(12) United States Patent
Sheppard et al.

(10) Patent No.: US 11,530,180 B2
(45) Date of Patent: Dec. 20, 2022

(54) ALPHA-5 BETA-1 INHIBITORS

(71) Applicants: The Regents of the University of California, Oakland, CA (US); Shanghai ChemPartner Co., Ltd., South San Francisco, CA (US)

(72) Inventors: Dean Sheppard, Oakland, CA (US); William F. DeGrado, San Francisco, CA (US); Hyunil Jo, Lafayette, CA (US); Aparna Sundaram, San Francisco, CA (US); Richard Beresis, San Francisco, CA (US)

(73) Assignees: The Regents of the University of California, Oakland, CA (US); Shanghai ChemPartner Co., Ltd., South San Francisco, CA (US)

(*) Notice: Subject to any disclaimer, the term of this patent is extended or adjusted under 35 U.S.C. 154(b) by 0 days.

(21) Appl. No.: 17/117,004

(22) Filed: Dec. 9, 2020

(65) Prior Publication Data
US 2021/0171455 A1  Jun. 10, 2021

Related U.S. Application Data
(60) Provisional application No. 62/946,358, filed on Dec. 10, 2019.

(51) Int. Cl.
| | | |
|---|---|---|
| C07C 279/18 | (2006.01) |
| C07C 279/28 | (2006.01) |
| C07C 317/14 | (2006.01) |
| C07D 239/14 | (2006.01) |
| C07D 265/08 | (2006.01) |
| C07D 265/16 | (2006.01) |
| C07D 265/36 | (2006.01) |
| C07D 295/155 | (2006.01) |
| C07D 311/68 | (2006.01) |
| C07D 401/12 | (2006.01) |
| C07D 403/12 | (2006.01) |
| C07D 413/12 | (2006.01) |
| C07D 417/12 | (2006.01) |
| C07D 471/04 | (2006.01) |
| A61K 31/337 | (2006.01) |
| A61K 31/704 | (2006.01) |
| C07D 235/16 | (2006.01) |
| C07D 213/74 | (2006.01) |
| C07D 233/88 | (2006.01) |
| C07D 215/42 | (2006.01) |
| C07D 279/06 | (2006.01) |

(52) U.S. Cl.
CPC .......... *C07C 279/18* (2013.01); *C07C 279/28* (2013.01); *C07C 317/14* (2013.01); *C07D 213/74* (2013.01); *C07D 215/42* (2013.01); *C07D 233/88* (2013.01); *C07D 235/16* (2013.01); *C07D 239/14* (2013.01); *C07D 265/08* (2013.01); *C07D 265/36* (2013.01); *C07D 279/06* (2013.01); *C07D 295/155* (2013.01); *C07D 311/68* (2013.01); *C07D 401/12* (2013.01); *C07D 403/12* (2013.01); *C07D 413/12* (2013.01); *C07D 417/12* (2013.01); *C07D 471/04* (2013.01); *C07C 2601/16* (2017.05)

(58) Field of Classification Search
CPC ... C07C 279/18; C07C 260/16; C07C 279/28; C07C 317/14; C07D 239/14; C07D 265/08; C07D 265/36; C07D 235/16; C07D 295/155; C07D 311/68; C07D 401/12; C07D 403/12; C07D 413/12; C07D 417/12; C07D 471/04; A61K 31/337; A61K 31/704
See application file for complete search history.

(56) References Cited

U.S. PATENT DOCUMENTS

| | | |
|---|---|---|
| 10,131,658 B2 | 11/2018 | DeGrado et al. |
| 10,214,522 B2 | 2/2019 | DeGrado et al. |
| 10,836,720 B2 | 11/2020 | Sheppard et al. |
| 2005/0203135 A1 | 9/2005 | Burdick et al. |

FOREIGN PATENT DOCUMENTS

WO   WO-2019/178248 A1   9/2019

OTHER PUBLICATIONS

Invitation to Pay Additional Fees dated Feb. 2, 2021, for PCT Application No. PCT/US2020/064114, filed Dec. 9, 2020, 2 pages.
Nair, R.V et al. (Jun. 18, 2018, e-published May 30, 2018). "A Photoactivatable $\alpha_5\beta_1$—Specific Integrin Ligand," *Chembiochem* 19(12):1280-1287; S1-S20 Supporting Information.
Heckmann, D. et al. (Jun. 16, 2008). "Rational design of highly active and selective ligands forthe $\alpha5\beta1$ integrin receptor," *ChemBioChem* 9(9):1397-1407.
International Search Report dated Apr. 29, 2021, for PCT Application No. PCT/US2020/064114, filed Dec. 9, 2020, 5 pages.
PubChem CID 68819682 (Nov. 30, 2012). Located at <https://pubchem.ncbi.nlm.nih.gov/compound/68819682> 10 pages.
Written Opinion dated Apr. 29, 2021, for PCT Application No. PCT/US2020/064114, filed Dec. 9, 2020, 5 pages.
Besse, B. et al. (Jan. 2013, e-published Aug. 16, 2012). "Phase Ib safety and pharmacokinetic study of volociximab, an anti-$\alpha5\beta1$ integrin antibody, in combination with carboplatin and paclitaxel in advanced non-small-cell lung cancer," *Ann Oncol* 24(1):90-96.

(Continued)

*Primary Examiner* — Bruck Kifle
(74) *Attorney, Agent, or Firm* — Mintz, Levin, Cohn, Ferris, Glovsky and Popeo, P.C.

(57) ABSTRACT

The disclosure provides, inter alia, alpha-5 beta-1 inhibitors, pharmaceutical compositions comprising alpha-5 beta-1 inhibitors, methods for treating diseases using alpha-5 beta-1 inhibitors, and processes for making alpha-5 beta-1 inhibitors.

21 Claims, No Drawings

(56) References Cited

OTHER PUBLICATIONS

Bhaskar, V. et al. (Nov. 27, 2007). "A function blocking anti-mouse integrin alpha5beta1 antibody inhibits angiogenesis and impedes tumor growth in vivo," *J Transl Med* 5:61.

Cianfrocca, M.E. et al. (Jun. 5, 2006). "Phase 1 trial of the antiangiogenic peptide ATN-161 (Ac-PHSCN-$NH_2$), a beta integrin antagonist, in patients with solid tumours," *Br J Cancer* 94(11):1621-1626.

Huang, R. et al. (Sep. 10, 2018). "The Protective Effect of a Long-Acting and Multi-Target HM-3-Fc Fusion Protein in Rheumatoid Arthritis," *Int J Mol Sci* 19(9):2683.

Kim, S. et al. (Apr. 2000). "Regulation of angiogenesis in vivo by ligation of integrin $\alpha 5\beta 1$ with the central cell-binding domain of fibronectin," *Am J Pathol* 156(4):1345-1362.

Stoeltzing, O. et al. (Apr. 20, 2003). "Inhibition of integrin alpha5beta1 function with a small peptide (ATN-161) plus continuous 5-FU infusion reduces colorectal liver metastases and improves survival in mice," *Int J Cancer* 104(4):496-503.

Sundaram, A. et al. (Jan. 3, 2017). "Targeting integrin $\alpha_5\beta_1$ ameliorates severe airway hyperresponsiveness in experimental asthma," *J Clin Invest* 127(1):365-374.

Wang, W. et al. (Sep. 14, 2011). "The antiangiogenic effects of integrin $\alpha 5\beta 1$ inhibitor (ATN-161) in vitro and in vivo," *Invest Ophthalmol Vis Sci* 52(10):7213-7220.

ALPHA-5 BETA-1 INHIBITORS

CROSS-REFERENCE TO RELATED APPLICATIONS

This application claims priority to U.S. Application No. 62/946,358 filed Dec. 10, 2019, the disclosure of which is incorporated by reference herein in its entirety.

STATEMENT AS TO RIGHTS TO INVENTIONS MADE UNDER FEDERALLY SPONSORED RESEARCH AND DEVELOPMENT

This invention was made with government support under grant nos. F32 HL112588, K08 HL124049, R01 HL102292, U19 AI070412, U19 AI077439 and U54 HL119893 awarded by The National Institutes of Health. The government has certain rights in this invention.

BACKGROUND

Despite its high prevalence, current therapeutic options for asthma are quite limited. There are a paucity of effective treatments for asthma. Pharmacological modulation of the α5β1 integrin by small molecules presents one route to test the role of the α5β1 integrin in asthma. There is a need in the art for potent, selective α5β1 integrin inhibitors. Provided herein are solutions to these and other problems in the art.

SUMMARY

The disclosure provides a compound of Formula (I) or a pharmaceutically acceptable salt thereof; pharmaceutical compositions comprising the compound of Formula (I) or a pharmaceutically acceptable salt thereof and a pharmaceutically acceptable excipient; and methods of treating asthma using these compounds and pharmaceutical compositions; wherein the compound of Formula (I) is:

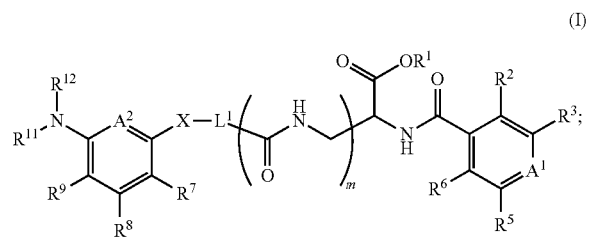

(I)

wherein the substituents are as defined herein. The compounds and compositions are useful to treat numerous diseases, including inflammatory disease and cancer.

These and other embodiments and aspects of the disclosure are described herein.

DETAILED DESCRIPTION

Definitions

Unless defined otherwise, technical and scientific terms used herein have the same meaning as commonly understood by a person of ordinary skill in the art. See, e.g., Singleton et al., Dictionary of Microbiology and Molecular Biology, 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). Any methods, devices and materials similar or equivalent to those described herein can be used in the practice of this disclosure. The following definitions are provided to facilitate understanding of certain terms used frequently herein and are not meant to limit the scope of the present disclosure.

Integrins are transmembrane proteins that mediate interactions between adhesion molecules on adjacent cells and/or the extracellular matrix (ECM). Integrins have diverse roles in several biological processes including, for example, cell migration during development and wound healing, cell differentiation, and apoptosis. Integrins typically exist as heterodimers consisting of α subunits (about 120-170 kDa in size) and β subunits (about 90-100 kDa in size).

The terms "α5β1" and "α5β1 integrin" refer to an integrin comprised of α5 subunit and a β1 subunit and is used according to its common, ordinary meaning. "α5β1" refers to proteins of the same or similar names, homologs, isoforms, and functional fragments thereof, so long as such fragments retain α5β1 integrin activity. The term includes any recombinant or naturally-occurring form of α5β1, or an α5β1 preprotein, or variants thereof that maintain α5β1 activity (e.g. within at least 30%, 40%, 50%, 60%, 70%, 80%, 90%, 95%, or 100% activity compared to wildtype α5β1). In aspects, α5 has the protein sequence corresponding to RefSeq NP_002196.3. In aspects, α5 has the protein sequence corresponding to the proteolytically processed mature version of RefSeq NP_002196.3. In aspects, α5 has the amino acid sequence corresponding to the reference number GI: 938148811. In aspects, β1 has the protein sequence corresponding to RefSeq NP_002202.2 In aspects, β1 has the amino acid sequence corresponding to the reference number GI: 19743813.

An "α5β1-inhibitor" as used herein refers to a composition (e.g. a compound, nucleic acid, polynucleotide, peptide, protein, or antibody) capable of reducing the activity of α5β1 integrin when compared to a control compound (e.g., known to have no reduction in α5β1 integrin activity) or the absence of the α5β1-inhibitor compound. An "α5β1-inhibitor compound" refers to a compound (e.g. compounds described herein) that reduce the activity of α5β1 integrin when compared to a control, such as absence of the compound or a compound with known inactivity.

An "α5β1-specific moiety", "specific," "specifically", "specificity", or the like of a composition (e.g. a compound, nucleic acid, polynucleotide, peptide, protein, or antibody) refers to the composition's ability to discriminate between particular molecular targets to a significantly greater extent than other proteins in the cell (e.g. a compound having specificity towards α5β1 integrin binds to α5β1 integrin whereas the same compound displays little-to-no binding to other integrins such as αvβ1, α8β1, α2β1, αvβ3, αvβ5, or αvβ6). An "α5β1-specific compound" refers to a compound (e.g. compounds described herein) having specificity towards α5β1 integrin.

The terms "α5β1-selective," "selective," or "selectivity" or the like of a compound refers to the composition's (e.g. a compound, nucleic acid, polynucleotide, peptide, protein, or antibody) ability to cause a particular action in a particular molecular target (e.g. a compound having selectivity toward α5β1 integrin would inhibit only α5β1). An "α5β1-selective compound" refers to a compound (e.g. compounds described herein) having selectivity towards α5β1 integrin.

The term "inhibition," "inhibit," "inhibiting" and the like in reference to a protein-inhibitor interaction means negatively affecting (e.g. decreasing) the activity or function of the protein relative to the activity or function of the protein in the absence of the inhibitor. In aspects, inhibition means negatively affecting (e.g. decreasing) the concentration or levels of the protein relative to the concentration or level of the protein in the absence of the inhibitor. In aspects, inhibition refers to reduction of a disease or symptoms of disease. In aspects, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In aspects, inhibition refers to a reduction of activity of a target protein resulting from a direct interaction (e.g. an inhibitor binds to the target protein). In aspects, inhibition refers to a reduction of activity of a target protein from an indirect interaction (e.g. an inhibitor binds to a protein that activates the target protein, thereby preventing target protein activation).

"Biological sample" refers to any biological sample taken from a subject. Biological samples include blood, plasma, serum, tumors, tissue, cells, and the like. In aspects, the biological sample is a blood sample. In aspects, the biological sample is a peripheral blood sample. Biological samples can be taken from a subject by methods known in the art, and can be analyzed by methods known in the art.

"Control," "suitable control," or "control experiment" is used in accordance with its plain ordinary meaning and refers to an experiment in which the subjects or reagents of the experiment are treated as in a parallel experiment except for omission of a procedure, reagent, or variable of the experiment. In aspects, the control is used as a standard of comparison in evaluating experimental effects. In aspects, a control is the measurement of the activity of a protein in the absence of a compound as described herein (including embodiments and examples). For example, a test sample can be taken from a patient suspected of having a given disease (e.g., asthma) and compared to samples from a known cancer patient, or a known normal (non-disease) individual. A control can also represent an average value gathered from a population of similar individuals, e.g., cancer patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters. In aspects, a control is a negative control. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The terms "treating" or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In aspects, treating is preventing. In aspects, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is not prophylactic treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, and other non-mammalian animals. In aspects, a patient is human.

A "effective amount," as used herein, is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). In these methods, the effective amount of the compounds described herein is an amount effective to accomplish the stated purpose of the method. An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control. For any compound described herein, the therapeutically effective amount can be initially determined from cell culture assays. Target concentrations will be those concentrations of active compound(s) that are capable of achieving the methods described herein, as measured using the methods described herein or known in the art. As is well known in the art, therapeutically effective amounts for use in humans can also be determined from animal models. For example, a dose for humans can be formulated to achieve a concentration that has been found to be effective in animals.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

The chemical structures and formulae set forth herein are constructed according to the standard rules of chemical valency known in the chemical arts. Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —$CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—S—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom. A heteroalkyl moiety may include two optionally different heteroatoms. A heteroalkyl moiety may include three optionally different heteroatoms. A heteroalkyl moiety may include four optionally different heteroatoms. A heteroalkyl moiety may include five optionally different heteroatoms. A heteroalkyl moiety may include up to 8 optionally different heteroatoms. The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— represents both —$C(O)_2R'$— and —$R'C(O)_2$—. As described above, heteroalkyl groups, as used herein, include those groups that are attached to the remainder of the molecule through a heteroatom, such as —C(O)R', —C(O)NR', —NR'R", —OR', —SR', and/or —$SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In aspects, monocyclic ring systems are cyclic hydrocarbon groups containing from 3 to 8 carbon atoms, where such groups can be saturated or unsaturated, but not aromatic. In aspects, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In aspects, bridged monocyclic rings contain a monocyclic cycloalkyl ring where two non adjacent carbon atoms of the monocyclic ring are linked by an alkylene bridge of between one and three additional carbon atoms (i.e., a bridging group of the form ($CH_2$), where w is 1, 2, or 3). Representative examples of bicyclic ring systems include, but are not limited to, bicyclo[3.1.1]-heptane, bicyclo[2.2.1]heptane, bicyclo[2.2.2]octane, bicyclo[3.2.2]nonane, bicyclo[3.3.1] nonane, and bicyclo[4.2.1]nonane. In aspects, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In aspects, the bridged or fused bicyclic cycloalkyl is attached to the parent molecular moiety through any carbon atom contained within the monocyclic cycloalkyl ring. In aspects, cycloalkyl groups are optionally substituted with one or two groups which are independently oxo or thia. In aspects, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In aspects, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In aspects, the multicyclic cycloalkyl is attached to the parent molecular moiety through any carbon atom contained within the base ring. In aspects, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In aspects, a cycloalkenyl is a monocyclic, bicyclic, or a multicyclic cycloalkenyl ring system. In aspects, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In aspects, bicyclic cycloalkenyl rings are bridged monocyclic rings or a fused bicyclic rings. In aspects, bridged monocyclic rings contain a monocyclic cycloalkenyl ring where two non adjacent carbon atoms of the monocyclic ring are linked by an alkylene bridge of between one and three additional carbon atoms (i.e., a bridging group of the form ($CH_2$)$_w$, where w is 1, 2, or 3). Representative examples of bicyclic cycloalkenyls include, but are not limited to, norbornenyl and bicyclo[2.2.2]oct 2 enyl. In aspects, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In aspects, the bridged or fused bicyclic cycloalkenyl is attached to the parent molecular moiety through any carbon atom contained within the monocyclic cycloalkenyl ring. In aspects, cycloalkenyl groups are optionally substituted with one or two groups which are independently oxo or thia. In aspects, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In aspects, the multicyclic cycloalkenyl is attached to the parent molecular moiety through any carbon atom contained within the base ring. In aspects, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of 0, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydro-benzofuran-2-yl, 2,3-dihydrobenzofuran-3-yl, indolin-1-yl, indolin-2-yl, indolin-3-yl, 2,3-dihydro-benzothien-2-yl, decahydroquinolinyl, decahydroisoquinolinyl, octahydro-1H-indolyl, and octahydrobenzofuranyl. In aspects, heterocyclyl groups are optionally substituted with one or two groups which are independently oxo or thia. In certain aspects, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In aspects, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3 g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol " ⌇ " and "—" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In aspects, the alkylarylene group has the formula:

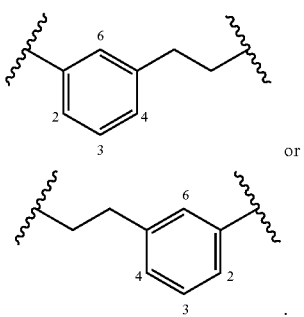

or

An alkylarylene moiety may be substituted (e.g., with a substituent group) on the alkylene moiety or the arylene linker (e.g., at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$, —SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In aspects, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R'")$_d$—, where s and d are independently integers of from 0 to 3, and X' is —O—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties: (A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and A "substituent group," as used herein, means a group selected from the following moieties: (B) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: (i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: (a) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In embodiments, each substituted group described in the compounds herein is substituted with at least one substituent group. In aspects, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In aspects, at least one or all of these groups are substituted with at least one size-limited substituent group. In aspects, at least one or all of these groups are substituted with at least one lower substituent group.

In embodiments, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In aspects, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and/or each substituted or unsubstituted heteroaryl is a substituted or unsubstituted 5 to 6 membered heteroaryl. In some aspects, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene. In aspects, the compound (e.g., nucleotide analogue) is a chemical species set forth in the Examples section, claims, aspects, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkyl ene, unsubstituted heteroalkylene, unsubstituted cycloalkylene, unsubstituted heterocycloalkylene, unsubstituted arylene, and/or unsubstituted heteroarylene, respectively). In aspects, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted aryl ene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In aspects, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group is optionally different. In aspects, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group is optionally different. In aspects, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group is optionally different. In aspects, if the substituted moiety is substituted with a plurality of groups selected from substituent groups, size-limited substituent groups, and lower substituent groups; each substituent group, size-limited substituent group, and/or lower substituent group is different.

Certain compounds of the disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the disclosure do not include those that are known in art to be too unstable to synthesize and/or isolate. The disclosure is meant to include compounds in racemic and optically pure forms. Optically active (R)- and (S)-, or (D)- and (L)-isomers may be prepared using chiral synthons or chiral reagents, or resolved using conventional techniques. When the compounds contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another. It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," "analogue" or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain compounds contain both basic and acidic functionalities that allow the compounds to be converted into either base or acid addition salts.

The compounds may exist as salts, such as with pharmaceutically acceptable acids. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art. The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the disclosure provides compounds which are in a prodrug form. Prodrugs of the compounds described herein are those compounds that readily undergo chemical changes under physiological conditions to provide the compounds disclosed herein. Prodrugs of the compounds described herein may be converted in vivo after administration. Additionally, prodrugs can be converted to the compounds of the disclosure by chemical or biochemical methods in an ex vivo environment, such as, for example, when contacted with a suitable enzyme or chemical reagent.

Certain compounds can exist in unsolvated forms as well as solvated forms, including hydrated forms. In general, the solvated forms are equivalent to unsolvated forms and are encompassed within the scope of the disclosure. Certain compounds may exist in multiple crystalline or amorphous forms. In general, all physical forms are equivalent for the uses contemplated by disclosure and are intended to be within the scope of the disclosure.

Compounds

In embodiments, the disclosure provides a compound of Formula (I) or a pharmaceutically acceptable salt thereof:

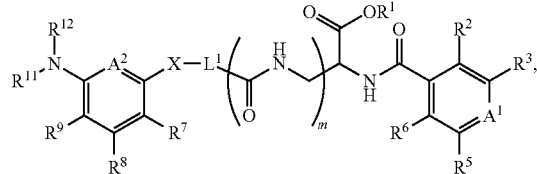

(I)

wherein the substituents are as defined herein.

In embodiments, the disclosure provides a compound of Formula (IIA) or a pharmaceutically acceptable salt thereof:

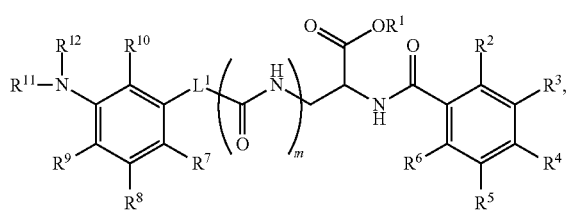

(IIA)

wherein the substituents are as defined herein.

In embodiments, the disclosure provides a compound of Formula (IIB) or a pharmaceutically acceptable salt thereof:

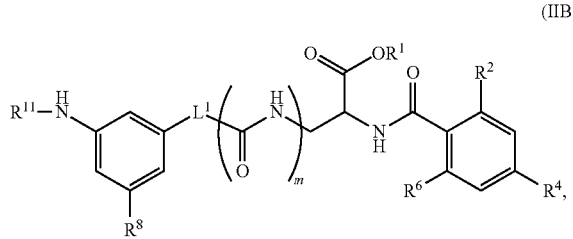

(IIB)

wherein the substituents are as defined herein.

In embodiments, the disclosure provides a compound of Formula (IIIA) or a pharmaceutically acceptable salt thereof:

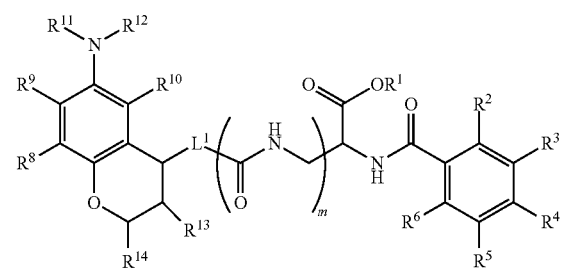

(IIIA)

wherein the substituents are as defined herein.

In embodiments, the disclosure provides a compound of Formula (IIIB) or a pharmaceutically acceptable salt thereof:

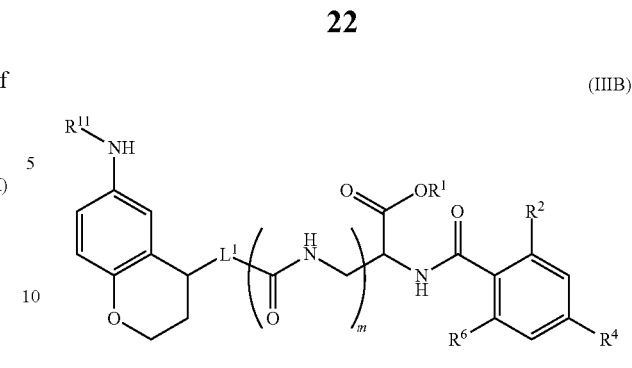

(IIIB)

wherein the substitutents are as defined herein.

Substituents

The following substituents refer to each of the compounds of Formula (I), (IIA), (IIB), (IIIA), and (IIIB).

m is an integer from 1 to 3. In aspects, m is 1 or 2. In aspects, m is 1. In aspects, m is 2. In aspects, m is 3.

$A^1$ is $C(R^4)$ or N. In aspects, $A^1$ is $C(R^4)$. In aspects, $A^1$ is N.

$A^2$ is $C(R^{10})$ or N. In aspects, $A^2$ is $C(R^{10})$. In aspects, $A^2$ is N.

In aspects, $A^1$ is $C(R^4)$ and $A^2$ is $C(R^{10})$. In aspects, $A^1$ is $C(R^4)$ and $A^2$ is N. In aspects, $A^1$ is N and $A^2$ is $C(R^{10})$. In aspects, $A^1$ is N and $A^2$ is N.

X is a bond, —$C(R^{15})(R^{16})$— or —$N(R^{15})$—. In aspects, X is a bond. In aspects, X is —$C(R^{15})(R^{16})$—. In aspects, X is —$N(R^{15})$—.

$R^1$ is hydrogen, substituted or unsubstituted aryl, substituted or unsubstituted heteroaryl, substituted or unsubstituted heterocycloalkyl, substituted or unsubstituted alkyl, substituted or unsubstituted heteroalkyl, substituted or unsubstituted cycloalkyl, or [P(=O)(OH)O—]$_n$, where n is an integer from 1 to 3. In aspects, $R^1$ is hydrogen. In aspects, $R^1$ is substituted or unsubstituted aryl. In aspects, $R^1$ is substituted or unsubstituted heteroaryl. In aspects, $R^1$ is substituted or unsubstituted heterocycloalkyl. In aspects, $R^1$ is substituted or unsubstituted alkyl. In aspects, $R^1$ is substituted or unsubstituted heteroalkyl. In aspects, $R^1$ is substituted or unsubstituted cycloalkyl.

In embodiments, $R^1$ is hydrogen, substituted or unsubstituted alkyl, substituted or unsubstituted heteroalkyl, substituted or unsubstituted cycloalkyl, or [P(=O)(OH)O—]$_n$, where n is an integer from 1 to 3. In aspects, $R^1$ is [P(=O)(OH)O—]$_n$, where n is 1. In aspects, $R^1$ is —[P(=O)(OH)O—]$_n$, where n is 2. In aspects, $R^1$ is [P(=O)(OH)O—]$_n$, where n is 3. In aspects, $R^1$ is hydrogen, substituted or unsubstituted alkyl, or substituted or unsubstituted cycloalkyl. In aspects, $R^1$ is hydrogen, unsubstituted alkyl, or unsubstituted cycloalkyl. In aspects, $R^1$ is hydrogen, unsubstituted $C_{1-10}$ alkyl, or unsubstituted $C_{4-8}$ cycloalkyl. In aspects, $R^1$ is hydrogen, unsubstituted $C_{1-8}$ alkyl, or unsubstituted $C_{5-6}$ cycloalkyl. In aspects, $R^1$ is hydrogen. In aspects, $R^1$ is unsubstituted $C_{1-12}$ alkyl. In aspects, $R^1$ is unsubstituted $C_{1-10}$ alkyl. In aspects, $R^1$ is unsubstituted $C_{1-8}$ alkyl. In aspects, $R^1$ is unsubstituted $C_{1-6}$ alkyl. In aspects, $R^1$ is unsubstituted $C_{1-4}$ alkyl. In aspects, $R^1$ is unsubstituted $C_{5-6}$ cycloalkyl.

In embodiments, $R^1$ is hydrogen, $R^{100}$-substituted or unsubstituted aryl (e.g. $C_6$-$C_{10}$ or $C_6$), $R^{100}$-substituted or unsubstituted heteroaryl (e.g. 5 to 10 membered, 5 to 9 membered, or 5 to 6 membered), $R^{100}$-substituted or unsubstituted heterocycloalkyl (e.g. 3 to 8 membered, 4 to 8 membered, or 5 to 6 membered), $R^{100}$-substituted or unsubstituted alkyl (e.g. $C_1$-$C_8$, $C_1$-$C_6$, or $C_1$-$C_4$), $R^{100}$-substituted or unsubstituted heteroalkyl (e.g. 2 to 10 membered, 2 to 8 membered, 2 to 6 membered heteroalkyl, or 2 to 4 membered heteroalkyl), $R^{100}$-substituted or unsubstituted cycloalkyl (e.g. $C_3$-$C_8$, $C_4$-$C_8$, or $C_5$-$C_6$), or —[P(=O)(OH)O—]$_n$, where n is an integer from 1 to 3. In aspects, $R^1$ is hydrogen. In aspects, $R^1$ is $R^{100}$-substituted or unsubstituted aryl (e.g. $C_6$-$C_{10}$ or $C_6$). In aspects, $R^1$ is $R^{100}$-substituted or unsubstituted heteroaryl (e.g. 5 to 10 membered, 5 to 9 membered, or 5 to 6 membered). In aspects, $R^1$ is $R^{100}$-substituted or unsubstituted heterocycloalkyl (e.g. 3 to 8 membered, 4 to 8 membered, or 5 to 6 membered). In aspects, $R^1$ is $R^{100}$-substituted or unsubstituted alkyl (e.g. $C_1$-$C_8$, $C_1$-$C_6$, or $C_1$-$C_4$). In aspects, $R^1$ is $R^{100}$-substituted or unsubstituted heteroalkyl (e.g. 2 to 10 membered, 2 to 8 membered, 2 to 6 membered heteroalkyl, or 2 to 4 membered). In aspects, $R^1$ is $R^{100}$-substituted or unsubstituted cycloalkyl (e.g. $C_3$-$C_8$, $C_4$-$C_8$, or $C_5$-$C_6$).

In embodiments, $R^1$ is hydrogen, $R^{100}$-substituted or unsubstituted alkyl (e.g. $C_1$-$C_8$, $C_1$-$C_6$, or $C_1$-$C_4$), $R^{100}$-substituted or unsubstituted heteroalkyl (e.g. 2 to 10 membered, 2 to 8 membered, 2 to 6 membered heteroalkyl, or 2 to 4 membered heteroalkyl), $R^{100}$-substituted or unsubstituted cycloalkyl (e.g. $C_3$-$C_8$, $C_4$-$C_8$, or $C_5$-$C_6$), or —[P(=O)(OH)O—]$_n$, where n is an integer from 1 to 3. In aspects, $R^1$ is $R^{100}$-substituted alkyl. In aspects, $R^1$ is $R^{100}$-substituted heteroalkyl. In aspects, $R^1$ is $R^{100}$-substituted cycloalkyl. In aspects, $R^1$ is $R^{100}$-substituted $C_1$-$C_8$, $C_1$-$C_6$, or $C_1$-$C_4$ alkyl. In aspects, $R^1$ is $R^{100}$-substituted 2 to 10 membered, 2 to 8 membered, 2 to 6 membered, or 2 to 4 membered heteroalkyl. In aspects, $R^1$ $R^{100}$-substituted $C_3$-$C_8$, $C_4$-$C_8$, or $C_5$-$C_6$ cycloakly.

$R^{100}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —N(O)$_2$, —$NHSO_2H$, —NHC(O)H, —NHC(O)OH, —NHOH, —$N_3$, $R^{101}$-substituted or unsubstituted alkyl (e.g. $C_1$-$C_8$, $C_1$-$C_6$, or $C_1$-$C_4$), $R^{101}$-substituted or unsubstituted heteroalkyl (e.g. 2 to 10 membered, 2 to 8 membered, 2 to 6 membered, or 2 to 4 membered), $R^{101}$-substituted or unsubstituted cycloalkyl (e.g. $C_3$-$C_8$, $C_4$-$C_8$, or $C_5$-$C_6$), $R^{101}$-substituted or unsubstituted heterocycloalkyl (e.g. 3 to 8 membered, 4 to 8 membered, or 5 to 6 membered), $R^{101}$-substituted or unsubstituted aryl (e.g. $C_6$-$C_{10}$ or $C_6$), or $R^{101}$-substituted or unsubstituted heteroaryl (e.g. 5 to 10 membered, 5 to 9 membered, or 5 to 6 membered).

$R^{101}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —N(O)$_2$, —$NHSO_2H$, —NHC(O)H, —NHC(O)OH, —NHOH, —$N_3$, unsubstituted alkyl (e.g. $C_1$-$C_8$, $C_1$-$C_6$, or $C_1$-$C_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. $C_3$-$C_8$, $C_4$-$C_8$, or $C_5$-$C_6$), unsubstituted heterocycloalkyl (e.g. 3 to 8 membered, 4 to 8 membered, or 5 to 6 membered), unsubstituted aryl (e.g. $C_6$-$C_{10}$ or $C_6$), or unsubstituted heteroaryl (e.g. 5 to 10 membered, 5 to 9 membered, or 5 to 6 membered).

$R^2$ is hydrogen, halogen, —$CX^2_3$, —$CHX^2_2$, —$CH_2X^2$, —$OCX^2_3$, —$OCH_2X^2$, —$OCHX^2_2$, —$SO_{n2}R^{2A}$, —$SO_{v2}NR^{2A}R^{2B}$, —CN, —C(O)$R^{2A}$, —C(O)O$R^{2A}$, —C(O)$NR^{2A}R^{2B}$, —O$R^{2A}$, —ON$R^{2A}R^{2B}$, —NHC(O)$NR^{2A}R^{2B}$, —N(O)$_{m2}$, —$NR^{2A}R^{2B}$, —$NHNR^{2A}R^{2B}$, —$NR^{2A}SO_2R^{2B}$, —$NR^{2A}$C(O)$R^{2B}$, —$NR^{2A}$C(O)O$R^{2B}$, —$NR^{2A}OR^{2B}$, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered). In aspects, $R^2$ is not unsubstituted alkyl. In aspects, $R^2$ is not substituted or unsubstituted alkyl.

In embodiments, $R^2$ is hydrogen, halogen, —$CHX^2_2$, —$CH_2X^2$, —$OCX^2_3$, —$OCH_2X^2$, —$OCHX^2_2$, —$SO_{n2}R^{2A}$, —$SO_{v2}NR^{2A}R^{2B}$, —CN, —C(O)$R^{2A}$, —C(O)O$R^{2A}$, —C(O)$NR^{2A}R^{2B}$, —O$R^{2A}$, —ON$R^{2A}R^{2B}$, —NHC(O)$NR^{2A}R^{2B}$, —N(O)$_{m2}$, —$NR^{2A}R^{2B}$, —$NHNR^{2A}R^{2B}$, —$NR^{2A}SO_2R^{2B}$, —$NR^{2A}$C(O)$R^{2B}$, —$NR^{2A}$C(O)O$R^{2B}$, —$NR^{2A}OR^{2B}$, —$N_3$, $R^{200}$-substituted or unsubstituted alkyl (e.g. $C_1$-$C_8$, $C_1$-$C_6$, or $C_1$-$C_4$), $R^{200}$-substituted or unsubstituted heteroalkyl (e.g. 2 to 10 membered, 2 to 8 membered, 4 to 8 membered, 2 to 6 membered, or 2 to 4 membered), $R^{200}$-substituted or unsubstituted cycloalkyl (e.g. $C_3$-$C_8$, $C_4$-$C_8$, or $C_5$-$C_6$), $R^{200}$-substituted or unsubstituted heterocycloalkyl (e.g. 3 to 8 membered, 4 to 8 membered, or 5 to 6 membered), $R^{200}$-substituted or unsubstituted aryl (e.g. $C_6$-$C_{10}$ or $C_6$), or $R^{200}$-substituted or unsubstituted heteroaryl (e.g. 5 to 10 membered, 5 to 9 membered, or 5 to 6 membered).

$R^{200}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —N(O)$_2$, —$NHSO_2H$, —NHC(O)H, —NHC(O)OH, —NHOH, —$N_3$, $R^{201}$-substituted or unsubstituted alkyl (e.g. $C_1$-$C_8$, $C_1$-$C_6$, or $C_1$-$C_4$), $R^{201}$-substituted or unsubstituted heteroalkyl (e.g. 2 to 10 membered, 2 to 8 membered, 4 to 8 membered, 2 to 6 membered, or 2 to 4 membered), $R^{201}$-substituted or unsubstituted cycloalkyl (e.g. $C_3$-$C_8$, $C_4$-$C_8$, or $C_5$-$C_6$), $R^{201}$-substituted or unsubstituted heterocycloalkyl (e.g. 3 to 8 membered, 4 to 8 membered, or 5 to 6 membered), $R^{201}$-substituted or unsubstituted aryl (e.g. $C_6$-$C_{10}$ or $C_6$), or $R^{201}$-substituted or unsubstituted heteroaryl (e.g. 5 to 10 membered, 5 to 9 membered, or 5 to 6 membered).

$R^{201}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —N(O)$_2$, —$NHSO_2H$, —NHC(O)H, —NHC(O)OH, —NHOH, —$N_3$, unsubstituted alkyl (e.g. $C_1$-$C_8$, $C_1$-$C_6$, or $C_1$-$C_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. $C_3$-$C_8$, $C_4$-$C_8$, or $C_5$-$C_6$), unsubstituted heterocycloalkyl (e.g. 3 to 8 membered, 4 to 8 membered, or 5 to 6 membered), unsubstituted aryl (e.g. $C_6$-$C_{10}$ or $C_6$), or unsubstituted heteroaryl (e.g. 5 to 10 membered, 5 to 9 membered, or 5 to 6 membered).

$R^{2A}$ and $R^{2B}$ are independently hydrogen, halogen, —$CF_3$, —$CBr_3$, —$CCl_3$, —$CI_3$, —$CHF_2$, —$CHBr_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, substituted or unsubstituted alkyl (e.g. C$_1$-C$_8$, C$_1$-C$_6$, or C$_1$-C$_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. C$_3$-C$_8$, C$_4$-C$_8$, or C$_5$-C$_6$), substituted or unsubstituted heterocycloalkyl (e.g. 3 to 8 membered, 4 to 8 membered, or 5 to 6 membered), substituted or unsubstituted aryl (e.g. C$_6$-C$_{10}$ or C$_6$), or substituted or unsubstituted heteroaryl (e.g. 5 to 10 membered, 5 to 9 membered, or 5 to 6 membered); R$^{2A}$ and R$^{2B}$ substituents bonded to the same nitrogen atom may optionally be joined to form a substituted or unsubstituted heterocycloalkyl (e.g. 3 to 8 membered, 4 to 8 membered, or 5 to 6 membered) or substituted or unsubstituted heteroaryl (e.g. 5 to 10 membered, 5 to 9 membered, or 5 to 6 membered).

In embodiments, R$^{2A}$ and R$^{2B}$ are independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, R$^{200}$-substituted or unsubstituted alkyl (e.g., C$_1$-C$_8$, C$_1$-C$_6$, or C$_1$-C$_4$), R$^{200}$-substituted or unsubstituted heteroalkyl (e.g., 2 to 10 membered, 2 to 8 membered, 4 to 8 membered, 2 to 6 membered, or 2 to 4 membered), R$^{200}$-substituted or unsubstituted cycloalkyl (e.g., C$_3$-C$_8$, C$_4$-C$_8$, or C$_5$-C$_6$), R$^{200}$-substituted or unsubstituted heterocycloalkyl (e.g., 3 to 8 membered, 4 to 8 membered, or 5 to 6 membered), R$^{200}$-substituted or unsubstituted aryl (e.g., C$_6$-C$_{10}$ or C$_6$), or R$^{200}$-substituted or unsubstituted heteroaryl (e.g., 5 to 10 membered, 5 to 9 membered, or 5 to 6 membered).

In embodiments, R$^2$ is halogen, —CHX$^2_2$, —CH$_2$X$^2$, —OCX$^2_3$, —OCH$_2$X$^2$, or —OCHX$^2_2$. In aspects, R$^2$ is halogen. In aspects, R$^2$ is chlorine. In aspects, R$^2$ is fluorine. In aspects, R$^2$ is bromine. In aspects, R$^2$ is iodine.

X$^2$ is halogen. In aspects, X$^2$ is bromine, chlorine, fluorine, or iodine. In aspects, X$^2$ is bromine. In aspects, X$^2$ is chlorine. In aspects, X$^2$ is fluorine. In aspects, X$^2$ is iodine. n2 is an integer from 0 to 4. In aspects, n2 is 0. In aspects, n2 is 1. In aspects, n2 is 2. In aspects, n2 is 3. In aspects, n2 is 4. m2 is 1 or 2. In aspects, m2 is 1. In aspects, m2 is 2. v2 is 1 or 2. In aspects, v2 is 1. In aspects, v2 is 2.

R$^3$ is hydrogen, halogen, —CX$^3_3$, —CHX$^3_2$, —CH$_2$X$^3$, —OCX$^3_3$, —OCH$_2$X$^3$, —OCHX$^3_2$, —SO$_{n3}$R$^{3A}$, —SO$_{v3}$NR$^{3A}$R$^{3B}$, —CN, —C(O)R$^{3A}$, —C(O)OR$^{3A}$, —C(O)NR$^{3A}$R$^{3B}$, —OR$^{3A}$, —ONR$^{3A}$R$^{3B}$, —NHC(O)NR$^{3A}$R$^{3B}$, —N(O)$_{m3}$, —NR$^{3A}$R$^{3B}$, —NHNR$^{3A}$R$^{3B}$, —NR$^{3A}$SO$_2$R$^{3B}$, —NR$^{3A}$C(O)R$^{3B}$, —NR$^{3A}$C(O)OR$^{3B}$, —NR$^{3A}$OR$^{3B}$, —N$_3$, substituted or unsubstituted alkyl (e.g. C$_1$-C$_8$, C$_1$-C$_6$, or C$_1$-C$_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. C$_3$-C$_8$, C$_4$-C$_8$, or C$_5$-C$_6$), substituted or unsubstituted heterocycloalkyl (e.g. 3 to 8 membered, 4 to 8 membered, or 5 to 6 membered), substituted or unsubstituted aryl (e.g. C$_6$-C$_{10}$ or C$_6$), or substituted or unsubstituted heteroaryl (e.g. 5 to 10 membered, 5 to 9 membered, or 5 to 6 membered). In aspects, R$^3$ is hydrogen.

In embodiments, R$^3$ is hydrogen, halogen, —CX$^3_3$, —CHX$^3_2$, —CH$_2$X$^3$, —OCX$^3_3$, —OCH$_2$X$^3$, —OCHX$^3_2$, —SO$_{n3}$R$^{3A}$, —SO$_{v3}$NR$^{3A}$R$^{3B}$, —CN, —C(O)R$^{3A}$, —C(O)OR$^{3A}$, —C(O)NR$^{3A}$R$^{3B}$, —OR$^{3A}$, —ONR$^{3A}$R$^{3B}$, —NHC(O)NR$^{3A}$R$^{3B}$, —N(O)$_{m3}$, —NR$^{3A}$R$^{3B}$, —NHNR$^{3A}$R$^{3B}$, —NR$^{3A}$SO$_2$R$^{3B}$, —NR$^{3A}$C(O)R$^{3B}$, —NR$^{3A}$C(O)OR$^{3B}$, —NR$^{3A}$OR$^{3B}$, —N$_3$, R$^{300}$-substituted or unsubstituted alkyl (e.g. C$_1$-C$_8$, C$_1$-C$_6$, or C$_1$-C$_4$), R$^{300}$-substituted or unsubstituted heteroalkyl (e.g. 2 to 10 membered, 2 to 8 membered, 4 to 8 membered, 2 to 6 membered, or 2 to 4 membered), R$^{300}$-substituted or unsubstituted cycloalkyl (e.g. C$_3$-C$_8$, C$_4$-C$_8$, or C$_5$-C$_6$), R$^{300}$-substituted or unsubstituted heterocycloalkyl (e.g. 3 to 8 membered, 4 to 8 membered, or 5 to 6 membered), R$^{300}$-substituted or unsubstituted aryl (e.g. C$_6$-C$_{10}$ or C$_6$), or R$^{300}$-substituted or unsubstituted heteroaryl (e.g. 5 to 10 membered, 5 to 9 membered, or 5 to 6 membered).

R$^{300}$ is halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, R$^{301}$-substituted or unsubstituted alkyl (e.g. C$_1$-C$_8$, C$_1$-C$_6$, or C$_1$-C$_4$), R$^{301}$-substituted or unsubstituted heteroalkyl (e.g. 2 to 10 membered, 2 to 8 membered, 4 to 8 membered, 2 to 6 membered, or 2 to 4 membered), R$^{301}$-substituted or unsubstituted cycloalkyl (e.g. C$_3$-C$_8$, C$_4$-C$_8$, or C$_5$-C$_6$), R$^{301}$-substituted or unsubstituted heterocycloalkyl (e.g. 3 to 8 membered, 4 to 8 membered, or 5 to 6 membered), R$^{301}$-substituted or unsubstituted aryl (e.g. C$_6$-C$_{10}$ or C$_6$), or R$^{301}$-substituted or unsubstituted heteroaryl (e.g. 5 to 10 membered, 5 to 9 membered, or 5 to 6 membered).

R$^{301}$ is halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, unsubstituted alkyl (e.g. C$_1$-C$_8$, C$_1$-C$_6$, or C$_1$-C$_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. C$_3$-C$_8$, C$_4$-C$_8$, or C$_5$-C$_6$), unsubstituted heterocycloalkyl (e.g. 3 to 8 membered, 4 to 8 membered, or 5 to 6 membered), unsubstituted aryl (e.g. C$_6$-C$_{10}$ or C$_6$), or unsubstituted heteroaryl (e.g. 5 to 10 membered, 5 to 9 membered, or 5 to 6 membered).

R$^{3A}$ and R$^{3B}$ are independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, substituted or unsubstituted alkyl (e.g. C$_1$-C$_8$, C$_1$-C$_6$, or C$_1$-C$_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. C$_3$-C$_8$, C$_4$-C$_8$, or C$_5$-C$_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered); $R^{3A}$ and $R^{3B}$ substituents bonded to the same nitrogen atom may optionally be joined to form a substituted or unsubstituted heterocycloalkyl (e.g. 3 to 8 membered, 4 to 8 membered, or 5 to 6 membered) or substituted or unsubstituted heteroaryl (e.g. 5 to 10 membered, 5 to 9 membered, or 5 to 6 membered).

In embodiments, $R^{3A}$ and $R^{3B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{300}$-substituted or unsubstituted alkyl (e.g., $C_1$-$C_8$, $C_1$-$C_6$, or $C_1$-$C_4$), $R^{300}$-substituted or unsubstituted heteroalkyl (e.g., 2 to 10 membered, 2 to 8 membered, 4 to 8 membered, 2 to 6 membered, or 2 to 4 membered), $R^{300}$-substituted or unsubstituted cycloalkyl (e.g., $C_3$-$C_8$, $C_4$-$C_8$, or $C_5$-$C_6$), $R^{300}$-substituted or unsubstituted heterocycloalkyl (e.g., 3 to 8 membered, 4 to 8 membered, or 5 to 6 membered), $R^{300}$-substituted or unsubstituted aryl (e.g., $C_6$-$C_{10}$ or $C_6$), or $R^{300}$-substituted or unsubstituted heteroaryl (e.g., 5 to 10 membered, 5 to 9 membered, or 5 to 6 membered).

$X^3$ is halogen. In aspects, $X^3$ is bromine, chlorine, fluorine, or iodine. In aspects, $X^3$ is bromine. In aspects, $X^3$ is chlorine. In aspects, $X^3$ is fluorine. In aspects, $X^3$ is iodine. n3 is an integer from 0 to 4. In aspects, n3 is 0. In aspects, n3 is 1. In aspects, n3 is 2. In aspects, n3 is 3. In aspects, n3 is 4. m3 is 1 or 2. In aspects, m3 is 1. In aspects, m3 is 2. v3 is 1 or 2. In aspects, v3 is 1. In aspects, v3 is 2.

$R^4$ is hydrogen, halogen, —$CX^4_3$, —$CHX^4_2$, —$CH_2X^4$, —$OCX^4_3$, —$OCH_2X^4$, —$OCHX^4_2$, —$SO_{n4}R^{4A}$, —$SO_{v4}NR^{4A}R^{4B}$, —CN, —$C(O)R^{4A}$, —$C(O)OR^{4A}$, —$C(O)NR^{4A}R^{4B}$, —$OR^{4A}$, —$ONR^{4A}R^{4B}$, —$NHC(O)NR^{4A}R^{4B}$, —$N(O)_{m4}$, —$NR^{4A}R^{4B}$, —$NHNR^{4A}R^{4B}$, —$NR^{4A}SO_2R^{4B}$, —$NR^{4A}C(O)R^{4B}$, —$NR^{4A}C(O)OR^{4B}$, —$NR^{4A}OR^{4B}$, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered).

In embodiments, $R^4$ is hydrogen, halogen, —$CX^4_3$, —$CHX^4_2$, —$CH_2X^4$, —$OCX^4_3$, —$OCH_2X^4$, —$OCHX^4_2$, —$SO_{n4}R^{4A}$, —$SO_{v4}NR^{4A}R^{4B}$, —CN, —$C(O)R^{4A}$, —$C(O)OR^{4A}$, —$C(O)NR^{4A}R^{4B}$, —$OR^{4A}$, —$ONR^{4A}R^{4B}$, —$NHC(O)NR^{4A}R^{4B}$, —$N(O)_{m4}$, —$NR^{4A}R^{4B}$, —$NR^{4A}SO_2R^{4B}$, —$NR^{4A}C(O)R^{4B}$, —$NR^{4A}C(O)OR^{4B}$, —$NR^{4A}OR^{4B}$, —$N_3$, $R^{400}$-substituted or unsubstituted alkyl (e.g. $C_1$-$C_8$, $C_1$-$C_6$, or $C_1$-$C_4$), $R^{400}$-substituted or unsubstituted heteroalkyl (e.g. 2 to 10 membered, 2 to 8 membered, 4 to 8 membered, 2 to 6 membered, or 2 to 4 membered), $R^{400}$-substituted or unsubstituted cycloalkyl (e.g. $C_3$-$C_8$, $C_4$-$C_8$, or $C_5$-$C_6$), $R^{400}$-substituted or unsubstituted heterocycloalkyl (e.g. 3 to 8 membered, 4 to 8 membered, or 5 to 6 membered), $R^{400}$-substituted or unsubstituted aryl (e.g. $C_6$-$C_{10}$ or $C_6$), or $R^{400}$-substituted or unsubstituted heteroaryl (e.g. 5 to 10 membered, 5 to 9 membered, or 5 to 6 membered).

$R^{400}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, $R^{401}$-substituted or unsubstituted alkyl (e.g. $C_1$-$C_8$, $C_1$-$C_6$, or $C_1$-$C_4$), $R^{401}$-substituted or unsubstituted heteroalkyl (e.g. 2 to 10 membered, 2 to 8 membered, 4 to 8 membered, 2 to 6 membered, or 2 to 4 membered), $R^{401}$-substituted or unsubstituted cycloalkyl (e.g. $C_3$-$C_8$, $C_4$-$C_8$, or $C_5$-$C_6$), $R^{401}$-substituted or unsubstituted heterocycloalkyl (e.g. 3 to 8 membered, 4 to 8 membered, or 5 to 6 membered), $R^{401}$-substituted or unsubstituted aryl (e.g. $C_6$-$C_{10}$ or $C_6$), or $R^{401}$-substituted or unsubstituted heteroaryl (e.g. 5 to 10 membered, 5 to 9 membered, or 5 to 6 membered).

$R^{401}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, unsubstituted alkyl (e.g. $C_1$-$C_8$, $C_1$-$C_6$, or $C_1$-$C_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. $C_3$-$C_8$, $C_4$-$C_8$, or $C_5$-$C_6$), unsubstituted heterocycloalkyl (e.g. 3 to 8 membered, 4 to 8 membered, or 5 to 6 membered), unsubstituted aryl (e.g. $C_6$-$C_{10}$ or $C_6$), or unsubstituted heteroaryl (e.g. 5 to 10 membered, 5 to 9 membered, or 5 to 6 membered).

$R^{4A}$ and $R^{4B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered); $R^{4A}$ and $R^{4B}$ substituents bonded to the same nitrogen atom may optionally be joined to form a substituted or unsubstituted heterocycloalkyl (e.g. 3 to 8 membered, 4 to 8 membered, or 5 to 6 membered) or substituted or unsubstituted heteroaryl (e.g. 5 to 10 membered, 5 to 9 membered, or 5 to 6 membered).

In embodiments, $R^{4A}$ and $R^{4B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{400}$-substituted or unsubstituted alkyl (e.g., $C_1$-$C_8$, $C_1$-$C_6$, or $C_1$-$C_4$), $R^{400}$-substituted or unsubstituted heteroalkyl (e.g., 2 to 10 membered, 2 to 8 membered, 4 to 8 membered, 2 to 6 membered, or 2 to 4 membered), $R^{400}$-substituted or unsubstituted cycloalkyl (e.g., $C_3$-$C_8$, $C_4$-$C_8$, or $C_5$-$C_6$), $R^{400}$-substituted or unsubstituted heterocycloalkyl (e.g., 3 to 8 membered, 4 to 8 membered, or 5 to 6 membered), $R^{400}$-substituted or unsubstituted aryl (e.g., $C_6$-$C_{10}$ or $C_6$), or $R^{400}$-substituted or unsubstituted heteroaryl (e.g., 5 to 10 membered, 5 to 9 membered, or 5 to 6 membered).

In aspects, $R^4$ is hydrogen. In aspects, $R^4$ is substituted or unsubstituted phenyl. In aspects, $R^4$ is $R^{400}$-substituted or unsubstituted phenyl. In aspects, $R^4$ is $R^{401}$-substituted or unsubstituted phenyl. In aspects, $R^4$ is unsubstituted phenyl. In aspects, $R^4$ is substituted phenyl. In aspects, $R^4$ is $R^{400}$-substituted phenyl. In aspects, $R^4$ is $R^{401}$-substituted phenyl.

In aspects, $R^4$ is substituted or unsubstituted aryl, substituted or unsubstituted heteroaryl, substituted or unsubstituted cycloakyl, or substituted or unsubstituted heterocycloalkyl. In aspects, $R^4$ is substituted or unsubstituted $C_{5-6}$ aryl, substituted or unsubstituted 5 or 6 membered heteroaryl, substituted or unsubstituted $C_{5-6}$ cycloalkyl, or substituted or unsubstituted 5 or 6 membered heterocycloalkyl. In aspects, $R^4$ is unsubstituted $C_{5-6}$ aryl. In aspects, $R^4$ is unsubstituted $C_5$ aryl. In aspects, $R^4$ is unsubstituted $C_6$ aryl. In aspects, $R^4$ is unsubstituted 5 or 6 membered heteroaryl. In aspects, $R^4$ is unsubstituted 5 membered heteroaryl. In aspects, $R^4$ is unsubstituted 6 membered heteroaryl. In aspects, $R^4$ is unsubstituted $C_{5-6}$ cycloakyl. In aspects, $R^4$ is unsubstituted $C_5$ cycloakyl. In aspects, $R^4$ is unsubstituted $C_6$ cycloakyl. In aspects, $R^4$ is unsubstituted 5 or 6 membered heterocycloalkyl. In aspects, $R^4$ is unsubstituted 5 membered heterocycloalkyl. In aspects, $R^4$ is unsubstituted 6 membered heterocycloalkyl.

In aspects, $R^4$ is $R^{400}$-substituted $C_{5-6}$ aryl. In aspects, $R^4$ is $R^{400}$-substituted $C_5$ aryl. In aspects, $R^4$ is $R^{400}$-substituted $C_6$ aryl. In aspects, $R^4$ is $R^{400}$-substituted 5 or 6 membered heteroaryl. In aspects, $R^4$ is $R^{400}$-substituted 5 membered heteroaryl. In aspects, $R^4$ is $R^{400}$-substituted 6 membered heteroaryl. In aspects, $R^4$ is $R^{400}$-substituted $C_{5-6}$ cycloakyl. In aspects, $R^4$ is $R^{400}$-substituted $C_5$ cycloalkyl. In aspects, $R^4$ is $R^{400}$-substituted $C_6$ cycloalkyl. In aspects, $R^4$ is $R^{400}$-substituted 5 or 6 membered heterocycloalkyl. In aspects, $R^4$ is $R^{400}$-substituted 5 membered heterocycloalkyl. In aspects, $R^4$ is $R^{400}$-substituted 6 membered heterocycloalkyl. In aspects, $R^4$ is $R^{401}$-substituted $C_{5-6}$ aryl. In aspects, $R^4$ is $R^{401}$-substituted $C_5$ aryl. In aspects, $R^4$ is $R^{401}$-substituted $C_6$ aryl. In aspects, $R^4$ is $R^{401}$-substituted 5 or 6 membered heteroaryl. In aspects, $R^4$ is $R^{401}$-substituted 5 membered heteroaryl. In aspects, $R^4$ is $R^{401}$-substituted 6 membered heteroaryl. In aspects, $R^4$ is $R^{400}$-substituted $C_{5-6}$ cycloakyl. In aspects, $R^4$ is $R^{401}$-substituted $C_5$ cycloalkyl. In aspects, $R^4$ is $R^{401}$-substituted $C_6$ cycloalkyl. In aspects, $R^4$ is $R^{401}$-substituted 5 or 6 membered heterocycloalkyl. In aspects, $R^4$ is $R^{401}$-substituted 5 membered heterocycloalkyl. In aspects, $R^4$ is $R^{401}$-substituted 6 membered heterocycloalkyl.

In aspects, $R^4$ is substituted or unsubstituted fused ring heteroaryl (e.g. 5 to 10 membered, 5 to 9 membered, or 5 to 6 membered). In aspects, $R^4$ is substituted or unsubstituted 5,6-fused ring heteroaryl. In aspects, $R^4$ is unsubstituted 5,6-fused ring heteroaryl. In aspects, $R^4$ is substituted or unsubstituted 6,6-fused ring heteroaryl. In aspects, $R^4$ is unsubstituted 6,6-fused ring heteroaryl.

$X^4$ halogen. In aspects, $X^4$ is bromine, chlorine, fluorine, or iodine. In aspects, $X^4$ is bromine. In aspects, $X^4$ is chlorine. In aspects, $X^4$ is fluorine. In aspects, $X^4$ is iodine. n4 is an integer from 0 to 4. In aspects, n4 is 0. In aspects, n4 is 1. In aspects, n4 is 2. In aspects, n4 is 3. In aspects, n4 is 4. m4 is 1 or 2. In aspects, m4 is 1. In aspects, m4 is 2. v4 is 1 or 2. In aspects, v4 is 1. In aspects, v4 is 2.

$R^5$ is hydrogen, halogen, $-CX^5_3$, $-CHX^5_2$, $-CH_2X^5$, $-OCX^5_3$, $-OCH_2X^5$, $-OCHX^5_2$, $-SO_{n5}R^{5A}$, $-SO_{v5}NR^{5A}R^{5B}$, $-CN$, $-C(O)R^{5A}$, $-C(O)OR^{5A}$, $-C(O)NR^{5A}R^{5B}$, $-OR^{5A}$, $-ONR^{5A}R^{5B}$, $-NHC(O)NR^{5A}R^{5B}$, $-N(O)_{m5}$, $-NR^{5A}R^{5B}$, $-NHNR^{5A}R^{5B}$, $-NR^{5A}SO_2R^{5B}$, $-NR^{5A}C(O)R^{5B}$, $-NR^{5A}C(O)OR^{5B}$, $-NR^{5A}OR^{5B}$, $-N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered). In aspects, $R^5$ is hydrogen.

In embodiments, $R^5$ is hydrogen, halogen, $-CX^5_3$, $-CHX^5_2$, $-CH_2X^5$, $-OCX^5_3$, $-OCH_2X^5$, $-OCHX^5_2$, $-SO_{n5}R^{5A}$, $-SO_{v5}NR^{5A}R^{5B}$, $-CN$, $-C(O)R^{5A}$, $-C(O)OR^{5A}$, $-C(O)NR^{5A}R^{5B}$, $-OR^{5A}$, $-ONR^{5A}R^{5B}$, $-NHC(O)NR^{5A}R^{5B}$, $-N(O)_{m5}$, $-NR^{5A}R^{5B}$, $-NHNR^{5A}R^{5B}$, $-NR^{5A}SO_2R^{5B}$, $-NR^{5A}C(O)R^{5B}$, $-NR^{5A}C(O)OR^{5B}$, $-NR^{5A}OR^{5B}$, $-N_3$, $R^{500}$-substituted or unsubstituted alkyl (e.g. $C_1$-$C_8$, $C_1$-$C_6$, or $C_1$-$C_4$), $R^{500}$-substituted or unsubstituted heteroalkyl (e.g. 2 to 10 membered, 2 to 8 membered, 4 to 8 membered, 2 to 6 membered, or 2 to 4 membered), $R^{500}$-substituted or unsubstituted cycloalkyl (e.g. $C_3$-$C_8$, $C_4$-$C_8$, or $C_5$-$C_6$), $R^{500}$-substituted or unsubstituted heterocycloalkyl (e.g. 3 to 8 membered, 4 to 8 membered, or 5 to 6 membered), $R^{500}$-substituted or unsubstituted aryl (e.g. $C_6$-$C_{10}$ or $C_6$), or $R^{500}$-substituted or unsubstituted heteroaryl (e.g. 5 to 10 membered, 5 to 9 membered, or 5 to 6 membered).

$R^{500}$ is halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-N(O)_2$, $-NHSO_2H$, $-NHC(O)H$, $-NHC(O)OH$, $-NHOH$, $-N_3$, $R^{501}$-substituted or unsubstituted alkyl (e.g. $C_1$-$C_8$, $C_1$-$C_6$, or $C_1$-$C_4$), $R^{501}$-substituted or unsubstituted heteroalkyl (e.g. 2 to 10 membered, 2 to 8 membered, 4 to 8 membered, 2 to 6 membered, or 2 to 4 membered), $R^{501}$-substituted or unsubstituted cycloalkyl (e.g. $C_3$-$C_8$, $C_4$-$C_8$, or $C_5$-$C_6$), $R^{501}$-substituted or unsubstituted heterocycloalkyl (e.g. 3 to 8 membered, 4 to 8 membered, or 5 to 6 membered), $R^{501}$-substituted or unsubstituted aryl (e.g. $C_6$-$C_{10}$ or $C_6$), or $R^{501}$-substituted or unsubstituted heteroaryl (e.g. 5 to 10 membered, 5 to 9 membered, or 5 to 6 membered).

$R^{501}$ is halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-N(O)_2$, $-NHSO_2H$, $-NHC(O)H$, $-NHC(O)OH$, $-NHOH$, $-N_3$, unsubstituted alkyl (e.g. $C_1$-$C_8$, $C_1$-$C_6$, or $C_1$-$C_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. $C_3$-$C_8$, $C_4$-$C_8$, or $C_5$-$C_6$), unsubstituted heterocycloalkyl (e.g. 3 to 8 membered, 4 to 8 membered, or 5 to 6 membered), unsubstituted aryl (e.g. $C_6$-$C_{10}$ or $C_6$), or unsubstituted heteroaryl (e.g. 5 to 10 membered, 5 to 9 membered, or 5 to 6 membered).

$R^{5A}$ and $R^{5B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered); $R^{5A}$ and $R^{5B}$ substituents bonded to the same nitrogen atom may optionally be joined to form a substituted or unsubstituted heterocycloalkyl (e.g. 3 to 8 membered, 4 to 8 membered, or 5 to 6 membered) or substituted or unsubstituted heteroaryl (e.g. 5 to 10 membered, 5 to 9 membered, or 5 to 6 membered).

In embodiments, $R^{5A}$ and $R^{5B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{500}$-substituted or unsubstituted alkyl (e.g., $C_1$-$C_8$, $C_1$-$C_6$, or $C_1$-$C_4$), $R^{500}$-substituted or unsubstituted heteroalkyl (e.g., 2 to 10 membered, 2 to 8 membered, 4 to 8 membered, 2 to 6 membered, or 2 to 4 membered), $R^{500}$-substituted or unsubstituted cycloalkyl (e.g., $C_3$-$C_8$, $C_4$-$C_8$, or $C_5$-$C_6$), $R^{500}$-substituted or unsubstituted heterocycloalkyl (e.g., 3 to 8 membered, 4 to 8 membered, or 5 to 6 membered), $R^{500}$-substituted or unsubstituted aryl (e.g., $C_6$-$C_{10}$ or $C_6$), or $R^{500}$-substituted or unsubstituted heteroaryl (e.g., 5 to 10 membered, 5 to 9 membered, or 5 to 6 membered).

$X^5$ is halogen. In aspects, $X^5$ is bromine, chlorine, fluorine, or iodine. In aspects, $X^5$ is bromine. In aspects, $X^5$ is chlorine. In aspects, $X^5$ is fluorine. In aspects, $X^5$ is iodine. n5 is an integer from 0 to 4. In aspects, n5 is 0. In aspects, n5 is 1. In aspects, n5 is 2. In aspects, n5 is 3. In aspects, n5 is 4. m5 is 1 or 2. In aspects, m5 is 1. In aspects, m5 is 2. v5 is 1 or 2. In aspects, v5 is 1. In aspects, v5 is 2.

$R^6$ is hydrogen, halogen, —$CX^6_3$, —$CHX^6_2$, —$CH_2X^6$, —$OCX^6_3$, —$OCH_2X^6$, —$OCHX^6_2$, —$SO_{n6}R^{6A}$, —$SO_{v6}NR^{6A}R^{6B}$, —CN, —$C(O)R^{6A}$, —$C(O)OR^{6A}$, —$C(O)NR^{6A}R^{6B}$, —$OR^{6A}$, —$ONR^{6A}R^{6B}$, —$NHC(O)NR^{6A}R^{6B}$, —$N(O)_{m6}$, —$NR^{6A}R^{6B}$, —$NHNR^{6A}R^{6B}$, —$NR^{6A}SO_2R^{6B}$, —$NR^{6A}C(O)R^{6B}$, —$NR^{6A}C(O)OR^{6B}$, —$NR^{6A}OR^{6B}$, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered). In aspects, $R^6$ is not unsubstituted alkyl. In aspects, $R^6$ is not substituted or unsubstituted alkyl.

In embodiments, $R^6$ is hydrogen, halogen, —$CHX^6_2$, —$CH_2X^6$, —$OCX^6_3$, —$OCH_2X^6$, —$OCHX^6_2$, —$SO_{n6}R^{6A}$, —$SO_{v6}NR^{6A}R^{6B}$, —CN, —$C(O)R^{6A}$, —$C(O)NR^{6A}R^{6B}$, —$OR^{6A}$, —$ONR^{6A}R^{6B}$, —$NHC(O)NR^{6A}R^{6B}$, —$N(O)_{m6}$, —$NR^{6A}R^{6B}$, —$NHNR^{6A}R^{6B}$, —$NR^{6A}SO_2R^{6B}$, —$NR^{6A}C(O)R^{6B}$, —$NR^{6A}C(O)OR^{6B}$, —$NR^{6A}OR^{6B}$, —$N_3$, $R^{600}$-substituted or unsubstituted alkyl (e.g. $C_1$-$C_8$, $C_1$-$C_6$, or $C_1$-$C_4$), $R^{600}$-substituted or unsubstituted heteroalkyl (e.g. 2 to 10 membered, 2 to 8 membered, 4 to 8 membered, 2 to 6 membered, or 2 to 4 membered), $R^{600}$-substituted or unsubstituted cycloalkyl (e.g. $C_3$-$C_8$, $C_4$-$C_8$, or $C_5$-$C_6$), $R^{600}$-substituted or unsubstituted heterocycloalkyl (e.g. 3 to 8 membered, 4 to 8 membered, or 5 to 6 membered), $R^{600}$-substituted or unsubstituted aryl (e.g. $C_6$-$C_{10}$ or $C_6$), or $R^{600}$-substituted or unsubstituted heteroaryl (e.g. 5 to 10 membered, 5 to 9 membered, or 5 to 6 membered). In aspects, $R^6$ is not an unsubstituted alkyl. In aspects, $R^6$ is not $R^{600}$-substituted or unsubstituted alkyl.

$R^{600}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, $R^{601}$-substituted or unsubstituted alkyl (e.g. $C_1$-$C_8$, $C_1$-$C_6$, or $C_1$-$C_4$), $R^{601}$-substituted or unsubstituted heteroalkyl (e.g. 2 to 10 membered, 2 to 8 membered, 4 to 8 membered, 2 to 6 membered, or 2 to 4 membered), $R^{601}$-substituted or unsubstituted cycloalkyl (e.g. $C_3$-$C_8$, $C_4$-$C_8$, or $C_5$-$C_6$), $R^{201}$-substituted or unsubstituted heterocycloalkyl (e.g. 3 to 8 membered, 4 to 8 membered, or 5 to 6 membered), $R^{601}$-substituted or unsubstituted aryl (e.g. $C_6$-$C_{10}$ or $C_6$), or $R^{601}$-substituted or unsubstituted heteroaryl (e.g. 5 to 10 membered, 5 to 9 membered, or 5 to 6 membered).

$R^{601}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, unsubstituted alkyl (e.g. $C_1$-$C_8$, $C_1$-$C_6$, or $C_1$-$C_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. $C_3$-$C_8$, $C_4$-$C_8$, or $C_5$-$C_6$), unsubstituted heterocycloalkyl (e.g. 3 to 8 membered, 4 to 8 membered, or 5 to 6 membered), unsubstituted aryl (e.g. $C_6$-$C_{10}$ or $C_6$), or unsubstituted heteroaryl (e.g. 5 to 10 membered, 5 to 9 membered, or 5 to 6 membered).

$R^{6A}$ and $R^{6B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered); $R^{6A}$ and $R^{6B}$ substituents bonded to the same nitrogen atom may optionally be joined to form a substituted or unsubstituted heterocycloalkyl (e.g. 3 to 8 membered, 4 to 8 membered, or 5 to 6 membered) or substituted or unsubstituted heteroaryl (e.g. 5 to 10 membered, 5 to 9 membered, or 5 to 6 membered).

In embodiments, $R^{6A}$ and $R^{6B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{200}$-substituted or unsubstituted alkyl (e.g., $C_1$-$C_8$, $C_1$-$C_6$, or $C_1$-$C_4$), $R^{600}$-substituted or unsubstituted heteroalkyl (e.g., 2 to 10 membered, 2 to 8 membered, 4 to 8 membered, 2 to 6 membered, or 2 to 4 membered), $R^{600}$-substituted or unsubstituted cycloalkyl (e.g., $C_3$-$C_8$, $C_4$-$C_8$, or $C_5$-$C_6$), $R^{600}$-substituted or unsubstituted heterocycloalkyl (e.g., 3 to 8 membered, 4 to 8 membered, or 5 to 6 membered), $R^{600}$-substituted or unsubstituted aryl (e.g., $C_6$-$C_{10}$ or $C_6$), or $R^{600}$-substituted or unsubstituted heteroaryl (e.g., 5 to 10 membered, 5 to 9 membered, or 5 to 6 membered).

In embodiments, $R^6$ is halogen, —$CX^6_3$, —$CHX^6_2$, —$CH_2X^6$, —$OCX^6_3$, —$OCH_2X^6$, or —$OCHX^6_2$. In aspects, $R^6$ is halogen. In aspects, $R^6$ is chlorine. $R^6$ is fluorine. $R^6$ is bromine. $R^6$ is iodine.

$X^6$ is halogen. In aspects, $X^6$ is bromine, chlorine, fluorine, or iodine. In aspects, $X^6$ is bromine. In aspects, $X^6$ is chlorine. In aspects, $X^6$ is fluorine. In aspects, $X^6$ is iodine. n6 is an integer from 0 to 4. In aspects, n6 is 0. In aspects, n6 is 1. In aspects, n6 is 2. In aspects, n6 is 3. In aspects, n6 is 4. m6 is 1 or 2. In aspects, m6 is 1. In aspects, m6 is 2. v6 is 1 or 2. In aspects, v6 is 1. In aspects, v6 is 2.

In embodiments, $R^2$ is halogen, —$CX^2_3$, —$CHX^2_2$, —$CH_2X^2$, —$OCX^2_3$, —$OCH_2X^2$, or —$OCHX^2_2$; and $R^6$ is halogen, —$CX^6_3$, —$CHX^6_2$, —$CH_2X^6$, —$OCX^6_3$, —$OCH_2X^6$, or —$OCHX^6_2$. In aspects, $X^2$ and $X^6$ are halogen. In aspects, $X^2$ and $X^6$ are chlorine. In aspects, $X^2$ and $X^6$ are fluorine. In aspects, $R^2$ is halogen, and $R^6$ is substituted or unsubstituted alkyl. In aspects, $R^2$ is chlorine or fluorine; and $R^6$ is unsubstituted $C_{1-4}$ alkyl. In aspects, $R^2$ and $R^6$ are halogen. In aspects, $R^2$ and $R^6$ are independently chlorine, fluorine, bromine, or iodine. In aspects, $R^2$ and $R^6$ are chlorine. In aspects, $R^2$ and $R^6$ are fluorine. In aspects, $R^2$ and $R^6$ are bromine. In aspects, $R^2$ and $R^6$ are iodine. In aspects, $R^2$ and $R^6$ are not substituted or unsubstituted alkyl. In aspects, $R^2$ and $R^6$ are the same. In aspects, $R^2$ and $R^6$ are different.

$R^7$ is hydrogen, halogen, —$CX^7_3$, —$CHX^7_2$, —$CH_2X^7$, —$OCX^7_3$, —$OCH_2X^7$, —$OCHX^7_2$, —$SO_{n7}R^{7A}$, —$SO_{v7}NR^{7A}R^{7B}$, —CN, —$C(O)R^{7A}$, —$C(O)OR^{7A}$, —$C(O)NR^{7A}R^{7B}$, —$OR^{7A}$, —$ONR^{7A}R^{7B}$, —$NHC(O)NR^{7A}R^{7B}$, —$N(O)_{m7}$, —$NR^{7A}R^{7B}$, —$NHNR^{7A}R^{7B}$, —$NR^{7A}SO_2R^{7B}$, —$NR^{7A}C(O)R^{7B}$, —$NR^{7A}C(O)OR^{7B}$, —$NR^{7A}OR^{7B}$, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered). In aspects, $R^7$ is hydrogen.

In embodiments, $R^7$ is hydrogen, halogen, —$CX^7_3$, —$CHX^7_2$, —$CH_2X^7$, —$OCX^7_3$, —$OCH_2X^7$, —$OCHX^7_2$, —$SO_{n7}R^{7A}$, —$SO_{v7}NR^{7A}R^{7B}$, —CN, —$C(O)R^{7A}$, —$C(O)OR^{7A}$, —$C(O)NR^{7A}R^{7B}$, —$OR^{7A}$, —$ONR^{7A}R^{7B}$, —NHC(O)$NR^{7A}R^{7B}$, —$N(O)_{m7}$, —$NR^{7A}R^{7B}$, —$NHNR^{7A}R^{7B}$, —$NR^{7A}SO_2R^{7B}$, —$NR^{7A}C(O)R^{7B}$, —$NR^{7A}C(O)OR^{7B}$, —$NR^{7A}OR^{7B}$, —$N_3$, $R^{700}$-substituted or unsubstituted alkyl (e.g. $C_1$-$C_8$, $C_1$-$C_6$, or $C_1$-$C_4$), $R^{700}$-substituted or unsubstituted heteroalkyl (e.g. 2 to 10 membered, 2 to 8 membered, 4 to 8 membered, 2 to 6 membered, or 2 to 4 membered), $R^{700}$-substituted or unsubstituted cycloalkyl (e.g. $C_3$-$C_8$, $C_4$-$C_8$, or $C_5$-$C_6$), $R^{700}$-substituted or unsubstituted heterocycloalkyl (e.g. 3 to 8 membered, 4 to 8 membered, or 5 to 6 membered), $R^{700}$-substituted or unsubstituted aryl (e.g. $C_6$-$C_{10}$ or $C_6$), or $R^{700}$-substituted or unsubstituted heteroaryl (e.g. 5 to 10 membered, 5 to 9 membered, or 5 to 6 membered).

$R^{700}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, $R^{701}$-substituted or unsubstituted alkyl (e.g. $C_1$-$C_8$, $C_1$-$C_6$, or $C_1$-$C_4$), $R^{701}$-substituted or unsubstituted heteroalkyl (e.g. 2 to 10 membered, 2 to 8 membered, 4 to 8 membered, 2 to 6 membered, or 2 to 4 membered), $R^{701}$-substituted or unsubstituted cycloalkyl (e.g. $C_3$-$C_8$, $C_4$-$C_8$, or $C_5$-$C_6$), $R^{701}$-substituted or unsubstituted heterocycloalkyl (e.g. 3 to 8 membered, 4 to 8 membered, or 5 to 6 membered), $R^{701}$-substituted or unsubstituted aryl (e.g. $C_6$-$C_{10}$ or $C_6$), or $R^{701}$-substituted or unsubstituted heteroaryl (e.g. 5 to 10 membered, 5 to 9 membered, or 5 to 6 membered).

$R^{701}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, unsubstituted alkyl (e.g. $C_1$-$C_8$, $C_1$-$C_6$, or $C_1$-$C_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. $C_3$-$C_8$, $C_4$-$C_8$, or $C_5$-$C_6$), unsubstituted heterocycloalkyl (e.g. 3 to 8 membered, 4 to 8 membered, or 5 to 6 membered), unsubstituted aryl (e.g. $C_6$-$C_{10}$ or $C_6$), or unsubstituted heteroaryl (e.g. 5 to 10 membered, 5 to 9 membered, or 5 to 6 membered).

$R^{7A}$ and $R^{7B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —N₃, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered); $R^{7A}$ and $R^{7B}$ substituents bonded to the same nitrogen atom may optionally be joined to form a substituted or unsubstituted heterocycloalkyl (e.g. 3 to 8 membered, 4 to 8 membered, or 5 to 6 membered) or substituted or unsubstituted heteroaryl (e.g. 5 to 10 membered, 5 to 9 membered, or 5 to 6 membered).

In embodiments, $R^{7A}$ and $R^{7B}$ are independently hydrogen, halogen, —CF₃, —CBr₃, —CCl₃, —CI₃, —CHF₂, —CHBr₂, —CHCl₂, —CHI₂, —CH₂F, —CH₂Br, —CH₂Cl, —CH₂I, —OCF₃, —OCBr₃, —OCCl₃, —OCI₃, —OCHF₂, —OCHBr₂, —OCHCl₂, —OCHI₂, —OCH₂F, —OCH₂Br, —OCH₂Cl, —OCH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, $R^{700}$-substituted or unsubstituted alkyl (e.g., $C_1$-$C_8$, $C_1$-$C_6$, or $C_1$-$C_4$), $R^{700}$-substituted or unsubstituted heteroalkyl (e.g., 2 to 10 membered, 2 to 8 membered, 4 to 8 membered, 2 to 6 membered, or 2 to 4 membered), $R^{700}$-substituted or unsubstituted cycloalkyl (e.g., $C_3$-$C_8$, $C_4$-$C_8$, or $C_5$-$C_6$), $R^{700}$-substituted or unsubstituted heterocycloalkyl (e.g., 3 to 8 membered, 4 to 8 membered, or 5 to 6 membered), $R^{400}$-substituted or unsubstituted aryl (e.g., $C_6$-$C_{10}$ or $C_6$), or $R^{700}$-substituted or unsubstituted heteroaryl (e.g., 5 to 10 membered, 5 to 9 membered, or 5 to 6 membered).

$X^7$ is halogen. In aspects, $X^7$ is bromine, chlorine, fluorine, or iodine. In aspects, $X^7$ is bromine. In aspects, $X^7$ is chlorine. In aspects, $X^7$ is fluorine. In aspects, $X^7$ is iodine. n7 is an integer from 0 to 4. In aspects, n7 is 0. In aspects, n7 is 1. In aspects, n7 is 2. In aspects, n7 is 3. In aspects, n7 is 4. m7 is 1 or 2. In aspects, m7 is 1. In aspects, m7 is 2. v7 is 1 or 2. In aspects, v7 is 1. In aspects, v7 is 2.

In embodiments, X is —C($R^{15}$)($R^{16}$)— and $R^7$ is bonded to $R^{15}$ together with the ring carbon atoms to which they are attached to form a substituted or unsubstituted cycloalkyl (e.g., $C_3$-$C_8$, $C_4$-$C_8$, or $C_5$-$C_6$), substituted or unsubstituted heterocycloalkyl (e.g., 3 to 8 membered, 4 to 8 membered, or 5 to 6 membered), or substituted or unsubstituted aryl (e.g., $C_6$-$C_{10}$ or $C_6$), or substituted or unsubstituted heteroaryl (e.g., 5 to 10 membered, 5 to 9 membered, or 5 to 6 membered). In aspects, $R^7$ bonded to $R^{15}$ together with the ring carbon atoms to which they are attached form the following fused ring structures:

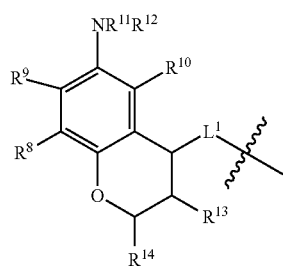

;

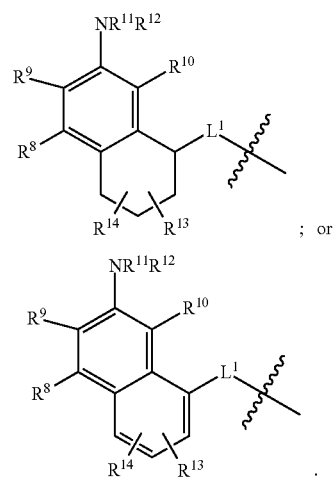

; or

In aspects, $R^{13}$ and $R^{14}$ are hydrogen. In aspects, $R^{16}$ is hydrogen. In aspects, $R^{13}$, $R^{14}$, and $R^{16}$ are hydrogen In embodiments, X is —N($R^{15}$)— and $R^7$ is bonded to $R^{15}$ together with the ring carbon atoms to which they are attached to form a substituted or unsubstituted cycloalkyl (e.g., $C_3$-$C_8$, $C_4$-$C_8$, or $C_5$-$C_6$), substituted or unsubstituted heterocycloalkyl (e.g., 3 to 8 membered, 4 to 8 membered, or 5 to 6 membered), or substituted or unsubstituted aryl (e.g., $C_6$-$C_{10}$ or $C_6$), or substituted or unsubstituted heteroaryl (e.g., 5 to 10 membered, 5 to 9 membered, or 5 to 6 membered). In aspects, $R^7$ bonded to $R^{15}$ together with the ring carbon atoms to which they are attached form the following fused ring structures:

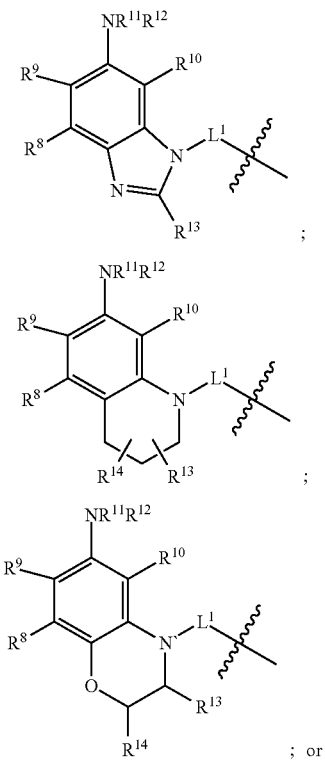

-continued

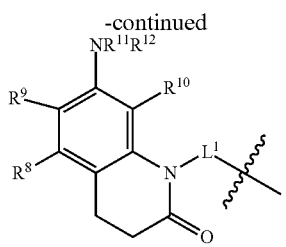

In aspects, $R^{13}$ and $R^{14}$ are hydrogen.

$R^8$ is hydrogen, halogen, —$CX^8{}_3$, —$CHX^8{}_2$, —$CH_2X^8$, —$OCX^8{}_3$, —$OCH_2X^8$, —$OCHX^8{}_2$, —$SO_{n8}R^{8A}$, —$SO_{v8}NR^{8A}R^{8B}$, —CN, —$C(O)R^{8A}$, —$C(O)OR^{8A}$, —$C(O)NR^{8A}R^{8B}$, —$OR^{8A}$, —$ONR^{8A}R^{8B}$, —$NHC(O)NR^{8A}R^{8B}$, —$N(O)_{m8}$, —$NR^{8A}R^{8B}$, —$NHNR^{8A}R^{8B}$, —$NR^{8A}SO_2R^{8B}$, —$NR^{8A}C(O)R^{8B}$, —$NR^{8A}C(O)OR^{8B}$, —$NR^{8A}OR^{8B}$, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered). In aspects, $R^8$ is hydrogen.

In embodiments, $R^1$ is hydrogen, halogen, —$CX^8{}_3$, —$CHX^8{}_2$, —$OCX^8{}_3$, —$OCH_2X^8$, —$OCHX^8{}_2$, —$SO_{n8}R^{8A}$, —$SO_{v8}NR^{8A}R^{8B}$, —CN, —$C(O)R^{8A}$, —$C(O)OR^{8A}$, —$C(O)NR^{8A}R^{8B}$, —$OR^{8A}$, —$ONR^{8A}R^{8B}$, —$NHC(O)NR^{8A}R^{8B}$, —$N(O)_{m8}$, —$NR^{8A}R^{8B}$, —$NHNR^{8A}R^{8B}$, —$NR^{8A}SO_2R^{8B}$, —$NR^{8A}C(O)R^{8B}$, —$NR^{8A}C(O)OR^{8B}$, —$NR^{8A}OR^{8B}$, —$N_3$, $R^{800}$-substituted or unsubstituted alkyl (e.g. $C_1$-$C_8$, $C_1$-$C_6$, or $C_1$-$C_4$), $R^{800}$-substituted or unsubstituted heteroalkyl (e.g. 2 to 10 membered, 2 to 8 membered, 4 to 8 membered, 2 to 6 membered, or 2 to 4 membered), $R^{800}$-substituted or unsubstituted cycloalkyl (e.g. $C_3$-$C_8$, $C_4$-$C_8$, or $C_5$-$C_6$), $R^{800}$-substituted or unsubstituted heterocycloalkyl (e.g. 3 to 8 membered, 4 to 8 membered, or 5 to 6 membered), $R^{800}$-substituted or unsubstituted aryl (e.g. $C_6$-$C_{10}$ or $C_6$), or $R^{400}$-substituted or unsubstituted heteroaryl (e.g. 5 to 10 membered, 5 to 9 membered, or 5 to 6 membered).

$R^{800}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —$NHC(O)H$, —$NHC(O)OH$, —NHOH, —$N_3$, $R^{801}$-substituted or unsubstituted alkyl (e.g. $C_1$-$C_8$, $C_1$-$C_6$, or $C_1$-$C_4$), $R^{801}$-substituted or unsubstituted heteroalkyl (e.g. 2 to 10 membered, 2 to 8 membered, 4 to 8 membered, 2 to 6 membered, or 2 to 4 membered), $R^{801}$-substituted or unsubstituted cycloalkyl (e.g. $C_3$-$C_8$, $C_4$-$C_8$, or $C_5$-$C_6$), $R^{801}$-substituted or unsubstituted heterocycloalkyl (e.g. 3 to 8 membered, 4 to 8 membered, or 5 to 6 membered), $R^{801}$-substituted or unsubstituted aryl (e.g. $C_6$-$C_{10}$ or $C_6$), or $R^{801}$-substituted or unsubstituted heteroaryl (e.g. 5 to 10 membered, 5 to 9 membered, or 5 to 6 membered).

$R^{801}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —$NHC(O)H$, —$NHC(O)OH$, —NHOH, —$N_3$, unsubstituted alkyl (e.g. $C_1$-$C_8$, $C_1$-$C_6$, or $C_1$-$C_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. $C_3$-$C_8$, $C_4$-$C_8$, or $C_5$-$C_6$), unsubstituted heterocycloalkyl (e.g. 3 to 8 membered, 4 to 8 membered, or 5 to 6 membered), unsubstituted aryl (e.g. $C_6$-$C_{10}$ or $C_6$), or unsubstituted heteroaryl (e.g. 5 to 10 membered, 5 to 9 membered, or 5 to 6 membered).

$R^{8A}$ and $R^{8B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —$NHC(O)H$, —$NHC(O)OH$, —NHOH, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered); $R^{8A}$ and $R^{8B}$ substituents bonded to the same nitrogen atom may optionally be joined to form a substituted or unsubstituted heterocycloalkyl (e.g. 3 to 8 membered, 4 to 8 membered, or 5 to 6 membered) or substituted or unsubstituted heteroaryl (e.g. 5 to 10 membered, 5 to 9 membered, or 5 to 6 membered).

In embodiments, $R^{8A}$ and $R^{8B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{800}$-substituted or unsubstituted alkyl (e.g., $C_1$-$C_8$, $C_1$-$C_6$, or $C_1$-$C_4$), $R^{800}$-substituted or unsubstituted heteroalkyl (e.g., 2 to 10 membered, 2 to 8 membered, 4 to 8 membered, 2 to 6 membered, or 2 to 4 membered), $R^{800}$-substituted or unsubstituted cycloalkyl (e.g., $C_3$-$C_8$, $C_4$-$C_8$, or $C_5$-$C_6$), $R^{800}$-substituted or unsubstituted heterocycloalkyl (e.g., 3 to 8 membered, 4 to 8 membered, or 5 to 6 membered), $R^{800}$-substituted or unsubstituted aryl (e.g., $C_6$-$C_{10}$ or $C_6$), or $R^{800}$-substituted or unsubstituted heteroaryl (e.g., 5 to 10 membered, 5 to 9 membered, or 5 to 6 membered).

$X^8$ is halogen. In aspects, $X^7$ is bromine, chlorine, fluorine, or iodine. In aspects, $X^8$ is bromine. In aspects, $X^8$ is chlorine. In aspects, $X^8$ is fluorine. In aspects, $X^8$ is iodine. n8 is an integer from 0 to 4. In aspects, n8 is 0. In aspects, n8 is 1. In aspects, n8 is 2. In aspects, n8 is 3. In aspects, n8 is 4. m8 is 1 or 2. In aspects, m8 is 1. In aspects, m8 is 2. v8 is 1 or 2. In aspects, v8 is 1. In aspects, v8 is 2.

$R^9$ is hydrogen, halogen, —$CX^9{}_3$, —$CHX^9{}_2$, —$CH_2X^9$, —$OCX^9{}_3$, —$OCH_2X^9$, —$OCHX^9{}_2$, —$SO_{n9}R^{9A}$, —$SO_{v9}NR^{9A}R^{9B}$, —CN, —$C(O)R^{9A}$, —$C(O)OR^{9A}$, —$C(C)NR^{9A}R^{9B}$, —$OR^{9A}$, —$ONR^{9A}R^{9B}$, —$NHC(O)NR^{9A}R^{9B}$, —$N(O)_{m9}$, —$NR^{9A}R^{9B}$, —$NHNR^{9A}R^{9B}$, —$NR^{9A}SO_2R^{9B}$, —$NR^{9A}C(O)R^{9B}$, —$NR^{9A}C(O)OR^{9B}$, —$NR^{9A}OR^{9B}$, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered). In aspects, $R^9$ is hydrogen.

In embodiments, $R^9$ is hydrogen, halogen, —$CX^9_3$, —$CHX^9_2$, —$CH_2X^9$, —$OCX^9_3$, —$OCH_2X^9$, —$OCHX^9_2$, —$SO_{n9}R^{9A}$, —$SO_{v9}NR^{9A}R^{9B}$, —CN, —$C(O)R^{9A}$, —$C(O)OR^{9A}$, —$C(O)NR^{9A}R^{9B}$, —$OR^{9A}$, —$ONR^{9A}R^{9B}$, —$NHC(O)NR^{9A}R^{9B}$, —$N(O)_{m9}$, —$NR^{9A}R^{9B}$, —$NHNR^{9A}R^{9B}$, —$NR^{9A}SO_2R^{9B}$, —$NR^{9A}C(O)R^{9B}$, —$NR^{9A}C(O)OR^{9B}$, —$NR^{9A}OR^{9B}$, —$N_3$, $R^{900}$-substituted or unsubstituted alkyl (e.g. $C_1$-$C_8$, $C_1$-$C_6$, or $C_1$-$C_4$), $R^{900}$-substituted or unsubstituted heteroalkyl (e.g. 2 to 10 membered, 2 to 8 membered, 4 to 8 membered, 2 to 6 membered, or 2 to 4 membered), $R^{900}$-substituted or unsubstituted cycloalkyl (e.g. $C_3$-$C_8$, $C_4$-$C_8$, or $C_5$-$C_6$), $R^{900}$-substituted or unsubstituted heterocycloalkyl (e.g. 3 to 8 membered, 4 to 8 membered, or 5 to 6 membered), $R^{900}$-substituted or unsubstituted aryl (e.g. $C_6$-$C_{10}$ or $C_6$), or $R^{900}$-substituted or unsubstituted heteroaryl (e.g. 5 to 10 membered, 5 to 9 membered, or 5 to 6 membered).

$R^{900}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, $R^{901}$-substituted or unsubstituted alkyl (e.g. $C_1$-$C_8$, $C_1$-$C_6$, or $C_1$-$C_4$), $R^{901}$-substituted or unsubstituted heteroalkyl (e.g. 2 to 10 membered, 2 to 8 membered, 4 to 8 membered, 2 to 6 membered, or 2 to 4 membered), $R^{901}$-substituted or unsubstituted cycloalkyl (e.g. $C_3$-$C_8$, $C_4$-$C_8$, or $C_5$-$C_6$), $R^{901}$-substituted or unsubstituted heterocycloalkyl (e.g. 3 to 8 membered, 4 to 8 membered, or 5 to 6 membered), $R^{901}$-substituted or unsubstituted aryl (e.g. $C_6$-$C_{10}$ or $C_6$), or $R^{901}$-substituted or unsubstituted heteroaryl (e.g. 5 to 10 membered, 5 to 9 membered, or 5 to 6 membered).

$R^{901}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, unsubstituted alkyl (e.g. $C_1$-$C_8$, $C_1$-$C_6$, or $C_1$-$C_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. $C_3$-$C_8$, $C_4$-$C_8$, or $C_5$-$C_6$), unsubstituted heterocycloalkyl (e.g. 3 to 8 membered, 4 to 8 membered, or 5 to 6 membered), unsubstituted aryl (e.g. $C_6$-$C_{10}$ or $C_6$), or unsubstituted heteroaryl (e.g. 5 to 10 membered, 5 to 9 membered, or 5 to 6 membered).

$R^{9A}$ and $R^{9B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered); $R^{9A}$ and $R^{9B}$ substituents bonded to the same nitrogen atom may optionally be joined to form a substituted or unsubstituted heterocycloalkyl (e.g. 3 to 8 membered, 4 to 8 membered, or 5 to 6 membered) or substituted or unsubstituted heteroaryl (e.g. 5 to 10 membered, 5 to 9 membered, or 5 to 6 membered).

In embodiments, $R^{9A}$ and $R^{9B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{900}$-substituted or unsubstituted alkyl (e.g., $C_1$-$C_8$, $C_1$-$C_6$, or $C_1$-$C_4$), $R^{900}$-substituted or unsubstituted heteroalkyl (e.g., 2 to 10 membered, 2 to 8 membered, 4 to 8 membered, 2 to 6 membered, or 2 to 4 membered), $R^{900}$-substituted or unsubstituted cycloalkyl (e.g., $C_3$-$C_8$, $C_4$-$C_8$, or $C_5$-$C_6$), $R^{900}$-substituted or unsubstituted heterocycloalkyl (e.g., 3 to 8 membered, 4 to 8 membered, or 5 to 6 membered), $R^{900}$-substituted or unsubstituted aryl (e.g., $C_6$-$C_{10}$ or $C_6$), or $R^{900}$-substituted or unsubstituted heteroaryl (e.g., 5 to 10 membered, 5 to 9 membered, or 5 to 6 membered).

$X^9$ is halogen. In aspects, $X^9$ is bromine, chlorine, fluorine, or iodine. In aspects, $X^9$ is bromine. In aspects, $X^9$ is chlorine. In aspects, $X^9$ is fluorine. In aspects, $X^9$ is iodine. n9 is an integer from 0 to 4. In aspects, n9 is 0. In aspects, n9 is 1. In aspects, n9 is 2. In aspects, n9 is 3. In aspects, n9 is 4. m9 is 1 or 2. In aspects, m9 is 1. In aspects, m9 is 2. v9 is 1 or 2. In aspects, v9 is 1. In aspects, v9 is 2.

In embodiments, $R^9$ is bonded to $R^{11}$ together with the ring carbon atoms to which they are attached to form substituted or unsubstituted heterocycloalkyl (e.g., 3 to 8 membered, 4 to 8 membered, or 5 to 6 membered), or substituted or unsubstituted heteroaryl (e.g., 5 to 10 membered, 5 to 9 membered, or 5 to 6 membered). In aspects, $R^9$ bonded to $R^{11}$ together with the ring carbon atoms to which they are attached form the following fused ring structures:

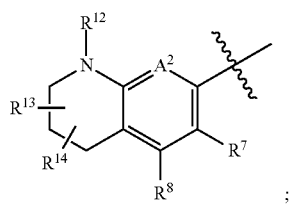

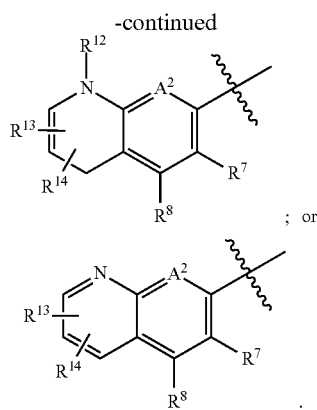

; or

In aspects, $R^{13}$ and $R^{14}$ are hydrogen. In aspects, $R^{12}$ is hydrogen. In aspects, $R^{12}$, $R^{13}$ and $R^{14}$ are hydrogen.

$R^{10}$ is hydrogen, halogen, —$CX^{10}_3$, —$CHX^{10}_2$, —$CH_2X^{10}$, —$OCX^{10}_3$, —$OCH_2X^{10}$, —$OCHX^{10}_2$, —$SO_{n10}R^{10A}$, —$SO_{v10}NR^{10A}R^{10B}$, —CN, —$C(O)R^{10A}$, —$C(O)OR^{10A}$, —$C(O)NR^{10A}R^{10B}$, —$OR^{10A}$, —$ONR^{10A}R^{10B}$, —$NHC(O)NR^{10A}R^{10B}$, —$N(O)_{m10}$, —$NR^{10A}R^{10B}$, —$NHNR^{10A}R^{10B}$, —$NR^{10A}SO_2R^{10B}$, —$NR^{10A}C(O)R^{10B}$, —$NR^{10A}C(O)OR^{10B}$, —$NR^{10A}OR^{10B}$, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered). In aspects, $R^{10}$ is hydrogen.

In embodiments, $R^{10}$ is hydrogen, halogen, —$CX^{10}_3$, —$CHX^{10}_2$, —$CH_2X^{10}$, —$OCX^{10}_3$, —$OCH_2X^{10}$, —$OCHX^{10}_2$, —$SO_{n10}R^{10A}$, —$SO_{v10}NR^{10A}R^{10B}$, —CN, —$C(O)R^{10A}$, —$C(O)OR^{10A}$, —$C(O)NR^{10A}R^{10B}$, —$OR^{10A}$, —$ONR^{10A}R^{10B}$, —$NHC(O)NR^{10A}R^{10B}$, —$N(O)_{m10}$, —$NR^{10A}R^{10B}$, —$NHNR^{10A}R^{10B}$, —$NR^{10A}SO_2R^{10B}$, —$NR^{10A}C(O)R^{10B}$, —$NR^{10A}C(O)OR^{10B}$, —$NR^{10A}OR^{10B}$, —$N_3$, $R^{101'}$-substituted or unsubstituted alkyl (e.g. $C_1$-$C_8$, $C_1$-$C_6$, or $C_1$-$C_4$), $R^{101'}$-substituted or unsubstituted heteroalkyl (e.g. 2 to 10 membered, 2 to 8 membered, 4 to 8 membered, 2 to 6 membered, or 2 to 4 membered), $R^{101'}$-substituted or unsubstituted cycloalkyl (e.g. $C_3$-$C_8$, $C_4$-$C_8$, or $C_5$-$C_6$), $R^{101'}$-substituted or unsubstituted heterocycloalkyl (e.g. 3 to 8 membered, 4 to 8 membered, or 5 to 6 membered), $R^{101'}$-substituted or unsubstituted aryl (e.g. $C_6$-$C_{10}$ or $C_6$), or $R^{101'}$-substituted or unsubstituted heteroaryl (e.g. 5 to 10 membered, 5 to 9 membered, or 5 to 6 membered).

$R^{101'}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —$NHC(O)H$, —$NHC(O)OH$, —NHOH, —$N_3$, $R^{102}$-substituted or unsubstituted alkyl (e.g. $C_1$-$C_8$, $C_1$-$C_6$, or $C_1$-$C_4$), $R^{102}$-substituted or unsubstituted heteroalkyl (e.g. 2 to 10 membered, 2 to 8 membered, 4 to 8 membered, 2 to 6 membered, or 2 to 4 membered), $R^{102}$-substituted or unsubstituted cycloalkyl (e.g. $C_3$-$C_8$, $C_4$-$C_8$, or $C_5$-$C_6$), $R^{102}$-substituted or unsubstituted heterocycloalkyl (e.g. 3 to 8 membered, 4 to 8 membered, or 5 to 6 membered), $R^{102}$-substituted or unsubstituted aryl (e.g. $C_6$-$C_{10}$ or $C_6$), or $R^{102}$-substituted or unsubstituted heteroaryl (e.g. 5 to 10 membered, 5 to 9 membered, or 5 to 6 membered).

$R^{102}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —$NHC(O)H$, —$NHC(O)OH$, —NHOH, —$N_3$, unsubstituted alkyl (e.g. $C_1$-$C_8$, $C_1$-$C_6$, or $C_1$-$C_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. $C_3$-$C_8$, $C_4$-$C_8$, or $C_5$-$C_6$), unsubstituted heterocycloalkyl (e.g. 3 to 8 membered, 4 to 8 membered, or 5 to 6 membered), unsubstituted aryl (e.g. $C_6$-$C_{10}$ or $C_6$), or unsubstituted heteroaryl (e.g. 5 to 10 membered, 5 to 9 membered, or 5 to 6 membered).

$R^{10A}$ and $R^{10B}$ are independently hydrogen, halogen, —$CF_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —$NHC(O)H$, —$NHC(O)OH$, —NHOH, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered); $R^{10A}$ and $R^{10B}$ substituents bonded to the same nitrogen atom may optionally be joined to form a substituted or unsubstituted heterocycloalkyl (e.g. 3 to 8 membered, 4 to 8 membered, or 5 to 6 membered) or substituted or unsubstituted heteroaryl (e.g. 5 to 10 membered, 5 to 9 membered, or 5 to 6 membered).

In embodiments, $R^{10A}$ and $R^{10B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{101'}$-substituted or unsubstituted alkyl (e.g., $C_1$-$C_8$, $C_1$-$C_6$, or $C_1$-$C_4$), $R^{101'}$-substituted or unsubstituted heteroalkyl (e.g., 2 to 10 membered, 2 to 8 membered, 4 to 8 membered, 2 to 6 membered, or 2 to 4 membered), $R^{101'}$-substituted or unsubstituted cycloalkyl (e.g., $C_3$-$C_8$, $C_4$-$C_8$, or $C_5$-$C_6$), $R^{101'}$-substituted or unsubstituted heterocycloalkyl (e.g., 3 to 8 membered, 4 to 8 membered, or 5 to 6 membered), $R^{101'}$-substituted or unsubstituted aryl (e.g., $C_6$-$C_{10}$ or $C_6$), or $R^{101'}$-substituted or unsubstituted heteroaryl (e.g., 5 to 10 membered, 5 to 9 membered, or 5 to 6 membered).

$X^{10}$ is halogen. In aspects, $X^{10}$ is bromine, chlorine, fluorine, or iodine. In aspects, $X^{10}$ is bromine. In aspects, $X^{10}$ is chlorine. In aspects, $X^{10}$ is fluorine. In aspects, $X^{10}$ is iodine. n10 is an integer from 0 to 4. In aspects, n10 is 0. In aspects, n10 is 1. In aspects, n10 is 2. In aspects, n10 is 3. In aspects, n10 is 4. m10 is 1 or 2. In aspects, m10 is 1. In aspects, m10 is 2. v10 is 1 or 2. In aspects, v10 is 1. In aspects, v10 is 2.

$R^{11}$ is hydrogen, halogen, —$CX^{11}_3$, —$CHX^{11}_2$, —$CH_2X^{11}$, —$OCX^{11}_3$, —$OCH_2X^{11}$, —$OCHX^{11}_2$, —$SO_{n11}R^{11A}$, —$SO_{v11}NR^{11A}R^{11B}$, —CN, —$C(O)R^{11A}$, —$C(O)OR^{11A}$, —$C(O)NR^{11A}R^{11B}$, —$OR^{11A}$, —$ONR^{11A}R^{11B}$, —$NHC(O)NR^{11A}R^{11B}$, —$N(O)_{m11}$, —$NR^{11A}R^{11B}$, —$NHNR^{11A}R^{11B}$, —$NR^{11A}SO_2R^{11B}$, —$NR^{11A}C(O)R^{11B}$, —$NR^{11A}C(O)OR^{11B}$, —$NR^{11A}OR^{11B}$, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered).

In embodiments, $R^{11}$ is hydrogen, halogen, —$CX^{11}_3$, —$CHX^{11}_2$, —$CH_2X^{11}$, —$OCX^{11}_3$, —$OCH_2X^{11}$, —$OCHX^{11}_2$, —$SO_{n11}R^{11A}$, —$SO_{v11}NR^{11A}R^{11B}$, —CN, —$C(O)R^{11A}$, —$C(O)OR^{11A}$, —$C(O)NR^{11A}R^{11B}$, —$OR^{11A}$, —$ONR^{11A}R^{11B}$, —$NHC(O)NR^{11A}R^{11B}$, —$N(O)_{m11}$, —$NR^{11A}R^{11B}$, —$NHNR^{11A}R^{11B}$, —$NR^{11A}SO_2R^{11B}$, —$NR^{11A}C(O)R^{11B}$, —$NR^{11A}C(O)OR^{11B}$, —$NR^{11A}OR^{11B}$, —$N_3$, $R^{111}$-substituted or unsubstituted alkyl (e.g. $C_1$-$C_8$, $C_1$-$C_6$, or $C_1$-$C_4$), $R^{110}$-substituted or unsubstituted heteroalkyl (e.g. 2 to 10 membered, 2 to 8 membered, 4 to 8 membered, 2 to 6 membered, or 2 to 4 membered), $R^{110}$-substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), $R^{110}$-substituted or unsubstituted aryl (e.g. $C_6$-$C_{10}$ or $C_6$), or $R^{110}$-substituted or unsubstituted heteroaryl (e.g. 5 to 10 membered, 5 to 9 membered, or 5 to 6 membered).

$R^{110}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, $R^{111}$-substituted or unsubstituted alkyl (e.g. $C_1$-$C_8$, $C_1$-$C_6$, or $C_1$-$C_4$), $R^{111}$-substituted or unsubstituted heteroalkyl (e.g. 2 to 10 membered, 2 to 8 membered, 4 to 8 membered, 2 to 6 membered, or 2 to 4 membered), $R^{111}$-substituted or unsubstituted cycloalkyl (e.g. $C_3$-$C_8$, $C_4$-$C_8$, or $C_5$-$C_6$), $R^{111}$-substituted or unsubstituted heterocycloalkyl (e.g. 3 to 8 membered, 4 to 8 membered, or 5 to 6 membered), $R^{111}$-substituted or unsubstituted aryl (e.g. $C_6$-$C_{10}$ or $C_6$), or $R^{111}$-substituted or unsubstituted heteroaryl (e.g. 5 to 10 membered, 5 to 9 membered, or 5 to 6 membered).

$R^{111}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, unsubstituted alkyl (e.g. $C_1$-$C_8$, $C_1$-$C_6$, or $C_1$-$C_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. $C_3$-$C_8$, $C_4$-$C_8$, or $C_5$-$C_6$), unsubstituted heterocycloalkyl (e.g. 3 to 8 membered, 4 to 8 membered, or 5 to 6 membered), unsubstituted aryl (e.g. $C_6$-$C_{10}$ or $C_6$), or unsubstituted heteroaryl (e.g. 5 to 10 membered, 5 to 9 membered, or 5 to 6 membered).

$R^{11A}$ and $R^{11B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered); $R^{11A}$ and $R^{11B}$ substituents bonded to the same nitrogen atom may optionally be joined to form a substituted or unsubstituted heterocycloalkyl (e.g. 3 to 8 membered, 4 to 8 membered, or 5 to 6 membered) or substituted or unsubstituted heteroaryl (e.g. 5 to 10 membered, 5 to 9 membered, or 5 to 6 membered).

In embodiments, $R^{11A}$ and $R^{11B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{110}$-substituted or unsubstituted alkyl (e.g., $C_1$-$C_8$, $C_1$-$C_6$, or $C_1$-$C_4$), $R^{110}$-substituted or unsubstituted heteroalkyl (e.g., 2 to 10 membered, 2 to 8 membered, 4 to 8 membered, 2 to 6 membered, or 2 to 4 membered), $R^{110}$-substituted or unsubstituted cycloalkyl (e.g., $C_3$-$C_8$, $C_4$-$C_8$, or $C_5$-$C_6$), $R^{110}$-substituted or unsubstituted heterocycloalkyl (e.g., 3 to 8 membered, 4 to 8 membered, or 5 to 6 membered), $R^{110}$-substituted or unsubstituted aryl (e.g., $C_6$-$C_{10}$ or $C_6$), or $R^{110}$-substituted or unsubstituted heteroaryl (e.g., 5 to 10 membered, 5 to 9 membered, or 5 to 6 membered).

$X^{11}$ is halogen. In aspects, $X^{11}$ is bromine, chlorine, fluorine, or iodine. In aspects, $X^{11}$ is bromine. In aspects, $X^{11}$ is chlorine. In aspects, $X^{11}$ is fluorine. In aspects, $X^{11}$ is iodine. n11 is an integer from 0 to 4. In aspects, n11 is 0. In aspects, n11 is 1. In aspects, n11 is 2. In aspects, n11 is 3. In aspects, n11 is 4. m11 is 1 or 2. In aspects, m11 is 1. In aspects, m11 is 2. v11 is 1 or 2. In aspects, v11 is 1. In aspects, v11 is 2.

In aspects, $R^{11}$ is substituted or unsubstituted alkyl, substituted or unsubstituted heteroalkyl, substituted or unsubstituted heteroaryl, or substituted or unsubstituted heterocycloalkyl. In aspects, $R^{11}$ is substituted or unsubstituted heteroalkyl. In aspects, $R^{11}$ is $R^{111}$-substituted or unsubstituted alkyl, $R^{111}$-substituted or unsubstituted heteroalkyl, $R^{111}$-substituted or unsubstituted heteroaryl, or $R^{111}$-substituted or unsubstituted heterocycloalkyl. In aspects, $R^{11}$ is $R^{111}$-substituted or unsubstituted heteroalkyl. In aspects, $R^{11}$ is $R^{112}$-substituted or unsubstituted alkyl, $R^{112}$-substituted or unsubstituted heteroalkyl, $R^{112}$-substituted or unsubstituted heteroaryl, or $R^{112}$-substituted or unsubstituted heterocycloalkyl. In aspects, $R^{11}$ is $R^{112}$-substituted or unsubstituted heteroalkyl.

In aspects, $R^{11}$ is

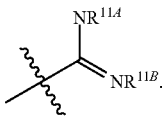

In aspects, $R^{11}$ is

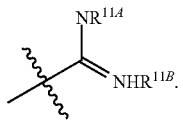

In aspects, $R^{11}$ is

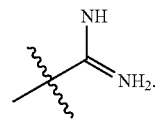

In aspects, $R^{11}$ is

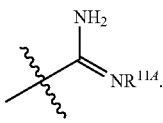

In aspects, $R^{11}$ is

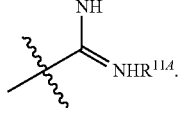

In aspects, $R^{11}$ is

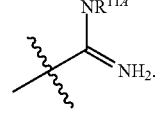

In aspects, $R^{11A}$ and $R^{11B}$ are hydrogen. In aspects, $R^{11A}$ and $R^{11B}$ are not hydrogen. In aspects, $R^{11A}$ is hydrogen and $R^{11B}$ is not hydrogen. In aspects, $R^{11A}$ is not hydrogen, and $R^{11B}$ is hydrogen. In aspects, $R^{11}$ is

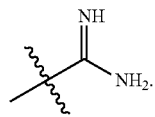

In aspects, $R^{11}$ is

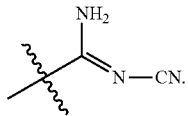 [SMILES: */C(N)=N/C#N]

In aspects, $R^{11}$ is

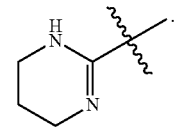 [SMILES: *C1=NCCCN1]

In aspects, $R^{11}$ is

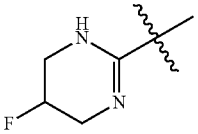

In aspects, $R^{11}$ is

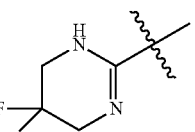

In aspects, $R^{11}$ is

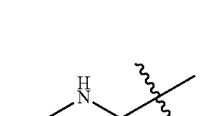

$R^{12}$ is a hydrogen, halogen, $-CX^{12}_3$, $-CHX^{12}_2$, $-CH_2X^{12}$, $-OCX^{12}_3$, $-OCH_2X^{12}$, $-OCHX^{12}_2$, $-SO_{n12}R^{12A}$, $-SO_{v12}NR^{12A}R^{12B}$, $-CN$, $-C(O)R^{12A}$, $-C(O)OR^{12A}$, $-C(O)NR^{12A}R^{12B}$, $-OR^{12A}$, $-ONR^{12A}R^{12B}$, $-NHC(O)NR^{12A}R^{12B}$, $-N(O)_{m12}$, $-NR^{12A}R^{12B}$, $-NHNR^{12A}R^{12B}$, $-NR^{12A}SO_2R^{12B}$, $-NR^{12A}C(O)R^{12B}$, $-NR^{12A}C(O)OR^{12B}$, $-NR^{12A}OR^{12B}$, $-N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered), or a bond. In aspects, $R^{12}$ is hydrogen. In aspects, $R^{12}$ is $NH_2$.

In embodiments, $R^{12}$ is hydrogen, halogen, $-CX^{12}{}_3$, $-CHX^{12}{}_2$, $-CH_2X^{12}$, $-OCX^{12}{}_3$, $-OCH_2X^{12}$, $-OCHX^{12}{}_2$, $-SO_{n12}R^{12A}$, $-SO_{v12}NR^{12A}R^{12B}$, $-CN$, $-C(O)R^{12A}$, $-C(O)OR^{12A}$, $-C(O)NR^{12A}R^{12B}$, $-OR^{12A}$, $-ONR^{12A}R^{12B}$, $-NHC(O)NR^{12A}R^{12B}$, $-N(O)_{m12}$, $-NR^{12A}R^{12B}$, $-NHNR^{12A}R^{12B}$, $-NR^{12A}SO_2R^{12B}$, $-NR^{12A}C(O)R^{12B}$, $-NR^{12A}C(O)OR^{12B}$, $-NR^{12A}OR^{12B}$, $-N_3$, $R^{111}$-substituted or unsubstituted alkyl (e.g. $C_1$-$C_8$, $C_1$-$C_6$, or $C_1$-$C_4$), $R^{120}$-substituted or unsubstituted heteroalkyl (e.g. 2 to 10 membered, 2 to 8 membered, 4 to 8 membered, 2 to 6 membered, or 2 to 4 membered), $R^{120}$-substituted or unsubstituted cycloalkyl (e.g. $C_3$-$C_8$, $C_4$-$C_8$, or $C_5$-$C_6$), $R^{120}$-substituted or unsubstituted heterocycloalkyl (e.g. 3 to 8 membered, 4 to 8 membered, or 5 to 6 membered), $R^{120}$-substituted or unsubstituted aryl (e.g. $C_6$-$C_{10}$ or $C_6$), or $R^{120}$-substituted or unsubstituted heteroaryl (e.g. 5 to 10 membered, 5 to 9 membered, or 5 to 6 membered).

$R^{120}$ is halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-N(O)_2$, $-NHSO_2H$, $-NHC(O)H$, $-NHC(O)OH$, $-NHOH$, $-N_3$, $R^{121}$-substituted or unsubstituted alkyl (e.g. $C_1$-$C_8$, $C_1$-$C_6$, or $C_1$-$C_4$), $R^{121}$-substituted or unsubstituted heteroalkyl (e.g. 2 to 10 membered, 2 to 8 membered, 4 to 8 membered, 2 to 6 membered, or 2 to 4 membered), $R^{121}$-substituted or unsubstituted cycloalkyl (e.g. $C_3$-$C_8$, $C_4$-$C_8$, or $C_5$-$C_6$), $R^{121}$-substituted or unsubstituted heterocycloalkyl (e.g. 3 to 8 membered, 4 to 8 membered, or 5 to 6 membered), $R^{121}$-substituted or unsubstituted aryl (e.g. $C_6$-$C_{10}$ or $C_6$), or $R^{121}$-substituted or unsubstituted heteroaryl (e.g. 5 to 10 membered, 5 to 9 membered, or 5 to 6 membered).

$R^{121}$ is halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-N(O)_2$, $-NHSO_2H$, $-NHC(O)H$, $-NHC(O)OH$, $-NHOH$, $-N_3$, unsubstituted alkyl (e.g. $C_1$-$C_8$, $C_1$-$C_6$, or $C_1$-$C_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. $C_3$-$C_8$, $C_4$-$C_8$, or $C_5$-$C_6$), unsubstituted heterocycloalkyl (e.g. 3 to 8 membered, 4 to 8 membered, or 5 to 6 membered), unsubstituted aryl (e.g. $C_6$-$C_{10}$ or $C_6$), or unsubstituted heteroaryl (e.g. 5 to 10 membered, 5 to 9 membered, or 5 to 6 membered).

$R^{12A}$ and $R^{12B}$ are independently hydrogen, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-N(O)_2$, $-NHSO_2H$, $-NHC(O)H$, $-NHC(O)OH$, $-NHOH$, $-N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered); $R^{12A}$ and $R^{12B}$ substituents bonded to the same nitrogen atom may optionally be joined to form a substituted or unsubstituted heterocycloalkyl (e.g. 3 to 8 membered, 4 to 8 membered, or 5 to 6 membered) or substituted or unsubstituted heteroaryl (e.g. 5 to 10 membered, 5 to 9 membered, or 5 to 6 membered).

In embodiments, $R^{12A}$ and $R^{12B}$ are independently hydrogen, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $R^{120}$-substituted or unsubstituted alkyl (e.g., $C_1$-$C_8$, $C_1$-$C_6$, or $C_1$-$C_4$), $R^{120}$-substituted or unsubstituted heteroalkyl (e.g., 2 to 10 membered, 2 to 8 membered, 4 to 8 membered, 2 to 6 membered, or 2 to 4 membered), $R^{120}$-substituted or unsubstituted cycloalkyl (e.g., $C_3$-$C_8$, $C_4$-$C_8$, or $C_5$-$C_6$), $R^{120}$-substituted or unsubstituted heterocycloalkyl (e.g., 3 to 8 membered, 4 to 8 membered, or 5 to 6 membered), $R^{120}$-substituted or unsubstituted aryl (e.g., $C_6$-$C_{10}$ or $C_6$), or $R^{120}$-substituted or unsubstituted heteroaryl (e.g., 5 to 10 membered, 5 to 9 membered, or 5 to 6 membered).

$X^{12}$ is halogen. In aspects, $X^{12}$ is bromine, chlorine, fluorine, or iodine. In aspects, $X^{12}$ is bromine. In aspects, $X^{12}$ is chlorine. In aspects, $X^{12}$ is fluorine. In aspects, $X^{12}$ is iodine. n12 is an integer from 0 to 4. In aspects, n12 is 0. In aspects, n12 is 1. In aspects, n12 is 2. In aspects, n12 is 3. In aspects, n12 is 4. m12 is 1 or 2. In aspects, m12 is 1. In aspects, m12 is 2. v12 is 1 or 2. In aspects, v12 is 1. In aspects, v12 is 2.

$R^{13}$ is hydrogen, halogen, $-CX^{13}{}_3$, $-CHX^{13}{}_2$, $-CH_2X^{13}$, $-OCX^{13}{}_3$, $-OCH_2X^{13}$, $-OCHX^{13}{}_2$, $-SO_{n13}R^{13A}$, $-SO_{v13}NR^{13A}R^{13B}$, $-CN$, $-C(O)R^{13A}$, $-C(O)OR^{13A}$, $-C(O)NR^{13A}R^{13B}$, $-OR^{13A}$, $-ONR^{13A}R^{13B}$, $-NHC(O)NR^{13A}R^{13B}$, $-N(O)_{m13}$, $-NR^{13A}R^{13B}$, $-NHNR^{13A}R^{13B}$, $-NR^{13A}SO_2R^{13B}$, $-NR^{13A}C(O)R^{13B}$, $-NR^{13A}C(O)OR^{13B}$, $-NR^{13A}OR^{13B}$, $-N_3$, oxo, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered). In aspects, $R^{13}$ is hydrogen.

In embodiments, $R^{13}$ is hydrogen, halogen, $-CX^{13}{}_3$, $-CHX^{13}{}_2$, $-CH_2X^{13}$, $-OCX^{13}{}_3$, $-OCH_2X^{13}$, $-OCHX^{13}{}_2$, $-SO_{n13}R^{13A}$, $-SO_{v13}NR^{13A}R^{13B}$, $-CN$, $-C(O)R^{13A}$, $-C(O)OR^{13A}$, $-C(O)NR^{13A}R^{13B}$, $-OR^{13A}$, $-ONR^{13A}R^{13B}$, $-NHC(O)NR^{13A}R^{13B}$, $-N(O)_{m13}$, $-NR^{13A}R^{13B}$, $-NHNR^{13A}R^{13B}$, $-NR^{13A}SO_2R^{13B}$, $-NR^{13A}C(O)R^{13B}$, $-NR^{13A}C(O)OR^{13B}$, $-NR^{13A}OR^{13B}$, $-N_3$, oxo, $R^{130}$-substituted or unsubstituted alkyl (e.g. $C_1$-$C_8$, $C_1$-$C_6$, or $C_1$-$C_4$), $R^{130}$-substituted or unsubstituted heteroalkyl (e.g. 2 to 10 membered, 2 to 8 membered, 4 to 8 membered, 2 to 6 membered, or 2 to 4 membered), $R^{130}$-substituted or unsubstituted cycloalkyl (e.g. $C_3$-$C_8$, $C_4$-$C_8$, or $C_5$-$C_6$), $R^{130}$-substituted or unsubstituted heterocycloalkyl (e.g. 3 to 8 membered, 4 to 8 membered, or 5 to 6 membered), $R^{130}$-substituted or unsubstituted aryl (e.g. $C_6$-$C_{10}$ or $C_6$), or $R^{130}$-substituted or unsubstituted heteroaryl (e.g. 5 to 10 membered, 5 to 9 membered, or 5 to 6 membered).

$R^{130}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —N(O)$_2$, —$NHSO_2H$, —NHC(O)H, —NHC(O)OH, —NHOH, —$N_3$, $R^{131}$-substituted or unsubstituted alkyl (e.g. $C_1$-$C_8$, $C_1$-$C_6$, or $C_1$-$C_4$), $R^{131}$-substituted or unsubstituted heteroalkyl (e.g. 2 to 10 membered, 2 to 8 membered, 4 to 8 membered, 2 to 6 membered, or 2 to 4 membered), $R^{131}$-substituted or unsubstituted cycloalkyl (e.g. $C_3$-$C_8$, $C_4$-$C_8$, or $C_5$-$C_6$), $R^{131}$-substituted or unsubstituted heterocycloalkyl (e.g. 3 to 8 membered, 4 to 8 membered, or 5 to 6 membered), $10^{31}$-substituted or unsubstituted aryl (e.g. $C_6$-$C_{10}$ or $C_6$), or $R^{131}$-substituted or unsubstituted heteroaryl (e.g. 5 to 10 membered, 5 to 9 membered, or 5 to 6 membered).

$R^{131}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —N(O)$_2$, —$NHSO_2H$, —NHC(O)H, —NHC(O)OH, —NHOH, —$N_3$, unsubstituted alkyl (e.g. $C_1$-$C_8$, $C_1$-$C_6$, or $C_1$-$C_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. $C_3$-$C_8$, $C_4$-$C_8$, or $C_5$-$C_6$), unsubstituted heterocycloalkyl (e.g. 3 to 8 membered, 4 to 8 membered, or 5 to 6 membered), unsubstituted aryl (e.g. $C_6$-$C_{10}$ or $C_6$), or unsubstituted heteroaryl (e.g. 5 to 10 membered, 5 to 9 membered, or 5 to 6 membered).

$R^{13A}$ and $R^{13B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —N(O)$_2$, —$NHSO_2H$, —NHC(O)H, —NHC(O)OH, —NHOH, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered); $R^{15A}$ and $R^{15B}$ substituents bonded to the same nitrogen atom may optionally be joined to form a substituted or unsubstituted heterocycloalkyl (e.g. 3 to 8 membered, 4 to 8 membered, or 5 to 6 membered) or substituted or unsubstituted heteroaryl (e.g. 5 to 10 membered, 5 to 9 membered, or 5 to 6 membered).

In embodiments, $R^{13A}$ and $R^{13B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, $R^{130}$-substituted or unsubstituted alkyl (e.g., $C_1$-$C_8$, $C_1$-$C_6$, or $C_1$-$C_4$), $R^{130}$-substituted or unsubstituted heteroalkyl (e.g., 2 to 10 membered, 2 to 8 membered, 4 to 8 membered, 2 to 6 membered, or 2 to 4 membered), $R^{130}$-substituted or unsubstituted cycloalkyl (e.g., $C_3$-$C_8$, $C_4$-$C_8$, or $C_5$-$C_6$), $R^{130}$-substituted or unsubstituted heterocycloalkyl (e.g., 3 to 8 membered, 4 to 8 membered, or 5 to 6 membered), $R^{130}$-substituted or unsubstituted aryl (e.g., $C_6$-$C_{10}$ or $C_6$), or $R^{130}$-substituted or unsubstituted heteroaryl (e.g., 5 to 10 membered, 5 to 9 membered, or 5 to 6 membered).

$X^{13}$ is halogen. In aspects, $X^{13}$ is bromine, chlorine, fluorine, or iodine. In aspects, $X^{13}$ is bromine. In aspects, $X^{13}$ is chlorine. In aspects, $X^{13}$ is fluorine. In aspects, $X^{13}$ is iodine. n13 is an integer from 0 to 4. In aspects, n13 is 0. In aspects, n13 is 1. In aspects, n13 is 2. In aspects, n13 is 3. In aspects, n13 is 4. m13 is 1 or 2. In aspects, m13 is 1. In aspects, m13 is 2. v13 is 1 or 2. In aspects, v13 is 1. In aspects, v13 is 2.

$R^{14}$ is hydrogen, halogen, —$CX^{14}_3$, —$CHX^{14}_2$, —$CH_2X^{14}$, —$OCX^{14}_3$, —$OCH_2X^{14}$, —$OCHX^{14}_2$, —$SO_{n14}R^{14A}$, —$SO_{v14}NR^{14A}R^{14B}$, —CN, —C(O)$R^{14A}$, —C(O)O$R^{14A}$, —C(O)N$R^{14A}R^{14B}$, —O$R^{14A}$, —ON$R^{14A}R^{14B}$, —NHC(O)N$R^{14A}R^{14B}$, —N(O)$_{m14}$, —N$R^{14A}R^{14B}$, —NHN$R^{14A}R^{14B}$, —N$R^{14A}SO_2R^{14B}$, —N$R^{14A}$C(O)$R^{14B}$, —N$R^{14A}$C(O)O$R^{14B}$, —N$R^{14A}$O$R^{14B}$, —$N_3$, oxo, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered). In aspects, $R^{14}$ is hydrogen.

In embodiments, $R^{14}$ is hydrogen, halogen, —$CX^{14}_3$, —$CHX^{14}_2$, —$CH_2X^{14}$, —$OCX^{14}_3$, —$OCH_2X^{14}$, —$OCHX^{14}_2$, —$SO_{n14}R^{14A}$, —$SO_{v14}NR^{14A}R^{14B}$, —CN, —C(O)$R^{14A}$, —C(O)O$R^{14A}$, —C(O)N$R^{14A}R^{14B}$, —O$R^{14A}$, —ON$R^{14A}R^{14B}$, —NHC(O)N$R^{14A}R^{14B}$, —N(O)$_{m14}$, —N$R^{14A}R^{14B}$, —NHN$R^{14A}R^{14B}$, —N$R^{14A}SO_2R^{14B}$, —N$R^{14A}$C(O)$R^{14B}$, —N$R^{14A}$C(O)O$R^{14B}$, —N$R^{14A}$O$R^{14B}$, —$N_3$, oxo, $R^{140}$-substituted or unsubstituted alkyl (e.g. $C_1$-$C_8$, $C_1$-$C_6$, or $C_1$-$C_4$), $R^{140}$-substituted or unsubstituted heteroalkyl (e.g. 2 to 10 membered, 2 to 8 membered, 4 to 8 membered, 2 to 6 membered, or 2 to 4 membered), $R^{140}$-substituted or unsubstituted cycloalkyl (e.g. $C_3$-$C_8$, $C_4$-$C_8$, or $C_5$-$C_6$), $R^{140}$-substituted or unsubstituted heterocycloalkyl (e.g. 3 to 8 membered, 4 to 8 membered, or 5 to 6 membered), $R^{140}$-substituted or unsubstituted aryl (e.g. $C_6$-$C_{10}$ or $C_6$), or $R^{140}$-substituted or unsubstituted heteroaryl (e.g. 5 to 10 membered, 5 to 9 membered, or 5 to 6 membered).

$R^{140}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, R$^{141}$-substituted or unsubstituted alkyl (e.g. C$_1$-C$_8$, C$_1$-C$_6$, or C$_1$-C$_4$), R$^{141}$-substituted or unsubstituted heteroalkyl (e.g. 2 to 10 membered, 2 to 8 membered, 4 to 8 membered, 2 to 6 membered, or 2 to 4 membered), R$^{141}$-substituted or unsubstituted cycloalkyl (e.g. C$_3$-C$_8$, C$_4$-C$_8$, or C$_5$-C$_6$), R$^{141}$-substituted or unsubstituted heterocycloalkyl (e.g. 3 to 8 membered, 4 to 8 membered, or 5 to 6 membered), R$^{141}$-substituted or unsubstituted aryl (e.g. C$_6$-C$_{10}$ or C$_6$), or R$^{141}$-substituted or unsubstituted heteroaryl (e.g. 5 to 10 membered, 5 to 9 membered, or 5 to 6 membered).

R$^{141}$ is halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, unsubstituted alkyl (e.g. C$_1$-C$_8$, C$_1$-C$_6$, or C$_1$-C$_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. C$_3$-C$_8$, C$_4$-C$_8$, or C$_5$-C$_6$), unsubstituted heterocycloalkyl (e.g. 3 to 8 membered, 4 to 8 membered, or 5 to 6 membered), unsubstituted aryl (e.g. C$_6$-C$_{10}$ or C$_6$), or unsubstituted heteroaryl (e.g. 5 to 10 membered, 5 to 9 membered, or 5 to 6 membered).

R$^{14A}$ and R$^{14B}$ are independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, substituted or unsubstituted alkyl (e.g. C$_1$-C$_8$, C$_1$-C$_6$, or C$_1$-C$_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. C$_3$-C$_8$, C$_4$-C$_8$, or C$_5$-C$_6$), substituted or unsubstituted heterocycloalkyl (e.g. 3 to 8 membered, 4 to 8 membered, or 5 to 6 membered), substituted or unsubstituted aryl (e.g. C$_6$-C$_{10}$ or C$_6$), or substituted or unsubstituted heteroaryl (e.g. 5 to 10 membered, 5 to 9 membered, or 5 to 6 membered); R$^{14A}$ and R$^{14B}$ substituents bonded to the same nitrogen atom may optionally be joined to form a substituted or unsubstituted heterocycloalkyl (e.g. 3 to 8 membered, 4 to 8 membered, or 5 to 6 membered) or substituted or unsubstituted heteroaryl (e.g. 5 to 10 membered, 5 to 9 membered, or 5 to 6 membered).

In embodiments, R$^{14A}$ and R$^{14B}$ are independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, R$^{140}$-substituted or unsubstituted alkyl (e.g., C$_1$-C$_8$, C$_1$-C$_6$, or C$_1$-C$_4$), R$^{140}$-substituted or unsubstituted heteroalkyl (e.g., 2 to 10 membered, 2 to 8 membered, 2 to 6 membered, or 2 to 4 membered), R$^{140}$-substituted or unsubstituted cycloalkyl (e.g., C$_3$-C$_8$, C$_4$-C$_8$, or C$_5$-C$_6$), R$^{140}$-substituted or unsubstituted heterocycloalkyl (e.g., 3 to 8 membered, 4 to 8 membered, or 5 to 6 membered), R$^{140}$-substituted or unsubstituted aryl (e.g., C$_6$-C$_{10}$ or C$_6$), or R$^{140}$-substituted or unsubstituted heteroaryl (e.g., 5 to 10 membered, 5 to 9 membered, or 5 to 6 membered).

X$^{14}$ is halogen. In aspects, X$^{14}$ is bromine, chlorine, fluorine, or iodine. In aspects, X$^{14}$ is bromine. In aspects, X$^{14}$ is chlorine. In aspects, X$^{14}$ is fluorine. In aspects, X$^{14}$ is iodine. n14 is an integer from 0 to 4. In aspects, n14 is 0. In aspects, n14 is 1. In aspects, n14 is 2. In aspects, n14 is 3. In aspects, n14 is 4. m14 is 1 or 2. In aspects, m14 is 1. In aspects, m14 is 2. v14 is 1 or 2. In aspects, v14 is 1. In aspects, v14 is 2.

R$^{15}$ is hydrogen, halogen, —CX$^{15}_3$, —CHX$^{15}_2$, —CH$_2$X$^{15}$, —OCX$^{15}_3$, —OCH$_2$X$^{15}$, —OCHX$^{15}_2$, —SO$_{n15}$R$^{15A}$, —SO$_{v15}$NR$^{15A}$R$^{15B}$, —CN, —C(O)R$^{15A}$, —C(O)OR$^{15A}$, —C(O)NR$^{15A}$R$^{15B}$, —OR$^{15A}$, —ONR$^{15A}$R$^{15B}$, —NHC(O)NR$^{15A}$R$^{15B}$, —N(O)$_{m15}$, —NR$^{15A}$R$^{15B}$, —NHNR$^{15A}$R$^{15B}$, —NR$^{15A}$SO$_2$R$^{15B}$, —NR$^{15A}$C(O)R$^{15B}$, —NR$^{15A}$C(O)OR$^{15B}$, —NR$^{15A}$OR$^{15B}$, —N$_3$, oxo, substituted or unsubstituted alkyl (e.g. C$_1$-C$_8$, C$_1$-C$_6$, or C$_1$-C$_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. C$_3$-C$_8$, C$_4$-C$_8$, or C$_5$-C$_6$), substituted or unsubstituted heterocycloalkyl (e.g. 3 to 8 membered, 4 to 8 membered, or 5 to 6 membered), substituted or unsubstituted aryl (e.g. C$_6$-C$_{10}$ or C$_6$), or substituted or unsubstituted heteroaryl (e.g. 5 to 10 membered, 5 to 9 membered, or 5 to 6 membered).

In embodiments, R$^{15}$ is hydrogen, halogen, —CX$^{15}_3$, —CHX$^{15}_2$, —CH$_2$X$^{15}$, —OCX$^{15}_3$, —OCH$_2$X$^{15}$, —OCHX$^{15}_2$, —SO$_{n15}$R$^{15A}$, —SO$_{v15}$NR$^{15A}$R$^{15B}$, —CN, —C(O)R$^{15A}$, —C(O)OR$^{15A}$, —C(O)NR$^{15A}$R$^{15B}$, —OR$^{15A}$, —ONR$^{15A}$R$^{15B}$, —NHC(O)NR$^{15A}$R$^{15B}$, —N(O)$_{m15}$, —NR$^{15A}$R$^{15B}$, —NHNR$^{15A}$R$^{15B}$, —NR$^{15A}$SO$_2$R$^{15B}$, —NR$^{15A}$C(O)R$^{15B}$, —NR$^{15A}$C(O)OR$^{15B}$, —NR$^{15A}$OR$^{15B}$, —N$_3$, oxo, R$^{150}$-substituted or unsubstituted alkyl (e.g. C$_1$-C$_8$, C$_1$-C$_6$, or C$_1$-C$_4$), R$^{150}$-substituted or unsubstituted heteroalkyl (e.g. 2 to 10 membered, 2 to 8 membered, 4 to 8 membered, 2 to 6 membered, or 2 to 4 membered), R$^{150}$-substituted or unsubstituted cycloalkyl (e.g. C$_3$-C$_8$, C$_4$-C$_8$, or C$_5$-C$_6$), R$^{150}$-substituted or unsubstituted heterocycloalkyl (e.g. 3 to 8 membered, 4 to 8 membered, or 5 to 6 membered), R$^{150}$-substituted or unsubstituted aryl (e.g. C$_6$-C$_{10}$ or C$_6$), or R$^{150}$-substituted or unsubstituted heteroaryl (e.g. 5 to 10 membered, 5 to 9 membered, or 5 to 6 membered).

R$^{150}$ is halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, R$^{151}$-substituted or unsubstituted alkyl (e.g. C$_1$-C$_8$, C$_1$-C$_6$, or C$_1$-C$_4$), R$^{151}$-substituted or unsubstituted heteroalkyl (e.g. 2 to 10 membered, 2 to 8 membered, 4 to 8 membered, 2 to 6 membered, or 2 to 4 membered), R$^{151}$-substituted or unsubstituted cycloalkyl (e.g. C$_3$-C$_8$, C$_4$-C$_8$, or C$_5$-C$_6$), R$^{151}$-substituted or unsubstituted heterocycloalkyl (e.g. 3 to 8 membered, 4 to 8 membered, or 5 to 6 membered), R$^{151}$-substituted or unsubstituted aryl (e.g.

$C_6$-$C_{10}$ or $C_6$), or $R^{151}$-substituted or unsubstituted heteroaryl (e.g. 5 to 10 membered, 5 to 9 membered, or 5 to 6 membered).

$R^{151}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, unsubstituted alkyl (e.g. $C_1$-$C_8$, $C_1$-$C_6$, or $C_1$-$C_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. $C_3$-$C_8$, $C_4$-$C_8$, or $C_5$-$C_6$), unsubstituted heterocycloalkyl (e.g. 3 to 8 membered, 4 to 8 membered, or 5 to 6 membered), unsubstituted aryl (e.g. $C_6$-$C_{10}$ or $C_6$), or unsubstituted heteroaryl (e.g. 5 to 10 membered, 5 to 9 membered, or 5 to 6 membered).

$R^{15A}$ and $R^{15B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered); $R^{15A}$ and $R^{15B}$ substituents bonded to the same nitrogen atom may optionally be joined to form a substituted or unsubstituted heterocycloalkyl (e.g. 3 to 8 membered, 4 to 8 membered, or 5 to 6 membered) or substituted or unsubstituted heteroaryl (e.g. 5 to 10 membered, 5 to 9 membered, or 5 to 6 membered).

In embodiments, $R^{15A}$ and $R^{15B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{150}$-substituted or unsubstituted alkyl (e.g., $C_1$-$C_8$, $C_1$-$C_6$, or $C_1$-$C_4$), $R^{150}$-substituted or unsubstituted heteroalkyl (e.g., 2 to 10 membered, 2 to 8 membered, 4 to 8 membered, 2 to 6 membered, or 2 to 4 membered), $R^{150}$-substituted or unsubstituted cycloalkyl (e.g., $C_3$-$C_8$, $C_4$-$C_8$, or $C_5$-$C_6$), $R^{150}$-substituted or unsubstituted heterocycloalkyl (e.g., 3 to 8 membered, 4 to 8 membered, or 5 to 6 membered), $R^{150}$-substituted or unsubstituted aryl (e.g., $C_6$-$C_{10}$ or $C_6$), or $R^{150}$-substituted or unsubstituted heteroaryl (e.g., 5 to 10 membered, 5 to 9 membered, or 5 to 6 membered).

$X^{15}$ is halogen. In aspects, $X^{15}$ is bromine, chlorine, fluorine, or iodine. In aspects, $X^{15}$ is bromine. In aspects, $X^{15}$ is chlorine. In aspects, $X^{15}$ is fluorine. In aspects, $X^{15}$ is iodine. n15 is an integer from 0 to 4. In aspects, n15 is 0. In aspects, n15 is 1. In aspects, n15 is 2. In aspects, n15 is 3.

In aspects, n15 is 4. m15 is 1 or 2. In aspects, m15 is 1. In aspects, m15 is 2. v15 is 1 or 2. In aspects, v15 is 1. In aspects, v15 is 2.

$R^{16}$ is hydrogen, halogen, —$CX^{16}_3$, —$CHX^{16}_2$, —$CH_2X^{16}$, —$OCX^{16}_3$, —$OCH_2X^{16}$, —$OCHX^{16}_2$, —$SO_{n16}R^{16A}$, —$SO_{v16}NR^{16A}R^{16B}$, —CN, —$C(O)R^{16A}$, —$C(O)OR^{16A}$, —$C(O)NR^{16A}R^{16B}$, —$OR^{16A}$, —$ONR^{16A}R^{16B}$, —$NHC(O)NR^{16A}R^{16B}$, —$N(O)_{m16}$, —$NR^{16A}R^{16B}$, —$NHNR^{16A}R^{16B}$, —$NR^{16A}SO_{16}R^{16B}$, —$NR^{16A}C(O)R^{16B}$, —$NR^{16A}C(O)OR^{16B}$, —$NR^{16A}OR^{16B}$, —$N_3$, substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered). In aspects, $R^{16}$ is hydrogen.

In embodiments, $R^{16}$ is hydrogen, halogen, —$CX^{16}_3$, —$CHX^{16}_2$, —$CH_{16}X^{16}$, —$OCX^{16}_3$, —$OCH_2X^{16}$, —$OCHX^{16}_2$, —$SO_{n16}R^{16A}$, —$SO_{v16}NR^{16A}R^{16B}$, —CN, —$C(O)R^{16A}$, —$C(O)OR^{16A}$, —$C(O)NR^{16A}R^{16B}$, —$OR^{16A}$, —$ONR^{16A}R^{16B}$, —$NHC(O)NR^{16A}R^{16B}$, —$N(O)_{m16}$, —$NR^{16A}R^{16B}$, —$NHNR^{16A}R^{16B}$, —$NR^{16A}SO_2R^{16B}$, —$NR^{16A}C(O)R^{16B}$, —$NR^{16A}C(O)OR^{16B}$, —$NR^{16A}OR^{16B}$, —$N_3$, $R^{160}$-substituted or unsubstituted alkyl (e.g. $C_1$-$C_8$, $C_1$-$C_6$, or $C_1$-$C_4$), $R^{160}$-substituted or unsubstituted heteroalkyl (e.g. 2 to 10 membered, 2 to 8 membered, 4 to 8 membered, 2 to 6 membered, or 2 to 4 membered), $R^{160}$-substituted or unsubstituted cycloalkyl (e.g. $C_3$-$C_8$, $C_4$-$C_8$, or $C_5$-$C_6$), $R^{160}$-substituted or unsubstituted heterocycloalkyl (e.g. 3 to 8 membered, 4 to 8 membered, or 5 to 6 membered), $R^{160}$-substituted or unsubstituted aryl (e.g. $C_6$-$C_{10}$ or $C_6$), or $R^{160}$-substituted or unsubstituted heteroaryl (e.g. 5 to 10 membered, 5 to 9 membered, or 5 to 6 membered).

$R^{160}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, $R^{161}$-substituted or unsubstituted alkyl (e.g. $C_1$-$C_8$, $C_1$-$C_6$, or $C_1$-$C_4$), $R^{161}$-substituted or unsubstituted heteroalkyl (e.g. 2 to 10 membered, 2 to 8 membered, 4 to 8 membered, 2 to 6 membered, or 2 to 4 membered), $R^{161}$-substituted or unsubstituted cycloalkyl (e.g. $C_3$-$C_8$, $C_4$-$C_8$, or $C_5$-$C_6$), $R^{161}$-substituted or unsubstituted heterocycloalkyl (e.g. 3 to 8 membered, 4 to 8 membered, or 5 to 6 membered), $R^{161}$-substituted or unsubstituted aryl (e.g. $C_6$-$C_{10}$ or $C_6$), or $R^{161}$-substituted or unsubstituted heteroaryl (e.g. 5 to 10 membered, 5 to 9 membered, or 5 to 6 membered).

$R^{161}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, unsubstituted alkyl (e.g. $C_1$-$C_8$, $C_1$-$C_6$, or $C_1$-$C_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. $C_3$-$C_8$, $C_4$-$C_8$, or $C_5$-$C_6$), unsubstituted heterocycloalkyl (e.g. 3 to 8 membered, 4 to 8 membered, or 5 to 6 membered), unsubstituted aryl (e.g. $C_6$-$C_{10}$ or $C_6$), or unsubstituted heteroaryl (e.g. 5 to 10 membered, 5 to 9 membered, or 5 to 6 membered).

$R^{16A}$ and $R^{16B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, substituted or unsubstituted alkyl (e.g. $C_1$-$C_8$, $C_1$-$C_6$, or $C_1$-$C_4$), substituted or unsubstituted heteroalkyl (e.g. 2 to 10 membered, 2 to 8 membered, 4 to 8 membered, 2 to 6 membered, or 2 to 4 membered), substituted or unsubstituted cycloalkyl (e.g. $C_3$-$C_8$, $C_4$-$C_8$, or $C_5$-$C_6$), substituted or unsubstituted heterocycloalkyl (e.g. 3 to 8 membered, 4 to 8 membered, or 5 to 6 membered), substituted or unsubstituted aryl (e.g. $C_6$-$C_{10}$ or $C_6$), or substituted or unsubstituted heteroaryl (e.g. 5 to 10 membered, 5 to 9 membered, or 5 to 6 membered); $R^{16A}$ and $R^{16B}$ substituents bonded to the same nitrogen atom may optionally be joined to form a substituted or unsubstituted heterocycloalkyl (e.g. 3 to 8 membered, 4 to 8 membered, or 5 to 6 membered) or substituted or unsubstituted heteroaryl (e.g. 5 to 10 membered, 5 to 9 membered, or 5 to 6 membered).

In embodiments, $R^{16A}$ and $R^{16B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{160}$-substituted or unsubstituted alkyl (e.g., $C_1$-$C_8$, $C_1$-$C_6$, or $C_1$-$C_4$), $R^{160}$-substituted or unsubstituted heteroalkyl (e.g., 2 to 10 membered, 2 to 8 membered, 4 to 8 membered, 2 to 6 membered, or 2 to 4 membered), $R^{160}$-substituted or unsubstituted cycloalkyl (e.g., $C_3$-$C_8$, $C_4$-$C_8$, or $C_5$-$C_6$), $R^{160}$-substituted or unsubstituted heterocycloalkyl (e.g., 3 to 8 membered, 4 to 8 membered, or 5 to 6 membered), $R^{160}$-substituted or unsubstituted aryl (e.g., $C_6$-$C_{10}$ or $C_6$), or $R^{160}$-substituted or unsubstituted heteroaryl (e.g., 5 to 10 membered, 5 to 9 membered, or 5 to 6 membered).

$X^{16}$ is halogen. In aspects, $X^{16}$ is bromine, chlorine, fluorine, or iodine. In aspects, $X^{16}$ is bromine. In aspects, $X^{16}$ is chlorine. In aspects, $X^{16}$ is fluorine. In aspects, $X^{16}$ is iodine. n16 is an integer from 0 to 4. In aspects, n16 is 0. In aspects, n16 is 1. In aspects, n16 is 2. In aspects, n16 is 3. In aspects, n16 is 4. m16 is 1 or 2. In aspects, m16 is 1. In aspects, m16 is 2. v16 is 1 or 2. In aspects, v16 is 1. In aspects, v16 is 2.

$L^1$ is a bond, —C(O)—, —C(O)O—, —O—, —S—, —NH—, —C(O)NH—, —NHC(O)—, —$S(O)_2$—, —S(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^1$ is a bond, —C(O)—, —C(O)O—, —O—, —S—, —NH—, —C(O)NH—, —NHC(O)—, —$S(O)_2$—, —S(O)NH—, $L^{11}$-substituted or unsubstituted alkylene, $L^{11}$-substituted or unsubstituted heteroalkylene, $L^{11}$-substituted or unsubstituted cycloalkylene, $L^{11}$-substituted or unsubstituted heterocycloalkylene, $L^{11}$-substituted or unsubstituted arylene, or $L^{11}$-substituted or unsubstituted heteroarylene $L^{11}$ is halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$N(O)_2$, —$NHSO_2H$, —NHC(O)H, —NHC(O)OH, —NHOH, —$N_3$, unsubstituted alkyl (e.g. $C_1$-$C_8$, $C_1$-$C_6$, or $C_1$-$C_4$), unsubstituted heteroalkyl (e.g. 2 to 10 membered, 2 to 8 membered, 4 to 8 membered, 2 to 6 membered, or 2 to 4 membered), unsubstituted cycloalkyl (e.g. $C_3$-$C_8$, $C_4$-$C_8$, or $C_5$-$C_6$), unsubstituted heterocycloalkyl (e.g. 3 to 8 membered, 4 to 8 membered, or 5 to 6 membered), unsubstituted aryl (e.g. $C_6$-$C_{10}$ or $C_6$), or unsubstituted heteroaryl (e.g. 5 to 10 membered, 5 to 9 membered, or 5 to 6 membered).

In aspects, $L^1$ is a bond, —NH—, substituted or unsubstituted alkyl, or substituted or unsubstituted heteroalkyl. In aspects, $L^1$ is a bond, —NH—, $L^{11}$-substituted or unsubstituted alkyl, or $L^{11}$-substituted or unsubstituted heteroalkyl. In aspects, $L^1$ is $L^{11}$-substituted alkyl. In aspects, $L^1$ is unsubstituted alkyl. In aspects, $L^1$ is $L^{11}$-substituted heteroalkyl. In aspects, $L^1$ is unsubstituted heteroalkyl.

In aspects, $L^1$ is a bond, —NH—, —$(CH_2)_{z1}$—NH—, —$(CH_2)_{z2}$—, or —$(CH_2)_{z3}$—N(($CH_2)_{z4}CH_3$)—C(=O)—. In aspects, z1, z2, and z3 are each independently an integer from 1 to 10; and z4 is an integer from 0 to 9. In aspects, z1, z2, and z3 are each independently an integer from 1 to 6; and z4 is an integer from 0 to 5. In aspects, z1, z2, and z3 are each independently an integer from 1 to 4; and z4 is an integer from 0 to 3. In aspects, $L^1$ is a bond. In aspects, $L^1$ is —NH—. In aspects, $L^1$ is —$(CH_2)_{z1}$—NH—, where z1 is an integer from 1 to 4. In aspects, $L^1$ is —$(CH_2)_{z2}$—, where z2 is an integer from 1 to 4. In aspects, $L^1$ is —$(CH_2)_{z3}$—N(($CH_2)_{z4}CH_3$)—C(=O)—; wherein z3 is an integer from 1 to 4, and z4 is an integer from 0 to 4.

In embodiments, the compound of Formula (I) is not

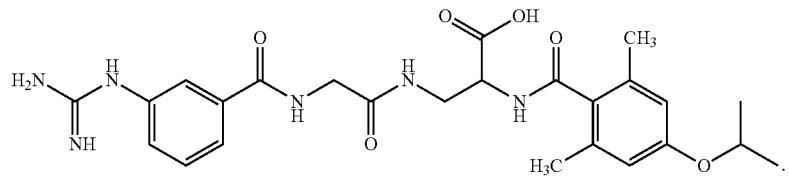 [SMILES: Cc1cc(OC(C)C)cc(C)c1C(=O)NC(CNC(=O)CNC(=O)c1cccc(NC(=N)N)c1)C(=O)O]

In embodiments of the compound of Formula (I), $R^2$ and $R^3$ are not simultaneously methyl. In embodiments of the compound of Formula (I), $R^2$ and $R^3$ are not simultaneously substituted or unsubstituted $C_{1-2}$ alkyl. In embodiments of the compound of Formula (I), $R^2$ and $R^3$ are not simultaneously unsubstituted $C_{1-2}$ alkyl. In embodiments of the compound of Formula (I), $R^2$ and $R^3$ are not simultaneously unsubstituted $C_{1-3}$ alkyl. In embodiments of the compound of Formula (I), $R^2$ and $R^3$ are not simultaneously unsubstituted $C_{1-4}$ alkyl. In embodiments of the compound of Formula (I), $R^2$ and $R^3$ are not simultaneously unsubstituted alkyl In embodiments of the compound of Formula (I), $R_4$ is not —O—CH(CH$_3$)$_2$ when $A^1$ is $C(R^4)$. In embodiments of the compound of Formula (I), $R_4$ is not a 3 membered heteroalkyl substituted with a $C_{1-3}$ alkyl when $A^1$ is $C(R^4)$. In embodiments of the compound of Formula (I), $R_4$ is not a 2 to 4 membered heteroalkyl substituted with a $C_{1-4}$ alkyl when $A^1$ is $C(R^4)$.

In embodiments, the disclosure provides a compound of Formula (1) or a pharmaceutically acceptable salt thereof:

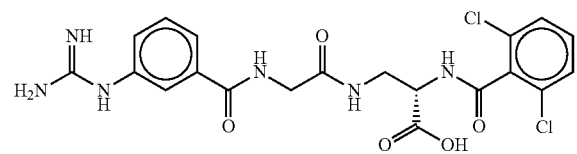

In embodiments, the disclosure provides a compound of Formula (2) or a pharmaceutically acceptable salt thereof:

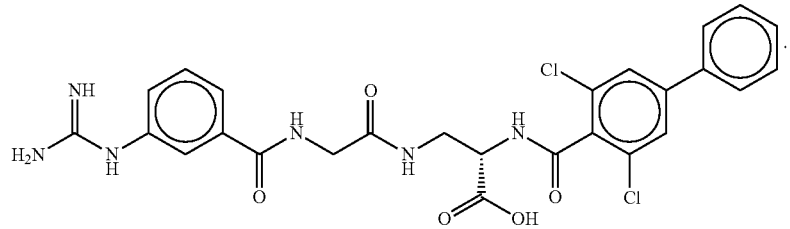

In embodiments, the disclosure provides a compound of Formula (3) or a pharmaceutically acceptable salt thereof:

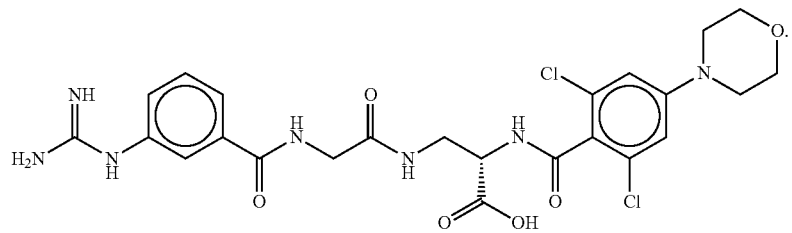

In embodiments, the disclosure provides a compound of Formula (4) or a pharmaceutically acceptable salt thereof:

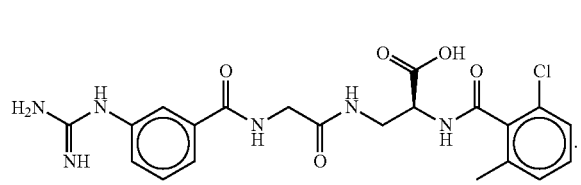

In embodiments, the disclosure provides a compound of Formula (5) or a pharmaceutically acceptable salt thereof:

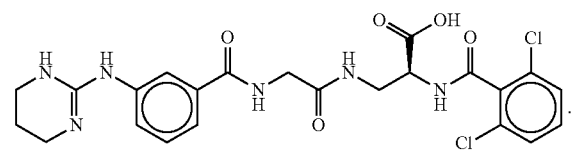

In embodiments, the disclosure provides a compound of Formula (6) or a pharmaceutically acceptable salt thereof:

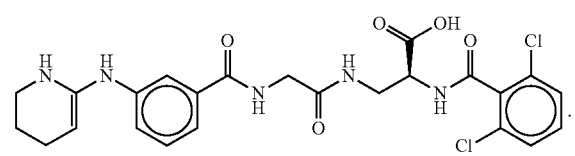

In embodiments, the disclosure provides a compound of Formula (7) or a pharmaceutically acceptable salt thereof:

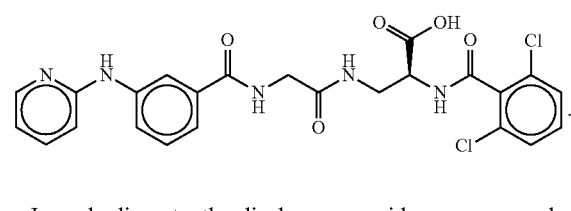

In embodiments, the disclosure provides a compound of Formula (8) or a pharmaceutically acceptable salt thereof:

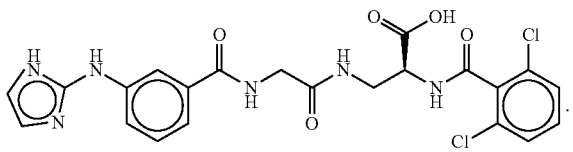

In embodiments, the disclosure provides a compound of Formula (9) or a pharmaceutically acceptable salt thereof:

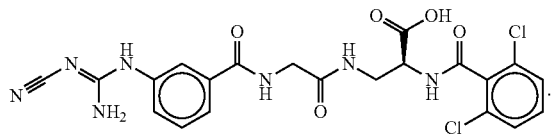

In embodiments, the disclosure provides a compound of Formula (10) or a pharmaceutically acceptable salt thereof:

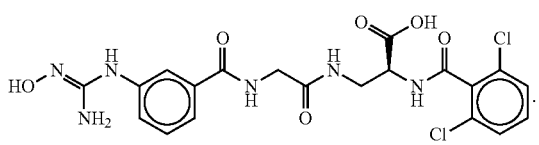

In embodiments, the disclosure provides a compound of Formula (11) or a pharmaceutically acceptable salt thereof:

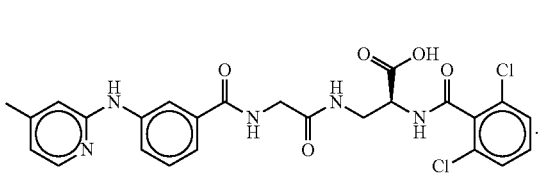

In embodiments, the disclosure provides a compound of Formula (12) or a pharmaceutically acceptable salt thereof:

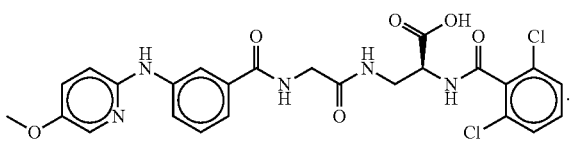

In embodiments, the disclosure provides a compound of Formula (13) or a pharmaceutically acceptable salt thereof:

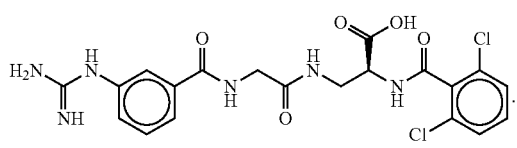

In embodiments, the disclosure provides a compound of Formula (14) or a pharmaceutically acceptable salt thereof:

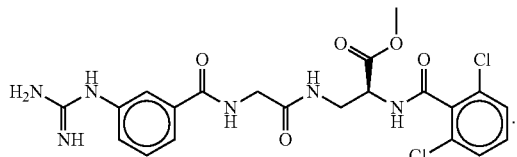

In embodiments, the disclosure provides a compound of Formula (15) or a pharmaceutically acceptable salt thereof:

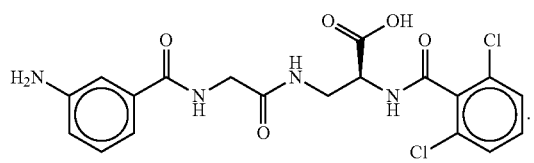

In embodiments, the disclosure provides a compound of Formula (16) or a pharmaceutically acceptable salt thereof:

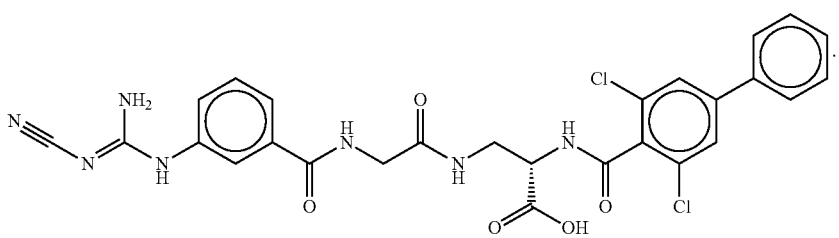

In embodiments, the disclosure provides a compound of Formula (17) or a pharmaceutically acceptable salt thereof:

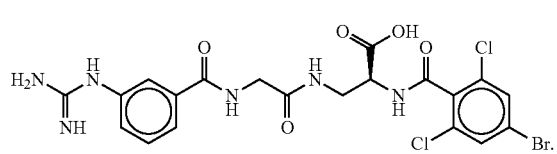

In embodiments, the disclosure provides a compound of Formula (18) or a pharmaceutically acceptable salt thereof:

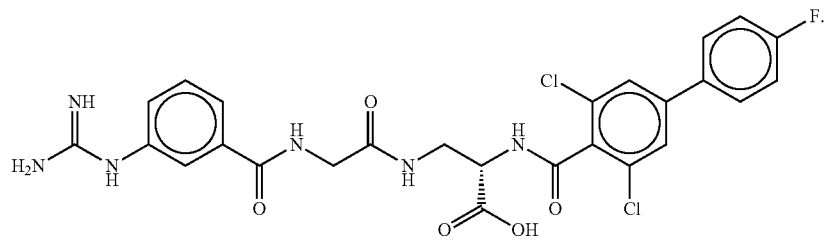

In embodiments, the disclosure provides a compound of Formula (19) or a pharmaceutically acceptable salt thereof:

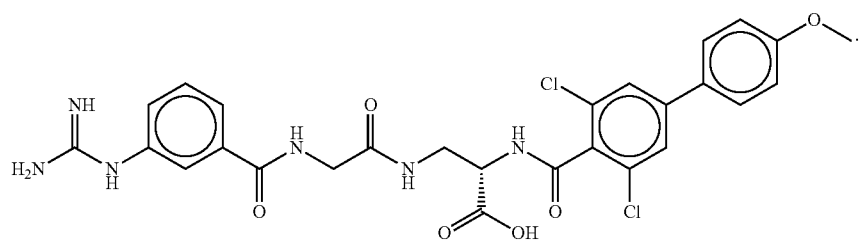

In embodiments, the disclosure provides a compound of Formula (20) or a pharmaceutically acceptable salt thereof:

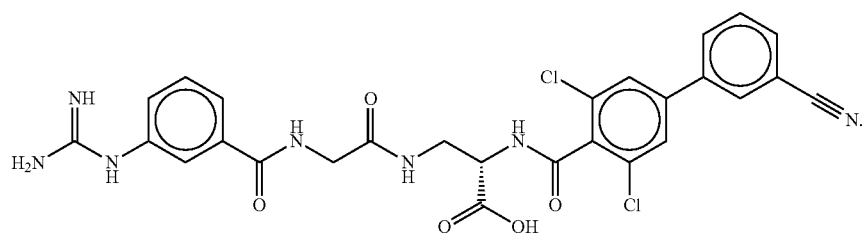

In embodiments, the disclosure provides a compound of Formula (21) or a pharmaceutically acceptable salt thereof:

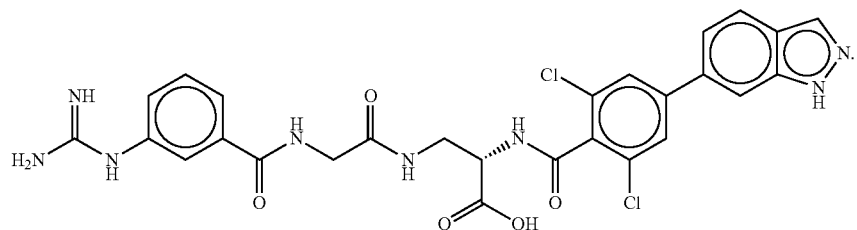

In embodiments, the disclosure provides a compound of Formula (22) or a pharmaceutically acceptable salt thereof:

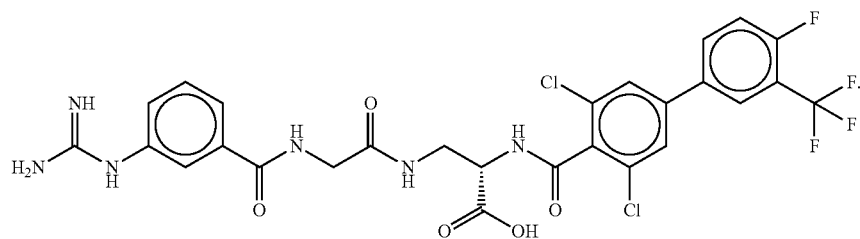

In embodiments, the disclosure provides a compound of Formula (23) or a pharmaceutically acceptable salt thereof:

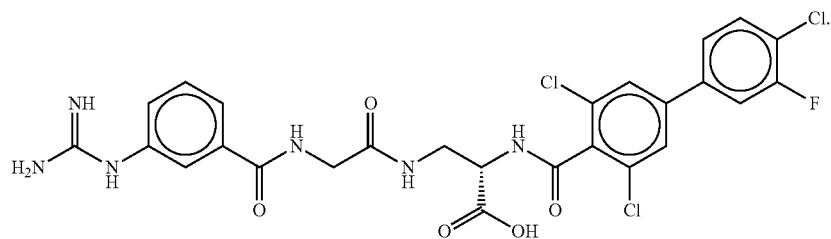

In embodiments, the disclosure provides a compound of Formula (24) or a pharmaceutically acceptable salt thereof:

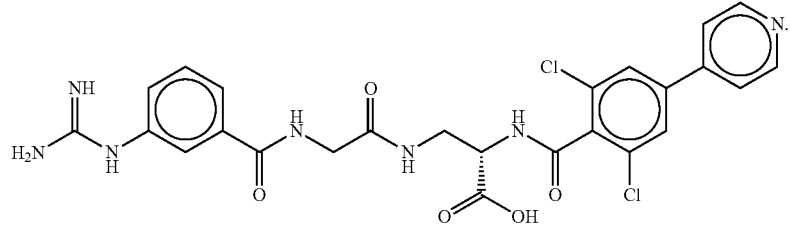

In embodiments, the disclosure provides a compound of Formula (25) or a pharmaceutically acceptable salt thereof:

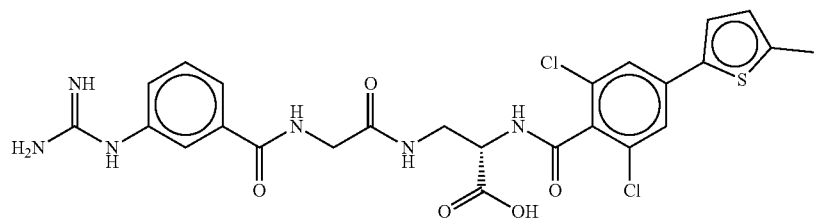

In embodiments, the disclosure provides a compound of Formula (26) or a pharmaceutically acceptable salt thereof:

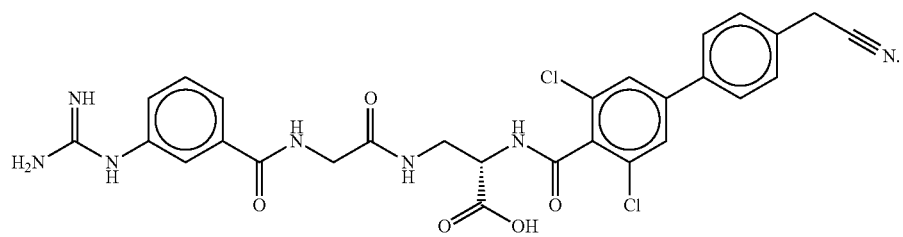

In embodiments, the disclosure provides a compound of Formula (27) or a pharmaceutically acceptable salt thereof:

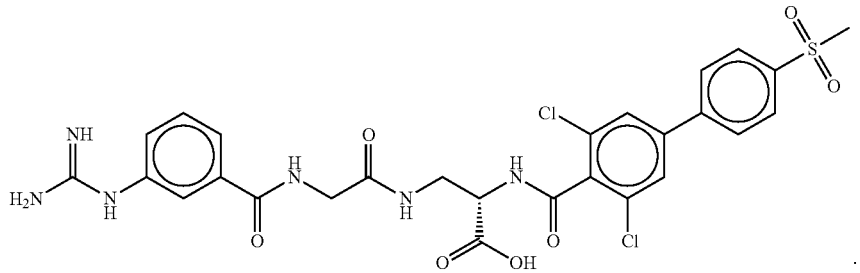

In embodiments, the disclosure provides a compound of Formula (28) or a pharmaceutically acceptable salt thereof:

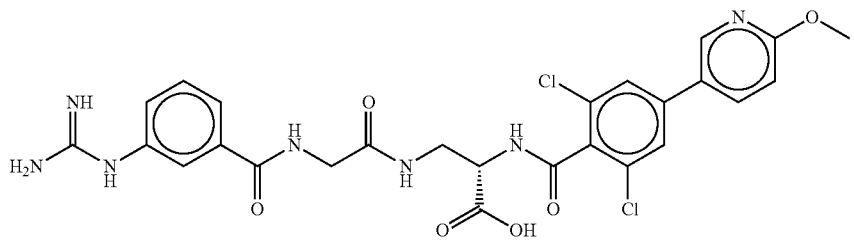

In embodiments, the disclosure provides a compound of Formula (29) or a pharmaceutically acceptable salt thereof:

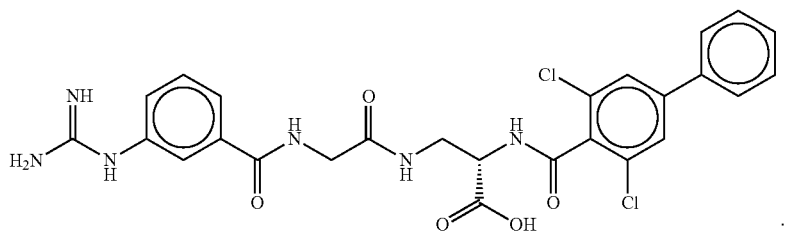

In embodiments, the disclosure provides a compound of Formula (30) or a pharmaceutically acceptable salt thereof:

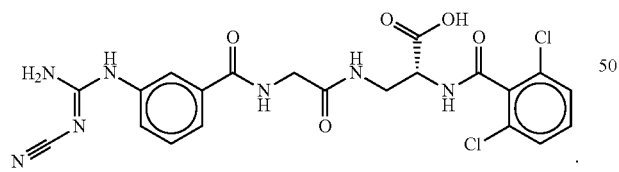

In embodiments, the disclosure provides a compound of Formula (31) or a pharmaceutically acceptable salt thereof:

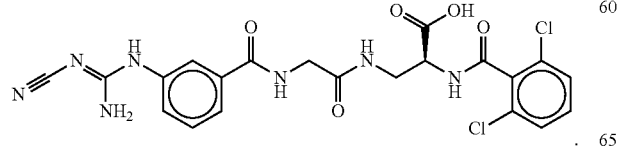

In embodiments, the disclosure provides a compound of Formula (32) or a pharmaceutically acceptable salt thereof:

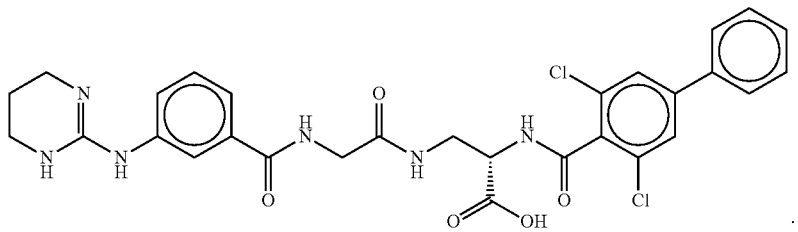

In embodiments, the disclosure provides a compound of Formula (33) or a pharmaceutically acceptable salt thereof:

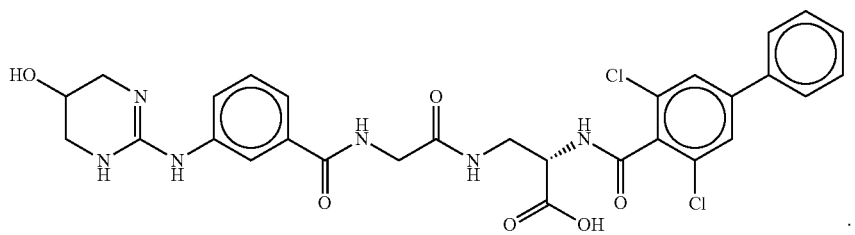

In embodiments, the disclosure provides a compound of Formula (34) or a pharmaceutically acceptable salt thereof:

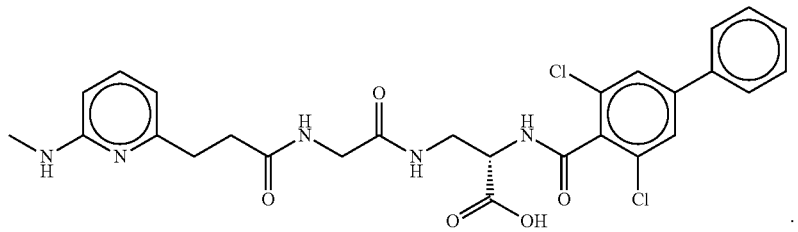

In embodiments, the disclosure provides a compound of Formula (35) or a pharmaceutically acceptable salt thereof:

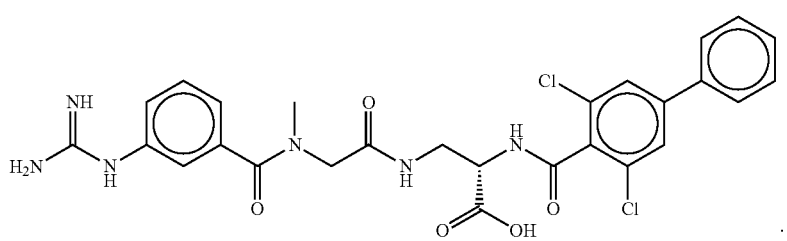

In embodiments, the disclosure provides a compound of Formula (36) or a pharmaceutically acceptable salt thereof:

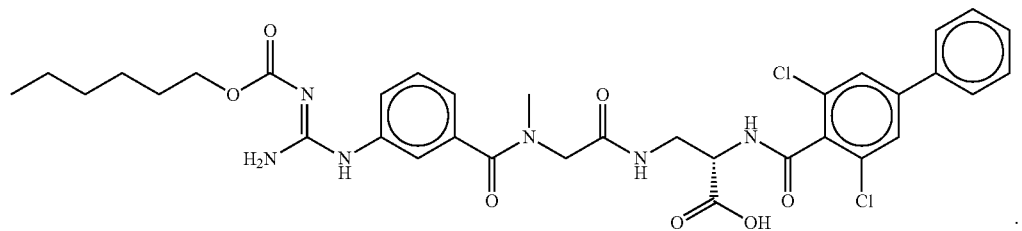

In embodiments, the disclosure provides a compound of Formula (37) or a pharmaceutically acceptable salt thereof:

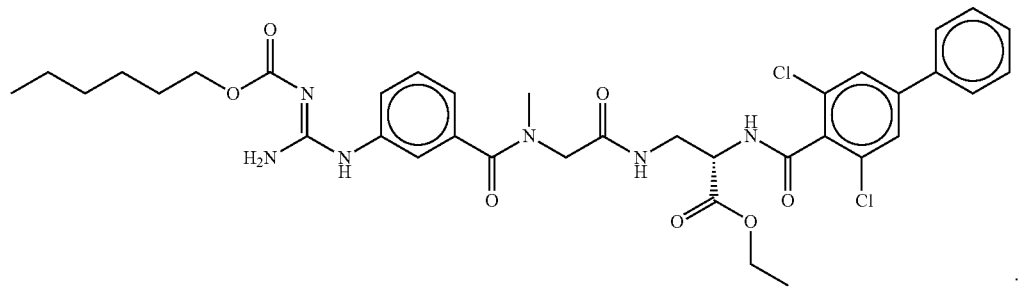

In embodiments, the disclosure provides a compound of Formula (38) or a pharmaceutically acceptable salt thereof:

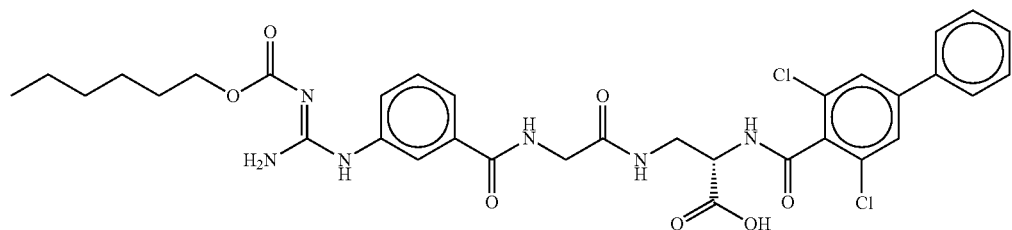

In embodiments, the disclosure provides a compound of Formula (39) or a pharmaceutically acceptable salt thereof:

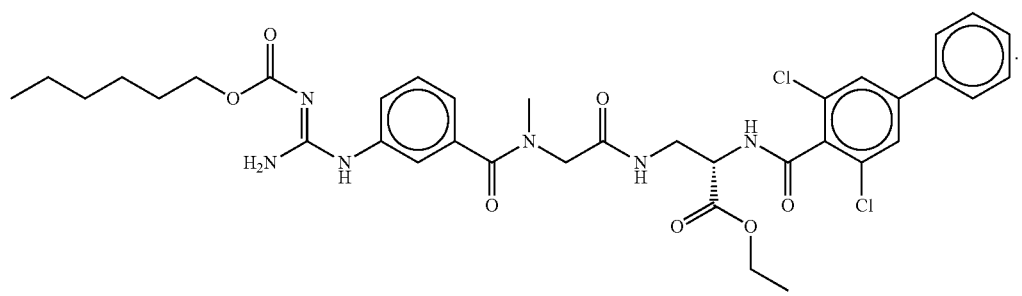

In embodiments, the disclosure provides a compound of Formula (40) or a pharmaceutically acceptable salt thereof:

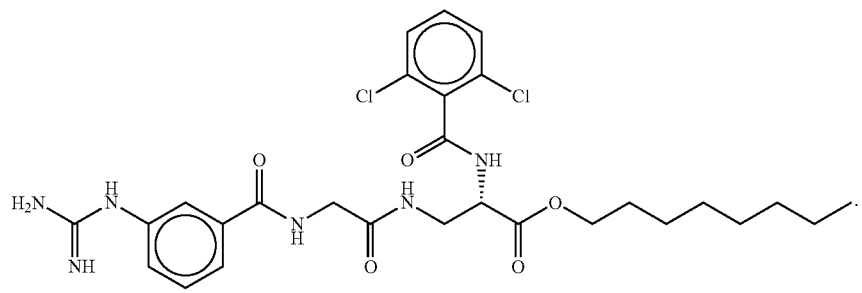

In embodiments, the disclosure provides a compound of Formula (41) or a pharmaceutically acceptable salt thereof:

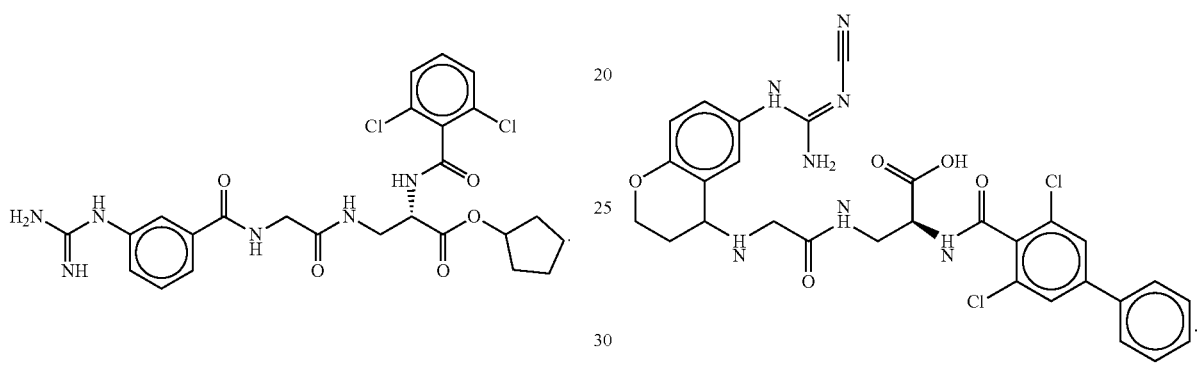

In embodiments, the disclosure provides a compound of Formula (42) or a pharmaceutically acceptable salt thereof:

In embodiments, the disclosure provides a compound of Formula (45) or a pharmaceutically acceptable salt thereof:

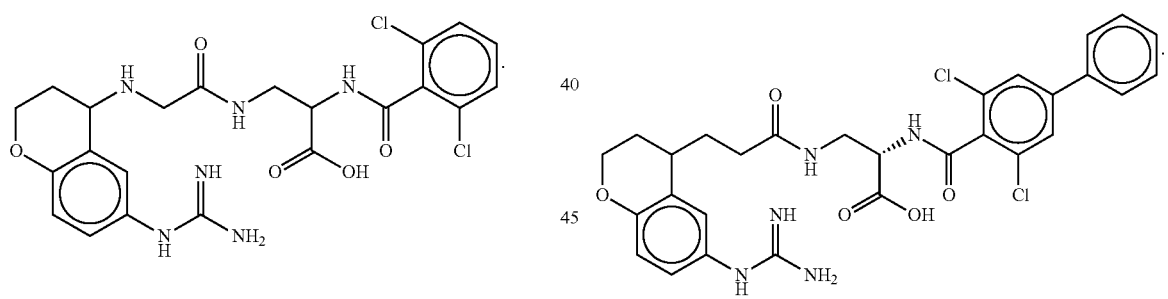

In embodiments, the disclosure provides a compound of Formula (43) or a pharmaceutically acceptable salt thereof:

In embodiments, the disclosure provides a compound of Formula (46) or a pharmaceutically acceptable salt thereof:

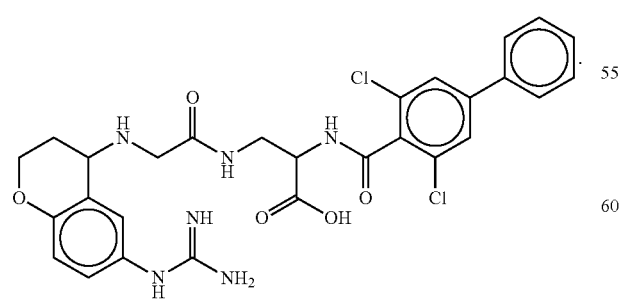

In embodiments, the disclosure provides a compound of Formula (44) or a pharmaceutically acceptable salt thereof:

In embodiments, the disclosure provides a compound of Formula (47) or a pharmaceutically acceptable salt thereof:

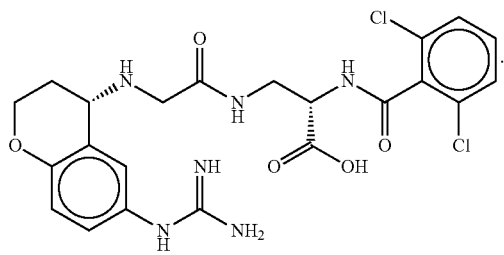

In embodiments, the disclosure provides a compound of Formula (48) or a pharmaceutically acceptable salt thereof:

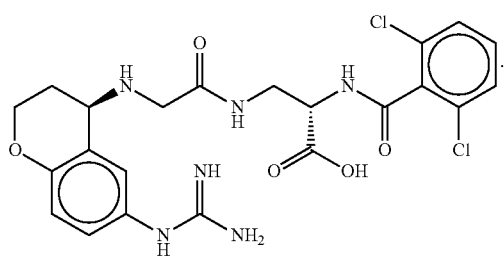

In embodiments, the disclosure provides a compound of Formula (49) or a pharmaceutically acceptable salt thereof:

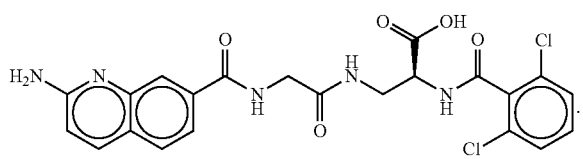

In embodiments, the disclosure provides a compound of Formula (50) or a pharmaceutically acceptable salt thereof:

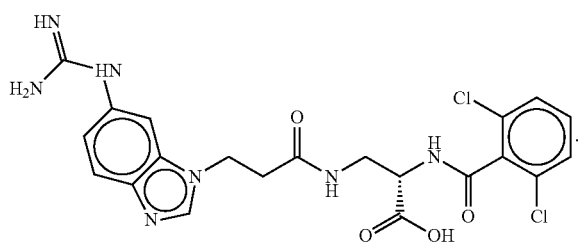

In embodiments, the disclosure provides a compound of Formula (51) or a pharmaceutically acceptable salt thereof:

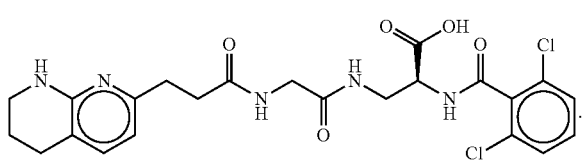

In embodiments, the disclosure provides a compound of Formula (52) or a pharmaceutically acceptable salt thereof:

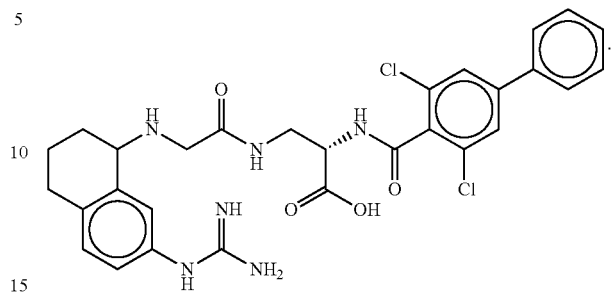

In embodiments, the disclosure provides a compound of Formula (53) or a pharmaceutically acceptable salt thereof:

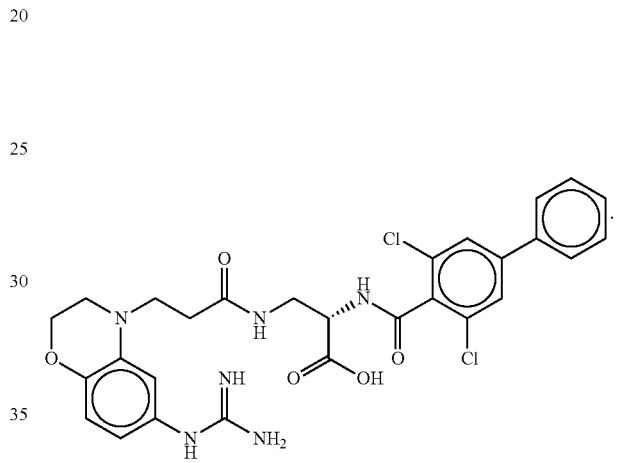

In embodiments, the disclosure provides a compound of Formula (54) or a pharmaceutically acceptable salt thereof:

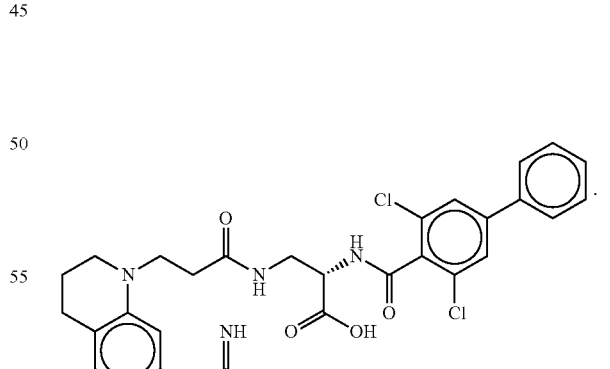

In embodiments, the disclosure provides a compound of Formula (55) or a pharmaceutically acceptable salt thereof:

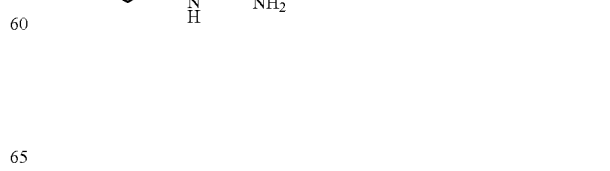

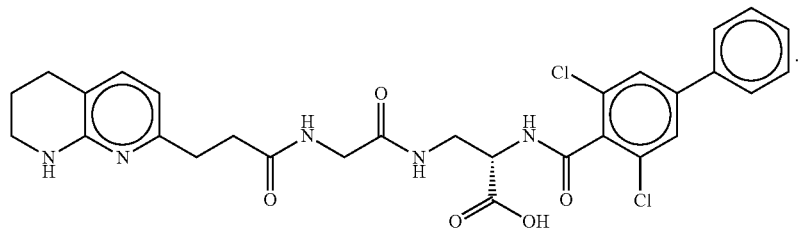

In embodiments, the disclosure provides a compound of Formula (56) or a pharmaceutically acceptable salt thereof:

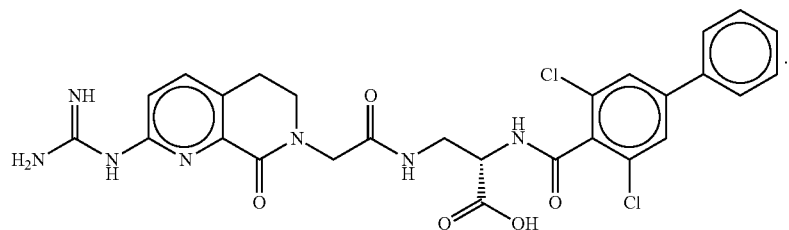

In embodiments, the disclosure provides a compound of Formula (57) or a pharmaceutically acceptable salt thereof:

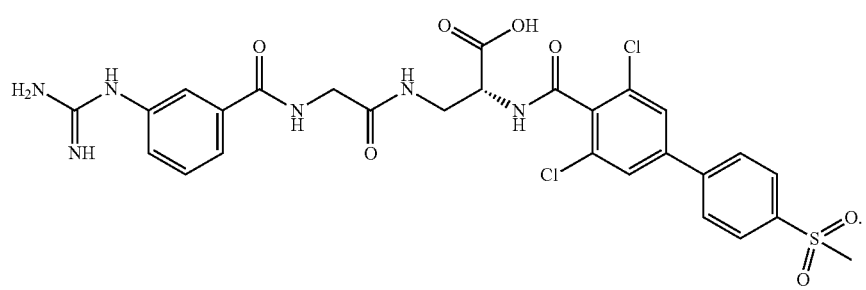 [SMILES: CS(=O)(=O)c1ccc(-c2cc(Cl)c(C(=O)N[C@H](CNC(=O)CNC(=O)c3cccc(NC(=N)N)c3)C(=O)O)c(Cl)c2)cc1]

In embodiments, the disclosure provides a compound of Formula (58) or a pharmaceutically acceptable salt thereof:

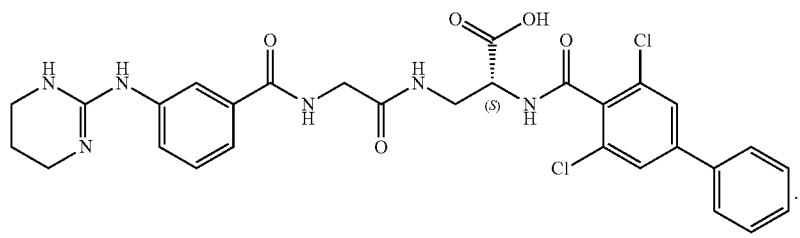

In embodiments, the disclosure provides a compound of Formula (59) or a pharmaceutically acceptable salt thereof:

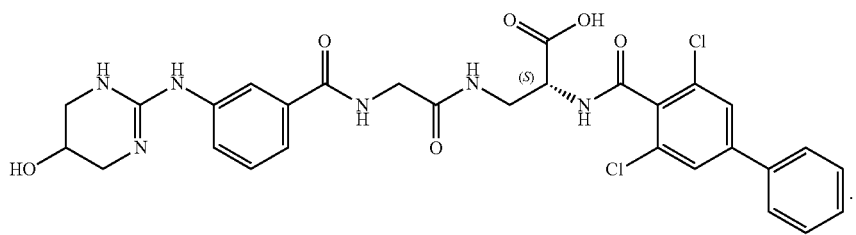

In embodiments, the disclosure provides a compound of Formula (60) or a pharmaceutically acceptable salt thereof:

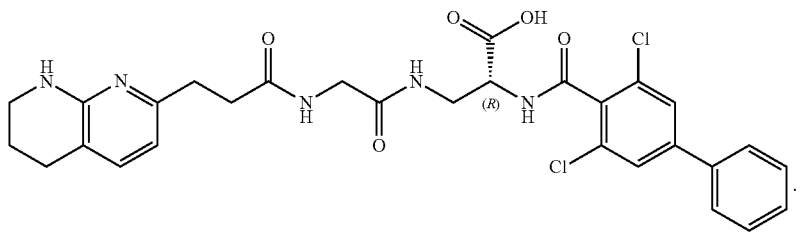

In embodiments, the disclosure provides a compound of Formula (61) or a pharmaceutically acceptable salt thereof:

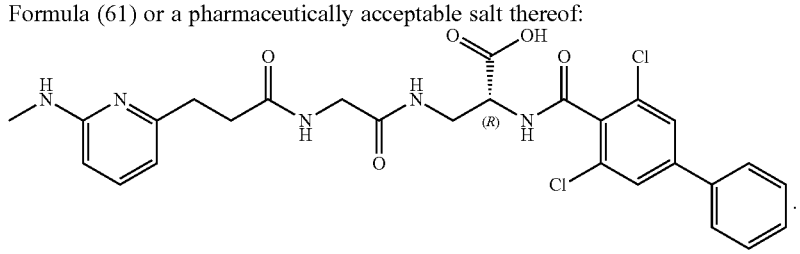

In embodiments, the disclosure provides a compound of Formula (62) or a pharmaceutically acceptable salt thereof:

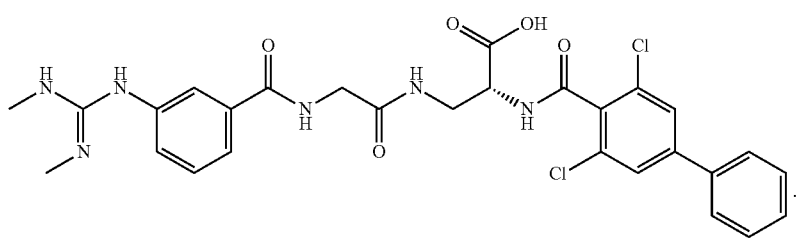 [SMILES: C/N=C(\NC)Nc1cccc(C(=O)NCC(=O)NC[C@@H](NC(=O)c2c(Cl)cc(-c3ccccc3)cc2Cl)C(=O)O)c1]

In embodiments, the disclosure provides a compound of Formula (63) or a pharmaceutically acceptable salt thereof:

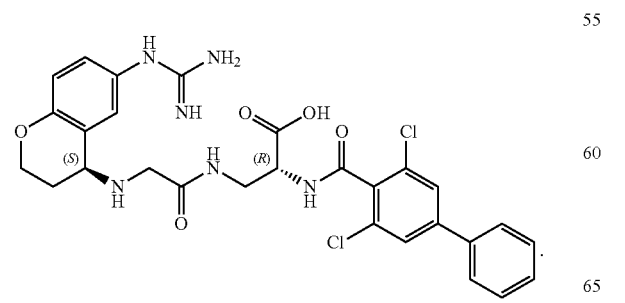

In embodiments, the disclosure provides a compound of Formula (64) or a pharmaceutically acceptable salt thereof:

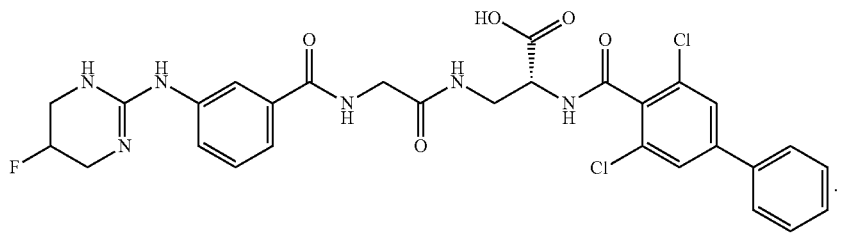 [SMILES: O=C(CNC(=O)c1cccc(NC2=NCC(F)CN2)c1)NC[C@@H](NC(=O)c1c(Cl)cc(-c2ccccc2)cc1Cl)C(=O)O]

In embodiments, the disclosure provides a compound of Formula (65) or a pharmaceutically acceptable salt thereof:

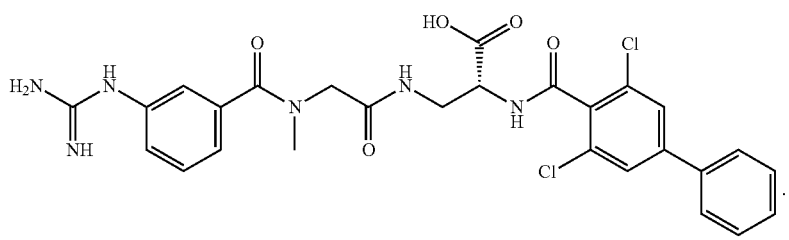 [SMILES: CN(CC(=O)NC[C@@H](NC(=O)c1c(Cl)cc(-c2ccccc2)cc1Cl)C(=O)O)C(=O)c1cccc(NC(=N)N)c1]

In embodiments, the disclosure provides a compound of Formula (66) or a pharmaceutically acceptable salt thereof:

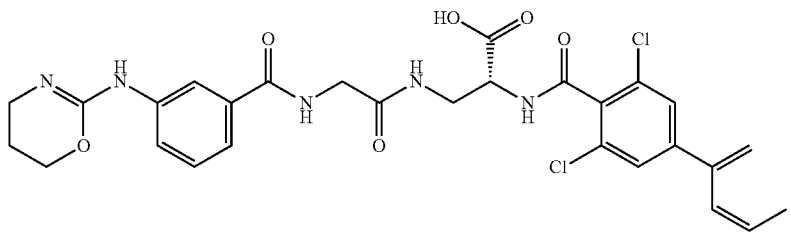

In embodiments, the disclosure provides a compound of Formula (67) or a pharmaceutically acceptable salt thereof:

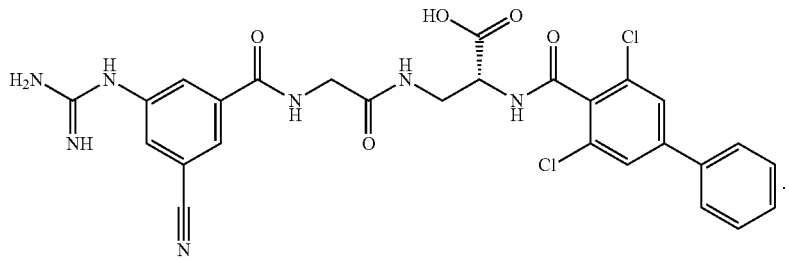 [SMILES: N#Cc1cc(NC(=N)N)cc(C(=O)NCC(=O)NC[C@@H](NC(=O)c2c(Cl)cc(-c3ccccc3)cc2Cl)C(=O)O)c1]

In embodiments, the disclosure provides a compound of Formula (68) or a pharmaceutically acceptable salt thereof:

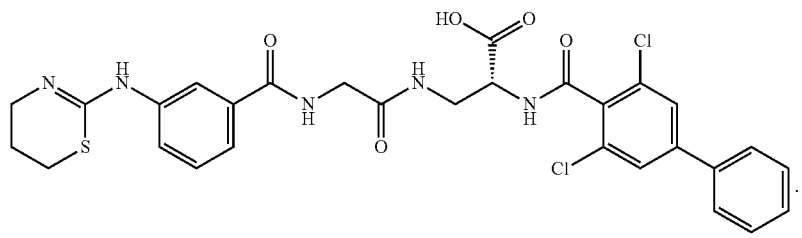 [SMILES: O=C(CNC(=O)c1cccc(NC2=NCCCS2)c1)NC[C@@H](NC(=O)c1c(Cl)cc(-c2ccccc2)cc1Cl)C(=O)O]

In embodiments, the disclosure provides a compound of Formula (69) or a pharmaceutically acceptable salt thereof:

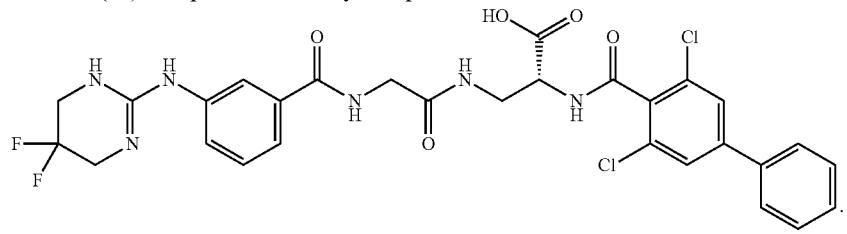

In embodiments, the disclosure provides a compound of Formula (70) or a pharmaceutically acceptable salt thereof:

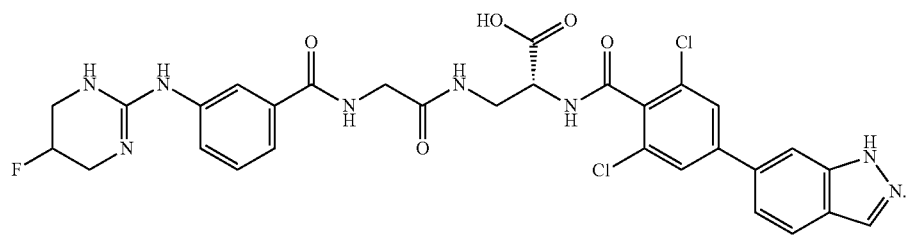 [SMILES: O=C(CNC(=O)c1cccc(NC2=NCC(F)CN2)c1)NC[C@@H](NC(=O)c1c(Cl)cc(-c2ccc3cn[nH]c3c2)cc1Cl)C(=O)O]

In embodiments, the disclosure provides a compound of Formula (71) or a pharmaceutically acceptable salt thereof:

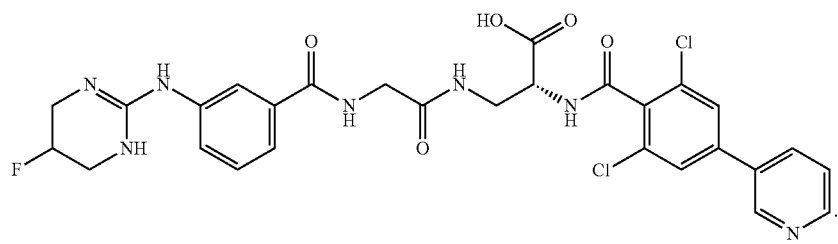 [SMILES: O=C(CNC(=O)c1cccc(NC2=NCC(F)CN2)c1)NC[C@@H](NC(=O)c1c(Cl)cc(-c2cccnc2)cc1Cl)C(=O)O]

In embodiments, the disclosure provides a compound of Formula (72) or a pharmaceutically acceptable salt thereof:

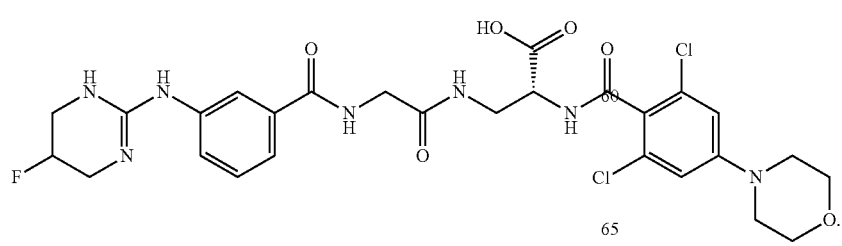 [SMILES: O=C(CNC(=O)c1cccc(NC2=NCC(F)CN2)c1)NC[C@@H](NC(=O)c1c(Cl)cc(N2CCOCC2)cc1Cl)C(=O)O]

In embodiments, the disclosure provides a compound of Formula (73) or a pharmaceutically acceptable salt thereof:

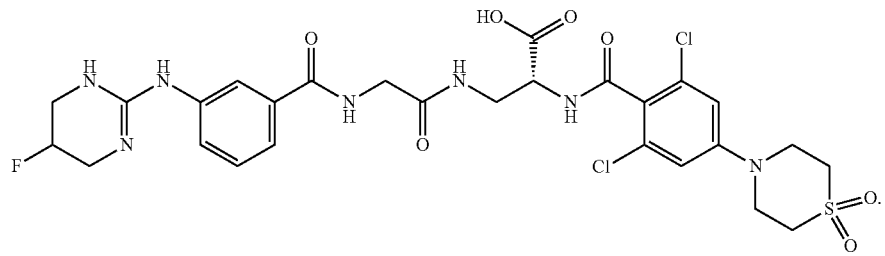 [SMILES: O=C(CNC(=O)c1cccc(NC2=NCC(F)CN2)c1)NC[C@@H](NC(=O)c1c(Cl)cc(N2CCS(=O)(=O)CC2)cc1Cl)C(=O)O]

In embodiments, the disclosure provides a compound of Formula (74) or a pharmaceutically acceptable salt thereof:

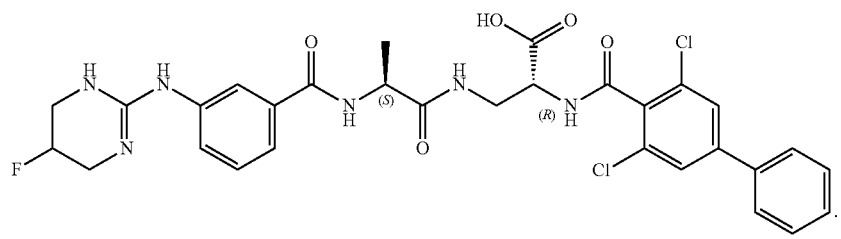

In embodiments, the disclosure provides a compound of Formula (75) or a pharmaceutically acceptable salt thereof:

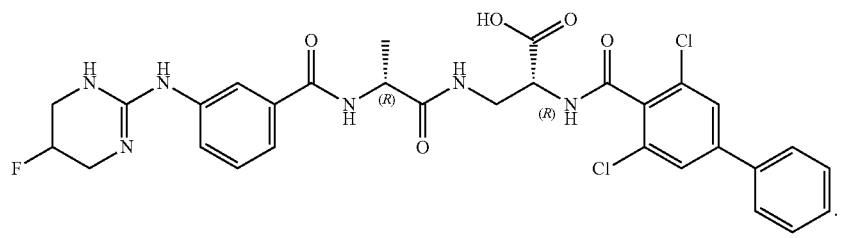

In embodiments, the disclosure provides a compound of Formula (76) or a pharmaceutically acceptable salt thereof:

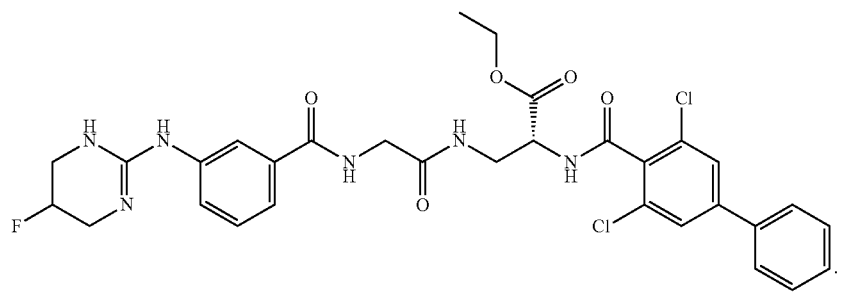 [SMILES: CCOC(=O)[C@@H](CNC(=O)CNC(=O)c1cccc(NC2=NCC(F)CN2)c1)NC(=O)c1c(Cl)cc(-c2ccccc2)cc1Cl]

In embodiments, the disclosure provides a compound of Formula (77) or a pharmaceutically acceptable salt thereof:

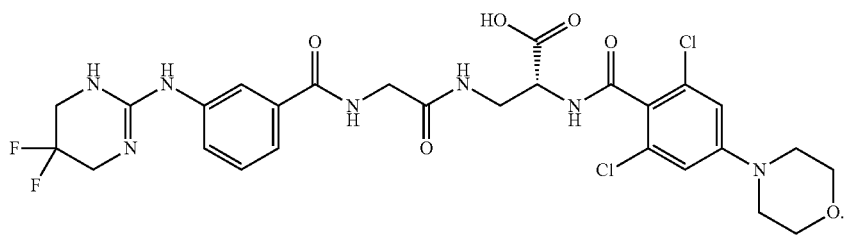 [SMILES: O=C(CNC(=O)c1cccc(NC2=NCC(F)(F)CN2)c1)NC[C@@H](NC(=O)c1c(Cl)cc(N2CCOCC2)cc1Cl)C(=O)O]

In embodiments, the disclosure provides a compound of Formula (78) or a pharmaceutically acceptable salt thereof:

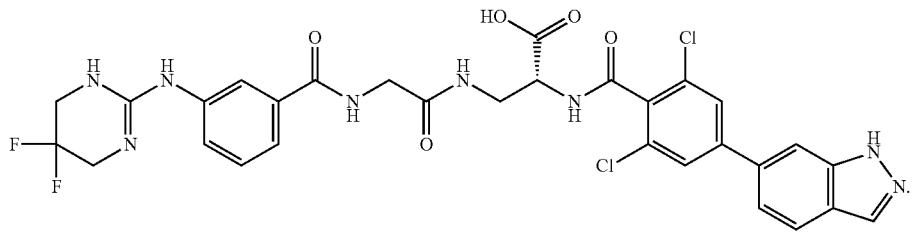 [SMILES: O=C(CNC(=O)c1cccc(NC2=NCC(F)(F)CN2)c1)NC[C@@H](NC(=O)c1c(Cl)cc(-c2ccc3cn[nH]c3c2)cc1Cl)C(=O)O]

Dose and Dosing Regimens

The dosage and frequency (single or multiple doses) of the α5β1 inhibitors administered to a subject can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and α5β1 inhibitors described herein. Adjustment and manipulation of established dosages (e.g., frequency and duration) are well within the ability of those skilled in the art.

For any composition and α5β1 inhibitors described herein, the effective amount can be initially determined from cell culture assays. Target concentrations will be those concentrations of α5β1 inhibitors that are capable of achieving the methods described herein, as measured using the methods described herein or known in the art. As is known in the art, effective amounts of α5β1 inhibitors for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages of the α5β1 inhibitors may be varied depending upon the requirements of the patient. The dose administered to a patient should be sufficient to affect a beneficial therapeutic response in the patient over time. The size of the dose also will be determined by the existence, nature, and extent of any adverse side-effects. Determination of the proper dosage for a particular situation is within the skill of the art. Generally, treatment is initiated with smaller dosages which are less than the optimum dose of the α5β1 inhibitor. Thereafter, the dosage is increased by small increments until the optimum effect under circumstances is reached. Dosage amounts and intervals can be adjusted individually to provide levels of the α5β1 inhibitors effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of α5β1 inhibitors by considering factors such as compound potency, relative bioavailability, patient body weight, presence and severity of adverse side effects.

In embodiments, the α5β1 inhibitors is administered to a patient at an amount of about 0.01 mg/kg to about 500 mg/kg. It is understood that where the amount is referred to as "mg/kg," the amount is milligram per kilogram body weight of the subject being administered with the α5β1 inhibitor. In aspects, the α5β1 inhibitor is administered to a patient in an amount from about 1 mg to about 500 mg per day, as a single dose, or in a dose administered two or three times per day. In aspects, the α5β1 inhibitor is administered to a patient in an amount from about 10 mg to about 100 mg per day, as a single dose, or in a dose administered two or three times per day.

Pharmaceutical Compositions

Provided herein are pharmaceutical compositions comprising a α5β1 inhibitor and a pharmaceutically acceptable excipient. The provided compositions are suitable for formulation and administration in vitro or in vivo. Suitable carriers and excipients and their formulations are described in Remington: The Science and Practice of Pharmacy, 21st Edition, David B. Troy, ed., Lippicott Williams & Wilkins (2005).

"Pharmaceutically acceptable excipient" and "pharmaceutically acceptable carrier" refer to a substance that aids the administration of an active agent to and absorption by a subject and can be included in the compositions of the disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In aspects, oral pharmaceutical compositions will comprise an inert diluent or edible carrier, or they may be enclosed in hard or soft shell gelatin capsule, or they may be compressed into tablets, or they may be incorporated directly with the food. For oral therapeutic administration, the active compounds may be incorporated with excipients and used in the form of ingestible tablets, buccal tablets, troches, capsules, elixirs, suspensions, syrups, wafers, and the like. The percentage of the compositions and preparations may, of course, be varied and may conveniently be between about 1 to about 75% of the weight of the unit. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

Methods of Treatment

The disclosure provides methods of treating a disease in a patient in need thereof by administering to the patient an effective amount of the compounds or compositions described herein to treat the disease. In aspects, the disclosure provides methods of treating an inflammatory disease in a patient in need thereof by administering to the patient an effective amount of the compounds or compositions described herein to treat the inflammatory disease. In aspects, the disclosure provides methods of treating asthma in a patient in need thereof by administering to the patient an effective amount of the compounds or compositions described herein to treat the asthma. In aspects, the disclosure provides methods of treating airway hyperresponsiveness in a patient in need thereof by administering to the patient an effective amount of the compounds or compositions described herein to treat the airway hyperresponsiveness. In aspects, the disclosure provides methods of treating cancer in a patient in need thereof by administering to the patient an effective amount of the compounds or compositions described herein to treat the cancer. In aspects, the disclosure provides methods of inhibiting angiogenesis in a patient in need thereof by administering to the patient an effective amount of the compounds or compositions described herein to inhibit angiogenesis.

"Disease" or "condition" refer to a state of being or health status of a patient or subject capable of being treated with a compound, pharmaceutical composition, or method provided herein. In some embodiments, the disease is asthma. The disease may be airway hyperresponsiveness. The disease may be airway hyperresponsiveness in asthma. The disease may be angiogenesis. The disease may be a cancer (e.g., ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer).

The term "inflammatory disease" refers to a disease or condition characterized by aberrant inflammation (e.g., an increased level of inflammation compared to a control such as a healthy person not suffering from a disease). Examples of inflammatory diseases include asthma, autoimmune diseases, arthritis, rheumatoid arthritis, psoriatic arthritis, juvenile idiopathic arthritis, multiple sclerosis, systemic lupus erythematosus, myasthenia gravis, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, ichthyosis, Graves ophthalmopathy, inflammatory bowel disease, Addison's disease, vitiligo, acne vulgaris, celiac disease, chronic prostatitis, inflammatory bowel disease, pelvic inflammatory disease, reperfusion injury, sarcoidosis, transplant rejection, graft-versus-host disease, interstitial cystitis, atherosclerosis, scleroderma, and atopic dermatitis.

The term "asthma" refers to any disease or condition characterized by inflammation within the circulatory system, often accompanied with wheezing, airway restriction, shortness of breath, chest tightness, and coughing. In aspects, asthma is characterized by airway hyperresponsiveness. In aspects, asthma is airway hyperresponsiveness. Asthma may refer inflammation in the bronchi and bronchioles. Asthma may refer to atopic asthma. Asthma may refer to non-atopic asthma.

The term "cancer" refers to all types of cancer, neoplasm or malignant tumors found in mammals, including leukemia, carcinomas and sarcomas. Exemplary cancers that may be treated with the compounds and pharmaceutical compositions described herein include breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, or melanoma. Other examples include, cancer of the thyroid, endocrine system, brain, breast, cervix, colon, head and neck, liver, kidney, lung, non-small cell lung, melanoma, mesothelioma, ovary, sarcoma, stomach, uterus or medulloblastoma, Hodgkin's disease, Non-Hodgkin's lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's disease of the nipple, phyllodes tumors, lobular carcinoma, ductal carcinoma, cancer of the pancreatic stellate cells, cancer of the hepatic stellate cells, or prostate cancer.

EXAMPLES

The following examples are for purposes of illustration and are not intended to limit the spirit or scope of the disclosure or claims.

Example 1

Cell Adhesion Assay. Evaluation of cell attachment to extracellular matrix proteins was performed as previously described by Yokosaki et al, *J. Biol. Chem.*, 271: (39): 24144-24150 (1996). Briefly, wells of non-tissue culture-treated polystyrene 96-well flat-bottom microtiter plates (Linbro/Titertek, Flow Laboratories, McLean, Va.) were coated by incubation with 100 µl of each substrate in PBS at 37° C. for 1 hour. 96-well flat-bottomed tissue culture plates were coated with human plasma fibronectin for 1 hour at 37° C. After incubation, wells were washed with PBS, then blocked with 1% bovine serum albumin (BSA) for one hour. Control wells were filled with 1% BSA. SW480 cells were detached using 10 mM EDTA and resuspended in serum-free DMEM. For blocking experiments, cells were incubated with 10 µg/ml of the antibody for 15 minutes at 4° C. before plating. The plates were centrifuged at 10 g for 5 minutes before incubation for 1 hour at 37° C. in humidified 5% $CO_2$. Nonadherent cells were removed by centrifugation (top side down) at 10 g for 5 minutes. Attached cells were stained with 0.5% crystal violet, and the wells were washed with PBS. The relative number of cells in each well was evaluated after solubilization in 40 µl of 2% Triton X-100 by measuring absorbance at 595 nm in a microplate reader. All determinations were carried out in triplicate. The results are shown in Table 1.

TABLE 1

| Compound | $IC_{50}$ |
|---|---|
| [chemical structure] | less than 100 nM |
| [chemical structure] | less than 100 nM |

TABLE 1-continued

| Compound | IC$_{50}$ |
|---|---|
| (structure) | less than 100 nM |
| (structure) | less than 100 nM |
| (structure) | less than 100 nM |
| (structure) | less than 100 nM |
| (structure) | less than 1,000 nM |
| (structure) | less than 1,000 nM |
| (structure) | less than 1,000 nM |

TABLE 1-continued

| Compound | IC$_{50}$ |
|---|---|
| 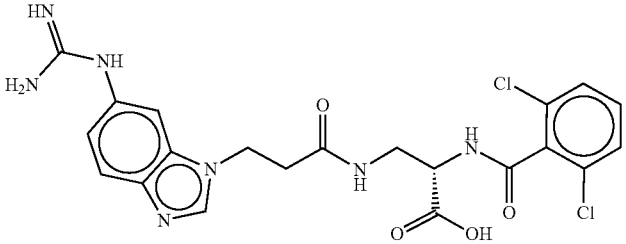 | less than 10,000 nM |
| 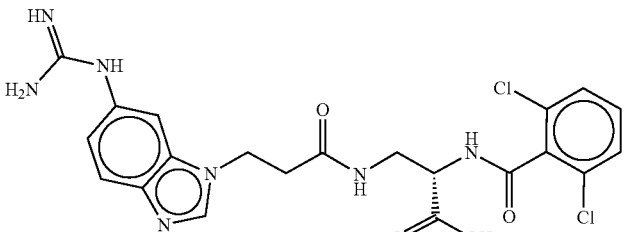 | less than 10,000 nM |
| 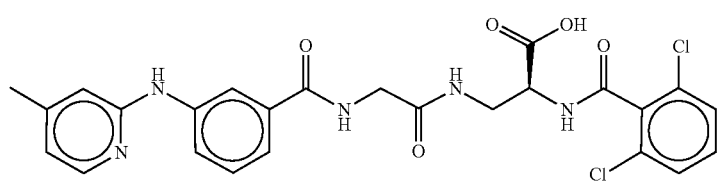 | less than 10,000 nM |
| 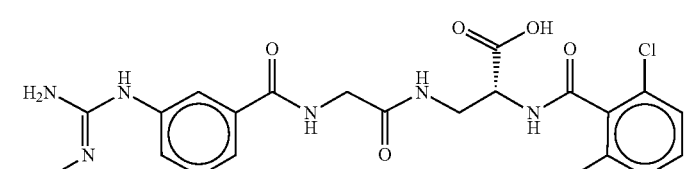 | less than 10,000 nM |
| 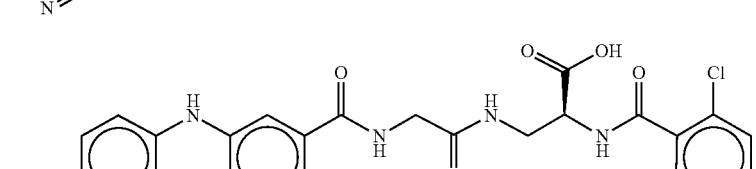 | less than 50,000 nM |

Measurement of tracheal smooth muscle contractility. Tracheal ring contraction studies were performed by dissecting mouse tracheal rings into 3-4 mm segments. After incubation with the indicated compound, the rings were equilibrated under 0.5 gm of applied tension, contracted with 60 mM KCl, and only rings that generated more than 1 mN of force were analyzed. After reequilibration, contractile responses to increasing doses of methacholine were evaluated. For analysis of the suppressive effects on IL-13 induced contractility, rings were treated with mouse IL-13 (100 ng/ml) for 12 hours at 37° C. in 5% $CO_2$. For relaxation experiments, rings were treated with mouse IL-13 (100 ng/ml) for 12 hours at 37° C. with 5% $CO_2$, then precontracted with $10^{-6}$ M Mch, and relaxation responses to increasing doses of isoproterenol in the presence of a compound were evaluated. For human bronchial rings, human lung tissue was obtained from lung transplant donors. Bronchi, 5-8 mm in diameter, were dissected free of connective tissue and cut into 4-mm-thick rings. The rings were stored overnight at 37° C. in 5% $CO_2$ in DMEM medium. Contraction was assessed as above, except a resting tension of 1 g was applied, the rings were first contracted with 120 mM KCl after equilibration for 2 hours, and only the rings that generated more than 2 mN tension were used for experiments. Rings were then washed and reequilibrated before contractile responses to increasing concentrations of Mch were evaluated.

Murine models of allergic airway disease. Six-week-old, sex-matched $C_{57}/B16$ mice were sensitized on days 0, 7, and 14 by i.p. injection of 50 µg OVA emulsified in 1 mg aluminum potassium sulfate. Subsequently, mice were anesthetized with isoflurane and i.n. challenged on 3 consecutive days (days 21, 22, and 23) by aspiration of 100 µg OVA dissolved in 40 µl saline. Twenty-four hours after the last challenge, mice were anesthetized with isoflurane and underwent computer-generated randomization to be given a compound or vehicle i.n. One hour after administration, mice were anesthetized with ketamine (100 mg/kg), xylazine (10 mg/kg), and acepromazine (3 mg/kg). Pulmonary resistance was determined by ventilator assessment after paralysis using invasive cannulation of the trachea. The scientists performing the experiment were blinded to the drug delivered throughout the experiment and during analysis of the experimental outcome. For experiments done on smooth-muscle conditional knockout mice, pulmonary resistance was assessed as above after treatment with doxycycline, but no compound was delivered prior to assessment.

Example 2

Experimental Procedures and Characterization Data

All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. $^1H$ chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration. LCMS spectra were obtained on an Agilent 1200 series 6110 or 6120 mass spectrometer with electrospray ionization and excepted as otherwise indicated, the general LCMS condition was as follows: Waters X Bridge C18 column (50 mm×4.6 mm×3.5 um), Flow Rate: 2.0 ml/min, the column temperature: 40° C.

SU15210-0002-01

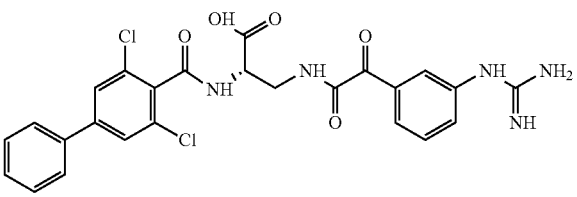

SU15210-0002-01

Chemical Formula: $C_{26}H_{24}Cl_2N_6O_5$
Molecular Weight: 571.41

Scheme: Route for SU15210-002-01

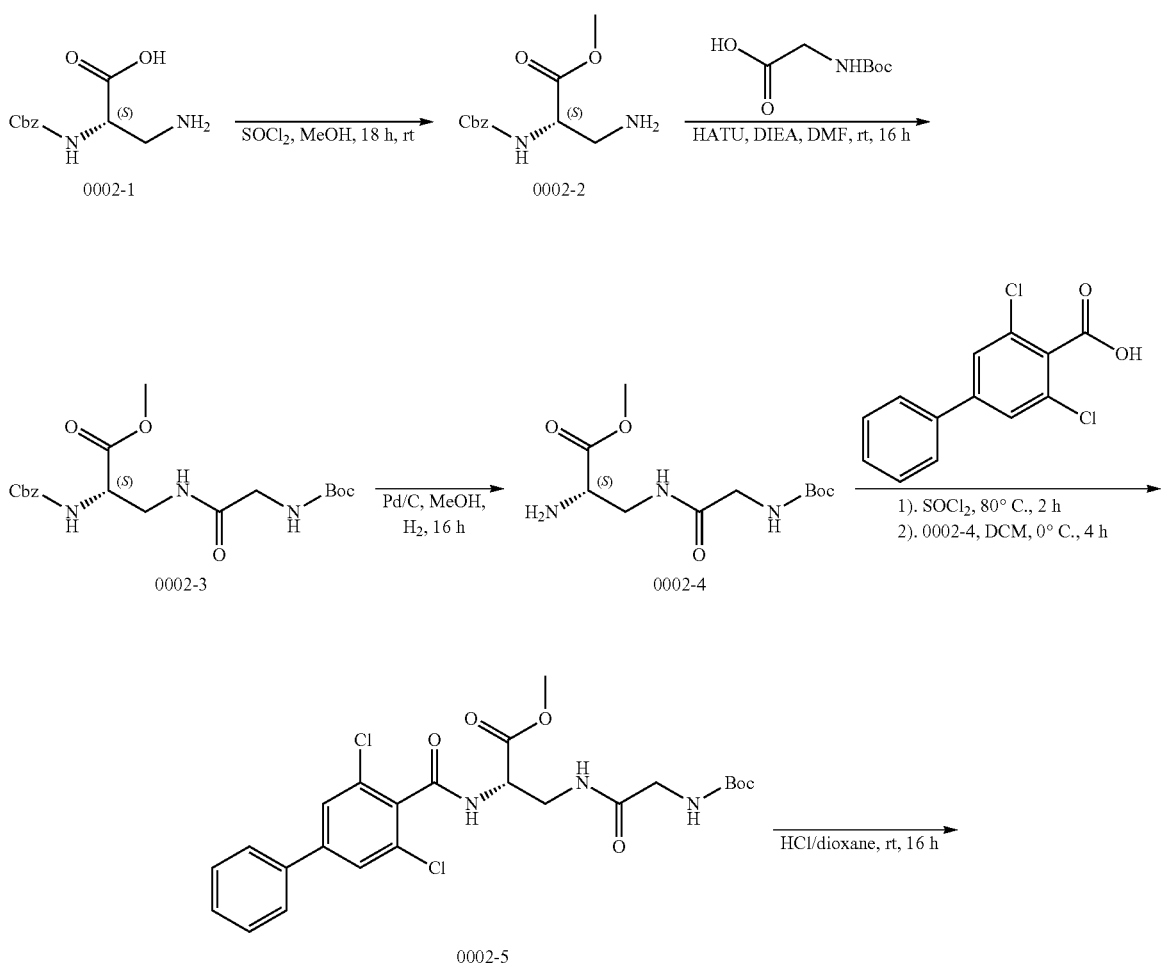

-continued
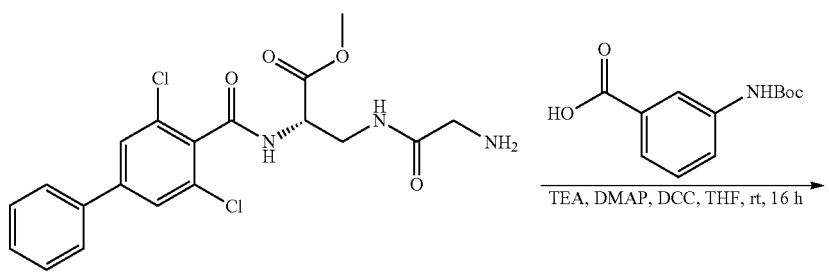
0002-6
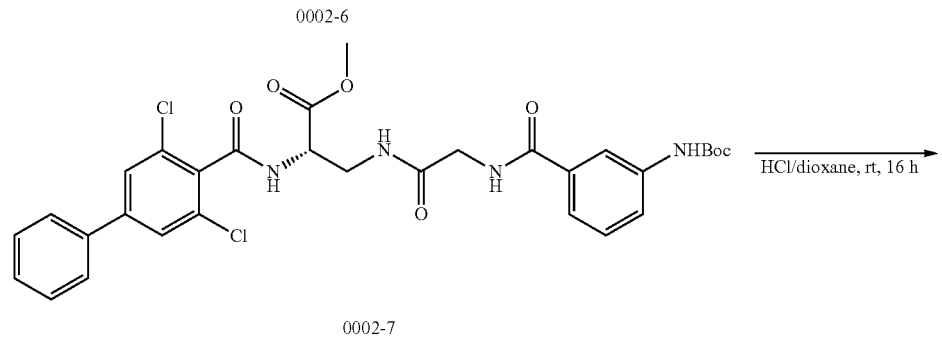
0002-7
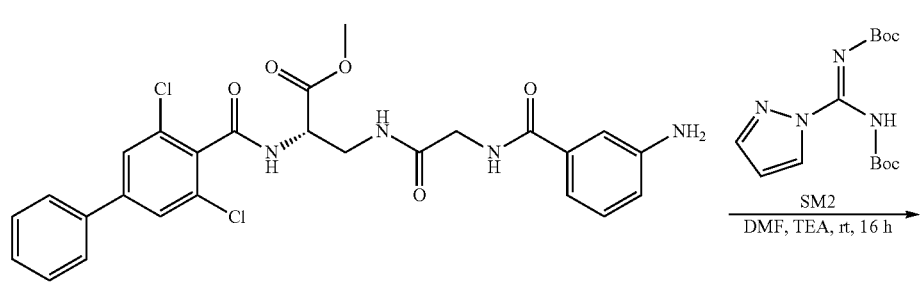
0002-8
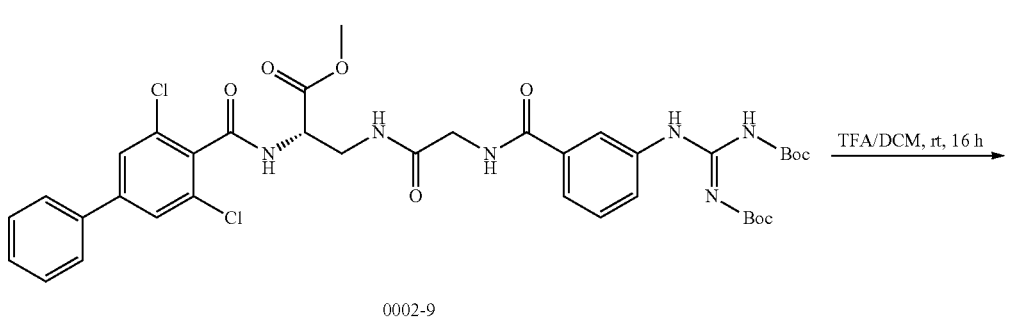
0002-9
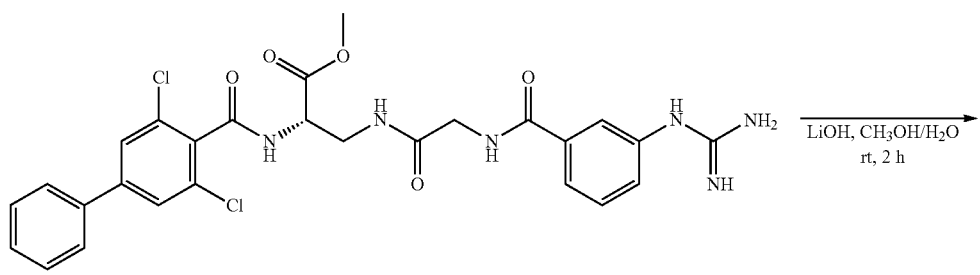
0002-10

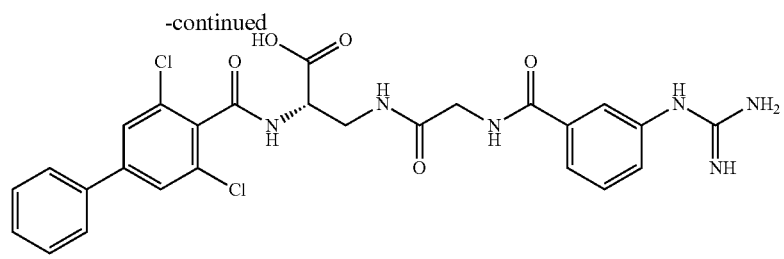

SU15210-0002-01

The Synthesis of (S)-methyl 3-amino-2-(benzyloxy-carbonylamino)propanoate (0002-2)

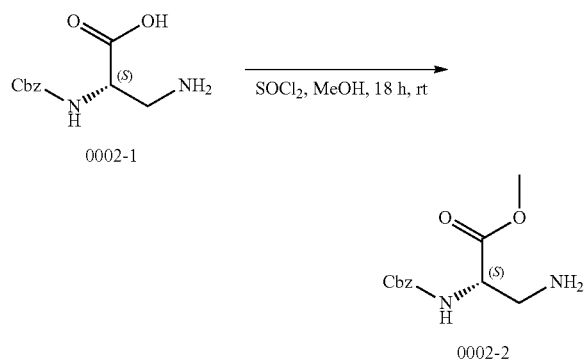

Thionyl chloride was (21.0 g, 192 mmol) added slowly to methanol (100 ml) with stirred at 0° C. in an ice bath, after stirred for 30 minutes. 0002-1 (20.0 g, 84 mmol) was added and the reaction was stirred overnight at room temperature. The solvent was removed in vacuo to give the desired product 0002-2 (20.0 g, 94.5% yield) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min. Purity is 96.5%. Rt=1.286 min; MS Calcd.: 252.7; MS Found: 253.7 [M+H]$^+$.

The Synthesis of (S)-methyl 13,13-dimethyl-3,8,11-trioxo-1-phenyl-2,12-dioxa-4,7,10-triazatetradecane-5-carboxylate (0002-3)

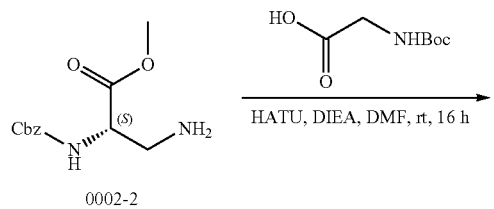

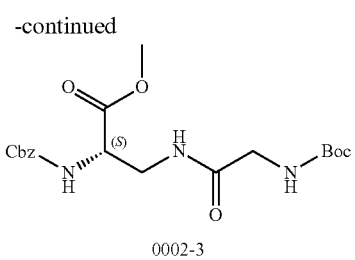

To a solution of 0002-2 (16.0 g, 64.0 mmol) in DMF (80.0 ml) was added 2-(tert-butoxycarbonylamino)acetic acid (11.2 g, 64.0 mmol), HATU (24.0 g, 64.0 mmol) and DIEA (24.0 g 192 mmol). The mixture was stirred at room temperature overnight. After the reaction was completed, the mixture was quenched with water, and then extracted with EA (100 mL×3). The organic layer was separated, dried over Na$_2$SO$_4$, and concentrated in vacuo. The residue was purified by column chromatography (PE/EA=1/1) to give 0002-3 (15.3 g, 59.1% yield) as yellow oil.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min. Purity is 97.0%. Rt=1.677 min; MS Calcd.: 409.7; MS Found: 410.7 [M+H]$^+$.

The Synthesis of (S)-methyl 2-amino-3-(2-(tert-butoxycarbonylamino)acetamido)propanoate (0002-4)

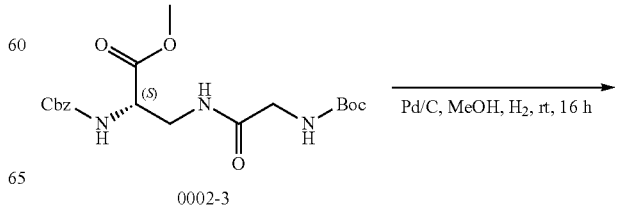

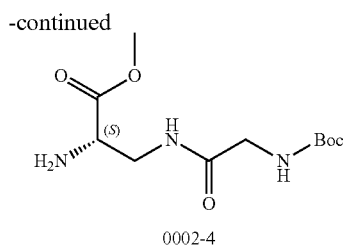

0002-4

To a solution of 0002-3 (15.3 g, 37.4 mmol) in MeOH (30.0 ml), was added and Pd/C (10%, 1.0 g) and the reaction mixture was stirred at rt for 16 h under $H_2$ atmosphere. After the reaction was completed, the reaction mixture was filtrated, the solvent is concentrated in vacuo to give the desired product 0002-4 (10.0 g, 97.3% yield) as yellow oil.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [$CH_3CN$+0.05% TFA] to 0% [water+0.05% TFA] and 100% [$CH_3CN$+0.05% TFA] in 1.6 min, then under this condition for 1.4 min, finally changed to 95% [water+0.05% TFA] and 5% [$CH_3CN$+0.05% TFA] in 0.05 min and under this condition for 0.7 min. Purity is 94.4%. Rt=1.135 min; MS Calcd.: 275.7; MS Found: 276.7 $[M+H]^+$.

The Synthesis of (S)-methyl 3-(2-(tert-butoxycarbonylamino)acetamido)-2-(3,5-dichlorobiphenyl-4-ylcarboxamido)propanoate (0002-5)

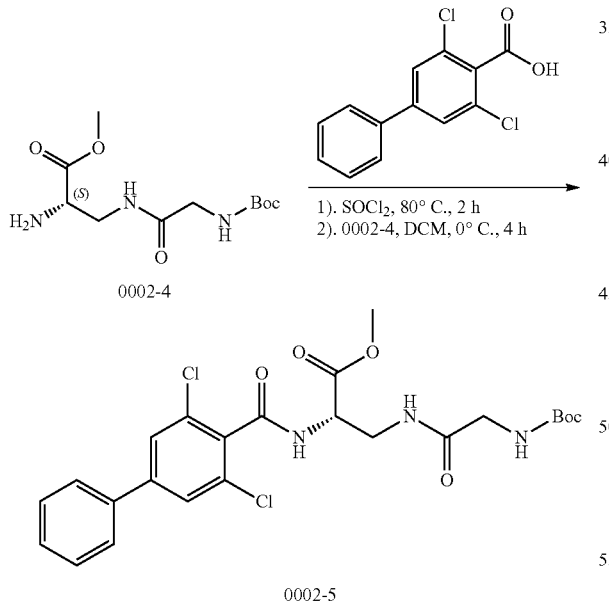

0002-5

To a solution of 3,5-dichlorobiphenyl-4-carboxylic acid (9.6 g, 36.3 mmol) in $SOCl_2$ (10 ml), stirred at 80° C. for 2 h then concentrated in vacuo to remove the solvent, then added 0002-4 (10.0 g, 36.3 mmol) and TEA (3.6 g, 36.3 mmol) in DCM (20.0 ml) at 0° C., the reaction mixture was stirred at this temperature for 4 h. After the reaction was completed, the mixture was quenched with water, and then extracted with EA (100 mL×3). The organic layer was separated, dried over $MgSO_4$ and concentrated in vacuo. The residue was purified by column chromatography (PE/EA=3:1) to give the desired product 0002-5 (8.0 g, 42.1% yield) as yellow oil.

Agilent LCMS 1200-6110, Column: Waters X-Bridge C18 (50 mm*4.6 mm*3.5 μm); Column Temperature: 40° C.; Flow Rate: 1.5 mL/min; Mobile Phase: from 95% [water+0.05% TFA] and 5% [$CH_3CN$+0.05% TFA] to 0% [water+0.05% TFA] and 100% [$CH_3CN$+0.05% TFA] in 1.5 min, then under this condition for 0.5 min, finally changed to 95% [water+0.05% TFA] and 5% [$CH_3CN$+0.05% TFA] in 0.1 min and under this condition for 0.1 min. Purity is 92.4%. Rt=1.878 min; MS Calcd.: 423.0; MS Found: 424.0 $[M+H]^+$.

The Synthesis of (S)-methyl 3-(2-aminoacetamido)-2-(3,5-dichlorobiphenyl-4-ylcarboxamido)propanoate (0002-6)

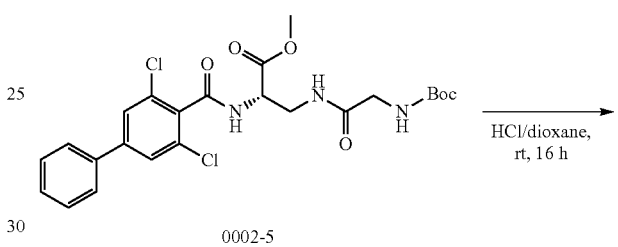

0002-5

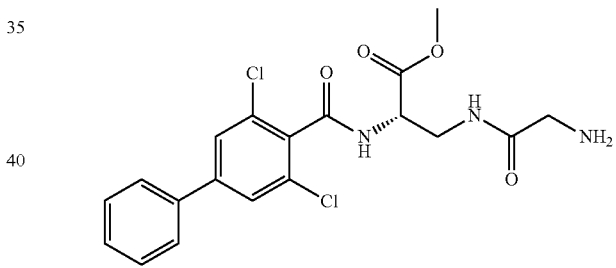

0002-6

To a solution of 0002-5 (1.1 g, 2.1 mmol) in HCl/dioxane (20.0 mL), the mixture was stirred at room temperature overnight. After the reaction was completed, the solvent was removed in vacuo to give 0002-6 (800.0 mg, 90.0%) as yellow oil.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [$CH_3CN$+0.05% TFA] to 0% [water+0.05% TFA] and 100% [$CH_3CN$+0.05% TFA] in 1.6 min, then under this condition for 1.4 min, finally changed to 95% [water+0.05% TFA] and 5% [$CH_3CN$+0.05% TFA] in 0.05 min and under this condition for 0.7 min. Purity is 94.0%. Rt=1.528 min; MS Calcd.: 423.0; MS Found: 423.9 $[M+H]^+$.

The Synthesis of (S)-methyl 3-(2-(3-(tert-butoxy-carbonylamino)-benzamido)acetamido)-2-(3,5-dichlorobiphenyl-4-ylcarboxamido)propanoate (0002-7)

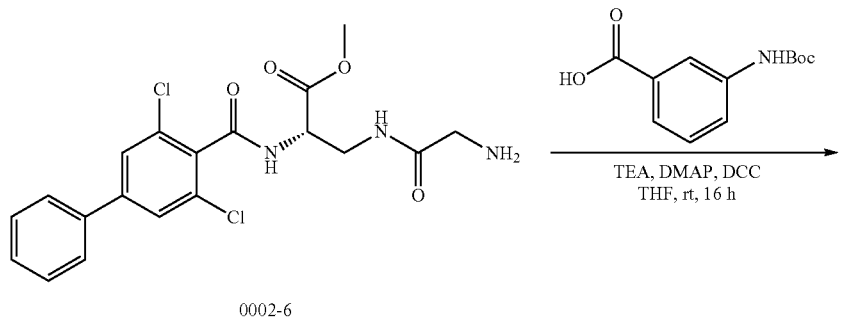

0002-6

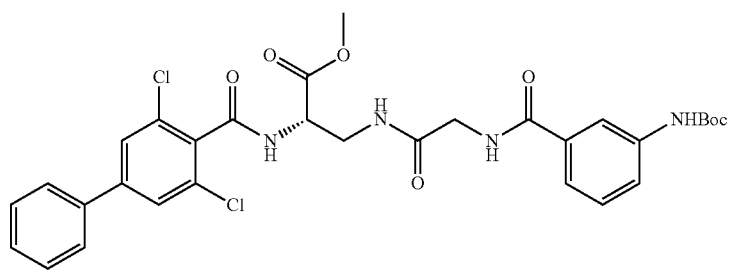

0002-7

To a solution of 0002-6 (800.0 mg, 1.9 mmol) in THF (10.0 mL), was added TEA (573.0 mg, 5.7 mmol), DMAP (20.0 mg, 0.2 mmol), DCC (389 mg, 1.9 mmol) and 3-(tert-butoxycarbonylamino)benzoic acid (450.3 mg, 1.0 mmol). The mixture was stirred at room temperature overnight. After the reaction was completed, the mixture was quenched with water, and then extracted with EA (20 mL×3). The organic layer was separated, dried over MgSO$_4$, and concentrated in vacuo. The residue was purified by column chromatography (PE/EA=2:1) to give 0002-7 (610 mg, 50.2% yield) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min. Purity is 95.1%. Rt=1.898 min; MS Calcd.: 642.7; MS Found: 643.7 [M+H]$^+$.

The Synthesis of (S)-methyl (S)-methyl 3-(2-(3-aminobenzamido)acetamido)-2-(3,5-dichlorobiphenyl-4-ylcarboxamido)propanoate (0002-8)

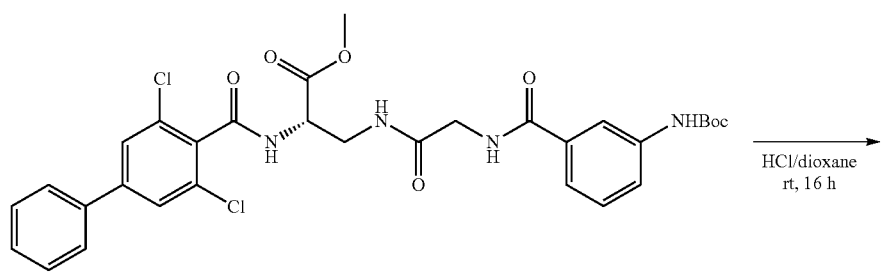

0002-7

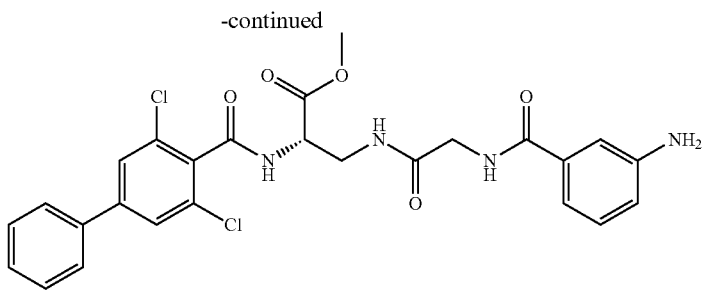

0002-8

To a solution of 0002-7 (610.0 mg, 0.9 mmol) in HCl/dioxane (20.0 mL), the mixture was stirred at room temperature overnight. After the reaction was completed, the solvent was removed in vacuo to give 0002-8 (500.0 mg, 97.3% yield) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH3CN+0.05% TFA] to 0% [water+0.05% TFA] and 100% [CH3CN+0.05% TFA] in 1.6 min, then under this condition for 1.4 min, finally changed to 95% [water+0.05% TFA] and 5% [CH3CN+0.05% TFA] in 0.05 min and under this condition for 0.7 min. Purity is 91.5%. Rt=1.576 min; MS Calcd.: 542.7; MS Found: 543.7 [M+H]$^+$.

The synthesis of (S,Z)-methyl 3-(2-(3-(2,3-bis(tert-butoxycarbonyl)guanidino)-benzamido)acetamido)-2-(3,5-dichlorobiphenyl-4-ylcarboxamido)propanoate (0002-9)

A mixture of tert-butyl (NE)-N-[(tert-butoxycarbonylamino)-pyrazol-1-yl-methylene]carbamate (SM2, 418.0 mg, 1.4 mmol), 0002-8 (500 mg, 0.9 mmol) and TEA (273.7 mg, 2.7 mmol) in DMF (10.0 mL) was stirred at room temperature overnight. After the reaction was completed, the reaction mixture was quenched with water and extracted with EA (20 mL×3). The organic layers were washed with brine, dried over MgSO$_4$ and concentrated in vacuo, the residue was purified by column chromatography (DCM/MeOH=20:1) to give 0002-9 (210.0 mg, 29.0% yield) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH3CN+0.05% TFA] to 0% [water+0.05% TFA] and 100% [CH3CN+0.05% TFA] in 1.6 min, then under this condition for 1.4 min, finally changed to 95% [water+0.05% TFA] and 5% [CH3CN+0.05% TFA] in 0.05 min and under this condition for 0.7 min. Purity is 83.8%. Rt=2.069 min; MS Calcd.: 784.7; MS Found: 785.7 [M+H]$^+$.

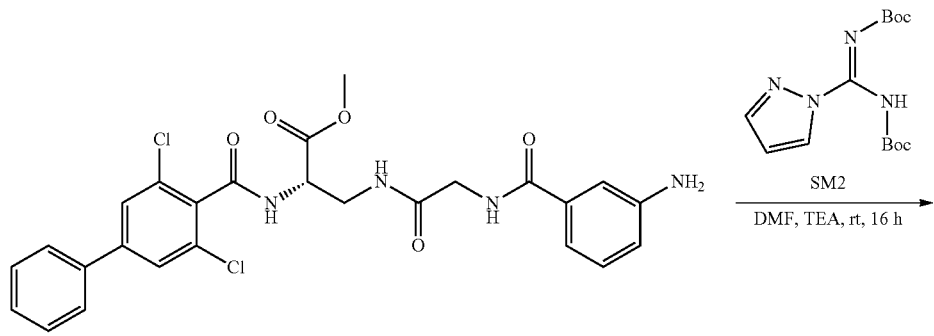

0002-8

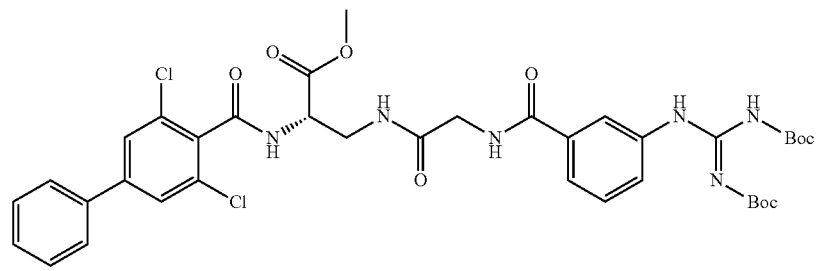

0002-9

The Synthesis of (S)-methyl 2-(3,5-dichlorobiphenyl-4-ylcarboxamido)-3-(2-(3-guanidinobenzamido)acetamido)propanoate (0002-10)

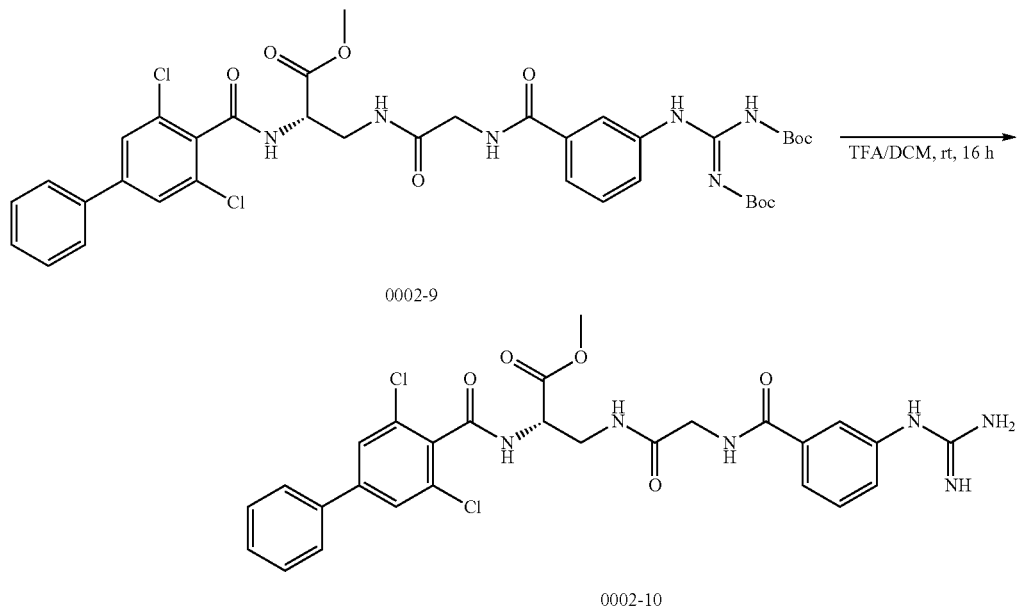

To a solution of 0002-9 (210.0 mg, 0.27 mmol) in TFA/DCM (2 mL/10 mL), the mixture was stirred at rt overnight. After the reaction was completed, the solvent was removed in vacuo to give 0002-10 (145.0 mg, 93.5% yield) as yellow oil.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH3CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH3CN+0.05% TFA] in 0.05 min and under this condition for 0.7 min. Purity is 91.4%. Rt=1.546 min; MS Calcd.: 584.7; MS Found: 585.7 [M+H]$^+$.

The Synthesis of (S)-2-(3,5-dichlorobiphenyl-4-ylcarboxamido)-3-(2-(3-guanidinobenzamido)acetamido)propanoic acid (SU15210-0002-01)

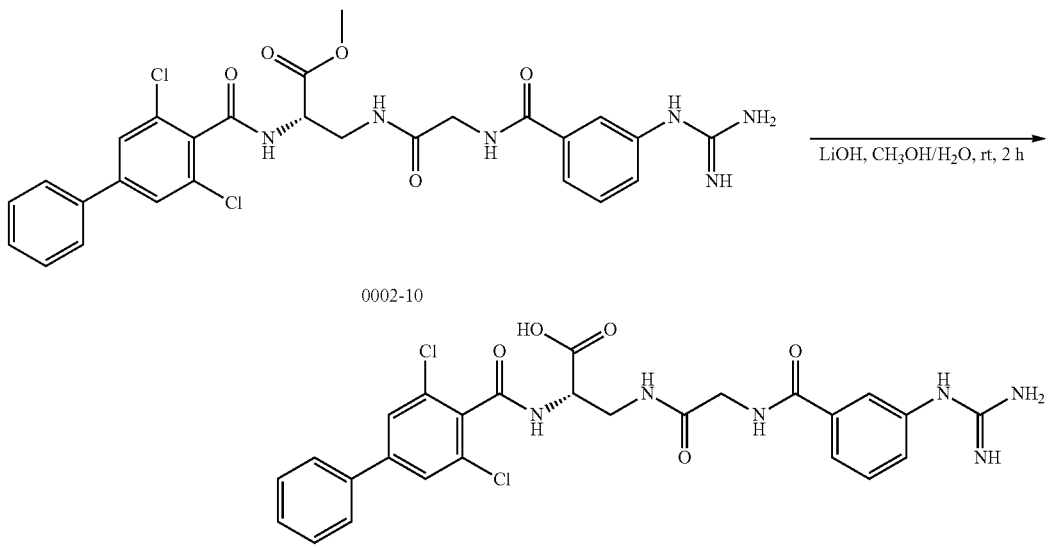

To a solution of 0002-10 (145.0 mg, 0.25 mmol) in MeOH/H$_2$O (10 mL/2 mL), was added LiOH (107.5 mg, 2.5 mmol). The reaction mixture was stirred at rt for 2 h, after the reaction was completed, the reaction mixture was concentrated and adjust pH to ~7.0 by HCl (1.0 N), then the reside was purified by pre-HPLC to give SU15210-0002-01 (110.0 mg, 78.0% yield) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH3CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH3CN+0.05% TFA] in 0.05 min and under this condition for 0.7 min. Purity is 100.0%. Rt=1.520 min; MS Calcd.: 570.8; MS Found: 571.8 [M+H]$^+$.

Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min. Purity is 98.9%. Rt=7.361 min.

$^1$H NMR (400 MHz, DMSO-d$_6$) δ 9.00 (t, J=6.0 Hz, 1H), 8.37 (d, J=3.2 Hz, 1H), 8.27 (s, 1H), 8.21 (d, J=7.2 Hz, 1H), 7.89-7.95 (m, 3H), 7.75-7.79 (m, 7H), 7.42-7.52 (m, 4H), 7.30 (d, J=8.0 Hz, 1H), 4.11 (q, J=6.8 Hz, 1H), 3.83 (d, J=8.4 Hz, 2H), 3.68-3.74 (m, 1H), 3.01 (t, J=9.6 Hz, 1H).

SU15210-0003

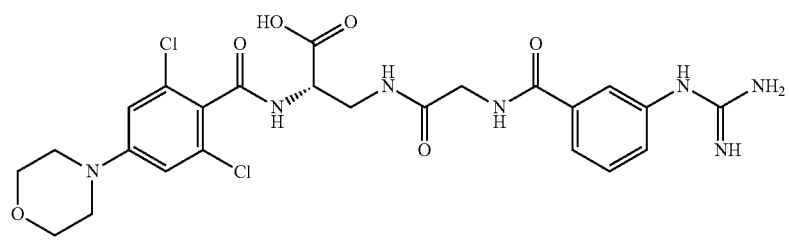

Chemical Formula: C$_{24}$H$_{27}$Cl$_2$N$_7$O$_6$
Molecular Weight: 580.42

Scheme: Route for SU15210-003

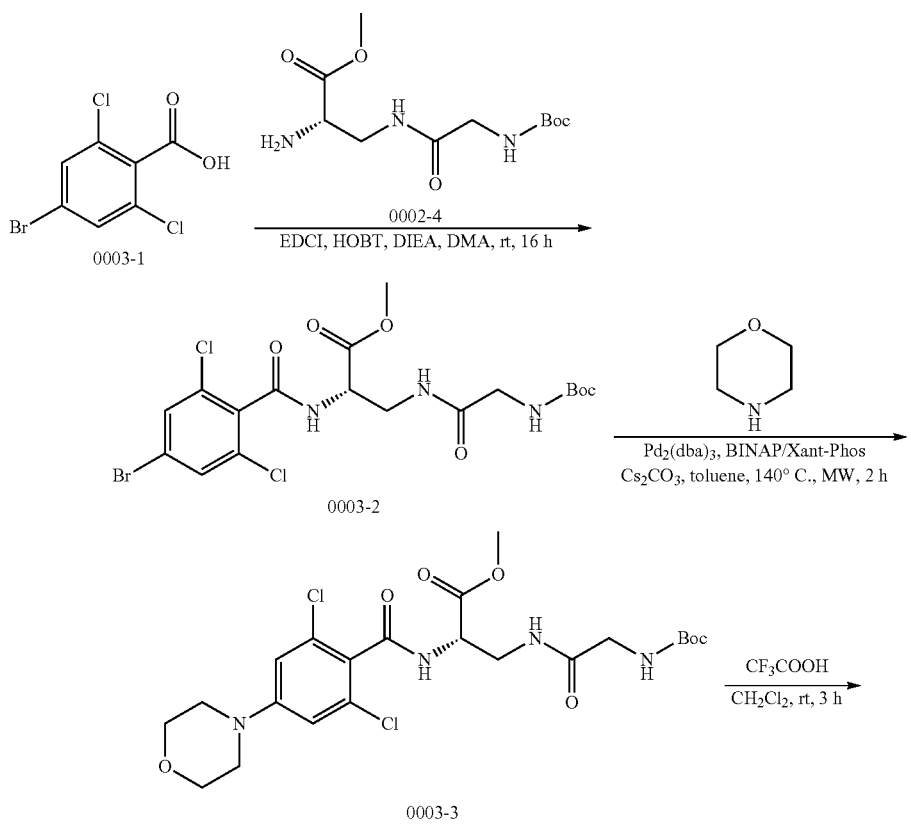

-continued
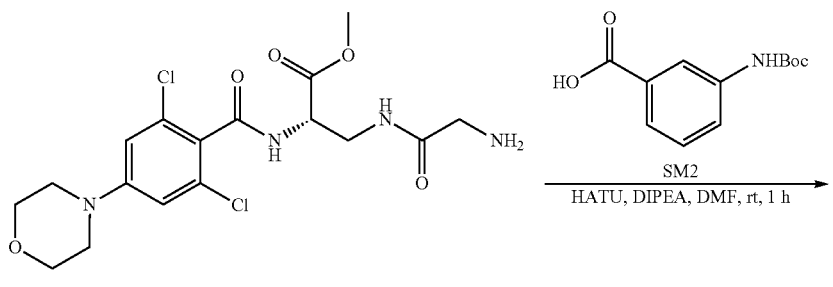
0003-4
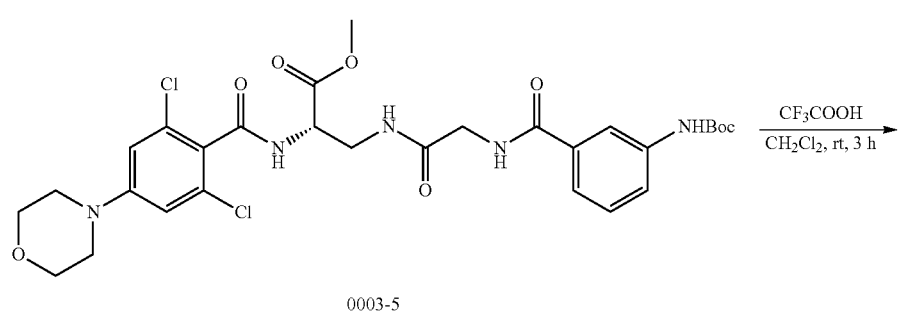
0003-5
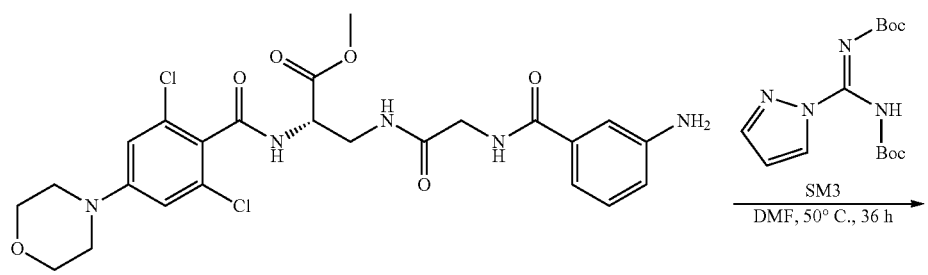
0003-6
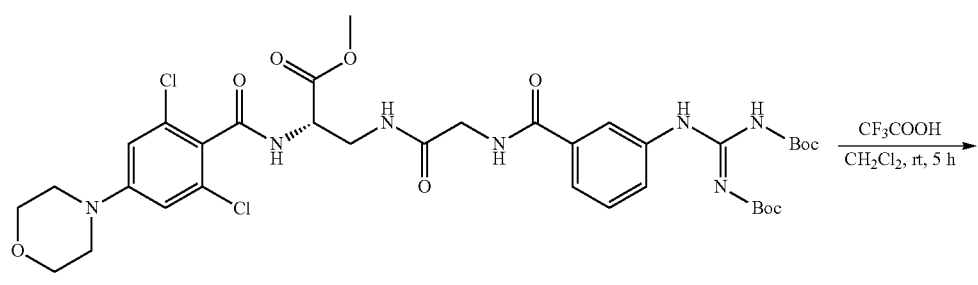
0003-7
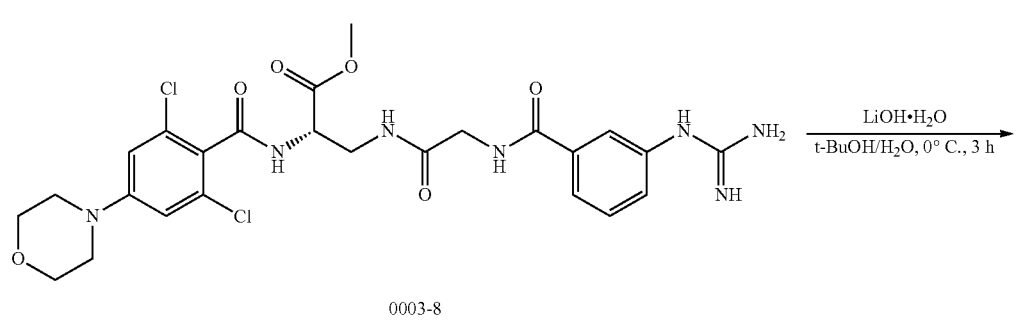
0003-8

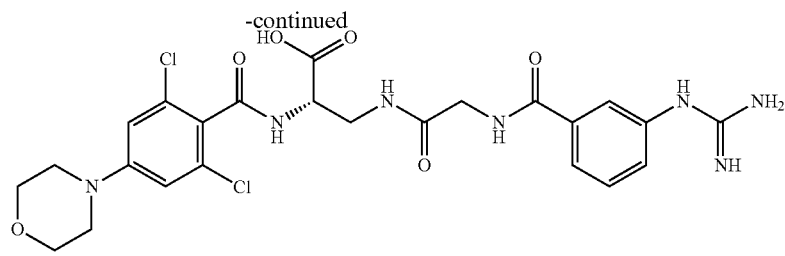

SU15210-0003

The Synthesis of (S)-methyl 2-(4-bromo-2,6-dichlorobenzamido)-3-(2-(tert-butoxycarbonylamino)acetamido)propanoate (0003-2)

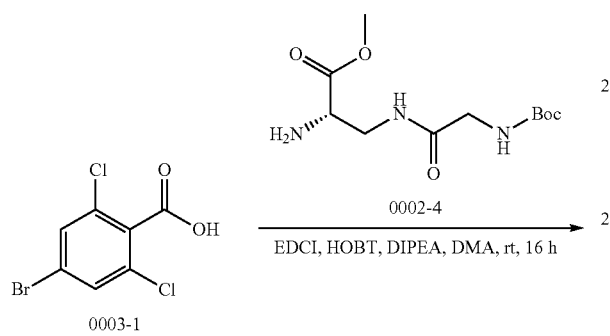

To a solution of compound 0003-1 (1.2 g, 4.5 mmol) in DMA (20 mL) was added EDCI (1.0 g, 5.4 mmol), HOBT (726.4 mg, 5.4 mmol), DIPEA (1.2 g, 9.0 mmol) and 0002-4 (1.2 g, 4.5 mmol). The mixture was stirred at rt for 16 h. After the consumption of starting material (by LCMS), the reaction solvent was quenched with water (100 mL), and extracted with EtOAc (40 mL×3), the organic layer was washed with saturated aqueous NaCl, collected the organic layer and dried over anhydrous $Na_2SO_4$, filtered and concentrated in vacuo, the crude was purified by CC (PE/EA=2/1) to get the product 0003-2 (1.2 g, yield: 52.3%) as a white solid.

The Synthesis of (S)-methyl 3-(2-(tert-butoxycarbonylamino)acetamido)-2-(2,6-dichloro-4-morpholinobenzamido)propanoate (0003-3)

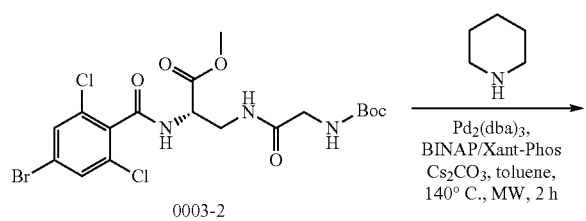

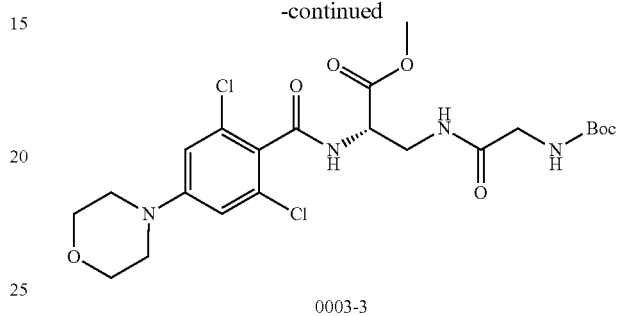

To a solution of compound 0003-2 (1.2 g, 2.3 mmol) in toluene (5 mL) was added $Pd_2(dba)_3$ (209.3 mg, 0.2 mmol), BINAP (142.3 mg, 0.2 mmol), Xant-Phos (132.2 mg, 0.2 mmol), $Cs_2CO_3$ (2.2 g, 6.9 mmol) and Morpholine (796.6 mg, 9.2 mmol). The reaction was stirred at 140° C. in MW for 2 h. After the reaction was finished, the reaction was filtered, the filtrate was concentrated in vacuo, the crude was dissolved in DMF and purified by prep-HPLC to give the product 0003-3 (183 mg, yield: 15.1%) as a white solid.

The Synthesis of (S)-methyl 3-(2-aminoacetamido)-2-(2,6-dichloro-4-morpholinobenzamido)propanoate (0003-4)

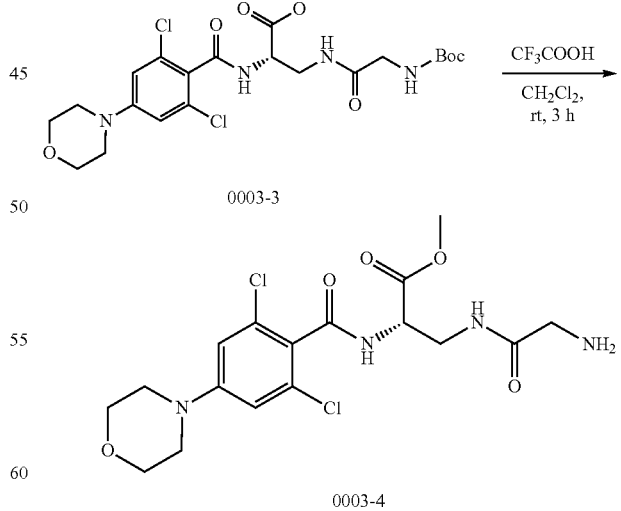

To a solution of compound 0003-3 (180.0 mg, 0.3 mmol) in DCM (5 mL) was added $CF_3COOH$ (1 mL), the mixture was stirred at rt for 3 h. After the consumption of starting material (by LCMS), the mixture was concentrated in vacuo to give the crude 0003-4 (146 mg, yield: 99.9%) as a white solid, which was used to the next step without further purification.

The Synthesis of (S)-methyl 3-(2-(3-(tert-butoxycarbonylamino)-benzamido)acetamido)-2-(2,6-dichloro-4-morpholinobenzamido)propanoate (0003-5)

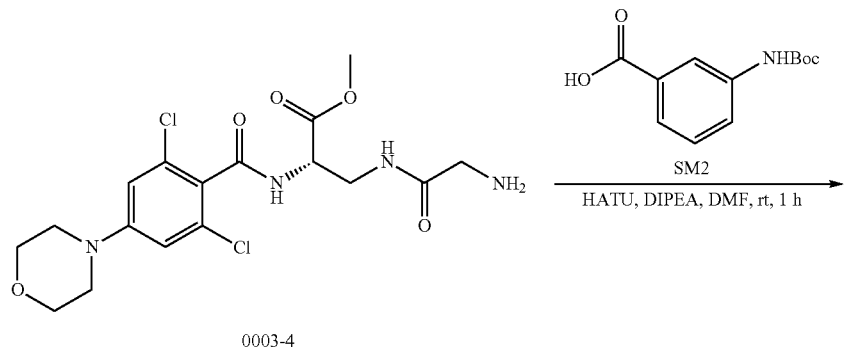

To a solution of compound 0003-4 (146.0 mg, 0.3 mmol) in DMF (5 mL) was added HATU (193.0 mg, 0.5 mmol), DIPEA (176.0 mg, 1.4 mmol) and SM2 (81.0 mg, 0.3 mmol). The mixture was stirred at rt for 1 h. After the reaction was finished (by LCMS), the mixture was purified by prep-HPLC to give the desired product 0003-5 (210.0 mg, yield: 95.4%) as a white solid.

The Synthesis of (S)-methyl 3-(2-(3-aminobenzamido)acetamido)-2-(2,6-dichloro-4-morpholinobenzamido)propanoate (0003-6)

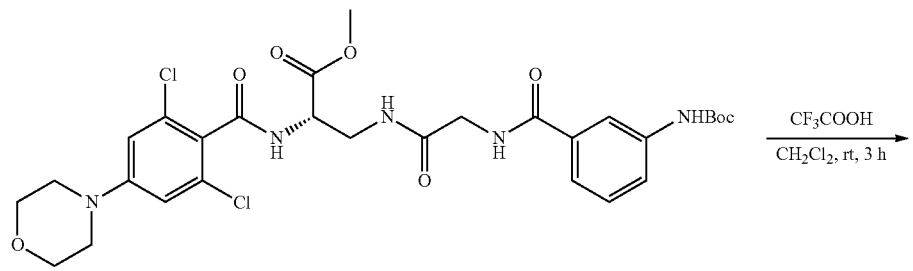

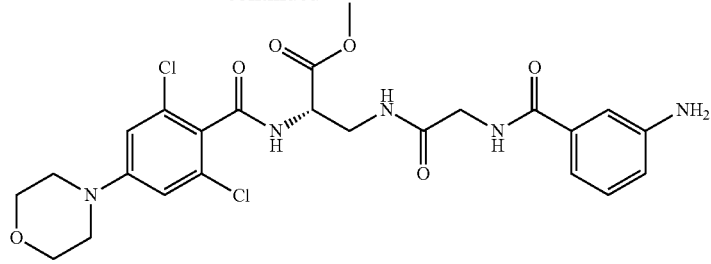

0003-6

To a solution of compound 0003-5 (210.0 mg, 0.3 mmol) in CH$_2$Cl$_2$ (5 mL) was added CF$_3$COOH (1 mL). The mixture was stirred at rt for 3 h. After the consumption of starting material (by LCMS), the mixture concentrated in vacuo to give the crude 0003-6 (174.0 mg, 97.8% yield) as a white solid, which was used to the next step without further purification.

The Synthesis of (S,Z)-methyl 3-(2-(3-(2,3-bis(tert-butoxycarbonyl)guanidino)-benzamido)acetamido)-2-(2,6-dichloro-4-morpholinobenzamido)propanoate (0003-7)

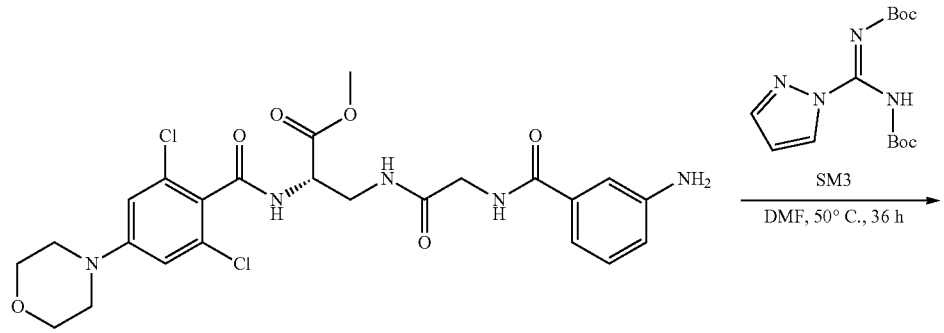

0003-6

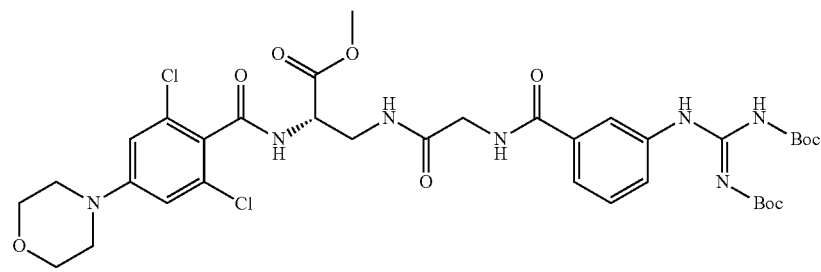

0003-7

To a solution of compound 0003-6 (174.0 mg, 0.3 mmol) in DMF (5 mL) was added SM3 (158.0 mg, 0.5 mmol), the mixture was stirred at 50° C. for 36 h. After the consumption of starting material (by LCMS), the mixture was purified by prep-HPLC to give the product 0003-7 (150.0 mg, 60.0% yield) as a white solid.

The Synthesis of (S)-methyl 2-(2,6-dichloro-4-morpholinobenzamido)-3-(2-(3-guanidinobenzamido)acetamido)propanoate (0003-8)

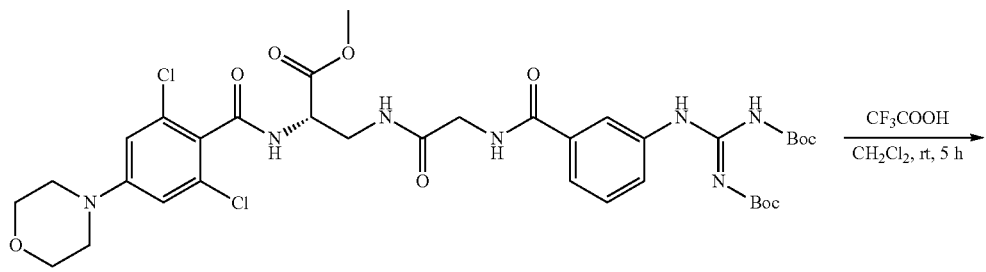

0003-7

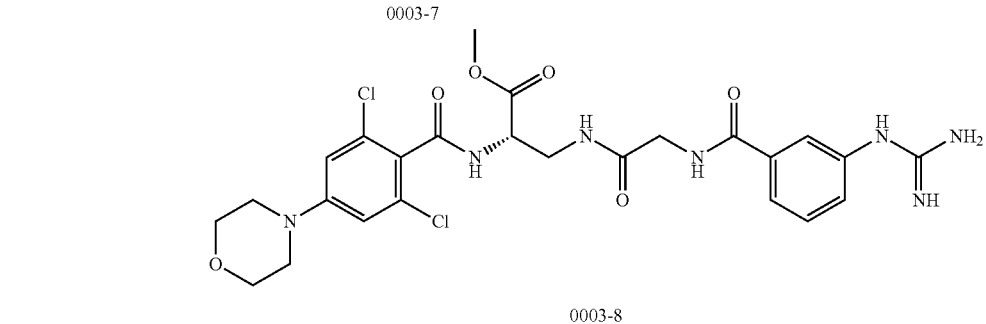

0003-8

To a solution of compound 0003-7 (150.0 mg, 0.2 mmol) in DCM (5 mL) was added CF$_3$COOH (1 mL). The mixture was stirred at rt for 5 h. After the consumption of starting material (by LCMS), the mixture concentrated in vacuo to give the crude 0003-8 (110 mg, 98.2% yield) as a white solid, which was used to the next step without further purification.

The Synthesis of (S)-2-(2,6-dichloro-4-morpholinobenzamido)-3-(2-(3-guanidinobenzamido)acetamido)propanoic acid (SU15210-0003)

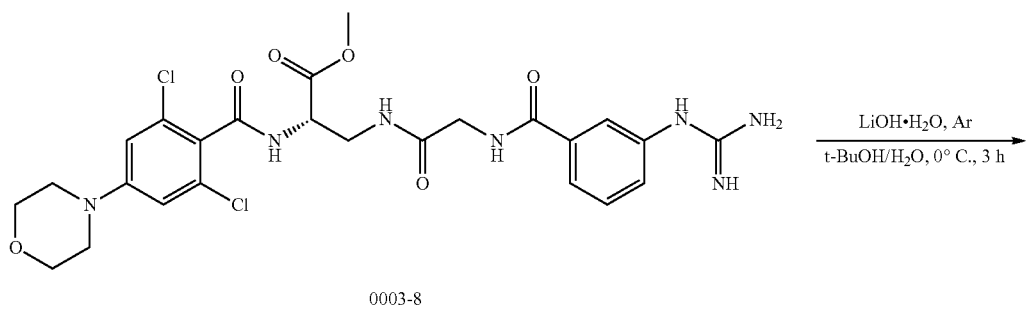

0003-8

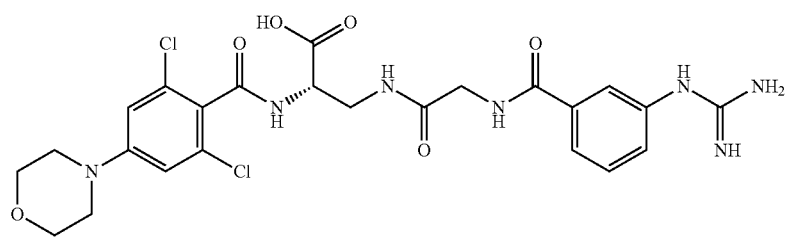

SU15210-0003

To a solution of compound 0003-8 (110.0 mg, 0.2 mmol) in t-BuOH (4 mL)/H₂O (2 mL), was added LiOH.H₂O (16.0 mg, 0.4 mmol). The mixture was stirred at 0° C. for 3 h. After the consumption of starting material (by LCMS), the reaction mixture was concentrated and adjust pH to ~7.0 by HCl (1.0 N), the mixture was freeze-drying to get the crude product, the crude was purified by prep-HPLC to give SU15210-0003 (9.5 mg, 8.8% yield) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% NH₄HCO₃] and 5% [CH₃CN+0.05% NH₄HCO₃] to 5% [water+0.05% NH₄HCO₃] and 95% [water+0.05% NH₄HCO₃] in 1.6 min, then under this condition for 1.4 min, finally changed to 95% [water+0.05% NH₄HCO₃] and 5% [CH₃CN+0.05% NH₄HCO₃] in 0.05 min and under this condition for 0.7 min), Purity: 93.22%, Rt=1.176 min; MS Calcd.: 579.0; MS Found: 580.2 [M+H]⁺.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% NH₄HCO₃] and 5% [CH₃CN+0.05% NH₄HCO₃] to 5% [water+0.05% NH₄HCO₃] and 95% [water+0.05% NH₄HCO₃] in 5.0 min, then under this condition for 1.0 min, finally changed to 95% [water+0.05% NH₄HCO₃] and 5% [CH₃CN+0.05% NH₄HCO₃] in 0.1 min and under this condition for 5 min), Purity: 95.78%, Rt=1.580 min.

¹H NMR (400 MHz, DMSO-d₆) δ 9.00 (t, J=5.2 Hz, 1H), 8.40-8.41 (m, 1H), 7.65-7.88 (m, 6H), 7.46 (t, J=7.6 Hz, 1H), 7.28 (d, J=8.0 Hz, 1H), 6.97 (s, 2H), 3.94-3.97 (m, 1H), 3.83 (d, J=5.2 Hz, 2H), 3.69-3.76 (m, 5H), 3.15-3.20 (m, 4H), 2.87-2.92 (m, 1H).

The Synthesis of (S)-methyl 1-(3,5-dimethylisoxazol-4-yl)-11,11-dimethyl-1,6,9-trioxo-10-oxa-2,5,8-triazadodecane-3-carboxylate (0004-2)

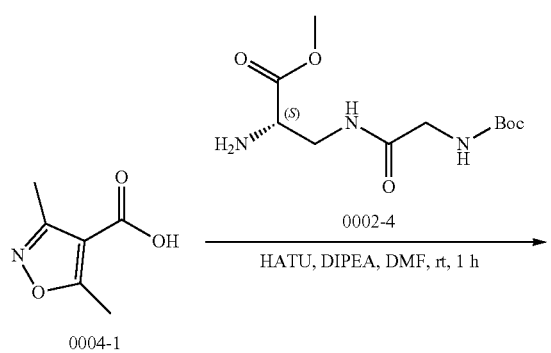

To a solution of compound 0004-1 (252.1 mg, 1.8 mmol) in DMF (15 mL) was added HATU (1.0 g, 2.7 mmol), DIPEA (462.0 mg, 3.6 mmol) and 0002-4 (491.8 mg, 1.8 mmol). The mixture was stirred at rt for 1 h. After the consumption of starting material (by LCMS), the reaction solvent was quenched with water (20 mL), and extracted with EtOAc (40 mL×3), the organic layer was washed with saturated aqueous NaCl (a.q.), collected the organic layer and dried over anhydrous Na₂SO₄, filtered and concentrated in vacuo, the crude was purified by CC (PE/EA=2:1) to give the product 0004-2 (484.0 mg, yield: 68.1%) as a white solid.

The Synthesis of (S)-methyl 3-(2-aminoacetamido)-2-(3,5-dimethylisoxazole-4-carboxamido)propanoate (0004-3)

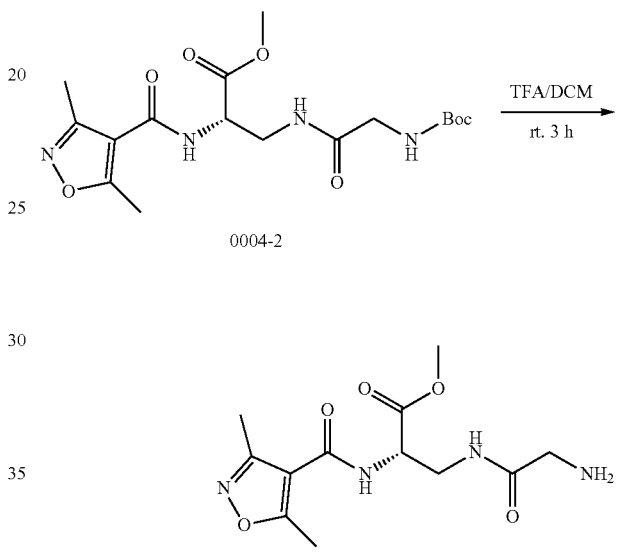

To a solution of compound 0004-2 (484.0 mg, 1.2 mmol) in DCM (5 mL) was added TFA (1 mL), the mixture was stirred at rt for 3 h. After the consumption of starting material (by LCMS), the mixture was concentrated in vacuo to give the crude 0004-3 (290.0 mg, yield: 82.3%) as a white solid, which was used to the next step without further purification.

The Synthesis of (S)-methyl 3-(2-(3-(tert-butoxycarbonylamino)-benzamido)acetamido)-2-(3,5-dimethylisoxazole-4-carboxamido)propanoate (0004-4)

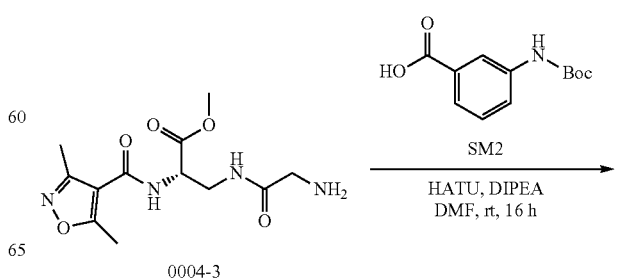

123
-continued

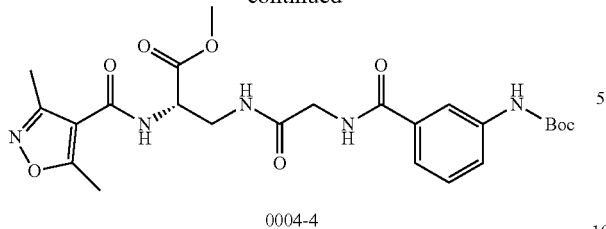

0004-4

To a solution of compound 0004-3 (290.0 mg, 1.2 mmol) in DMF (5 mL) was added HATU (696.0 mg, 1.8 mmol), DIPEA (631.0 mg, 4.8 mmol) and SM2 (364.0 mg, 1.2 mmol). The mixture was stirred at rt for 1 h. After the reaction was finished (by LCMS), the mixture was purified directly by prep-HPLC to get the desired product 0004-4 (560.0 mg, yield: 88.7%) as a white solid.

The Synthesis of (S)-methyl 3-(2-(3-aminobenzamido)acetamido)-2-(3,5-dimethylisoxazole-4-carboxamido)propanoate (0004-5)

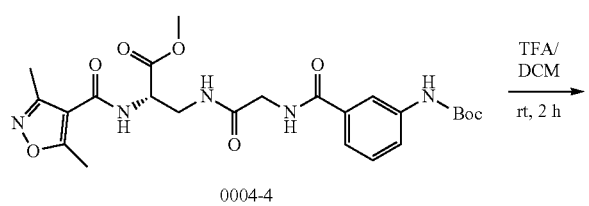

0004-4

124
-continued

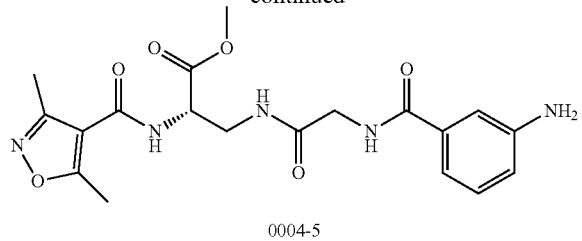

0004-5

To a solution of compound 0004-4 (560.0 mg, 1.1 mmol) in DCM (5 mL) was added TFA (1 mL), the mixture was stirred at rt for 2 h. After the consumption of starting material (by LCMS), the mixture was concentrated in vacuo to give the crude 0004-5 (451.0 mg, 99.8% yield) as a white solid, which was used to the next step without further purification.

The Synthesis of (S,Z)-methyl 3-(2-(3-(2,3-bis(tert-butoxycarbonyl)guanidino)-benzamido)acetamido)-2-(3,5-dimethylisoxazole-4-carboxamido)propanoate (0004-6)

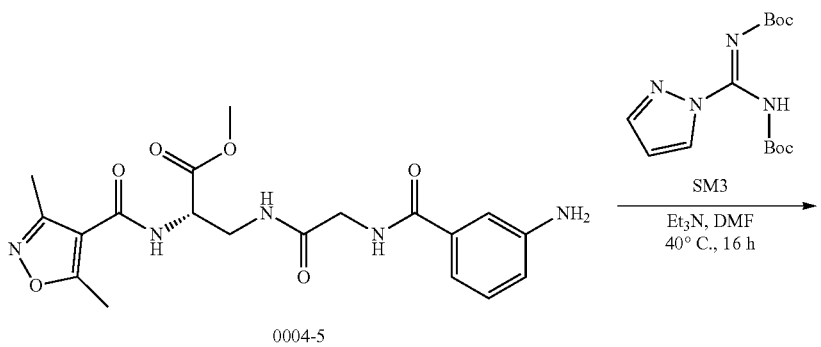

0004-5

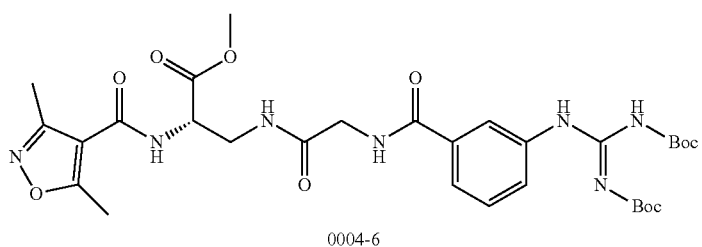

0004-6

To a solution of compound 0004-5 (451.0 mg, 1.1 mmol) in DMF (5 mL) was added TEA (328.0 mg, 3.3 mmol), SM3 (674.0 mg, 2.2 mmol), The mixture was stirred at 50° C. for 36 h. After the consumption of starting material (by LCMS), the mixture was purified directly by prep-HPLC to get the product 0004-6 (270.0 mg, 37.9% yield) as a white solid.

The Synthesis of (S)-methyl 2-(3,5-dimethylisoxazole-4-carboxamido)-3-(2-(3-guanidinobenzamido)acetamido)propanoate (0004-7)

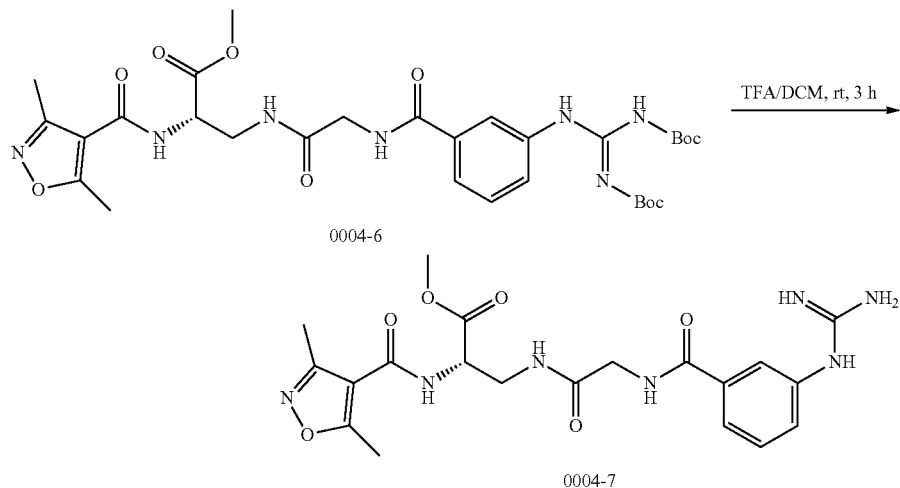

To a solution of compound 0004-6 (180.0 mg, 0.3 mmol) in DCM (5 mL) was added TFA (1 mL), the mixture was stirred at rt for 3 h. After the consumption of starting material (by LCMS), the mixture was concentrated in vacuo to give the crude 0004-7 (125.0 mg, 99.7% yield) as a white solid, which was used to the next step without further purification.

The Synthesis of (S)-2-(3,5-dimethylisoxazole-4-carboxamido)-3-(2-(3-guanidinobenzamido)acetamido)propanoic acid (SU15210-0004)

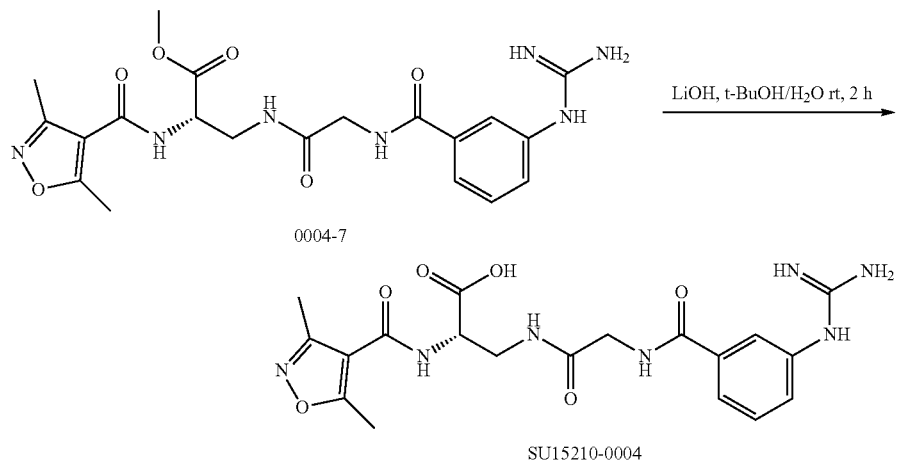

To a solution of compound 0004-7 (125.0 mg, 0.3 mmol) in t-BuOH (4 mL)/H$_2$O (2 mL), was added LiOH.H$_2$O (25.2 mg, 0.6 mmol). The mixture was stirred at 0° C. for 3 h. After the consumption of starting material (by LCMS), the reaction mixture was concentrated and adjust pH to 7.0 by HCl (1.0 N), the mixture was freeze-drying to get the crude product, the crude was purified by prep-HPLC to give SU15210-0004 (64.0 mg, 52.9% yield) as a white solid.

LC-MS (Agilent LCMS 1200-6110, Column: Waters X-Bridge C18 (50 mm*4.6 mm*3.5 µm); Column Temperature: 40° C.; Flow Rate: 2.0 mL/min; Mobile Phase: from 95% [water+0.05% NH$_4$HCO$_3$] and 5% [CH$_3$CN+0.05% NH$_4$HCO$_3$] to 5% [water+0.05% NH$_4$HCO$_3$] and 95% [water+0.05% NH$_4$HCO$_3$] in 1.6 min, then under this condition for 1.4 min, finally changed to 95% [water+0.05% NH$_4$HCO$_3$] and 5% [CH$_3$CN+0.05% NH$_4$HCO$_3$] in 0.05 min and under this condition for 0.7 min), Purity: 98.84%, Rt=0.410 min; MS Calcd.: 445.0; MS Found: 446.2 [M+H]$^+$.

HPLC (Agilent HPLC 1200; Column: L-column2 ODS (150 mm*4.6 mm*5.0 µm); Column Temperature: 40° C.; Flow Rate: 1.0 mL/min; Mobile Phase: from 95% [water+0.05% NH$_4$HCO$_3$] and 5% [CH$_3$CN+0.05% NH$_4$HCO$_3$] to 5% [water+0.05% NH$_4$HCO$_3$] and 95% [water+0.05% NH$_4$HCO$_3$] in 5.0 min, then under this condition for 1.0 min, finally changed to 95% [water+0.05% NH$_4$HCO$_3$] and 5% [CH$_3$CN+0.05% NH$_4$HCO$_3$] in 0.1 min and under this condition for 5 min), Purity: 98.79%, Rt=1.123 min.

$^1$H NMR (400 MHz, DMSO-d$_6$) δ 11.08 (brs, 1H), 8.90 (t, J=6.4 Hz, 1H), 8.14 (t, J=5.2 Hz, 1H), 7.87-8.10 (m, 3H), 7.65-7.70 (m, 2H), 7.57 (d, J=7.2 Hz, 1H), 7.45-7.49 (m, 1H), 7.30 (d, J=8.4 Hz, 1H), 4.10 (q, J=6.8 Hz, 1H), 3.77-3.87 (m, 2H), 3.35-3.52 (m, 2H), 2.53 (s, 3H), 2.30 (s, 3H).

SU15210-0005-01

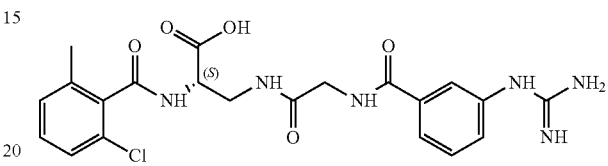

SU15210-0005-01

Chemical Formula: C$_{21}$H$_{23}$ClN$_6$O$_5$
Molecular Weight: 474.90

Scheme: Route for SUI15210-005-01

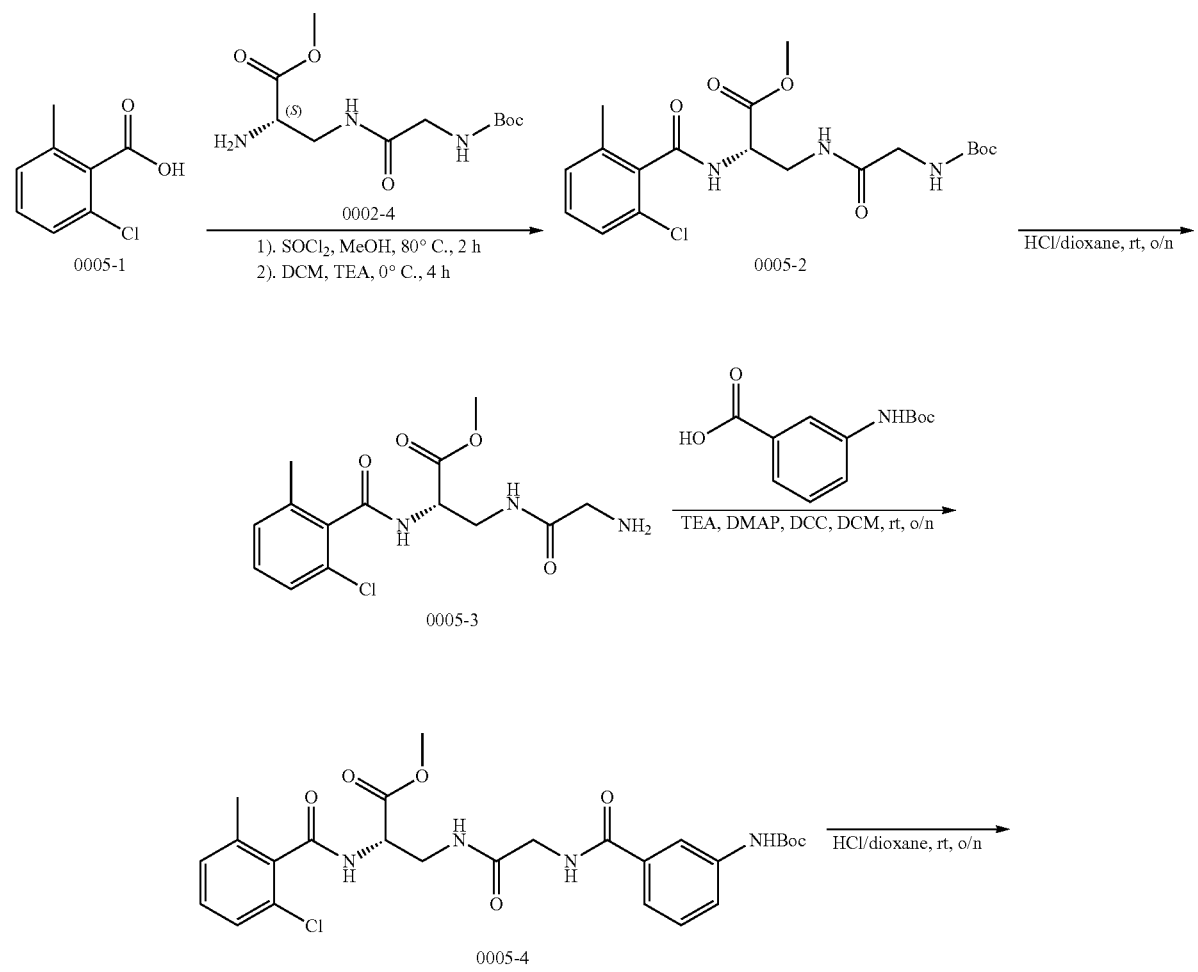

-continued

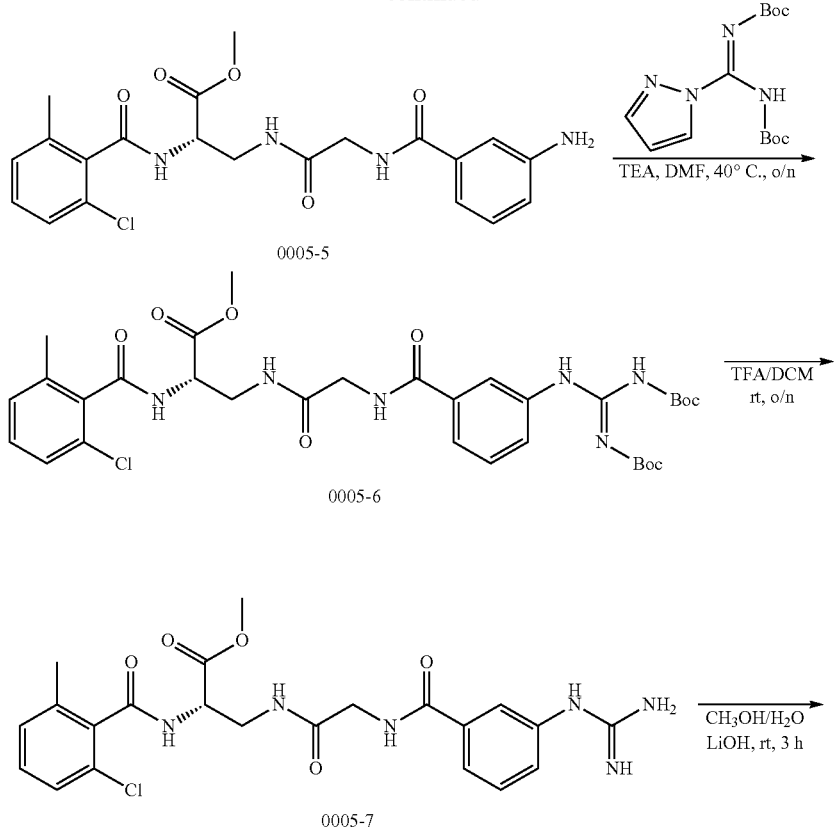

The Synthesis of (S)-methyl 3-(2-(tert-butoxycarbonylamino)acetamido)-2-(2-chloro-6-methylbenzamido)propanoate (0005-2)

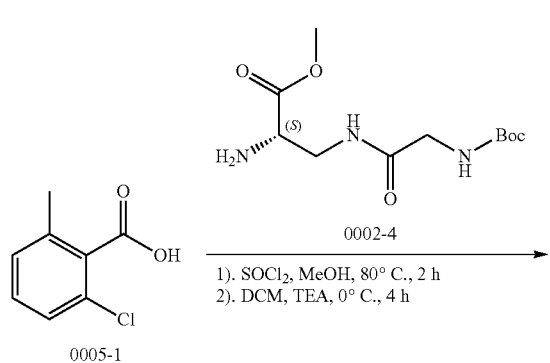

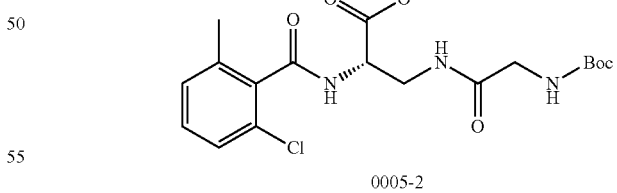

To a solution of 0005-1 (2.0 g, 11.7 mmol) in thionyl chloride (20 mL), the reaction mixture was stirred at 80° C. for 2 h, then concentrated in vacuo to remove the solvent, to thus was dissolved in DCM (20.0 ml), added 0002-4 (3.2 g, 11.7 mmol) and TEA (2.4 g, 2.4 mmol) at 0° C., the reaction was stirred for 4 h at 0° C., after the reaction was completed (by LCMS), the mixture was quenched with water, and then extracted with EA (20.0 mL×3). The organic layer was separated, dried over MgSO₄, and concentrated in vacuo.

The residue was purified by column chromatography (PE/EA=2:1) to give 0005-2 (2.8 g, 56.5% yield) as yellow oil.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 0% [water+0.05% TFA] and 100% [CH₃CN+0.05% TFA] in 1.6 min, then under this condition for 1.4 min, finally changed to 95% [water+0.05% TFA] and 5% [CH₃CN+0.05% TFA] in 0.05 min and under this condition for 0.7 min. Purity: 96.9%. Rt=1.620 min; MS Calcd.: 427.7; MS Found: 428.7 [M+H]⁺.

The Synthesis of (S)-methyl 3-(2-aminoacetamido)-2-(2-chloro-6-methylbenzamido)propanoate (0005-3)

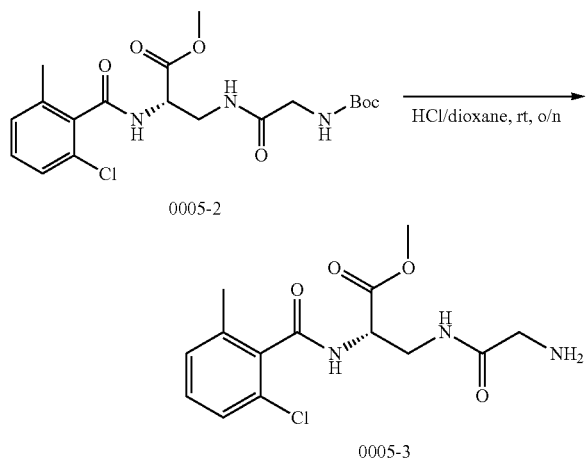

To a solution of 0005-2 (2.8 g, 6.6 mmol) in HCl/dioxane (20 mL), the mixture was stirred at room temperature overnight. After the reaction was completed, the solvent was removed in vacuo to give 0005-3 (2.0 g, 93.5% yield) as yellow oil.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 0% [water+0.05% TFA] and 100% [CH₃CN+0.05% TFA] in 1.6 min, then under this condition for 1.4 min, finally changed to 95% [water+0.05% TFA] and 5% [CH₃CN+0.05% TFA] in 0.05 min and under this condition for 0.7 min. Purity: 91.2%. Rt=1.235 min; MS Calcd.: 327.7; MS Found: 328.7 [M+H]⁺.

The Synthesis of (S)-methyl 3-(2-(3-(tert-butoxycarbonylamino)-benzamido)acetamido)-2-(2-chloro-6-methylbenzamido)propanoate (0005-4)

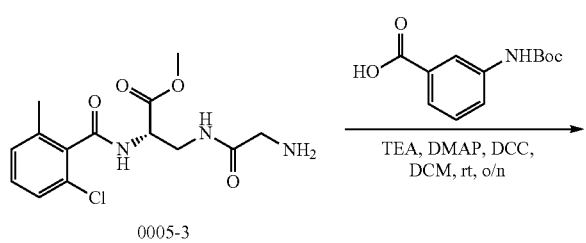

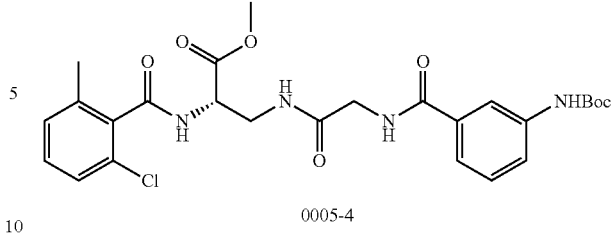

To a solution of 0005-3 (2.0 g, 6.1 mmol) in DCM (20 mL), was added TEA (919.0 mg, 9.1 mmol), DMAP (72.0 mg, 0.6 mmol), DCC (1.2 g, 6.1 mmol) and 3-(tert-butoxycarbonylamino)benzoic acid (1.5 g, 6.1 mmol). The mixture was stirred at room temperature overnight. After the reaction was completed, the mixture was quenched with water, and then extracted with EA (20 mL×3). The organic layer was separated, dried over MgSO₄, and concentrated in vacuo. The residue was purified by column chromatography (PE/EA=2:1) to give 0005-4 (1.1 g, 33.3% yield) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 0% [water+0.05% TFA] and 100% [CH₃CN+0.05% TFA] in 1.6 min, then under this condition for 1.4 min, finally changed to 95% [water+0.05% TFA] and 5% [CH₃CN+0.05% TFA] in 0.05 min and under this condition for 0.7 min. Purity: 97.8%. Rt=1.705 min; MS Calcd.: 546.7; MS Found: 547.7 [M+H]⁺.

The Synthesis of (S)-methyl 3-(2-(3-aminobenzamido)acetamido)-2-(2-chloro-6-methylbenzamido)propanoate (0005-5)

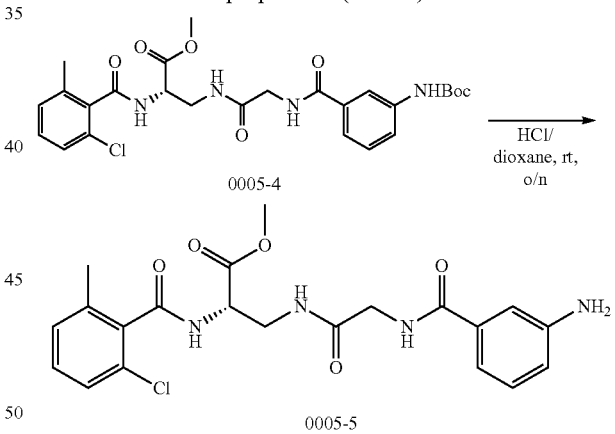

To a solution of 0005-5 (1.1 g, 2.0 mmol) in HCl/dioxane (20 mL), the mixture was stirred at room temperature overnight. After the reaction was completed, the solvent was removed in vacuo to give 0005-5 (850.0 mg, 94.7% yield) as yellow oil.

Agilent LCMS 1200-6110, Column: Waters X-Bridge C18 (50 mm*4.6 mm*3.5 μm); Column Temperature: 40° C.; Flow Rate: 1.5 mL/min; Mobile Phase: from 95% [water+0.05% TFA] and 5% [CH₃CN+0.05% TFA] to 0% [water+0.05% TFA] and 100% [CH₃CN+0.05% TFA] in 1.5 min, then under this condition for 0.5 min, finally changed to 95% [water+0.05% TFA] and 5% [CH₃CN+0.05% TFA] in 0.1 min and under this condition for 0.1 min. Purity: 90.0%. Rt=1.297 min; MS Calcd.: 446.0; MS Found: 447.0 [M+H]⁺.

The Synthesis of (S,Z)-methyl 3-(2-(3-(2,3-bis(tert-butoxycarbonyl)guanidino)-benzamido)acetamido)-2-(2-chloro-6-methylbenzamido)propanoate (0005-6)

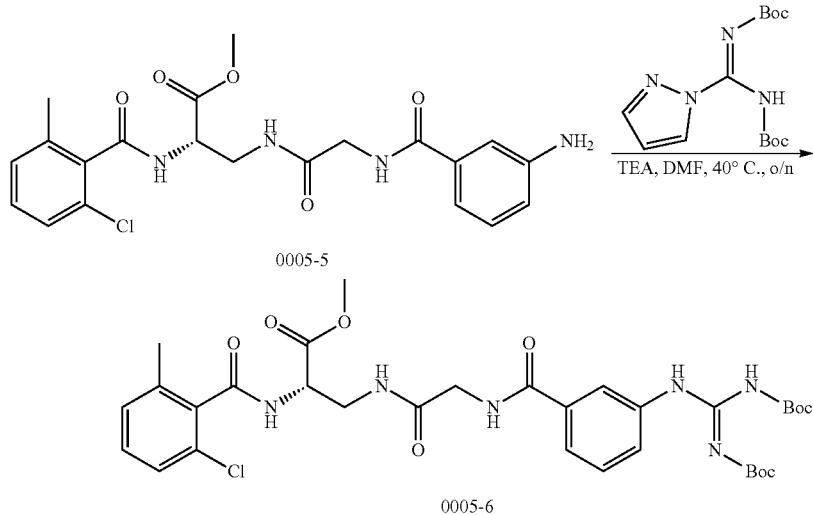

A mixture of tert-butyl (NE)-N-[(tert-butoxycarbonylamino)-pyrazol-1-yl-methylene]carbamate (837.0 mg, 2.7 mmol), 0005-5 (850.0 mg, 1.8 mmol) and TEA (273.7 mg, 2.7 mmol) in DMF (10 mL) was stirred at 40° C. overnight. After the reaction was completed, the reaction mixture was quenched with water and extracted with EA (20 mL×3). The organic layers were washed with brine, dried over MgSO$_4$ and concentrated in vacuo, the residue was purified by column chromatography (DCM/MeOH=20:1) to give 0005-6 (311.0 mg, 24.8% yield) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min. Purity: 95.6%. Rt=2.287 min; MS Calcd.: 688.7; MS Found: 689.7 [M+H]$^+$.

The Synthesis of (S)-methyl 2-(2-chloro-6-methylbenzamido)-3-(2-(3-guanidinobenzamido)acetamido)propanoate (0005-7)

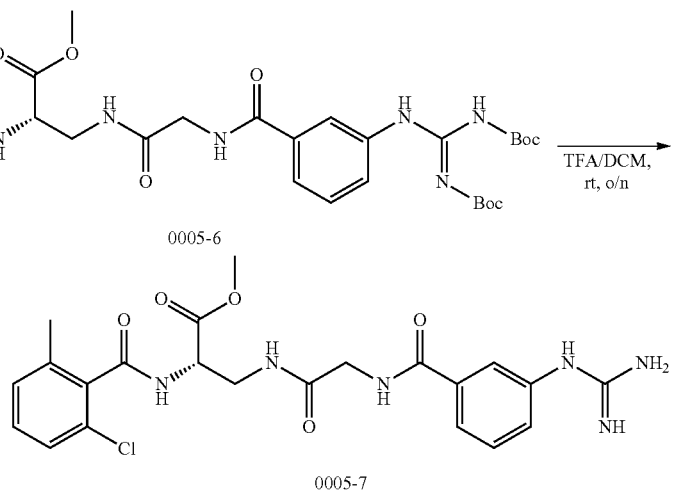

To a solution of 0005-6 (311.0 mg, 0.5 mmol) in TFA/DCM (2 mL/10 mL), the mixture was stirred at rt overnight. After the reaction was completed, the solvent was removed in vacuo to give 0005-7 (180.0 mg, 81.8% yield) as yellow oil.

The Synthesis of (S)-2-(2-chloro-6-methylbenzamido)-3-(2-(3-guanidinobenzamido)acetamido)propanoic acid (SU15210-0005-01)

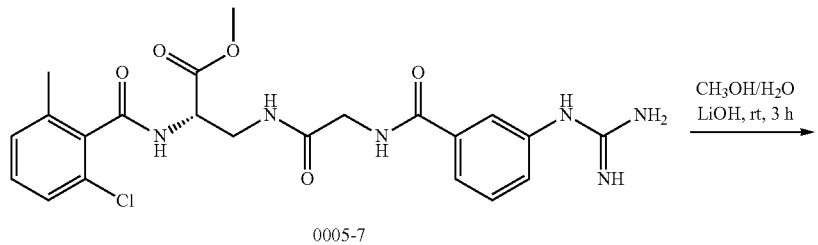

0005-7

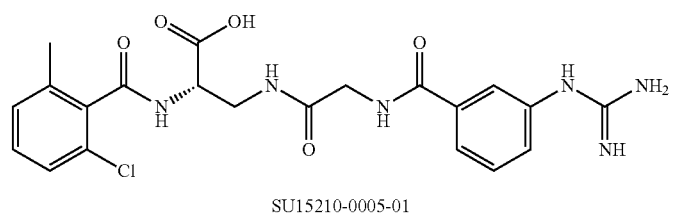 [SMILES: Cc1cccc(Cl)c1C(=O)N[C@@H](CNC(=O)CNC(=O)c1cccc(NC(=N)N)c1)C(=O)O]

SU15210-0005-01

To a solution of 0005-7 (180.0 mg, 0.37 mmol) in MeOH/H$_2$O (10 mL/2 mL), was added LiOH (155.5 mg, 3.7 mmol). The reaction mixture was stirred at rt for 3 h, after the reaction was completed, the reaction mixture was concentrated and adjust pH to ~7.0 by HCl (1.0 N), then the reside was purified by pre-HPLC to give SU15210-0005-01 (130.0 mg, 73.0% yield) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH3CN+0.05% TFA] in 1.6 min, then under this condition for 1.4 min, finally changed to 95% [water+0.05% TFA] and 5% [CH3CN+0.05% TFA] in 0.05 min and under this condition for 0.7 min. Purity is 96.7%. Rt=1.205 min; MS Calcd.: 474.0; MS Found: 475.0 [M+H]$^+$.

Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min. Purity is 99.9%. Rt=4.827 min.

$^1$HNMR (400 MHz, DMSO-d$_6$) δ 10.98 (br s., 1H), 8.98 (t, J=6.0 Hz, 1H), 8.36 (d, J=2.8 Hz, 1H), 7.87-7.92 (m, 4H), 7.76 (s, 1H), 7.66 (d, J=7.6 Hz, 1H), 7.47 (t, J=7.6 Hz, 1H), 7.25-7.31 (m, 3H), 7.17-7.20 (m, 1H), 4.09-4.14 (m, 1H), 3.83-3.84 (m, 2H), 3.58-3.64 (m, 1H), 3.07-3.11 (m, 1H), 2.28 (s, 3H).

SU15210-0006-01

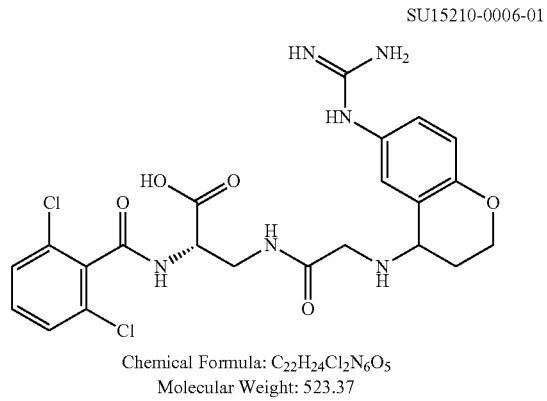 [SMILES: N=C(N)Nc1ccc2c(c1)C(NCC(=O)NC[C@H](NC(=O)c1c(Cl)cccc1Cl)C(=O)O)CCO2]

SU15210-0006-01

Chemical Formula: C$_{22}$H$_{24}$Cl$_2$N$_6$O$_5$
Molecular Weight: 523.37

Scheme: Route for SU15210-0006-01

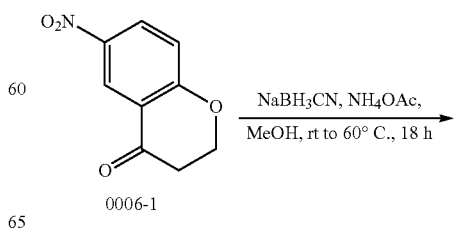

0006-1

NaBH$_3$CN, NH$_4$OAc, MeOH, rt to 60° C., 18 h

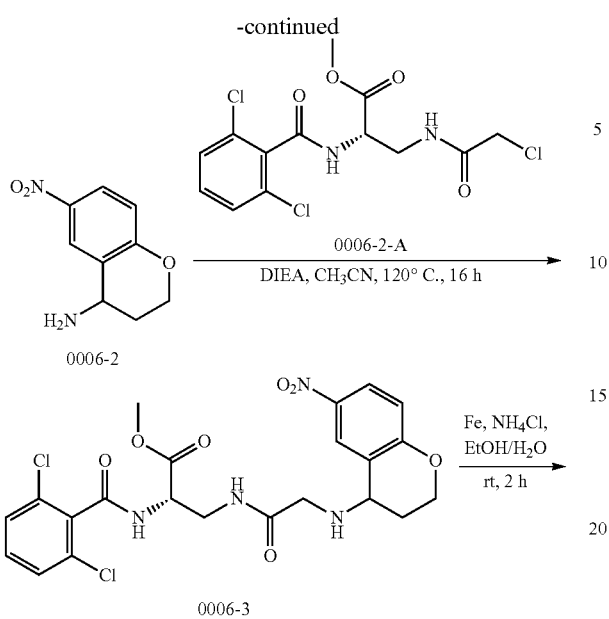

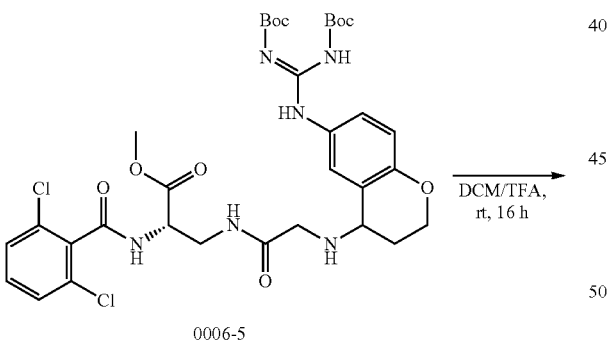

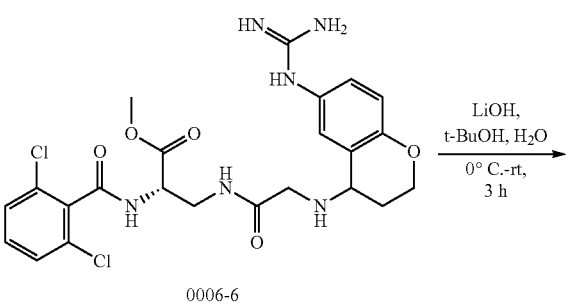

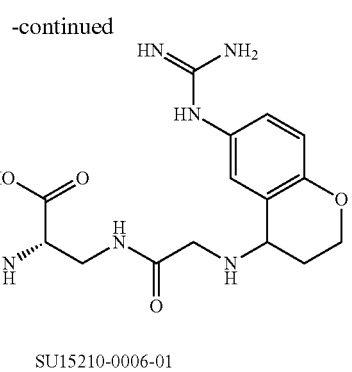

The Synthesis of 6-nitrochroman-4-amine (0006-2)

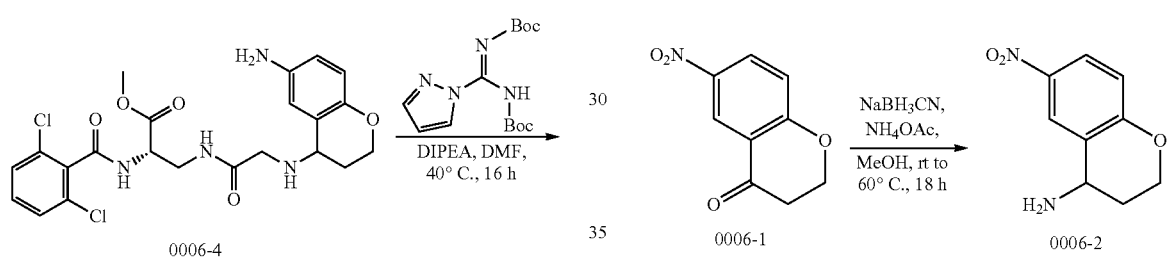

To a solution of 0006-1 (2.0 g, 10.35 mmol) in MeOH (20 mL) was added NaBH$_3$CN (3.2 g, 51.77 mmol), NH$_4$OAc (3.7 g, 51.77 mmol) and HOAc (61.8 mg, 1.03 mmol) at room temperature. The reaction mixture was then heated to 60° C. and stirred for 18 h. After the reaction was finished, the solvent was removed in vacuum, the residual was dissolved in water (20 mL) and EA (20 mL), then Na$_2$CO$_3$ was added to adjust the pH=~10.0, the organic layer was then separated and the water phase was extracted with EA (20 mL×3), the organic phase was combined and washed with water then brine, dried over Na$_2$SO$_4$, concentrated and purified by prep-HPLC to give 0006-2 (1.1 g, 55% yield) as a yellow solid.

Agilent LCMS 1200-6120, Column: Halo C18 (50 mm*4.6 mm*2.7 μm); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity: 92.12%. Rt=0.381 min; MS Calcd.: 194.2; MS Found: 195.2 [M+H]$^+$.

The Synthesis of (2S)-methyl 2-(2,6-dichlorobenzamido)-3-(2-(6-nitrochroman-4-ylamino) acetamido) propanoate (0006-3)

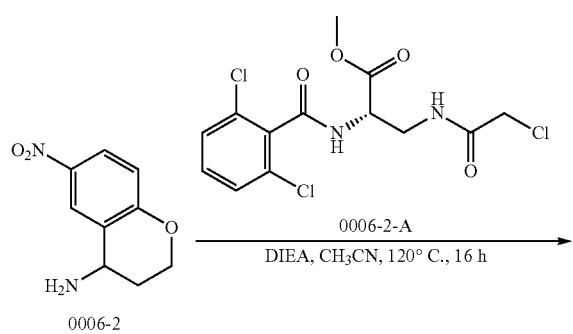

0006-2

0006-2-A

DIEA, CH₃CN, 120° C., 16 h

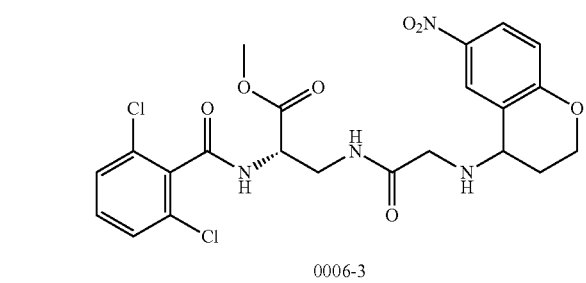

0006-3

To a solution of 0006-2-A (1.0 g, 2.72 mmol) and 0006-2 (528.24 mg, 2.72 mmol) in ACN (10 mL), DIPEA (351.57 mg, 2.72 mmol, 473.81 uL) was added, the solution was stirred at 120° C. for overnight in a sealed tube, concentrated to remove the solvent and purified by prep-HPLC to give 0006-3 (800 mg, 55.98% yield) as a light yellow solid.

Agilent LCMS 1200-6120, Column: Waters X-Bridge C18 (50 mm*4.6 mm*3.5 μm); Column Temperature: 30° C.; Flow Rate: 2.0 mL/min; Mobile Phase: from 95% [water+0.2% NH₃ 7M in MeOH] and 5% [CH₃CN] to 0% [water+0.2% NH₃ 7 M in MeOH] and 100% [CH₃CN] in 1.6 min, then under this condition for 1.4 min, finally changed to 95% [water+0.2% NH₃ 7 M in MEOH] and 5% [CH₃CN] in 0.1 min and under this condition for 0.7 min. Purity: 88.57%. Rt=1.955 min; MS Calcd.: 525.6; MS Found: 526.6 [M+H]⁺.

The Synthesis of (2S)-methyl 3-(2-(6-aminochroman-4-ylamino)acetamido)-2-(2,6-dichlorobenzamido) propanoate (0006-4)

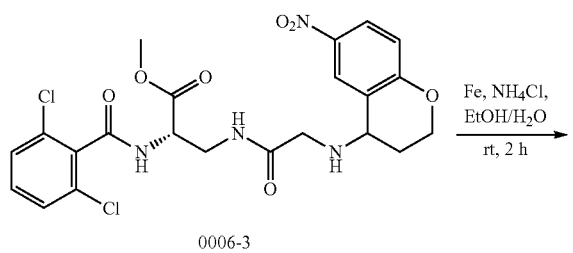

0006-3

Fe, NH₄Cl, EtOH/H₂O
rt, 2 h

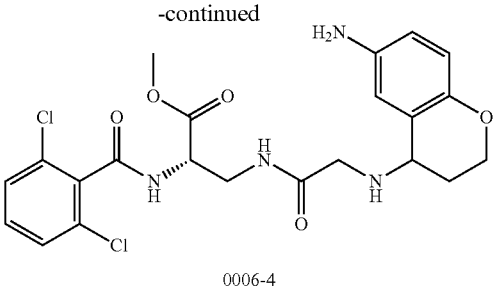

0006-4

To a solution of 0006-3 (800 mg, 1.52 mmol) in EtOH (10 mL) was added NH₄Cl (sat. aq. 5 mL) and iron powder (851 mg, 15.2 mmol), the mixture was stirred at room temperature for 2 h. Basified with Na₂CO₃ to pH~10, filtrated, the residue was washed with MeOH (20 mL×3), the filtrate was combined and concentrated then purified by prep-HPLC to give 0006-4 (500 mg, 66% yield) as a white solid.

Agilent LCMS 1200-6120, Column: Halo C18 (50 mm*4.6 mm*2.7 μm); Column Temperature: 40° C.; Flow Rate: 3.0 mL/min; Mobile Phase: from 95% [water+10 mM TFA] and 5% [CH₃CN] to 0% [water+10 mM TFA] and 100% [CH₃CN] in 0.8 min, then under this condition for 0.4 min, finally changed to 95% [water+10 mM TFA] and 5% [CH₃CN] in 0.01 min. Purity: 100%. Rt=0.448 min; MS Calcd.: 494.6; MS Found: 495.6 [M+H]⁺.

The Synthesis of (2S)-methyl 3-(2-(6-((Z)-2,3-bis (tert-butoxycarbonyl)guanidino)-chroman-4-ylamino) acetamido)-2-(2,6-dichlorobenzamido) propanoate (0006-5)

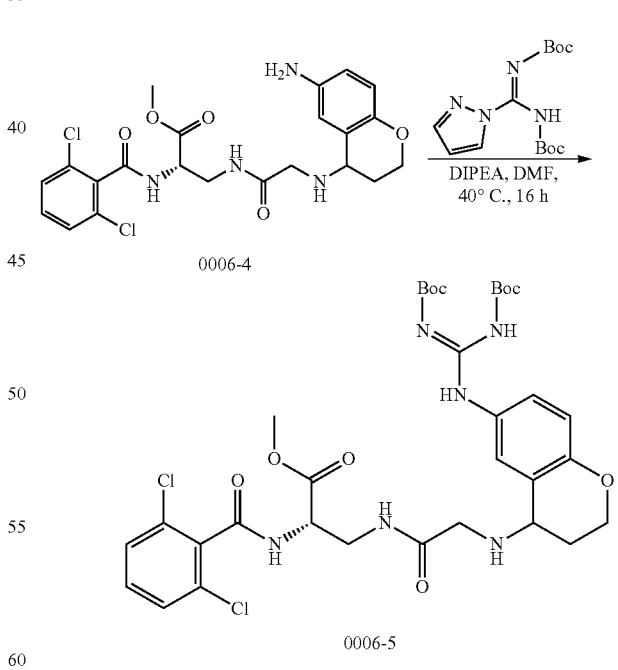

0006-4

DIPEA, DMF, 40° C., 16 h 0006-5

To a solution of 0006-4 (500 mg, 1.01 mmol) in DMF (5 mL) was added DIPEA (260 mg, 2.02 mmol) and tert-butyl (1H-pyrazol-1-yl)methylenedicarbamate (626 mg, 2.02 mmol), the solution was heated to 40° C. and stirred for overnight. The residue was purified by prep-HPLC to give 0006-5 (230 mg, 30% yield) as a white solid.

Agilent LCMS 1200-6120, Column: Halo C18 (50 mm*4.6 mm*2.7 μm); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity: 83.41%. Rt=0.735 min; MS Calcd.: 737.3; MS Found: 738.3 [M+H]$^+$.

The Synthesis of (2S)-methyl 2-(2,6-dichlorobenzamido)-3-(2-(6 guanidinochroman-4-ylamino) acetamido)propanoate (0006-6)

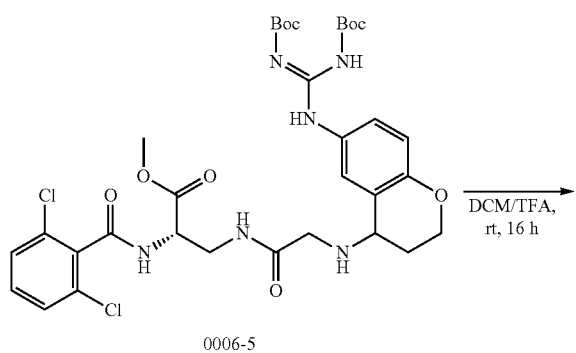

0006-5

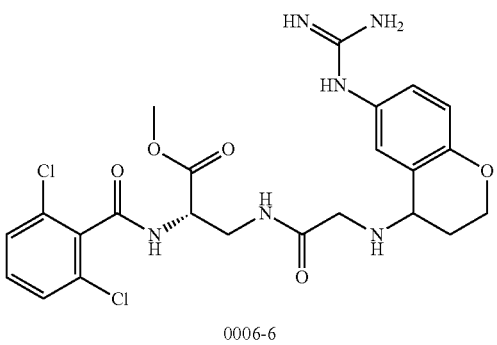

0006-6

A solution of 0006-5 (230 mg, 0.31 mmol) in DCM (5 mL) was added TFA (357 mg, 3.1 mmol), the solution was stirred at room temperature for overnight, then concentrated to give the crude 0006-6 (202 mg, 100% yield) as a brown solid, which was used for the next step directly.

Agilent LCMS 1200-6120, Column: Halo C18 (50 mm*4.6 mm*2.7 μm); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity: 93.00%. Rt=0.481 min; MS Calcd.: 536.1; MS Found: 537.3 [M+H]$^+$.

The Synthesis of (2S)-2-(2,6-dichlorobenzamido)-3-(2-(6 guanidinochroman-4-ylamino)acetamido) propanoic acid (SU15210-0006)

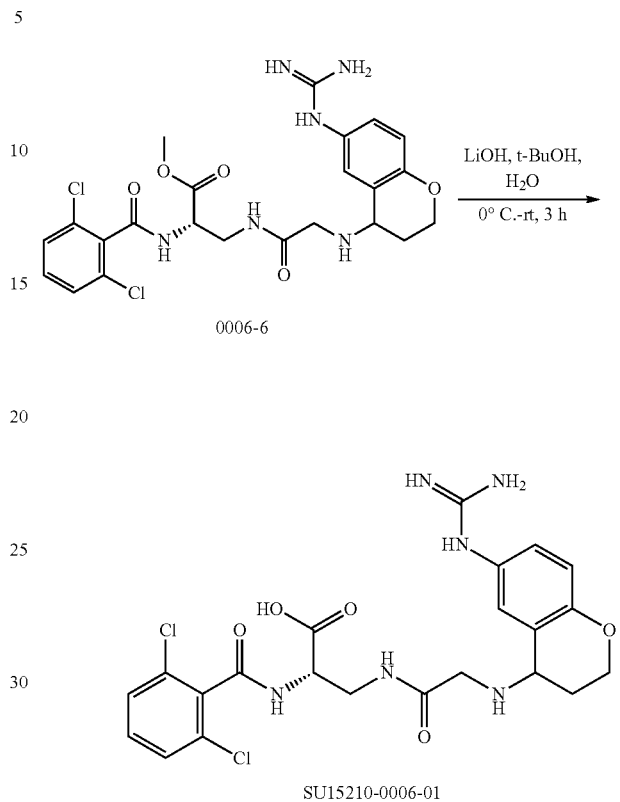

SU15210-0006-01

To a solution of 0006-6 (202 mg, 0.31 mmol) in t-BuOH/H$_2$O (3 mL/1 mL), was added LiOH (118 mg, 2.8 mmol), the reaction mixture was stirred at rt for 3 h, after the reaction was completed, the reaction mixture was concentrated and adjust pH to 2.0 by HCl (1.0 N), then the reside was purified by prep-HPLC to give SU15210-0006-01 (115.0 mg, 78.8% yield) as a white solid.

Agilent LCMS 1200-6120, Column: Waters X-Bridge-C18 (50 mm*4.6 mm*3.5 μm); Column Temperature: 40° C.; Flow Rate: 2.0 mL/min; Mobile Phase: from 95% [water+10 mM TFA] and 5% [CH$_3$CN] to 0% [water+10 mM TFA] and 100% [CH$_3$CN] in 1.6 min, then under this condition for 1.4 min, finally changed to 95% [water+10 mM TFA] and 5% [CH$_3$CN] in 0.1 min. Purity: 100%. Rt=1.402 min; MS Calcd.: 523.7; MS Found: 524.7 [M+H]$^+$.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH$_4$HCO$_3$] and 5% [CH$_3$CN] to 0% [water+0.1% NH$_4$HCO$_3$] and 100% [CH$_3$CN] in 10 min, then under this condition for 5 min, finally changed to 95% [water+0.1% NH$_4$HCO$_3$] and 5% [CH$_3$CN] in 0.1 min and under this condition for 5 min. Purity: 100%. Rt=5.560 min.

$^1$HNMR (400 MHz, DMSO-d$_6$) δ 10.73-10.80 (m, 1H), 8.46-8.51 (m, 1H), 8.04-8.18 (m, 1H), 7.56 (s, 4H), 7.38-7.47 (m, 3H), 7.31 (s, 1H), 6.97-7.01 (m, 1H), 6.73-6.76 (m, 1H), 4.24-4.34 (m, 2H), 4.08-4.12 (m, 1H), 3.71 (t, J=4.8 Hz, 1H), 3.48-3.59 (m, 2H), 3.15 (q, J=16.8 Hz, 3H), 1.89-1.93 (m, 1H), 1.78-1.81 (m, 1H).

SU15210-0007-01
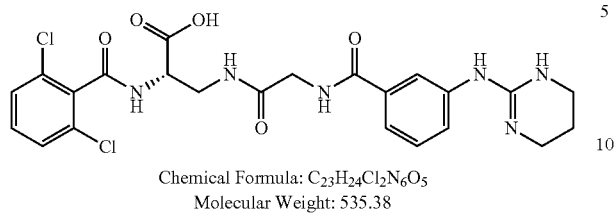
Chemical Formula: C₂₃H₂₄Cl₂N₆O₅
Molecular Weight: 535.38
The Synthesis of 2-(methylthio)-1,4,5,6-tetrahydropyrimidine (0007-2)
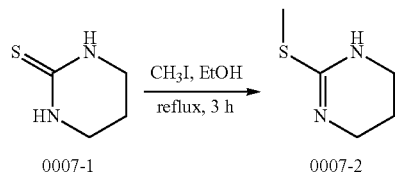
Scheme: Route for SU15210-0007-01
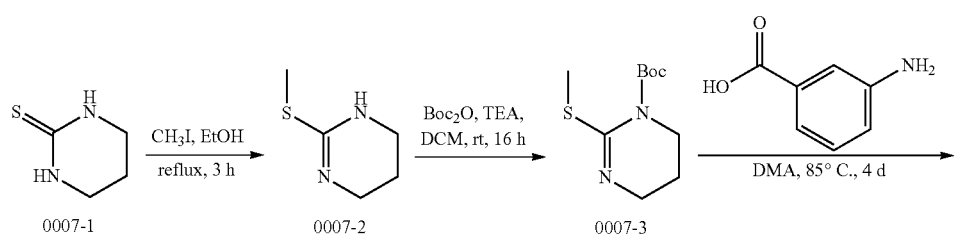
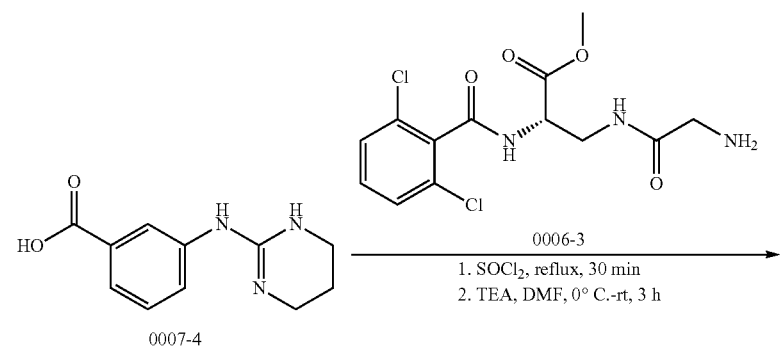
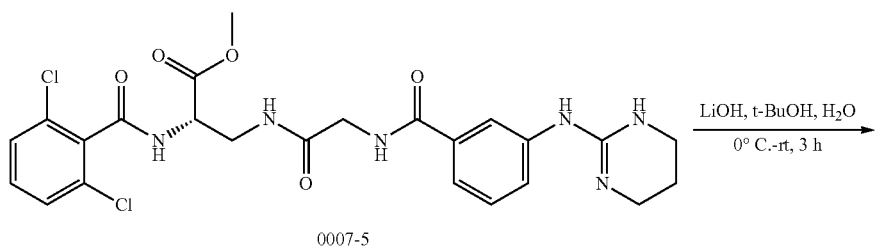
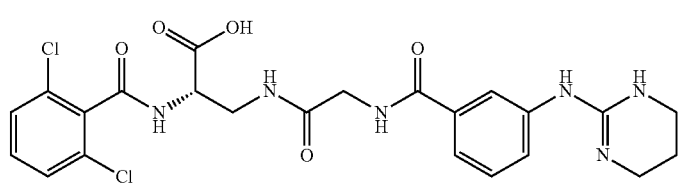

To a solution of 0007-1 (5.0 g, 43.1 mmol) in EtOH (50 mL) was added CH₃I (8.9 g, 51.7 mmol). The solution was heated to reflux and stirred for 3 h. After the reaction was finished, the solvent was removed in vacuum to get 2-(methylthio)-1,4,5,6-tetrahydropyrimidine (0007-2) (5.6 g, 100% yield) as a yellow solid which was used for the next step directly.

The Synthesis of tert-butyl 2-(methylthio)-5,6-dihydropyrimidine-1(4H)-carboxylate (0007-3)

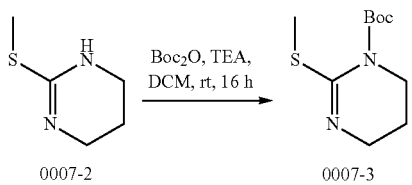

To a solution of 0007-2 (5.0 g, 38.5 mmol) in DCM (50 mL), was added TEA (7.77 g, 77.0 mmol) and Boc₂O (10.08 g, 46.2 mmol) at 0° C., the reaction was then allowed to warm to room temperature and stirred for overnight. Water (50 mL) was added and the organic layer was separated and washed with brine, dried over Na₂SO₄, concentrated and purified by silica gel column to give 0007-3 (8.0 g, 90.1% yield) as colorless oil.

Agilent LCMS 1200-6120, Column: Halo C18 (30 mm*4.6 mm*2.7 µm); Column Temperature: 40° C.; Flow Rate: 3.0 mL/min; Mobile Phase: from 95% [water+10 mM TFA] and 5% [CH₃CN] to 0% [water+10 mM TFA] and 100% [CH₃CN] in 0.8 min, then under this condition for 0.4 min, finally changed to 95% [water+10 mM TFA] and 5% [CH₃CN] in 0.01 min. Purity: 96.34%. Rt=0.475 min; MS Calcd.: 230.1; MS Found: 231.2 [M+H]⁺.

The Synthesis of 3-(1,4,5,6-tetrahydropyrimidin-2-ylamino)benzoic acid (0007-4)

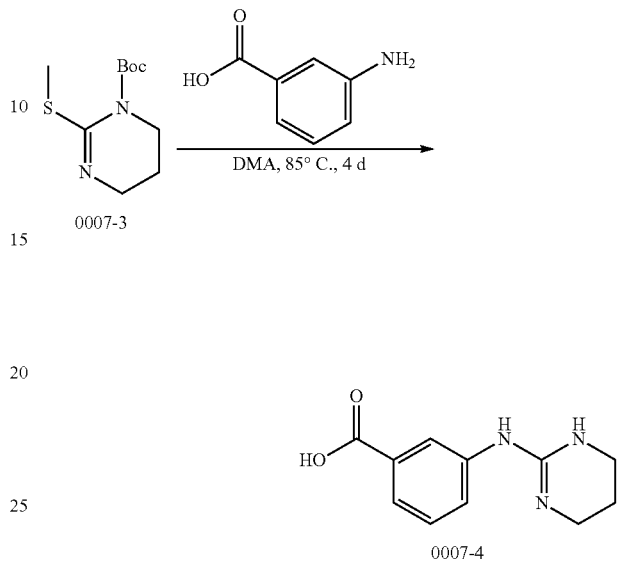

To a solution of 0007-3 (3.0 g, 13.0 mmol) in DMA (20 mL) was added 3-aminobenzoic acid (3.6 g, 26.1 mmol), the solution was stirred at 85° C. for 4 days. The precipitate was filtrated and washed with ethyl acetate then dry in vacuum to give 0007-4 (1.1 g, 38% yield) as a white solid.

Agilent LCMS 1200-6120, Column: Halo C18 (50 mm*4.6 mm*2.7 µm); Column Temperature: 40° C.; Flow Rate: 3.0 mL/min; Mobile Phase: from 95% [water+10 mM TFA] and 5% [CH₃CN] to 0% [water+10 mM TFA] and 100% [CH₃CN] in 0.8 min, then under this condition for 0.4 min, finally changed to 95% [water+10 mM TFA] and 5% [CH₃CN] in 0.01 min. Purity: 100%. Rt=0.357 min; MS Calcd.: 219.2; MS Found: 220.2 [M+H]⁺.

The Synthesis of (S)-methyl 2-(2,6-dichlorobenzamido)-3-(2-(3-(1,4,5,6-tetrahydropyrimidin-2-ylamino)benzamido)acetamido)propanoate (0007-5)

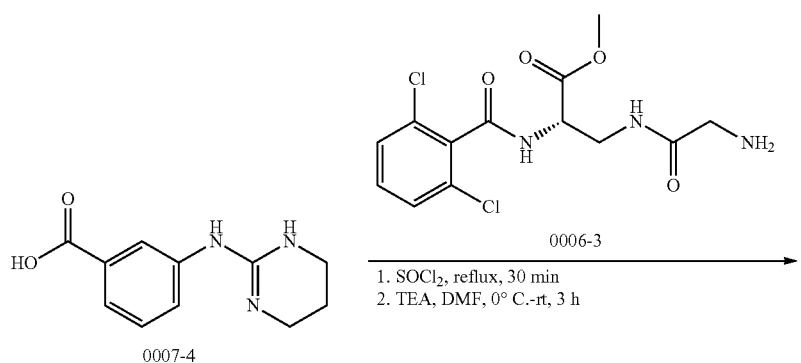

-continued

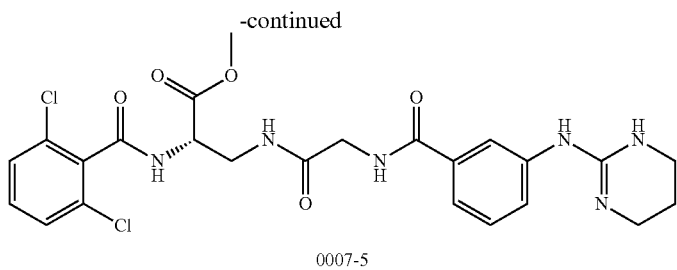

0007-5

A solution of 0007-4 (200 mg, 0.91 mmol) in SOCl₂ (2.0 mL) was heated at reflux for 30 min, then concentrated to remove the excessive SOCl₂ then dissolved in dry DCM (2.0 mL), the solution was added to a mixture of 0006-3 (317 mg, 0.91 mmol) and TEA (184 mg, 1.82 mmol) in dry DMF (3.0 mL) at 0° C., the solution was then allowed to warm to room temperature and stirred for 3 h. Concentrated and purified by prep-HPLC to give 0007-5 (150 mg, 30% yield) as a white solid.

The Synthesis of (S)-2-(2,6-dichlorobenzamido)-3-(2-(3-(1,4,5,6-tetrahydropyrimidin-2-ylamino) benzamido)acetamido)propanoic acid (SU15210-0007)

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH₄HCO₃] and 5% [CH₃CN] to 0% [water+0.1% NH₄HCO₃] and 100% [CH₃CN] in 10 min, then under this condition for 5 min, finally changed to 95% [water+0.1% NH₄HCO₃] and 5% [CH₃CN] in 0.1 min and under this condition for 5 min. Purity: 99.01%. Rt=6.560 min.

¹H NMR (400 MHz, DMSO-d₆) δ 12.08 (s, 1H), 9.34 (s, 2H), 8.92-8.93 (m, 1H), 8.40-8.48 (m, 2H), 7.88 (s, 1H), 7.39-7.54 (m, 5H), 7.28 (d, J=7.6 Hz, 1H), 4.28 (q, J=7.6 Hz, 1H), 4.01-4.08 (m, 1H), 3.68-3.86 (m, 2H), 3.14-3.21 (m, 2H), 2.95-3.12 (m, 3H), 1.70 (s, 2H).

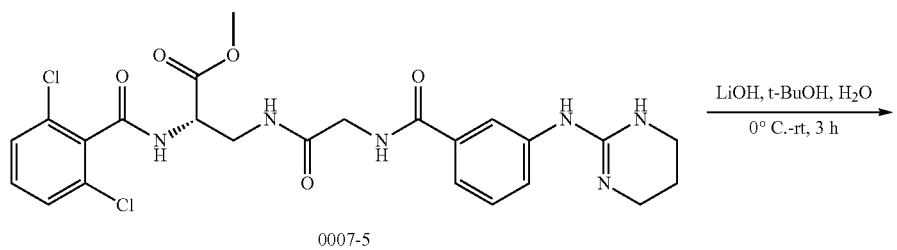

0007-5

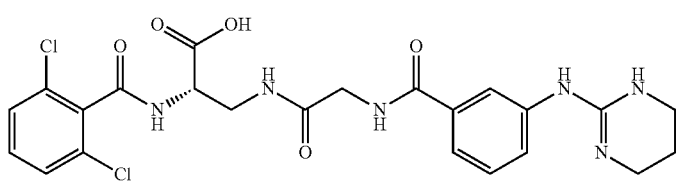

SU15210-0007-01

To a solution of compound 0007-5 (202 mg, 0.31 mmol) in t-BuOH (3 mL) and water (1 mL) was added LiOH.H₂O (15 mg, 0.62 mmol), the mixture was stirred in Ar atmosphere at 0° C. for 3 h. After the consumption of starting material (by LCMS), the mixture was concentrated and the solution was adjusted to pH=2 by addition of aqueous HCl (1 N) and the mixture was purified by prep-HPLC to give product SU15210-0007-01 (80 mg, 55% yield) as a white solid.

Agilent LCMS 1200-6120, Column: Waters X-Bridge-C18 (50 mm*4.6 mm*3.5 μm); Column Temperature: 40° C.; Flow Rate: 2.0 mL/min; Mobile Phase: from 95% [water+10 mM TFA] and 5% [CH₃CN] to 0% [water+10 mM TFA] and 100% [CH₃CN] in 1.6 min, then under this condition for 1.4 min, finally changed to 95% [water+10 mM TFA] and 5% [CH₃CN] in 0.1 min. Purity: 99.31%. Rt=1.298 min; MS Calcd.: 534.1; MS Found: 535.1 [M+H]⁺.

SU15210-0010

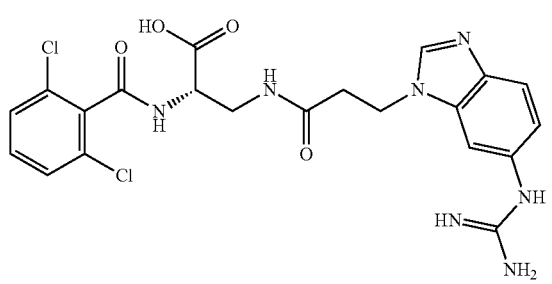

Chemical Formula: C₂₁H₂₁Cl₂N₇O₄
Molecular Weight: 506.34

Scheme: Route for SU15210-0010
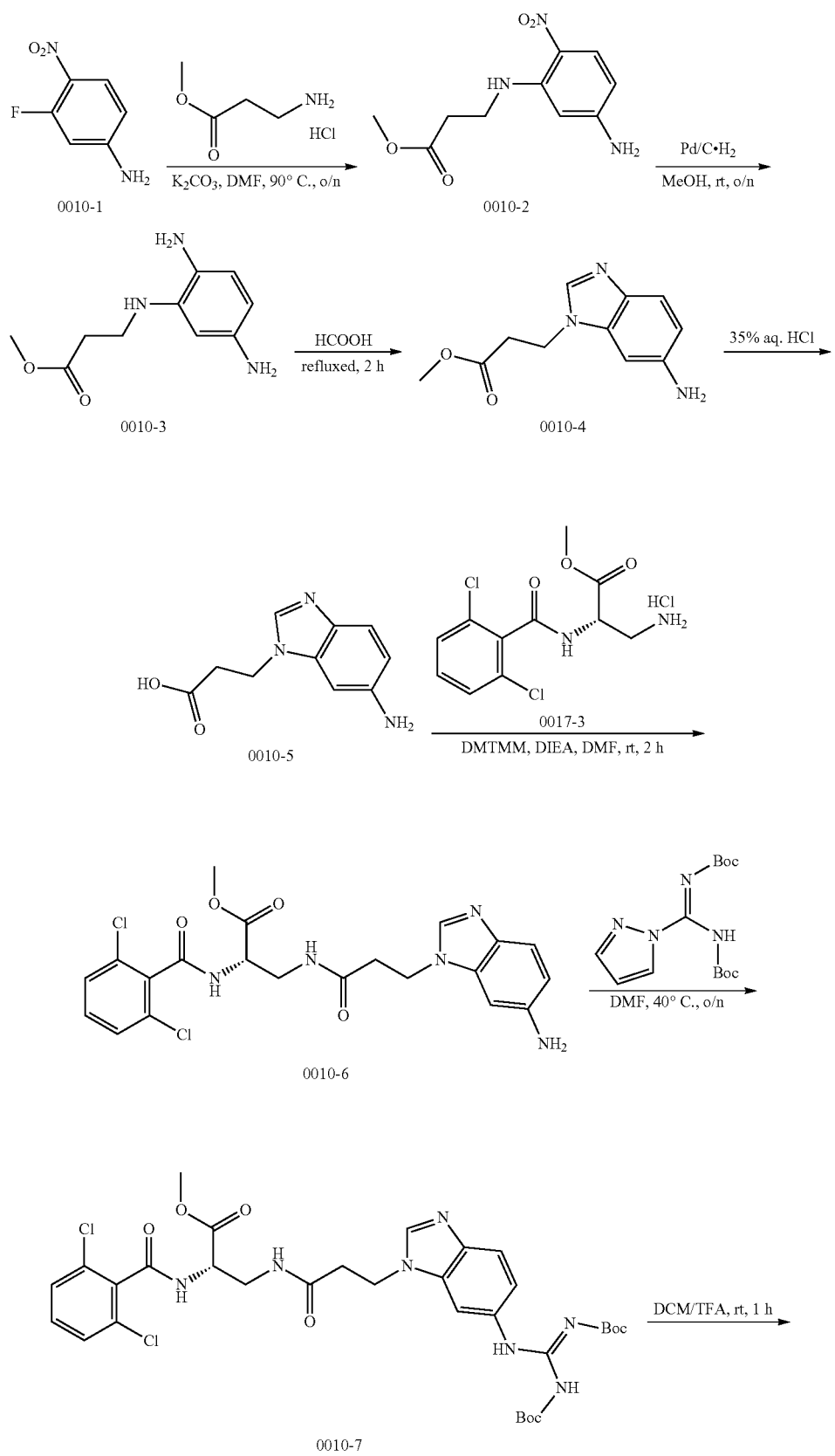

-continued

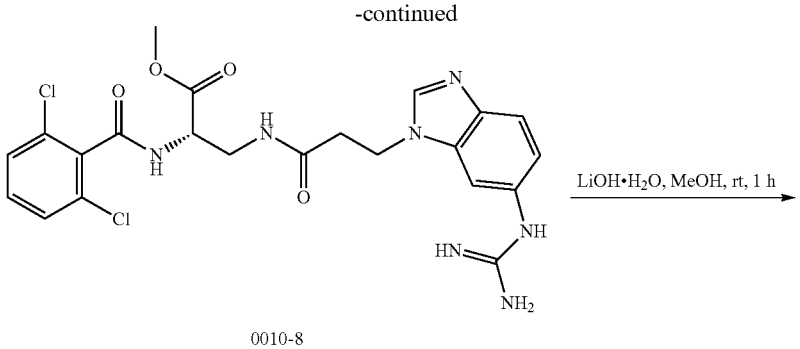

0010-8

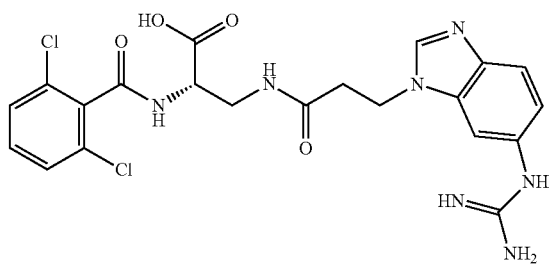

SU15210-0010-01

The Synthesis of methyl 3-(5-amino-2-nitrophenylamino)propanoate (0010-2)

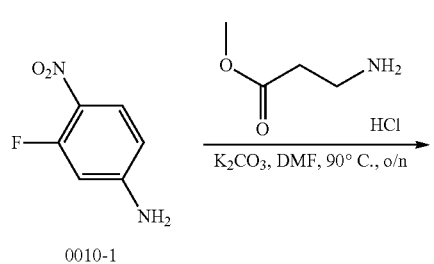

0010-1

0010-2

The Synthesis of methyl 3-(2,5-diaminophenylamino)propanoate (0010-3)

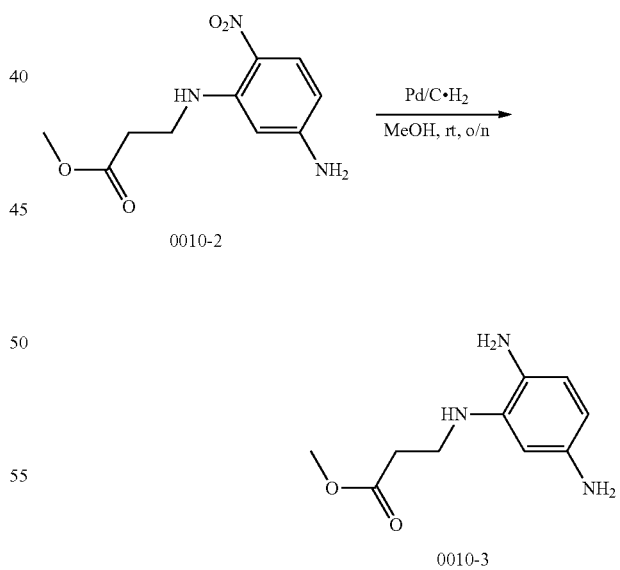

0010-2

0010-3

To a solution of 3-fluoro-4-nitro-aniline (3 g, 19.22 mmol) in DMF (30 mL) was added K₂CO₃ (5.31 g, 38.43 mmol). The mixture was stirred at 90° C. overnight. The mixture was cooled down to room temperature, poured into ice water and extracted with EA (100 mL×2). The combined organic layers was dried over Na₂SO₄, filtered and concentrated to give 0010-2 (4.5 g, crude) as brown oil.

To a solution of 0010-2 (4.5 g, 18.81 mmol) in MeOH (60 mL), was added Pd/C (450 mg), the reaction mixture was stirred overnight under hydrogen atmosphere (1.0 atm). The solid was filtered, the filtrate was concentrated and evaporated to give 0010-3 (3.50 g, 88.92% yield) as a brown solid.

The Synthesis of methyl 3-(6-amino-1H-benzo[d]imidazol-1-yl)propanoate (0010-4)

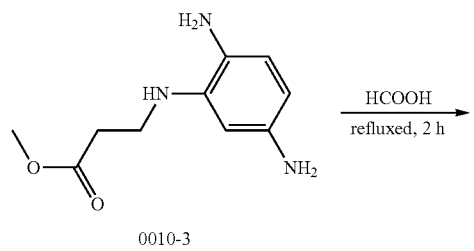

The mixture of 0010-3 (3.5 g, 16.73 mmol) in formic acid (10 mL), the reaction mixture was refluxed for 2 h. The solvent was removed and the residue was purified by c.c (PE/EA=2:1) to give 0010-4 (1.5 g, 40.90% yield) as a brown solid.

The Synthesis of 3-(6-amino-1H-benzo[d]imidazol-1-yl)propanoic acid (0010-5)

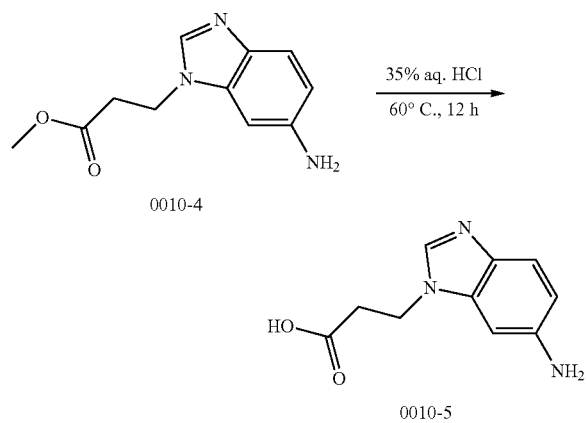

The mixture of 0010-4 (500 mg, 2.28 mmol) in HCl (3 mL, 10 N), was stirred at 60° C. for 12 h. The mixture was cooled down to room temperature and evaporated to give 0010-5 (300 mg, 64.04% yield) as a gray solid.

The Synthesis of (S)-methyl 3-(3-(6-amino-1H-benzo[d]imidazol-1-yl)propanamido)-2-(2,6-dichlorobenzamido)propanoate (0010-6)

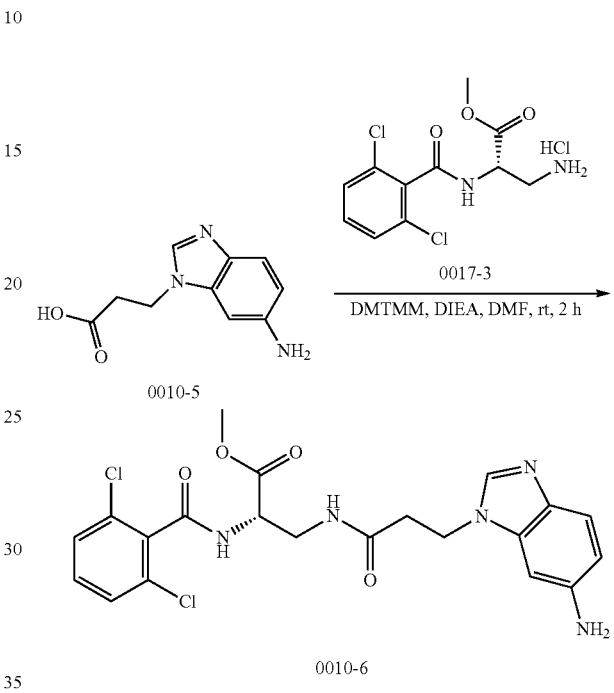

To a solution of 0010-5 (300 mg, 1.46 mmol), 0017-3 (478.90 mg, 1.46 mmol) and DIEA (591.72 mg, 5.85 mmol) in DMF (10 mL) was added DMTMM (485.44 mg, 1.75 mmol), the mixture was stirred at room temperature for 2 hr. After the reaction was finished (by LCMS), the reaction solvent was removed in vacuo, the crude was purified directly by prep-HPLC to get the desired product 0010-6 (300 mg, 42.90% yield) as a white solid.

The Synthesis of (S,Z)-methyl 3-(3-(6-(2,3-bis(tert-butoxycarbonyl)guanidino)-1H-benzo[d]imidazol-1-yl)propanamido)-2-(2,6-dichlorobenzamido)propanoate (0010-7)

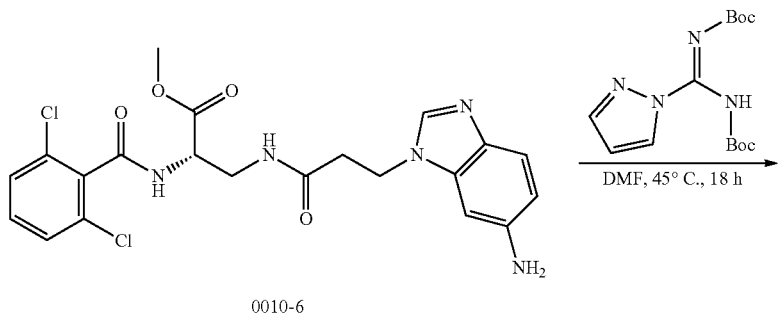

-continued

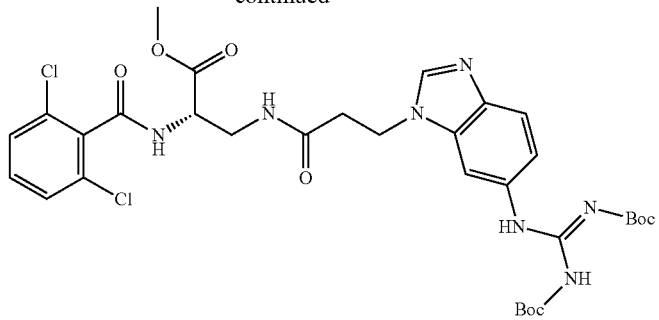

0010-7

The mixture of 0010-6 (300 mg, 627.18 umol) and tert-butyl (NE)-N-[(tert-butoxycarbonylamino)-pyrazol-1-yl-methylene]carbamate (253.04 mg, 815.34 umol) in DMF (5 mL), the reaction mixture was stirred at 45° C. for 18 h. The mixture was cooled down to room temperature and purified by prep-HPLC to give 0010-7 (230 mg, 50.89% yield) as a white solid.

The Synthesis of (S)-methyl 2-(2,6-dichlorobenzamido)-3-(3-(6 guanidino-1H-benzo[d]imidazol-1-yl)propanamido)propanoate (0010-8)

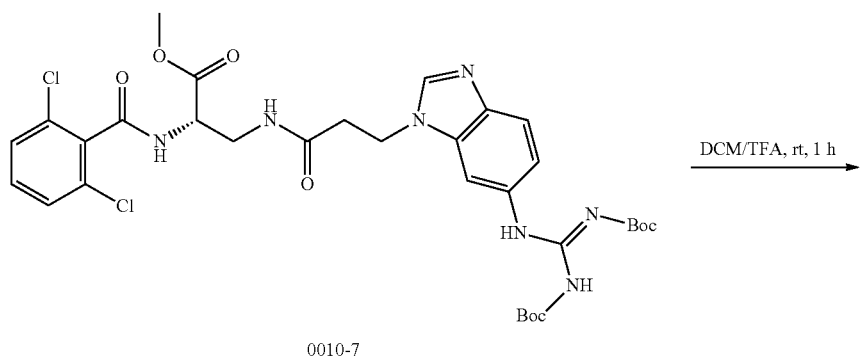

0010-7

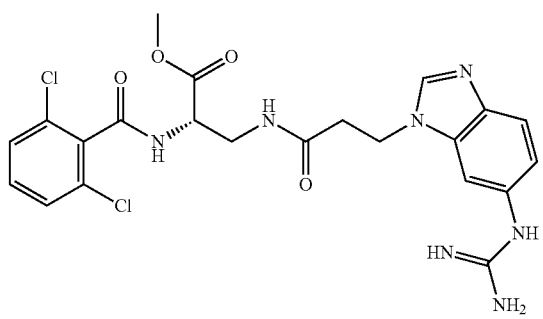

0010-8

To a solution of 0010-7 (120 mg, 166.53 umol) in DCM (5 mL), was added 2,2,2-trifluoroacetic acid (2 mL) dropwise. The mixture was stirred at room temperature for 1 hr, the solvent was removed in vacuo to give 0010-8 (90 mg, crude) as a yellow solid, which was used for the next step without further purification.

The Synthesis of (S)-2-(2,6-dichlorobenzamido)-3-(3-(6 guanidino-1H-benzo[d]imidazol-1-yl)propanamido)propanoic acid (SU15210-0010)

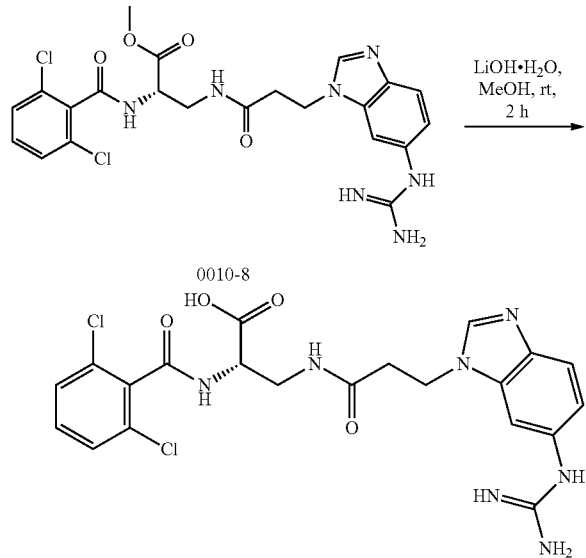

To a solution of compound 0010-8 (86.66 mg, 166.53 umol) in MeOH (2 mL), was added lithium hydroxide hydrate (34.94 mg, 832.65 umol), the mixture was stirred at room temperature for 3 h. After the consumption of starting material (by LCMS), the mixture was concentrated and the solution was adjusted to pH=2 by addition of aqueous HCl (1 N) and the mixture was purified by prep-HPLC to give product SU15210-0010-01 (30 mg, 35.58% yield) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min), Purity: 100.0%, Rt=1.201 min; MS Calcd.: 505.1; MS Found: 506.0 $[M+H]^+$.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [$CH_3CN$+0.1% TFA] to 0% [water+0.1% TFA] and 100% [$CH_3CN$+0.1% TFA] in 10 min, then under this condition for 5 min, finally changed to 95% [water+0.1% TFA] and 5% [$CH_3CN$+0.1% TFA] in 0.1 min and under this condition for 5 min), Purity: 96.17%, Rt=4.566 min.

$^1$H NMR (400 MHz, DMSO-$d_6$) δ 11.52 (brs, 1H), 8.19 (s, 1H), 8.15 (d, J=7.6 Hz, 1H), 7.76 (brs, 3H), 7.70 (t, J=5.0 Hz, 1H), 7.61 (d, J=8.4 Hz, 1H), 7.38-7.47 (m, 4H), 7.01 (dd, J=8.4 Hz, 1.6 Hz, 1H), 4.38-4.45 (m, 2H), 4.20-4.24 (m, 1H), 3.48-3.54 (m, 1H), 3.24-3.30 (m, 1H), 2.60 (t, J=6.4 Hz, 2H).

SU15210-0011

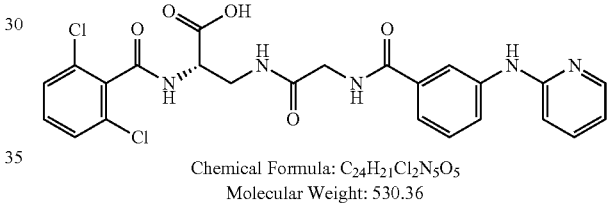

Chemical Formula: $C_{24}H_{21}Cl_2N_5O_5$
Molecular Weight: 530.36

Scheme: Route for SU15210-0011

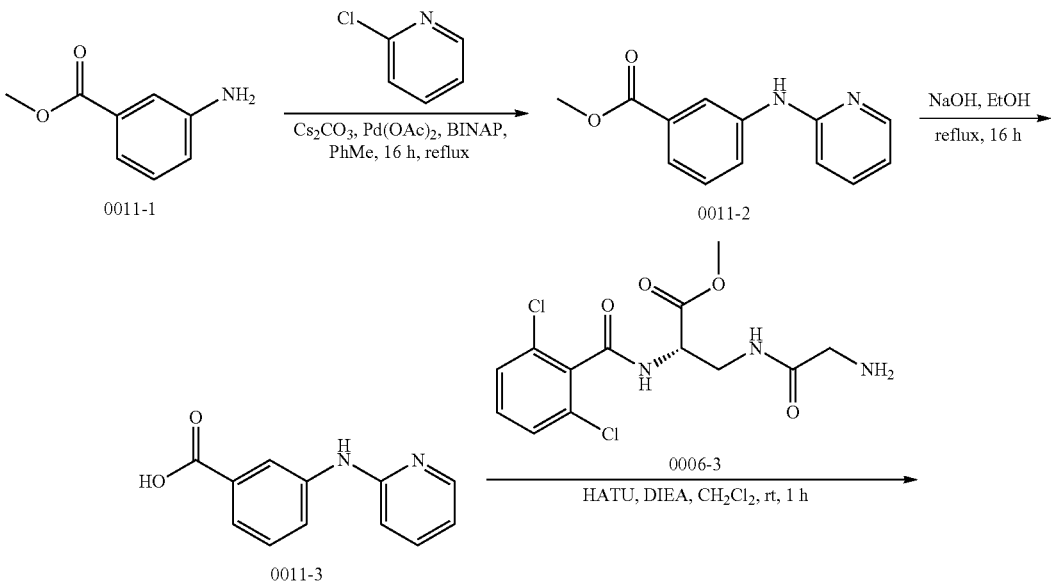

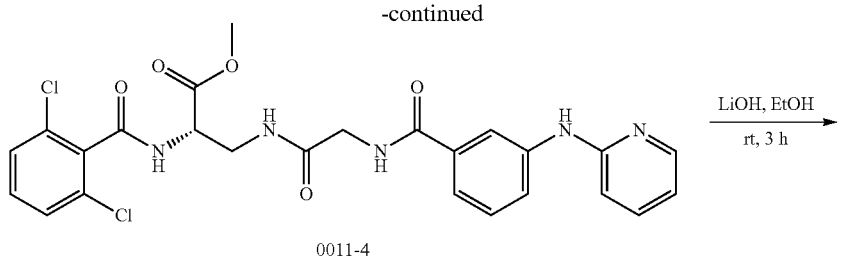

0011-4

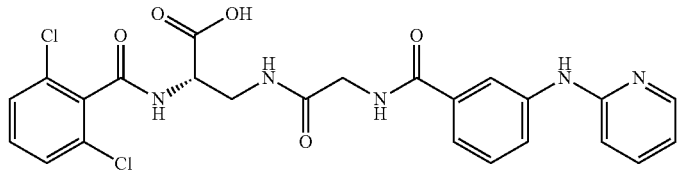

SU15210-0011-01

The Synthesis of methyl 3-(pyridin-2-ylamino)benzoate (0011-2)

The Synthesis of 3-(pyridin-2-ylamino)benzoic acid (0011-3)

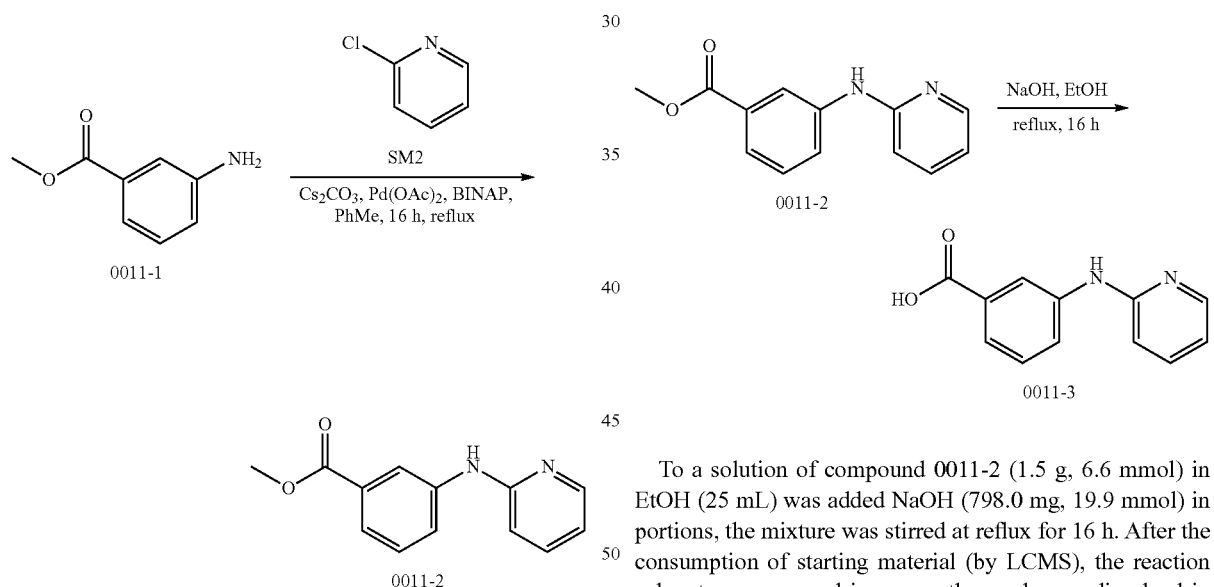

To a solution of compound 0011-2 (1.5 g, 6.6 mmol) in EtOH (25 mL) was added NaOH (798.0 mg, 19.9 mmol) in portions, the mixture was stirred at reflux for 16 h. After the consumption of starting material (by LCMS), the reaction solvent was removed in vacuo, the crude was dissolved in water (15 mL) and adjust pH to 3.0 by HCl (1.0 N), the mixture was filtered, the filter cake was collected and dried over freeze-drying to give the product 0011-3(1.2 g, 85.3% yield) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05 TFA] in 0.8 min, then under this condition for 0.4 min, finally changed to 0% [water+0.05% TFA] and 100% [CH$_3$CN+0.05% TFA] to 95% [water+0.05% TFA] and 5% [CH$_3$CN+0.05% TFA] in 0.01 min, Purity: 90.23%, Rt=0.379 min; MS Calcd.: 214.0; MS Found: 215.2 [M+H]$^+$.

To a solution of compound 0011-1 (1.5 g, 10.0 mmol) in toluene (50 mL) was added Pd(OAc)$_2$ (225.0 mg, 1.0 mmol), BINAP (623.0 mg, 1.0 mmol), Cs$_2$CO$_3$ (6.5 g, 20.0 mmol) and SM2 (1.2 g, 11.0 mmol). The mixture was stirred at reflux for 16 h. After the consumption of starting material (by LCMS), the reaction solvent was removed in vacuo, the crude was purified directly by prep-HPLC to get the product 0011-2 (1.5 g, yield: 65.8%) as a brown solid.

The Synthesis of (S)-methyl 2-(2,6-dichlorobenzamido)-3-(2-(3-(pyridin-2-ylamino)benzamido)acetamido)propanoate (0011-4)

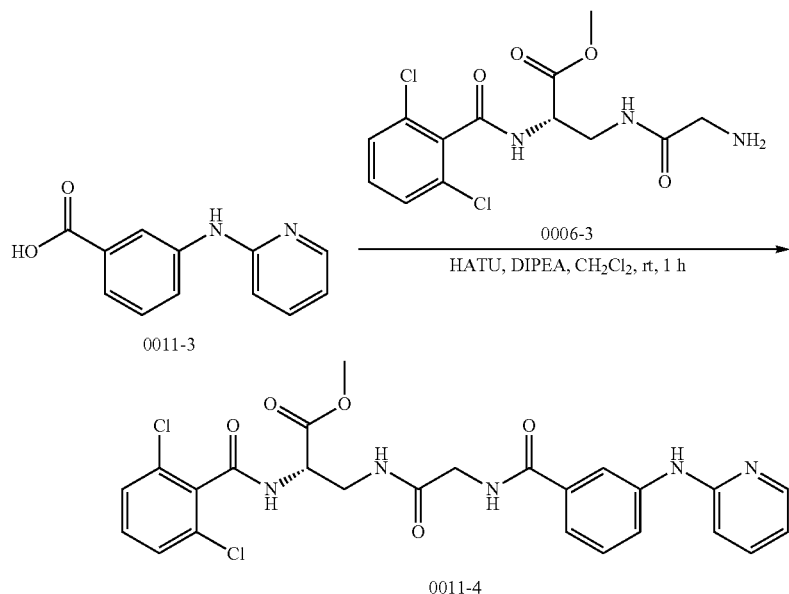

To a solution of compound 0011-3 (386.0 mg, 1.8 mmol) in DCM (20 mL) was added HATU (875.0 mg, 2.3 mmol), DIPEA (776.0 mg, 6.0 mmol) and 0006-3 (520.0 mg, 1.8 mmol). The mixture was stirred at rt for 1 h. After the reaction was finished (by LCMS), the reaction solvent was removed in vacuo, the crude was purified directly by prep-HPLC to get the desired product 0011-4 (750.0 mg, yield: 76.6%) as a white solid.

The Synthesis of (S)-2-(2,6-dichlorobenzamido)-3-(2-(3-(pyridin-2-ylamino)benzamido)acetamido)propanoic acid (SU15210-0011)

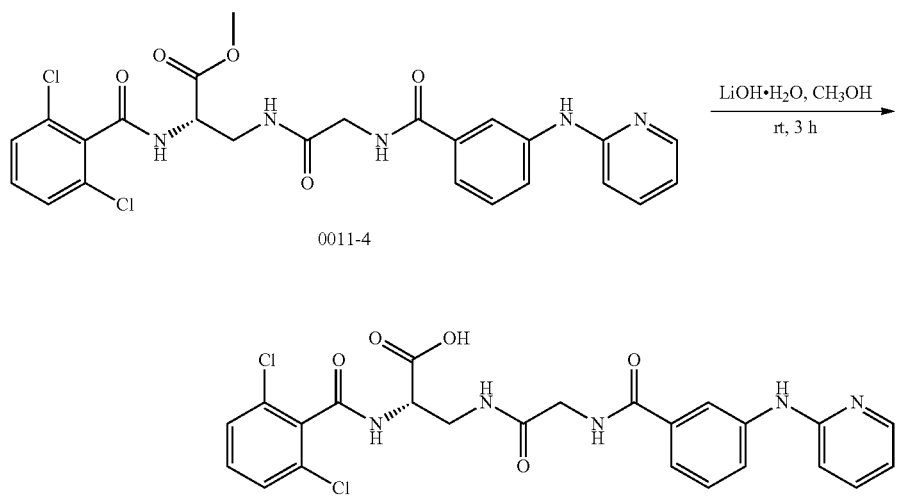

To a solution of compound 0011-4 (435.0 mg, 0.8 mmol) in CH$_3$OH (5 mL) was added LiOH.H$_2$O (168.0 mg, 4.0 mmol). The mixture was stirred at rt for 3 h. After the consumption of starting material (by LCMS), the reaction mixture was concentrated in vacuo, the crude was dissolved with 5 mL H$_2$O, 1N HCl was added to adjust pH=2~3, the mixture was freeze-drying to get the crude product, the crude was further purified by prep-HPLC to give the SU15210-0011 (69.8 mg, 16.5% yield) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 5% [water+0.05% TFA] and 95% [water+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min), Purity: 98.40%, Rt=1.247 min; MS Calcd.: 529.0; MS Found: 529.9 [M+H]$^+$.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH$_3$CN+0.05% TFA] to 5% [water+0.05% TFA] and 95% [water+0.05% TFA] in 10 min, then under this condition for 5 min, finally changed to 95% [water+0.05% TFA] and 5% [CH$_3$CN+0.05% TFA] in 0.1 min and under this condition for 5 min), Purity: 100%, Rt=5.162 min.

$^1$H NMR (400 MHz, DMSO-d$_6$) δ 9.72 (brs, 1H), 8.98 (d, J=8.0 Hz, 1H), 8.68 (t, J=8.0 Hz, 1H), 8.11-8.12 (m, 1H), 8.05 (s, 1H), 7.94 (t, J=5.6 Hz, 1H), 7.75-7.82 (m, 2H), 7.41-7.56 (m, 5H), 6.98 (d, J=8.0 Hz, 1H), 6.88 (t, J=6.0 Hz, 1H), 4.57 (q, J=7.6 Hz, 1H), 3.80-3.93 (m, 2H), 3.52-3.56 (m, 1H), 3.40-3.44 (m, 1H).

SU15210-0012

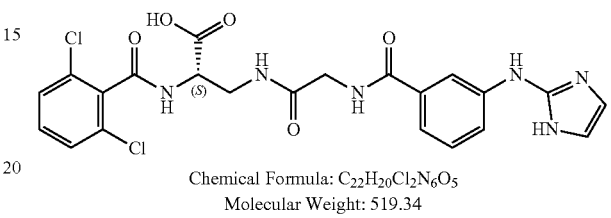

Chemical Formula: C$_{22}$H$_{20}$Cl$_2$N$_6$O$_5$
Molecular Weight: 519.34

Scheme: Route for SU15210-0012

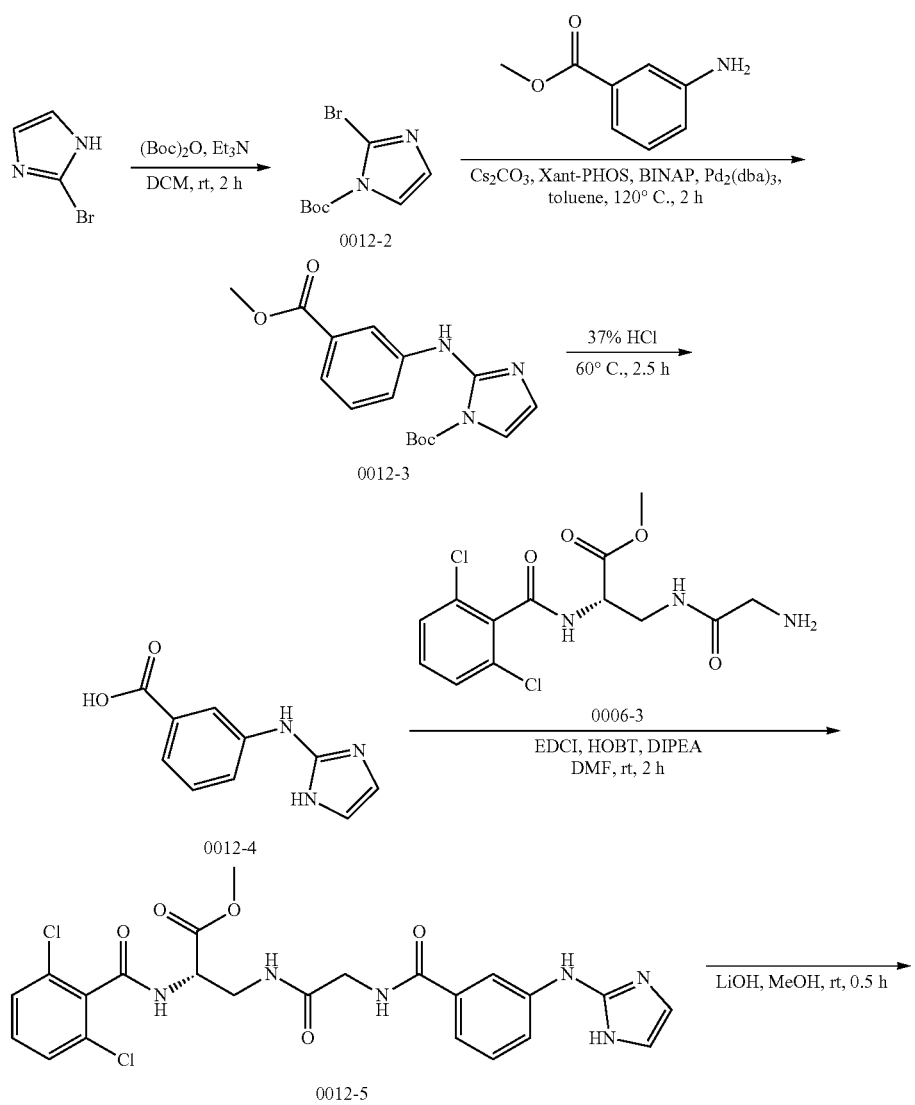

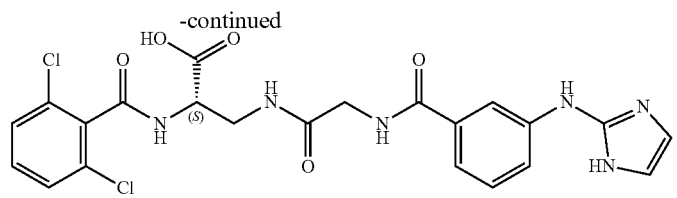

SU15210-0012

The Synthesis of tert-butyl 2-bromoimidazole-1-carboxylate (0012-2)

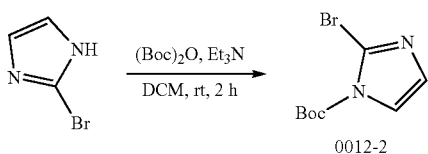

To a stirred solution of 2-bromo-1H-imidazole (5 g, 34.0 mmol) in DMF (50 ml) was added TEA (10.3 g, 102.1 mmol) and di-tert-butyl dicarbonate (11.1 g, 51.0 mmol) at 0° C. The resulting reaction mixture was stirred for 2 h at rt. Then added water, the aqueous phase was extracted with dichloromethane, the combined organic phases were dried over anhydrous sodium sulfate, filtered, and concentrated in vacuo to give the desired product 0012-2 (5.5 g, yield: 65%) as yellow oil.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05 TFA] in 0.8 min, then under this condition for 0.4 min, finally changed to 0% [water+0.05% TFA] and 100% [CH$_3$CN+0.05% TFA] to 95% [water+0.05% TFA] and 5% [CH$_3$CN+0.05% TFA] in 0.01 min, Purity: 100.0%, Rt=0.668 min; MS Calcd.: 246.0; MS Found: 247.3 [M+H]$^+$.

The Synthesis of tert-butyl 2-(3-methoxycarbonylanilino)imidazole-1-carboxylate (0012-3)

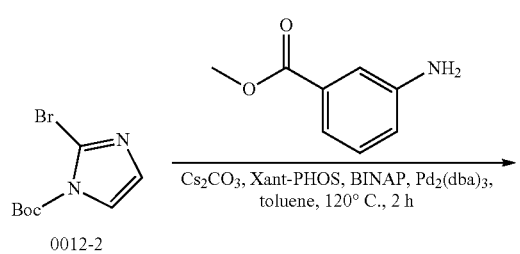

To a solution of compound 0012-2 (1 g, 4.05 mmol) in toluene (20 mL) was added methyl 3-aminobenzoate (0.35 g, 2.32 mmol), Xant-PHOS (234.17 mg, 404.71 umol), BINAP (252.00 mg, 404.71 umol), cesium carbonate (1.32 g, 4.05 mmol) and Pd$_2$(dba)$_3$ (370.60 mg, 404.71 umol). The mixture was stirred at reflux for 2 h. After the consumption of starting material (by LCMS), the reaction solvent was removed in vacuo, the crude was purified directly by prep-HPLC to get the product 0012-3 (120 mg, 9.34% yield) as a white solid.

The Synthesis of 3-(1H-imidazol-2-ylamino)benzoic acid (0012-4)

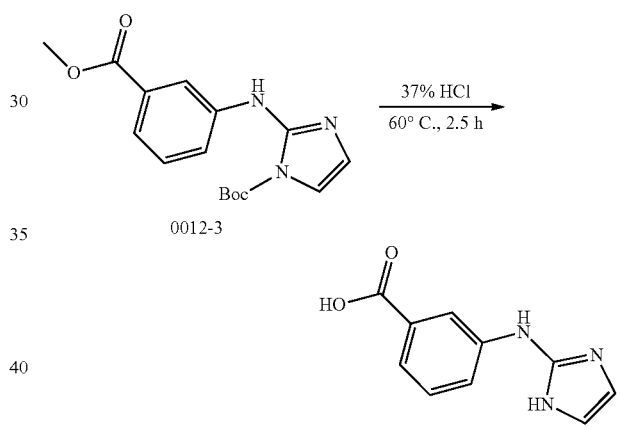

To a solution of 0012-3 (50 mg, 157.56 umol) in 37% HCl (2 mL), the mixture was stirred at 60° C. for 2.5 h. After the reaction was completed, the solvent was removed in vacuo to give 0012-4 (30 mg, 93.70% yield) as a white solid.

The Synthesis of methyl (2S)-2-[(2,6-dichlorobenzoyl)amino]-3-[[2-[[3-(1H-imidazol-2-ylamino)benzoyl]amino]acetyl]amino]propanoate (0012-5)

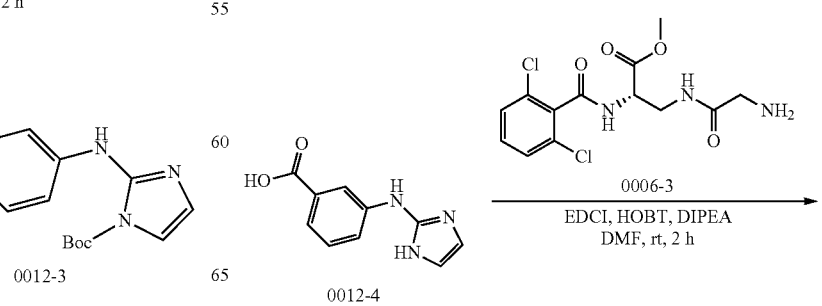

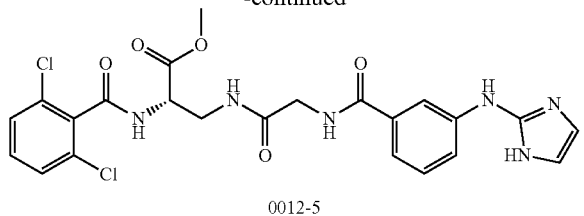

0012-5

To a solution of 0006-3 (170.60 mg, 369.10 umol) in DMF (2 mL) was added in DIPEA (95.40 mg, 738.20 umol), 0012-4 (30 mg, 147.64 umol), HOBT (99.75 mg, 738.20 umol) and EDCI (390.00 mg, 2.03 mmol). The mixture was stirred at rt for 24 h. After the reaction was completed, the mixture was purified by prep-HPLC to get the product 0012-5 (5 mg, 6.35% yield) as a yellow solid.

The Synthesis of (2S)-2-[(2,6-dichlorobenzoyl)amino]-3-[[2-[[3-(1H-imidazol-2-ylamino)benzoyl]amino]acetyl]amino]propanoic acid (SU15210-0012)

to 95% [water+0.05% TFA] and 5% [CH$_3$CN+0.05% TFA] in 0.05 min and under this condition for 0.7 min). Purity: 96.58%, Rt=1.412 min; MS Calcd.: 518.1; MS Found: 519.1 [M+H]$^+$.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH$_3$CN+0.05% TFA] to 5% [water+0.05% TFA] and 95% [water+0.05% TFA] in 10 min, then under this condition for 5 min, finally changed to 95% [water+0.05% TFA] and 5% [CH$_3$CN+0.05% TFA] in 0.1 min and under this condition for 5 min). Purity: 96.77%, Rt=4.996 min.

$^1$H NMR (400 MHz, CD$_3$OD+D$_2$O) δ 8.56 (s, 1H), 7.82 (s, 1H), 7.59 (d, J=7.6 Hz, 1H), 7.49 (t, J=7.6 Hz, 1H), 7.31-7.43 (m, 4H), 6.97 (s, 1H), 4.59-4.63 (m, 1H) 4.06 (d, J=7.2 Hz, 2H), 3.70 (d, J=5.6 Hz, 2H).

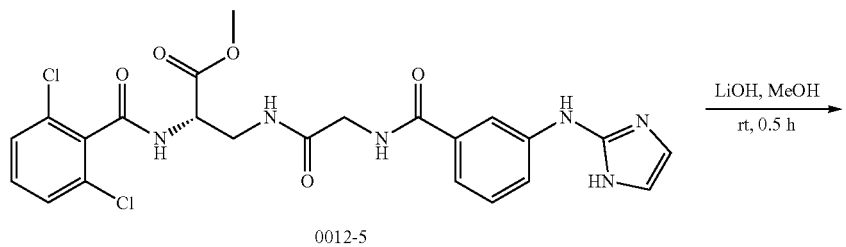

0012-5

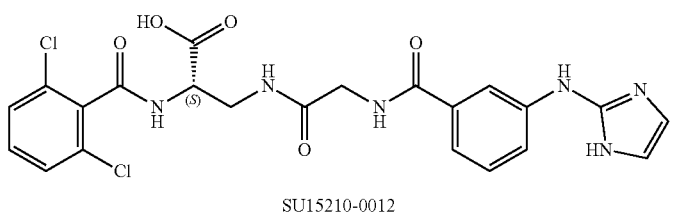

SU15210-0012

To a solution of compound 0012-5 (120.0 mg, 0.2 mmol) in CH$_3$OH (2 mL) was added LiOH.H$_2$O (1 g, 23.8 mmol). The mixture was stirred at rt for 0.5 h. After the consumption of starting material (by LCMS), the reaction mixture was concentrated in vacuo, the crude was dissolved with H$_2$O (5 mL), 1N HCl was added to adjust pH=2~3, the mixture was freeze-drying to get the crude product, the crude was further purified by prep-HPLC to give the SU15210-0012 (5 mg, 4.2% yield) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 5% [water+0.05% TFA] and 95% [water+0.05% TFA] in 1.6 min, then under this condition for 1.4 min, finally changed

SU15210-0013-01

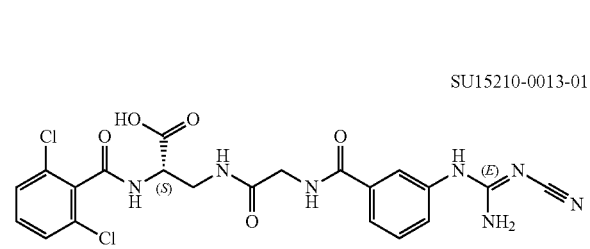

Chemical Formula: C$_{21}$H$_{19}$Cl$_2$N$_7$O$_5$
Molecular Weight: 520.33

Scheme: Route for SU15210-0013-01
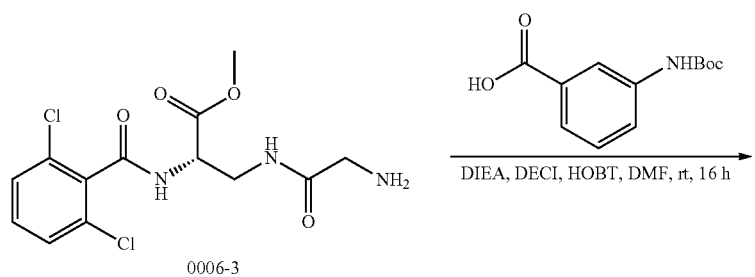
0006-3
DIEA, DECI, HOBT, DMF, rt, 16 h
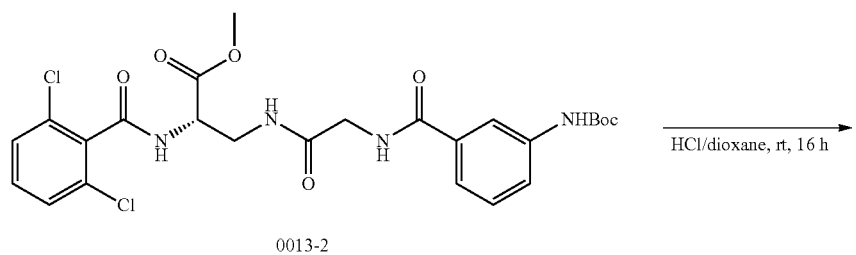
0013-2
HCl/dioxane, rt, 16 h
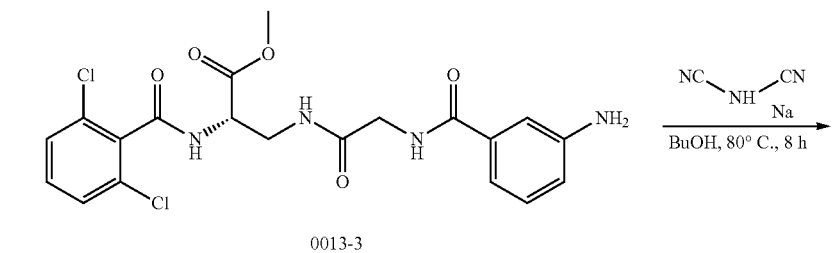
0013-3
$\underset{\text{BuOH, 80° C., 8 h}}{\overset{\text{NC}\diagdown\underset{\text{NH}}{}\diagup\text{CN, Na}}{\longrightarrow}}$
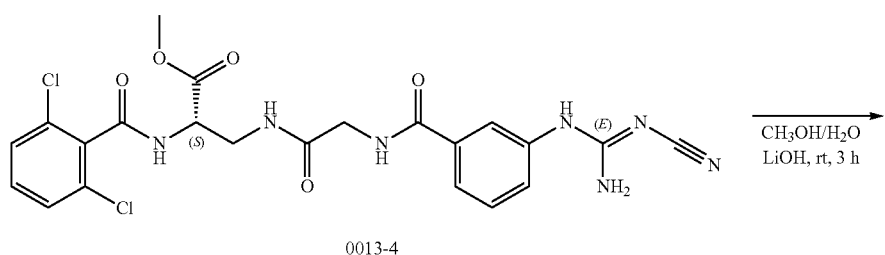
0013-4
CH₃OH/H₂O
LiOH, rt, 3 h
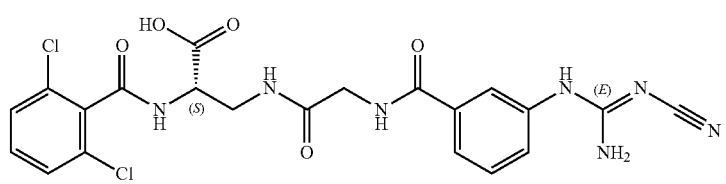
SU15210-0013-01

The Synthesis of (S)-methyl 3-(2-(3-(tert-butoxycarbonylamino)benzamido)acetamido)-2-(2,6-dichlorobenzamido)propanoate (0013-2)

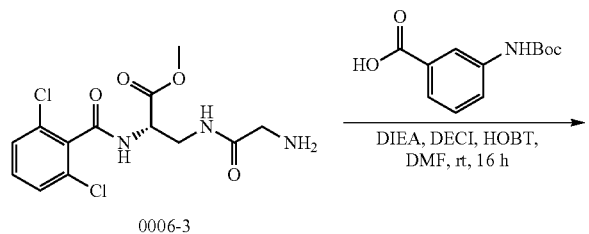

To a solution of 0006-3 (1.0 g, 2.9 mmol) in DCM (20 mL) was added 3-(tert-butoxycarbonylamino)benzoic acid (680.0 mg, 2.9 mmol), TEA (290.6 mg, 2.9 mmol), DMAP (170.0 mg, 1.5 mmol) and DCC (600 mg, 2.9 mmol). Then stirred the mixture at room temperature overnight, after the reaction was completed (by LCMS), the reaction mixture was quenched with water (20 mL), and extracted with DCM (20 mL×3). The organic layers were washed with brine, dried over MgSO$_4$ and concentrated in vacuo, the residue was purified by column chromatography (PE/EA=2:1) to give 0013-2 (750.0 mg, 46.0% yield) as colorless oil.

The Synthesis of (S)-methyl 3-(2-(3-aminobenzamido)acetamido)-2-(2,6-dichlorobenzamido)propanoate (0013-3)

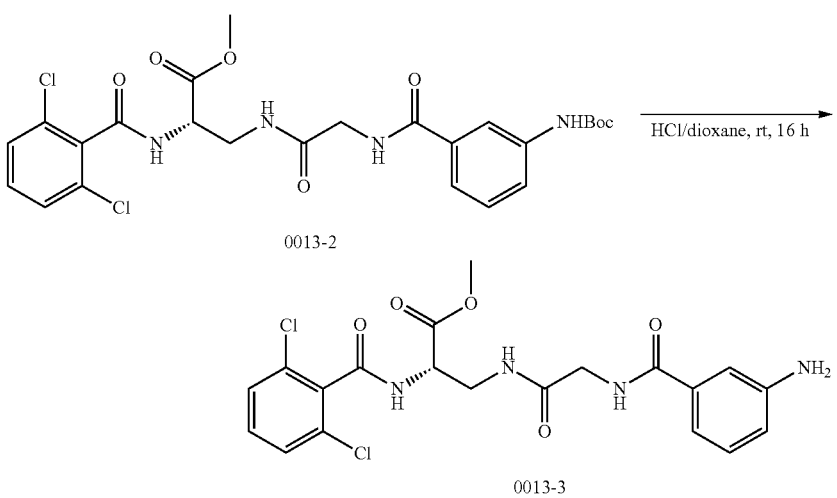

To a solution of 0013-2 (750.0 mg, 1.3 mmol) in HCl/dioxane (10 mL), the mixture was stirred at room temperature overnight. After the reaction was completed, the solvent was removed in vacuo to give 0013-3 (550.0 mg, 89.1% yield) as yellow oil.

The Synthesis of (S,E)-methyl 3-(2-(3-(2-cyanoguanidino)benzamido)acetamido)-2-(2,6-dichlorobenzamido)propanoate (0013-4)

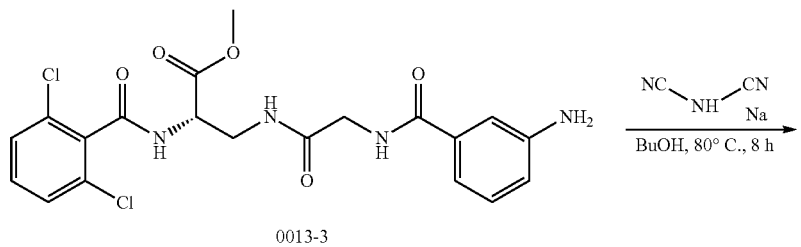

-continued

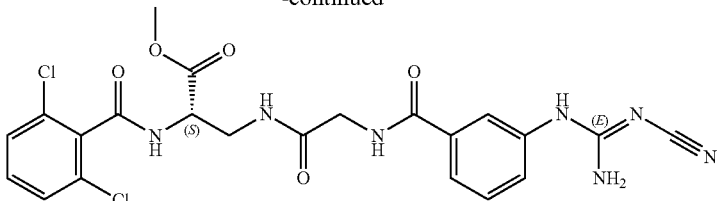

0013-4

To a solution of 0013-3 (750.0 mg, 1.6 mmol) in BuOH (10 mL) was added (dicyanoamino)sodium (288.0 mg, 3.2 mmol), stirred the mixture at 60° C. for 8 h. After the reaction was completed, the reaction mixture was quenched with water, and extracted with DCM (20 mL×3). The organic layers were washed with brine, dried over MgSO₄ and concentrated in vacuo, the residue was purified by prep-HPLC to give 0013-4 (150.0 mg, 17.5% yield) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 0% [water+0.05% TFA] and 100% [CH₃CN+0.05% TFA] in 1.6 min, then under this condition for 1.4 min, finally changed to 95% [water+0.05% TFA] and 5% [CH₃CN+0.05% TFA] in 0.05 min and under this condition for 0.7 min. Purity: 89.1%. Rt=1.401 min; MS Calcd.: 533.0; MS Found: 534.0 [M+H]⁺.

The Synthesis of (S,E)-3-(2-(3-(2-cyanoguanidino)benzamido)acetamido)-2-(2,6-dichlorobenzamido)propanoic acid (SU15210-0013-01)

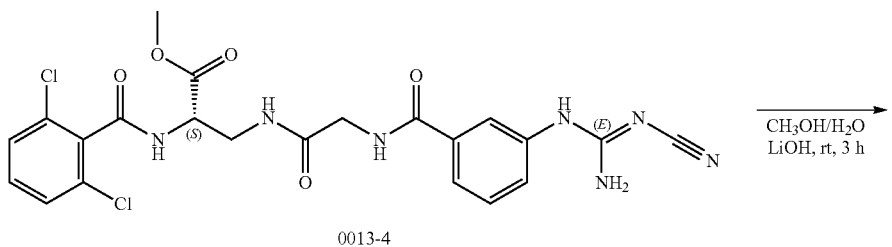

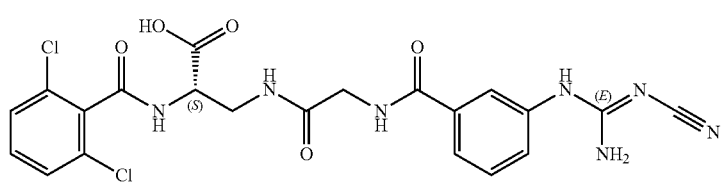

SU15210-0013-01

To a solution of 0013-4 (150.0 mg, 0.28 mmol) in MeOH/H₂O (10 mL/2 mL), was added LiOH (117.6 mg, 2.8 mmol). The reaction mixture was stirred at rt for 3 h, after the reaction was completed, the reaction mixture was concentrated and adjust pH to ~7.0 by HCl (1.0 N), then the reside was purified by prep-HPLC to give SU15210-0013-01 (115.0 mg, 78.8% yield) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Purity: 99.5%. Rt=1.119 min; MS Calcd.: 519.0; MS Found: 520.0 [M+H]⁺.

Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH₃CN+0.1% TFA] to 0% [water+0.1% TFA] and 100% [CH₃CN+0.1% TFA] in 10 min, then under this condition for 5 min, finally changed to 95% [water+0.1% TFA] and 5% [CH₃CN+0.1% TFA] in 0.1 min and under this condition for 5 min. Purity: 98.7%. Rt=5.365 min.

¹H NMR (400 MHz, DMSO-d₆) δ 12.83 (s, 1H), 9.27 (s, 1H), 8.91 (d, J=7.6 Hz, 1H), 8.72 (t, J=5.6 Hz, 1H), 7.93 (t, J=5.6 Hz, 1H), 7.81 (s, 1H), 7.38-7.59 (m, 6H), 7.12 (s, 2H), 4.50-4.53 (m, 1H), 3.79-3.91 (m, 2H), 3.49-3.53 (m, 1H), 3.34-3.42 (m, 1H).

SU15210-0015
The Synthesis of methyl 3-(4-methylpyridin-2-ylamino)benzoate (0015-2)
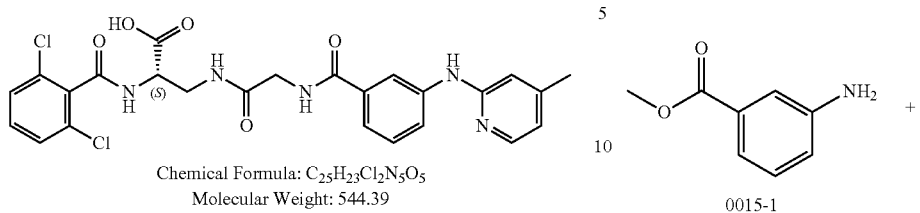
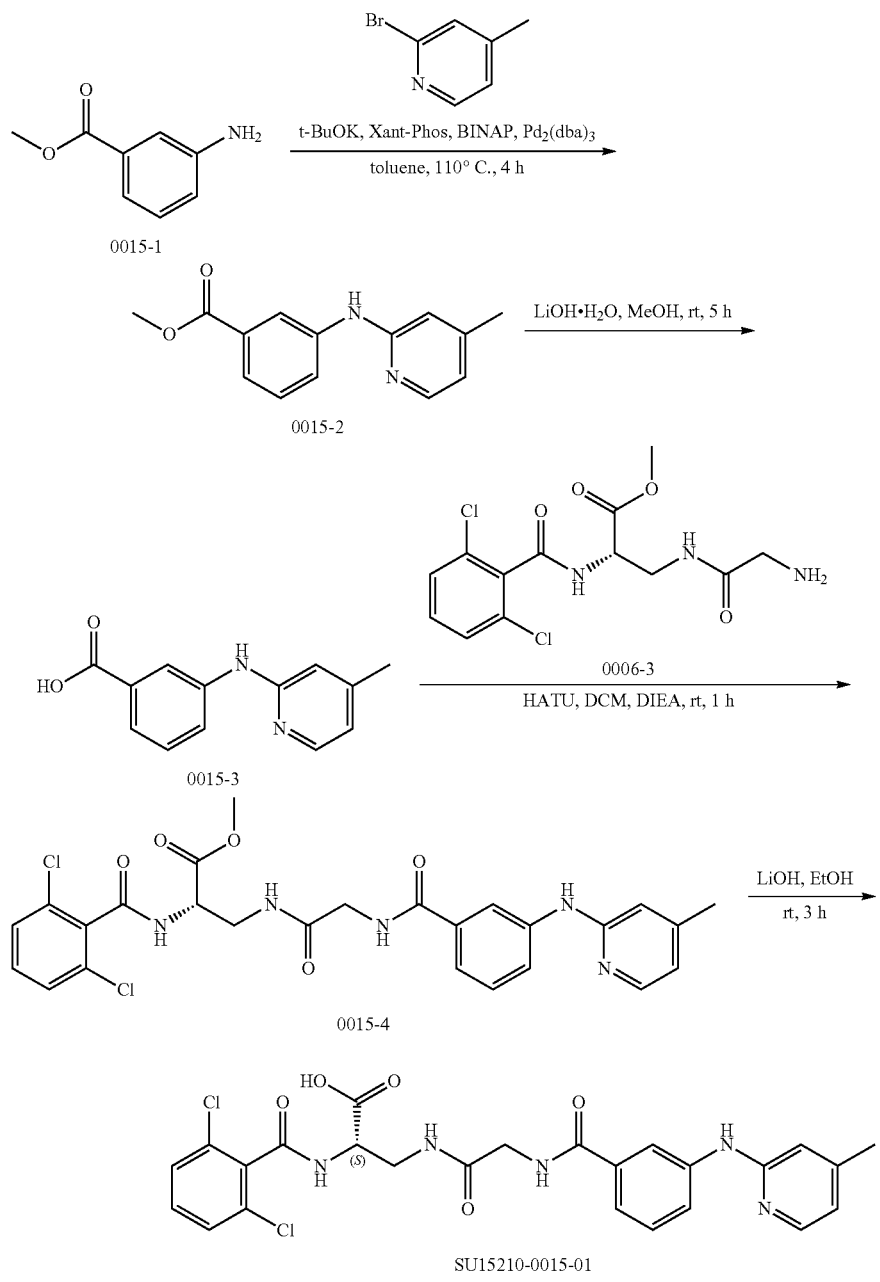

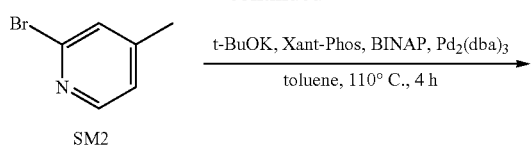

The Synthesis of 3-(4-methylpyridin-2-ylamino)benzoic acid (0015-3)

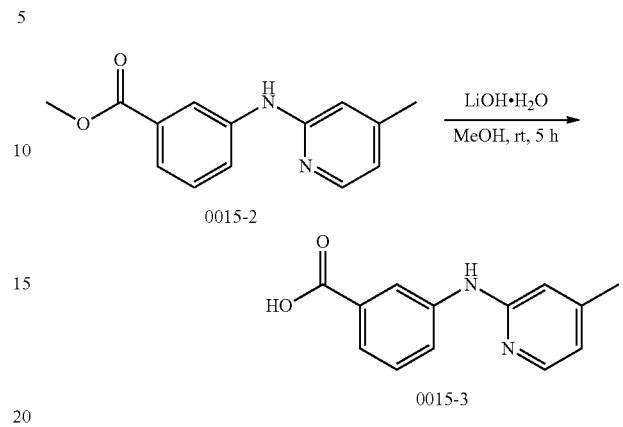

To a solution of compound 0015-1 (1.0 g, 6.6 mmol) in toluene (50 mL) was added Pd$_2$(dba)$_3$ (606.0 mg, 0.7 mmol), BINAP (413.0 mg, 0.7 mmol), Xant-Phos (383.0 mg, 0.7 mmol), t-BuOK (1.5 g, 13.2 mmol) and SM2 (1.2 g, 6.6 mmol). The reaction mixture was stirred at 110° C. for 4 h. After the consumption of starting material (by LCMS), the reaction solvent was removed in vacuo, the crude was purified directly by prep-HPLC to get the product 0015-2 (600 mg, yield: 37.5%) as a brown solid.

To a solution of compound 0015-2 (600 mg, 2.5 mmol) in MeOH (25 mL) was added LiOH.H$_2$O (210 mg, 5.0 mmol) in portions, the mixture was stirred at rt for 5 h. After the consumption of starting material (by LCMS), the reaction solvent was removed in vacuo, the crude was dissolved in 15 mL H$_2$O, 1N HCl was added dropwised to adjust pH=3~4, the mixture was purified by prep-HPLC to get the product 0015-3 (500 mg, 88.5% yield) as a brown solid.

The Synthesis of (S)-methyl 2-(2,6-dichlorobenzamido)-3-(2-(3-(4-methylpyridin-2-ylamino)benzamido)acetamido)propanoate (0015-4)

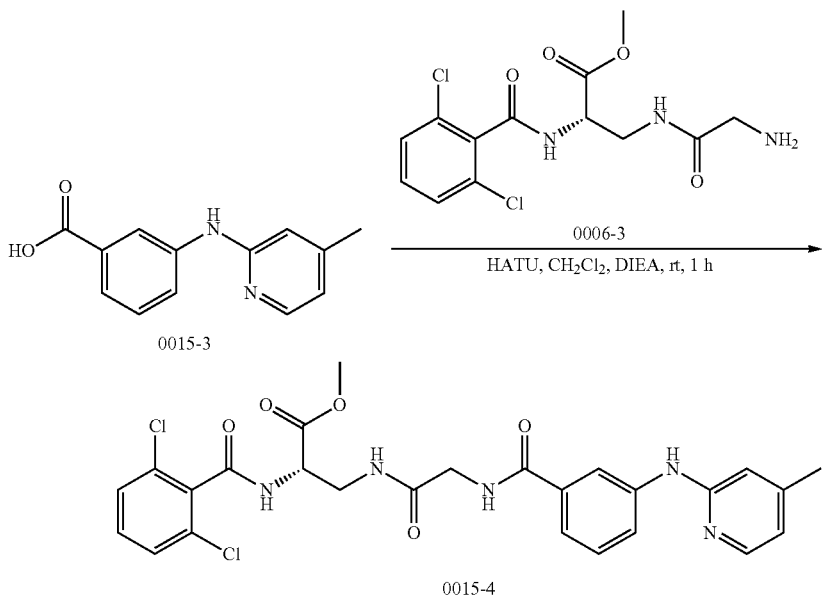

To a solution of compound 0015-3 (165.0 mg, 0.7 mmol) in DCM (10 mL) was added HATU (343.0 mg, 0.9 mmol), DIEA (279.0 mg, 2.1 mmol) and 0006-3 (208.0 mg, 0.6 mmol). The mixture was stirred at rt for 1 h. After the reaction was finished (by LCMS), the reaction solvent was removed in vacuo, the crude was purified directly by prep-HPLC to get the desired product 0015-4 (300.0 mg, yield: 89.8%) as a white solid.

The Synthesis of (S)-2-(2,6-dichlorobenzamido)-3-(2-(3-(4-methylpyridin-2-ylamino)benzamido)acetamido)propanoic acid (SU15210-0015)

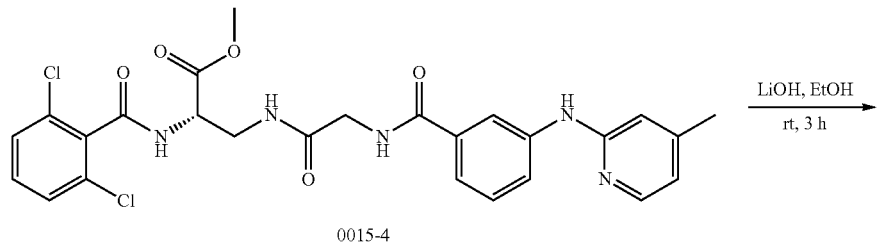

To a solution of compound 0015-4 (300.0 mg, 0.5 mmol) in ethanol (5 mL) was added LiOH·H₂O (113.0 mg, 2.7 mmol). The mixture was stirred at rt for 3 h. After the consumption of starting material (by LCMS), the reaction mixture was concentrated in vacuo, the crude was dissolved with 5 mL H₂O, 1N HCl was added to adjust pH=2~3, the mixture was freeze-drying to get the crude product, which was further purified by prep-HPLC to give SU15210-0015 (85.1 mg, 29.1% yield) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 5% [water+0.05% TFA] and 95% [water+0.05% TFA] in 1.6 min, then under this condition for 1.4 min, finally changed to 95% [water+0.05% TFA] and 5% [CH₃CN+0.05% TFA] in 0.05 min and under this condition for 0.7 min), Purity: 99.42%, Rt=1.292 min; MS Calcd.: 543.0; MS Found: 543.8 [M+H]⁺.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH₃CN+0.05% TFA] to 5% [water+0.05% TFA] and 95% [water+0.05% TFA] in 10 min, then under this condition for 5 min, finally changed to 95% [water+0.05% TFA] and 5% [CH₃CN+0.05% TFA] in 0.1 min and under this condition for 5 min), Purity: 100.00%, Rt=5.428 min.

¹H NMR (400 MHz, DMSO-d₆) δ 12.83 (brs, 1H), 9.93 (brs, 1H), 8.98 (d, J=8.0 Hz, 1H), 8.72 (d, J=5.6 Hz, 1H), 7.93-7.98 (m, 3H), 7.64-7.71 (m, 2H), 7.41-7.52 (m, 4H), 6.83-6.87 (m, 2H), 4.58 (q, J=7.2 Hz, 1H), 3.81-3.94 (m, 2H), 3.51-3.56 (m, 1H), 3.36-3.43 (m, 1H), 2.34 (s, 3H).

SU15210-0016

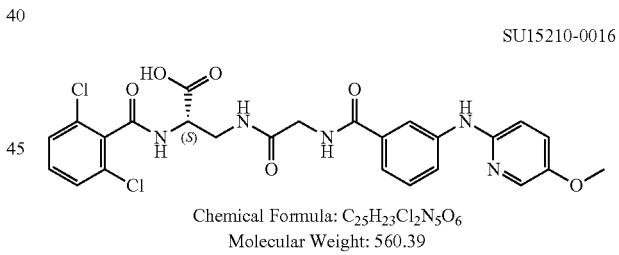

Chemical Formula: C₂₅H₂₃Cl₂N₅O₆
Molecular Weight: 560.39

Scheme: Route for SU15210-0016

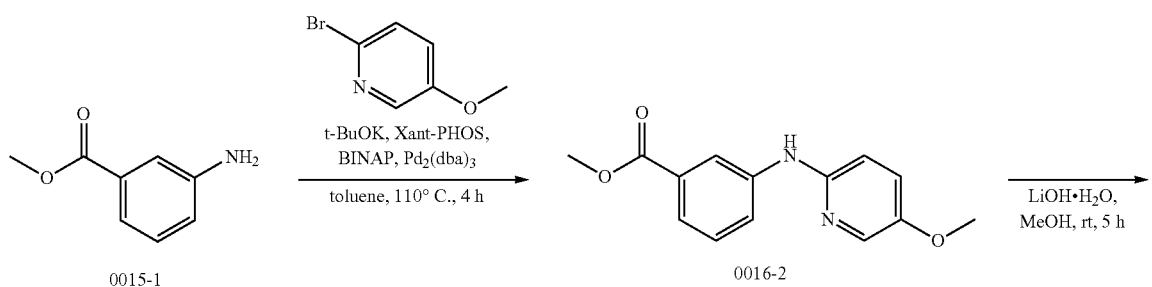

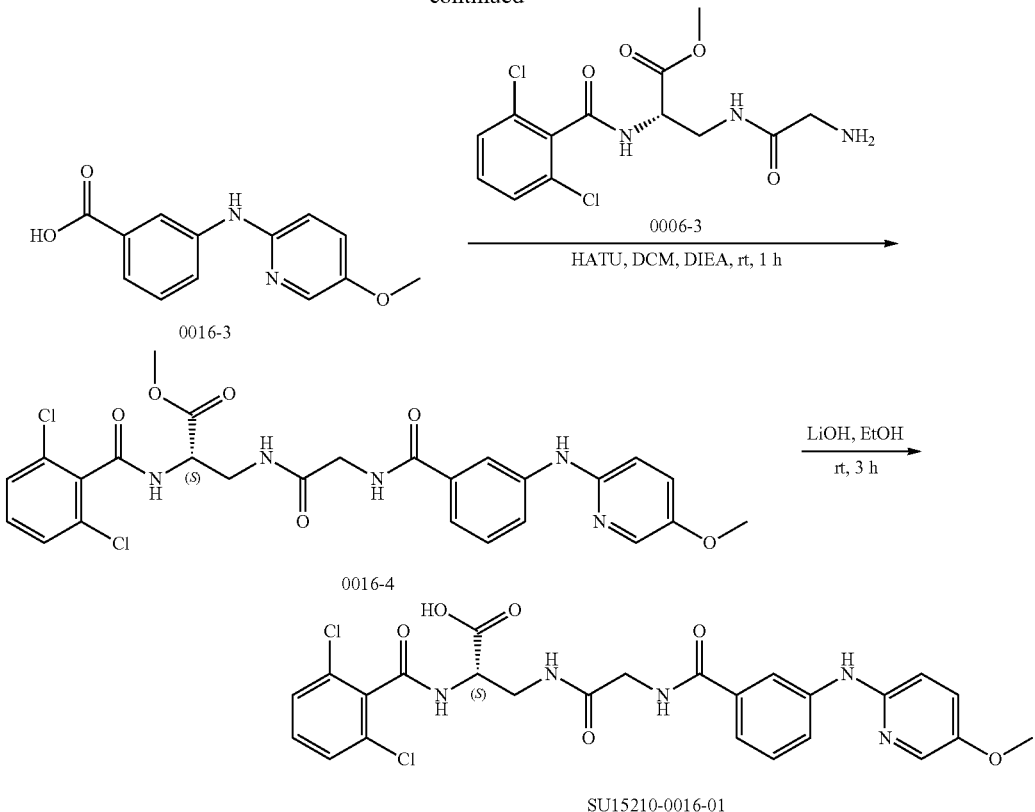

The Synthesis of methyl 3-(5-methoxypyridin-2-ylamino)benzoate (0016-2)

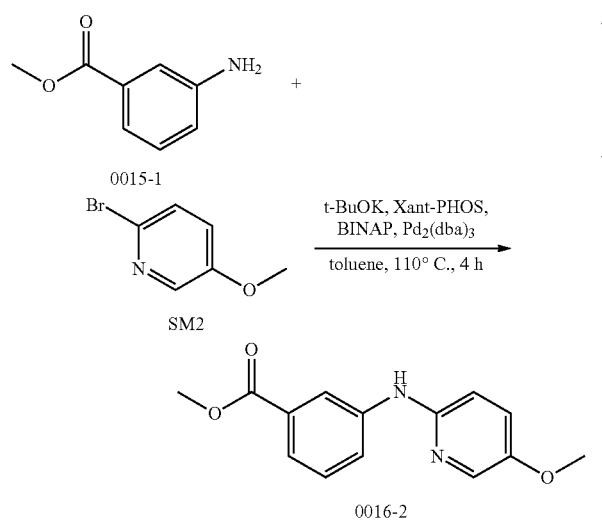

To a solution of compound 0015-1 (1.0 g, 6.6 mmol) in toluene (50 mL) was added Pd$_2$(dba)$_3$ (606.0 mg, 0.7 mmol), BINAP (413.0 mg, 0.7 mmol), Xant-Phos (383.0 mg, 0.7 mmol), t-BuOK (1.5 g, 13.2 mmol) and SM2 (1.2 g, 6.6 mmol). The mixture was stirred at 110° C. for 4 h. After the consumption of starting material (by LCMS), the reaction solvent was removed in vacuo, the crude was purified directly by prep-HPLC to get the product 0016-2 (500 mg, yield: 37.5%) as a brown solid.

The Synthesis of 3-(5-methoxypyridin-2-ylamino)benzoic acid (0016-3)

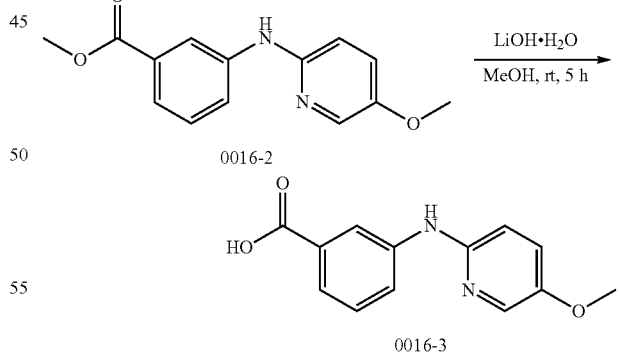

To a solution of compound 0015-2 (500 mg, 1.9 mmol) in MeOH (20 mL) was added LiOH.H$_2$O (406.0 mg, 9.7 mmol) in portions, The mixture was stirred at rt for 5 h. After the consumption of starting material (by LCMS), the reaction solvent was removed in vacuo, the crude was dissolved in 15 mL H$_2$O, 1N HCl was dropwisely to adjust pH=3~4, the mixture was purified by prep-HPLC to give the product 0016-3 (400 mg, 84.7% yield) as a brown solid.

The Synthesis of (S)-methyl 2-(2,6-dichlorobenzamido)-3-(2-(3-(5-methoxypyridin-2-ylamino)benzamido)acetamido)propanoate (0016-4)

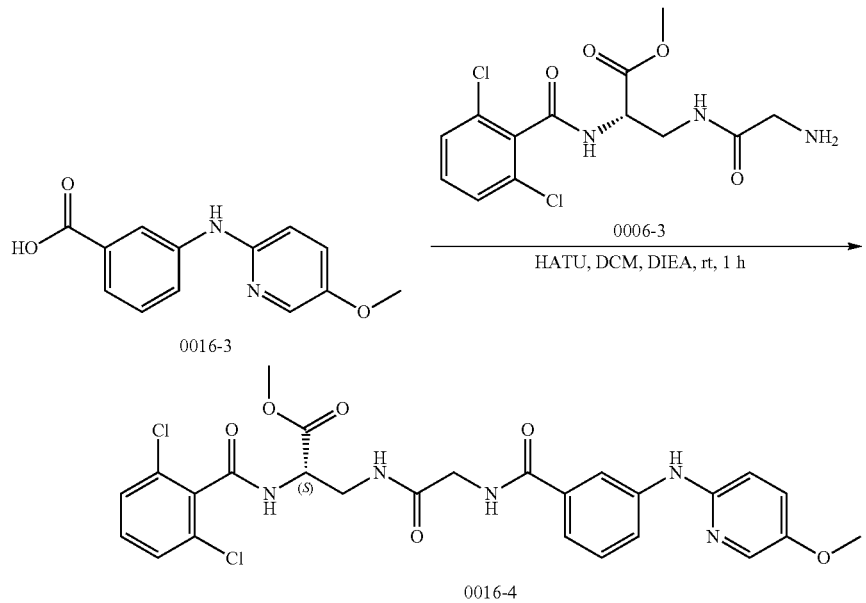

To a solution of compound 0016-3 (176.0 mg, 0.7 mmol) in DCM (10 mL) was added HATU (343.0 mg, 0.9 mmol), DIPEA (279.0 mg, 2.1 mmol) and 0006-3 (208.0 mg, 0.6 mmol). The mixture was stirred at rt for 1 h. After the reaction was finished (by LCMS), the reaction solvent was removed in vacuo, the crude was purified directly by prep-HPLC to give the desired product 0016-4 (310.0 mg, yield: 90.1%) as a white solid.

The Synthesis of (S)-2-(2,6-dichlorobenzamido)-3-(2-(3-(5-methoxypyridin-2-ylamino)benzamido)acetamido)propanoic acid (SU15210-0016)

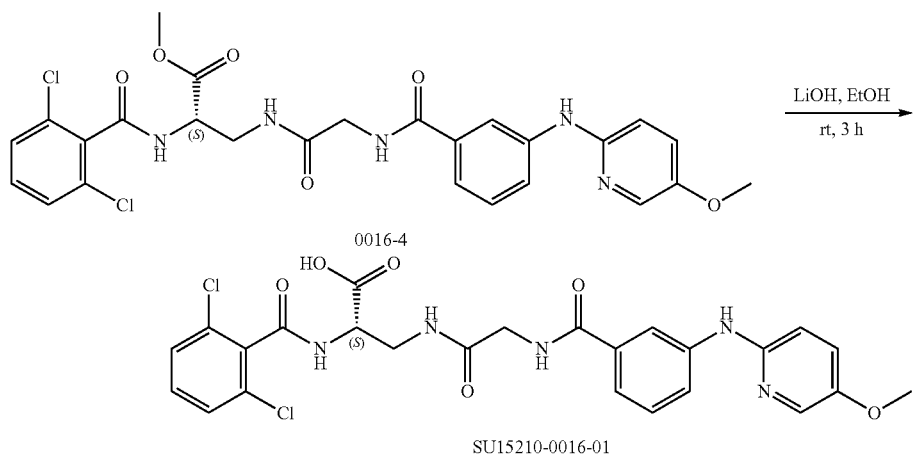

To a solution of compound 0016-4 (310.0 mg, 0.5 mmol) in ethanol (5 mL) was added LiOH.H$_2$O (113.0 mg, 2.7 mmol). The mixture was stirred at rt for 3 h. After the consumption of starting material (by LCMS), the reaction mixture was concentrated in vacuo, the crude was dissolved with 5 mL H$_2$O, 1N HCl was added to adjust pH=2~3, the mixture was freeze-drying to give the crude product, the crude was purified by prep-HPLC to give SU15210-0016 (116.8 mg, 38.6% yield) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 5% [water+0.05% TFA] and 95% [water+0.05% TFA] in 1.6 min, then under this condition for 1.4 min, finally changed to 95% [water+0.05% TFA] and 5% [CH$_3$CN+0.05% TFA]

in 0.05 min and under this condition for 0.7 min), Purity: 97.96%, Rt=1.308 min; MS Calcd.: 559.0; MS Found: 559.8 [M+H]⁺.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH₃CN+0.05% TFA] to 5% [water+0.05% TFA] and 95% [water+0.05% TFA] in 10 min, then under this condition for 5 min, finally changed to 95% [water+0.05% TFA] and 5% [CH₃CN+0.05% TFA] in 0.1 min and under this condition for 5 min), Purity: 100%, Rt=5.530 min.

¹H NMR (400 MHz, DMSO-d₆) δ 12.83 (brs, 1H), 9.17 (brs, 1H), 8.98 (d, J=7.6 Hz, 1H), 8.60 (t, J=6.0 Hz, 1H), 7.98 (1H, s), 7.88-7.93 (m, 2H), 7.81 (d, J=7.6 Hz, 1H), 7.32-7.51 (m, 6H), 6.90 (d, J=9.2 Hz, 1H), 4.56 (q, J=7.2 Hz, 1H), 3.79-3.92 (m, 2H), 3.77 (s, 3H), 3.52-3.56 (m, 1H), 3.39-3.44 (m, 1H).

SU15210-0047-01

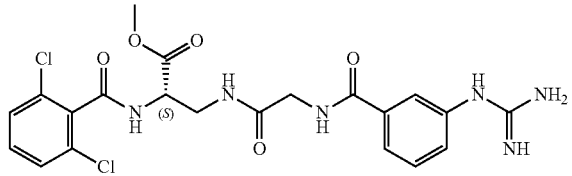

Chemical Formula: C₂₁H₂₂Cl₂N₆O₅
Molecular Weight: 509.34

Scheme: Route for SU15210-0047-01

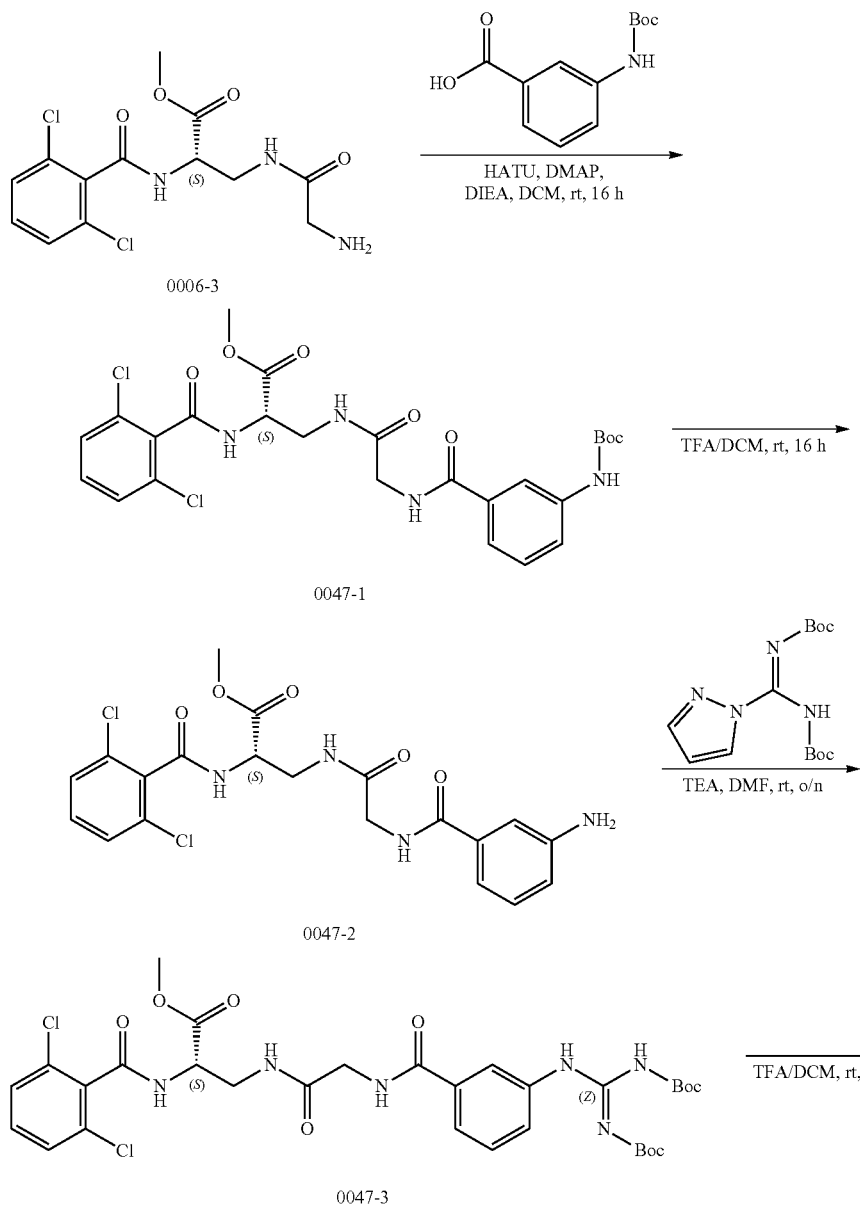

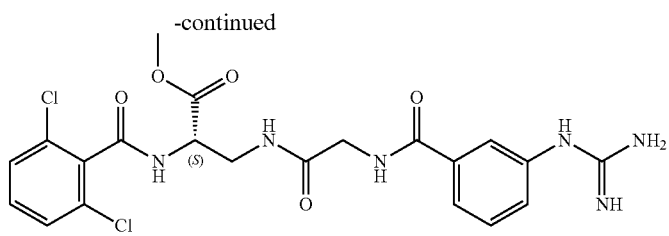

SU15210-0047-01

The Synthesis of (S)-methyl 3-(2-(3-(tert-butoxy-carbonylamino)benzamido)acetamido)-2-(2,6-dichlorobenzamido)propanoate (0047-1)

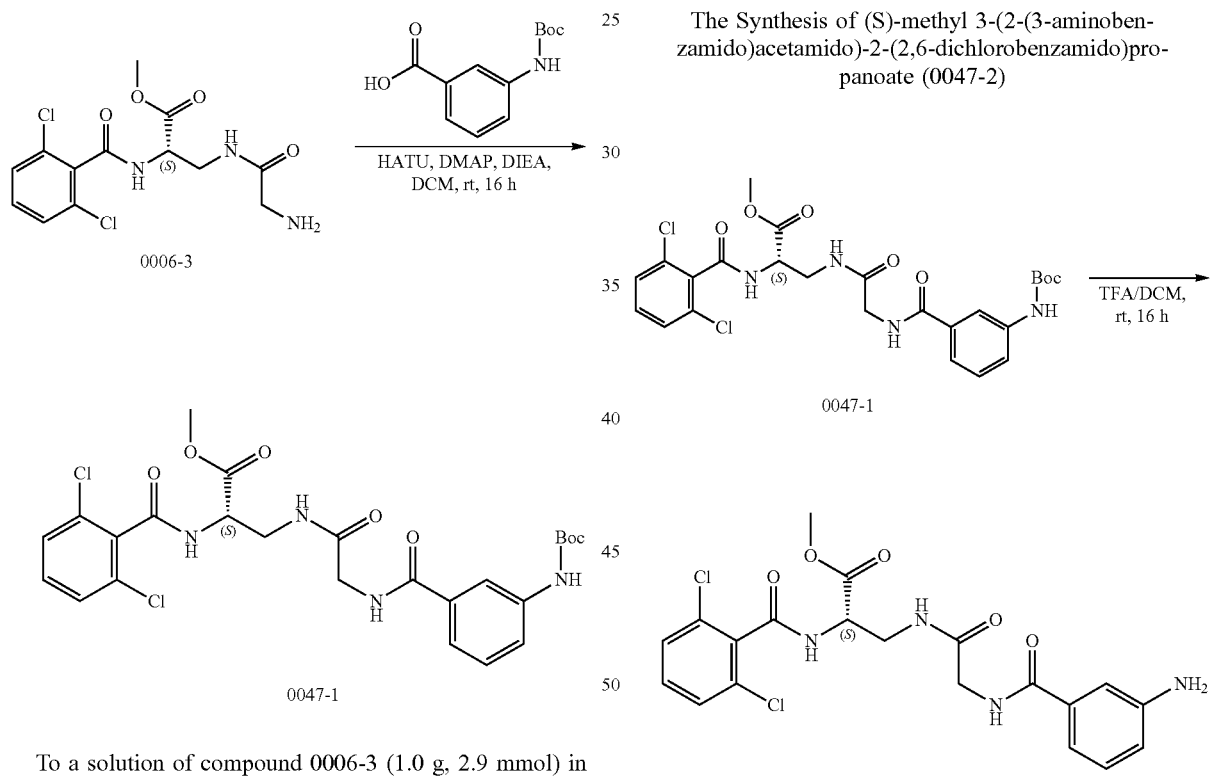

To a solution of compound 0006-3 (1.0 g, 2.9 mmol) in DCM (20 mL) was added 3-(tert-butoxycarbonylamino) benzoic acid (680.0 mg, 2.9 mmol), TEA (290.6 mg, 2.9 mmol), DMAP (170.0 mg, 1.5 mmol) and DCC (600 mg, 2.9 mmol). The mixture was stirred at rt for 16 h. After the reaction was finished (by LCMS), the reaction solvent was removed in vacuo, the crude was purified directly by prep-HPLC to get the desired product 0047-1 (750.0.0 mg, yield 46.0%) as colorless oil.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min. Purity: 97.3%. Rt=0.723 min; MS Calcd.: 566.7; MS Found: 567.7 [M+H]$^+$.

The Synthesis of (S)-methyl 3-(2-(3-aminobenzamido)acetamido)-2-(2,6-dichlorobenzamido)propanoate (0047-2)

To a solution of 0047-1 (750.0 mg, 1.3 mmol) in TFA/DCM (2 mL/10 mL), the mixture was stirred at rt overnight. After the reaction was completed, the solvent was removed in vacuo to give 0047-2 (550.0 mg, yield: 89.1%) as yellow oil.

The Synthesis of (S,Z)-methyl 3-(2-(3-(2,3-bis(tert-butoxycarbonyl)guanidino)benzamido)acetamido)-2-(2,6-dichlorobenzamido)propanoate (0047-3)

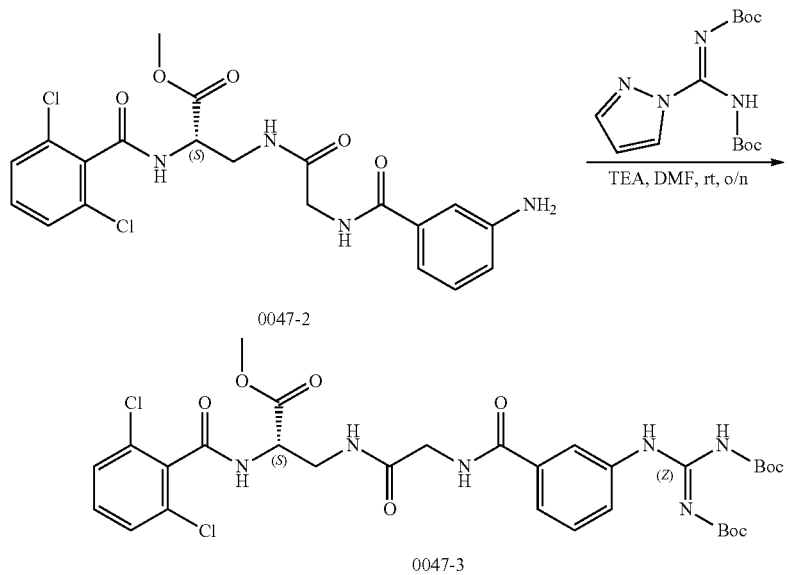

0047-3

A mixture of tert-butyl (NE)-N-[(tert-butoxycarbonylamino)-pyrazol-1-yl-methylene]carbamate (187.0 mg, 0.64 mmol), 0047-2 (200 mg, 0.43 mmol) and TEA (82.0 mg, 0.8 mmol) in DMF (10 mL) was stirred at 40° C. overnight. After the reaction was completed, the reaction mixture was quenched with water and extracted with EA (20 mL×3). The organic layers were washed with brine, dried over MgSO$_4$ and concentrated in vacuo, the residue was purified by column chromatography (DCM/MeOH=20:1) to give 0047-3 (80.0 mg, yield: 26.4%) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min. Purity: 97.9%. Rt=0.785 min; MS Calcd.: 708.7; MS Found: 709.7 [M+H]$^+$.

The Synthesis of (S)-methyl 2-(2,6-dichlorobenzamido)-3-(2-(3-guanidinobenzamido)acetamido) propanoate (SU15210-0047-01)

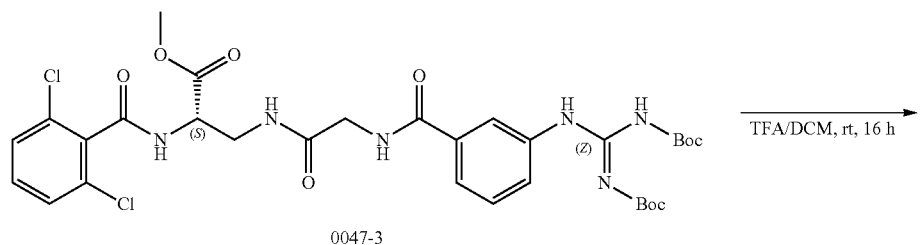

0047-3

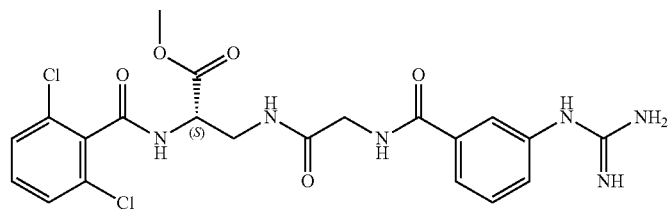

SU15210-0047-01

To a solution of 0047-3 (80.0 mg, 0.11 mmol) in TFA/DCM (2 mL/10 mL), the mixture was stirred at rt overnight. After the reaction was completed, the solvent was removed in vacuo, the residue was further purified by prep-HPLC to give SU15210-0047-01 (35.0 mg, yield: 61.0%) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 96.7%. Rt=1.259 min; MS Calcd.: 508.1; MS Found: 509.1 [M+H]$^+$.

Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min. Purity: 95.2%. Rt=5.304 min.

$^1$H NMR (400 MHz, DMSO-d$_6$) δ 10.91 (brs, 1H), 8.56 (t, J=6.0 Hz, 1H), 7.92 (t, J=6.0 Hz, 1H), 7.21-7.50 (m, 7H), 6.91 (d, J=8.0 Hz, 1H), 5.32-5.61 (brs, 3H), 4.57 (t, J=6.8 Hz, 1H), 3.79 (t, J=5.6 Hz, 2H), 3.63 (s, 3H), 3.48-3.53 (m, 1H), 3.35-3.41 (m, 1H).

SU15210-0048-01

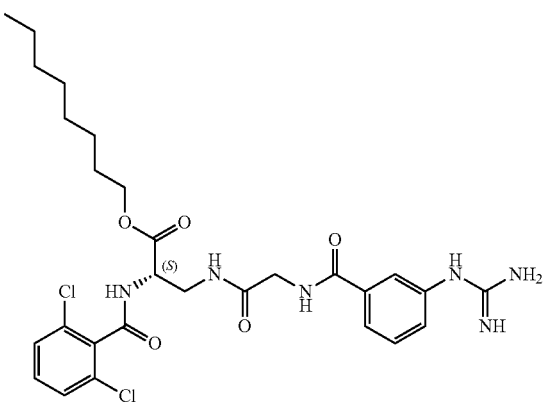

SU15210-0048-01

Chemical Formula: C$_{28}$H$_{36}$Cl$_2$N$_6$O$_5$
Molecular Weight: 607.53

Scheme: Route for SU15210-0048-01

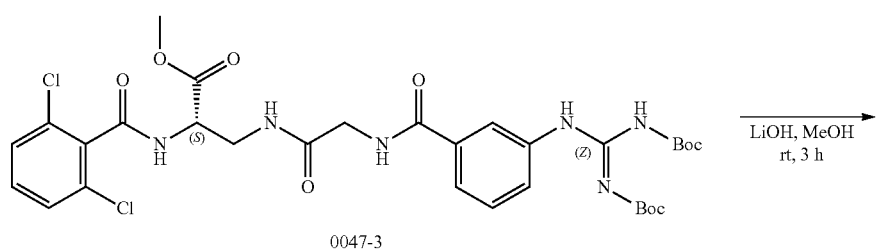

0047-3

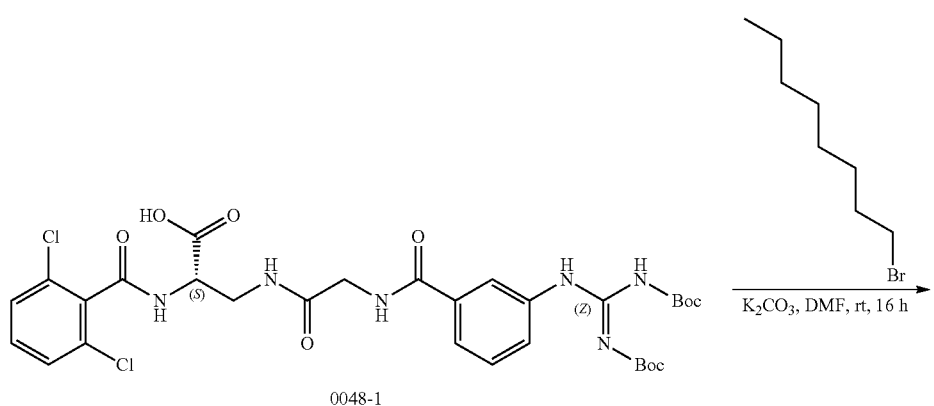

0048-1

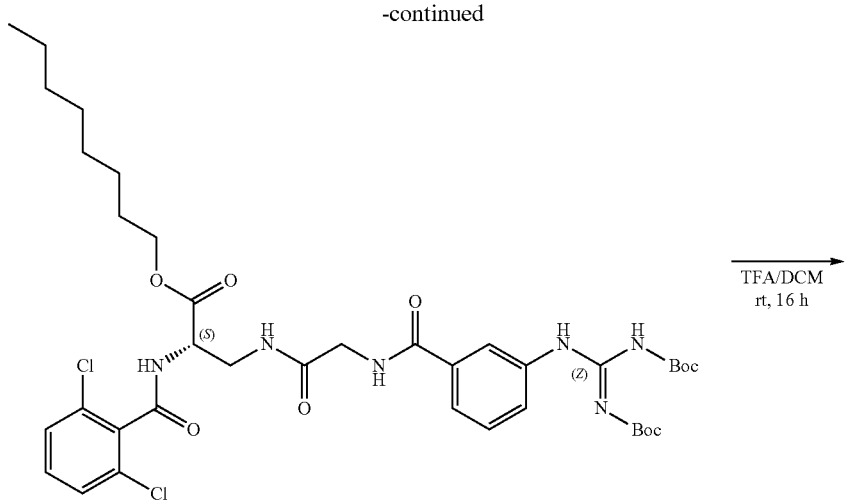
0048-2
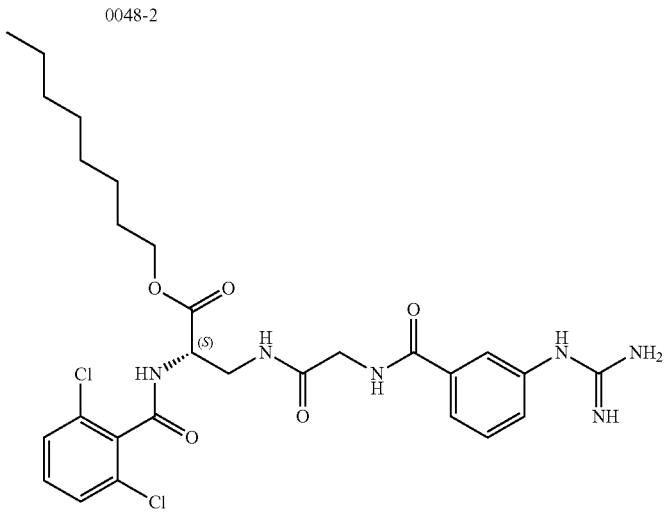
SU15210-0048-01
The Synthesis of (S,Z)-3-(2-(3-(2,3-bis(tert-butoxy-carbonyl)guanidino)-benzamido)acetamido)-2-(2,6-dichlorobenzamido)propanoic acid (0048-1)
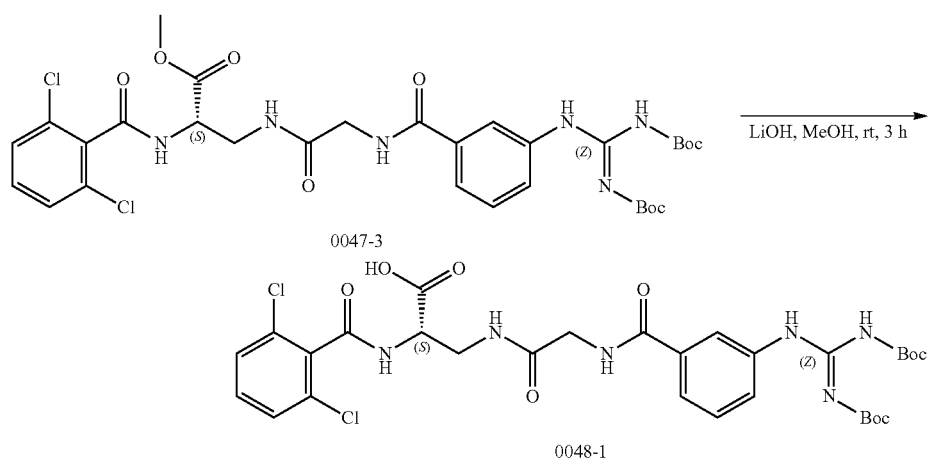

To a solution of compound 0047-3 (600.0 mg, 0.8 mmol) in methanol (5 mL) was added LiOH.H$_2$O (67.2 mg, 1.6 mmol). The mixture was stirred at rt for 3 h. After the consumption of starting material (by LCMS), the reaction mixture was concentrated in vacuo, the crude was dissolved with 5 mL H$_2$O, 1N HCl was added to adjust pH=7~8, the mixture was freeze-drying to give 0048-1 (550.0 mg, yield: 93.2%) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min. Purity: 98.1%. Rt=1.828 min; MS Calcd.: 694.7; MS Found: 695.7 [M+H]$^+$.

The Synthesis of (S,Z)-octyl 3-(2-(3-(2,3-bis(tert-butoxycarbonyl)guanidino)-benzamido)acetamido)-2-(2,6-dichlorobenzamido)propanoate (0048-2)

To a solution of 0048-1 (200.0 mg, 0.3 mmol) in DMF (10.0 ml), was added 1-bromooctane (115.0 mg, 0.6 mmol) and K$_2$CO$_3$ (69.0 mg, 0.5 mmol). The reaction mixture was stirred at room temperature overnight. After the reaction was completed (by LCMS), the reaction mixture was quenched with water, and extracted with (DCM). The organic layers were washed with brine, dried over MgSO$_4$ and concentrated in vacuo to give 0048-2 (200.0 mg, yield: 86.0%) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min. Purity: 87.4%. Rt=2.211 min; MS Calcd.: 806.7; MS Found: 807.7 [M+H]$^+$.

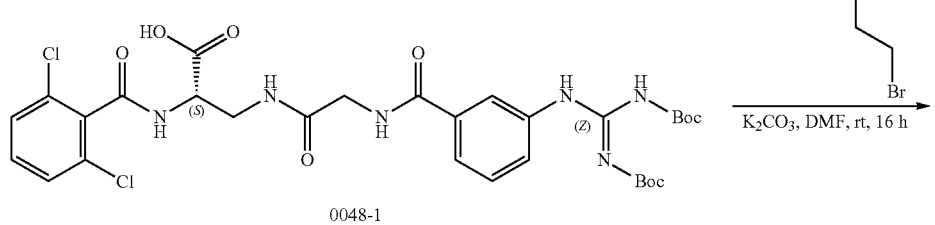

0048-1

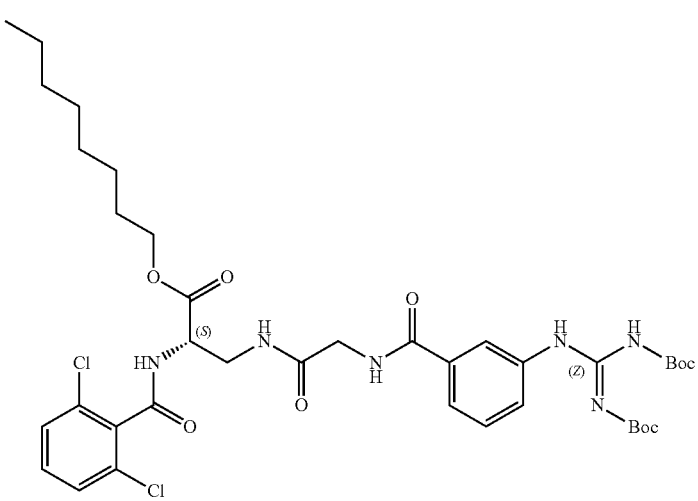

0048-2

The Synthesis of (S)-octyl 2-(2,6-dichlorobenzamido)-3-(2-(3-guanidinobenzamido)acetamido)propanoate (SU15210-0048-01)

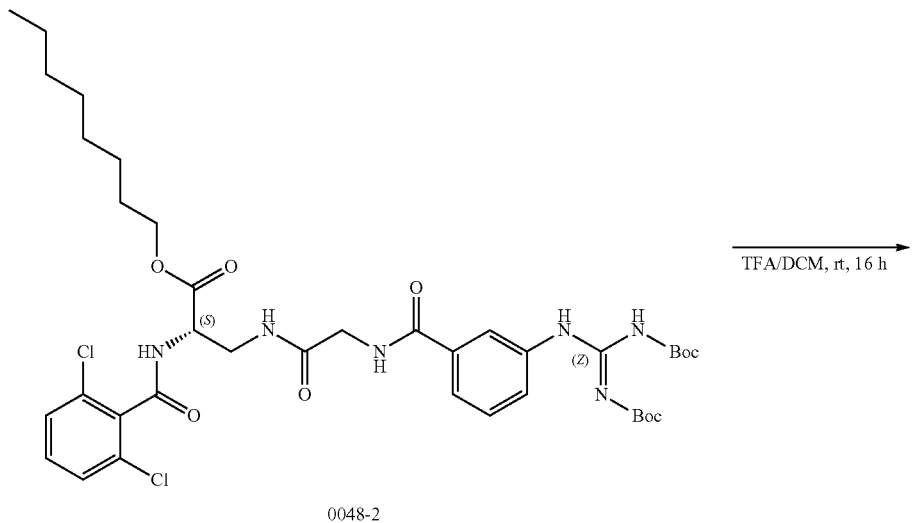

0048-2

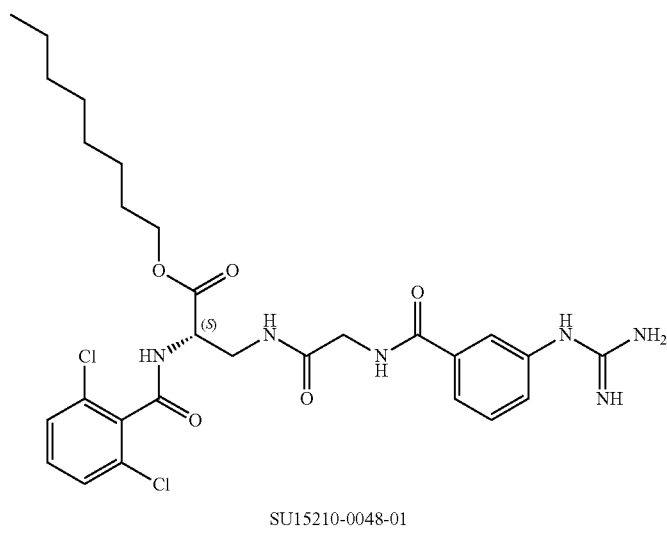

SU15210-0048-01

To a solution of 0048-2 (200.0 mg, 0.3 mmol) in TFA/DCM (2 mL/10 mL), the mixture was stirred at rt overnight. After the reaction was completed, the solvent was removed in vacuo, the residue was further purified by prep-HPLC to give SU15210-0048-01 (110.0 mg, yield: 73.3%) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 90% [(total 10 mM AcONH$_4$) H$_2$O/MeCN=900/100 (v/v)] and 10% [(total 10 mM AcONH$_4$) H$_2$O/MeCN=100/900 (v/v)] to 10% [(total 10 mM AcONH$_4$) H$_2$O/MeCN=900/100 (v/v)] and 90% [(total 10 mM AcONH$_4$) H$_2$O/MeCN=100/900 (v/v)] in 1.6 min, then under this condition for 2.4 min, finally changed to 90% [(total 10 mM AcONH$_4$) H$_2$O/MeCN=900/100 (v/v)] and 10% [(total 10 mM AcONH$_4$) H$_2$O/MeCN=100/900 (v/v)] in 0.1 min and under this condition for 0.7 min. Purity is 97.1%. Rt=2.044 min; MS Calcd.: 606.2; MS Found: 607.2 [M+H]$^+$.

Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min. Purity is 96.2%. Rt=8.635 min.

$^1$HNMR (400 MHz, DMSO-d$_6$) δ 9.04 (d, J=7.2 Hz, 1H), 8.53 (t, J=5.6 Hz, 1H), 7.90 (t, J=5.6 Hz, 1H), 7.40-7.50 (m, 3H), 7.21-7.31 (m, 3H), 6.89-6.91 (m, 1H), 5.27-5.29 (m, 3H), 4.58-4.60 (m, 1H), 4.04 (t, J=6.8 Hz, 2H), 3.79 (t, J=6.4 Hz, 2H), 3.48-3.55 (m, 1H), 3.34-3.41 (m, 2H), 1.52-1.59 (m, 2H), 1.23-1.29 (m, 10H), 0.81-0.85 (m, 3H).

SU15210-0049-01
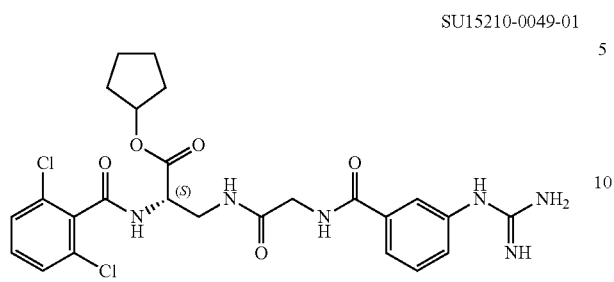
Chemical Formula: $C_{25}H_{28}Cl_2N_6O_5$
Molecular Weight: 563.43
Scheme: Route for SU15210-0049-01
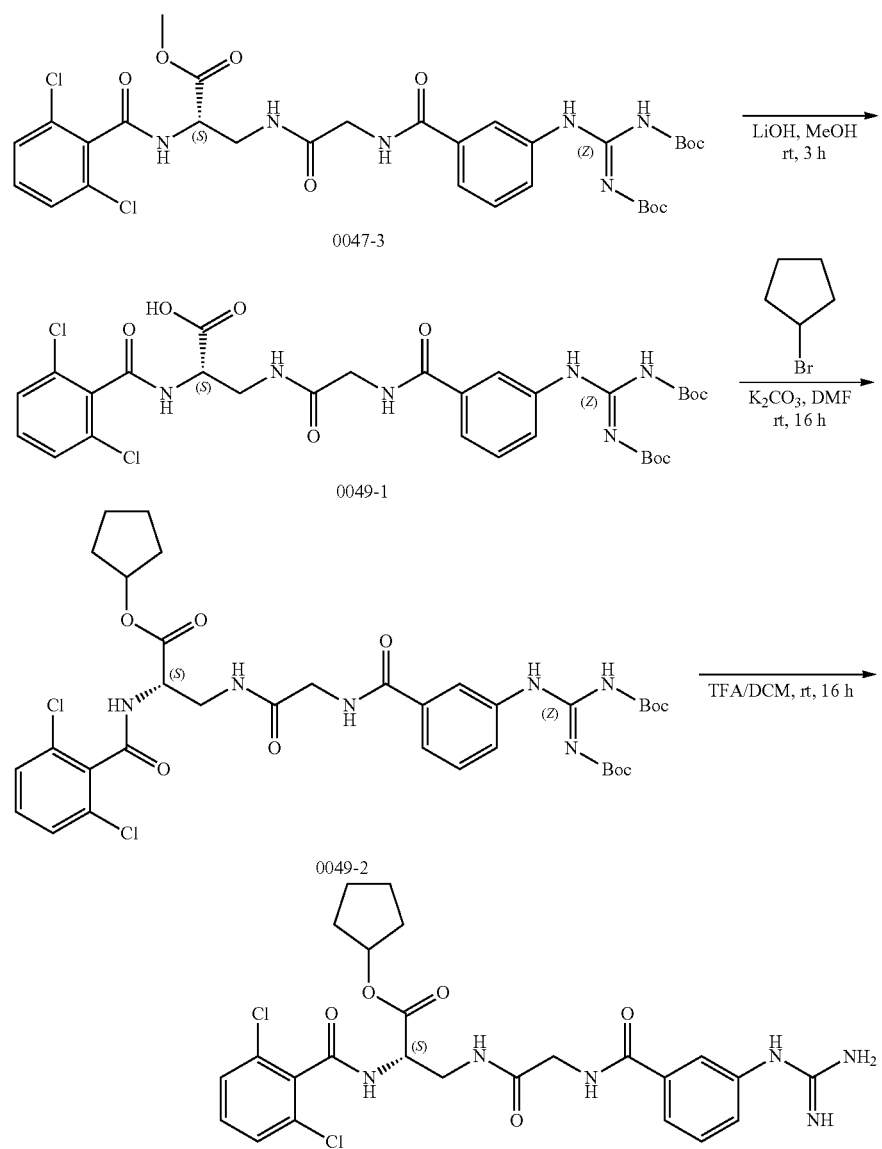

The Synthesis of (S,Z)-3-(2-(3-(2,3-bis(tert-butoxycarbonyl)guanidino)-benzamido)acetamido)-2-(2,6-dichlorobenzamido)propanoic acid (0049-1)

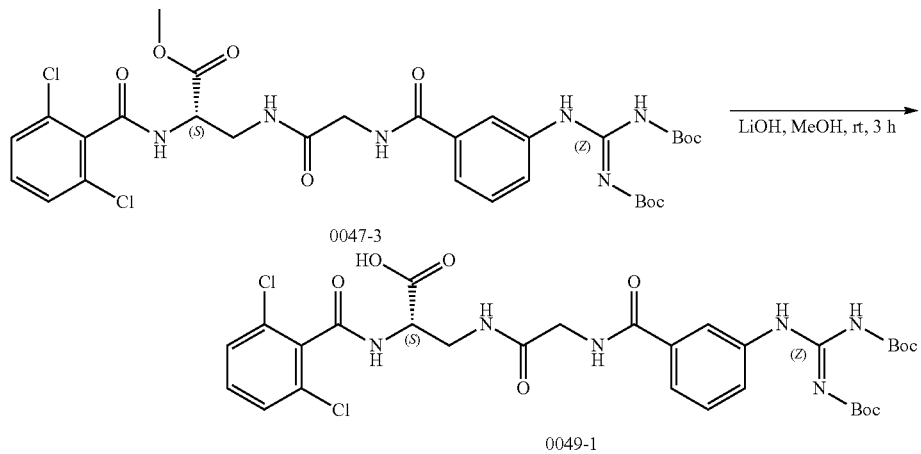

To a solution of compound 0047-3 (600.0 mg, 0.8 mmol) in methanol (10 mL) was added LiOH.H₂O (67.2 mg, 1.6 mmol). The mixture was stirred at rt for 3 h. After the consumption of starting material (by LCMS), the reaction mixture was concentrated in vacuo, the crude was dissolved with 5 mL H₂O, 1N HCl was added to adjust pH=7~8, the mixture was freeze-drying to give 0048-1 (550.0 mg, yield: 93.2%) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 0% [water+0.05% TFA] and 100% [CH₃CN+0.05% TFA] in 1.6 min, then under this condition for 1.4 min, finally changed to 95% [water+0.05% TFA] and 5% [CH₃CN+0.05% TFA] in 0.05 min and under this condition for 0.7 min. Purity: 98.1%. Rt=1.828 min; MS Calcd.: 694.7; MS Found: 695.7 [M+H]⁺.

The Synthesis of (S,Z)-cyclopentyl 3-(2-(3-(2,3-bis(tert-butoxycarbonyl)guanidino)-benzamido)acetamido)-2-(2,6-dichlorobenzamido)propanoate (0049-2)

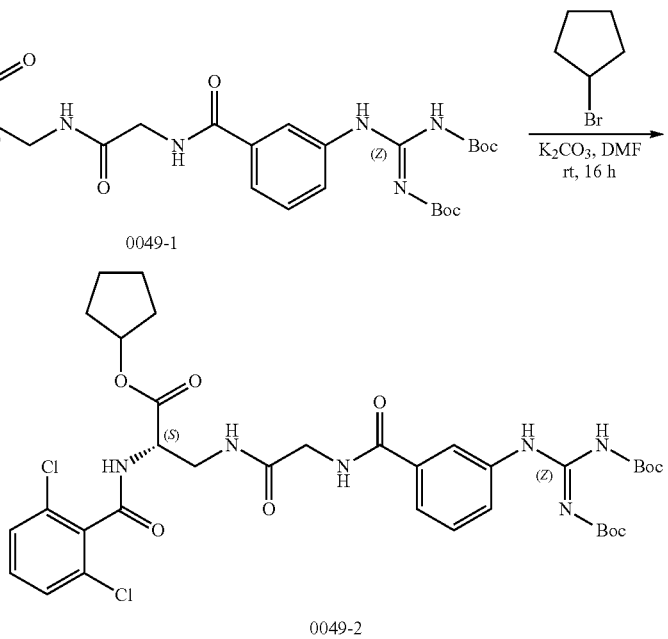

To a solution of 0049-1 (200.0 mg, 0.3 mmol) in DMF (10.0 ml), was added bromocyclopentane (88.2 mg, 0.6 mmol) and K$_2$CO$_3$ (69.0 mg, 0.5 mmol). The reaction mixture was stirred at room temperature overnight. After the reaction was completed (by LCMS), the reaction mixture was quenched with water, and extracted with (DCM). The organic layers were washed with brine, dried over MgSO$_4$ and concentrated in vacuo, the crude was further purified by prep-HPLC to give 0049-2 (120.0 mg, yield: 54.5%) as a white solid.

Agilent LCMS 1200-6110, Column: Waters X-Bridge C18 (50 mm*4.6 mm*3.5 μm); Column Temperature: 40° C.; Flow Rate: 1.5 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.5 min, then under this condition for 0.5 min, finally changed to 95% [water+0.05% TFA] and 5% [CH$_3$CN+0.05% TFA] in 0.1 min and under this condition for 0.1 min. Purity: 96.7%. Rt=0.856 min; MS Calcd.: 762.7; MS Found: 763.7 [M+H]$^+$.

The Synthesis of (S)-cyclopentyl 2-(2,6-dichlorobenzamido)-3-(2-(3-guanidinobenzamido)acetamido)propanoate (SU15210-0049-01)

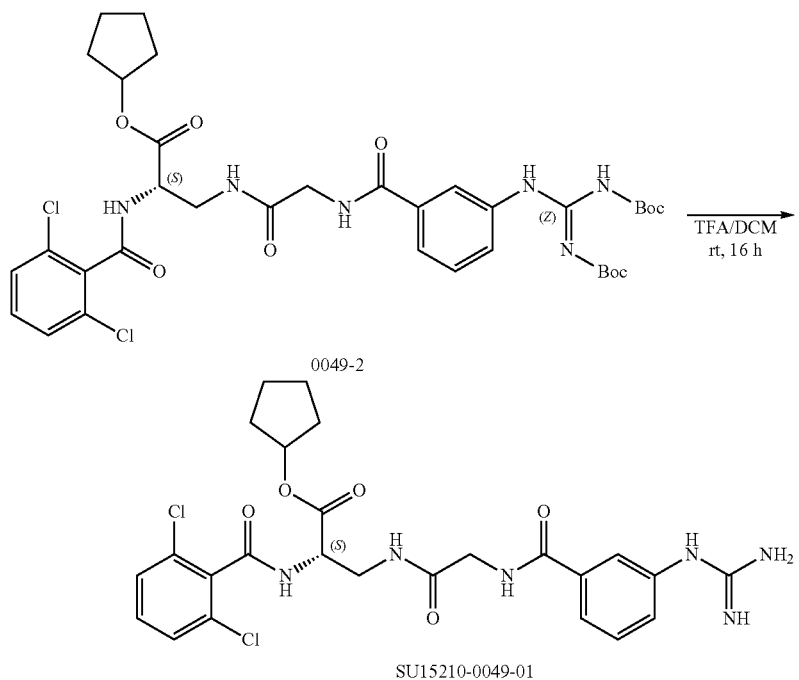

To a solution of 0049-2 (120.0 mg, 0.3 mmol) in TFA/DCM (2 mL/10 mL), the mixture was stirred at rt overnight. After the reaction was completed, the solvent was removed in vacuo, the residue was further purified by prep-HPLC to give SU15210-0049-01 (50.0 mg, yield: 56.5%) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity is 100.0%. Rt=10515 min; MS Calcd.: 562.1; MS Found: 563.1[M+H]$^+$.

Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 100.0%. Rt=7.493 min.

$^1$H NMR (400 MHz, DMSO-d$_6$) δ 9.03 (s, 1H), 8.53 (t, J=5.6 Hz, 1H), 7.89 (t, J=5.6 Hz, 1H), 7.41-7.51 (m, 3H), 7.22-7.31 (m, 3H), 6.90 (d, J=7.6 Hz, 1H), 5.23-5.27 (m, 3H), 5.09 (t, J=6.4 Hz, 1H), 4.54 (s, 1H), 3.80 (t, J=6.4 Hz, 2H), 3.48-3.54 (m, 1H), 3.35-3.42 (m, 1H), 1.77-1.81 (m, 2H), 1.64-1.65 (m, 4H), 1.52-1.54 (s, 2H), 1.22 (s, 1H).

SU15210-0050-01

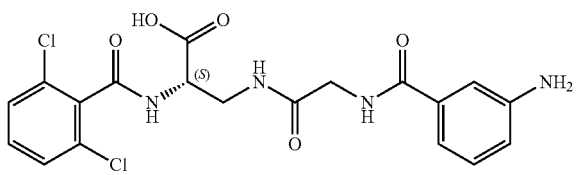

Chemical Formula: C$_{19}$H$_{18}$Cl$_2$N$_4$O$_5$
Molecular Weight: 453.28

Scheme: Route for SU15210-0050-01

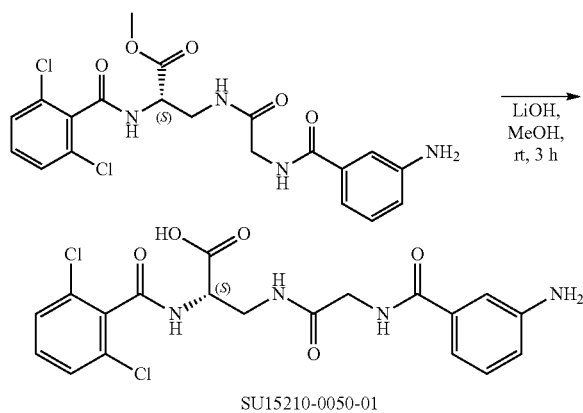

SU15210-0050-01

The Synthesis of (S)-3-(2-(3-aminobenzamido)acetamido)-2-(2,6-dichlorobenzamido)propanoic acid (SU15210-0050-01)

To a solution of compound 0047-2 (100.0 mg, 0.2 mmol) in methanol (10 mL) was added LiOH.H$_2$O (84.0 mg, 2.0 mmol). The mixture was stirred at rt for 3 h. After the consumption of starting material (by LCMS), the reaction mixture was concentrated in vacuo, the crude was dissolved with 5 mL H$_2$O, 1N HCl was added to adjust pH=7~8, the mixture was freeze-drying and further purified by prep-HPLC to give SU15210-0050-01 (70.0 mg, yield: 72.2%) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min. Purity: 100.0%. Rt=1.176 min; MS Calcd.: 452.1; MS Found: 453.1 [M+H]$^+$.

Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 10 min, then under this condition for 5 min, finally changed to 95% [water+0.05% TFA] and 5% [CH$_3$CN+0.05% TFA] in 0.1 min and under this condition for 5 min. Purity: 97.7%. Rt=4.791 min.

$^1$HNMR (400 MHz, DMSO-d$_6$) δ 8.89 (d, J=6.0 Hz, 1H), 8.42 (t, J=6.0 Hz, 1H), 7.87 (t, J=5.6 Hz, 1H), 7.41-7.51 (m, 4H), 6.98-7.10 (m, 4H), 6.69 (dd, J=7.6 Hz, 2.0 Hz, 1H), 5.21-5.25 (m, 1H), 4.50 (q, J=6.8 Hz, 1H), 3.75-3.87 (m, 2H), 3.42-3.54 (m, 2H).

SU15210-0063

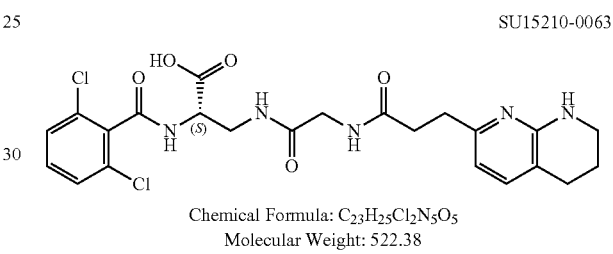

Chemical Formula: C$_{23}$H$_{25}$Cl$_2$N$_5$O$_5$
Molecular Weight: 522.38

Scheme: Route for SU15210-0063

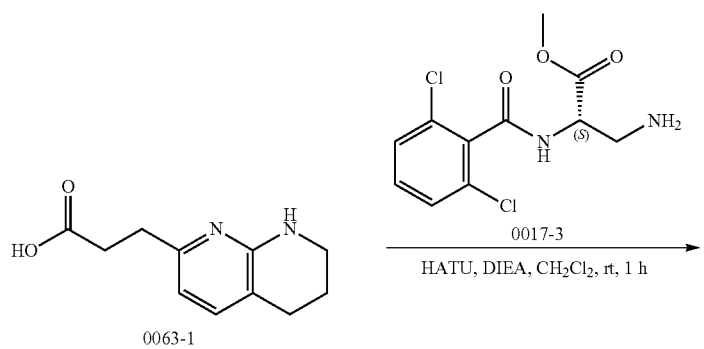

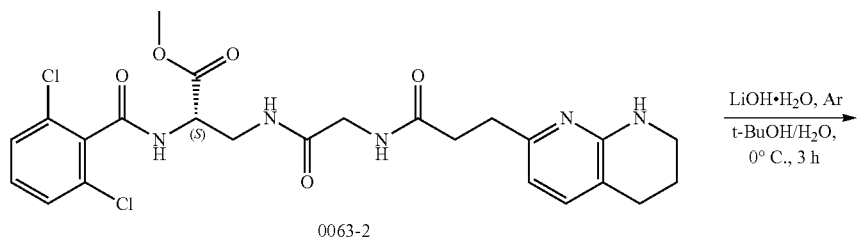

0063-2

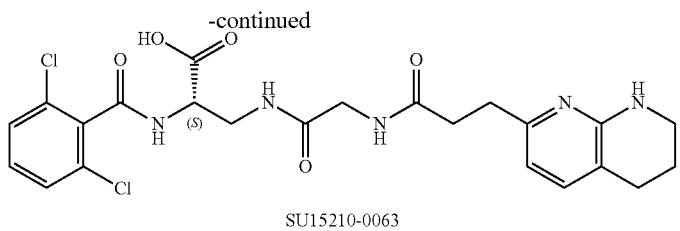

SU15210-0063

The Synthesis of (S)-methyl 2-(2,6-dichlorobenzamido)-3-(2-(3-(5,6,7,8-tetrahydro-1,8-naphthyridin-2-yl)propanamido)acetamido)propanoate (0063-2)

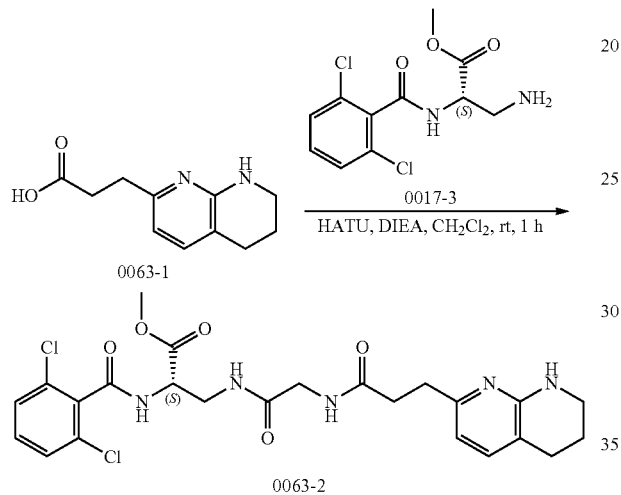

To a solution of compound 0063-1 (206.0 mg, 1.0 mmol) in CH$_2$Cl$_2$ (10 mL) was added HATU (571.0 mg, 1.5 mmol), DIEA (389.0 mg, 3.0 mmol) and 0017-3 (417 mg, 1.2 mmol). The mixture was stirred at rt for 1 h. After the consumption of starting material (by LCMS), the reaction solvent was quenched with 20 mL water, and extracted with EtOAc (30×3 mL), the organic layer was washed with saturated aqueous NaCl, collected the organic layer and dried over anhydrous Na$_2$SO$_4$, filtered and concentrated in vacuo, the crude was purified by CC to get the product 0063-2 (340.0 mg, yield: 63.6%) was get as a white solid.

The Synthesis of (S)-2-(2,6-dichlorobenzamido)-3-(2-(3-(5,6,7,8-tetrahydro-1,8-naphthyridin-2-yl)propanamido)acetamido)propanoic acid (SU15210-0063)

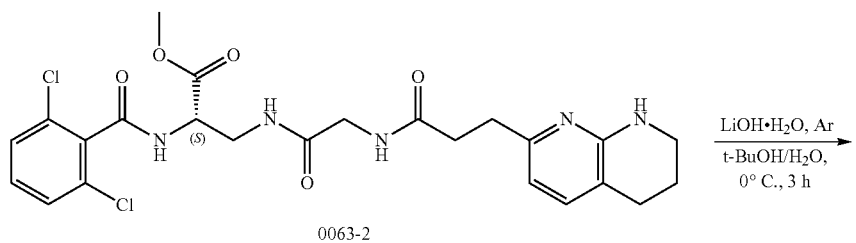

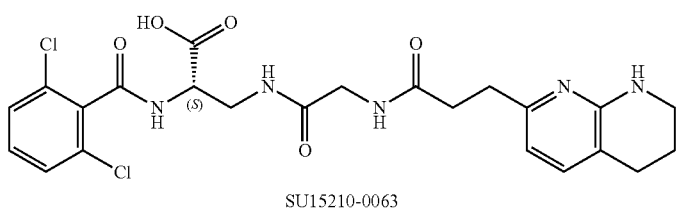

SU15210-0063

To a solution of compound 0063-2 (200.0 mg, 0.4 mmol) in t-BuOH (4 mL) and H₂O (2 mL) was added LiOH.H₂O (32.0 mg, 0.8 mmol). The mixture was stirred at 0° C. for 3 h. After the consumption of starting material (by LCMS), the mixture concentrated in vacuo, the crude was dissolved with 5 mL H₂O, 1N HCl was added to PH=2-3, the mixture was freeze-drying to get the crude product, the crude was purified by prep-HPLC to get the SU15210-0063 (36.5 mg, 18.9% yield) as white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 5% [water+0.05% TFA] and 95% [water+0.05% TFA] in 1.6 min, then under this condition for 1.4 min, finally changed to 95% [water+0.05% TFA] and 5% [CH₃CN+0.05% TFA] in 0.05 min and under this condition for 0.7 min), Purity: 100.00%, Rt=1.259 min; MS Calcd.: 521.0; MS Found: 522.2 [M+H]⁺.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH₃CN+0.05% TFA] to 5% [water+0.05% TFA] and 95% [water+0.05% TFA] in 10 min, then under this condition for 5 min, finally changed to 95% [water+0.05% TFA] and 5% [CH₃CN+0.05% TFA] in 0.1 min and under this condition for 5 min), Purity: 96.65%, Rt=5.459 min.

¹H NMR (400 MHz, CD₃OD) δ 7.35-7.49 (m, 4H), 6.57 (d, J=7.2 Hz, 1H), 4.56-4.59 (m, 1H), 3.84-3.88 (m, 1H), 3.69-3.77 (m, 2H), 3.44-3.54 (m, 3H), 2.98-3.03 (m, 2H), 2.77 (t, J=6.0 Hz, 2H), 2.63 (t, J=6.8 Hz, 2H), 1.88-1.93 (m, 2H).

SU15210-0090

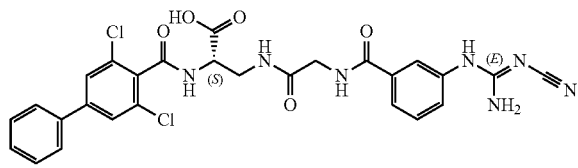

Chemical Formula: C₂₇H₂₃Cl₂N₇O₅
Molecular Weight: 596.42

Scheme: Route for intermediate of SU15210-0090-5

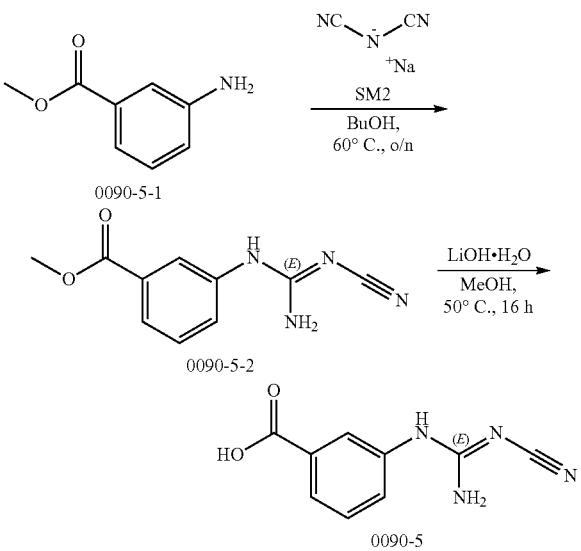

Scheme: Route for SU15210-0090

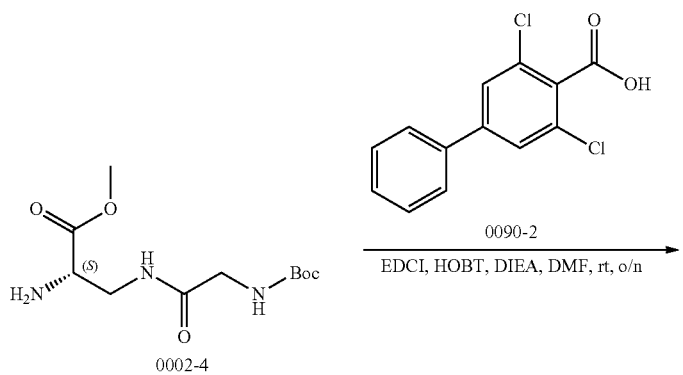

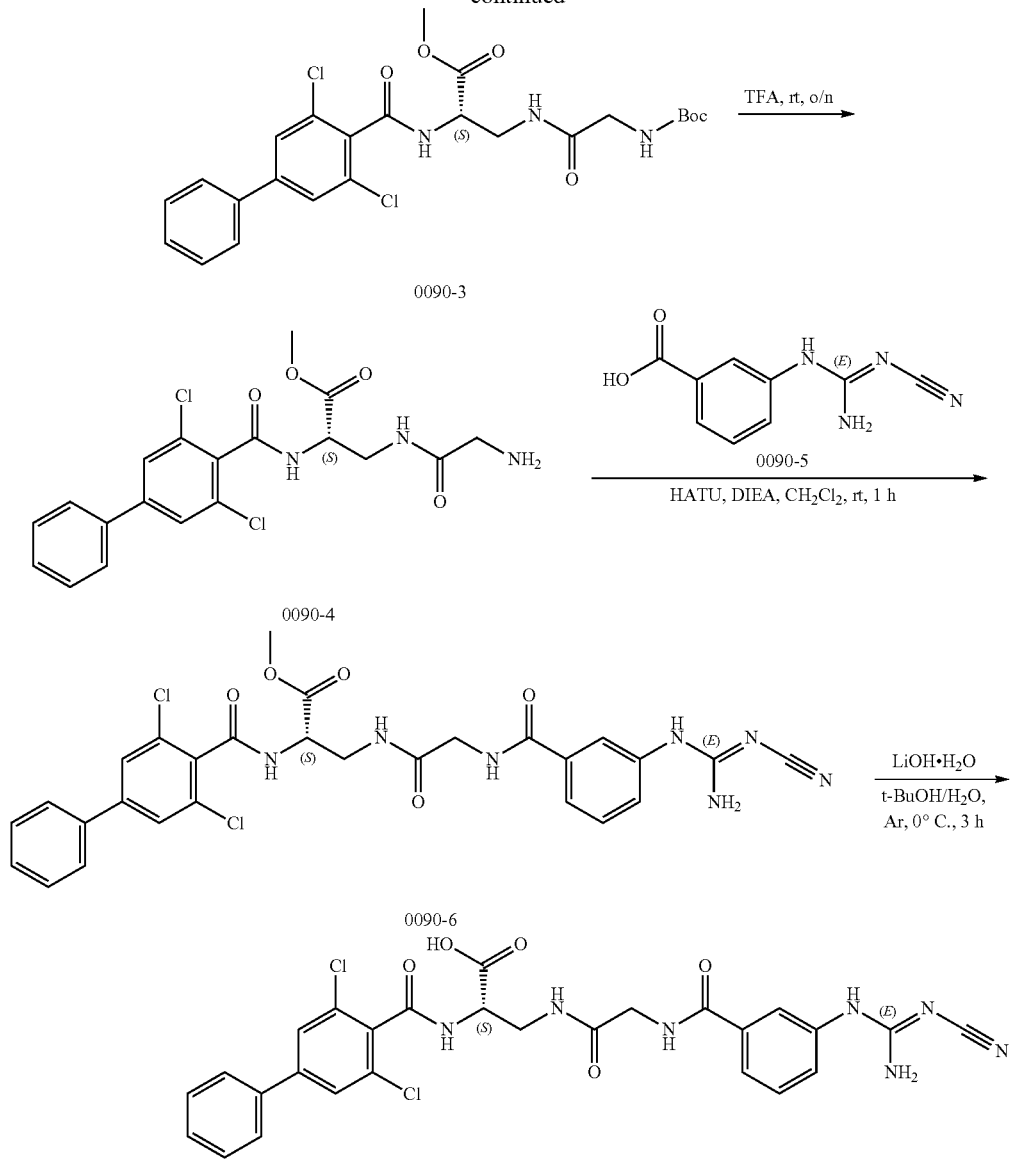

The Synthesis of (E)-methyl 3-(2-cyanoguanidino) benzoate (0090-5-2)

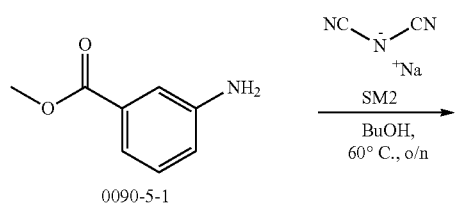

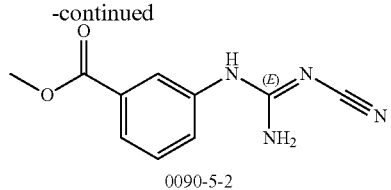

To a solution of compound 0090-5-1 (3.0 g, 20.0 mmol) in BuOH (60 mL) and H₂O (6 mL) was added SM2 (2.7 g, 30.0 mmol). The mixture was stirred at rt for 16 h. After the consumption of starting material (by LCMS), the reaction was concentrated, the crude was quenched with water (100 mL) and extracted with EtOAc (40 mL×3), the organic layer was washed with saturated aqueous NaCl, collected the organic layer and dried over anhydrous Na₂SO₄, filtered and concentrated in vacuo, the crude was purified by CC (PE/EA=3/1) to get the product 0090-5-2 (200.0 mg, yield: 4.58%) as a white solid.

The Synthesis of (E)-3-(2-cyanoguanidino)benzoic acid (0090-5)

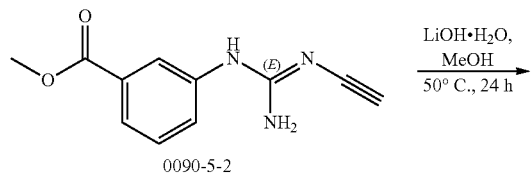

To a solution of compound 0090-5-2 (200.0 g, 0.9 mmol) in MeOH (5 mL) was added LiOH.H₂O (76.2 mg, 1.8 mmol). The reaction was stirred at 50° C. for 24 h. After the reaction was finished, the reaction mixture was concentrated and adjust pH to 2.0 by HCl (1.0 N), the mixture was filtered, the filter cake was collected and dried by freeze-drying to give the product 0090-5 (110 mg, yield: 59.4%) as a white solid.

The Synthesis of (S)-methyl 3-(2-(tert-butoxycarbonylamino)acetamido)-2-(3,5-dichlorobiphenyl-4-ylcarboxamido)propanoate (0090-3)

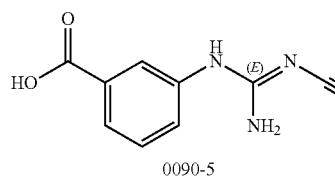

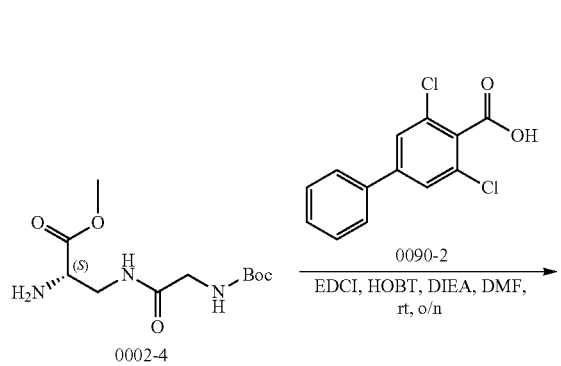

To a solution of compound 0002-4 (1.3 g, 4.8 mmol) in DMF (15 mL) was added EDCI (1.1 g, 5.8 mmol), HOBT (783.3 mg, 5.8 mmol), DIEA (1.3 g, 9.7 mmol) and 0090-2 (1.3 g, 4.8 mmol). The mixture was stirred at rt for overnight. After the reaction was finished (by LCMS), the reaction solvent was quenched with water (100 mL), and extracted with EtOAc (40 mL×3), the organic layer was washed with saturated aqueous NaCl, collected the organic layer and dried over anhydrous Na₂SO₄, filtered and concentrated in vacuo, the crude was purified by CC (PE/EA=4/1) to get the product 0090-3 (1.5 g, yield: 59.2%) as a white solid.

The Synthesis of (S)-methyl 3-(2-aminoacetamido)-2-(3,5-dichlorobiphenyl-4-ylcarboxamido)propanoate (0090-4)

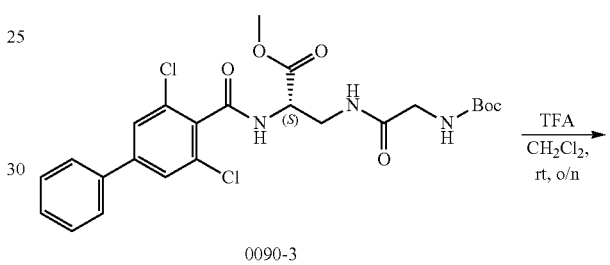

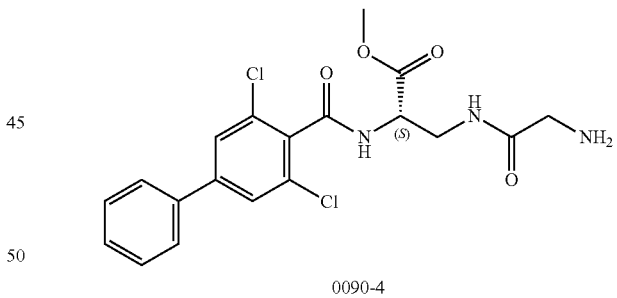

To a solution of compound 0090-3 (1.3 g, 2.5 mmol) in CH₂Cl₂ (20 mL) was added TFA (4 mL). The mixture was stirred at rt for overnight. After the reaction was finished (by LCMS), the mixture was concentrated in vacuo to give the desired product 0090-4 (1.0 g, yield: 96.9%) as a white solid.

The Synthesis of (S,E)-methyl 3-(2-(3-(2-cyanoguanidino)benzamido)acetamido)-2-(3,5-dichlorobiphenyl-4-ylcarboxamido)propanoate (0090-6)

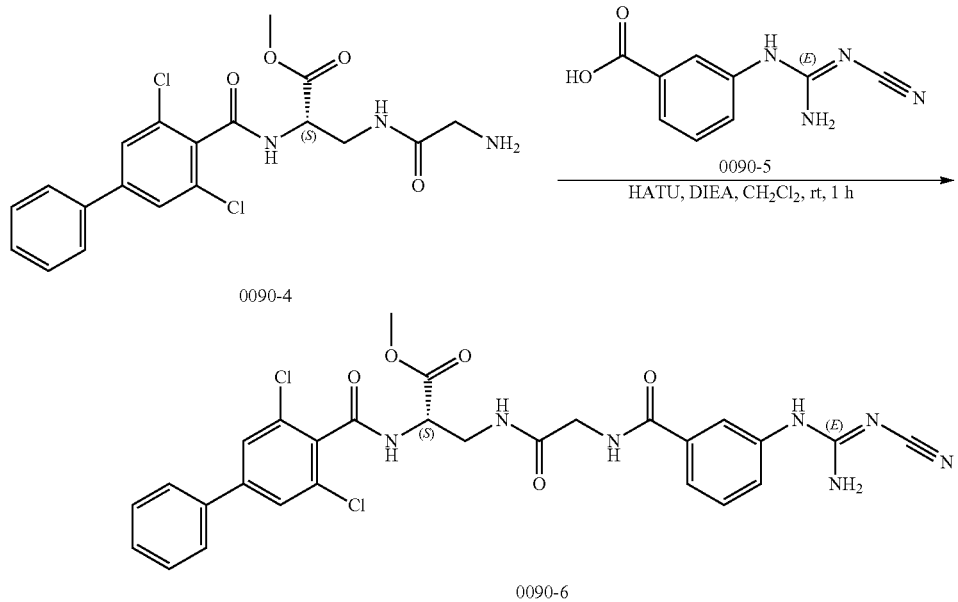

To a solution of compound 0090-5 (110.0 mg, 0.5 mmol) in CH$_2$Cl$_2$ (10 mL) was added HATU (307.3 mg, 0.8 mmol), DIEA (140.0 mg, 1.1 mmol) and 0090-4 (290.0 mg, 0.5 mmol). The mixture was stirred at rt for 1 h. After the reaction was finished (by LCMS), the mixture was purified by prep-HPLC to give the desired product 0090-6 (110.0 mg, yield: 33.5%) as a white solid.

The Synthesis of (S,E)-3-(2-(3-(2-cyanoguanidino)benzamido)acetamido)-2-(3,5-dichlorobiphenyl-4-ylcarboxamido)propanoic acid (SU15210-0090)

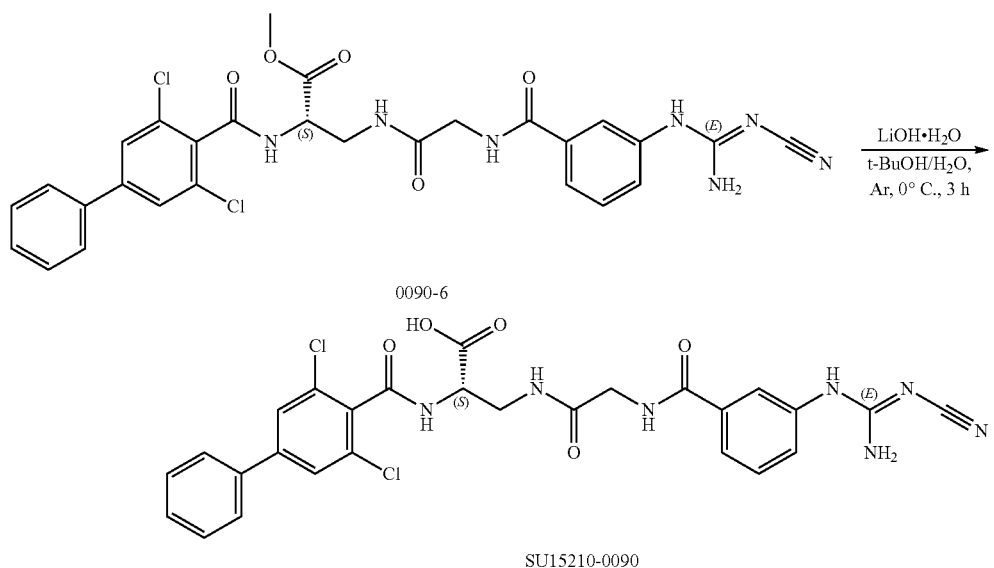

To a solution of compound 0090-6 (110.0 mg, 0.2 mmol) in t-BuOH (4 mL)/H$_2$O (2 mL), was added LiOH.H$_2$O (16.0 mg, 0.4 mmol). The mixture was stirred at 0° C. under Ar atmosphere for 3 h. After the consumption of starting material (by LCMS), the reaction mixture was concentrated and adjust pH to 2.0 by HCl (1.0 N), the mixture was freeze-drying to get the crude product, the crude was purified by prep-HPLC to give SU15210-0090 (60.0 mg, 55.8% yield) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH3CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH3CN+0.05% TFA] in 0.05 min and under this condition for 0.7 min. Purity is 100.0%. Rt=1.528 min; MS Calcd.: 595.0; MS Found: 596.0 [M+H]$^+$.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min. Purity is 100.00%. Rt=6.999 min.

$^1$H NMR (400 MHz, DMSO-d$_6$) δ 9.93 (brs, 1H), 8.69-8.76 (m, 1H), 8.46-8.64 (m, 1H), 7.98 (t, J=5.2 Hz, 1H), 7.80-7.91 (m, 1H), 7.73-7.75 (m, 4H), 7.25-7.52 (m, 9H), 4.28 (q, J=6.4 Hz, 1H), 3.78-3.91 (m, 2H), 3.47-3.60 (m, 2H).

SU15210-0091-01

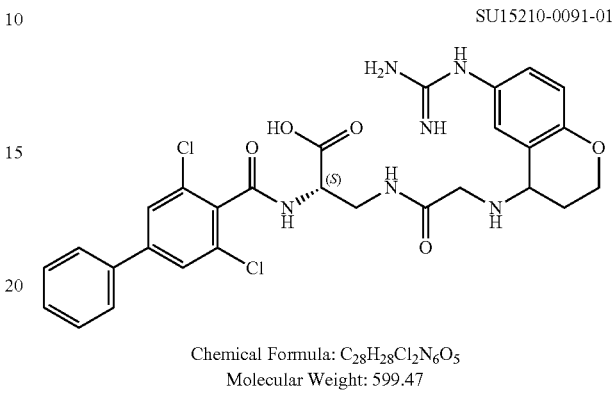

Chemical Formula: C$_{28}$H$_{28}$Cl$_2$N$_6$O$_5$
Molecular Weight: 599.47

Scheme: Route for SU15210-0091-01

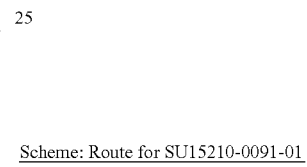

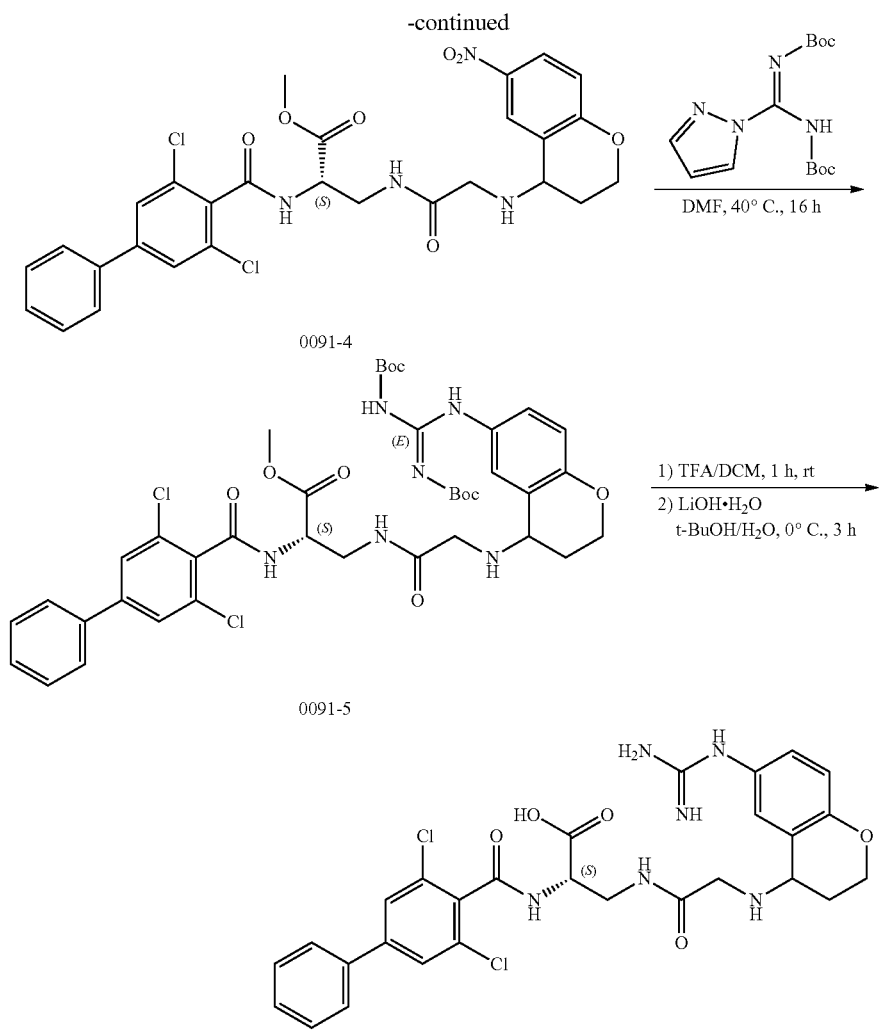

0091-4

0091-5

SU15210-0091-01

The Synthesis of (S)-methyl 3-(2-chloroacetamido)-2-(3,5-dichlorobiphenyl-4-ylcarboxamido)propanoate (0091-2)

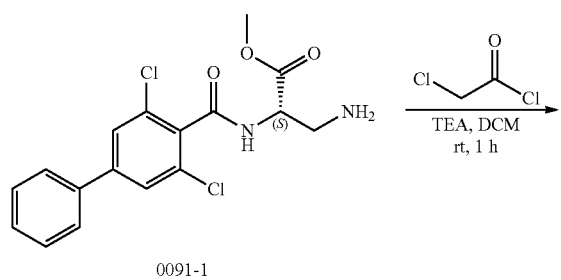

0091-1

0091-2

To a solution of compound 0091-1 (3 g, 8.17 mmol) in DCM (10 mL) was added 2-chloroacetyl chloride (1.01 g, 8.99 mmol) and TEA (2.48 g, 24.51 mmol). The mixture was stirred at room temperature for 1 h. After the consumption of starting material (by LCMS), the reaction solvent was removed in vacuo, the crude was purified directly by column chromatography (petrol ether/EtOAc=1/1) to give 0091-2 (2.5 g, 69% yield) as a white solid.

Agilent LCMS 1200-6110, Column: Waters X-Bridge C18 (30 mm*4.6 mm*2.7 μm); Column Temperature: 40° C.; Flow Rate: 3.0 mL/min; Mobile Phase: from 95%

[water+0.05% TFA] and 5% [CH₃CN+0.05% TFA] to 0% [water+0.05% TFA] and 100% [CH₃CN+0.05% TFA] in 0.8 min, then under this condition for 0.4 min, finally changed to 95% [water+0.05% TFA] and 5% [CH₃CN+0.05% TFA] in 0.1 min. Purity: 87.1%. Rt=0.760 min; MS Calcd.: 443.7; MS Found: 444.7 [M+H]⁺.

The Synthesis of (2S)-methyl 2-(3,5-dichlorobiphenyl-4-ylcarboxamido)-3-(2-(6-nitrochroman-4-ylamino)acetamido)propanoate (0091-3)

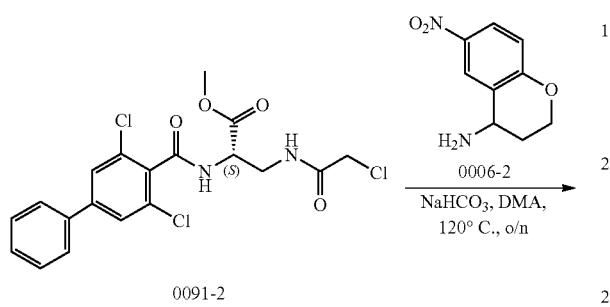

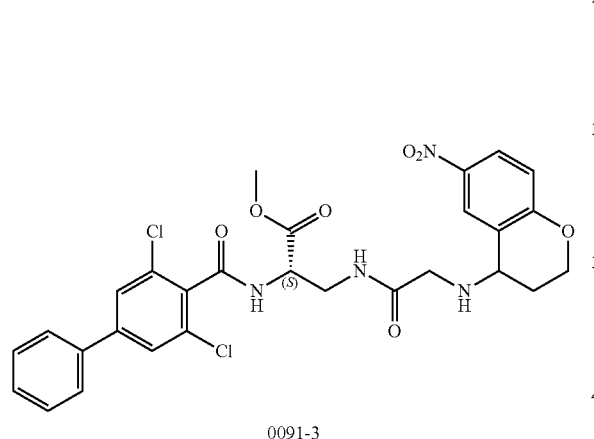

The Synthesis of (2S)-methyl 3-(2-(6-aminochroman-4-ylamino)acetamido)-2-(3,5-dichlorobiphenyl-4-ylcarboxamido)propanoate (0091-4)

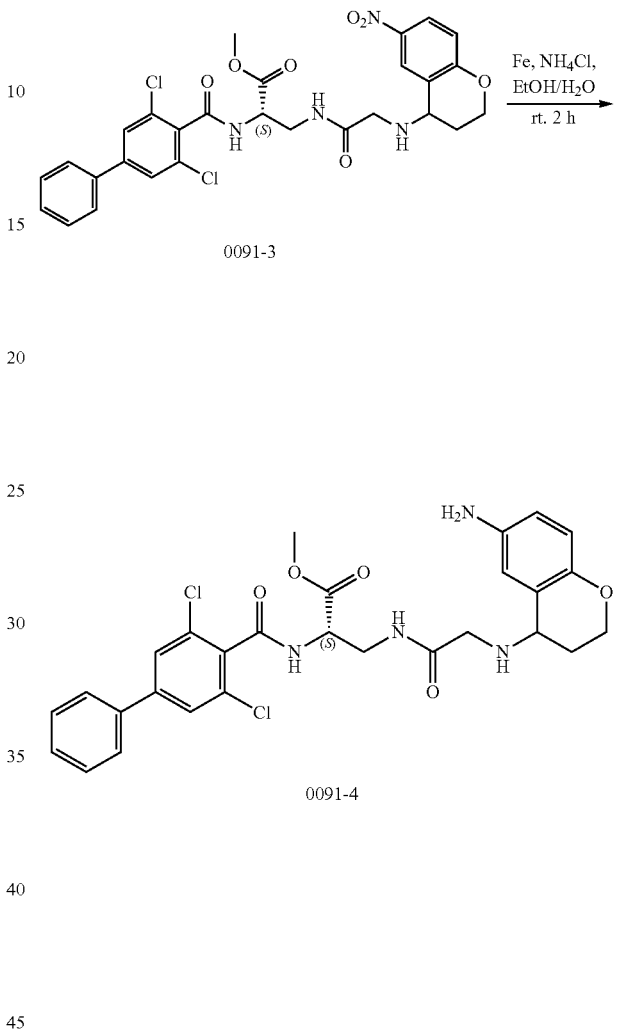

To a solution of compound 0091-2 (3 g, 8.17 mmol) in DMA (3 mL) was added 6-nitrochroman-4-amine (1.05 g, 5.41 mmol) and NaHCO₃ (757.35 mg, 9.01 mmol). The mixture was stirred at 120° C. overnight. After the reaction was completed, the mixture was quenched with water, and then extracted with EA (30 mL×3). The organic layer was separated, dried over Na₂SO₄, and concentrated in vacuo. The residue was purified by prep-HPLC to give 0091-3 (0.9 g, 33% yield) as a yellow solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Purity: 99.4%. Rt=2.176 min; MS Calcd.: 600.1; MS Found: 601.2 [M+H]⁺.

To a solution of 0091-3 (0.9 g, 1.49 mmol) in EtOH/H₂O (5 mL, 5/1) was added Fe (83.29 mg, 1.49 mmol) and NH₄Cl (239.1 mg, 4.47 mmol). The mixture was stirred at room temperature for 1 h. After the reaction was completed, the mixture was quenched with water and then extracted with EA (30 mL×3). The organic layer was separated, dried over Na₂SO₄, and concentrated in vacuo. The residue was purified by Prep-HPLC to give 0091-4 (0.82 g, 96% yield) as a yellow solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Purity: 91.9%. Rt=1.977 min; MS Calcd.: 570.1; MS Found: 571.2 [M+H]⁺.

The Synthesis of (2 S)-methyl 3-(2-(6-((E)-2,3-bis(tert-butoxycarbonyl)guanidino) chroman-4-yl amino)acetamido)-2-(3,5-dichlorobiphenyl-4-yl carboxamido) propanoate (0091-5)

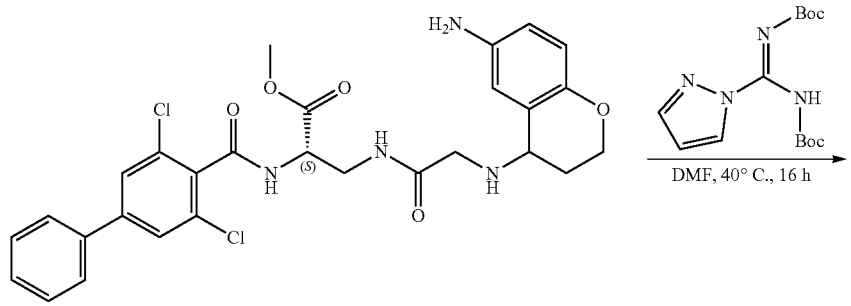

0091-4

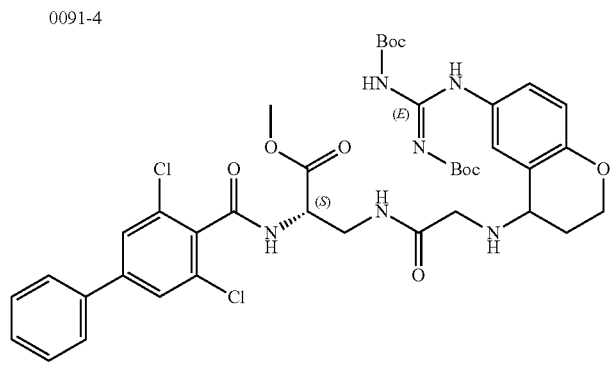

0091-5

To a solution of 0091-4 (0.75 g, 1.31 mmol) in DMF (5 ml) was added (E)-tert-butyl (1H-pyrazol-1-yl)methylenedicarbamate (488.78 mg, 1.57 mmol). The mixture was stirred at 40° C. for 16 hr. After the reaction was completed, the mixture was quenched with water, and then extracted with EA (30 mL×3). The organic layer was separated, dried over Na$_2$SO$_4$, and concentrated in vacuo. The residue was purified by prep-HPLC to give 0091-5 (0.5 g, 47% yield) as a white solid.

The Synthesis of (2S)-2-(3,5-dichlorobiphenyl-4-ylcarboxamido)-3-(2-(6-guanidinochroman-4-yl amino)acetamido)propanoic acid (SU15210-0091-01)

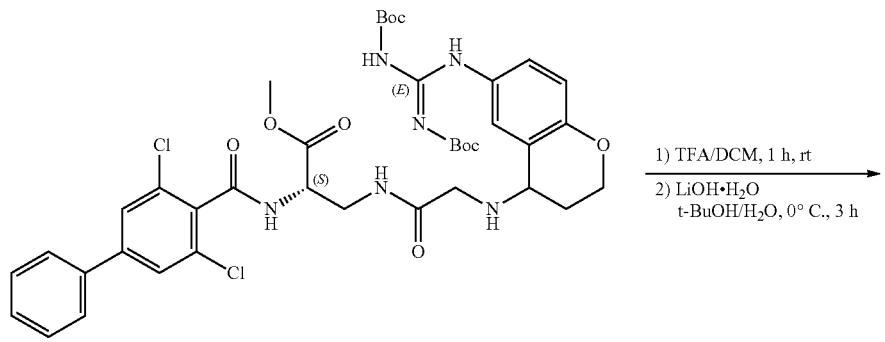

0091-5

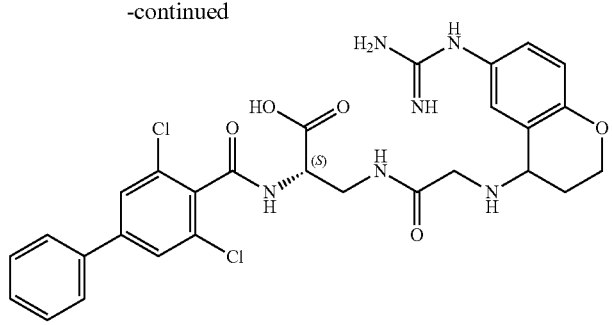

SU15210-0091-01

To a solution of 0091-5 (0.5 g, 0.62 mmol) in DCM (5 mL) was added TFA (70.06 mg, 0.62 mmol). The mixture was stirred at room temperature for 1 h. Then mixture was concentrated in vacuo, the crude in t-BuOH/H$_2$O (5 mL, 5/1) was added LiOH.H$_2$O (130.20 mg, 3.10 mmol). The mixture was stirred at 0° C. for 3 h. The reaction mixture was concentrated in vacuo, the crude was dissolved with 5 mL H$_2$O, 1N HCl was added to adjust pH=2~3, the mixture was freeze-drying to get the crude product, the crude was further purified by prep-HPLC to give the SU15210-0091-01 (99.8 mg, 27% yield) as a white solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 98.2%. Rt=1,606 min; MS Calcd.: 598.1; MS Found: 599.2 [M+H]$^+$.

Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 96.7%. Rt=7.484 min.

$^1$H NMR (400 MHz, DMSO-d$_6$) δ 8.16-8.31 (m, 2H), 7.74-7.77 (m, 5H), 7.44-7.52 (m, 4H), 7.32-7.34 (m, 1H), 6.99-6.70 (m, 1H), 6.66-6.71 (m, 1H), 4.14-4.27 (m, 2H), 4.04-4.09 (m, 1H), 3.64-3.72 (m, 2H), 3.02-3.26 (m, 3H), 2.78-2.84 (m, 1H), 1.95-2.02 (m, 1H), 1.78-1.81 (m, 1H).

SU15210-0094

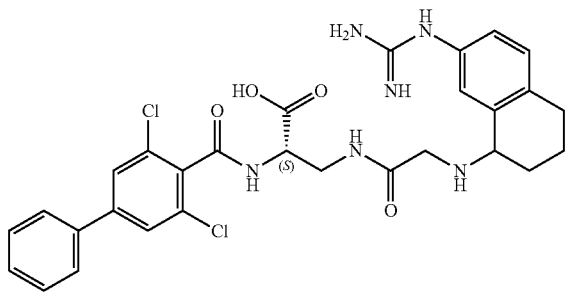

SU15210-0094

Chemical Formula: C$_{29}$H$_{30}$Cl$_2$N$_6$O$_4$
Molecular Weight: 597.49

Scheme: Route for SU15210-0094

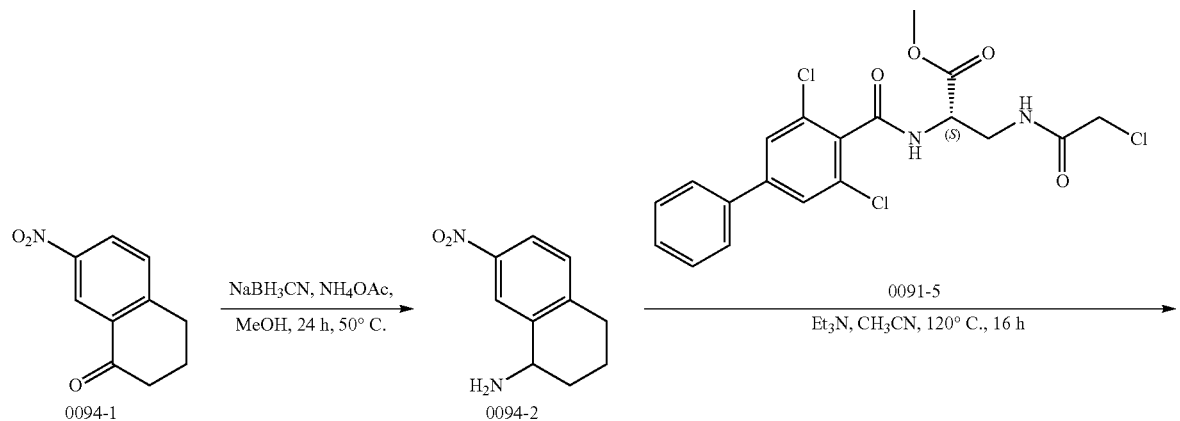

-continued
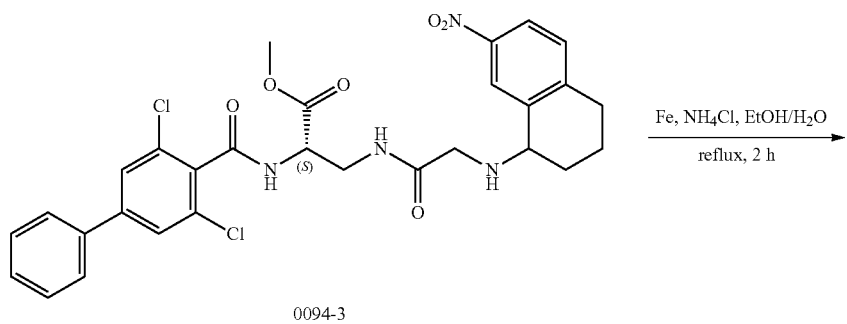
0094-3
Fe, NH₄Cl, EtOH/H₂O
reflux, 2 h
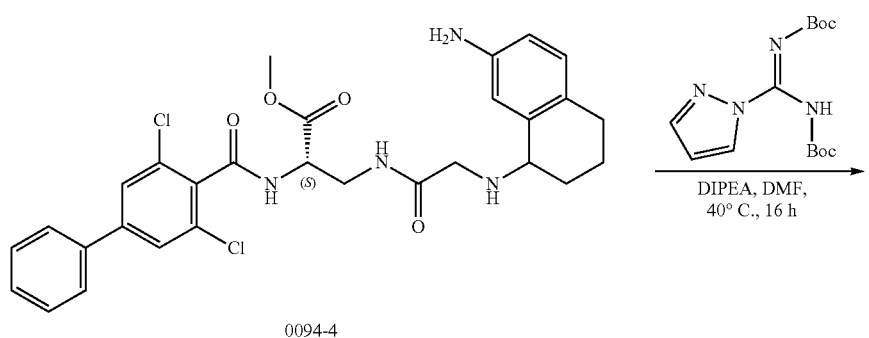
0094-4
DIPEA, DMF,
40° C., 16 h
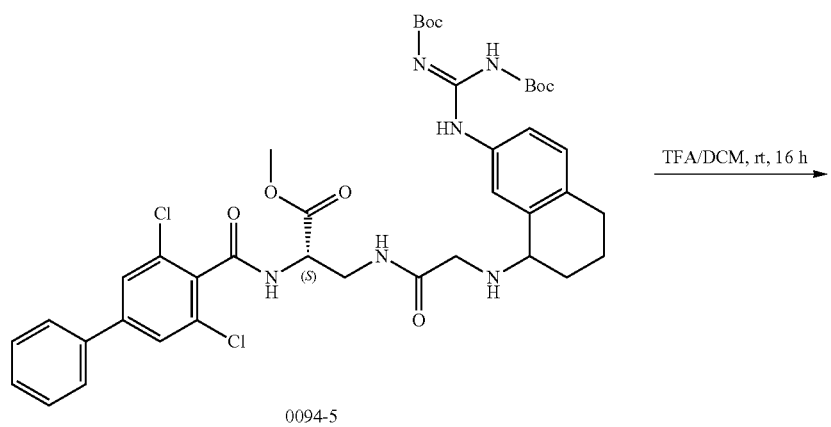
0094-5
TFA/DCM, rt, 16 h
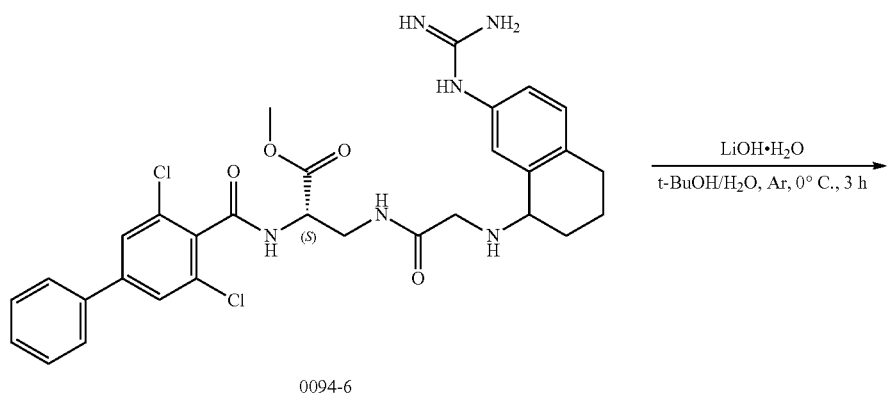
0094-6
LiOH·H₂O
t-BuOH/H₂O, Ar, 0° C., 3 h

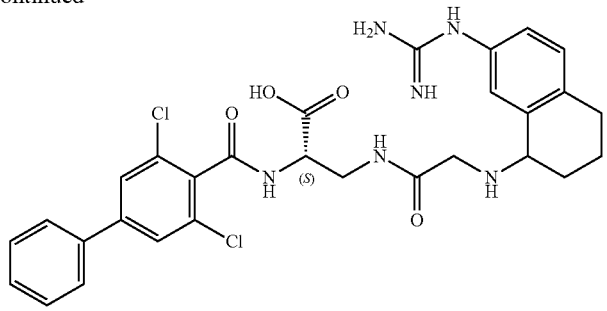

SU15210-0094

The Synthesis of 7-nitro-1,2,3,4-tetrahydronaphthalen-1-amine (0094-2)

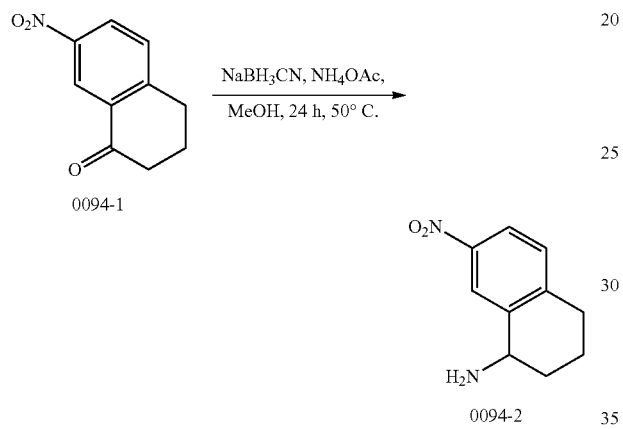

To a solution of compound 0094-1 (2.0 g, 10.5 mmol) in MeOH (50 mL) was added NH₄OAc (4.0 g, 52.3 mmol). The mixture was stirred at 50° C. for 30 min, then NaBH₃CN (3.3 g, 52.3 mmol) was added in portions, the mixture was stirred at 50° C. for 24 h. After the consumption of starting material (by LCMS), the reaction was concentrated, the crude was quenched with water (100 mL) and extracted with EtOAc (40 mL×3), the organic layer was washed with saturated aqueous NaCl, collected the organic layer and dried over anhydrous Na₂SO₄, filtered and concentrated in vacuo, the crude was purified by prep-HPLC to get the product 0094-2 (1.2 g, yield: 59.7%) as a brown solid.

The Synthesis of (2S)-methyl 2-(3,5-dichlorobiphenyl-4-ylcarboxamido)-3-(2-(7-nitro-1,2,3,4-tetrahydronaphthalen-1-ylamino)acetamido)propanoate (0094-3)

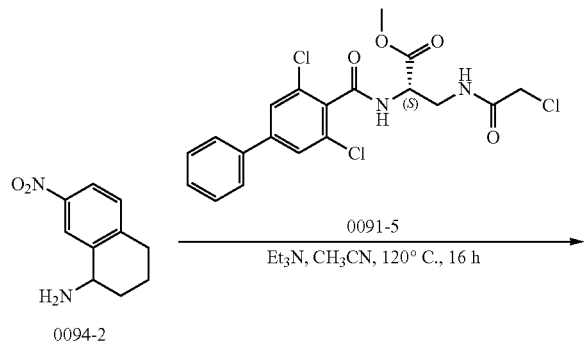

To a solution of compound 0094-2 (192.0 mg, 1.0 mmol) in CH₃CN (10 mL) was added Et₃N (101.0 mg, 1.0 mmol) and 0091-5 (442.0 mg, 1.0 mmol). The reaction was stirred at 120° C. for 16 h. After the reaction was finished, the reaction mixture was concentrated, the crude was purified by CC (PE/EtA=35%) to give the product 0094-3 (250.0 mg, yield: 41.8%) as a white solid.

The Synthesis of (2S)-methyl 3-(2-(7-amino-1,2,3,4-tetrahydronaphthalen-1-ylamino)acetamido)-2-(3,5-dichlorobiphenyl-4-ylcarboxamido)propanoate (0094-4)

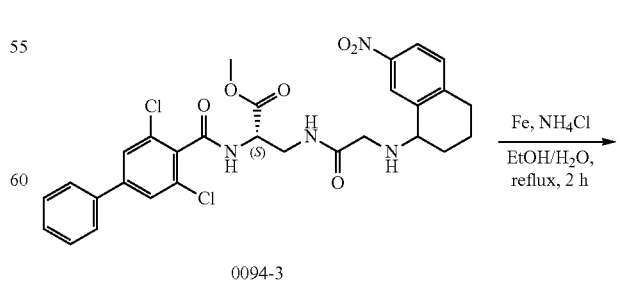

-continued

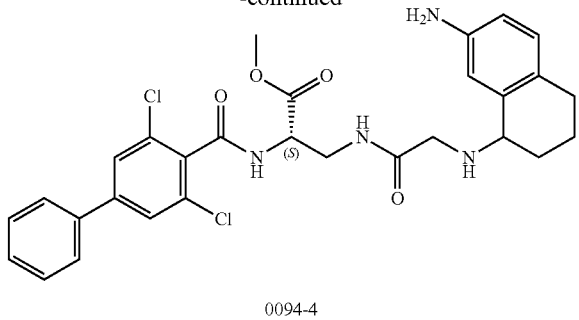

0094-4

To a solution of compound 0094-3 (250.0 mg, 0.4 mmol) in EtOH (10 mL) and H₂O (5 mL) was added iron powder (116.7 mg, 2.1 mmol) and NH₄Cl (112.0 mg, 2.1 mmol). The mixture was stirred at reflux for 2 h. After the reaction was finished (by LCMS), the reaction was filtered, the filtrate was concentrated in vacuo, the crude was quenched in 30 mL H₂O, extracted with CH₂Cl₂ (25 mL×3), the organic layer was washed with saturated aqueous NaCl, collected the organic layer and dried over anhydrous Na₂SO₄, filtered and concentrated in vacuo, the crude was purified by CC (CH₂Cl₂/MeOH=5%) to get the product 0094-4 (210.0 g, yield: 88.6%) as a white solid.

The Synthesis of (2 S)-methyl 3-(2-(7-((Z)-2,3-bis(tert-butoxycarbonyl)guanidino)-1,2,3,4-tetrahydronaphthalen-1-yl amino)acetamido)-2-(3,5-dichlorobiphenyl-4-ylcarboxamido)propanoate (0094-5)

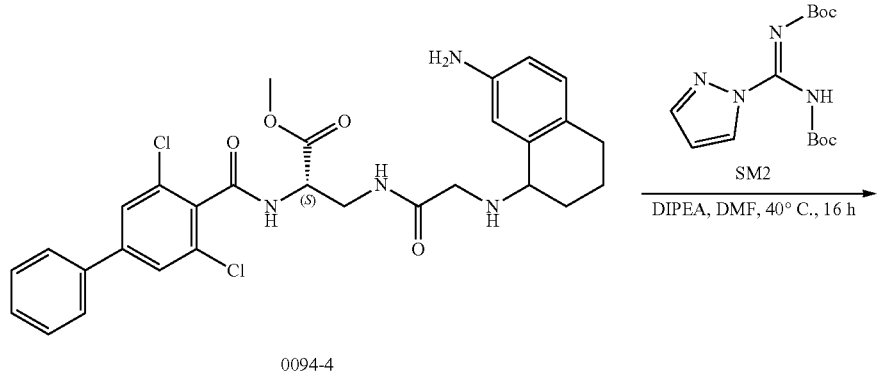

To a solution of compound 0094-4 (210.0 mg, 0.4 mmol) in DMF (5 mL) was added DIPEA (114.0 mg, 1.0 mmol) and SM2 (175.0 mg, 0.6 mmol). The mixture was stirred at 40° C. for 16 h. After the reaction was finished (by LCMS), the mixture was purified directly by prep-HPLC to give the product 0094-5 (120.0 g, yield: 39.4%) as a white solid.

The Synthesis of (2S)-methyl 2-(3,5-dichlorobiphenyl-4-ylcarboxamido)-3-(2-(7-guanidino-1,2,3,4-tetrahydronaphthalen-1-ylamino)acetamido)propanoate (0094-6)

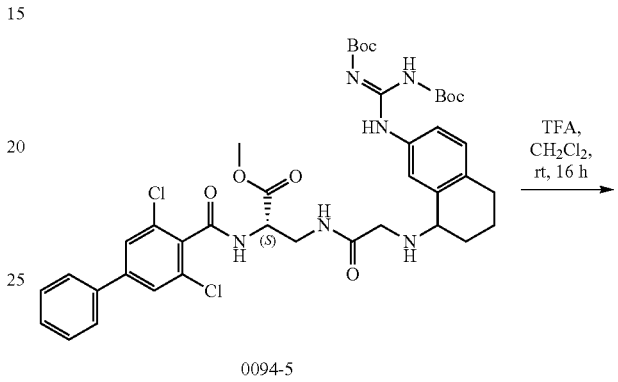

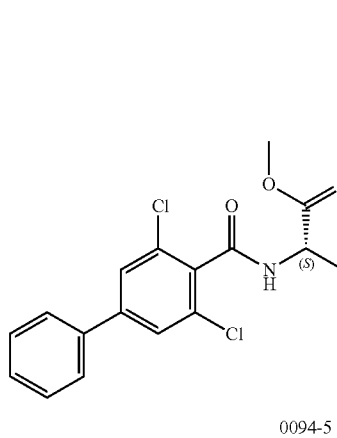

0094-5

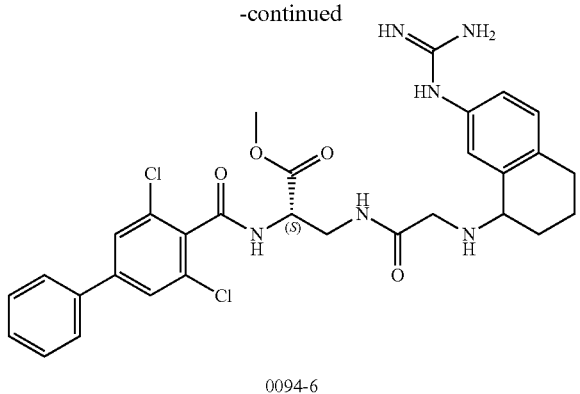

0094-6

To a solution of compound 0094-5 (170.0 mg, 0.2 mmol) in CH₂Cl₂ (5 mL) was added TFA (1.5 g, 13.0 mmol). The mixture was stirred at rt for 16 h. After the reaction was finished (by LCMS), the mixture was concentrated to give the desired product 0094-6 (110.0 mg, yield: 85.9%) as a white solid.

The Synthesis of (2S)-2-(3,5-dichlorobiphenyl-4-ylcarboxamido)-3-(2-(7 guanidino-1,2,3,4-tetrahydronaphthalen-1-ylamino)acetamido)propanoic acid (SU15210-0094)

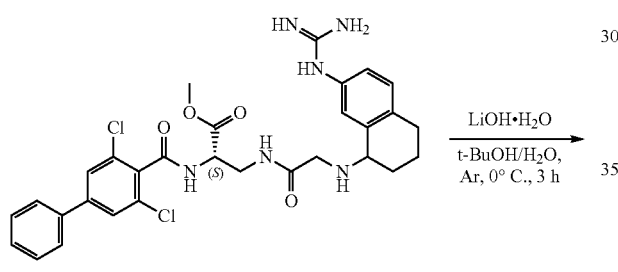

0094-6

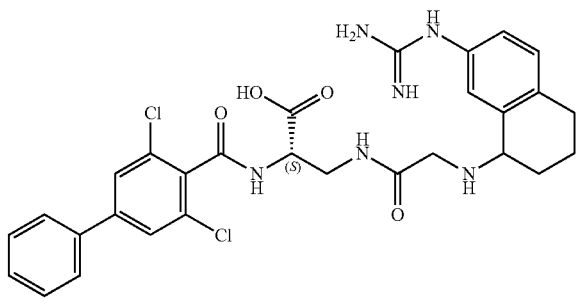

SU15210-0094

To a solution of compound 0094-6 (110.0 mg, 0.2 mmol) in t-BuOH (4 mL)/H₂O (2 mL), was added LiOH.H₂O (16.0 mg, 0.4 mmol). The mixture was stirred at 0° C. under Ar atmosphere for 3 h. After the consumption of starting material (by LCMS), the reaction mixture was concentrated and adjust pH to 2.0 by HCl (1.0 N), the mixture was freeze-drying to get the crude product, the crude was purified by prep-HPLC to give SU15210-0094 (17.0 mg, 15.82% yield) as a white solid.

LC-MS (Agilent LCMS 1200-6110, Column: Waters X-Bridge C18 (50 mm*4.6 mm*3.5 µm); Column Temperature: 40° C.; Flow Rate: 2.0 mL/min; Mobile Phase: from 95% [water+0.05% NH₄HCO₃] and 5% [CH₃CN+0.05% NH₄HCO₃] to 5% [water+0.05% NH₄HCO₃] and 95% [water+0.05% NH₄HCO₃] in 1.6 min, then under this condition for 1.4 min, finally changed to 95% [water+0.05% NH₄HCO₃] and 5% [CH₃CN+0.05% NH₄HCO₃] in 0.05 min and under this condition for 0.7 min), Purity: 97.22%, Rt=1.820 min; MS Calcd.: 596.0; MS Found: 597.2 [M+H]⁺.

HPLC (Agilent HPLC 1200; Column: L-column2 ODS (150 mm*4.6 mm*5.0 µm); Column Temperature: 40° C.; Flow Rate: 1.0 mL/min; Mobile Phase: from 95% [water+0.05% NH₄HCO₃] and 5% [CH₃CN+0.05% NH₄HCO₃] to 5% [water+0.05% NH₄HCO₃] and 95% [water+0.05% NH₄HCO₃] in 5.0 min, then under this condition for 1.0 min, finally changed to 95% [water+0.05% NH₄HCO₃] and 5% [CH₃CN+0.05% NH₄HCO₃] in 0.1 min and under this condition for 5 min), Purity: 95.13%, Rt=7.860 min.

¹H NMR (400 MHz, DMSO-d₆ and D₂O) δ 7.70-7.74 (m, 4H), 7.39-7.52 (m, 4H), 6.99-7.05 (m, 2H), 4.17-4.25 (m, 1H), 3.55-3.71 (m, 2H), 3.22-3.33 (m, 1H), 2.98-3.12 (m, 2H), 2.52-2.66 (m, 2H), 1.82-1.87 (m, 2H), 1.53-1.58 (m, 2H).

SU15210-0096

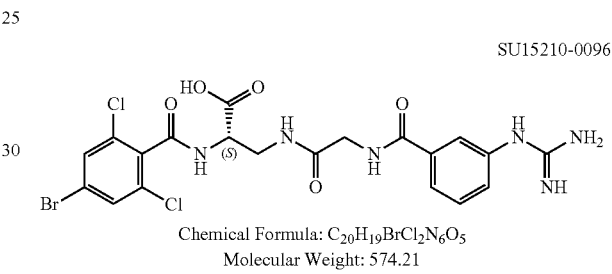

Chemical Formula: C₂₀H₁₉BrCl₂N₆O₅
Molecular Weight: 574.21

Scheme: Route for intermediate of SU15210-0096-3A

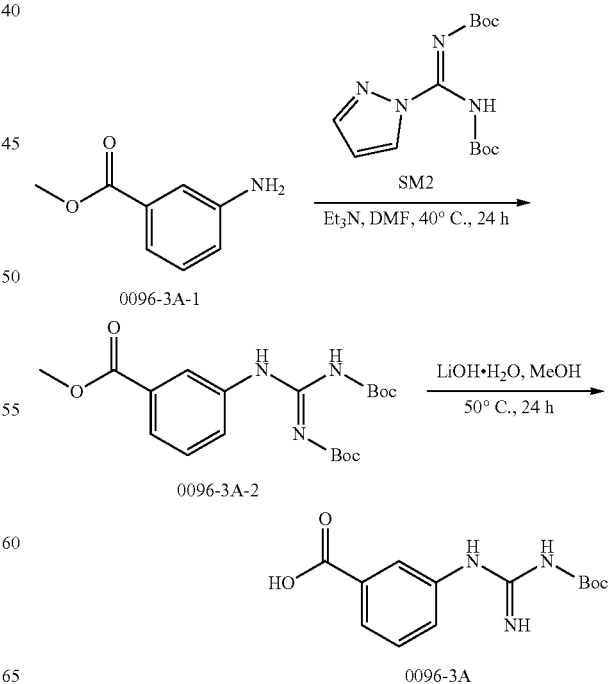

Scheme: Route for intermediate of SU15210-0096
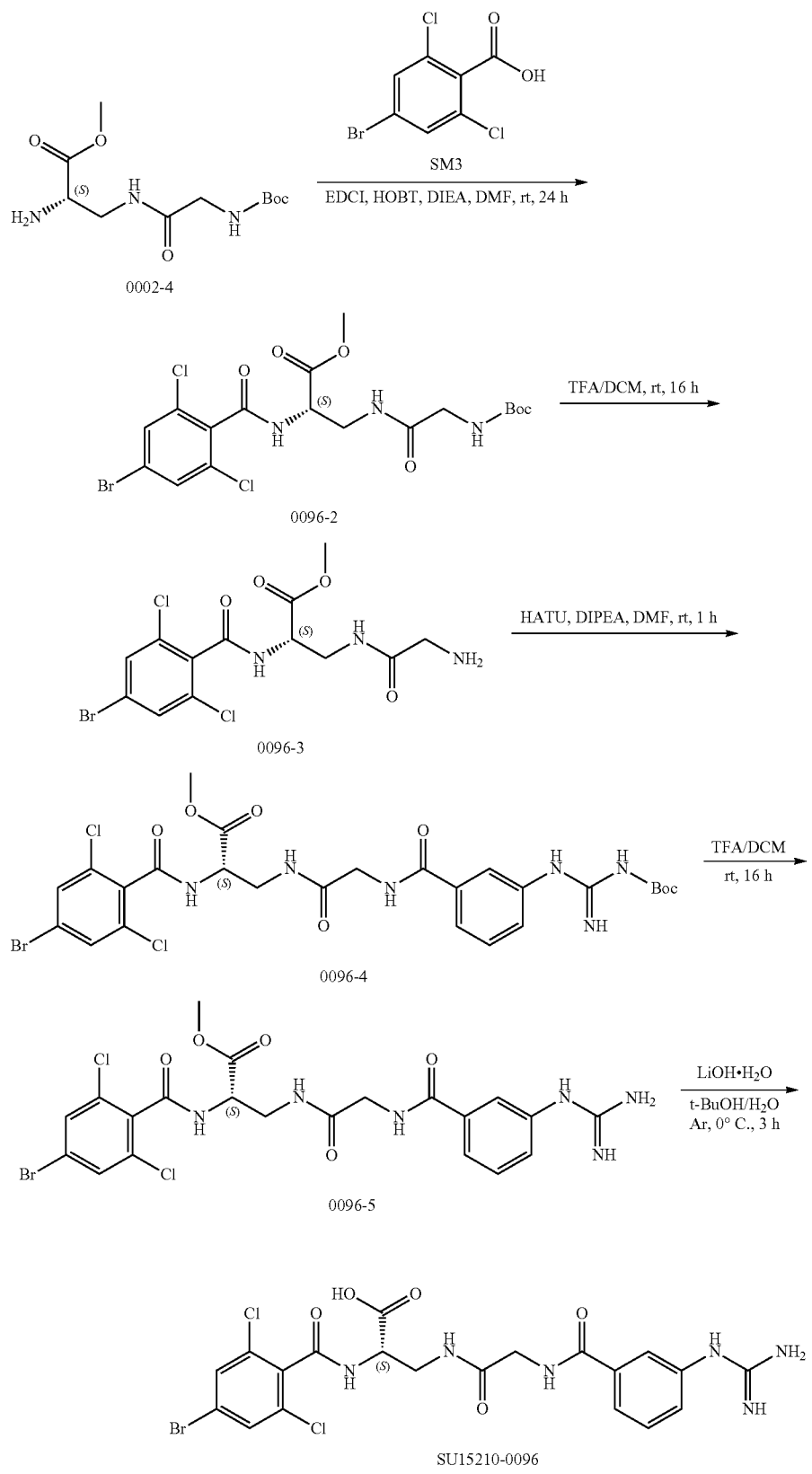

The Synthesis of (Z)-methyl 3-(2,3-bis(tert-butoxycarbonyl)guanidino)benzoate (0096-3A-2)

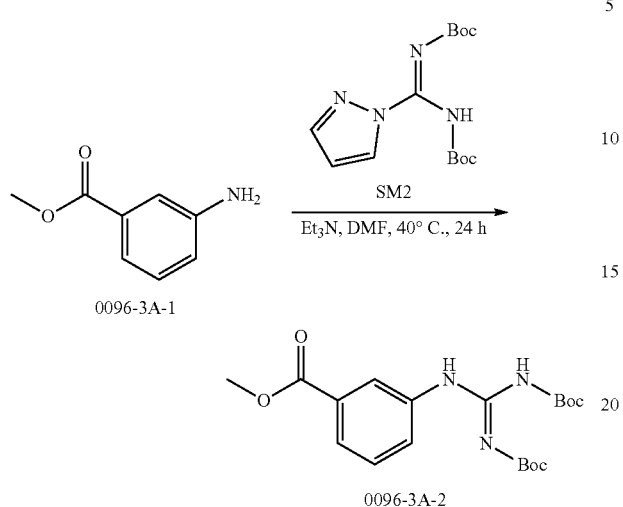

To a solution of compound 0096-3A-1 (6.0 g, 40.0 mmol) in DMF (30 mL) was added Et$_3$N (8.1 g, 80.0 mmol) and SM2 (14.9 g, 48.0 mmol). The mixture was stirred at 40° C. for 24 h. After the consumption of starting material (by LCMS), the reaction was purified directly by prep-HPLC to get the product 0096-3A-2 (12.5 g, yield: 79.4%) as a white solid.

The Synthesis of 3-(3-(tert-butoxycarbonyl)guanidino)benzoic acid (0096-3A)

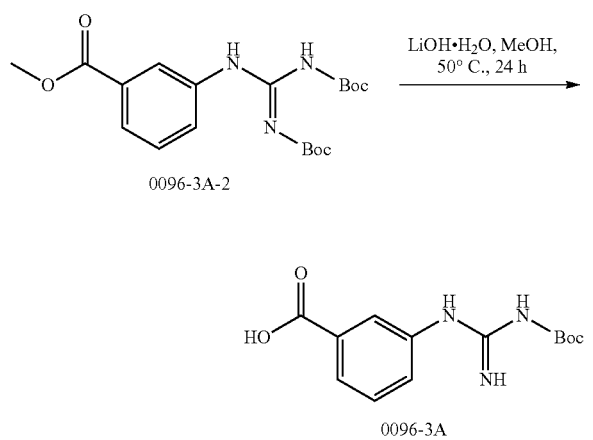

To a solution of compound 0096-3A-2 (8.9 g, 22.6 mmol) in MeOH (50 mL) was added LiOH·H$_2$O (1.9 g, 45.2 mmol). The reaction was stirred at 50° C. for 24 h. After the reaction was finished, the reaction mixture was concentrated, the crude was dissolved in 50 mL H$_2$O and adjust pH to 2.0 by HCl (1.0 N), the mixture was purified directly by prep-HPLC to give the product 0096-3A (6.3 g, yield: 91.9%) as a white solid.

The Synthesis of (S)-methyl 2-(4-bromo-2,6-dichlorobenzamido)-3-(2-(tert-butoxycarbonylamino)acetamido)propanoate (0096-2)

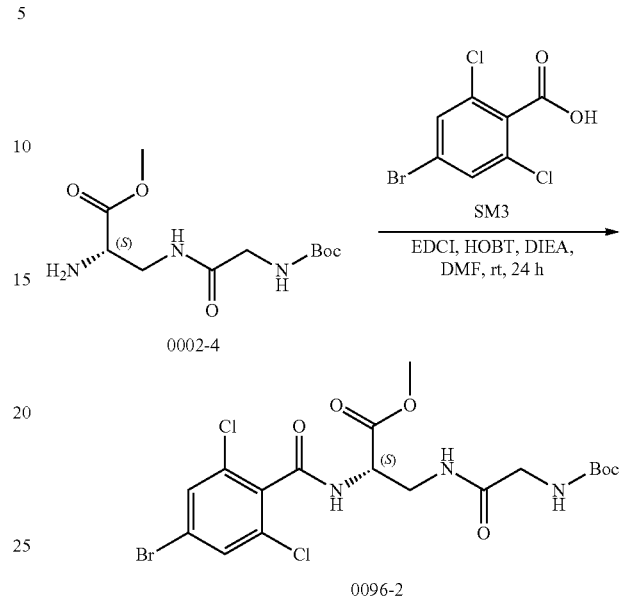

To a solution of compound 0002-4 (551.0 mg, 1.0 mmol) in DMF (10 mL) was added EDCI (461.0 mg, 2.4 mmol), HOBT (325.0 mg, 2.4 mmol), DIEA (259.0 mg, 2.0 mmol) and SM3 (539.0 mg, 1.0 mmol). The mixture was stirred at rt for 24 h. After the reaction was finished (by LCMS), the reaction solvent was quenched with water (100 mL) and extracted with EtOAc (40 mL×3), the organic layer was washed with saturated aqueous NaCl, collected the organic layer and dried over anhydrous Na$_2$SO$_4$, filtered and concentrated in vacuo, the crude was purified by CC (PE/EA=2/1) to get the product 0096-2 (410.0 mg, yield: 78.1%) as a white solid.

The Synthesis of (S)-methyl 3-(2-aminoacetamido)-2-(4-bromo-2,6-dichlorobenzamido)propanoate (0096-3)

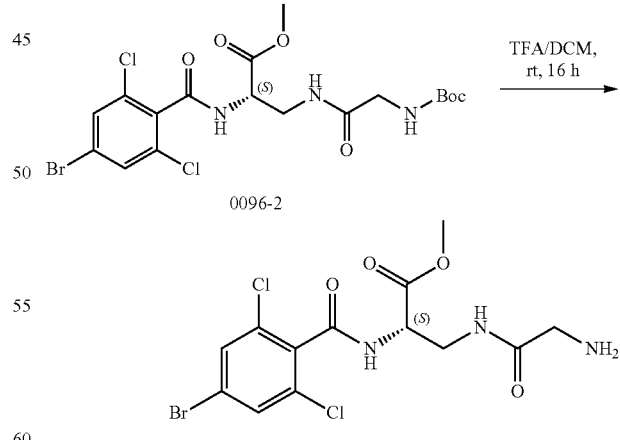

To a solution of compound 0096-2 (3.9 g, 7.4 mmol) in DCM (50 mL) was added TFA (5 mL). The mixture was stirred at rt for 16 h. After the reaction was finished (by LCMS), the reaction was concentrated to give the product 0096-3 (3.0 g, yield: 95.0%) as a white solid.

The Synthesis of (S)-methyl 2-(4-bromo-2,6-dichlorobenzamido)-3-(2-(3-(3-(tert-butoxycarbonyl)guanidino)benzamido)acetamido)propanoate (0096-4)

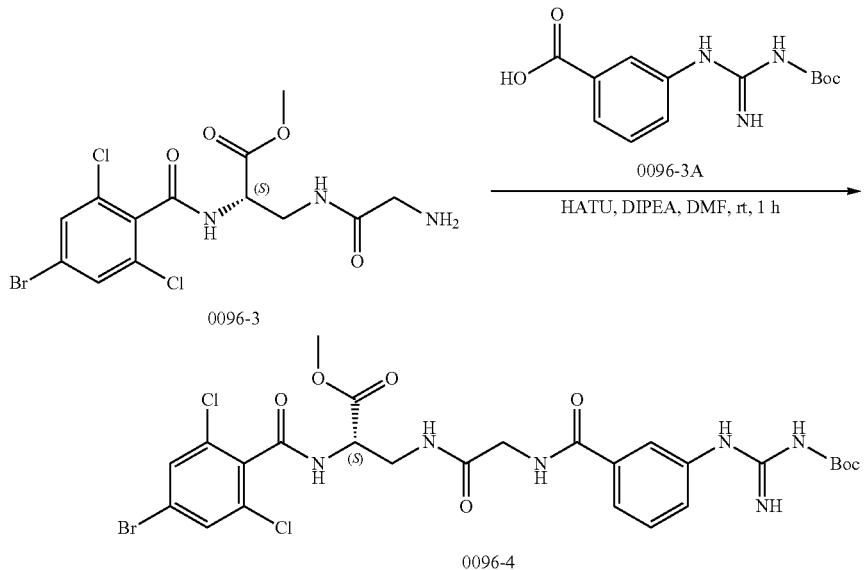

To a solution of compound 0096-3A (896.0 mg, 3.2 mmol) in DMF (30 mL) was added HATU (1.8 g, 4.8 mmol), DIEA (829.0 mg, 6.4 mmol) and 0096-3 (1.4 g, 3.2 mmol). The mixture was stirred at rt for 1 h. After the reaction was finished (by LCMS), the mixture was purified by prep-HPLC to give the desired product 0096-4 (750.0 mg, yield: 39.5%) as a white solid.

The Synthesis of (S)-methyl 2-(4-bromo-2,6-dichlorobenzamido)-3-(2-(3-guanidinobenzamido)acetamido)propanoate (0096-5)

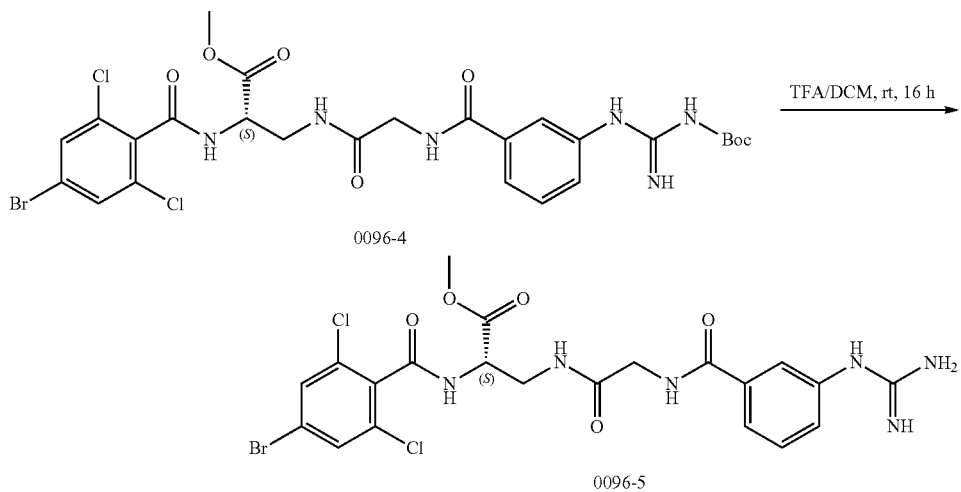

To a solution of compound 0096-4 (2.2 g, 3.2 mmol) in DCM (30 mL) was added TFA (6 mL). The mixture was stirred at rt for 16 h. After the reaction was finished (by LCMS), the mixture was concentrated to give the product 0096-5 (1.8 g, yield: 95.8%) as a white solid.

The Synthesis of (S)-2-(4-bromo-2,6-dichlorobenzamido)-3-(2-(3-guanidinobenzamido)acetamido)propanoic acid (SU15210-0096)

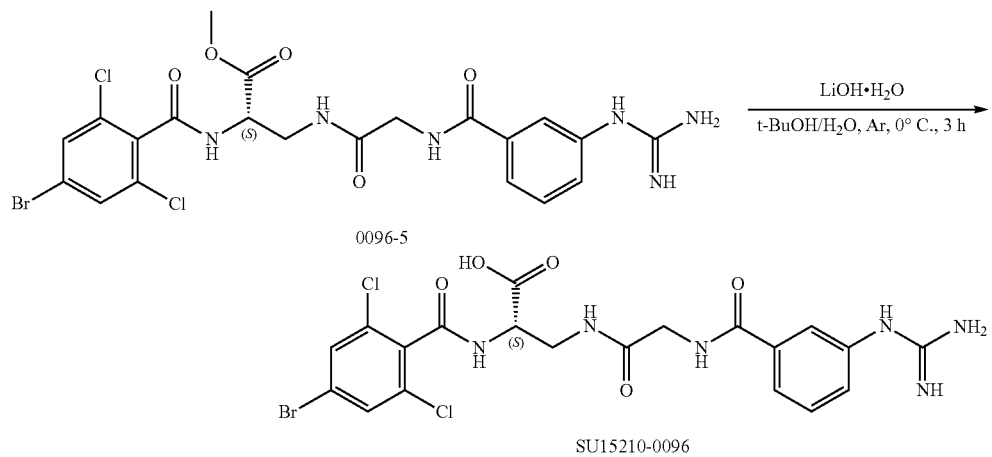

To a solution of compound 0096-5 (120.0 mg, 0.2 mmol) in t-BuOH (4 mL)/H₂O (2 mL), was added LiOH.H₂O (16.0 mg, 0.4 mmol). The mixture was stirred at 0° C. under Ar protected for 3 h. After the consumption of starting material (by LCMS), the reaction mixture was concentrated and adjust pH to 2.0 by HCl (1.0 N), the mixture was freeze-drying to get the crude product, the crude was purified by prep-HPLC to give SU15210-0096 (35.0 mg, 29.9% yield) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 0% [water+0.05% TFA] and 100% [CH₃CN+0.05 TFA] in 1.6 min, then under this condition for 1.4 min, finally changed to 95% [water+0.05% TFA] and 5% [CH3CN+0.05% TFA] in 0.05 min and under this condition for 0.7 min. Purity is 100.0%. Rt=1.318 min; MS Calcd.: 572.0; MS Found: 573.0 [M+H]⁺.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH₃CN+0.1% TFA] to 0% [water+0.1% TFA] and 100% [CH₃CN+0.1% TFA] in 10 min, then under this condition for 5 min, finally changed to 95% [water+0.1% TFA] and 5% [CH₃CN+0.1% TFA] in 0.1 min and under this condition for 5 min. Purity is 100.00%. Rt=5.694 min.

¹H NMR (400 MHz, DMSO-d₆) δ 11.06 (brs, 1H), 8.96 (t, J=6.0 Hz, 1H), 8.26-8.33 (m, 2H), 7.89-8.06 (m, 4H), 7.66-7.80 (m, 4H), 7.46 (t, J=7.6 Hz, 1H), 7.29 (d, J=7.6 Hz, 1H), 4.11 (q, J=7.6 Hz, 1H), 3.78-3.88 (m, 2H), 3.61-3.67 (m, 1H), 3.02-3.06 (m, 2H).

SU15210-0101

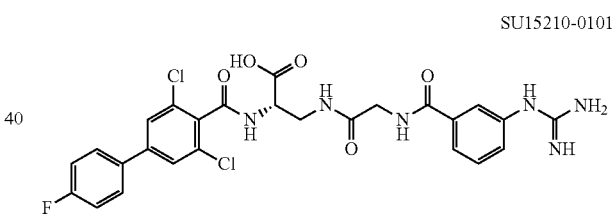

Chemical Formula: C₂₆H₂₃Cl₂FN₆O₅
Molecular Weight: 589.40

Scheme: Route for SU15210-0101

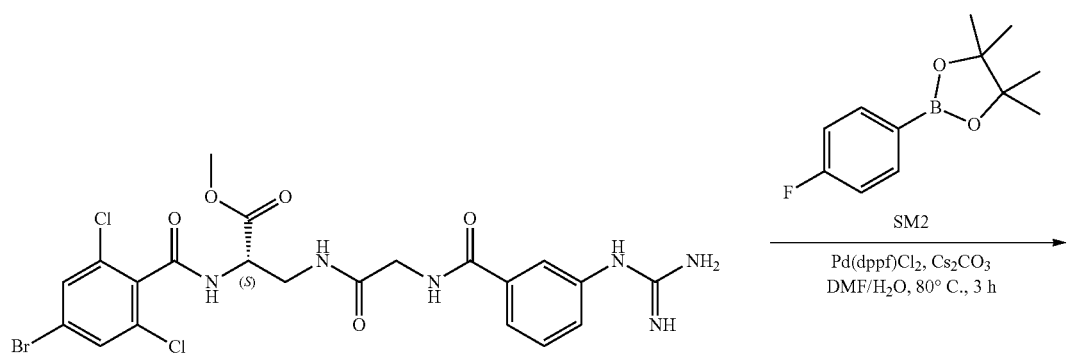

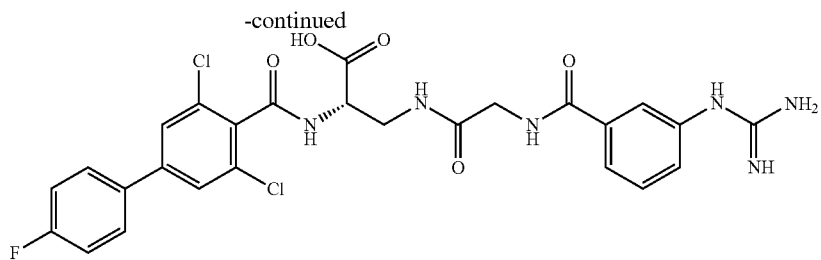

SU15210-0101-01

The Synthesis of (S)-2-(3,5-dichloro-4'-fluorobiphenyl-4-ylcarboxamido)-3-(2-(3-guanidinobenzamido)acetamido)propanoic acid (SU15210-0101)

A solution of 0096-5 (118.0 mg, 0.20 mmol) in DMF (5 mL) and H₂O (0.5 mL) was added Pd(dppf)Cl₂ (15.0 mg, 0.02 mmol), Cs₂CO₃ (130.0 mg, 0.40 mmol) and SM2 (53.3 mg, 0.24 mmol). The reaction mixture stirred at 80° C. for 3 h. After the consumption of starting material (by LCMS), the reaction mixture was adjust pH to 2.0 by HCl (1.0 N), the mixture was purified directly by prep-HPLC to get the product SU15210-0101 (17.0 mg, yield: 14.4%) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% NH₄HCO₃] and 5% [CH₃CN+0.05% NH₄HCO₃] to 5% [water+0.05% NH₄HCO₃] and 95% [water+0.05% NH₄HCO₃] in 1.6 min, then under this condition for 1.4 min, finally changed to 95% [water+0.05% NH₄HCO₃] and 5% [CH₃CN+0.05% NH₄HCO₃] in 0.05 min and under this condition for 0.7 min), Purity: 97.15%, Rt=1.554 min; MS Calcd.: 588.0; MS Found: 589.2 [M+H]⁺.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% NH₄HCO₃] and 5% [CH₃CN+0.05% NH₄HCO₃] to 5% [water+0.05% NH₄HCO₃] and 95% [water+0.05% NH₄HCO₃] in 5.0 min, then under this condition for 1.0 min, finally changed to 95% [water+0.05% NH₄HCO₃] and 5% [CH₃CN+0.05% NH₄HCO₃] in 0.1 min and under this condition for 5 min), Purity: 98.74%, Rt=6.652 min.

¹HNMR (400 MHz, DMSO-d₆) δ 10.95 (brs, 1H), 8.97 (t, J=6.0 Hz, 1H), 8.19-8.31 (m, 2H), 7.67-7.94 (m, 10H), 7.47 (t, J=7.6 Hz, 1H), 7.29-7.34 (m, 3H), 4.12 (q, J=5.6 Hz, 1H), 3.84-3.91 (m, 2H), 3.66-3.73 (m, 1H), 3.04 (t, J=9.6 Hz, 1H).

SU15210-0102

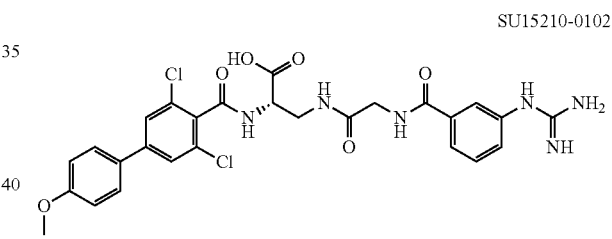

Chemical Formula: C₂₇H₂₆Cl₂N₆O₆
Molecular Wight: 601.44

Scheme: Route for SU15210-0102

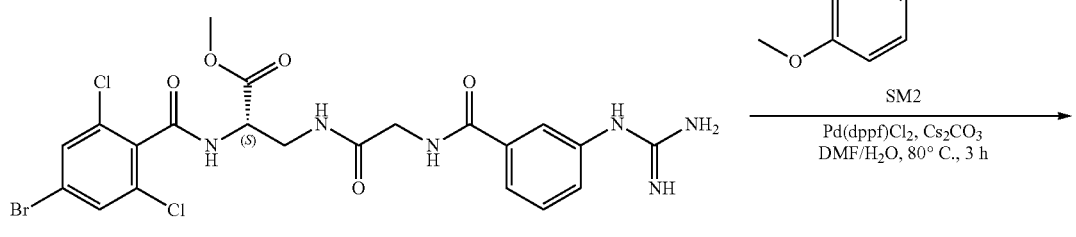

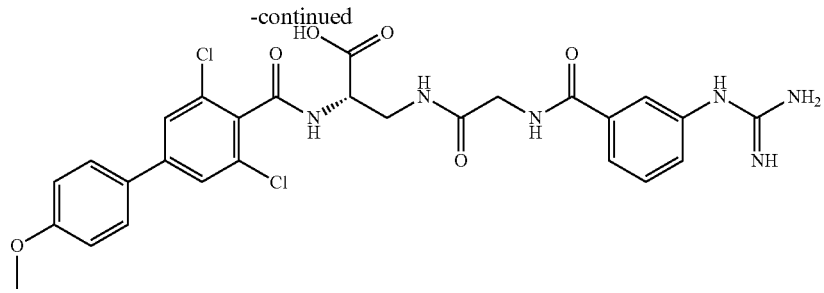

SU15210-0102

The Synthesis of (S)-2-(3,5-dichloro-4'-methoxybiphenyl-4-ylcarboxamido)-3-(2-(3-guanidinobenzamido)acetamido)propanoic acid (SU15210-0102)

A solution of 0096-5 (176.0 mg, 0.30 mmol) in DMF (5 mL) and H$_2$O (0.5 mL) was added Pd(dppf)Cl$_2$ (22.0 mg, 0.03 mmol), Cs$_2$CO$_3$ (196.0 mg, 0.60 mmol) and SM2 (84.0 mg, 0.36 mmol). The reaction mixture stirred at 80° C. for 3 h. After the consumption of starting material (by LCMS), the reaction mixture was adjust pH to 2.0 by HCl (1.0 N), the mixture was purified directly by prep-HPLC to get the product SU15210-0102 (72.0 mg, yield: 39.9%) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 5% [water+0.05% TFA] and 95% [water+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min), Purity: 99.52%, Rt=1.466 min; MS Calcd.: 600.0; MS Found: 601.2 [M+H]$^+$.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH$_3$CN+0.05% TFA] to 5% [water+0.05% TFA] and 95% [water+0.05% TFA] in 10 min, then under this condition for 5 min, finally changed to 95% [water+0.05% TFA] and 5% [CH$_3$CN+0.05% TFA] in 0.1 min and under this condition for 5 min), Purity: 100%, Rt=6.522 min.

$^1$HNMR (400 MHz, DMSO-d$_6$) δ 11.02 (brs, 1H), 8.97 (t, J=6.0 Hz, 1H), 8.14-8.29 (m, 2H), 7.83-7.96 (m, 4H), 7.67-7.76 (m, 6H), 7.46 (t, J=8.0 Hz, 1H), 7.28-7.34 (m, 1H), 7.01-7.05 (m, 2H), 4.13 (q, J=6.0 Hz, 1H), 3.85 (d, J=5.2 Hz, 2H), 3.81 (s, 3H), 3.66-3.73 (m, 1H), 3.05 (t, J=9.6 Hz, 1H).

SU15210-0103

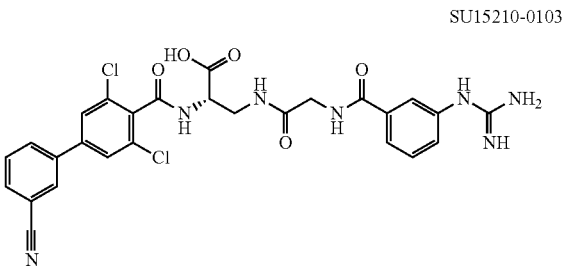

SU15210-0103

Chemical Formula: C$_{27}$H$_{23}$Cl$_2$N$_7$O$_5$
Molecular Weight: 596.42

Scheme: Route for SU15210-0103

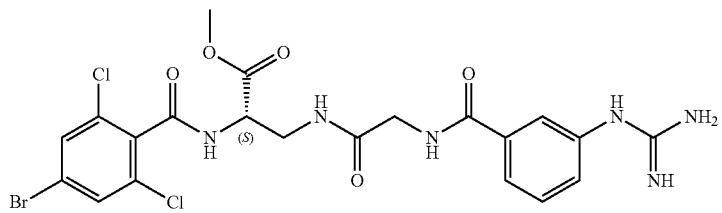 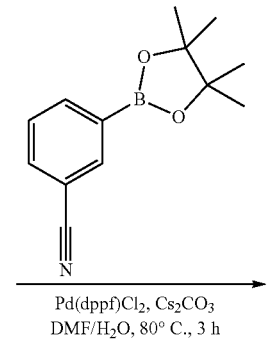

Pd(dppf)Cl$_2$, Cs$_2$CO$_3$
DMF/H$_2$O, 80° C., 3 h 0096-5

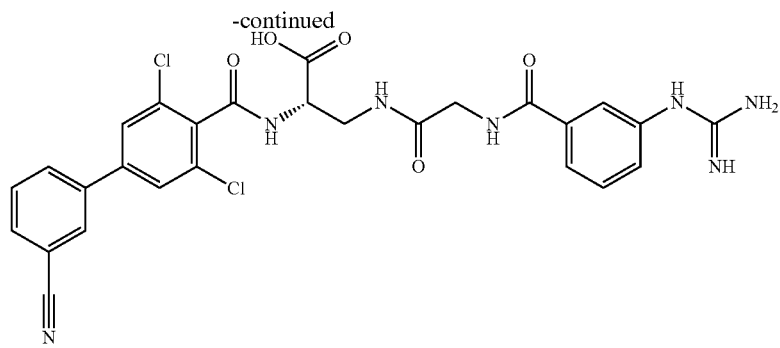

SU15210-0103

The Synthesis of (S)-2-(3,5-dichloro-4'-methoxybiphenyl-4-ylcarboxamido)-3-(2-(3-guanidinobenzamido)acetamido)propanoic acid (SU15210-0103)

A solution of 0096-5 (176.0 mg, 0.30 mmol) in DMF (5 mL) and H₂O (0.5 mL) was added Pd(dppf)Cl₂ (22.0 mg, 0.03 mmol), Cs₂CO₃ (196.0 mg, 0.60 mmol) and SM2 (84.0 mg, 0.36 mmol). The reaction mixture stirred at 80° C. for 3 h. After the consumption of starting material (by LCMS), the reaction mixture was adjust pH to 2.0 by HCl (1.0 N), the mixture was purified directly by prep-HPLC to get the product SU15210-0103 (47.0 mg, yield: 26.27%) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 5% [water+0.05% TFA] and 95% [water+0.05% TFA] in 1.6 min, then under this condition for 1.4 min, finally changed to 95% [water+0.05% TFA] and 5% [CH₃CN+0.05% TFA] in 0.05 min and under this condition for 0.7 min), Purity: 98.96%, Rt=1.406 min; MS Calcd.: 595.0; MS Found: 596.1 [M+H]⁺.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH₃CN+0.05% TFA] to 5% [water+0.05% TFA] and 95% [water+0.05% TFA] in 10 min, then under this condition for 5 min, finally changed to 95% [water+0.05% TFA] and 5% [CH₃CN+0.05% TFA] in 0.1 min and under this condition for 5 min), Purity: 100%, Rt=6.207 min.

¹H NMR (400 MHz, DMSO-d₆) δ 11.12 (brs, 1H), 8.95 (t, J=5.2 Hz, 1H), 8.23-8.32 (m, 3H), 8.11-8.16 (m, 1H), 7.76-8.08 (m, 6H), 7.65-7.73 (m, 4H), 7.44 (t, J=8.0 Hz, 1H), 7.26-7.31 (m, 1H), 4.11-4.17 (m, 1H), 3.80-3.91 (m, 2H), 3.66-3.72 (m, 1H), 3.07 (t, J=9.6 Hz, 1H).

SU15210-0105-01

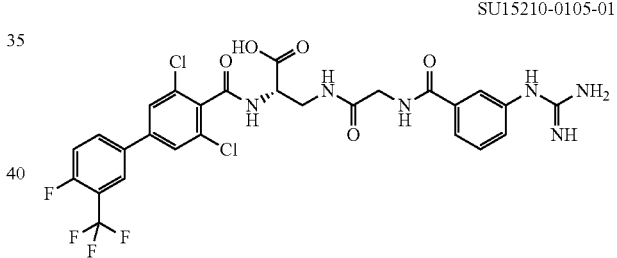

Chemical Formula: C₂₇H₂₂Cl₂F₄N₅O₅
Molecular Weight: 657.40

Scheme: Route for SU15210-0105-01

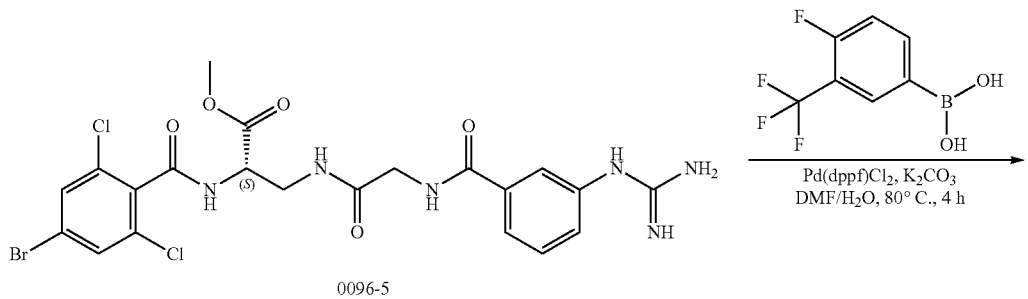

-continued

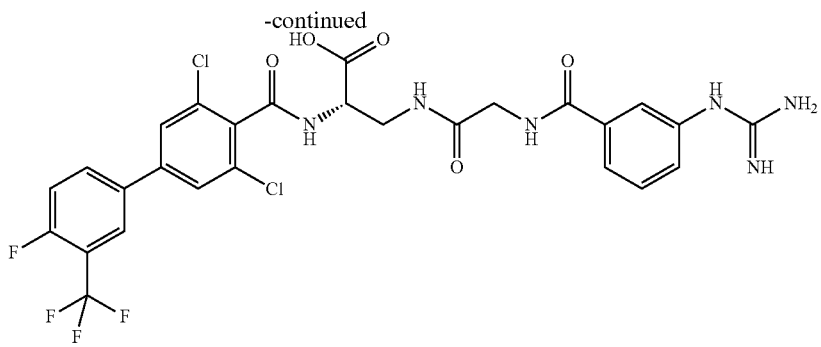

SU15210-0105-01

The Synthesis of (S)-2-(3,5-dichloro-4'-fluoro-3'-(trifluoromethyl)biphenyl-4-ylcarboxamido)-3-(2-(3 guanidinobenzamido)acetamido)propanoic acid (SU15210-0105-01)

A solution of 0096-5 (117 mg, 0.2 mmol), 4-fluoro-3-(trifluoromethyl)phenylboronic acid (83.2 mg, 0.4 mmol), Pd(dppf)Cl₂ (14.6 mg, 0.02 mmol) and K₂CO₃ (104 mg, 0.8 mmol) were suspended in DMF (3 mL) and water (0.3 mL). The reaction mixture was heated to 80° C. and stirred for 4 h. After the reaction was finished, 1N HCl was added to adjust pH=2~3, filtrated, the filtrate was purified directly by pre-HPLC to give SU15210-0105-01 (40 mg, yield: 38.20%) as a white solid.

Agilent LCMS 105-63314, Column: Waters X-Bridge C18 (50 mm*4.6 mm*3.5 μm); Column Temperature: 40° C.; F Flow Rate: 2.0 mL/min; Mobile Phase: from 95% [water+0.05% TFA] and 5% [CH₃CN+0.05% TFA] to 0% [water+0.05% TFA] and 100% [CH₃CN+0.05% TFA] in 3.0 min, then under this condition for 1.6 min, finally changed to 0% [water+0.05% TFA] and 100% [CH₃CN+0.05% TFA] in 0.05 min and under this condition for 1.4 min. Purity: 96.57%. Rt=1.595 min; MS Calcd.: 656.1; MS Found: 657.1 [M+H]⁺.

Agilent HPLC 1200; Column: Waters X-Bridge C18 (150 mm*4.6 mm*3.5 μm); Column Temperature: 40° C.; Flow Rate: 1.0 mL/min; Mobile Phase: from 95% [water+0.1% TFA] and 5% [CH₃CN+0.1% TFA] to 0% [water+0.1% TFA] and 100% [CH₃CN+0.1% TFA] in 10 min, then under this condition for 10 min, finally changed to 95% [water+0.1% TFA] and 5% [CH₃CN+0.1% TFA] in 0.1 min and under this condition for 5 min. Purity: 95.74%. Rt=7.342 min.

¹H NMR (400 MHz, DMSO-d₆) δ 11.50 (br s, 1H), 9.01 (s, 1H), 8.13-8.53 (m, 8H), 7.91 (s, 2H), 7.61-7.77 (m, 3H), 7.44 (t, J=7.6 Hz, 1H), 7.28 (d, J=8.4 Hz, 1H), 4.05-4.09 (m, 1H), 3.83-3.85 (m, 2H), 3.71-3.73 (m, 1H), 2.98-3.03 (m, 1H).

SU15210-0106-01

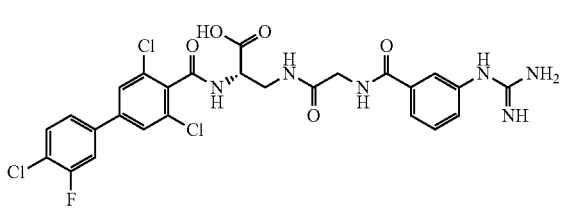

Chemical Formula: C₂₆H₂₂Cl₃FN₆O₅
Molecular Weight: 623.85

Scheme: Route for SU15210-0106-01

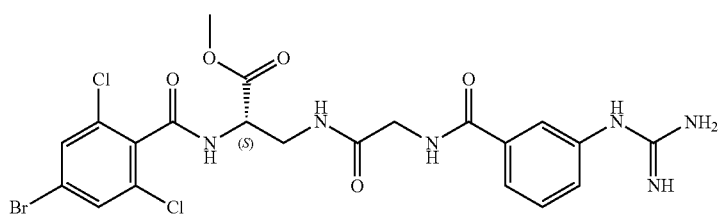 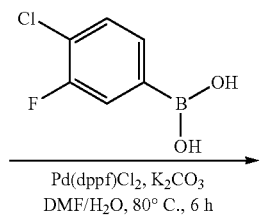

Pd(dppf)Cl₂, K₂CO₃
DMF/H₂O, 80° C., 6 h 0096-5

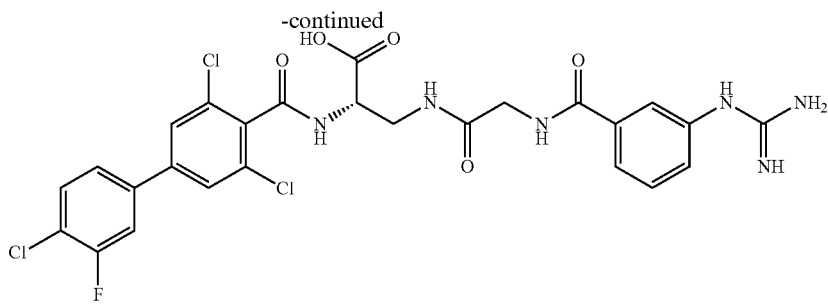

SU15210-0106-01

The Synthesis of (S)-3-(2-(3 guanidinobenzamido) acetamido)-2-(3,4',5-trichloro-3'-fluorobiphenyl-4-ylcarboxamido)propanoic acid (SU15210-0106-01)

A solution of 0096-5 (175.8 mg, 0.3 mmol), 4-chloro-3-fluorophenylboronic acid (104.6 mg, 0.4 mmol), Pd(dppf)Cl$_2$ (21.6 mg, 0.03 mmol) and K$_2$CO$_3$ (156 mg, 1.2 mmol) were suspended in DMF (3 mL) and water (0.3 mL). The reaction mixture was heated to 80° C. and stirred for 6 h. After the reaction was finished (by LCMS), 1N HCl was added to adjust pH=2~3, filtrated, the filtrate was purified directly by prep-HPLC to give the product SU15210-0106-01 (100 mg, yield: 52.4%) as a white solid.

Agilent LCMS 1200-1 Column: Waters X-Bridge C18 (50 mm*4.6 mm*3.5 μm); Column Temperature: 40° C.; F Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 3.0 min, then under this condition for 1.6 min, finally changed to 0% [water+0.05% TFA] and 100% [CH$_3$CN+0.05% TFA] in 0.05 min and under this condition for 1.4 min. Purity: 97.66%. Rt=1.562 min; MS Calcd.: 622.07; MS Found: 625.1 [M+H]$^+$.

Agilent HPLC 1200; Column: Waters X-Bridge C18 (150 mm*4.6 mm*3.5 μm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 10 min, finally changed to 95% [water+0.1% TFA] and 5% [CH$_3$CN+0.1% TFA] in 0.1 min and under this condition for 5 min. Purity: 94.17%. Rt=7.122 min.

$^1$H NMR (400 MHz, DMSO-d$_6$) δ 8.94-8.96 (m, 1H), 8.00-8.29 (m, 4H), 7.37-7.85 (m, 10H), 7.20-7.22 (m, 1H), 4.05-4.07 (m, 1H), 3.83-3.84 (m, 2H), 3.69-3.77 (m, 1H), 2.85-3.01 (m, 1H).

SU15210-0108-01

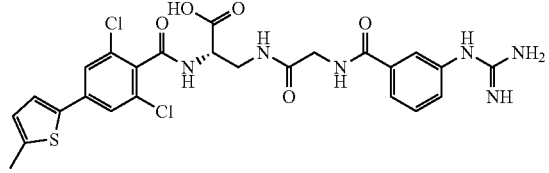

SU15210-0108-01

Chemical Formula: C$_{25}$H$_{24}$Cl$_2$N$_5$O$_5$S
Molecular Weight: 591.47

Scheme: Route for SU15210-0108-01

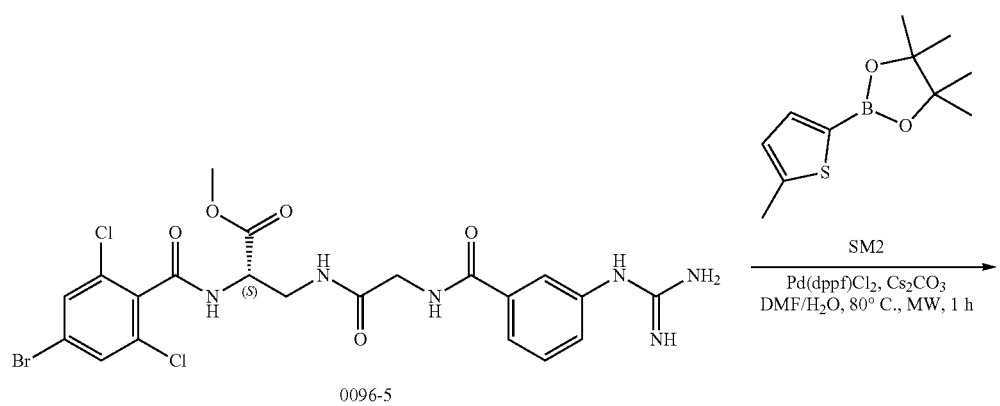

0096-5

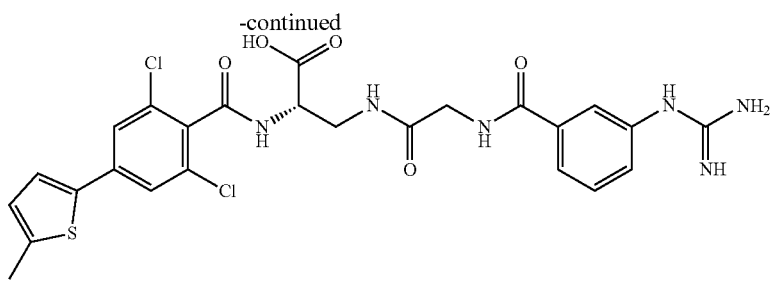

SU15210-0108-01

The Synthesis of (S)-2-(2,6-dichloro-4-(5-methyl-thiophen-2-yl)benzamido)-3-(2-(3-guanidinobenzamido)acetamido)propanoic acid (SU15210-0108-01)

To a solution of compound 0096-5 (0.2 g, 340.00 umol) in DMF/H$_2$O (3 mL, 2/1) was added SM2 (114.30 mg, 510.00 umol), Cs$_2$CO$_3$ (332.33 mg, 1.02 mmol) and Pd(dppf)Cl$_2$ (24.88 mg, 34.00 umol). The mixture was stirred at 80° C. under MW for 1 h. After the consumption of starting material (by LCMS), the crude was purified by prep-HPLC to give SU15210-0108-01 (0.06 g, 29.8% yield) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min. Purity: 100.0%. Rt=1.507 min; MS Calcd.: 590.1; MS Found: 591.0 [M+H]$^+$.

Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min. Purity: 97.1%. Rt=6.761 min.

$^1$H NMR (400 MHz, CD$_3$OD-d$_4$) δ 8.52 (s, 1H), 7.82-7.85 (m, 2H), 7.57 (s, 2H), 7.53-7.56 (m, 1H), 7.40-7.43 (m, 1H), 7.32 (d, J=3.6 Hz, 1H), 6.80-6.81 (m, 1H), 4.55-4.59 (m, 1H), 3.67-4.06 (m, 3H), 2.51 (s, 3H).

SU15210-0109-01

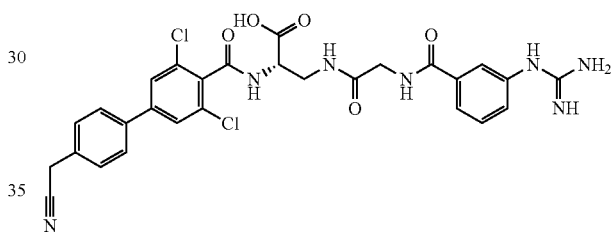

Chemical Formula: C$_{28}$H$_{25}$Cl$_2$N$_7$O$_5$
Molecular Weight: 610.45

Scheme: Route for SU15210-0109-01

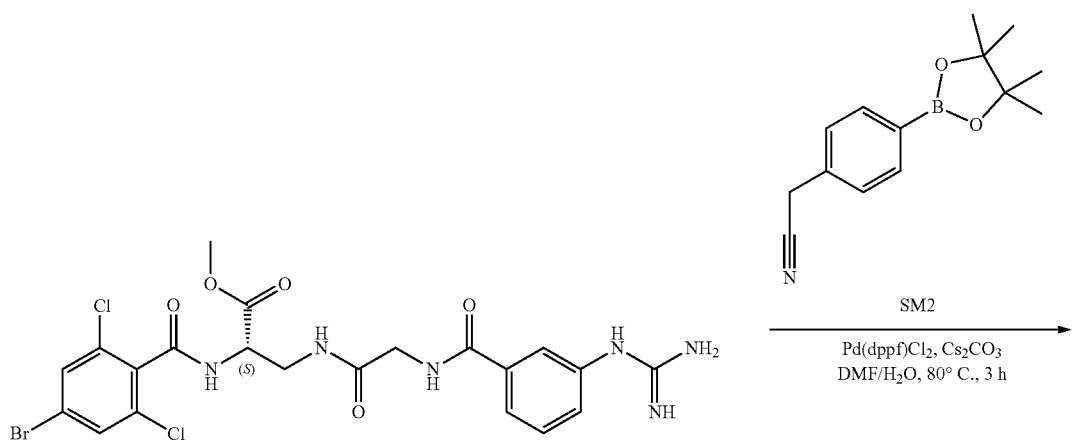

-continued

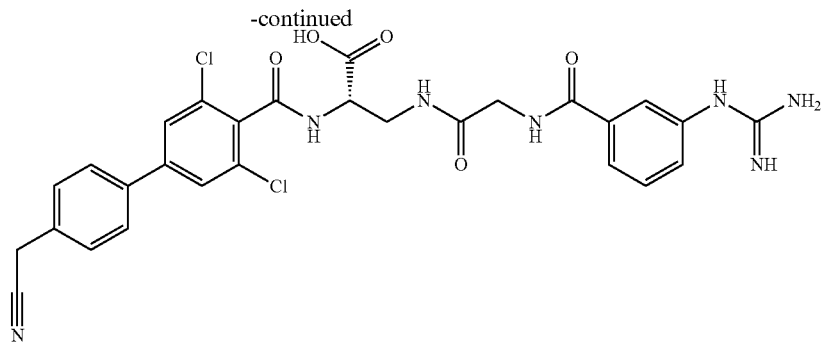

SU15210-0109-01

The Synthesis of (S)-2-(3,5-dichloro-4'-(cyanomethyl)biphenyl-4-ylcarboxamido)-3-(2-(3-guanidinobenzamido)acetamido)propanoic acid (SU15210-0109-01)

To a solution of compound 0065-5 (0.2 g, 0.34 mmol) in DMF/H$_2$O (5 mL, 4/1) was added SM2 (123.98 mg, 0.51 mmol), Pd(dppf)Cl$_2$ (21.95 mg, 0.03 mmol) and Cs$_2$CO$_3$ (331.50 mg, 1.02 mmol). The mixture was stirred at 80° C. for 3 h under N$_2$ atmosphere. After the consumption of starting material (by LCMS), the reaction solvent was quenched with water (100 mL), and extracted with EtOAc (30 mL×3), the organic layer was washed with saturated aqueous NaCl, collected the organic layer and dried over anhydrous Na$_2$SO$_4$, filtered and concentrated in vacuo, the crude was purified by prep-HPLC to give SU15210-0109-01 (70 mg, 34% yield) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min. Purity: 98.0%. Rt=1.384 min; MS Calcd.: 609.1; MS Found: 610.3 [M+H]$^+$.

Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min. Purity: 88.5%. Rt=6.018 min.

$^1$H NMR (400 MHz, DMSO-d$_6$) δ 9.00 (t, J=6.0 Hz, 1H), 8.52 (s, 1H), 8.38 (s, 1H), 7.94-8.05 (m, 3H), 7.77-7.79 (m, 5H), 7.61-7.67 (t, 1H), 7.43-7.46 (m, 3H), 7.25 (d, J=8.4 Hz, 1H), 4.09 (s, 2H), 3.97 (brs, 1H), 3.72-3.88 (m, 3H), 2.88 (brs, 1H), 1.93-2.00 (m, 1H).

SU15210-0111-01

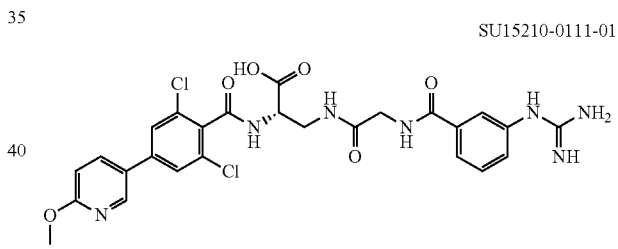

Chemical Formula: C$_{26}$H$_{25}$Cl$_2$N$_7$O$_6$
Molecular Weight: 602.43

Scheme: Route for SU15210-0111-01

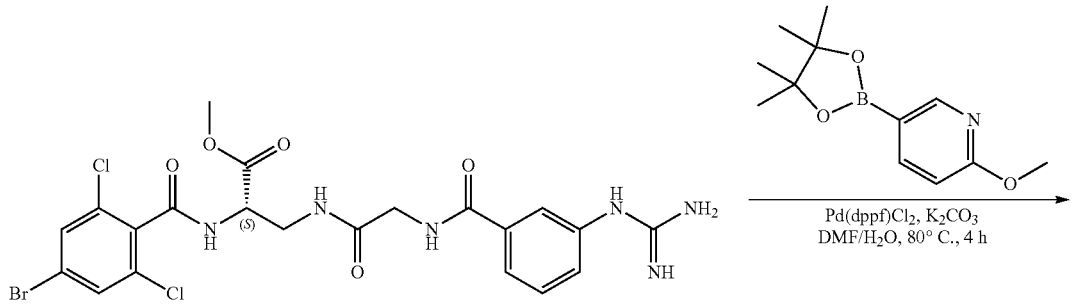

-continued

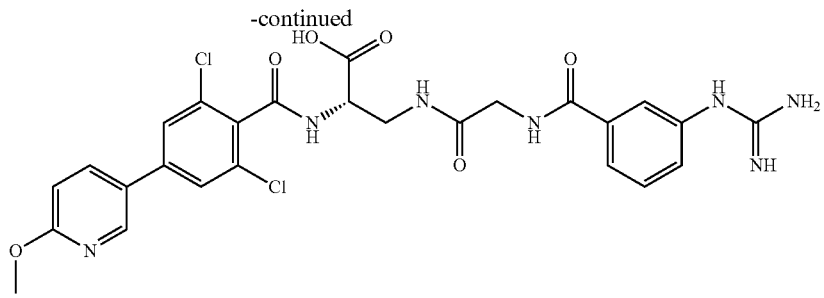

SU15210-0111-01

The Synthesis of (S)-2-(2,6-dichloro-4-(6-methoxy-pyridin-3-yl)benzamido)-3-(2-(3-guanidinobenzamido)acetamido)propanoic acid (SU15210-0111-01)

A solution of 0096-5 (175.8 mg, 0.3 mmol), 4-fluoro-3-(trifluoromethyl)phenylboronic acid (141 mg, 0.6 mmol), Pd(dppf)Cl$_2$ (21.9 mg, 0.03 mmol) and K$_2$CO$_3$ (165.6 mg, 1.2 mmol) were suspended in DMF (3 mL) and water (0.3 mL). The reaction mixture was heated to 80° C. and stirred for 4 h. After the reaction was finished (by LCMS), 1N HCl was added to adjust pH=2~3, filtrated, the filtrate was purified directly by prep-HPLC to give the product SU15210-0111-01 (70 mg, yield: 53.24%) as a white solid.

Agilent LCMS 105-63314, Column: Waters X-Bridge C18 (50 mm*4.6 mm*3.5 μm); Column Temperature: 40° C.; F Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 3.0 min, then under this condition for 1.6 min, finally changed to 0% [water+0.05% TFA] and 100% [CH$_3$CN+0.05% TFA] in 0.05 min and under this condition for 1.4 min. Purity: 100%. Rt=1.366 min; MS Calcd.: 602.1; MS Found: 604.1 [M+H]$^+$.

Agilent HPLC 1200; Column: Waters X-Bridge C18 (150 mm*4.6 mm*3.5 μm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 10 min, finally changed to 95% [water+0.1% TFA] and 5% [CH$_3$CN+0.1% TFA] in 0.1 min and under this condition for 5 min. Purity: 97.32%. Rt=5.925 min.

$^1$H NMR (400 MHz, DMSO-d$_6$) δ 9.01 (t, J=5.6 Hz, 1H), 8.59 (d, J=2.4 Hz, 1H), 8.36-8.47 (m, 2H), 8.08-8.19 (m, 5H), 7.78-7.80 (m, 3H), 7.64-7.69 (m, 1H), 7.46 (t, J=7.6 Hz, 1H), 7.28 (d, J=8.0 Hz, 1H), 6.92 (d, J=8.4 Hz, 1H), 4.03-4.06 (m, 1H), 3.90 (s, 3H), 3.84 (d, J=5.6 Hz, 2H), 3.68-3.77 (m, 1H), 2.95-2.97 (m, 1H).

SU15210-0122-01

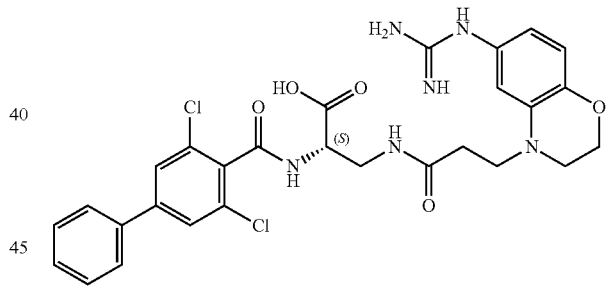

Chemical Formula: C$_{28}$H$_{28}$Cl$_2$N$_6$O$_5$
Molecular Weight: 599.47

Scheme: Route for SU15210-0122-01

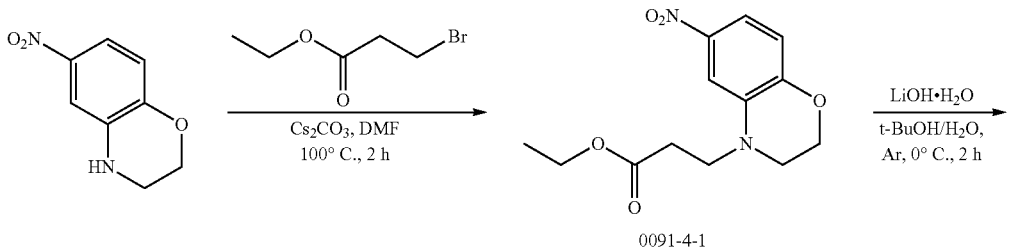

0091-4-1

-continued
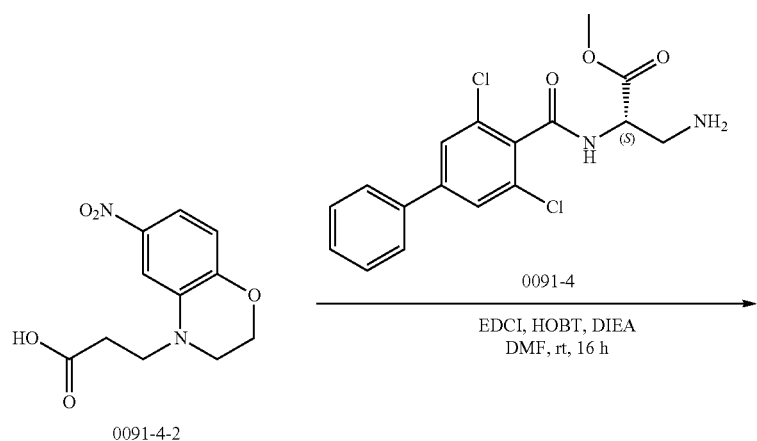
0091-4-2
EDCI, HOBT, DIEA
DMF, rt, 16 h
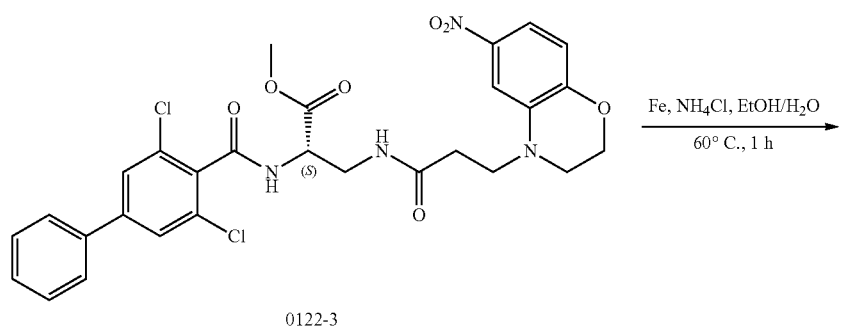
0122-3
Fe, NH₄Cl, EtOH/H₂O
60° C., 1 h
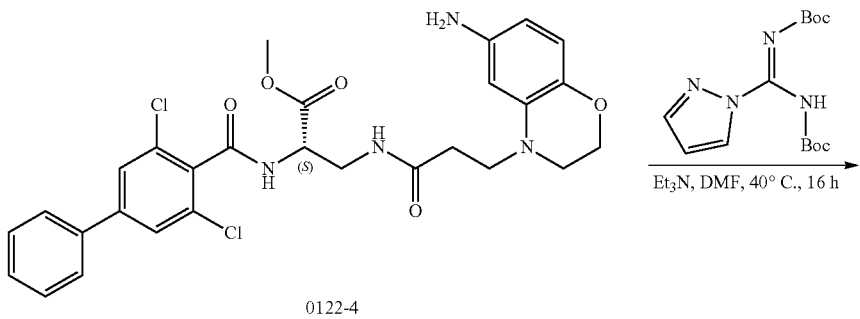
0122-4
Et₃N, DMF, 40° C., 16 h
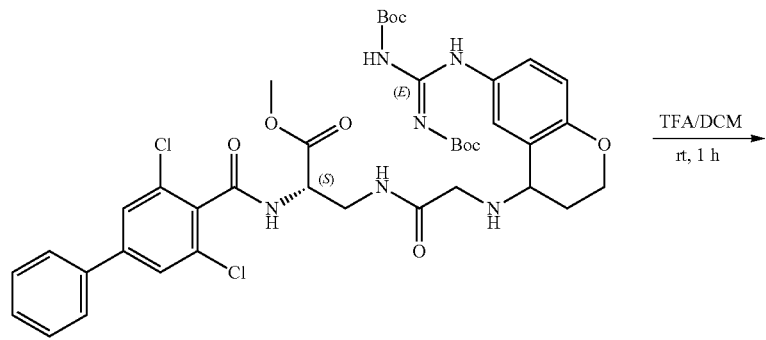
0122-5
TFA/DCM
rt, 1 h

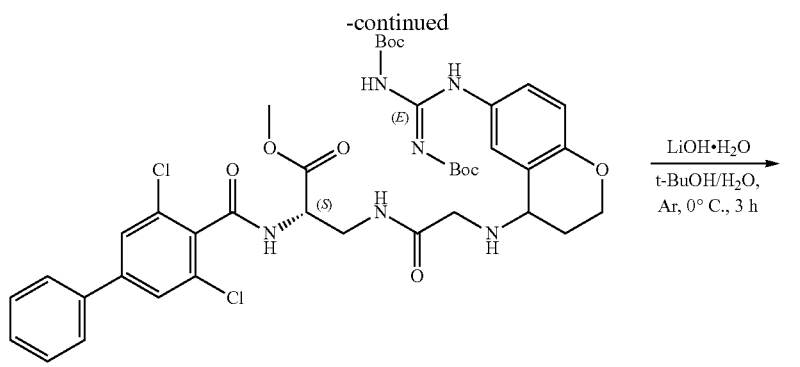

0122-5

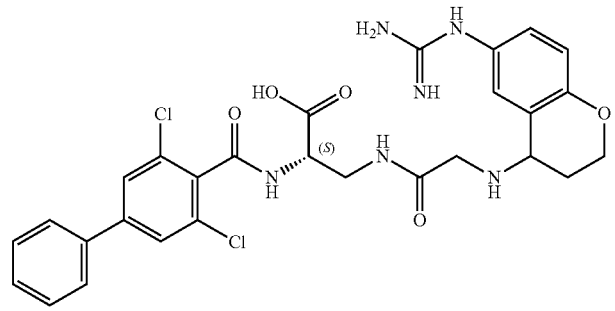

SU15210-0122-01

The Synthesis of ethyl 3-(6-nitro-2H-benzo[b][1,4]oxazin-4(3H)-yl)propanoate (0091-4-1)

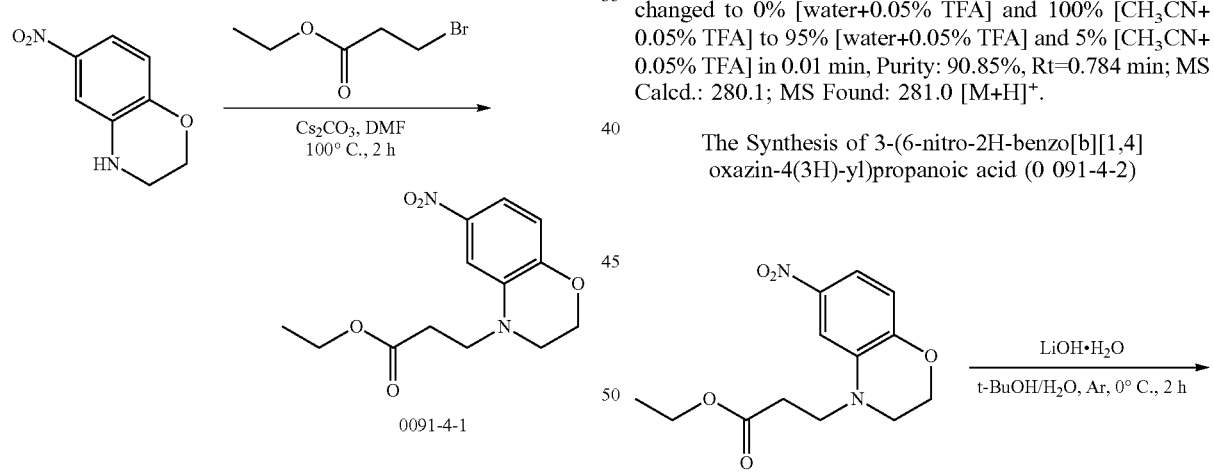

To a solution of 6-nitro-3,4-dihydro-2H-1,4-benzoxazine (1.08 g, 5.99 mmol) in DMF (12 mL) was added $Cs_2CO_3$ (5.86 g, 17.98 mmol) and ethyl 3-bromo propanoate (2.17 g, 11.99 mmol), the mixture was heat to 100° C. and stirred for 2 h. After the consumption of starting material (by LCMS), the reaction solvent was quenched with water (100 mL) and extracted with EtOAc (60 mL×3), the organic layer was washed with saturated aqueous NaCl, collected the organic layer and dried over anhydrous $Na_2SO_4$, filtered and concentrated in vacuo, the crude product was purified by c.c. (0-20% EtOAct/Hexane) to give 0091-4-1 (1.3 g, yield: 77.4%) as red oil.

LC-MS (Agilent LCMS 1200-6110, Column: Waters X-Bridge C18 (30 mm*4.6 mm*2.7 μm); Column Temperature: 40° C.; Flow Rate: 3.0 mL/min; Mobile Phase: rom 95% [water+0.05% TFA] and 5% [$CH_3CN$+0.05% TFA] to 0% [water+0.05% TFA] and 100% [$CH_3CN$+0.05% TFA] in 0.8 min, then under this condition for 0.4 min, finally changed to 0% [water+0.05% TFA] and 100% [$CH_3CN$+0.05% TFA] to 95% [water+0.05% TFA] and 5% [$CH_3CN$+0.05% TFA] in 0.01 min, Purity: 90.85%, Rt=0.784 min; MS Calcd.: 280.1; MS Found: 281.0 $[M+H]^+$.

The Synthesis of 3-(6-nitro-2H-benzo[b][1,4]oxazin-4(3H)-yl)propanoic acid (0 091-4-2)

To a solution of compound 0091-4-1 (2.1 g, 7.49 mmol) in t-BuOH (20 mL) and water (10 mL), $LiOH.H_2O$ (628.61 mg, 14.98 mmol) was added and the mixture was stirred at 0° C. for 2 h. Then the mixture was concentrated and added aqueous HCl (1N, 3 mL), extracted with EtOAc (30 mL×4), the combined organic layers were concentrated to give 0091-4-2 (1.3 g, yield: 68.8%) as a red solid.

LC-MS (Agilent LCMS 1200-6110, Column: Waters X-Bridge C18 (30 mm*4.6 mm*2.7 μm); Column Temperature: 40° C.; Flow Rate: 3.0 mL/min; Mobile Phase: from 95% [water+0.05% TFA] and 5% [CH$_3$CN+0.05% TFA] to 0% [water+0.05% TFA] and 100% [CH$_3$CN+0.05 TFA] in 0.8 min, then under this condition for 0.4 min, finally changed to 0% [water+0.05% TFA] and 100% [CH$_3$CN+0.05% TFA] to 95% [water+0.05% TFA] and 5% [CH$_3$CN+0.05% TFA] in 0.01 min, Purity: 95.43%, Rt=0.675 min; MS Calcd.: 252.1; MS Found: 253.0 [M+H]$^+$.

The Synthesis of (5)-methyl 2-(3,5-dichlorobiphenyl-4-ylcarboxamido)-3-(3-(6-nitro-2H-benzo[b][1,4]oxazin-4(3H)-yl)propanamido)propanoate (0122-3)

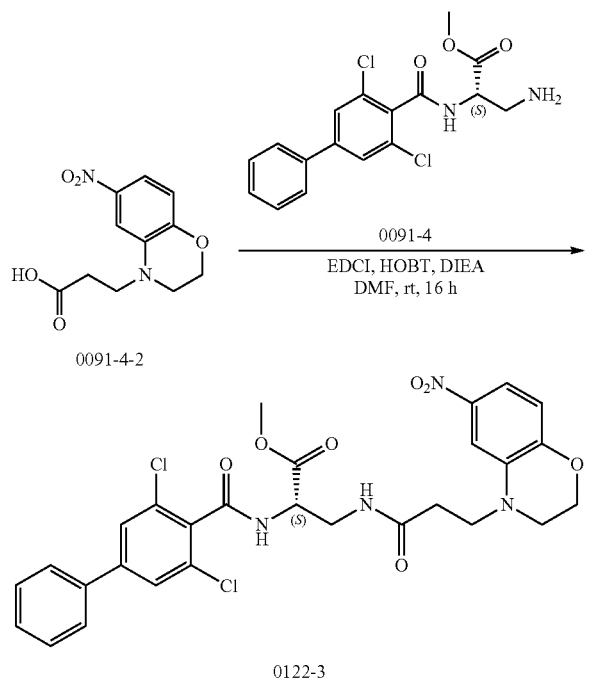

To a solution of compound 0091-4-2 (1.05 g, 4.16 mmol) in DMF (10 mL), was added EDCI (1.60 g, 8.33 mmol), HOBT (1.13 g, 8.33 mmol) and DIEA (1.61 g, 12.49 mmol, 2.18 mL). The mixture was stirred at rt for 16 h. After the consumption of starting material (by LCMS), the mixture was quenched with water (15 mL) and extracted with EtA (30 mL×4), the combined organic layer was dried over anhydrous Na$_2$SO$_4$, filtered and concentrated in vacuo. The crude was purified by c.c. (EA/PE=1:3) to give the product 0122-3 (1.8 g, yield: 71.9%) as a yellow solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 0% water [0.1 mol/L NH$_4$HCO$_3$] and 100% CH$_3$CN to 95% water [0.1 mol/L NH$_4$HCO$_3$] and CH$_3$CN in 0.01 min, Purity: 97.39%, Rt=2.342 min; MS Calcd.: 600.1; MS Found: 601.2 [M+H]$^+$.

The Synthesis of (5)-methyl 3-(3-(6-amino-2H-benzo[b][1,4]oxazin-4(3H) yl)propanamido)-2-(3,5-dichlorobiphenyl-4-ylcarboxamido)propanoate (0122-4)

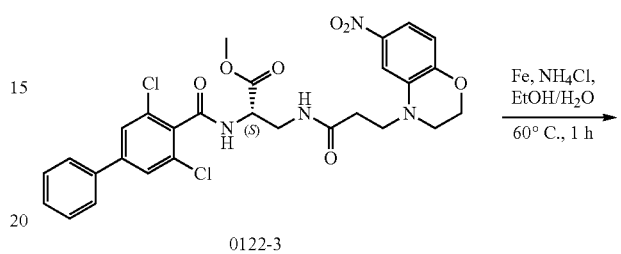

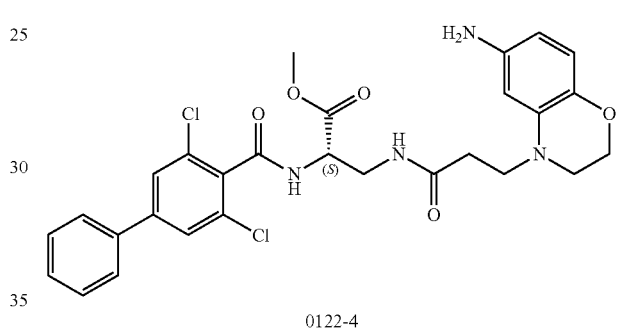

To a solution of compound 0122-3 (400 mg, 665 umol) in EtOH (5 mL) and H$_2$O (0.5 mL) was added iron powder (742.30 mg, 14.42 mmol) and NH$_4$Cl (355.76 mg, 6.65 mmol). The mixture was stirred at 60° C. for 1 h. After the reaction was finished (by LCMS), the reaction was filtered, the filtrate was concentrated in vacuo, the crude was quenched in H$_2$O (30 mL), extracted with CH$_2$Cl$_2$ (25 mL×3), the organic layer was washed with saturated aqueous NaCl, collected the organic layer and dried over anhydrous Na$_2$SO$_4$, filtered and concentrated in vacuo, the crude was purified by c.c. (CH$_2$Cl$_2$/MeOH=5%) to give the product 0122-4 (310 mg, 80.12% yield) as a brown solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% water [0.1 mol/L NH$_4$HCO$_3$] and CH$_3$CN to water [0.1 mol/L NH$_4$HCO$_3$] and CH$_3$CN in 1.6 min, then under this condition for 1.4 min, finally changed to 0% water [0.1 mol/L NH$_4$HCO$_3$] and 100% CH$_3$CN to 95% water [0.1 mol/L NH$_4$HCO$_3$] and 5% CH$_3$CN in 0.01 min, Purity: 85.21%, Rt=2.112 min; MS Calcd.: 570.1; MS Found: 571.1 [M+H]$^+$.

The Synthesis of (S,E)-methyl 3-(3-(6-(2,3-bis(tert-butoxycarbonyl)guanidino)-2H-benzo[b][1,4]oxazin-4(3H)-yl)propanamido)-2-(3,5-dichlorobiphenyl-4-yl carboxamido)propanoate (0122-5)

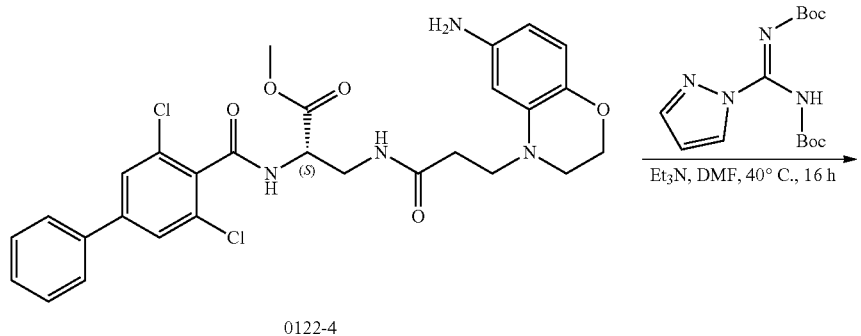

0122-4

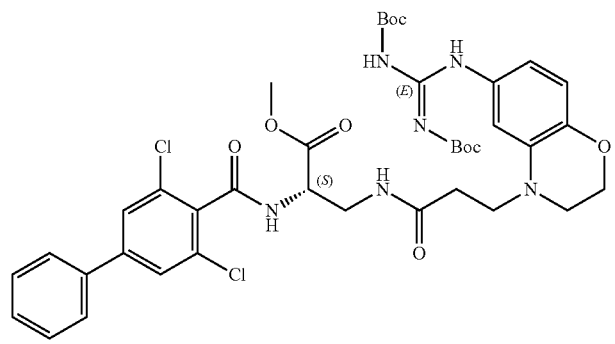

0122-5

To a solution of compound 0122-4 (360 mg, 629.98 umol) in DMF (5 mL) was added (E)-tert-butyl (1H-pyrazol-1-yl)methylenedicarbamate (293.27 mg, 944.96 umol) and TEA (191.24 mg, 1.89 mmol, 263.42 uL), the reaction mixture was stirred at 40° C. for 16 h. After the reaction was finished (by LCMS), the crude was purified by prep-HPLC to give the product 0122-5 (510.0 mg, yield: 55.0%) as a yellow solid.

The Synthesis of (9-methyl 2-(3,5-dichlorobiphenyl-4-ylcarboxamido)-3-(3-(6-guanidino-2H-benzo[b][1,4]oxazin-4(3H)-yl)propanamido)propanoate (0122-6)

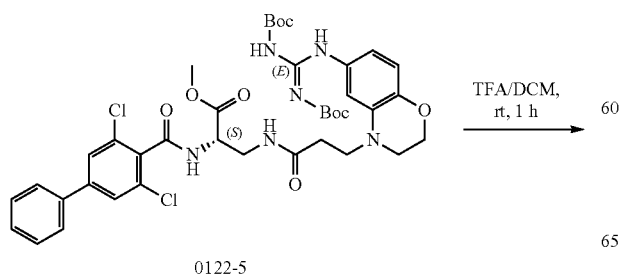

0122-5

-continued

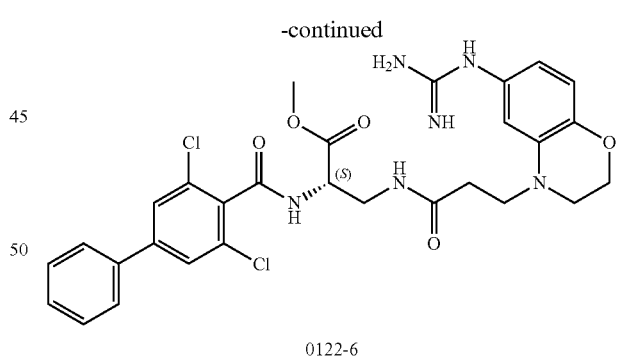

0122-6

To a solution of compound 0122-5 (360 mg, 629.98 umol) in DCM (5 mL) was added TFA (1.48 g, 12.98 mmol, 1 mL) at 0° C. and the mixture was stirred at rt for 2 h. After the consumption of the starting material (by LCMS), the reaction solvent was removed and the crude 0122-6 (250 mg, yield: 94.4%) was used for next step without purification.

The Synthesis of (S)-2-(3,5-dichlorobiphenyl-4-ylcarboxamido)-3-(3-(6 guanidino-2H-benzo[b][1,4]oxazin-4(3H)-yl)propanamido)propanoic acid (SU15210-0122-01)

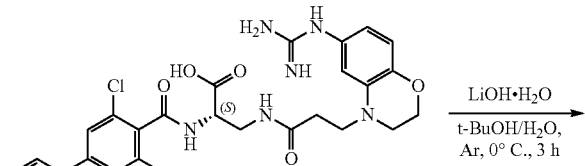

0122-6

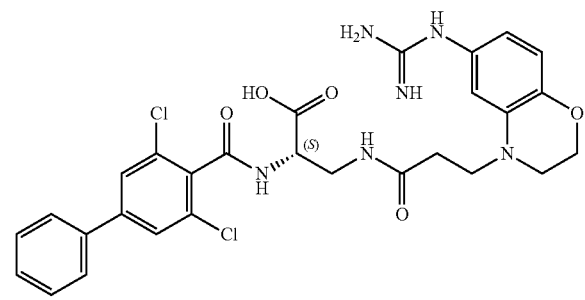

SU15210-0122-01

To a solution of compound 0122-6 (200 mg, 326.00 umol) in t-BuOH (4 mL) and water (2 mL) was added LiOH.H₂O (27.36 mg, 652.01 umol), the mixture was stirred in Ar atmosphere at 0° C. for 2 h. After the consumption of starting material (by LCMS), the mixture was concentrated and the solution was adjusted to pH=6 by addition of aqueous HCl (1 N) and the mixture was purified by prep-HPLC to give the product SU15210-0122-01 (106 mg, yield: 54.24%) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 5% [water+0.05% TFA] and 95% [water+0.05% TFA] in 1.6 min, then under this condition for 1.4 min, finally changed to 95% [water+0.05% TFA] and 5% [CH₃CN+0.05% TFA] in 0.05 min and under this condition for 0.7 min), Purity: 96.09%, Rt=1.570 min; MS Calcd.: 598.2; MS Found: 599.2 [M+H]⁺.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH₃CN+0.05% TFA] to 5% [water+0.05% TFA] and 95% [water+0.05% TFA] in 10 min, then under this condition for 5 min, finally changed to 95% [water+0.05% TFA] and 5% [CH₃CN+0.05% TFA] in 0.1 min and under this condition for 5 min), Purity: 94.27%, Rt=7.082 min.

¹H NMR (400 MHz, DMSO-d₆) δ 11.82 (d, J=2.8 Hz, 1H), 8.40 (d, J=8.0 Hz, 1H), 7.72-7.75 (m, 6H), 7.40-7.55 (m, 7H), 6.64 (d, J=8.0 Hz, 1H), 6.40 (dd, J=8.4 Hz, 2.4 Hz, 1H), 6.31 (s, 1H), 4.23-4.28 (m, 1H), 4.14 (s, 2H), 3.41-3.56 (m, 4H), 3.26-3.27 (m, 1H), 2.27-2.31 (m, 2H).

SU15210-0123-01

SU15210-0123-01

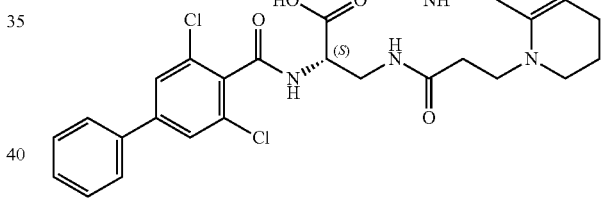

Chemical Formula: C₂₉H₃₀Cl₂N₆O₄
Molecular Weight: 597.49

Scheme 1: Route for SU15210-0123-01

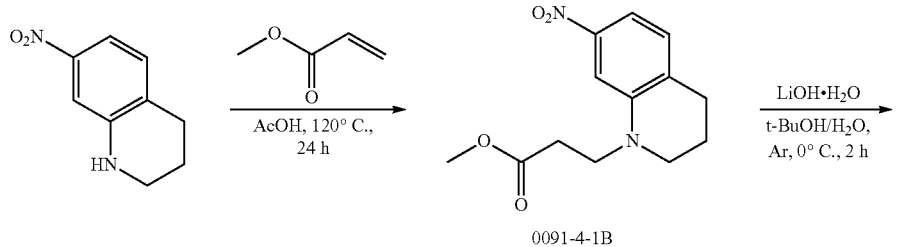

0091-4-1B

-continued
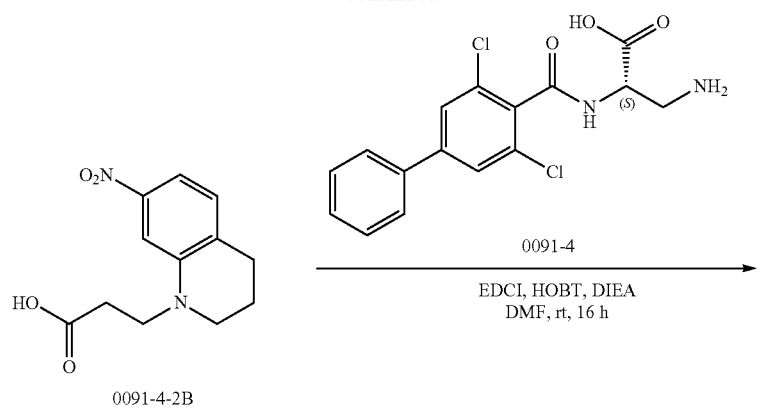
0091-4-2B
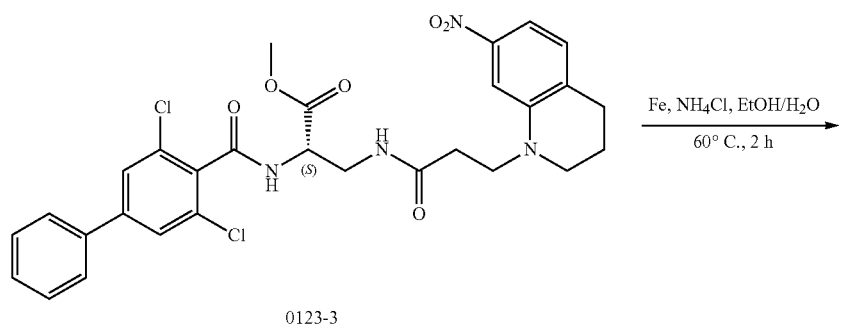
0123-3
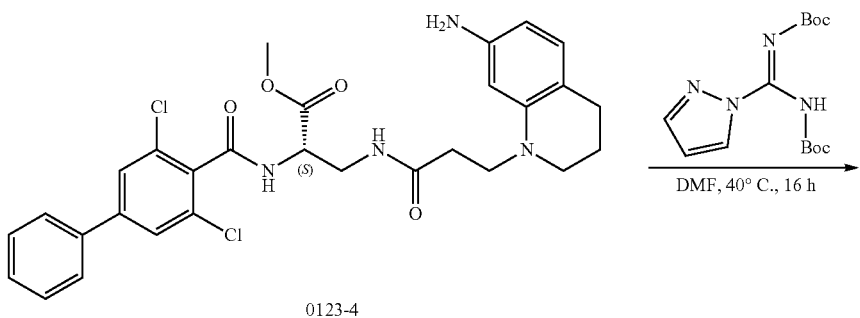
0123-4
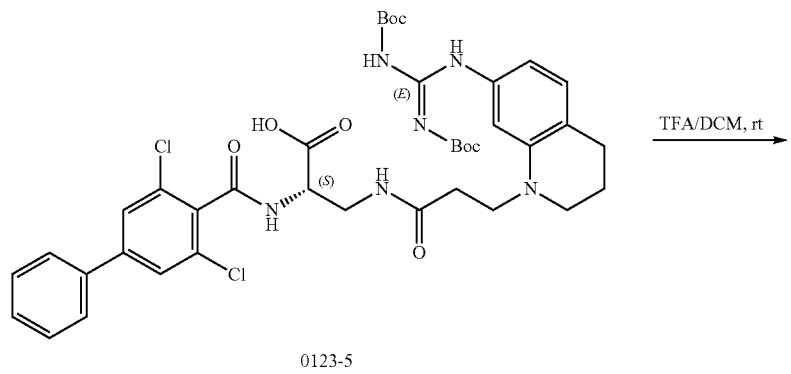
0123-5

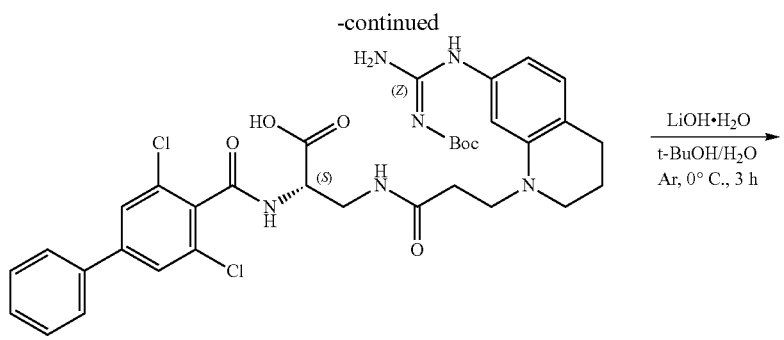

0123-6

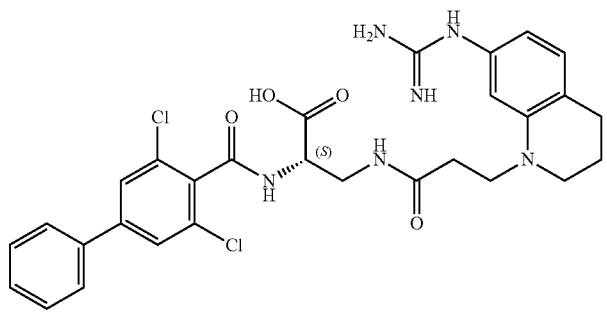

SU15210-0123-01

The Synthesis of methyl 3-(7-nitro-3,4-dihydroquinolin-1(2H)-yl)propanoate (0091-4-1B)

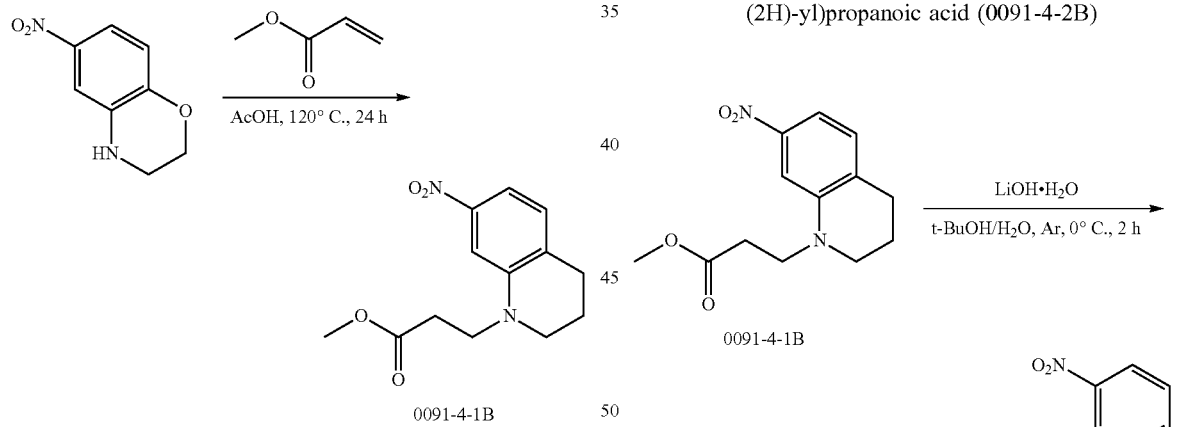

To a solution of 7-nitro-1,2,3,4-tetrahydroquinoline (2.14 g, 11.99 mmol) in AcOH (30 mL) was added methyl prop-2-enoate (3.10 g, 35.96 mmol, 3.24 mL) and the mixture was heat to 120° C. and stirred for 24 h. After the consumption of starting material (by LCMS), the reaction concentrated in vacuo, and the crude product was purified by c.c. (PE/EA=6:1) to give 0091-4-1B (2.2 g, 69.44% yield) as a red solid.

LC-MS (Agilent LCMS 1200-6110, Column: Waters X-Bridge C18 (30 mm*4.6 mm*2.7 μm); Column Temperature: 40° C.; Flow Rate: 3.0 mL/min; Mobile Phase: rom 95% [water+0.05% TFA] and 5% [CH$_3$CN+0.05% TFA] to 0% [water+0.05% TFA] and 100% [CH$_3$CN+0.05% TFA] in 0.8 min, then under this condition for 0.4 min, finally changed to 0% [water+0.05% TFA] and 100% [CH$_3$CN+0.05% TFA] to 95% [water+0.05% TFA] and 5% [CH$_3$CN+0.05% TFA] in 0.01 min, Purity: 94.61%, Rt=0.839 min; MS Calcd.: 364.1; MS Found: 265.0 [M+H]$^+$.

The Synthesis of 3-(7-nitro-3,4-dihydroquinolin-1(2H)-yl)propanoic acid (0091-4-2B)

To a solution of compound 0091-4-1B (2.2 g, 8.32 mmol) in t-BuOH (8 mL) and water (4 mL), LiOH.H$_2$O (628.61 mg, 14.98 mmol) was added and the mixture was stirred at 0° C. for 2 h. Then the mixture was concentrated and added aqueous HCl (1 N, 3 mL), extracted with EtOAc (30 mL×4) and the combined organic layers were concentrated in vacuo to give 0091-4-2B (1.97 g, 94.56% yield) as a red solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 0.8 min, then under this condition for 0.4 min, finally changed to 0% [water+0.05% TFA] and 100% [CH$_3$CN+0.05% TFA] to 95% [water+0.05% TFA] and 5% [CH$_3$CN+0.05% TFA] in 0.01 min, Purity: 96.97%, Rt=1.70 min; MS Calcd.: 250.1; MS Found: 251.2 [M+H]$^+$.

The Synthesis of (9-methyl 2-(3,5-dichlorobiphenyl-4-ylcarboxamido)-3-(3-(7-nitro-3,4-dihydroquinolin-1(2H)-yl)propanamido)propanoate (0123-3)

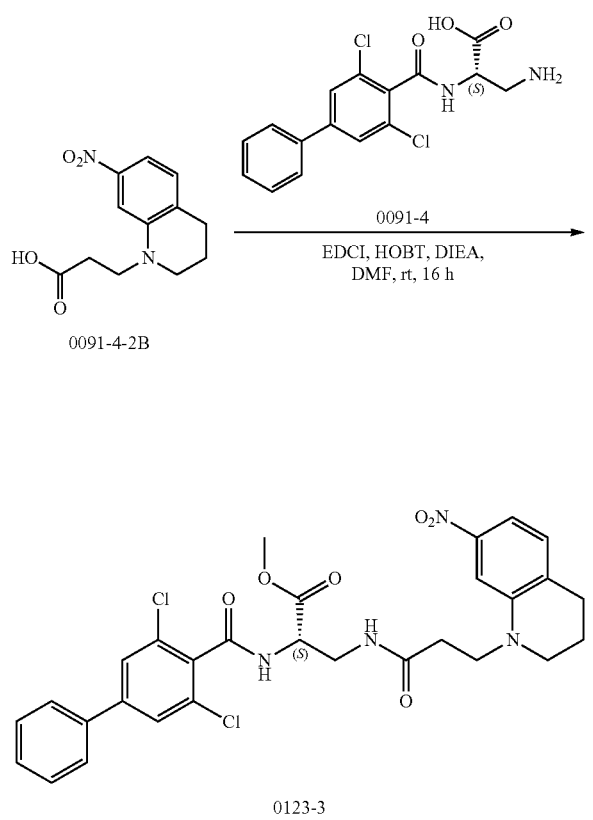

To a solution of compound 0091-4-2B (0.75 g, 3.00 mmol) in DMF (10 mL), were added EDCI (2.29 g, 6.00 mmol), HOBT (1.16 g, 9.00 mmol) and DIEA (1.16 g, 9.00 mmol, 1.57 mL) and the mixture was stirred at rt for 15 min. Then 0091-4 (1.10 g, 3.00 mmol) was added into the mixture and the mixture was stirred at rt for 16 h. After the consumption of starting material (by LCMS), the mixture was quenched with water (15 mL), and extracted with EtOAc (30 mL×4), combined the organic layer and dried over anhydrous Na$_2$SO$_4$, filtered and concentrated in vacuo. The crude was purified by c.c. (EA/PE=30%) to get the product 0123-3 (1.61 g, 89.52% yield) as a yellow solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [0.1 mol/L NH$_4$HCO$_3$] and 5% CH$_3$CN to 0% [water+0.05% TFA] and 100% CH$_3$CN in 1.6 min, then under this condition for 1.4 min, finally changed to 0% water [0.1 mol/L NH$_4$HCO$_3$] and 100% CH$_3$CN to 95% water [0.1 mol/L NH$_4$HCO$_3$] and CH$_3$CN in 0.01 min, Purity: 93.91%, Rt=2.449 min; MS Calcd.: 598.1; MS Found: 599.1 [M+H]$^+$.

The Synthesis of (9-methyl 3-(3-(7-amino-3,4-dihydroquinolin-1(2H)-yl)propanamido)-2-(3,5-dichlorobiphenyl-4-ylcarboxamido)propanoate (0123-4)

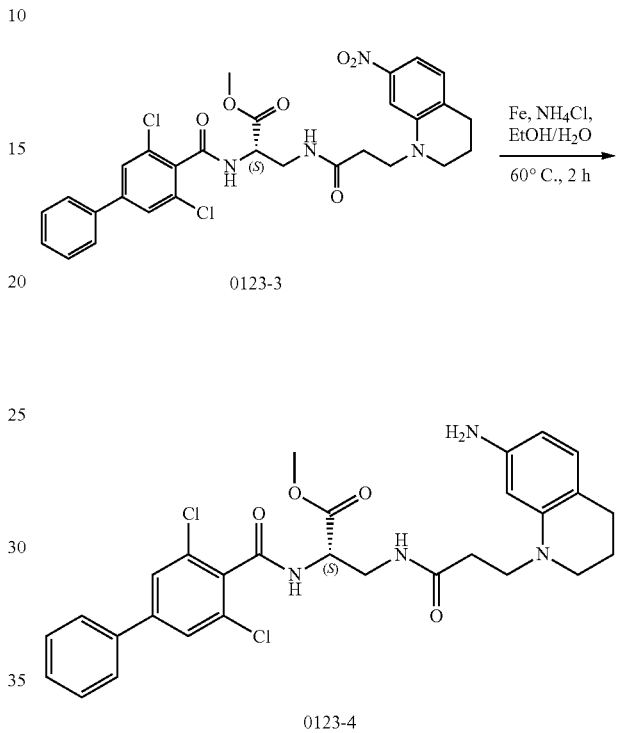

To a solution of compound 0123-3 (480 mg, 800.72 umol) in EtOH (5 mL) and H$_2$O (0.5 mL) was added iron powder (670.74 mg, 12.01 mmol) and NH$_4$Cl (428.32 mg, 8.01 mmol). The mixture was stirred at 60° C. for 2 h. After the reaction was finished (by LCMS), the reaction was filtered, the filtrate was concentrated in vacuo, the crude was quenched in H$_2$O (30 mL), extracted with CH$_2$Cl$_2$ (25 mL×3), the organic layer was washed with saturated aqueous NaCl, collected the organic layer and dried over anhydrous Na$_2$SO$_4$, filtered and concentrated in vacuo, the crude was purified by c.c. (CH$_2$Cl$_2$/MeOH=5%) to give the product 0123-4 (405 mg, 88.82% yield) as a brown solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% water [0.1 mol/L NH$_4$HCO$_3$] and CH$_3$CN to water [0.1 mol/L NH$_4$HCO$_3$] and CH$_3$CN in 1.6 min, then under this condition for 1.4 min, finally changed to 0% water [0.1 mol/L NH$_4$HCO$_3$] and 100% CH$_3$CN to 95% water [0.1 mol/L NH$_4$HCO$_3$] and 5% CH$_3$CN in 0.01 min, Purity: 68.72%, Rt=2.270 min; MS Calcd.: 568.2; MS Found: 569.2 [M+H]$^+$.

The Synthesis of (S,E)-3-(3-(7-(2,3-bis(tert-butoxycarbonyl)guanidino)-3,4-dihydroquinolin-1(2H)-yl)propanamido)-2-(3,5-dichlorobiphenyl-4-ylcarboxamido)propanoic acid (0123-5)

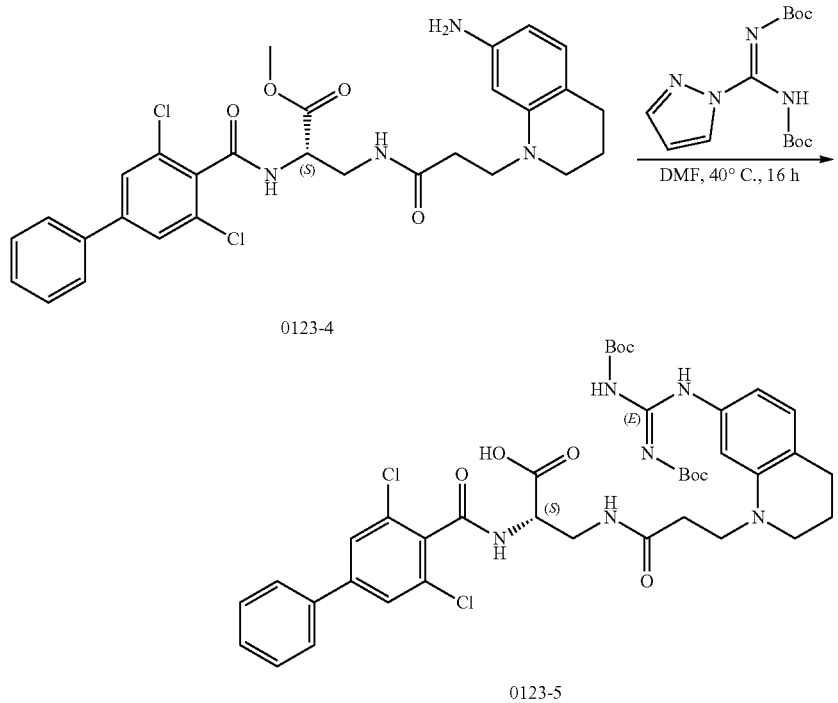

To a solution of compound 0123-4 (405 mg, 711.18 umol) in DMF (5 mL) was added (E)-tert-butyl (1H-pyrazol-1-yl)methylenedicarbamate (331.07 mg, 1.07 mmol) and TEA (191.24 mg, 1.89 mmol, 263.42 uL) and the mixture was stirred at 50° C. for 16 h. After the reaction was finished (by LCMS), the crude was purified by prep-HPLC to get product 0123-5 (310 mg, 53.70% yield) as a yellow solid.

The Synthesis of (9-methyl 2-(3,5-dichlorobiphenyl-4-ylcarboxamido)-3-(3-(7-guanidino-3,4-dihydroquinolin-1(2H)-yl)propanamido)propanoate (0123-6)

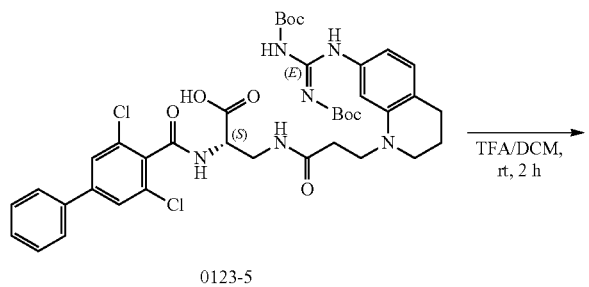

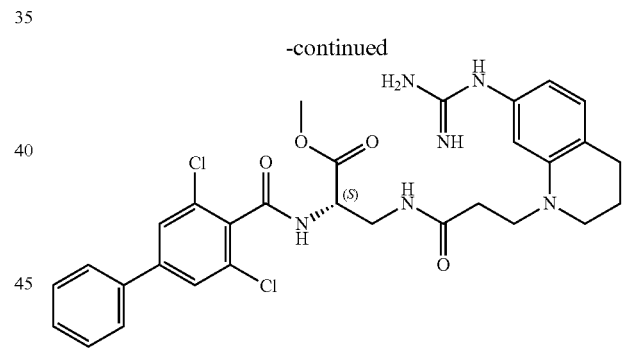

To a solution of compound 0123-5 (310 mg, 381.89 umol) in DCM (5 mL) was added 2,2,2-trifluoroacetic acid (435.44 mg, 3.82 mmol) was added at 0° C. and the mixture was stirred at rt for 2 h. After the consumption of starting material (by LCMS), the reaction solvent was removed in vacuo to give 0123-6 (233 mg, yield: 97.7%), which was used for next step without purification.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 5% [water+0.05% TFA] and 95% [water+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min), Purity: 100.0%, Rt=1.708 min; MS Calcd.: 610.2; MS Found: 610.9 [M+H]$^+$.

The Synthesis of (S)-2-(3,5-dichlorobiphenyl-4-ylcarboxamido)-3-(3-(7 guanidino-3,4-dihydroquinolin-1(2H)-yl)propanamido)propanoic acid (SU15210-0123-01)

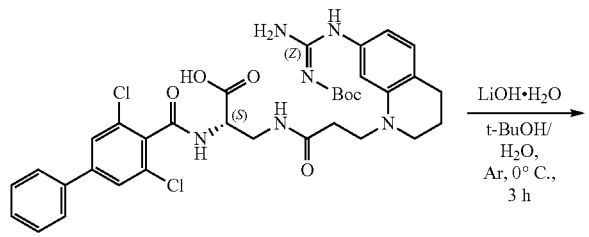

0123-6

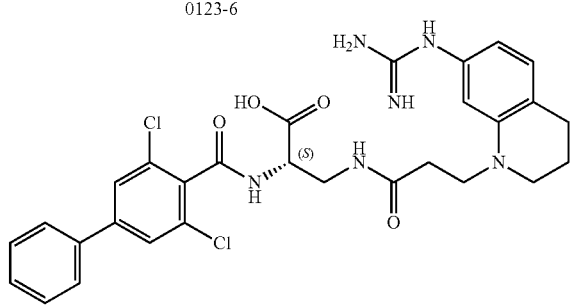

SU15210-0123-01

To a solution of compound 0123-6 (200 mg, 326.00 umol) in t-BuOH (2 mL) and water (1 mL) was added LiOH.H₂O (40 mg, 1.2 mmol) and the mixture was stirred in Ar atmosphere at 0° C. for 2 h. After the consumption of starting material (by LCMS), the mixture was concentrated. The solution was adjusted to pH=6 by addition of aqueous HCl (1 N) and the crude was purified by prep-HPLC to get product SU15210-0123-01 (36 mg, 15.81% yield) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 5% [water+0.05% TFA] and 95% [water+0.05% TFA] in 1.6 min, then under this condition for 1.4 min, finally changed to 95% [water+0.05% TFA] and 5% [CH₃CN+0.05% TFA] in 0.05 min and under this condition for 0.7 min), Purity: 94.58%, Rt=1.634 min; MS Calcd.: 596.2; MS Found: 597.2 [M+H]⁺.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH₃CN+0.05% TFA] to 5% [water+0.05% TFA] and 95% [water+0.05% TFA] in 5 min, then under this condition for 1 min, finally changed to 95% [water+0.05% TFA] and 5% [CH₃CN+0.05% TFA] in 0.1 min and under this condition for 5 min), Purity: 94.27%, Rt=2.959 min.

¹H NMR (400 MHz, DMSO-d₆) δ 12.13 (s, 1H), 8.26 (d, J=8.0 Hz, 1H), 7.73-7.80 (m, 6H), 7.43-7.57 (m, 7H), 6.87 (d, J=3.6 Hz, 1H), 6.39 (dd, J=7.4 Hz, 1.6 Hz, 1H), 6.16 (d, J=1.2 Hz, 1H), 4.27-4.28 (m, 1H), 3.53-3.59 (m, 1H), 3.39-3.46 (m, 2H), 3.19-3.22 (m, 2H), 2.62-2.66 (m, 2H), 2.27-2.32 (m, 2H), 1.79-1.85 (m, 2H).

SU15210-0130

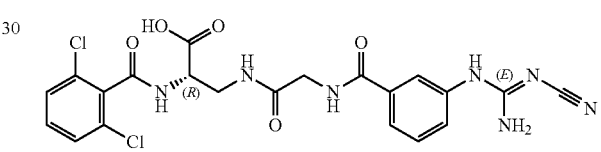

Chemical Formula: C₂₁H₁₉Cl₂N₇O₅
Molecular Weight: 520.33

Scheme: Route for SU15210-0130

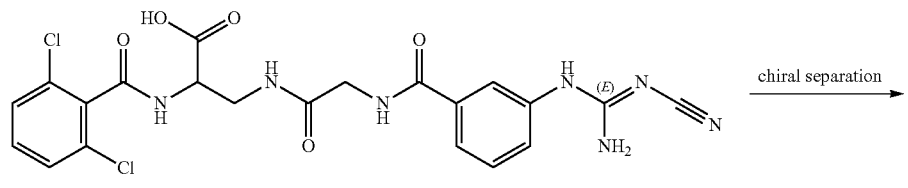

SU15210-0013 chiral separation →

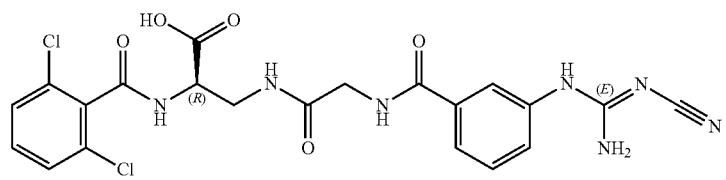

SU15210-0130

The Synthesis of (R,E)-3-(2-(3-(2-cyanoguanidino)benzamido)acetamido)-2-(2,6-dichlorobenzamido)propanoic acid (SU15210-0130)

The target SU15210-0013 was further purified by SFC to get the product SU15210-0130 (7.1 mg, peak A) as a white solid.

LC-MS (Agilent LCMS 1200-6110, Column: Waters X-Bridge C18 (50 mm*4.6 mm*3.5 µm); Column Temperature: 40° C.; Flow Rate: 2.0 mL/min; Mobile Phase: from 95% [water+0.05% TFA] and 5% [CH$_3$CN+0.05% TFA] to 5% [water+0.05% TFA] and 95% [water+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min), Purity: 99.05%, Rt=1.259 min; MS Calcd.: 519.0; MS Found: 520.0 [M+H]$^+$.

HPLC (Agilent HPLC 1200; Column: L-column2 ODS (150 mm*4.6 mm*5.0 µm); Column Temperature: 40° C.; Flow Rate: 1.0 mL/min; Mobile Phase: from 95% [water+0.05% TFA] and 5% [CH$_3$CN+0.05% TFA] to 5% [water+0.05% TFA] and 95% [water+0.05% TFA] in 10 min, then under this condition for 5 min, finally changed to 95% [water+0.05% TFA] and 5% [CH$_3$CN+0.05% TFA] in 0.1 min and under this condition for 5 min), Purity: 100.00%, Rt=6.353 min.

$^1$H NMR (400 MHz, DMSO-d$_6$) δ 10.13 (s, 1H), 8.82 (t, J=6.0 Hz, 1H), 8.05-8.12 (m, 2H), 7.82 (s, 1H), 7.37-7.53 (m, 8H), 7.29 (t, J=7.6 Hz, 1H), 4.06 (q, J=6.8 Hz, 1H), 3.82 (d, J=6.0 Hz, 2H), 3.65-3.72 (m, 1H), 3.08-3.12 (m, 1H).

SU15210-0131

The Synthesis of (S,E)-3-(2-(3-(2-cyanoguanidino)benzamido)acetamido)-2-(2,6-dichlorobenzamido)propanoic acid (SU15210-0131)

The target SU15210-0013 was further purified by SFC to get the product SU15210-0131 (10.3 mg, peak B) as a white solid.

LC-MS (Agilent LCMS 1200-6110, Column: Waters X-Bridge C18 (50 mm*4.6 mm*3.5 µm); Column Temperature: 40° C.; Flow Rate: 2.0 mL/min; Mobile Phase: from 95% [water+0.05% TFA] and 5% [CH$_3$CN+0.05% TFA] to 5% [water+0.05% TFA] and 95% [water+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min), Purity: 99.31%, Rt=1.261 min; MS Calcd.: 519.0; MS Found: 520.0 [M+H]$^+$.

HPLC (Agilent HPLC 1200; Column: L-column2 ODS (150 mm*4.6 mm*5.0 µm); Column Temperature: 40° C.; Flow Rate: 1.0 mL/min; Mobile Phase: from 95% [water+0.05% TFA] and 5% [CH$_3$CN+0.05% TFA] to 5% [water+0.05% TFA] and 95% [water+0.05% TFA] in 10 min, then under this condition for 5 min, finally changed to 95% [water+0.05% TFA] and 5% [CH$_3$CN+0.05% TFA] in 0.1 min and under this condition for 5 min), Purity: 100.00%, Rt=5.350 min.

$^1$H NMR (400 MHz, DMSO-d$_6$) δ 9.57 (s, 1H), 8.63-8.75 (m, 2H), 7.97 (s, 1H), 7.82 (s, 1H), 7.34-7.57 (m, 7H), 7.25 (s, 2H), 4.38 (q, J=6.0 Hz, 1H), 3.79-3.90 (m, 2H), 3.39-3.54 (m, 2H).

SU15210-0132

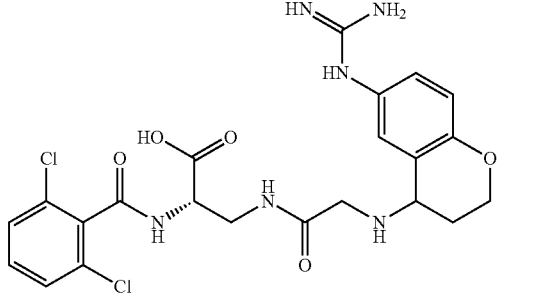

SU15210-0132

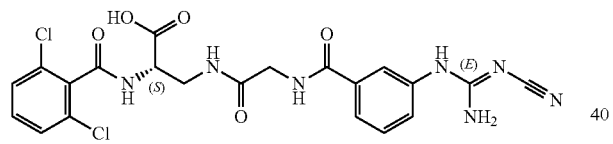

SU15210-0131

Chemical Formula: C$_{21}$H$_{19}$Cl$_2$N$_7$O$_5$
Molecular Weight: 520.33

Chemical Formula: C$_{22}$H$_{24}$Cl$_2$N$_6$O$_5$
Molecular Weight: 523.37

Scheme: Route for SU15210-0131

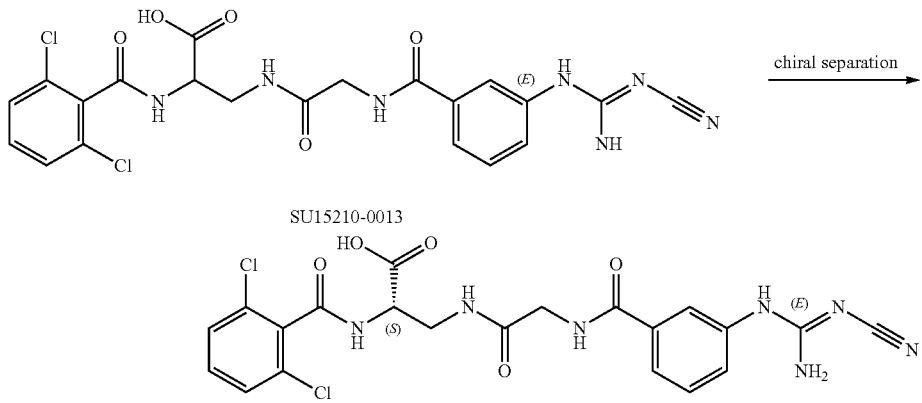

Scheme: Route for SU15210-0132

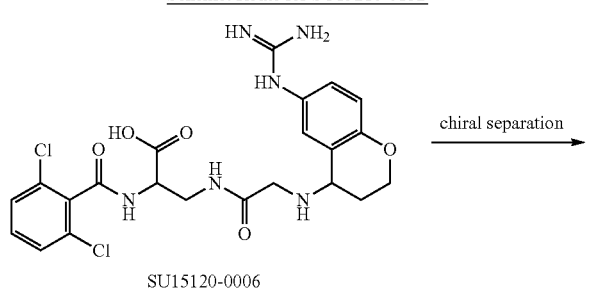

SU15120-0006

→ chiral separation

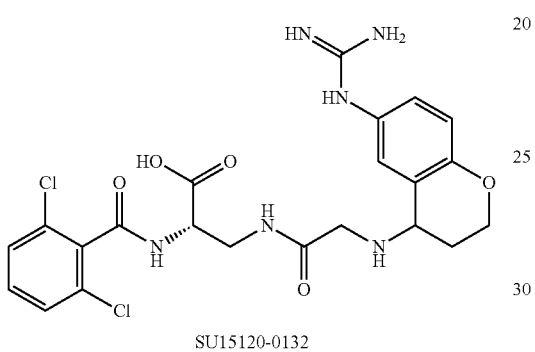

SU15120-0132

The Synthesis of (2S)-2-(2,6-dichlorobenzamido)-3-(2-(6 guanidinochroman-4-ylamino)acetamido)propanoic acid (SU15210-0132)

The target SU15210-0006 was further purified by SFC to get the product SU15210-0132 (4.8 mg) as a white solid.
LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% $NH_4HCO_3$] and 5% [$CH_3CN$+0.05% $NH_4HCO_3$] to 5% [water+0.05% $NH_4HCO_3$] and 95% [water+0.05% $NH_4HCO_3$] in 1.6 min, then under this condition for 1.4 min, finally changed to 95% [water+0.05% $NH_4HCO_3$] and 5% [$CH_3CN$+0.05% $NH_4HCO_3$] in 0.05 min and under this condition for 0.7 min), Purity: 99.33%, Rt=1.238 min; MS Calcd.: 522.0; MS Found: 523.1 [M+H]$^+$.
HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% $NH_4HCO_3$] and 5% [$CH_3CN$+0.05% $NH_4HCO_3$] to 5% [water+0.05% $NH_4HCO_3$] and 95% [water+0.05% $NH_4HCO_3$] in 5.0 min, then under this condition for 1.0 min, finally changed to 95% [water+0.05% $NH_4HCO_3$] and 5% [$CH_3CN$+0.05% $NH_4HCO_3$] in 0.1 min and under this condition for 5 min), Purity: 99.35%, Rt=5.440 min.

$^1$H NMR (400 MHz, DMSO-$d_6$) δ 11.50 (br s, 1H), 8.10-8.46 (m, 7H), 7.36-7.47 (m, 4H), 6.97-6.99 (m, 1H), 6.70 (d, J=8.8 Hz, 1H), 4.25-4.29 (m, 1H), 4.02-4.20 (m, 2H), 3.63-3.74 (m, 2H), 3.07-3.27 (m, 3H), 1.95-1.99 (m, 1H), 1.76-1.78 (m, 1H).

Example 3

Table 2 provides the IC50 (nM) results of an alpha-5-beta-1 integrin cell adhesion assay for the compounds shown. The assay was performed following the procedures set forth in Example 1 and as described by Yokosaki et al, J. Biol. Chem., 271: (39): 24144-24150 (1996).

TABLE 2

| Compound | IC50 (nM) |
| --- | --- |
| SU15210-0110-01 | <100 nM |
| SU15210-0147-01 | <100 nM |
| SU15210-0150-01 | <100 nM |
| SU15210-0151-01 | 101-1000 nM |
| SU15210-0152-01 | 1001-10000 nM |
| SU15210-0193-01 | 101-1000 nM |
| SU15210-0200 | <100 nM |
| SU15210-0202-01 | 101-1000 nM |
| SU15210-0203-01 | <100 nM |
| SU15210-0205-01 | <100 nM |
| SU15210-0206-01 | <100 nM |
| SU15210-0230-01 | <100 nM |
| SU15210-0238-01 | <100 nM |
| SU15210-0241-01 | <100 nM |
| SU15210-0248-01 | <100 nM |
| SU15210-0253-01 | <100 nM |
| SU15210-0254 | 101-1000 nM |
| SU15210-0271-01 | <100 nM |
| SU15210-0272-01 | <100 nM |

Example 4

All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. 1H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration.

Scheme: Route for SU15210-0110-01

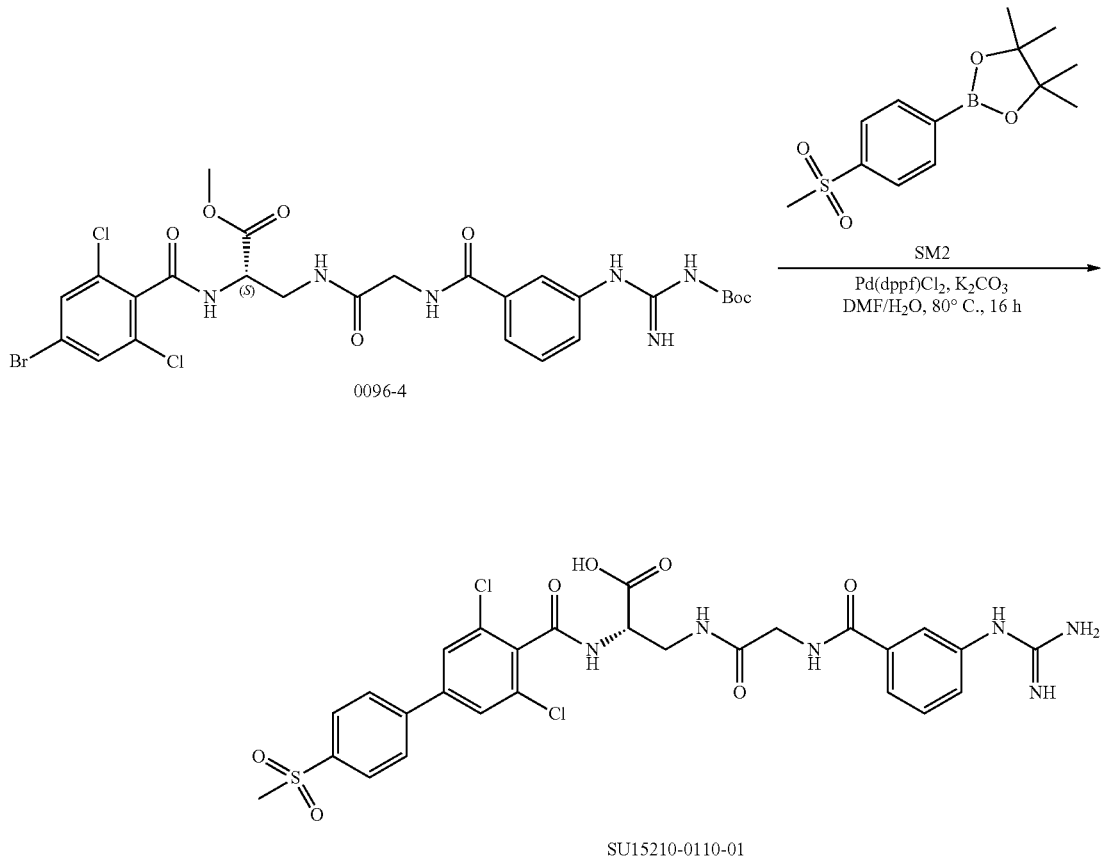

0096-4

SU15210-0110-01

The Synthesis of (S)-2-(3,5-dichloro-4'-(methyl-sulfonyl)biphenyl-4-ylcarboxamido)-3-(2-(3 guanidinobenzamido)acetamido)propanoic acid (SU15210-0110-01)

To a solution of 0096-4 (176.5 mg, 0.3 mmol) in DMF/H$_2$O (5 mL/0.5 mL) was added Pd(dppf)Cl$_2$ (22.0 mg, 30.0 umol), K$_2$CO$_3$ (124.4 mg, 0.9 mmol) and SM2 (127.0 mg, 0.5 mmol), the reaction was stirred at 80° C. for 16 h. After the consumption of starting material (detected by LCMS), the reaction mixture was adjusted pH to 2.0 by HCl (1.0 N), the mixture was purified directly by prep-HPLC to get the product SU15210-0110-01 (79.6 mg, 40.9% yield) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% NH$_4$HCO$_3$] and 5% [CH$_3$CN+0.05% NH$_4$HCO$_3$] to 5% [water+0.05% NH$_4$HCO$_3$] and 95% [water+0.05% NH$_4$HCO$_3$] in 1.6 min, then under this condition for 1.4 min, finally changed to 95% [water+0.05% NH$_4$HCO$_3$] and 5% [CH$_3$CN+0.05% NH$_4$HCO$_3$] in 0.05 min and under this condition for 0.7 min), Purity: 98.04%, Rt=1.121 min; MS Calcd.: 648.0; MS Found: 649.2 [M+H]$^+$.

Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min. Purity is 96.10%. Rt=5.449 min.

$^1$H NMR (400 MHz, DMSO-d$_6$) δ 11.14 (brs, 1H), 8.93 (s, 1H), 8.22-8.24 (m, 2H), 7.58-8.04 (m, 11H), 7.41 (t, J=8.0 Hz, 1H), 7.23 (d, J=7.6 Hz, 1H), 4.10 (q, J=6.4 Hz, 1H), 3.82 (d, J=4.0 Hz, 2H), 3.65-3.71 (m, 1H), 3.26 (s, 3H), 3.03 (t, J=9.6 Hz, 1H).

$^1$H NMR (400 MHz, DMSO-d$_6$ and D$_2$O) δ 7.96-8.02 (m, 4H), 7.84 (s, 2H), 7.62-7.68 (m, 2H), 7.43 (t, J=7.6 Hz, 1H), 7.25 (d, J=8.0 Hz, 1H), 4.10 (q, J=2.0 Hz, 1H), 3.82 (s, 2H), 3.58-3.65 (m, 1H), 3.23 (s, 3H), 3.06-3.11 (m, 1H).

Scheme: Route for SU15210-0147-01
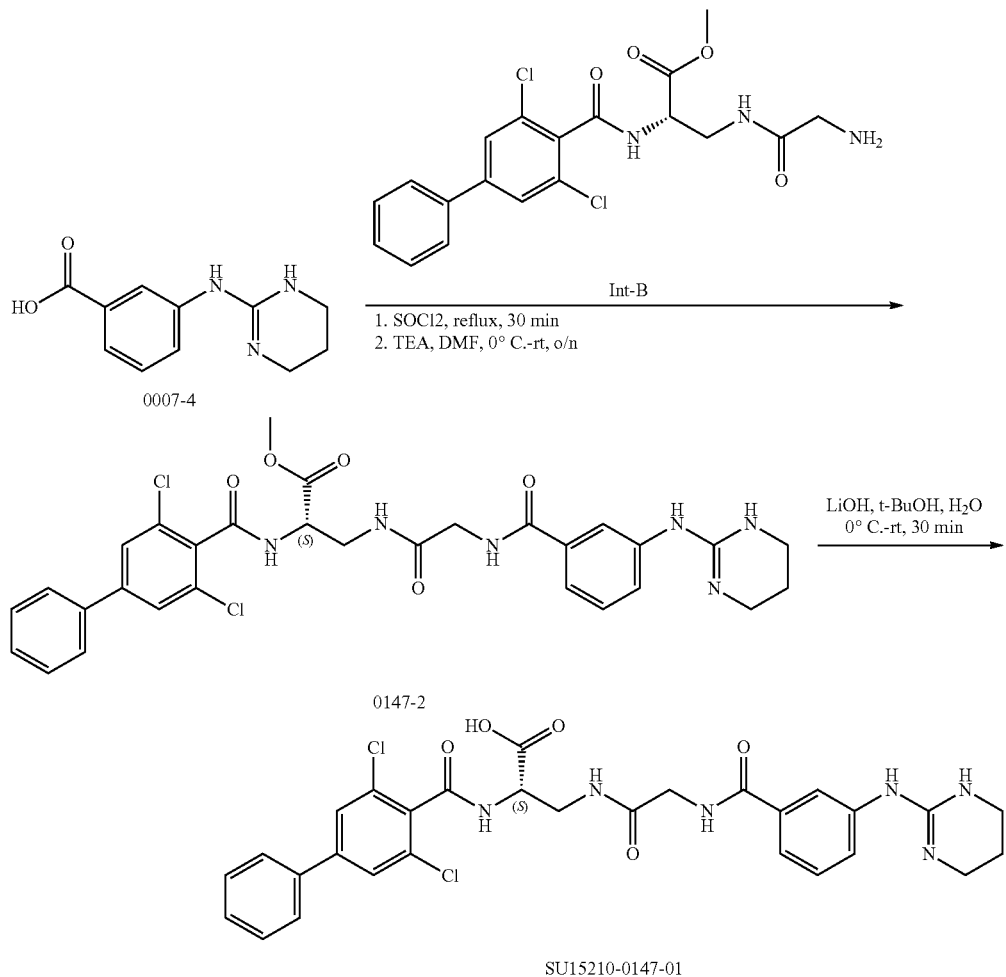
The Synthesis of (S)-methyl 2-(3,5-dichlorobiphe-nyl-4-ylcarboxamido)-3-(2-(3-(1,4,5,6-tetrahydropy-rimidin-2-ylamino)benzamido)acetamido)propanoate (0147-2)
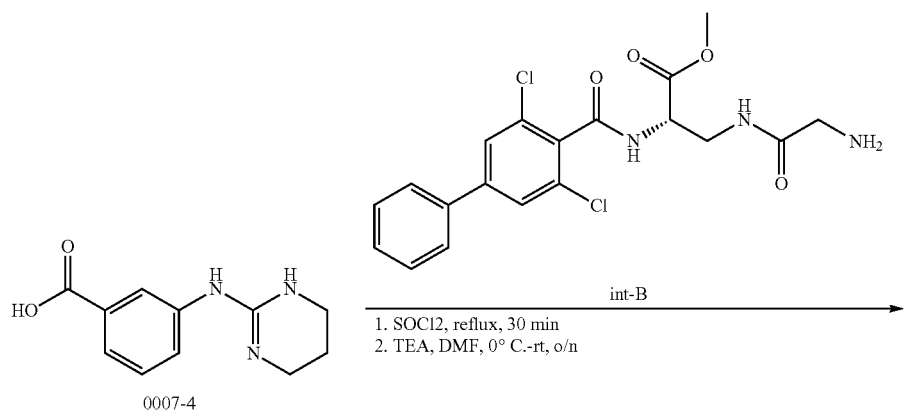

-continued

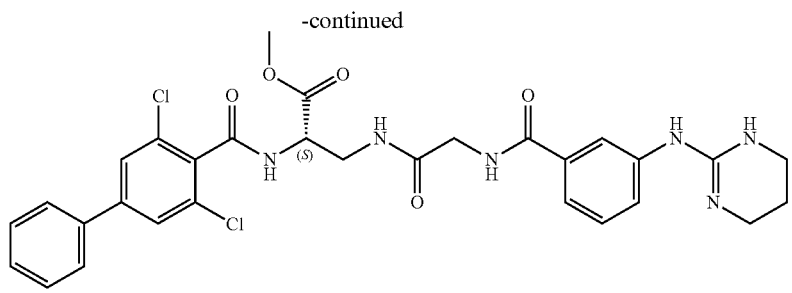

0147-2

A solution of 0007-4 (100 mg, 0.46 mmol) in SOCl$_2$ (5 mL) was stirred at reflux for 30 min, then remove the excess SOCl$_2$ under reduced pressure. The residue was then added to a solution of int-B (194 mg, 0.46 mmol) and TEA (186 mg, 1.84 mmol) in DMF (5 mL) at 0° C., the solution was then allowed to warm to room temperature and stirred for overnight. The solution was poured into water (50 mL), collected the precipitate by filtration, the solid was dried then purified by prep-HPLC to get 0147-02 (60 mg, 21% yield) as a white solid.

The Synthesis of (S)-2-(3,5-dichlorobiphenyl-4-ylcarboxamido)-3-(2-(3-(1,4,5,6-tetrahydropyrimidin-2-ylamino)benzamido)acetamido)propanoic acid (SU15210-0147-01)

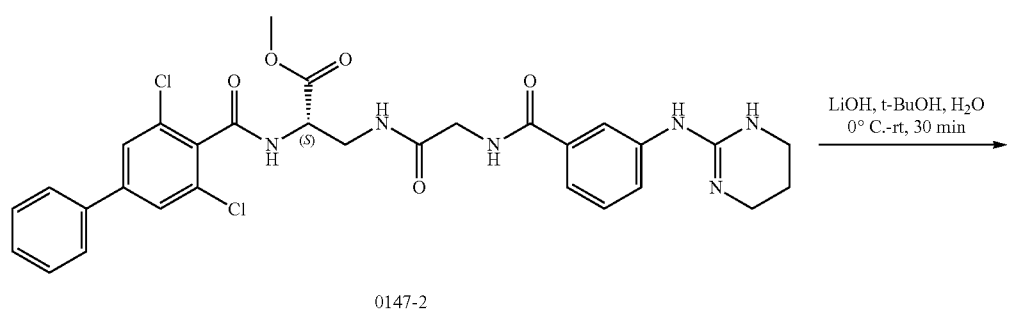

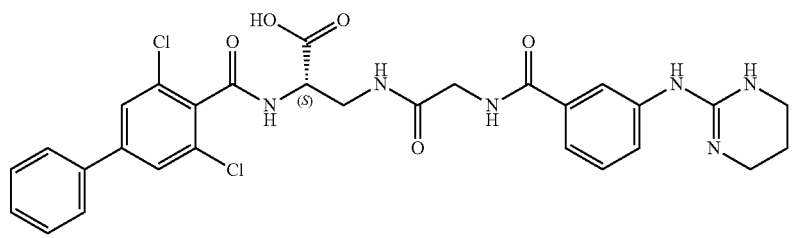

SU15210-0147-01

A solution of 0147-2 (60 mg, 0.096 mmol) in t-BuOH (3 mL) and H$_2$O (1 mL) was added LiOH (4.6 mg, 0.19 mmol) at 0° C. and stirred for 30 min. Acidified by 1 N HCl aq. to pH~2, concentrated and purified by prep-HPLC to get SU15210-0147-01 (25 mg, 42% yield) as a white solid.

Agilent LCMS 1200-6120, Column: Waters X-Bridge-C18 (50 mm*4.6 mm*3.5 µm); Column Temperature: 40° C.; Flow Rate: 2.0 mL/min; Mobile Phase: from 95% [water+10 mM TFA] and 5% [CH$_3$CN] to 0% [water+10 mM TFA] and 100% [CH$_3$CN] in 1.6 min, then under this condition for 1.4 min, finally changed to 95% [water+10 mM TFA] and 5% [CH$_3$CN] in 0.1 min. Purity is 100%. Rt=1.448 min; MS Calcd.: 610.1; MS Found: 611.1 [M+H]$^+$.

Agilent HPLC 1200; Column: Waters X-Bridge C18 (50 mm*4.6 mm*3.5 µm); Column Temperature: 30° C.; Flow Rate: 2.0 mL/min; Mobile Phase: from 95% [water+0.1% NH$_4$HCO$_3$] and 5% [CH$_3$CN] to 0% [water+0.1% NH$_4$HCO$_3$] and 100% [CH$_3$CN] in 10 min, then under this condition for 5 min, finally changed to 95% [water+0.1% NH$_4$HCO$_3$] and 5% [CH$_3$CN] in 0.1 min and under this condition for 5 min. Purity is 100%. Rt=6.689 min.

$^1$H NMR (400 MHz, DMSO-d$_6$) δ 11.63 (br, 1H), 9.15 (br, 2H), 8.87 (q, J=5.6 Hz, 1H), 8.43-8.3 (m, 2H), 7.84 (s, 1H), 7.79-7.70 (m, 4H), 7.53-7.37 (m, 5H), 7.29-7.21 (m, 1H), 4.23-4.17 (m, 1H), 3.96-3.81 (m, 2H), 3.76-3.68 (m, 1H), 3.18-2.99 (m, 5H), 1.79-1.65 (m, 2H).

Scheme: Route for SU15210-0150-01
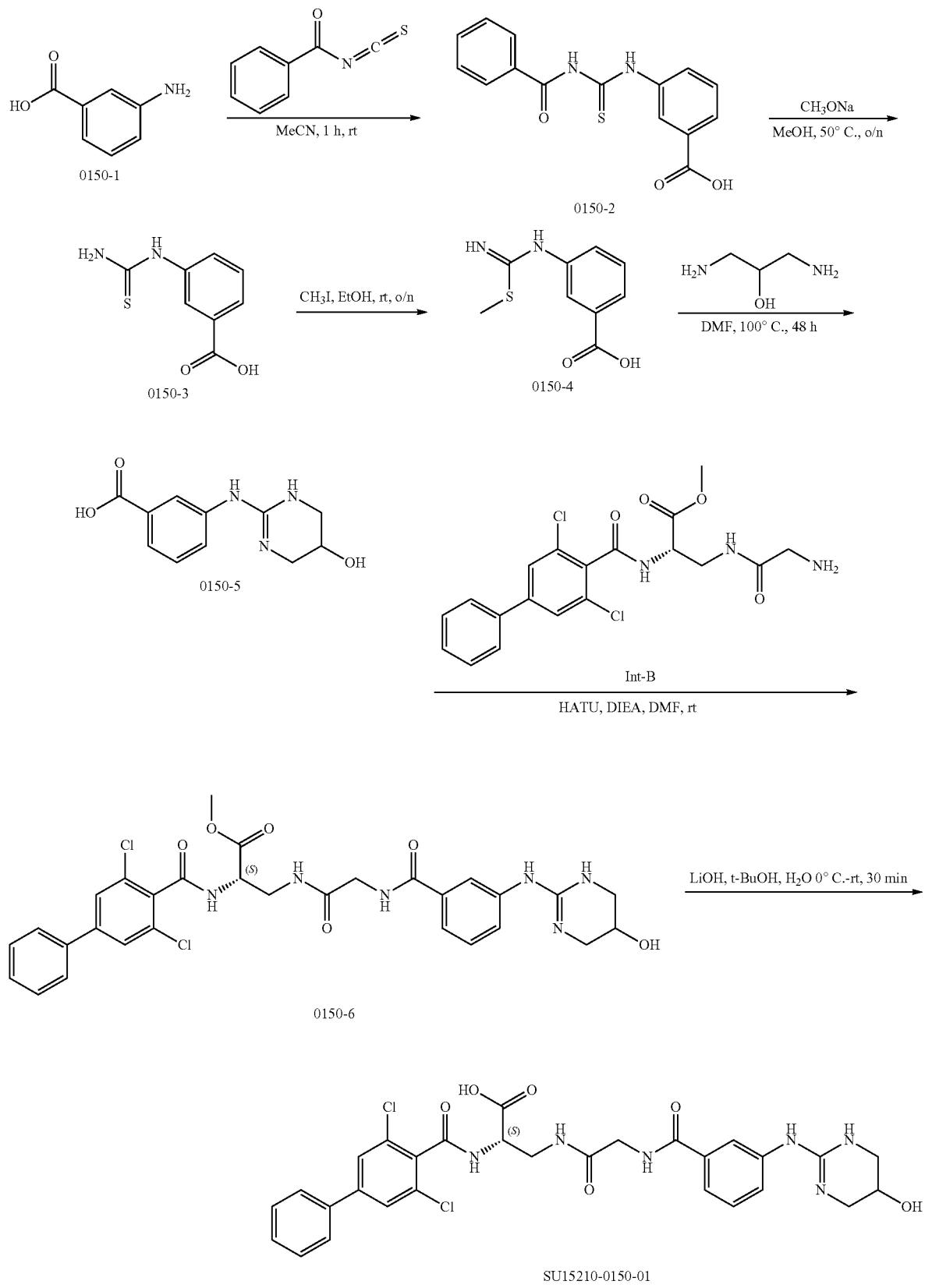

The Synthesis of 3-(3-benzoylthioureido)benzoic acid (0150-2)

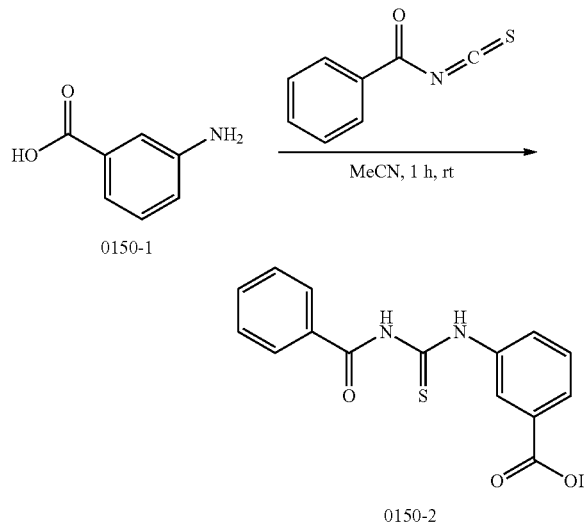

A solution of 0150-1 (5.0 g, 36.5 mmol) and benzoyl isothiocyanate (5.9 g, 36.5 mmol) in acetonitrile (50 mL) was stirred at room temperature for 1 h. Filtrate the precipitate and washed with acetonitrile, dried to get 0150-2 (8.5 g, 77% yield) as a yellow solid.

The Synthesis of 3-thioureidobenzoic acid (0150-3)

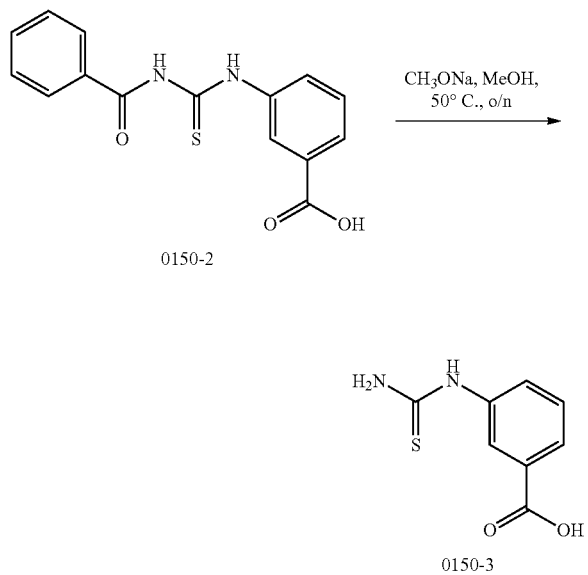 [SMILES: O=C(O)c1cccc(NC(=S)NC(=O)c2ccccc2)c1 ; NC(=S)Nc1cccc(C(=O)O)c1]

To a solution of 0150-2 (2.0 g, 6.67 mmol) in methanol (20 mL) was added $CH_3ONa$ (0.72 g, 13.3 mmol), the solution was stirred at 50° C. for overnight. Concentrated to remove the solvent, the residual was dissolved in water (10 mL), cooled to 0° C., acidified with concentrated HCl to pH~5, collected the precipitate and dried to give 0150-3 (1.1 g, 84% yield) as an off-white solid.

The Synthesis of 3-(imino(methylthio)methylamino)benzoic acid (0154-4)

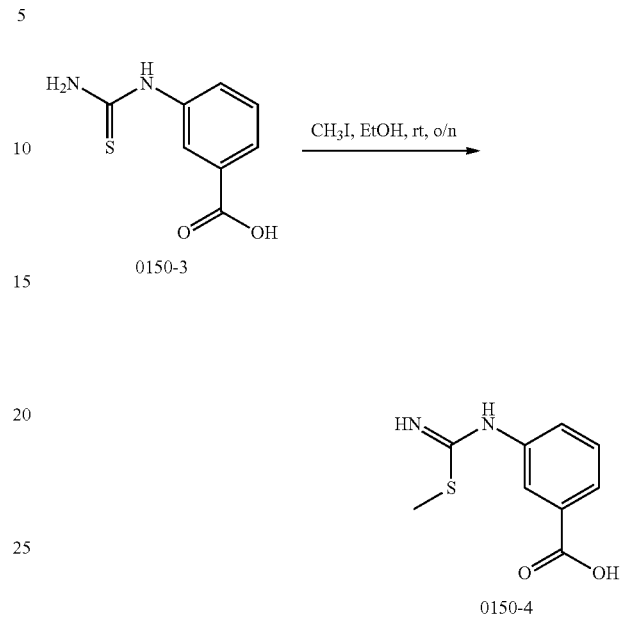

To a solution of 0150-3 (1.1 g, 5.61 mmol) in ethanol (10 mL) was added $CH_3I$ (0.8 g, 5.61 mmol), the solution was stirred at room temperature for overnight. Concentrated to give 0150-4 (1.2 g, 100% yield) as a yellow solid.

The Synthesis of 3-(5-hydroxy-1,4,5,6-tetrahydro-pyrimidin-2-ylamino)benzoic acid (0150-5)

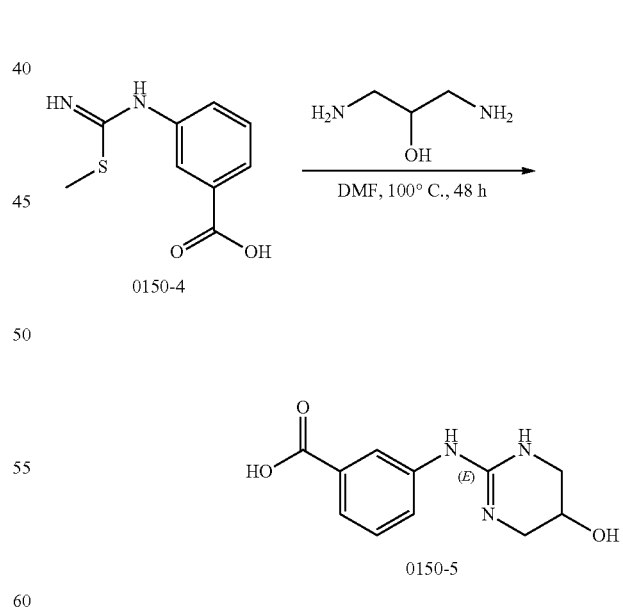

To a solution of 0150-4 (1.2 g, 5.7 mmol) in DMF (6 mL) was added 1,3-diaminopropan-2-ol (1.0 g, 11.4 mmol), the solution was stirred at 100° C. for 48 hours. Cooled to room temperature and filter the precipitate, wash the precipitate with ethyl acetate and dried to get 0150-5 (0.3 g, 22% yield) as an off-white solid.

The Synthesis of (2S)-methyl 2-(3,5-dichlorobiphenyl-4-ylcarboxamido)-3-(2-(3-(5-hydroxy-1,4,5,6-tetrahydropyrimidin-2-ylamino)benzamido)acetamido)propanoate (0150-6)

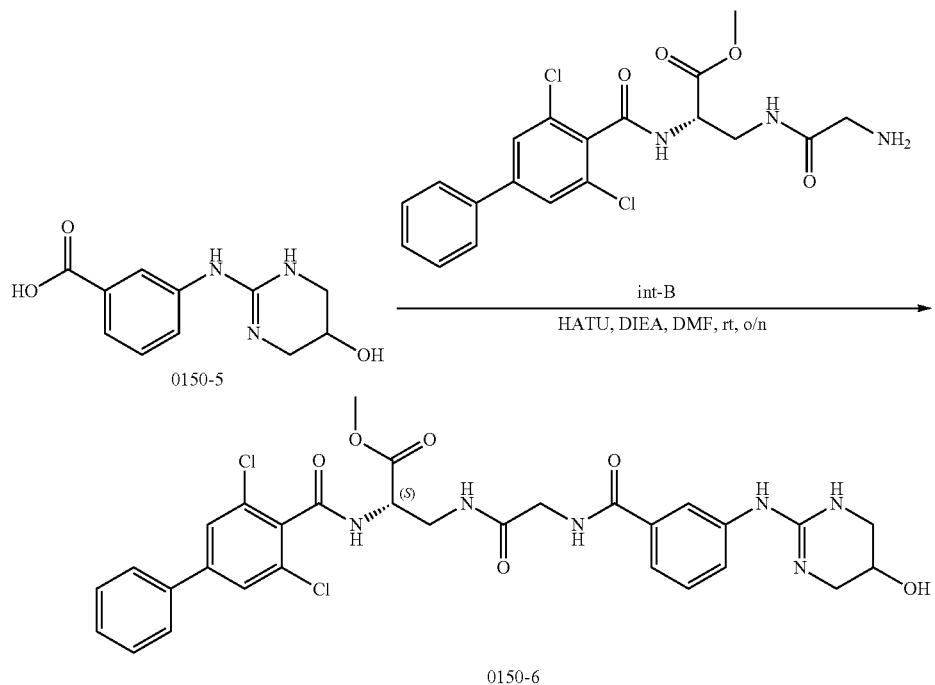

To a solution of 0150-5 (100 mg, 0.43 mmol) in DMF (5 mL) was added int-B (180 mg, 0.43 mmol), HATU (163 mg, 0.43 mmol) and DIPEA (111 mg, 0.86 mmol). The solution was stirred at room temperature for overnight. The solution was poured into water (30 mL), filter the precipitate then purified by prep-HPLC to give 0150-6 (60 mg, 22% yield) as a white solid.

The Synthesis of (2 S)-2-(3,5-dichlorobiphenyl-4-yl carboxamido)-3-(243-(5-hydroxy-1,4,5,6-tetrahydropyrimidin-2-yl amino)benzamido)acetamido)propanoic acid (SU15210-0150-01)

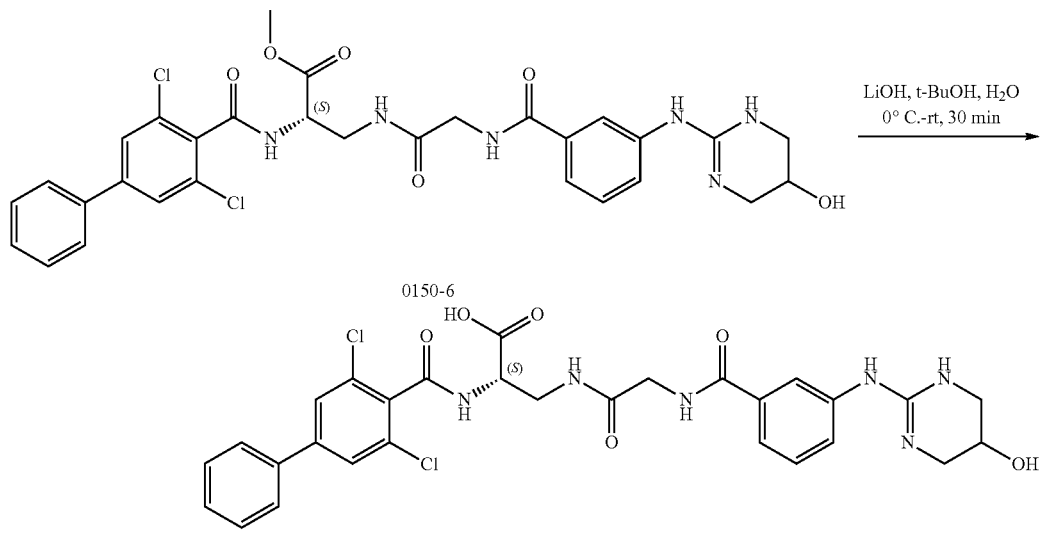

A solution of 0150-6 (60 mg, 0.093 mmol) in t-BuOH (3 mL) and H₂O (1 mL) was added LiOH (4.8 mg, 0.20 mmol) at 0° C. and stirred for 30 min. Acidified by 1 N HCl aq. to pH~2, concentrated and purified by prep-HPLC to get SU15210-0150-01 (30 mg, 51% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [CH₃CN] to 0% [water+10 mM TFA] and 100% [CH₃CN] in 1.6 min, then under this condition for 1.4 min, finally changed to 95% [water+10 mM TFA] and 5% [CH₃CN] in 0.1 min. Purity is 100%. Rt=1.396 min; MS Calcd.: 626.1; MS Found: 627.1 [M+H]⁺.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH₄HCO₃] and 5% [CH₃CN] to 0% [water+0.1% NH₄HCO₃] and 100% [CH₃CN] in 10 min, then under this condition for 5 min, finally changed to 95% [water+0.1% NH₄HCO₃] and 5% [CH₃CN] in 0.1 min and under this condition for 5 min. Purity is 100%. Rt=6.451 min.

$^1$H NMR (400 MHz, DMSO-d₆) δ 11.13 (br, 1H), 8.99 (br, 1H), 8.90 (t, J=5.6 Hz, 1H), 8.29-8.22 (m, 2H), 7.76-7.70 (m, 5H), 7.58 (d, J=8.0 Hz, 1H), 7.49-7.39 (m, 4H), 7.25 (d, J=8.0 Hz, 1H), 5.57 (br, 1H), 4.13 (q, J=7.6 Hz, 1H), 4.02-3.99 (m, 1H), 3.87-3.79 (m, 2H), 3.72-3.66 (m, 1H), 3.29-3.23 (m, 3H), 3.19-3.12 (m, 2H), 3.07-3.02 (m, 1H).

0.7 mmol) and DIPEA (236.5 mg, 1.8 mmol), the reaction mixture was stirred at rt for 15 min, then, 0002-6 (250.3 mg, 0.6 mmol) was added into reaction mixture, the reaction was stirred at rt for 16 h. After the reaction was finished, the reaction mixture was purified directly by prep-HPLC to get the product SU15210-0151-01 (46.5 mg, 12.7% yield) as white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% NH₄HCO₃] and 5% [CH₃CN+0.05% NH₄HCO₃] to 5% [water+0.05% NH₄HCO₃] and 95% [water+0.05% NH₄HCO₃] in 1.6 min, then under this condition for 1.4 min, finally changed to 95% [water+0.05% NH₄HCO₃] and 5% [CH₃CN+0.05% NH₄HCO₃] in 0.05 min and under this condition for 0.7 min), Purity: 100.00%, Rt=1.531 min; MS Calcd.: 597.0; MS Found: 598.0 [M+H]⁺.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% NH₄HCO₃] and 5% [CH₃CN+0.05% NH₄HCO₃] to 5% [water+0.05% NH₄HCO₃] and 95% [water+0.05% NH₄HCO₃] in 5.0 min, then under this condition for 1.0 min, finally changed to 95% [water+0.05% NH₄HCO₃] and 5% [CH₃CN+0.05% NH₄HCO₃] in 0.1 min and under this condition for 5 min), Purity: 100.00%, Rt=7.483 min.

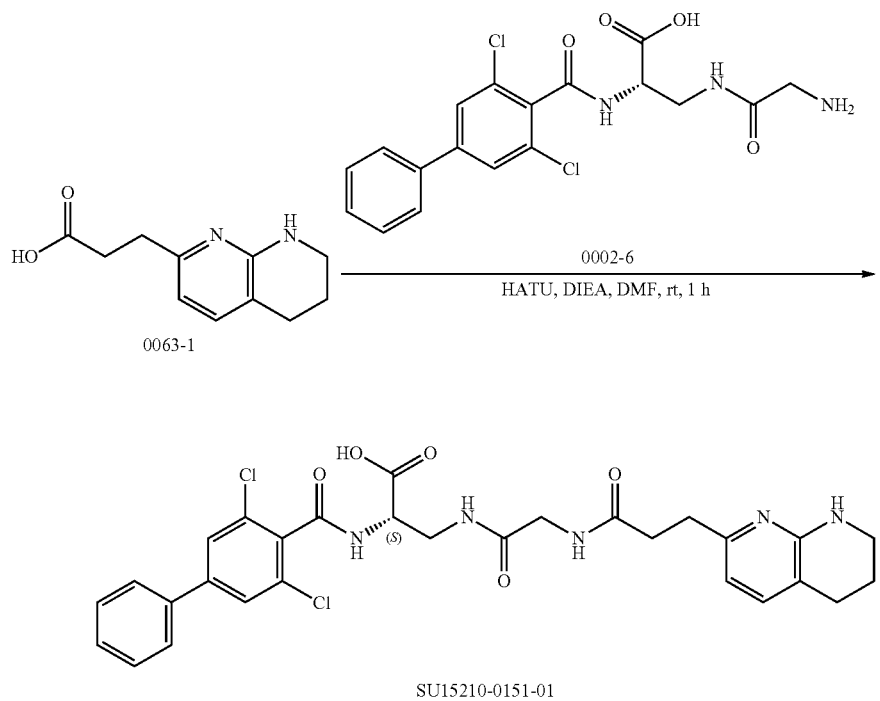

Scheme: Route for SU15210-0151-01

The Synthesis of (S)-2-(3,5-dichloro-[1,1'-biphenyl]-4-carboxamido)-3-(2-(3-(5,6,7,8-tetrahydro-1,8-naphthyridin-2-yl)propanamido)acetamido)propanoic acid (SU15210-0151-01)

To a solution of 0063-1 (151.0 mg, 0.7 mmol) in DMF (10 mL) was added EDCI (140.3 g, 07 mmol), HOBT (99.0 g, $^1$H NMR (400 MHz, DMSO-d₆) δ 8.57 (m, 1H), 8.29 (t, J=6.0 Hz, 1H), 7.96 (t, J=4.8 Hz, 1H), 7.73-7.77 (m, 4H), 7.41-7.50 (m, 3H), 7.09-7.18 (m, 2H), 6.31 (d, J=7.6 Hz, 1H), 4.29 (q, J=6.8 Hz, 1H), 3.48-3.69 (m, 6H), 2.71 (t, J=7.6 Hz, 2H), 2.59 (t, J=6.0 Hz, 2H), 2.42-2.47 (m, 2H), 1.72-1.74 (m, 2H).

Scheme: Route for SU15210-0152-01

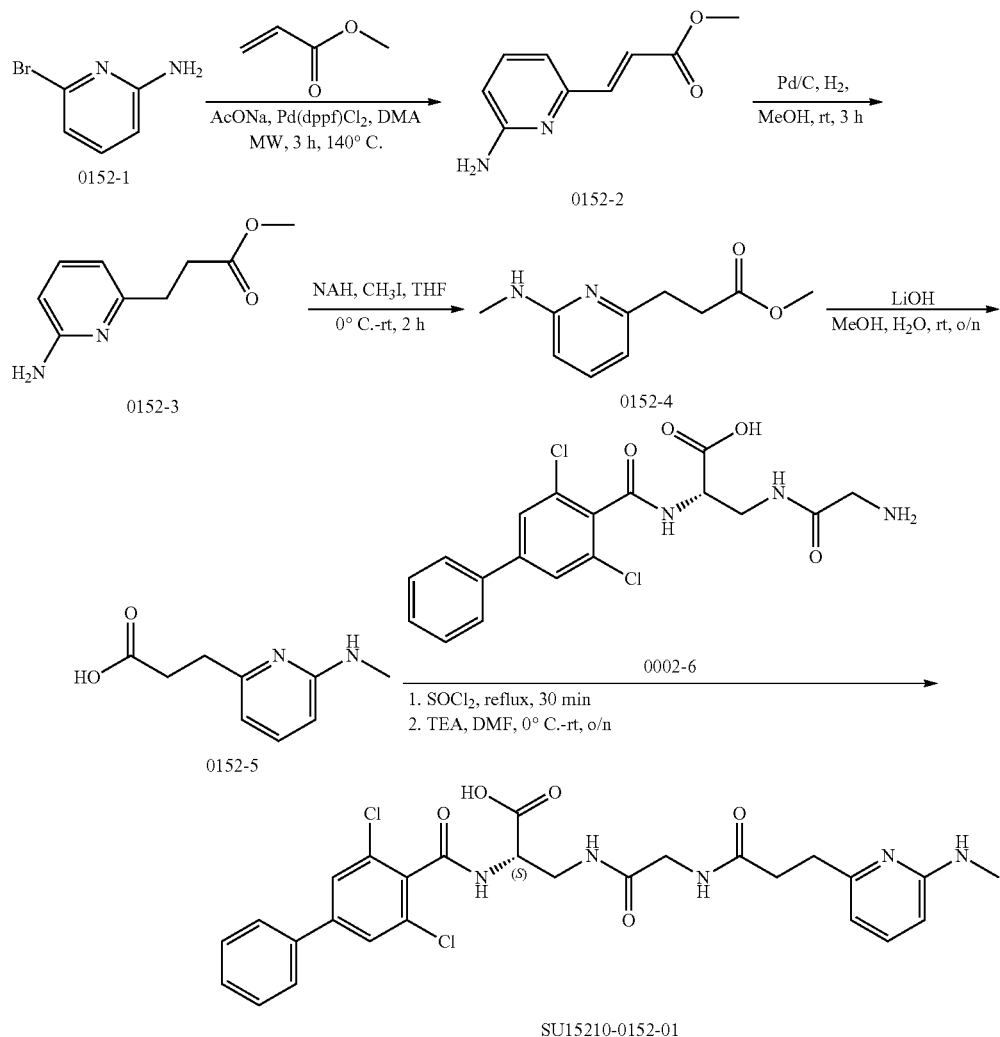

The Synthesis of (E)-methyl 3-(6-aminopyridin-2-yl)acrylate (0152-2)

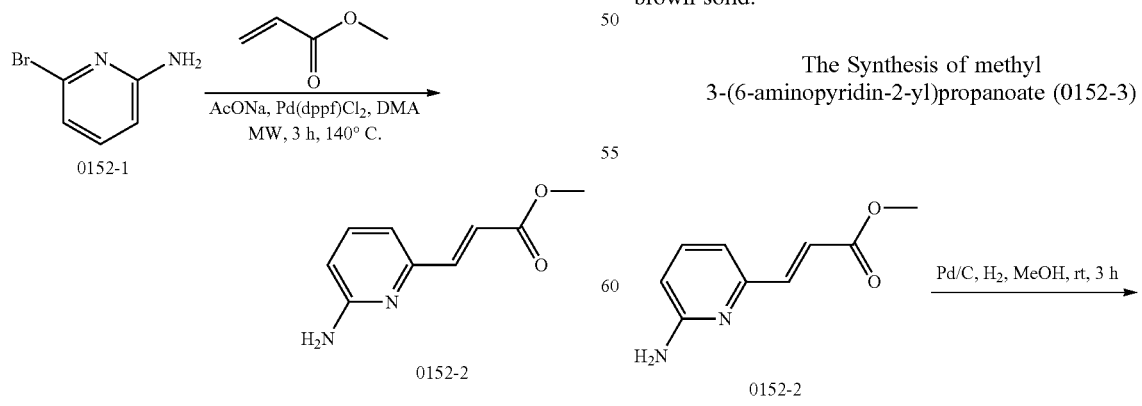

To a solution of 0152-1 (3.0 g, 17.3 mmol) in DMA (15 mL) was added methyl acrylate (3.0 g, 34.6 mmol), sodium acetate (2.8 g, 34.60 mmol) and Pd(dppf)Cl$_2$, the mixture was stirred under microwave at 140° C. for 3 h. Cooled to room temperature and filter, the filtrate was concentrated then purified by CC give 0152-2 (0.9 g, 29% yield) as a brown solid.

The Synthesis of methyl 3-(6-aminopyridin-2-yl)propanoate (0152-3)

-continued

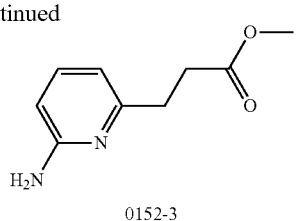

0152-3

To a solution of 0152-2 (200 mg, 1.12 mmol) in MeOH (10 mL) was added Pd/C (40 mg), the mixture was stirred under H₂ at room temperature for 3 h. When the reaction was completed, filtrate to remove the catalyst, the filtrate was concentrate to give 0152-3 (210 mg, 100%) as a brown oil.

The Synthesis of methyl 3-(6-(methylamino)pyridin-2-yl)propanoate (0152-4)

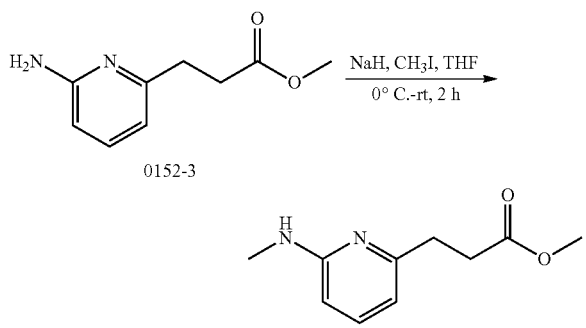

To a solution of 0152-3 (220 mg, 1.22 mmol) in dry THF (10 mL) was added NaH (60 in oil) (53 mg, 1.46 mmol) at 0° C., the mixture was stirred at 0° C. for 30 min, then iodomethane (207 mg, 1.46 mmol) was added drop wise. The mixture was then allowed to warm to room temperature and stirred for 2 h. Then water was added, the mixture was extracted with EA (10 mL×2), the organic phase was separated and washed with water then brine, dried over Na₂SO₄, concentrated and purified by CC to give 0152-4 (110 mg, 47%) as a white solid.

The Synthesis of 3-(6-(methylamino)pyridin-2-yl)propanoic acid (0152-5)

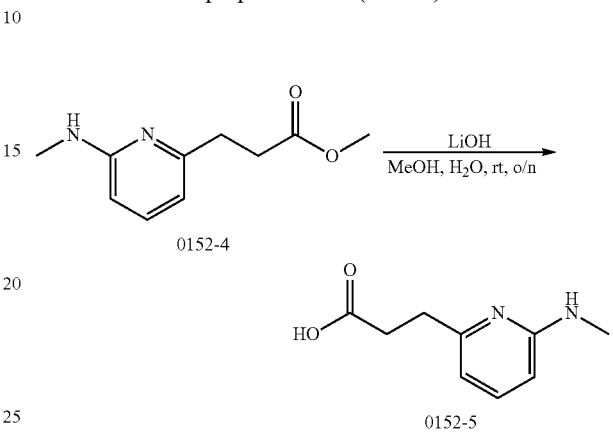

To a solution of 0152-4 (110 mg, 0.57 mmol) in MeOH (5 mL) and H₂O (1.5 mL) was added LiOH (27 mg, 1.14 mmol), the solution was stirred at room temperature for overnight. Concentrated to remove MeOH, acidified by 1N HCl aq. to pH~2, then purified by prep-HPLC to give 0152-5 (95 mg, 93% yield) as a white solid.

The Synthesis of (S)-2-(3,5-dichlorobiphenyl-4-ylcarboxamido)-3-(2-(3-(6-(methylamino)pyridin-2-yl)propanamido)acetamido)propanoic acid (SU15210-0152-01)

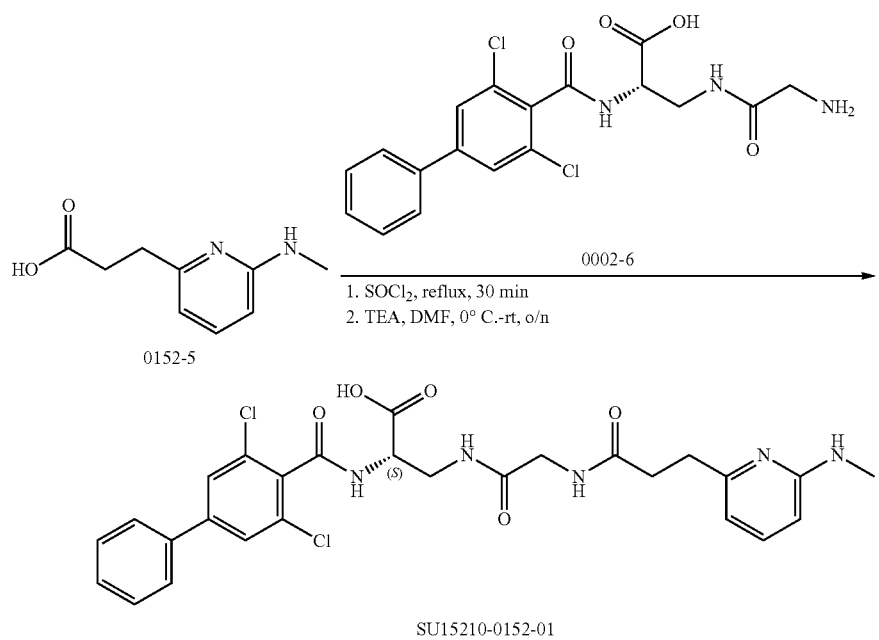

A solution of 0152-5 (95 mg, 0.53 mmol) in SOCl₂ (5 mL) was stirred at reflux for 30 min, then remove the excess SOCl₂ under reduced pressure. The residue was then added to a solution of 0002-6 (216 mg, 0.53 mmol) and TEA (214 mg, 2.12 mmol) in DMF (5 mL) at 0° C., the solution was then allowed to warm to room temperature and stirred for overnight. Poured the solution into water (50 mL), collected the precipitate by filtration, the solid was dried then purified by prep-HPLC to get SU15210-0152-01 (35 mg, 12% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [CH₃CN] to 0% [water+10 mM TFA] and 100% [CH₃CN] in 1.6 min, then under this condition for 1.4 min, finally changed to 95% [water+10 mM TFA] and 5% [CH₃CN] in 0.1 min. Purity is 97.87%. Rt=1.501 min; MS Calcd.: 571.2; MS Found: 572.2 [M+H]⁺.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH₄HCO₃] and 5% [CH₃CN] to 0% [water+0.1% NH₄HCO₃] and 100% [CH₃CN] in 10 min, then under this condition for 5 min, finally changed to 95% [water+0.1% NH₄HCO₃] and 5% [CH₃CN] in 0.1 min and under this condition for 5 min. Purity is 95.74%. Rt=6.621 min.

$^1$H NMR (400 MHz, DMSO-d₆) δ 8.33 (t, J=6.0 Hz, 1H), 8.27 (br, 1H), 8.27 (d, J=8.0 Hz, 1H), 7.82 (d, J=6.0 Hz, 1H), 7.76-7.73 (m, 4H), 7.50-7.40 (m, 3H), 7.23 (t, J=8.0 Hz, 1H), 6.33-6.29 (m, 2H), 6.18 (d, J=8.0 Hz, 1H), 3.85-3.80 (m, 1H), 3.68-3.62 (m, 1H), 3.61 (d, J=5.6 Hz, 2H), 3.02-2.95 (m, 1H), 2.78-2.73 (m, 2H), 2.71 (d, J=4.8 Hz, 3H), 2.53-2.49 (m, 2H).

Scheme: Route for SU15210-0193-01

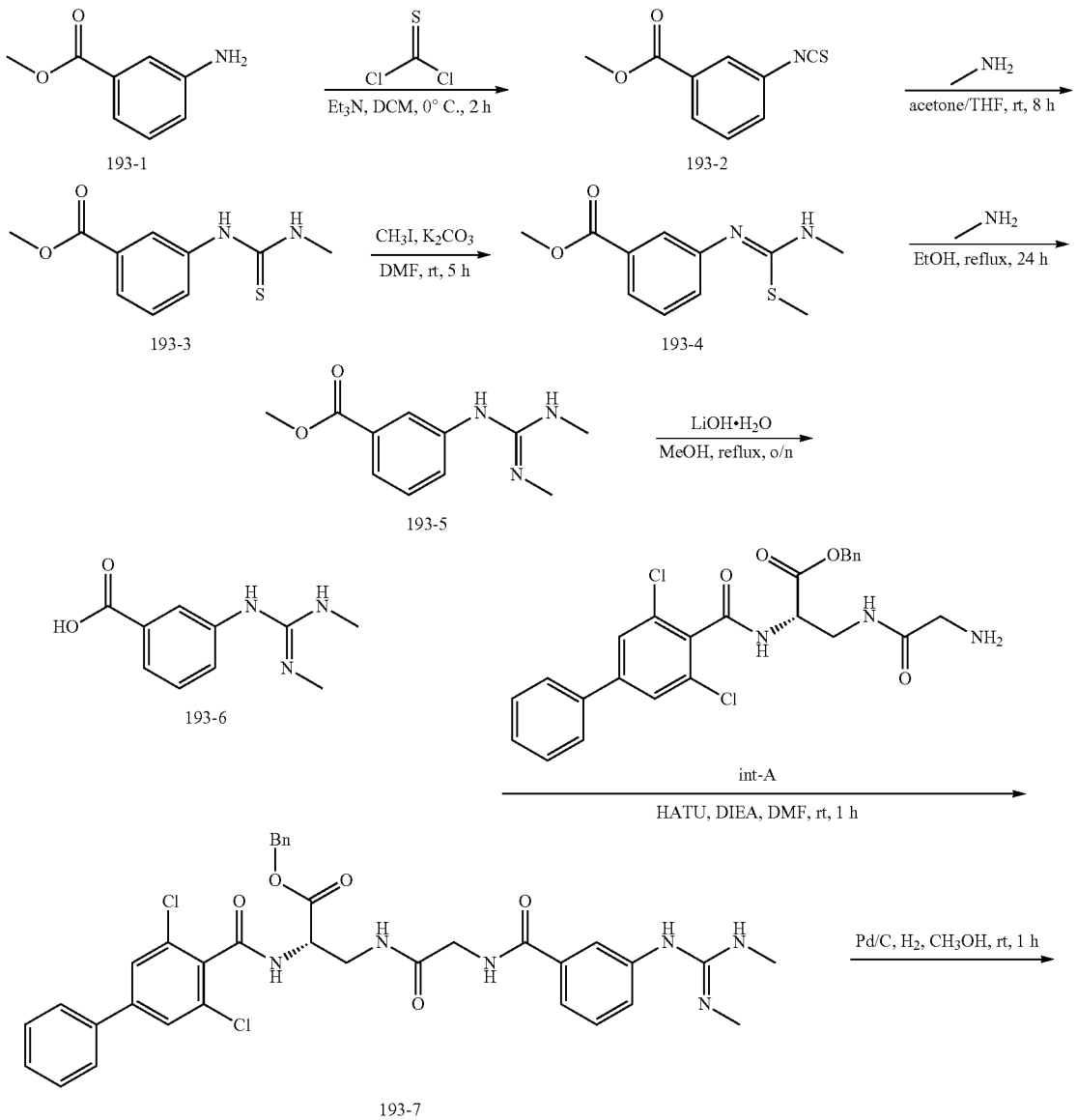

-continued

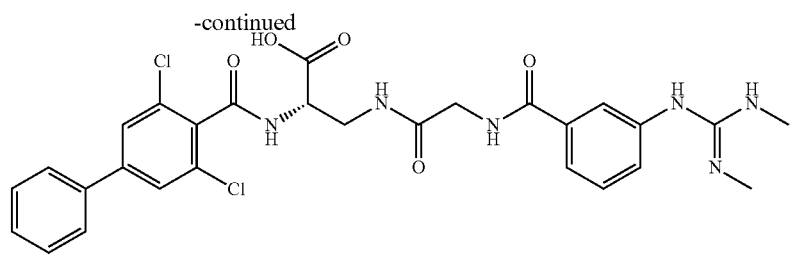

SU15210-0193-01

The Synthesis of methyl 3-isothiocyanatobenzoate (193-2)

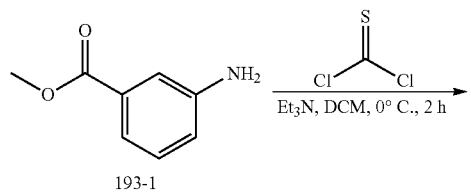

To a solution of 193-1 (1.5 g, 10.0 mmol) in CH₂Cl₂ (50 mL) was added Et₃N (3.0 g, 30.0 mmol) and thiocarbonyl dichloride (1.4 g, 12.0 mmol) was dropwise slowly in 0° C., the reaction was stirred at 0° C. for 2 h. After the consumption of starting material (detected by LCMS), the reaction was concentrated in vacuo, the crude was dissolved in 20 mL H₂O, extracted with CH₂Cl₂ (25 mL×3), combined the organic layer, dried over Na₂SO₄, filtered and concentrated in vacuo, the crude was purified by CC (EtOAc/PE=1015) to get the product 193-2 (1.8 g, 91.1% yield) as brown oil.

The Synthesis of methyl 3-(3-methylthioureido)benzoate (193-3)

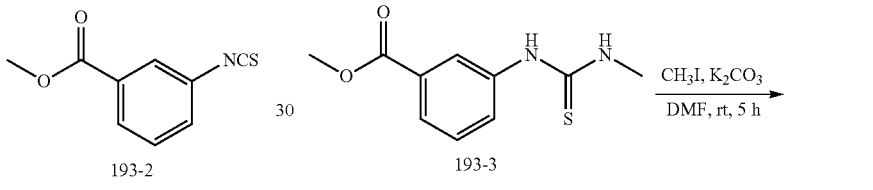

To a solution of 193-2 (2.1 g, 11.0 mmol) in acetone (5 mL) was dropwise methanamine (684.0 mg, 22.0 mmol, 2.5 M in THF), the reaction was stirred in a closed reactor and at 25° C. for 8 h. After the consumption of starting material, the reaction solvent was removed in vacuo, the crude was purified directly by CC (EtOAc/PE=25%~30%) to get the product 193-3 (1.7 g, 68.9% yield) as a white solid.

The Synthesis of (Z)-methyl 3-((methylamino)(methylthio)methyleneamino)benzoate (193-4)

To a solution of methyl 193-4 (1.7 g, 7.6 mmol) in DMF (20 mL) was added K₂CO₃ (2.1 g, 15.2 mmol) and CH₃I (2.2 g, 15.2 mmol), the reaction was stirred at rt for 5 h. After the consumption of starting material, the reaction was quenched with H₂O (150 mL), extracted with EtOAc (30 mL×3), combined the organic layer and dried over Na₂SO₄, filtered and concentrated in vacuo, the crude was purified by CC (EtOAc/PE=25%~30%) to get the product 193-4 (1.4 g, 77.5% yield) as a white solid.

The Synthesis of (E)-methyl 3-(2,3-dimethylguanidino)benzoate (193-5)

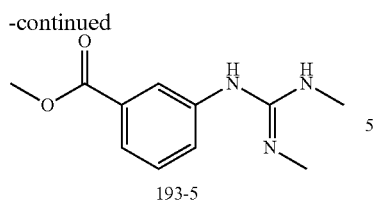

193-5

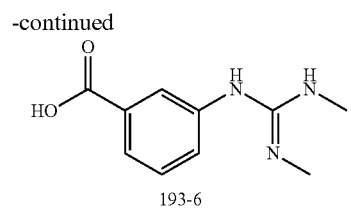

193-6

To a solution of 193-4 (1.5 g, 6.34 mmol) in EtOH (5 mL) was dropwise methanamine (396.2 mg, 2.5M in THF), the reaction was stirred in a closed reactor and for 24 h in 75° C. After the consumption of starting material, the reaction solvent was removed in vacuo, the crude was purified by prep-HPLC to get the product 193-5 (1.1 g, 78.0% yield) as a white solid.

The Synthesis of
(E)-3-(2,3-dimethylguanidino)benzoic acid (193-6)

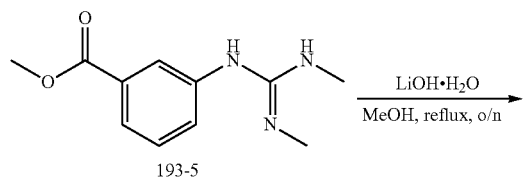

To a solution of 193-5 (1.1 g, 5.0 mmol) in CH$_3$OH (15 mL) was added LiOH.H$_2$O (626.0 mg, 14.9 mmol), the reaction was stirred at 70° C. for overnight. After the consumption of starting material, the reaction was concentrated in vacuo, the crude was dissolved with H$_2$O (5 mL), 1N HCl was added to adjust pH=3~4, the mixture was purified directly by prep-HPLC to get the product 193-6 (550.0 mg, 53.4% yield) as white solid.

The Synthesis of (S,E)-benzyl 2-(3,5-dichlorobiphenyl-4-ylcarboxamido)-3-(2-(3-(2,3-dimethylguanidino)benzamido)acetamido)propanoate (193-7)

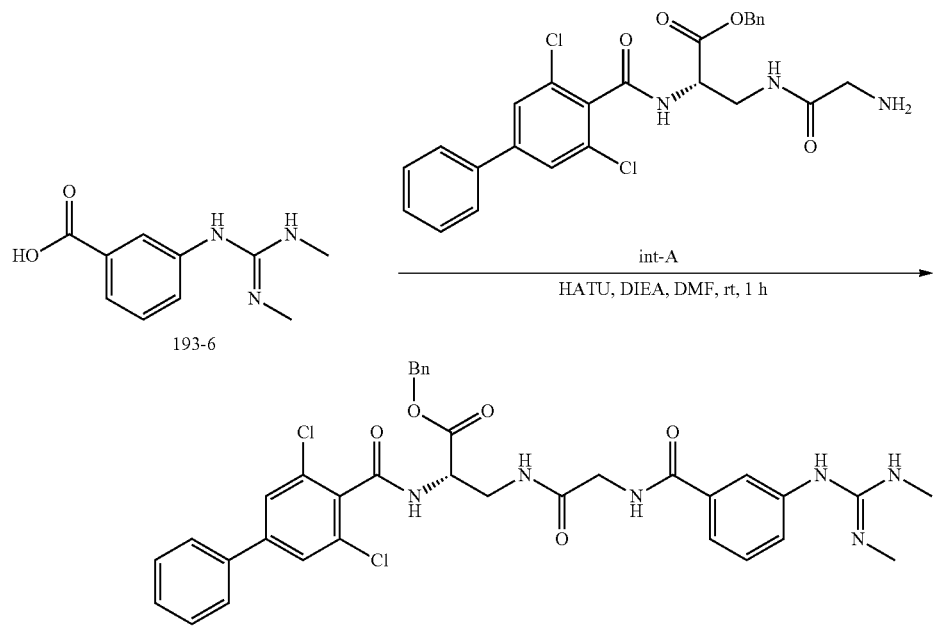

To a solution of 193-6 (104.0 mg, 0.5 mmol) in DMF (10 mL) was added HATU (286.0 mg, 0.8 mmol), DIPEA (130.0 mg, 1.0 mmol) and int-A (251.0 mg, 0.5 mmol), the reaction was stirred at rt for 1 h. After the reaction was finished (detected by LCMS), the reaction was quenched with 100 mL H$_2$O, extracted with EtOAc (25 mL×3), combined the organic layer, dried over Na$_2$SO$_4$, filtered and concentrated in vacuo, the crude was purified by prep-HPLC to get the product 193-7 (280.0 mg, 81.2% yield) as a white solid.

The Synthesis of (S,E)-2-(3,5-dichlorobiphenyl-4-ylcarboxamido)-3-(2-(3-(2,3-dimethylguanidino)benzamido)acetamido)propanoic acid (SU15210-0193-01)

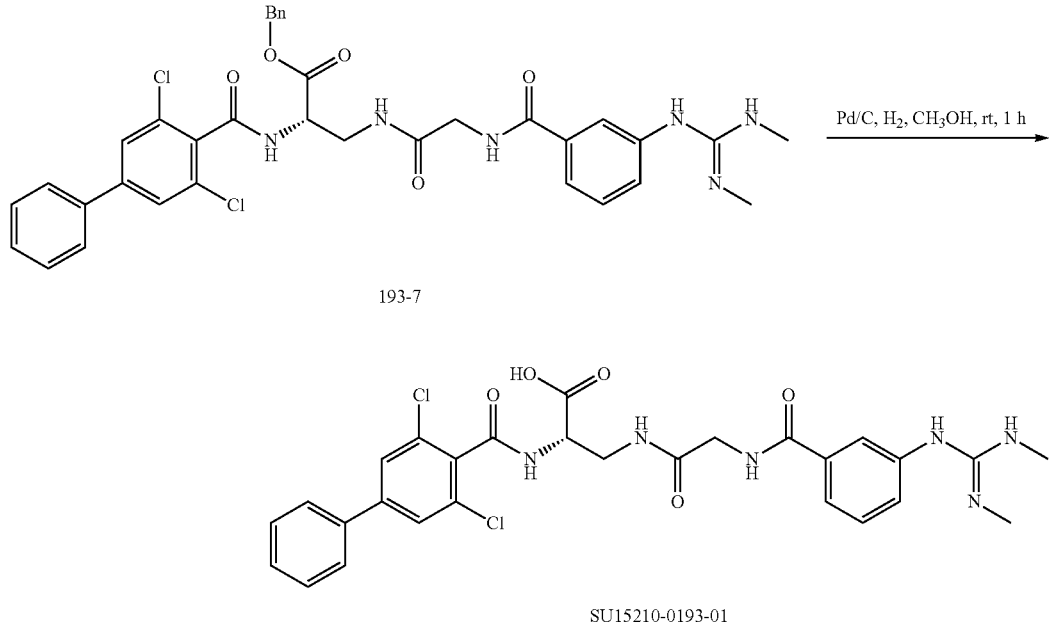 [SMILES: C/N=C(\NC)Nc1cccc(C(=O)NCC(=O)NC[C@H](NC(=O)c2c(Cl)cc(-c3ccccc3)cc2Cl)C(=O)OCc2ccccc2)c1 ; "Pd/C, H2, CH3OH, rt, 1 h" ; C/N=C(\NC)Nc1cccc(C(=O)NCC(=O)NC[C@H](NC(=O)c2c(Cl)cc(-c3ccccc3)cc2Cl)C(=O)O)c1]

To a solution of 193-7 (150.0 mg, 0.2 mmol) in CH$_3$OH (10 mL) was added Pd/C (150 mg, 1.4 mmol), the reaction was stirred under H$_2$ protected and at rt for 1 h. After the consumption of starting material (detected by LCMS), the reaction was filtered, the filtrated was concentrated in vacuo, the crude was purified directly by prep-HPLC to get the product SU15210-0193-01 (50.0 mg, 38.3% yield) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% NH$_4$HCO$_3$] and 5% [CH$_3$CN+0.05% NH$_4$HCO$_3$] to 5% [water+0.05% NH$_4$HCO$_3$] and 95% [water+0.05% NH$_4$HCO$_3$] in 1.6 min, then under this condition for 1.4 min, finally changed to 95% [water+0.05% NH$_4$HCO$_3$] and 5% [CH$_3$CN+0.05% NH$_4$HCO$_3$] in 0.05 min and under this condition for 0.7 min), Purity: 100.00%, Rt=1.441 min; MS Calcd.: 598.0; MS Found: 599.2 [M+H]$^+$.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% NH$_4$HCO$_3$] and 5% [CH$_3$CN+0.05% NH$_4$HCO$_3$] to 5% [water+0.05% NH$_4$HCO$_3$] and 95% [water+0.05% NH$_4$HCO$_3$] in 5.0 min, then under this condition for 1.0 min, finally changed to 95% [water+0.05% NH$_4$HCO$_3$] and 5% [CH$_3$CN+0.05% NH$_4$HCO$_3$] in 0.1 min and under this condition for 5 min), Purity: 100.00%, Rt=6.612 min.

$^1$H NMR (400 MHz, DMSO-d$_6$) δ 9.11 (s, 1H), 8.37 (s, 1H), 7.85-8.25 (m, 4H), 7.72-7.79 (m, 5H), 7.43-7.54 (m, 4H), 7.38 (d, J=7.2 Hz, 1H), 3.96 (q, J=6.8 Hz, 1H), 3.74-3.85 (m, 3H), 2.95 (t, J=10.0 Hz, 1H), 2.85 (s, 6H).

Scheme: Route for SU15210-0195

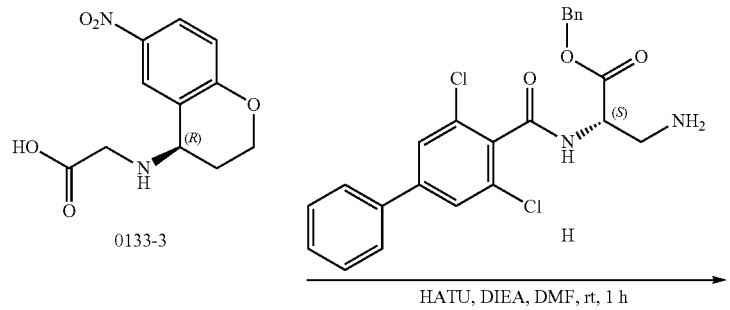

-continued
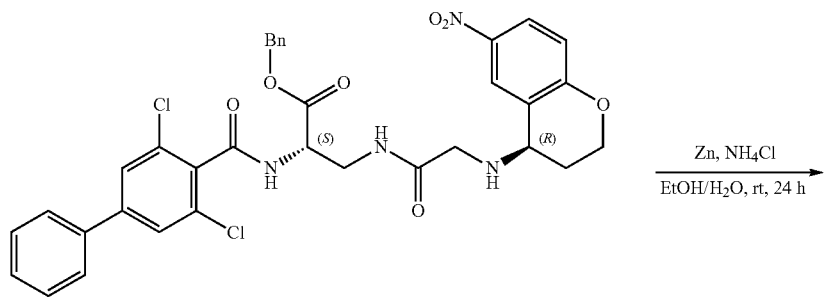
0195-2
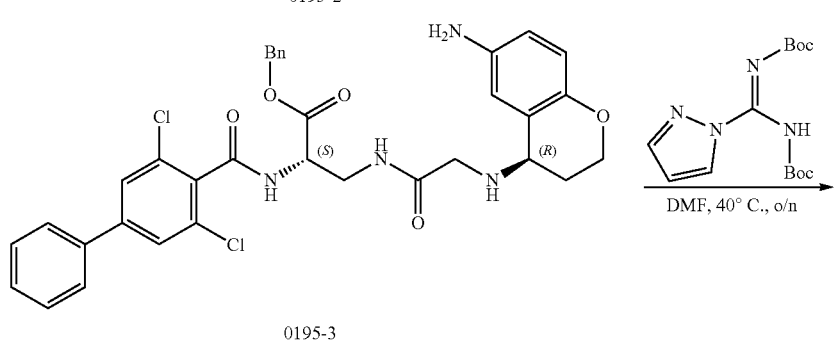
0195-3
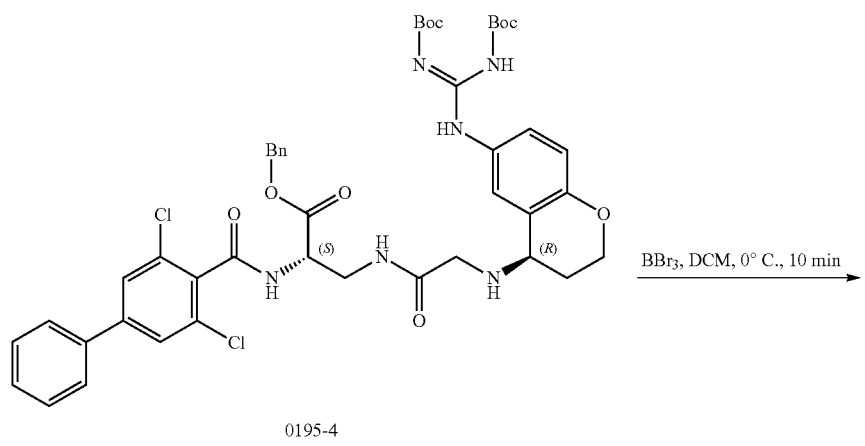
0195-4
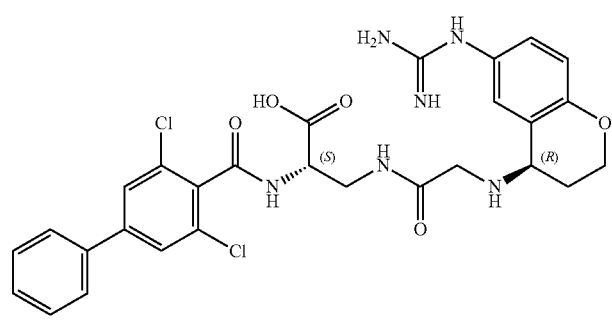
SU15210-0195

311

The Synthesis of (S)-benzyl 2-(3,5-dichlorobiphenyl-4-ylcarboxamido)-3-(2-((R)-6-nitrochroman-4-ylamino)acetamido)propanoate (0195-2)

312

The Synthesis of (S)-benzyl 3-(2-((R)-6-aminochroman-4-ylamino)acetamido)-2-(3,5-dichlorobiphenyl-4-ylcarboxamido)propanoate (0195-3)

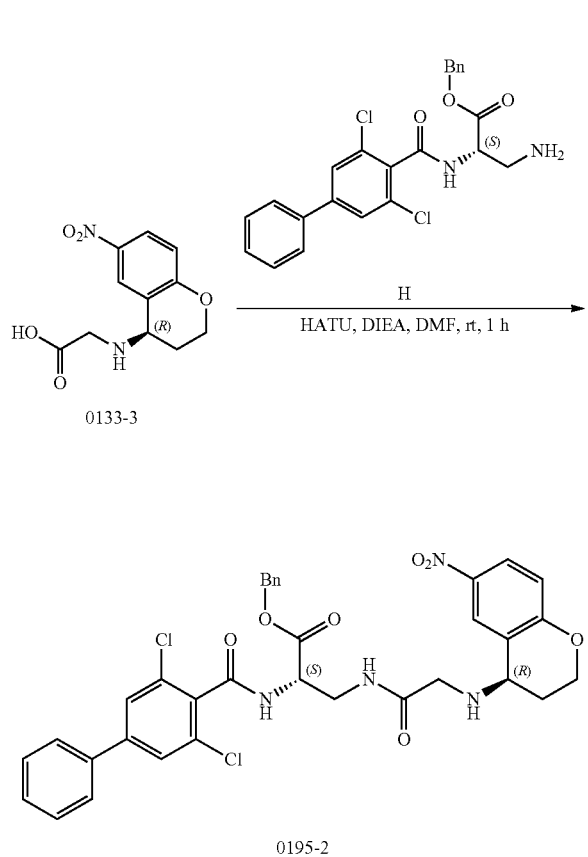

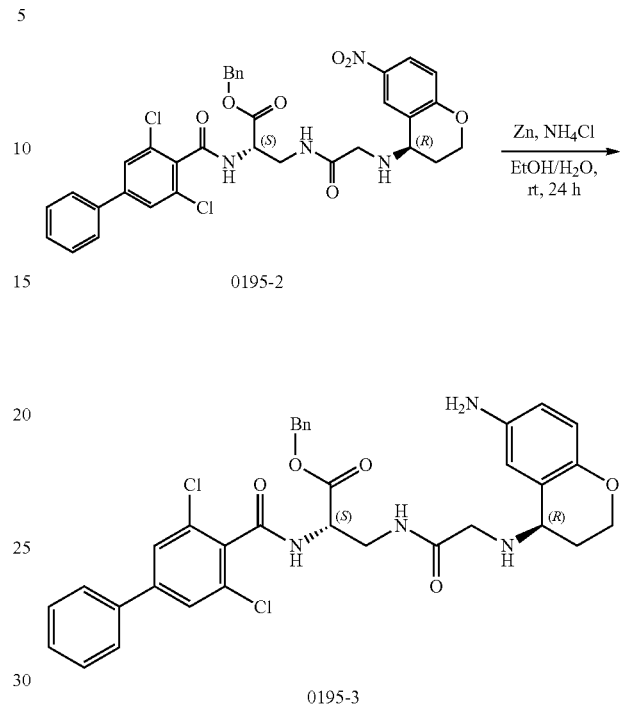

To a solution of compound 0133-2 (500 mg, 1.98 mmol) and intermediate H (879 mg, 1.98 mmol) was added DIEA (769 mg, 5.95 mmol, 1.04 mL) and HATU (1.52 g, 3.96 mmol), and this mixture was allowed to stir at room temperature for 1 h. After the consumption starting material (by LCMS), water (100 mL) was added, extracted with ethyl acetate (100 mL×3), washed with water (100 mL×3), dried and concentrated. The crude product was purified by C.C. (50%-100% ethyl acetate in hexane) to give 0195-2 (1.3 g, yield: 96.79%) as a white solid.

To a solution of compound 0195-2 (400 mg, 590 umol) in EtOH (150 mL) was added zinc dust (193 mg, 2.95 mmol) and a solution of ammonia hydrochloride (316 mg, 5.90 mmol) in water (5 mL). And this mixture was allowed to stir at room temperature for 24 h. After the reaction finished (by LCMS), the mixture was filtered and concentrated. The residue was dissolved in ethyl acetate (50 mL) and extracted with ethyl acetate (20 mL×3). The organics was dried over $Na_2SO_4$ and concentrated. The crude was purified by pre-HPLC to get 0195-3 (270 mg, yield: 70.63%) as a light-yellow solid.

The Synthesis of (S)-benzyl 3-(2-((R)-6-((Z)-2,3-bis(tert-butoxycarbonyl)guanidino)-chroman-4-ylamino)acetamido)-2-(3,5-dichlorobiphenyl-4-ylcarboxamido)propanoate (0195-4)

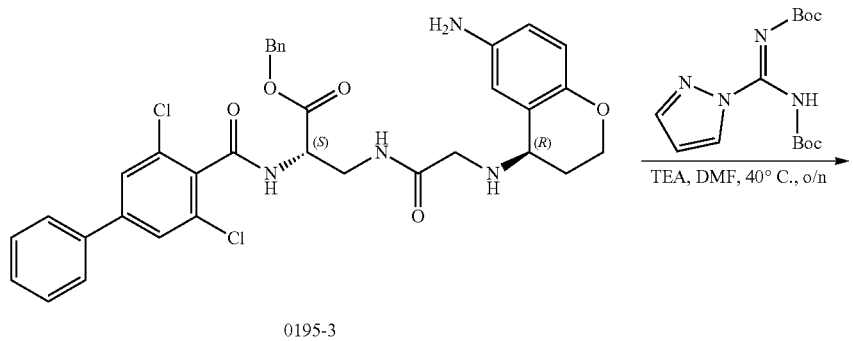

0195-3

-continued

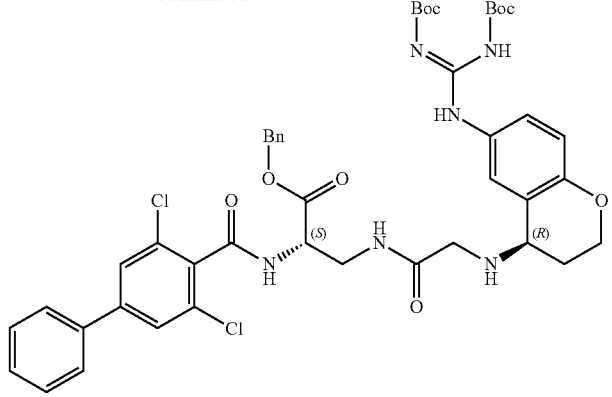

0195-4

To a solution of compound 0195-3 (260 mg, 402 umol) in DMF (15 mL) was added (E)-tert-butyl (1H-pyrazol-1-yl)methylenedicarbamate (187 mg, 602 umol) and TEA (81 mg, 803 umol) and allowed this mixture to stir at 40° C. for overnight. After the consumption of starting material, the mixture was quenched with water (20 mL), extracted with ethyl acetate (20 mL×3), washed with water (20 mL×3), dried and concentrated. The crude product was purified by pre-HPLC to get 0195-4 (120 mg, yield: 33.59%) as a white solid.

The Synthesis of (S)-2-(3,5-dichlorobiphenyl-4-ylcarboxamido)-3-(2-((R)-6-guanidinochroman-4-ylamino)acetamido)propanoic acid (SU15210-0195)

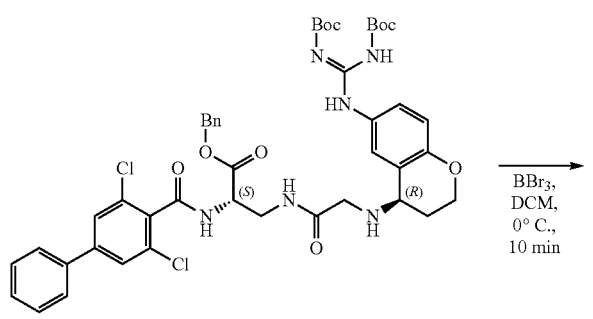

0195-4

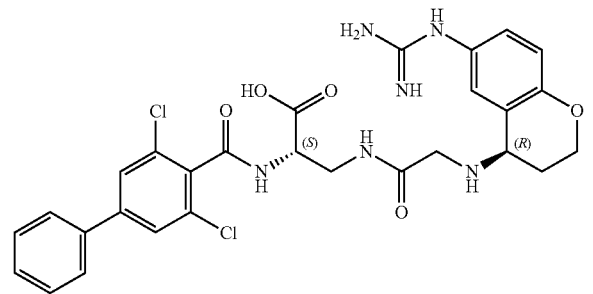

SU15210-0195

To a solution of compound 0195-4 (60 mg, 67 umol) in DCM (5 mL) was added a solution of boron tribromide in DCM (0.6 mL, 1 M) at 0° C. over 5 min, then the mixture was stirred at 0° C. for 10 min. After the consumption of starting material (by LCMS), this mixture was concentrated under reduced pressure. The crude product was purified by pre-HPLC to get SU15210-0195 (12 mg, yield: 29.69%) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min), Purity: 96.52%, Rt=1.501 min; MS Found: 599.2 [M+H]$^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 0.7 min), Purity: 94.27%, Rt=7.420 min; MS Found: 699.2 [M+H]$^+$.

$^1$H NMR (400 MHz, DMSO-d$_6$) δ 10.84 (br, 1H), 8.58 (t, J=5.2 Hz, 1H), 8.19 (d, J=6.8 Hz, 1H), 7.73-7.81 (m, 8H), 7.42-7.51 (m, 3H), 7.34 (d, J=2.4 Hz, 1H), 6.92 (dd, J=2.4 Hz, J=8.8 Hz, 1H), 6.71 (d, J=8.8 Hz, 1H), 4.22-4.28 (m, 1H), 4.04-4.12 (m, 2H), 3.65-3.72 (m, 2H), 3.52-3.58 (m, 1H), 3.10-3.30 (m, 2H), 2.67-2.71 (m, 1H), 1.85 (d, J=4.4 Hz, 2H).

Scheme: Route for SU15210-0200
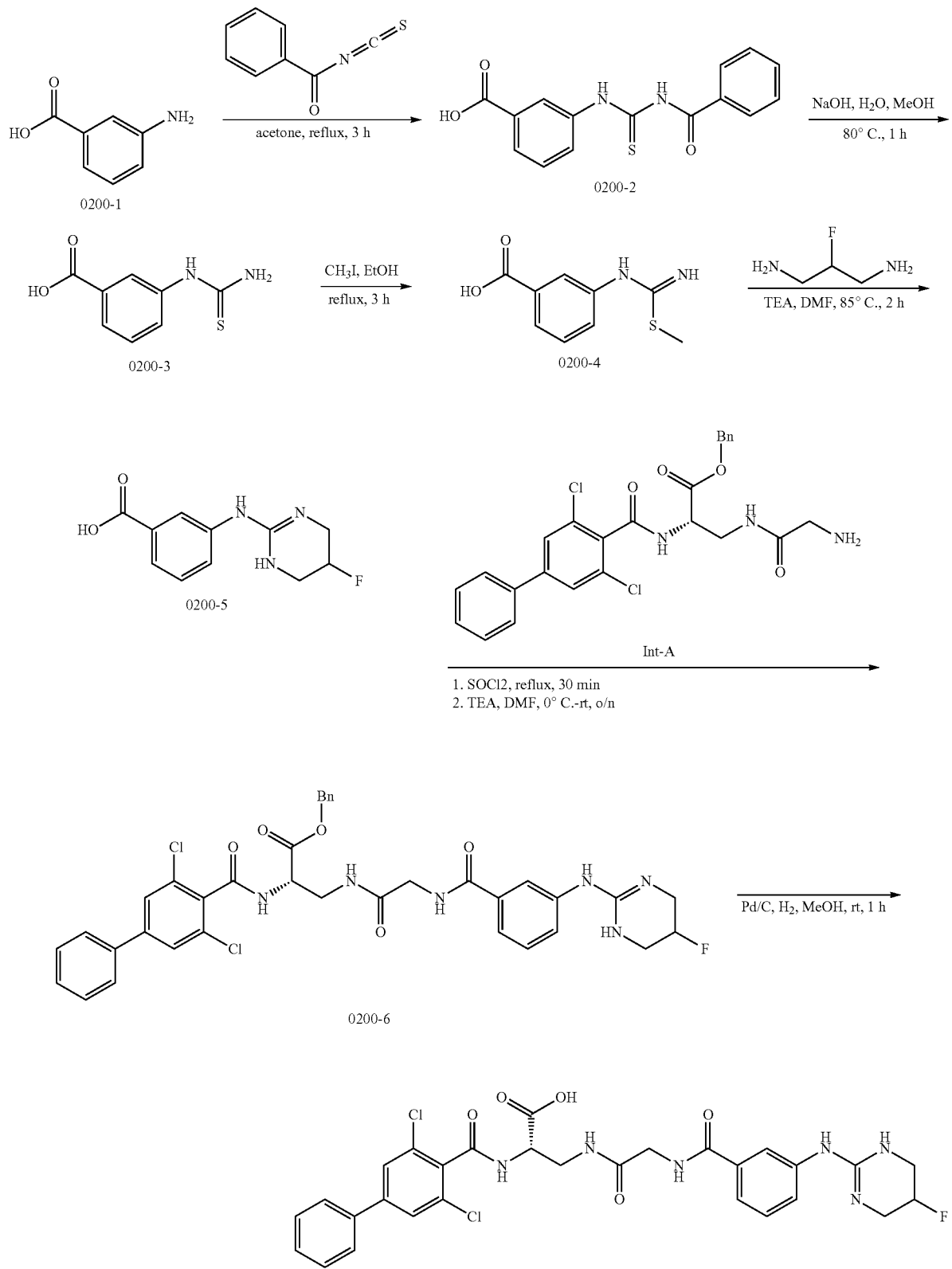
SU15210-0200

The Synthesis of 3-(3-benzoylthioureido)benzoic acid (0200-2)

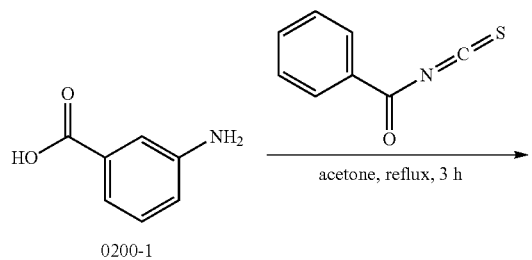

0200-1

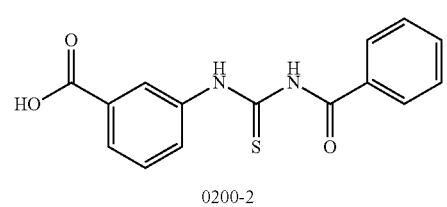

0200-2

A solution of 0200-1 (2.0 g, 14.60 mmol) and added benzoyl isothiocyanate (2.4 g, 14.60 mmol) in acetone (20 mL) was stirred at reflux for 3 h. Cooled to room temperature and concentrated to remove the solvent, the residue was recrystallized from ethyl acetate, dried in vacuum to give 0238-3 (3.8 g, 86% yield) as a yellow solid.

The Synthesis of 3-thioureidobenzoic acid (0200-3)

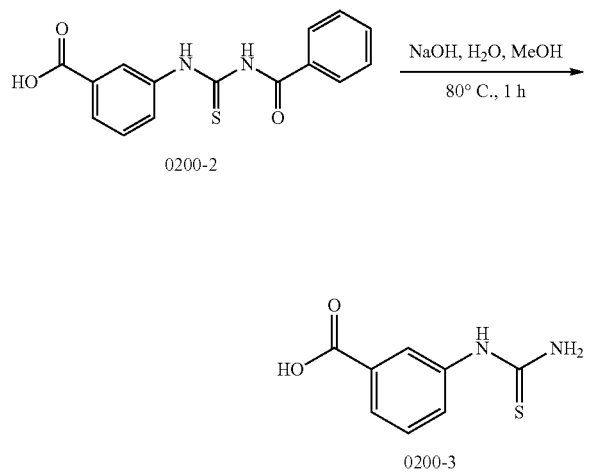

To a solution of 0200-2 (3.8 g, 12.67 mmol) in MeOH (30 mL) was added NaOH (aq. 1 N, 30 mL), the solution was stirred at 80° C. for 1 h. When the reaction was completed, cooled to room temperature and concentrated to remove the organic solution, the residue solution was acidized by 1 N HCl aq. to pH 3, extracted with EA, the organic phase was separated and dried over Na$_2$SO$_4$, concentrated to give 0200-3 (2.2 g, 88%) as a yellow solid.

The Synthesis of 3-(imino(methylthio)methylamino)benzoic acid (0200-4)

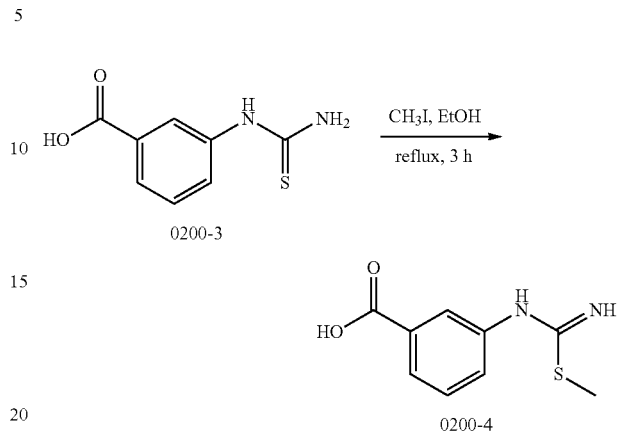

To a solution of 0200-3 (2.2 g, 11.22 mmol) in EtOH (30 mL) was added CH$_3$I (1.8 g, 12.34 mmol), the solution was stirred at reflux for 3 h. Concentrated to remove the solvent to give 0200-4 (2.4 g, 100%) as a yellow solid.

The Synthesis of 3-(5-fluoro-1,4,5,6-tetrahydropyrimidin-2-ylamino)benzoic acid (0200-5)

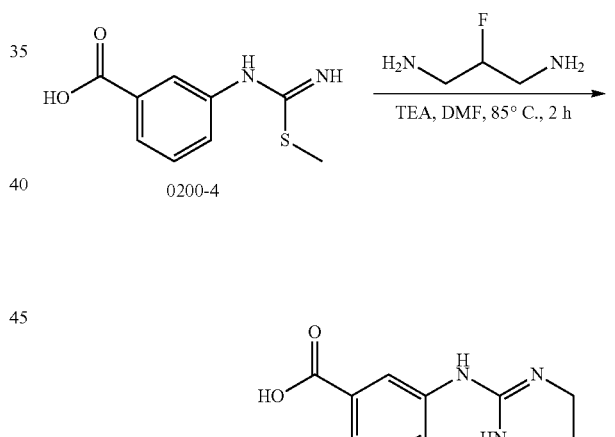

To a solution of 0200-4 (200 mg, 0.95 mmol) in DMF (5 mL) was added 2-fluoropropane-1,3-diamine (105 mg, 1.14 mmol) and TEA (288 mg, 2.85 mmol). The solution was stirred at 85° C. for 2 h. Cooled to room temperature and collected the precipitate by filtration, the solid was washed with ethyl acetate (10 mL) then dried in vacuum to give 0200-5 (130 mg, 58% yield) as an off-white solid.

The Synthesis of (2S)-benzyl 2-(3,5-dichlorobiphenyl-4-ylcarboxamido)-3-(2-(3-(5-fluoro-1,4,5,6-tetrahydropyrimidin-2-ylamino)benzamido)acetamido)propanoate (0200-6)

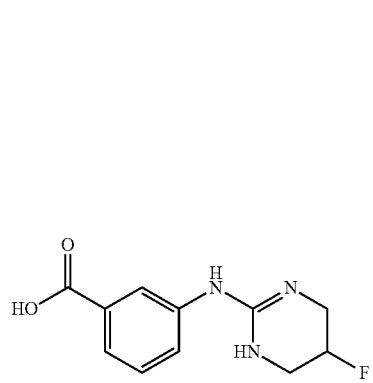

0200-5

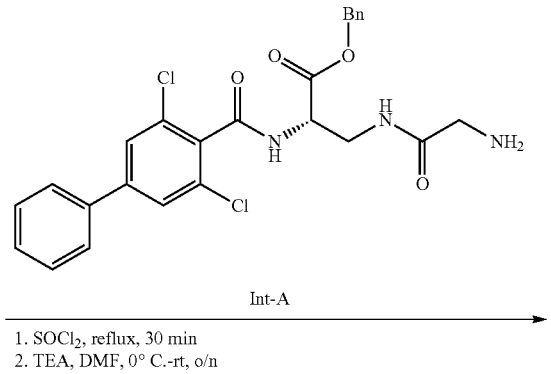

Int-A

1. SOCl₂, reflux, 30 min
2. TEA, DMF, 0° C.-rt, o/n

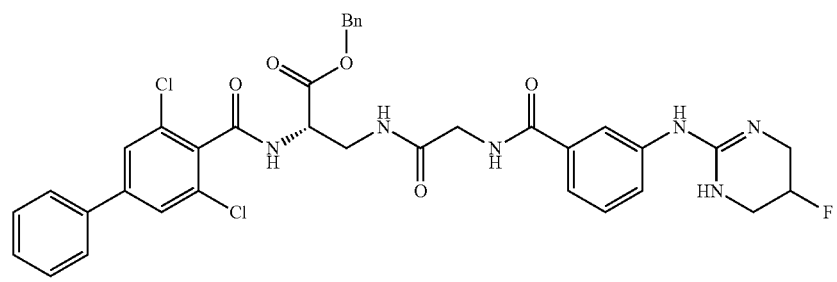

0200-6

A solution of 0200-5 (130 mg, 0.55 mmol) in SOCl₂ (5 mL) was stirred at reflux for 30 min, then removed the excess SOCl₂ under reduced pressure. The residue was then added to a solution of int-A (275 mg, 0.55 mmol) and TEA (222 mg, 2.20 mmol) in DMF (5 mL) at 0° C., the solution was then allowed to warm to room temperature and stirred for overnight. Poured the solution into water (50 ml), collected the precipitate by filtration, the solid was dried then purified by CC (0% to 10% MeOH in DCM) to get 0200-6 (220 mg, 56% yield) as a white solid.

The Synthesis of (S)-2-(3,5-dichlorobiphenyl-4-ylcarboxamido)-3-(2-(3-(5,5-difluoro-1,4,5,6-tetrahydropyrimidin-2-ylamino)benzamido)acetamido)propanoic acid (SU15210-0200)

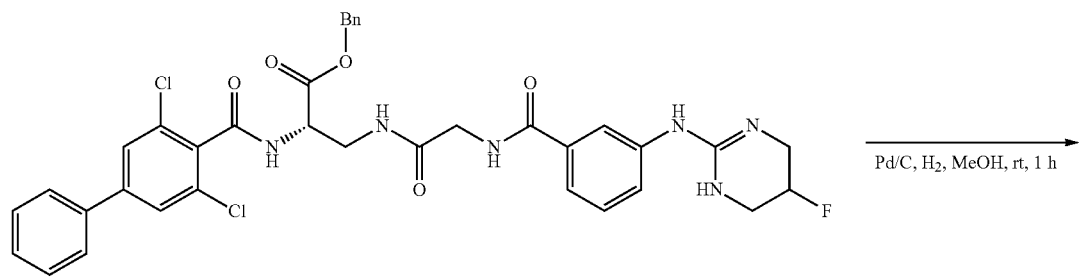

0200-6

Pd/C, H₂, MeOH, rt, 1 h

-continued

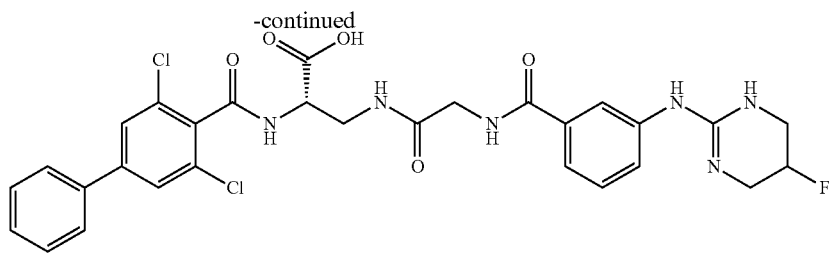

SU15210-0200

To a solution of 0200-6 (100 mg, 0.13 mmol) in MeOH (5.0 mL) was added Pd/C (10 mg). The mixture was stirred under H₂ in balloon at room temperature for 1 h. When the reaction completed, filtrated to remove the catalyst, the filtrate was concentrated and purified by prep-HPLC to get SU15210-00200 (25 mg, 28% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [CH₃CN] to 0% [water+10 mM TFA] and 100% [CH₃CN] in 1.6 min, then under this condition for 1.4 min, finally changed to 95% [water+10 mM TFA] and 5% [CH₃CN] in 0.1 min. Purity is 100%. Rt=1.502 min; MS Calcd.: 628.2; MS Found: 629.2 [M+H]⁺.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% NH₄HCO₃] and 5% [CH₃CN] to 0% [water+0.1% NH₄HCO₃] and 100% [CH₃CN] in 10 min, then under this condition for 5 min, finally changed to 95% [water+0.1% NH₄HCO₃] and 5% [CH₃CN] in 0.1 min and under this condition for 5 min. Purity is 99.10%. Rt=6.647 min.

¹H NMR (400 MHz, DMSO-d₆) δ 9.60 (br, 1H), 8.95 (t, J=5.6 Hz, 1H), 8.27 (d, J=8.0 Hz, 1H), 8.16 (s, 1H), 7.74-7.77 (m, 5H), 7.67 (d, J=8.0 Hz, 1H), 7.42-7.52 (m, 4H), 7.29 (d, J=8.0 Hz, 1H), 5.25 (d, J=46.8 Hz, 1H), 4.17 (q, J=6.4 Hz, 1H), 3.85 (d, J=6.4 Hz, 2H), 3.50-3.67 (m, 4H), 3.33-3.44 (m, 2H), 3.14 (t, J=8.0 Hz, 1H).

Scheme: Route for SU15210-0202-01

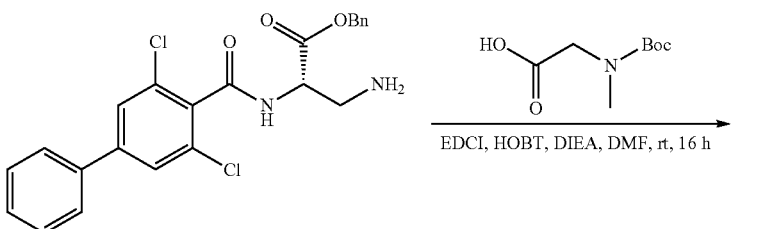

int-H

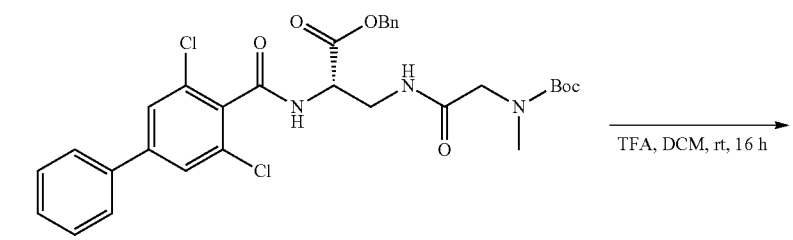

0202-2

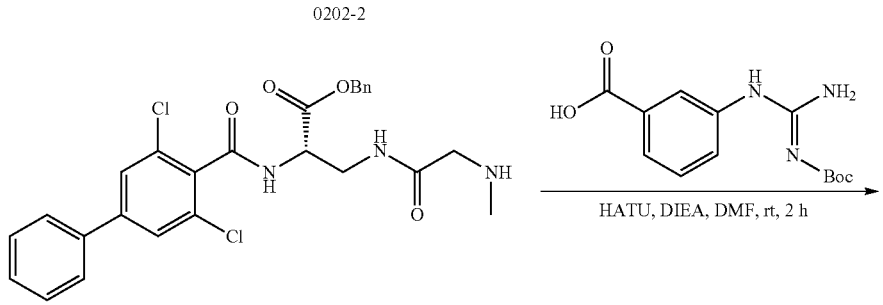

0202-3

-continued

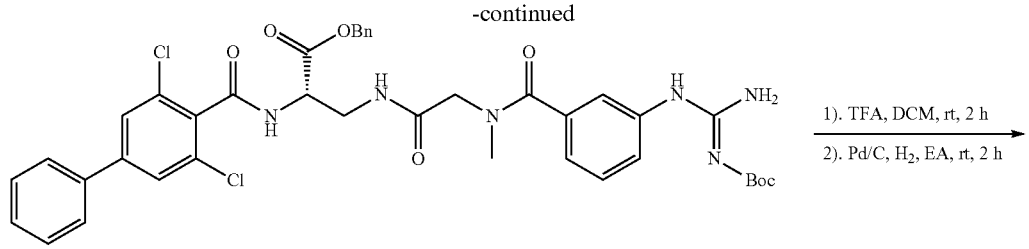

0202-4

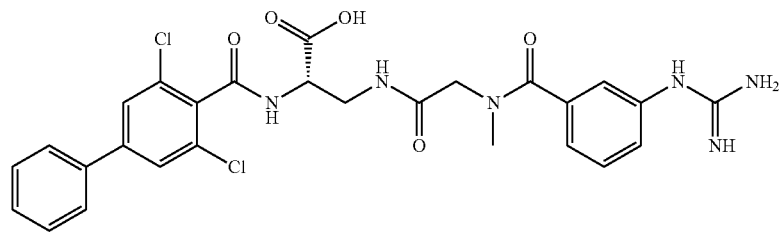

SU15210-0202-01

The Synthesis of (S)-benzyl 3-(2-(tert-butoxycarbonyl(methyl)amino)acetamido)-2-(3,5-dichlorobiphenyl-4-ylcarboxamido) propanoate (0202-2)

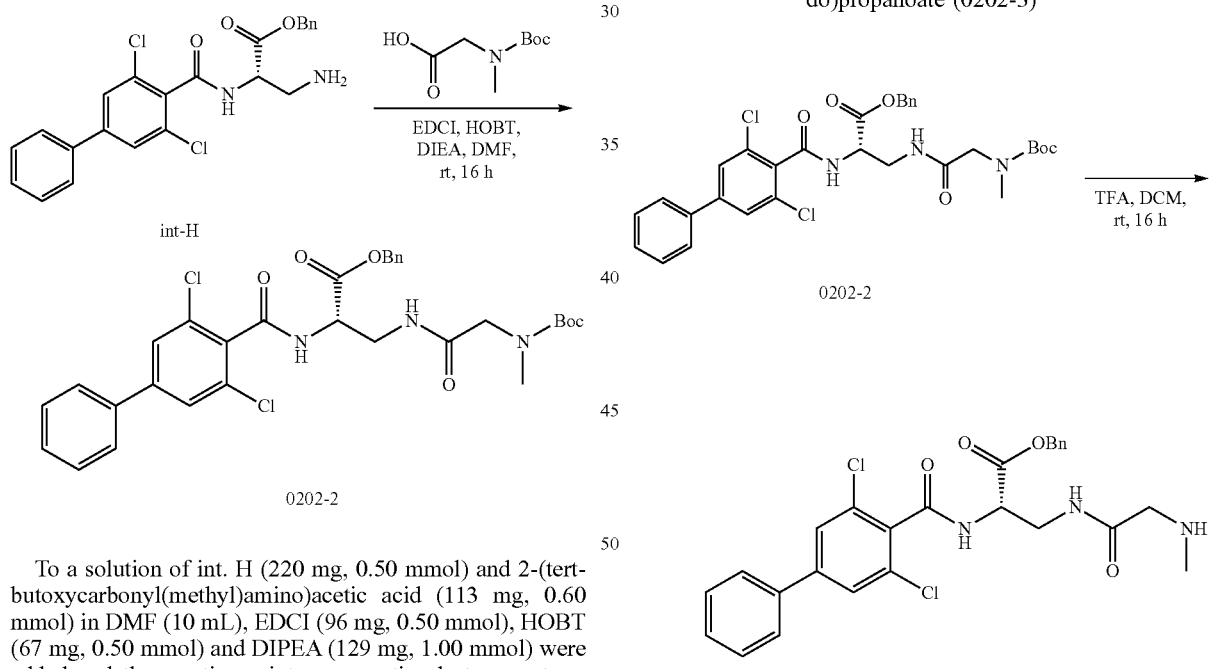

To a solution of int. H (220 mg, 0.50 mmol) and 2-(tert-butoxycarbonyl(methyl)amino)acetic acid (113 mg, 0.60 mmol) in DMF (10 mL), EDCI (96 mg, 0.50 mmol), HOBT (67 mg, 0.50 mmol) and DIPEA (129 mg, 1.00 mmol) were added and the reaction mixture was stirred at room temperature for 16 hours. After the reaction was finished, the solvent was diluted by water (50 mL) and extracted by EA (50 mL). Then the EA layer was washed by saturated salt water and dried by anhydrous $Na_2SO_4$, the organic layer was concentrated in vacuo and purified by Flash to get 0202-2 (130 mg, 43% yield) as a yellow solid.

Agilent LCMS 1200-6120, Column: Halo C18 (30 mm*4.6 mm*2.7 μm); Column Temperature: 40° C.; Flow Rate: 3.0 mL/min; Mobile Phase: from 95% [water+10 mM TFA] and 5% [$CH_3CN$] to 0% [water+10 mM TFA] and 100% [$CH_3CN$] in 0.8 min, then under this condition for 0.4 min, finally changed to 95% [water+10 mM TFA] and 5% [$CH_3CN$] in 0.01 min. Purity is 81.46%. Rt=0.846 min; MS Calcd.: 613.7; MS Found: 614.7 [M+H]$^+$.

The Synthesis of (S)-benzyl 2-(3,5-dichlorobiphenyl-4-ylcarboxamido)-3-(2-(methylamino) acetamido)propanoate (0202-3)

To a solution of 0202-2 (130 mg, 0.21 mmol) in DCM (10 mL), TFA (3 mL) was and the solution was stirred at room temperature for 16 hours. After the reaction was finished, the solution was concentrated in vacuo and purified by CC. to get 0202-3 (95 mg, 87% yield) as a white solid.

The Synthesis of (S,E)-benzyl 3-(2-(3-(2-(tert-butoxycarbonyl)guanidino)-N-methylbenzamido)acetamido)-2-(3,5-dichlorobiphenyl-4-ylcarboxamido)propanoate (0202-4)

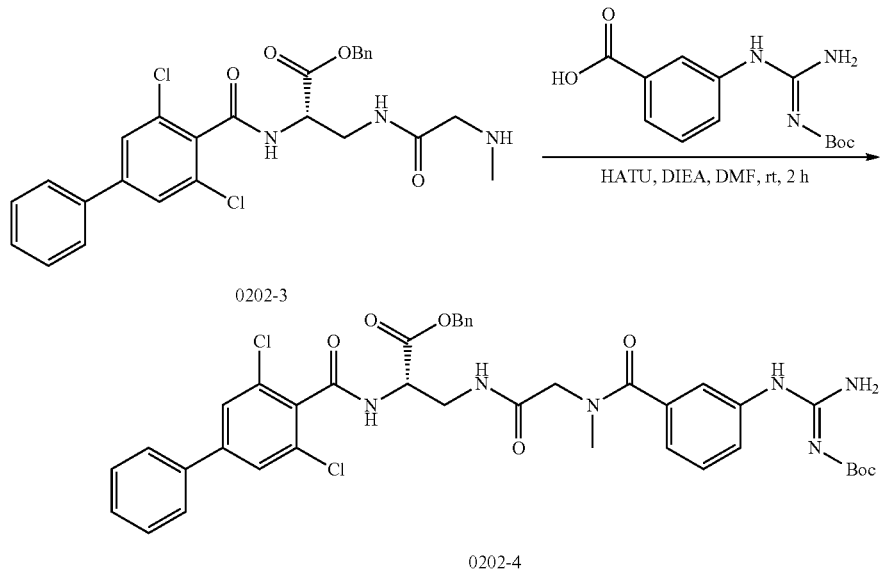

To a solution of 0202-3 (95 mg, 0.19 mmol) and (E)-3-(2-(tert-butoxycarbonyl)guanidino) benzoic acid (64 mg, 0.23 mmol) in DMF (5 mL), HATU (72 mg, 0.19 mmol) and DIPEA (74 mg, 0.57 mmol) were and the mixture was stirred at room temperature for 2 hours. After the reaction was finished, the solvent was diluted by water (50 mL) and extracted by EA (50 mL). Then the EA layer was washed by saturated salt water and dried by anhydrous Na$_2$SO$_4$, the organic layer was concentrated in vacuo and purified by Flash to get 0202-4 (70 mg, 48.8% yield) as a white solid.

Agilent LCMS 1200-6120, Column: Halo C18 (30 mm*4.6 mm*2.7 μm); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity is 88.8%. Rt=0.733 min; MS Calcd.: 774.7; MS Found: 775.7 [M+H]$^+$.

The Synthesis of (S)-2-(3,5-dichlorobiphenyl-4-ylcarboxamido)-3-(2-(3 guanidino-N-methylbenzamido) acetamido)propanoic acid (SU15210-0202-01)

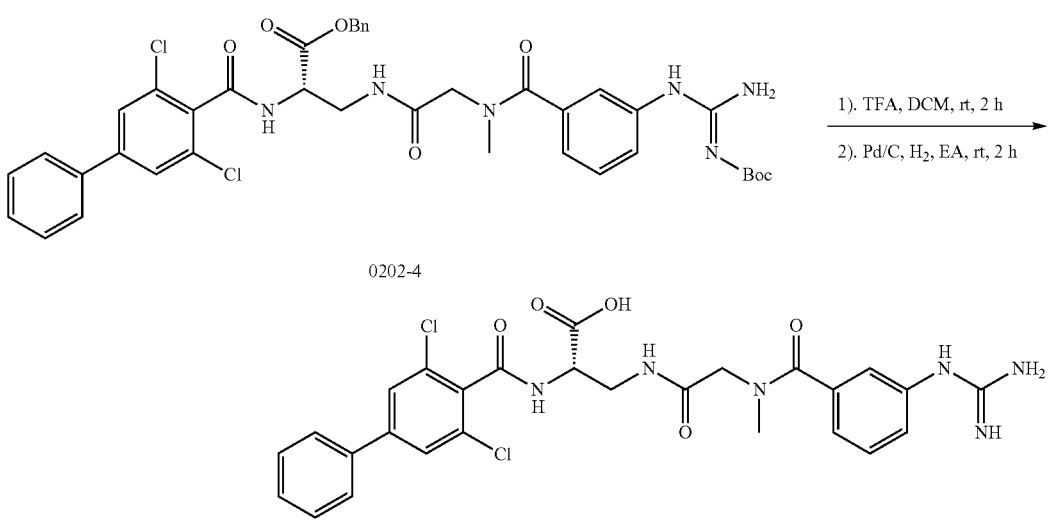

To a solution of 0202-4 (70 mg, 0.09 mmol) in DCM (5 mL), TFA (1 mL) was added and the mixture was stirred at room temperature for 2 hours. After the reaction was finished, the solution was concentrated in vacuo. Then the solid was dissolved in EA (5 mL) and Pd/C (20 mg) was added and the mixture was still stirred at room temperature for 2 hours under hydrogen atmosphere. After the reaction was finished, the mixture was filtered and the solution was concentrated in vacuo and purified by pre-HPLC directly to get SU15210-0202-01 (4 mg, 7.6% yield) as a white solid.

Agilent LCMS 1200-6120, Column: Waters X-Bridge-C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+ 10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min. Purity is 100%. Rt=1.518 min; MS Calcd.: 584.7; MS Found: 585.7 [M+H]$^+$.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% $NH_4HCO_3$] and 5% [$CH_3CN$] to 0% [water+0.1% $NH_4HCO_3$] and 100% [$CH_3CN$] in 10 min, then under this condition for 5 min, finally changed to 95% [water+0.1% $NH_4HCO_3$] and 5% [$CH_3CN$] in 0.1 min and under this condition for 5 min. Purity is 98.33%. Rt=6.712 min.

$^1$H NMR (400 MHz, DMSO-$d_6$) δ 8.29 (d, J=8.8 Hz, 1H), 7.87-7.75 (m, 8H), 7.52-7.45 (m, 5H), 7.38 (d, J=7.2 Hz, 1H), 7.29 (d, J=7.6 Hz, 1H), 7.06 (s, 1H), 4.34 (s, 1H), 3.91 (d, J=17.6 Hz, 1H), 3.77 (d, J=18.0 Hz, 1H), 3.61-3.49 (m, 1H), 2.97 (s, 3H), 2.34-2.32 (m, 2H).

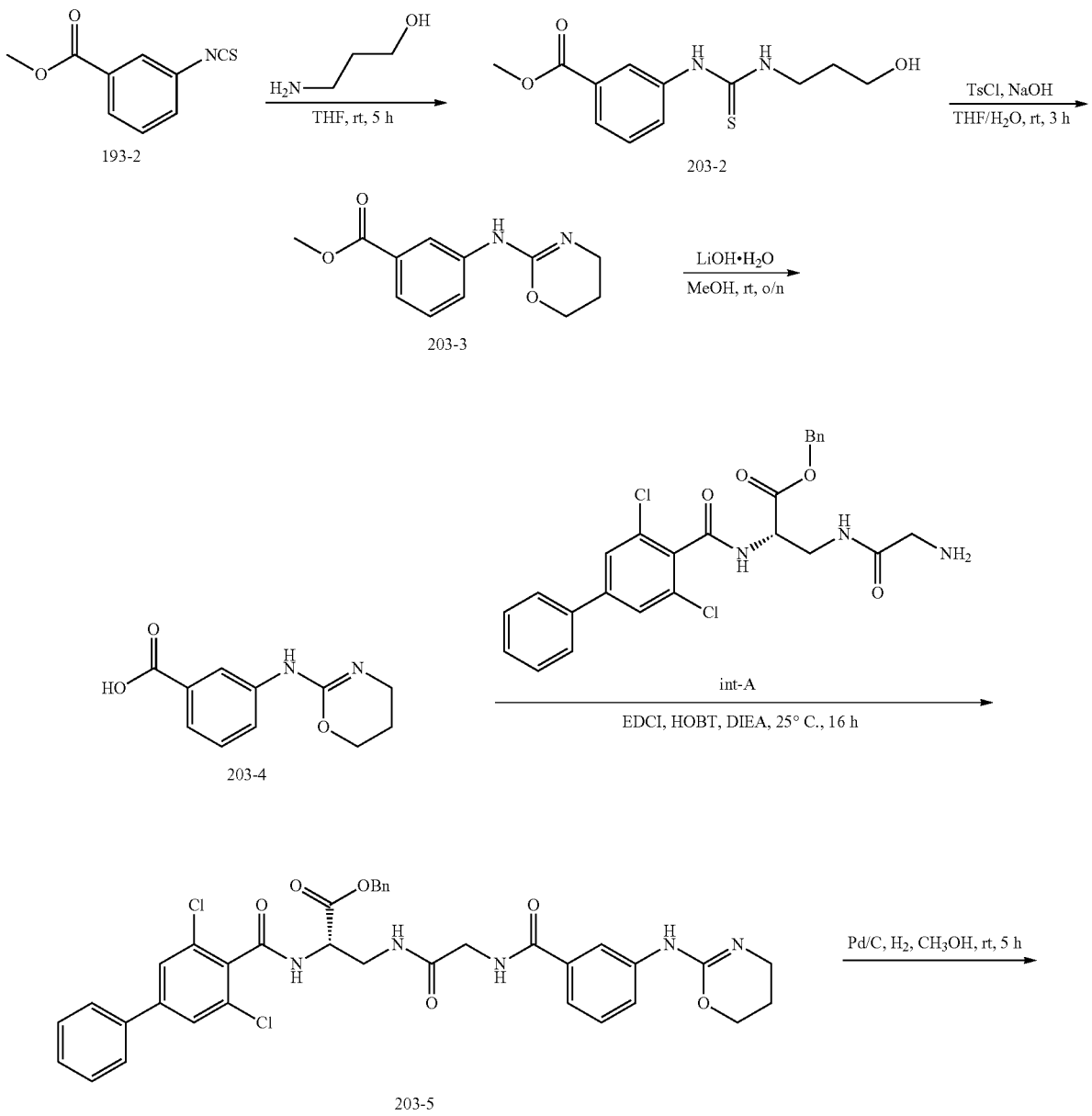

-continued

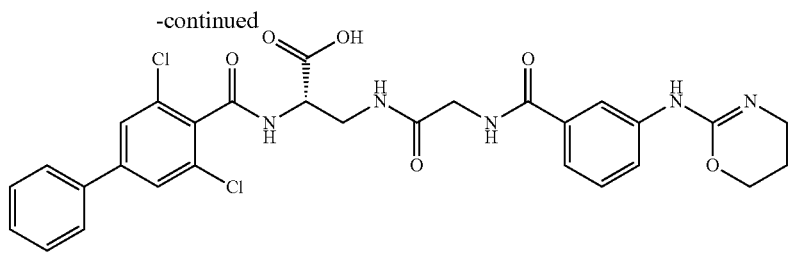

SU15210-0203-01

The Synthesis of methyl 3-(3-(3-hydroxypropyl)thioureido)benzoate (203-2)

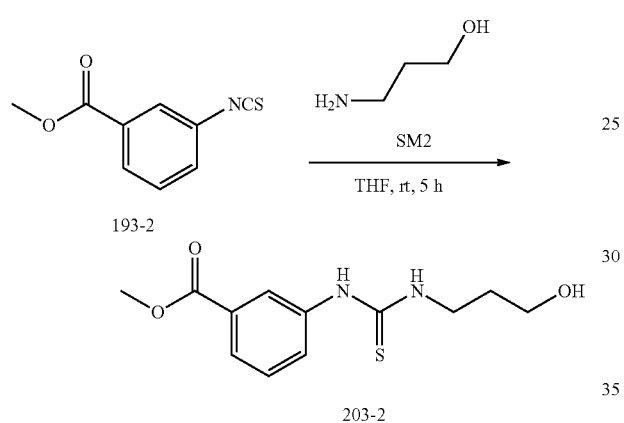

To a solution of 193-2 (516.0 mg, 2.7 mmol) in Acetone (20 mL) was added SM2 (301.0 mg, 4.0 mmol), the reaction was stirred at rt for 5 h. After the consumption of starting material (detected by LCMS), the reaction was quenched with 20 mL H₂O, extracted with EtOAc (25 mL×3), combined the organic layer and dried over anhydrous Na₂SO₄, filtered and concentrated in vacuo, the crude 203-2 (680.0 mg, 94.9% yield) was get as white solid and used directly for next step without further purification.

The Synthesis of methyl 3-(5,6-dihydro-4H-1,3-oxazin-2-ylamino)benzoate (203-3)

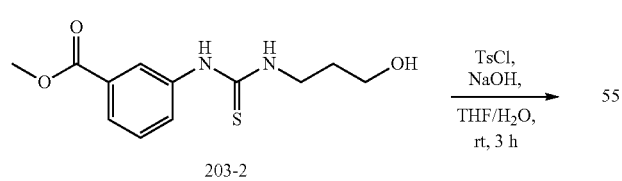

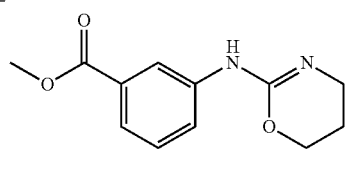

To a solution of 203-2 (654.0 mg, 2.4 mmol) in the mixture solvent of THF (24 mL) and H₂O (6 mL), was added NaOH (243.7 mg, 6.1 mmol) and TsCl (604.0 mg, 3.2 mmol) in 0° C., the reaction was stirred at rt for 3 h. After the consumption of starting material (detected by LCMS), the reaction was quenched with 30 mL H₂O, extracted with EtOAc (30 mL×3), combined the organic layer and dried over anhydrous Na₂SO₄, filtered and concentrated in vacuo, the crude was purified by CC (CH₃OH/CH₂Cl₂=5%~8%) to get the product 203-3 (550.0 mg, 96.3% yield) as a white solid.

The Synthesis of 3-(5,6-dihydro-4H-1,3-oxazin-2-ylamino)benzoic acid (203-4)

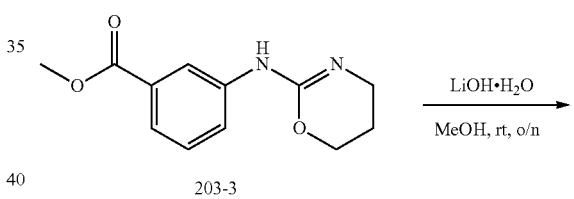

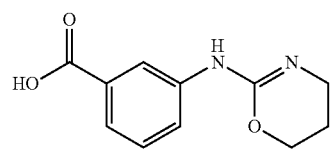

To a solution of 203-3 (588.0 mg, 2.5 mmol) in CH₃OH (10 mL) was added LiOH.H₂O (316.0 mg, 7.5 mmol), the reaction was stirred at reflux for overnight. After the consumption of starting material, the reaction was concentrated in vacuo, the crude was dissolved with 5 mL H₂O, 1N HCl was added to adjust pH=3~4, the mixture was purified by prep-HPLC to get the product 203-4 (480.0 mg, 86.8% yield) as white solid.

The Synthesis of (S)-benzyl 2-(3,5-dichlorobiphe-
nyl-4-ylcarboxamido)-3-(2-(3-(5,6-dihydro-4H-1,3-
oxazin-2-ylamino)benzamido)acetamido)propanoate
(203-5)

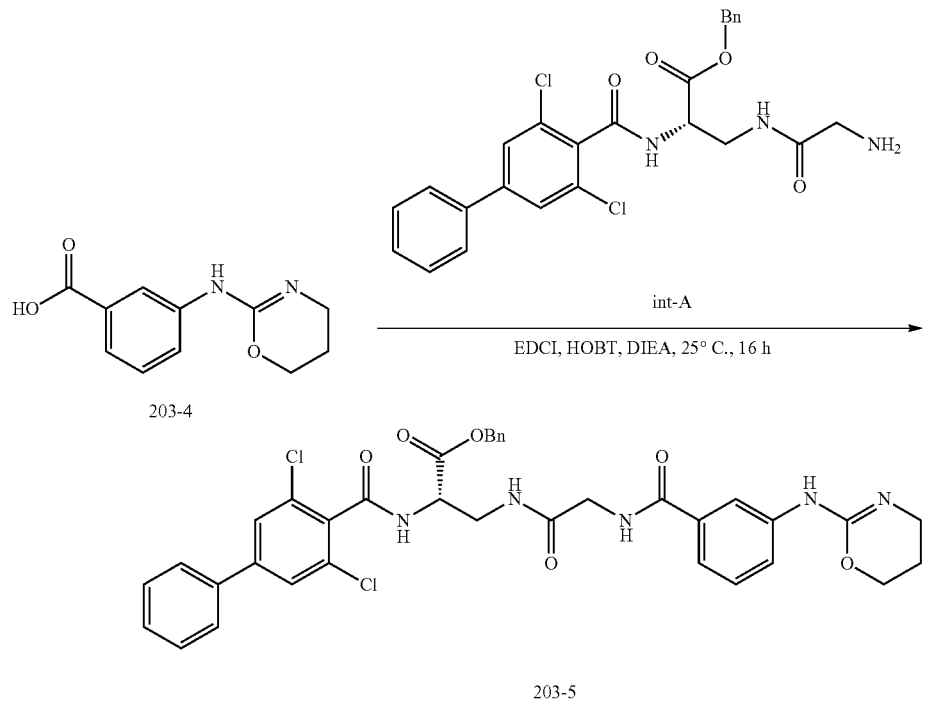

To a solution of 203-4 (110.0 mg, 0.5 mmol) in DMF (10 mL) was added EDCI (115.0 mg, 0.6 mmol), HOBT (81.0 mg, 0.6 mmol), DIPEA (194.0 mg, 1.5 mmol) and int-A (250.0 mg, 0.5 mmol), the reaction was stirred at 25° C. for 16 h. After the reaction was finished (detected by LCMS), the reaction was quenched with 100 mL $H_2O$, extracted with EtOAc (25 mL×3), combined the organic layer and dried over anhydrous $Na_2SO_4$, filtered and concentrated, the crude was purified by prep-HPLC to get the product 203-5 (65.0 mg, 18.5% yield) as a white solid.

The Synthesis of (S)-2-(3,5-dichlorobiphenyl-4-
ylcarboxamido)-3-(2-(3-(5,6-dihydro-4H-1,3-oxazin-
2-ylamino)benzamido)acetamido)propanoic acid
(SU15210-0203-01)

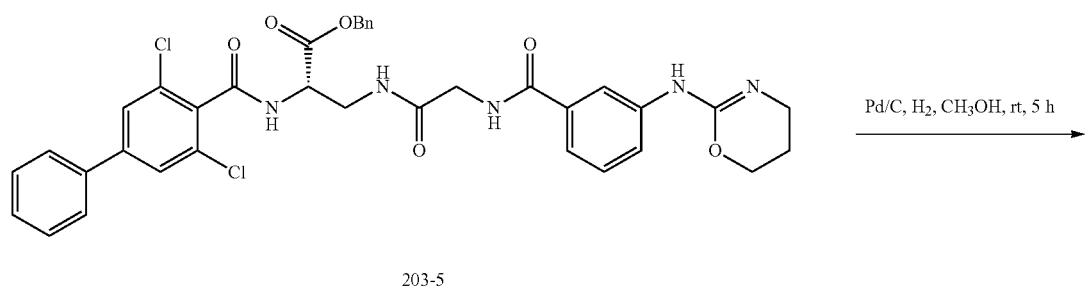

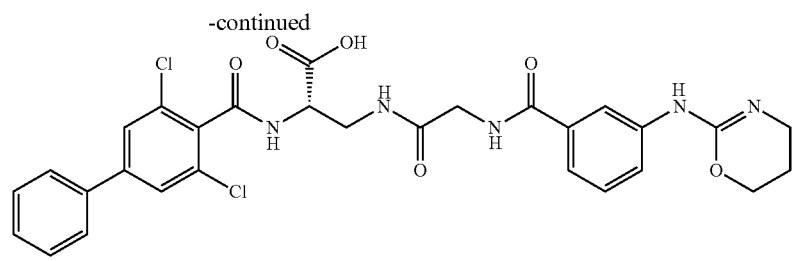

SU15210-0203-01

To a solution of 203-5 (65.0 mg, 0.1 mmol) in CH₃OH (5 mL) was added Pd/C (65.0 mg, 0.6 mmol), the reaction was stirred under H$_2$ protected and at rt for 5 h. After the consumption of starting material (detected by LCMS), the reaction was filtered, the filtrated was concentrated in vacuo, the crude was purified directly by prep-HPLC to get the product SU15210-0203-01 (15.0 mg, 26.5% yield) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% NH$_4$HCO$_3$] and 5% [CH$_3$CN+0.05% NH$_4$HCO$_3$] to 5% [water+0.05% NH$_4$HCO$_3$] and 95% [water+0.05% NH$_4$HCO$_3$] in 1.6 min, then under this condition for 1.4 min, finally changed to 95% [water+0.05% NH$_4$HCO$_3$] and 5% [CH$_3$CN+0.05% NH$_4$HCO$_3$] in 0.05 min and under this condition for 0.7 min), Purity: 98.55%, Rt=1.440 min; MS Calcd.: 611.0; MS Found: 612.1 [M+H]$^+$.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% NH$_4$HCO$_3$] and 5% [CH$_3$CN+0.05% NH$_4$HCO$_3$] to 5% [water+0.05% NH$_4$HCO$_3$] and 95% [water+0.05% NH$_4$HCO$_3$] in 5.0 min, then under this condition for 1.0 min, finally changed to 95% [water+0.05% NH$_4$HCO$_3$] and 5% [CH$_3$CN+0.05% NH$_4$HCO$_3$] in 0.1 min and under this condition for 5 min), Purity: 100.00%, Rt=6.633 min.

$^1$H NMR (400 MHz, DMSO-d$_6$) δ 8.66-8.74 (m, 2H), 8.17 (s, 1H), 7.97 (s, 1H), 7.75-7.83 (m, 5H), 7.42-7.52 (m, 5H), 7.29 (t, J=7.6 Hz, 1H), 4.43 (q, J=6.8 Hz, 1H), 4.32 (t, J=4.4 Hz, 2H), 3.80-3.87 (m, 2H), 3.32-3.55 (m, 4H), 1.90 (t, J=5.2 Hz, 2H).

Scheme: Route for SU15210-0205-01

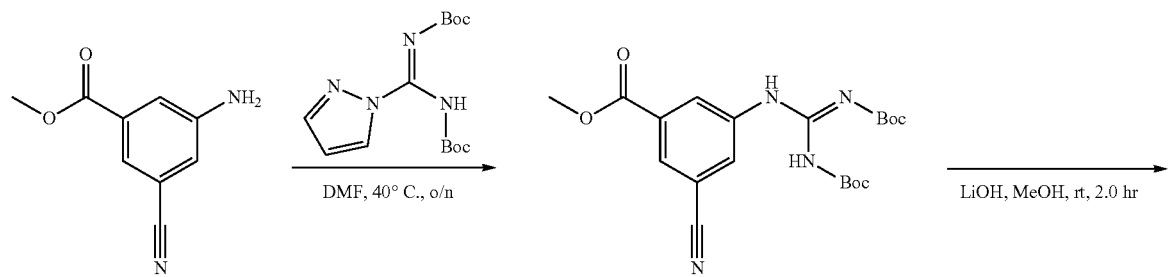

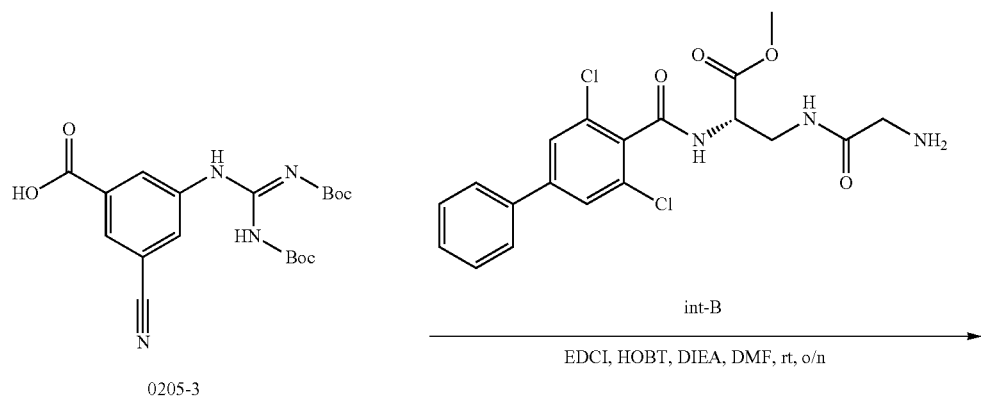

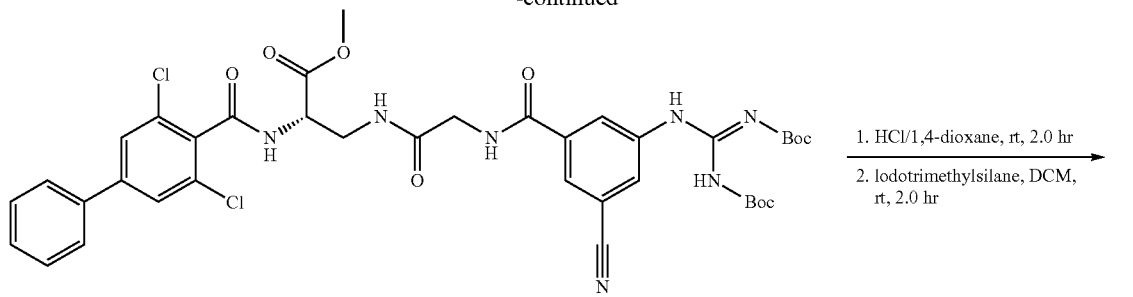

0205-4

1. HCl/1,4-dioxane, rt, 2.0 hr
2. Iodotrimethylsilane, DCM, rt, 2.0 hr

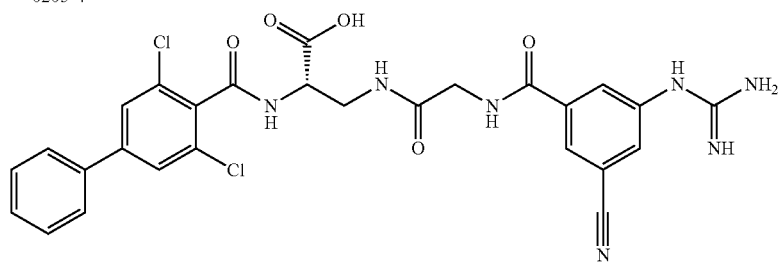

SU15210-0205-01

The Synthesis of (Z)-methyl 3-(2,3-bis(tert-butoxy-carbonyl)guanidino)-5-cyanobenzoate (0205-2)

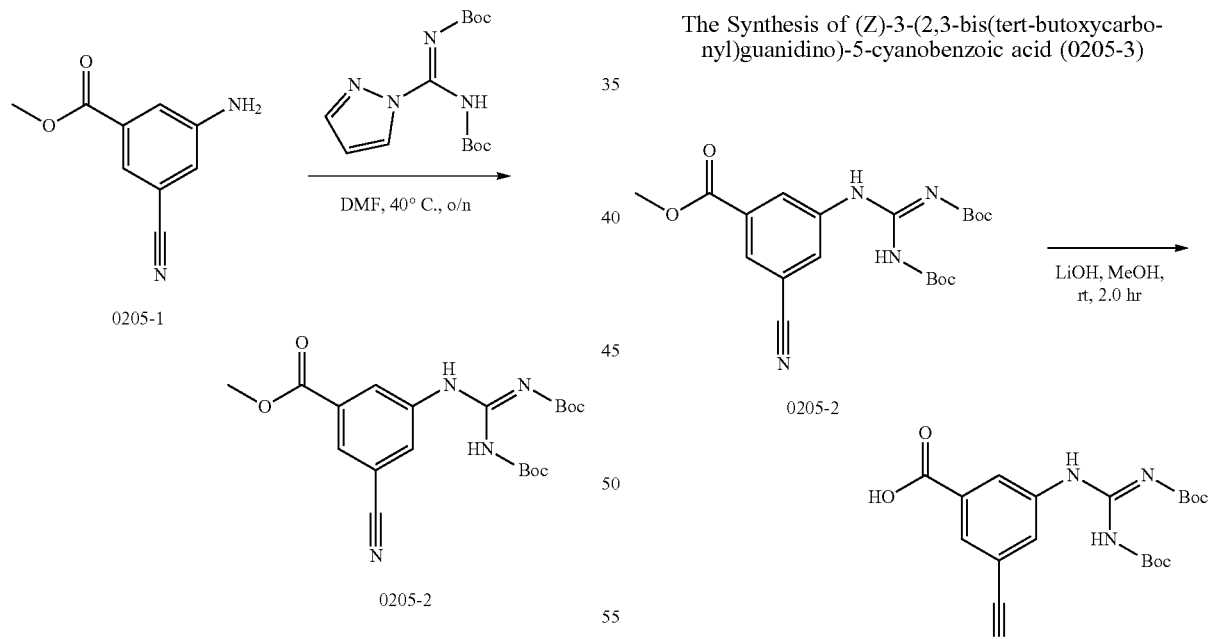

To a solution of methyl 3-amino-5-cyanobenzoate (0205-1) (500 mg, 2.84 mmol) in DMF (5 mL), (E)-tert-butyl (1H-pyrazol-1-yl)methylenedicarbamate (880 mg, 2.84 mmol) was added and the reaction mixture was then stirred at 40° C. for overnight. After the reaction was finished, the solvent was filtered and the liquid was concentrated in vacuo and the solid was collected and purified by CC. to get 0205-2 (620 mg, 52.2% yield) as a yellow solid.

Agilent LCMS 1200-6120, Column: Halo C18 (30 mm*4.6 mm*2.7 μm); Column Temperature: 40° C.; Flow Rate: 3.0 mL/min; Mobile Phase: from 95% [water+10 mM TFA] and 5% [CH$_3$CN] to 0% [water+10 mM TFA] and 100% [CH$_3$CN] in 0.8 min, then under this condition for 0.4 min, finally changed to 95% [water+10 mM TFA] and 5% [CH$_3$CN] in 0.01 min. Purity is 95.06%. Rt=0.928 min; MS Calcd.: 418.7; MS Found: 419.7 [M+H]$^+$.

The Synthesis of (Z)-3-(2,3-bis(tert-butoxycarbo-nyl)guanidino)-5-cyanobenzoic acid (0205-3)

To a solution of 0205-2 (360 mg, 0.86 mmol) in MeOH (10 mL), LiOH (30 mg, 1.29 mmol) was and the mixture was stirred at room temperature for 2 hours. After the reaction was finished, the solution was concentrated in vacuo and the crude product was dissolved in water (20 mL), 2 M HCl solution was added to adjust the pH to 3-4, then the solution was filtered and dried to get 0205-3 (230 mg, 66.1% yield) as a yellow solid.

The Synthesis of (S,Z)-methyl 3-(2-(3-(2,3-bis(tert-butoxycarbonyl)guanidino)-5-cyanobenzamido)acetamido)-2-(3,5-dichlorobiphenyl-4-ylcarboxamido)propanoate (0205-4)

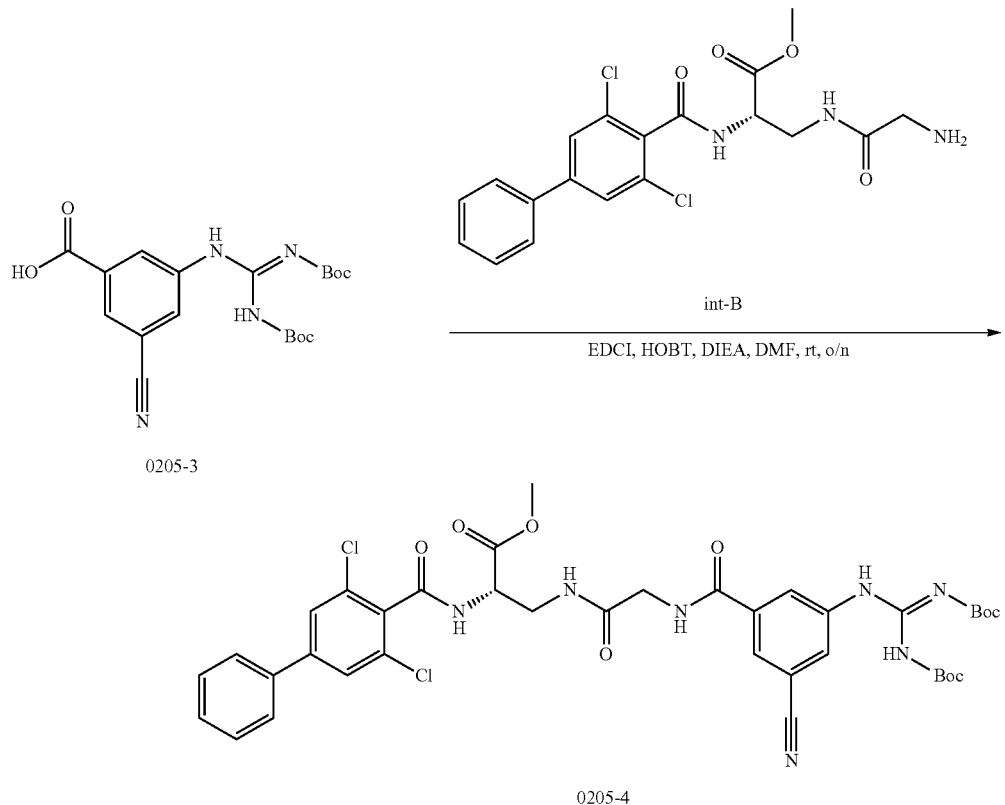

0205-3

0205-4

To a solution of 0205-3 (150 mg, 0.37 mmol) and int-B (157 mg, 0.37 mmol) in DMF (5 mL), EDCI (28 mg, 0.37 mmol), HOBT (50 mg, 0.37 mmol) and DIPEA (96 mg, 0.74 mmol) were added and the mixture was stirred at room temperature for overnight. After the reaction was finished, the solvent was diluted by water (50 mL) and extracted by EA (50 mL). Then the EA layer was washed by saturated salt water and dried by anhydrous $Na_2SO_4$, the organic layer was concentrated in vacuo and purified by CC. to get 0205-4 (100 mg, 33.3% yield) as brown oil.

The Synthesis of (S)-3-(2-(3-cyano-5 guanidinobenzamido)acetamido)-2-(3,5-dichlorobiphenyl-4-ylcarboxamido)propanoic acid (SU15210-0205-01)

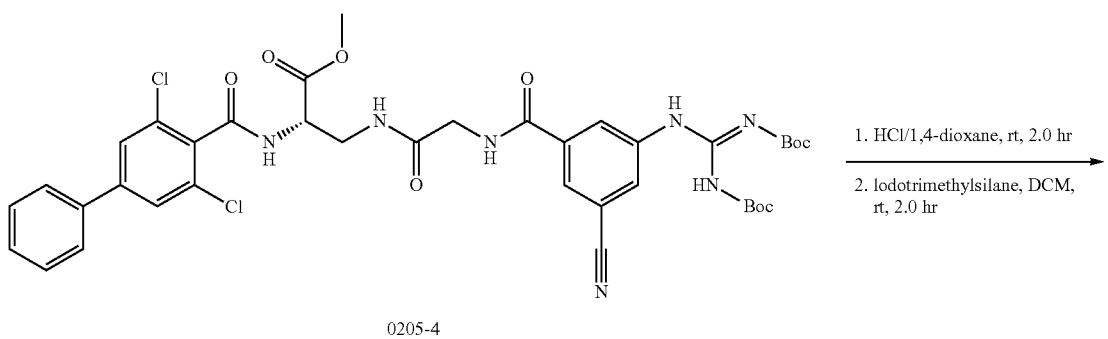

0205-4

1. HCl/1,4-dioxane, rt, 2.0 hr
2. Iodotrimethylsilane, DCM, rt, 2.0 hr

-continued

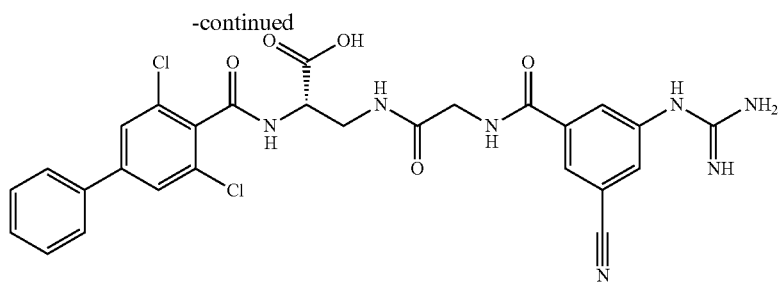

SU15210-0205-01

To a solution of 0205-4 (100 mg, 0.12 mmol) in 1,4-dioxane solution of HCl (4 M) (5 mL), the solution was stirred at room temperature for 2 hours. After the reaction was finished, the solution was concentrated in vacuo. Then the solid was dissolved in DCM (5 mL) and Iodotrimethylsilane (24 mg, 0.12 mmol) was added and the mixture was still stirred at room temperature for 2 hours. After the reaction was finished, the mixture was filtered and the solution was concentrated in vacuo and purified by pre-HPLC directly to get SU15210-0205-01 (3 mg, 4.1% yield) as a yellow solid.

Agilent LCMS 1200-6120, Column: Waters X-Bridge-C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min. Purity is 100%. Rt=1.419 min; MS Calcd.: 595.7; MS Found: 596.7 $[M+H]^+$.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% $NH_4HCO_3$] and 5% [$CH_3CN$] to 0% [water+0.1% $NH_4HCO_3$] and 100% [$CH_3CN$] in 10 min, then under this condition for 5 min, finally changed to 95% [water+0.1% $NH_4HCO_3$] and 5% [$CH_3CN$] in 0.1 min and under this condition for 5 min. Purity is 100%. Rt=6.544 min.

$^1$H NMR (400 MHz, DMSO-$d_6$) δ 9.23-9.15 (m, 1H), 8.41-8.27 (m, 2H), 8.08 (s, 1H), 8.02 (s, 1H), 7.80-7.75 (m, 7H), 7.52-7.45 (m, 3H), 4.24-4.17 (m, 1H), 3.90-3.83 (m, 2H), 3.71-3.60 (m, 2H), 3.09 (s, 1H), 2.71-2.62 (m, 1H), 2.33 (s, 1H).

Scheme: Route for SU15210-0230-01

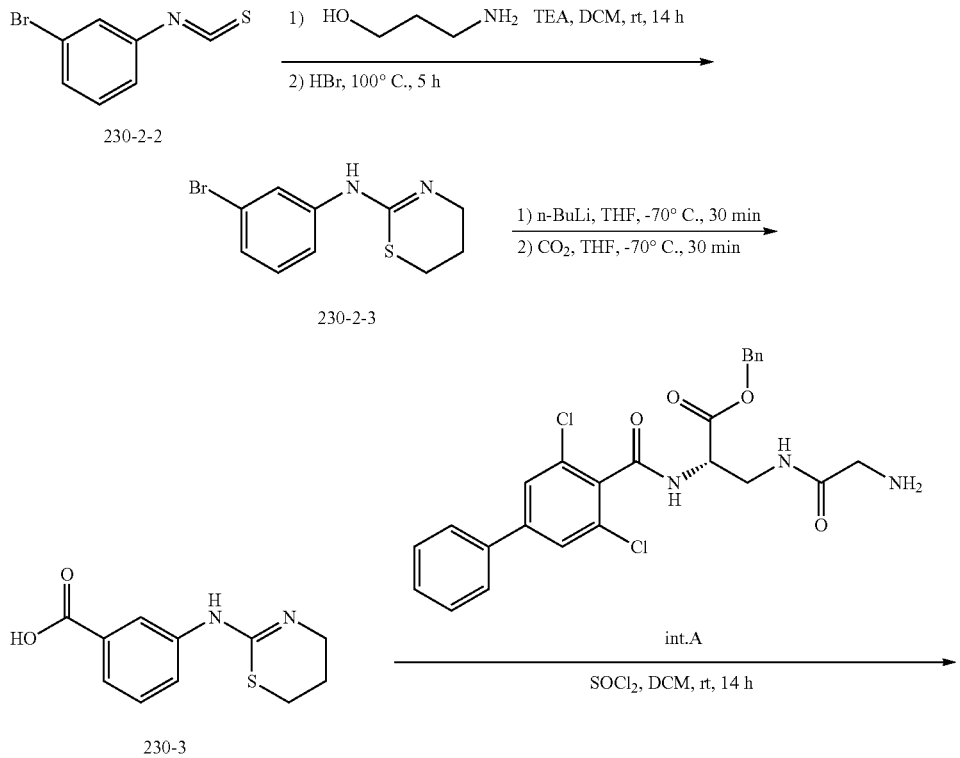

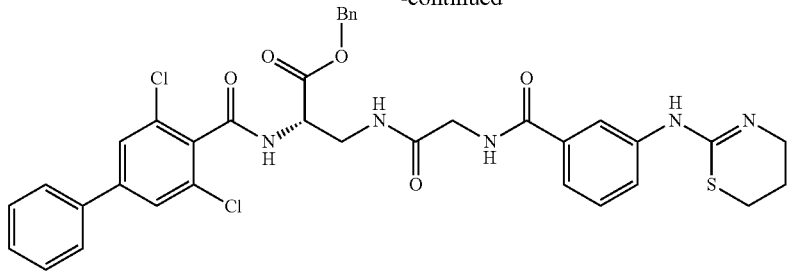

230-4

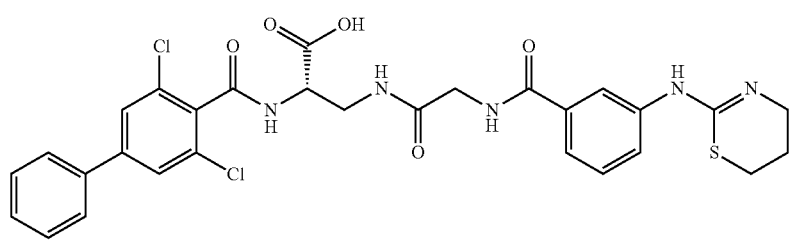

SU15210-0230-01

The Synthesis of N-(3-bromophenyl)-5,6-dihydro-4H-1,3-thiazin-2-amine (230-2-3)

The Synthesis of 3-(5,6-dihydro-4H-1,3-thiazin-2-ylamino)benzoic acid (230-3)

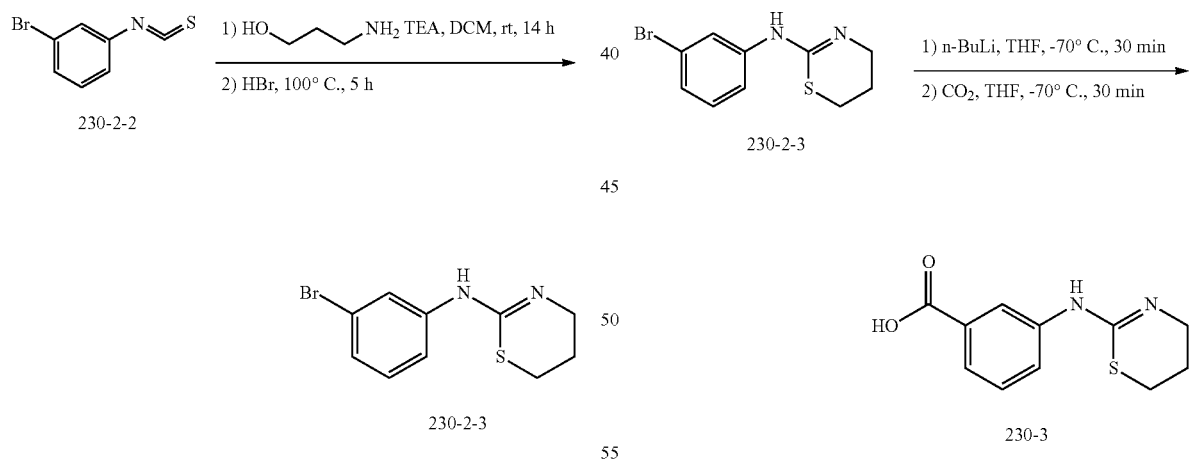

To a stirred solution of 3-aminopropan-1-ol (526 mg, 7.01 mmol) in DCM was added TEA (1062 mg, 10.51 mmol) and 230-2-2 (1.5 g, 7.01 mmol), the solution was stirred at rt for 14 h, concentrated and dissolved in HBr (60 mL), heated to 100° C. and stirred for 5 h, concentrated in vacuo to remove the solvent, then added $K_2CO_3$ (aq) until pH=9, the solid was collected by filtration and washed with water, dried to give 230-2-3 (1.2 g, 63.2% yield) as an off-white solid.

To the solution of 230-2-3 (370 mg, 1.36 mmol) in THF (8 mL) was added n-BuLi (1.64 mmol) at −70° C., the mixture was stirred at −70° C. for 30 min, the mixture was stirred under $CO_2$ atmosphere (1 atm) at −70° C. for 30 min, concentrated and purified by prep-HPLC to give 230-3 (287 mg, 89.1% yield) as a gray solid.

The Synthesis of (S)-benzyl 2-(3,5-dichlorobiphenyl-4-ylcarboxamido)-3-(2-(3-(5,6-dihydro-4H-1,3-thiazin-2-ylamino)benzamido)acetamido)propanoate (230-4)

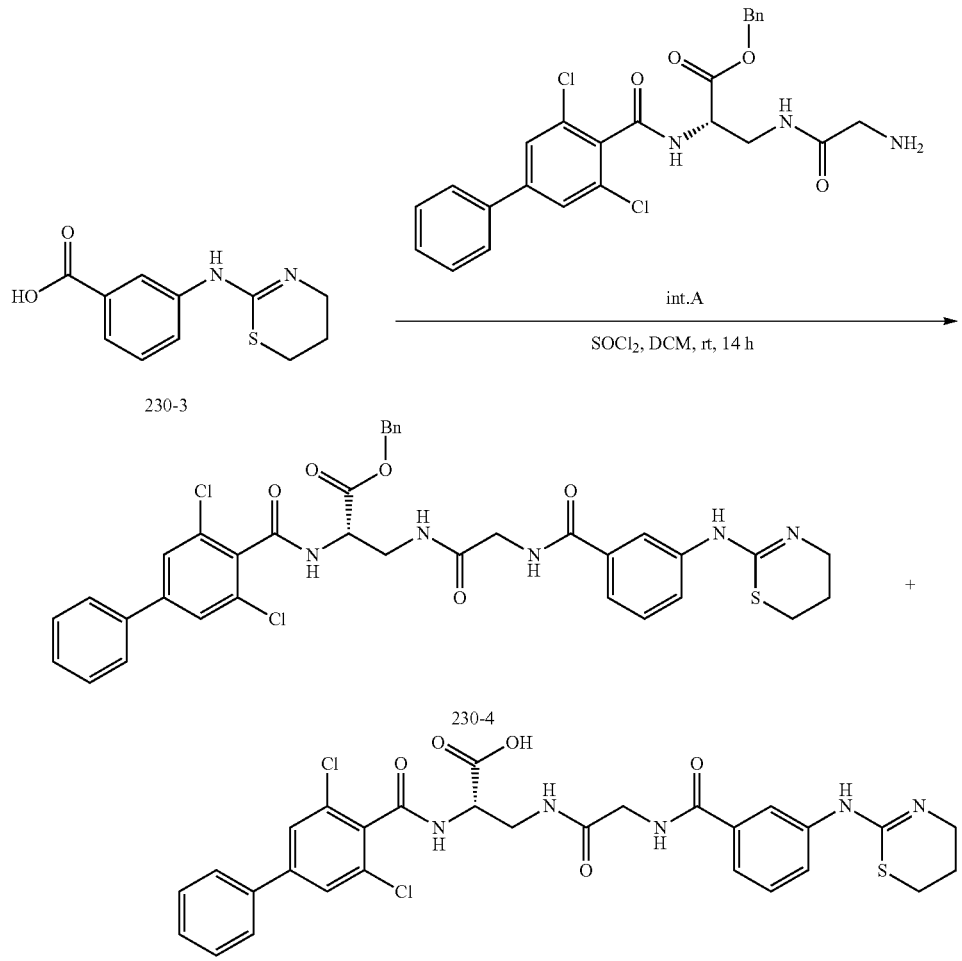

To a solution of 230-3 (100 mg, 0.42 mmol) was dissolved in SOCl₂ (1 mL), the solution was stirred at 50° C. for 2 h, concentrated and dissolved in DCM (4 mL), int.A (210 mg, 0.42 mmol) was added at rt, stirred for 5 min, TEA (212 mg, 2.1 mmol) was added dropwise, the mixture was stirred at rt for 14 h, LCMS detected both intermediate 230-4 and final compound SU15210-0230-01. The reaction mixture was concentrated and purified with prep-HPLC to give intermediate 230-4 (38 mg, yield: 12.5%) as a white solid and compound SU15210-0230-01 (17 mg, yield: 6.6%) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: A: Water (0.05% TFA) B: ACN (0.05% TFA); Gradient: B from 5% to 100% for 1.6 min and hold 100% for 1.4 min. Purity: 99.77%, $R_t$=1.515 min; MS Calcd.: 627.11; MS Found: 628.1 [M+H]⁺.

HPLC (Agilent HPLC 1200, Column: WATERS)(Bridge (150 mm*4.6 mm*3.5 um); Column Temperature: 40° C.; Flow Rate: 1.0 mL/min; Mobile Phase: A: Water (0.05% TFA) B: ACN (0.05% TFA); Gradient: Pump1:B from 5% to 100% for 10 min and hold 100% for 5.0 min. Purity: 99.29%, Rt=6.692 min.

¹H NMR (400 MHz, DMSO-$d_6$) δ 8.91 (d, J=7.6 Hz, 1H), 8.56 (t, J=5.6 Hz, 1H), 7.92 (t, J=5.6 Hz, 1H), 7.75-7.80 (m, 5H), 7.38-7.52 (m, 5H), 7.26 (t, J=7.6 Hz, 1H), 4.52 (q, J=7.2 Hz, 1H), 3.77-3.90 (m, 2H), 3.43-3.52 (m, 5H), 3.03 (t, J=5.6 Hz, 2H), 1.83 (s, 2H).

Scheme: Route for SU15210-0238-01

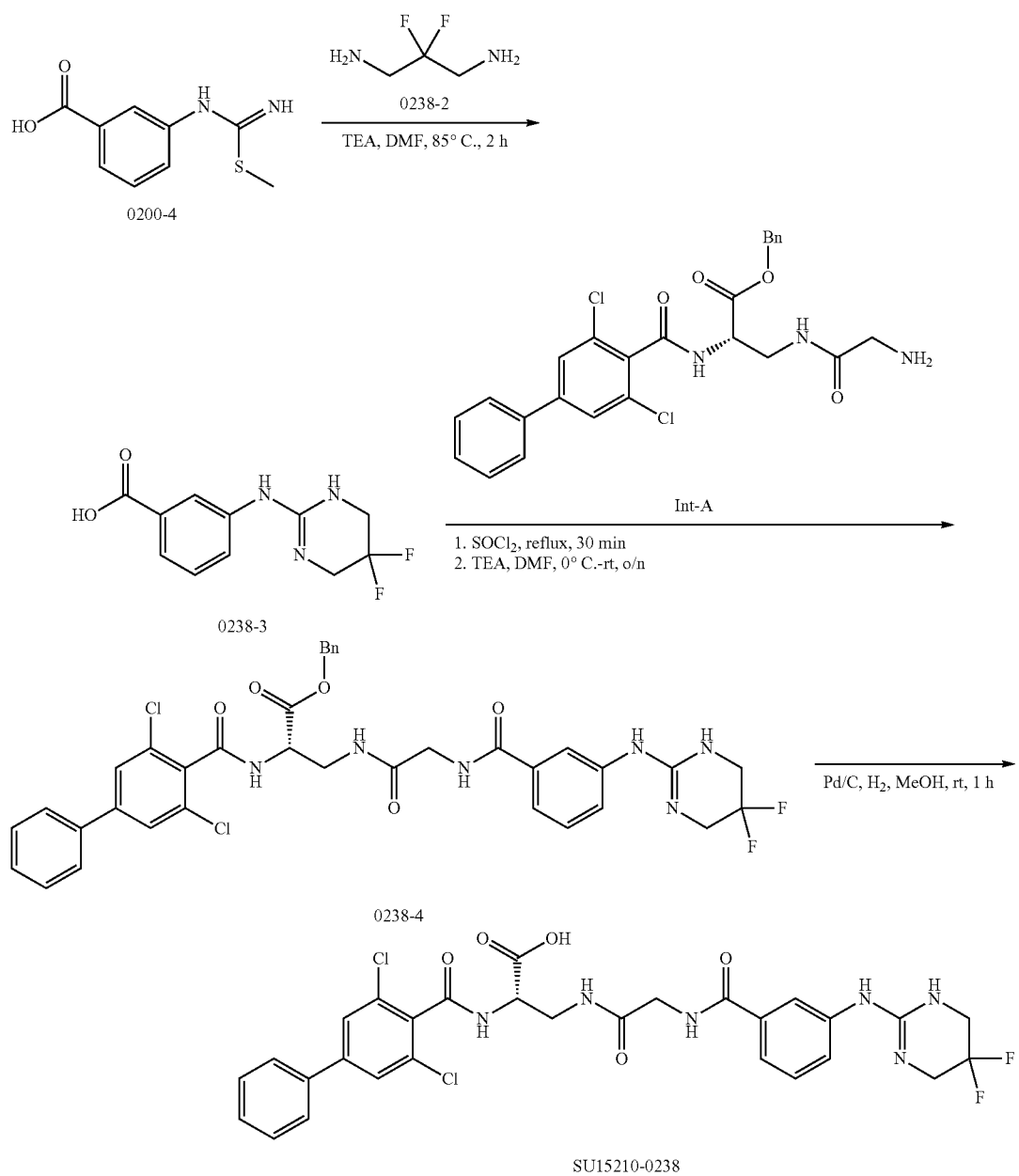

The Synthesis of 3-(5,5-difluoro-1,4,5,6-tetrahydro-pyrimidin-2-ylamino)benzoic acid (0238-3)

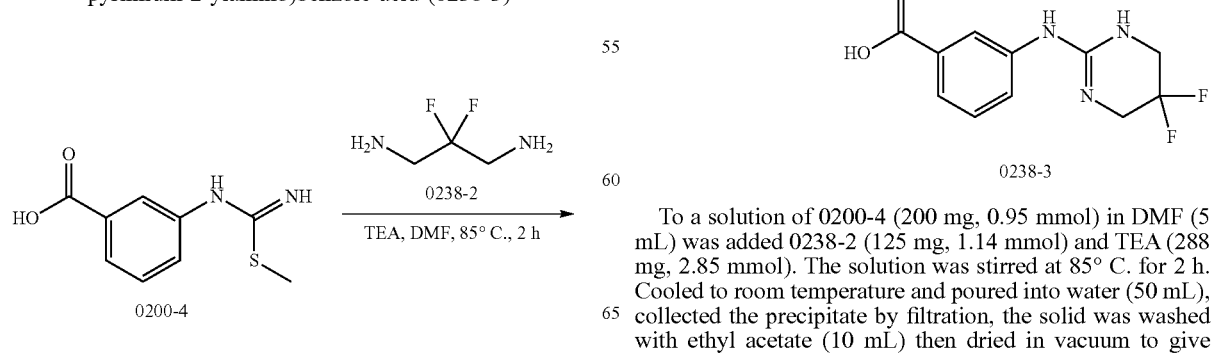

To a solution of 0200-4 (200 mg, 0.95 mmol) in DMF (5 mL) was added 0238-2 (125 mg, 1.14 mmol) and TEA (288 mg, 2.85 mmol). The solution was stirred at 85° C. for 2 h. Cooled to room temperature and poured into water (50 mL), collected the precipitate by filtration, the solid was washed with ethyl acetate (10 mL) then dried in vacuum to give 0238-3 (150 mg, 62% yield) as an off-white solid.

The Synthesis of (S)-benzyl 2-(3,5-dichlorobiphenyl-4-ylcarboxamido)-3-(2-(3-(5,5-difluoro-1,4,5,6-tetrahydropyrimidin-2-ylamino)benzamido)acetamido)propanoate (0238-3)

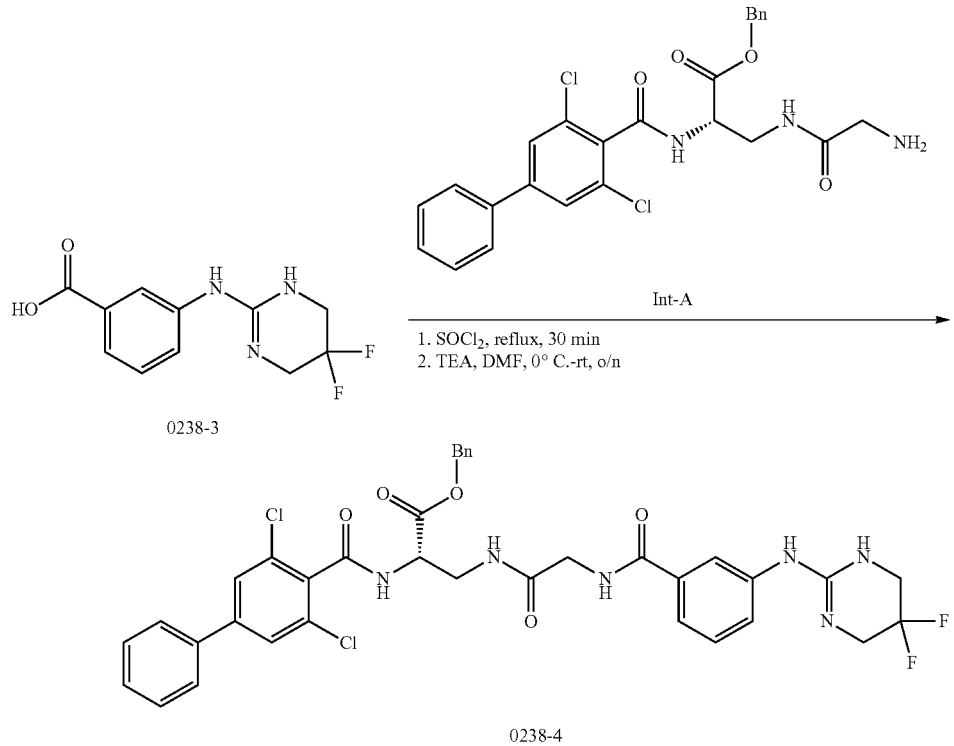

A solution of 0238-3 (150 mg, 0.59 mmol) in SOCl$_2$ (5 mL) was stirred at reflux for 30 min, then concentrated under reduced pressure to remove the excess SOCl$_2$. The residue was then added to a solution of int-A (295 mg, 0.59 mmol) and TEA (238 mg, 2.36 mmol) in DMF (5 mL) at 0° C., the solution was then allowed to warm to room temperature and stirred for overnight. Poured the solution into water (50 ml), collected the precipitate by filtration, the solid was dried and purified by CC (0% to 10% MeOH in DCM) to get 0238-4 (240 mg, 55% yield) as a white solid.

The Synthesis of (S)-2-(3,5-dichlorobiphenyl-4-ylcarboxamido)-3-(2-(3-(5,5-difluoro-1,4,5,6-tetrahydropyrimidin-2-ylamino)benzamido)acetamido) propanoic acid (SU15210-0238)

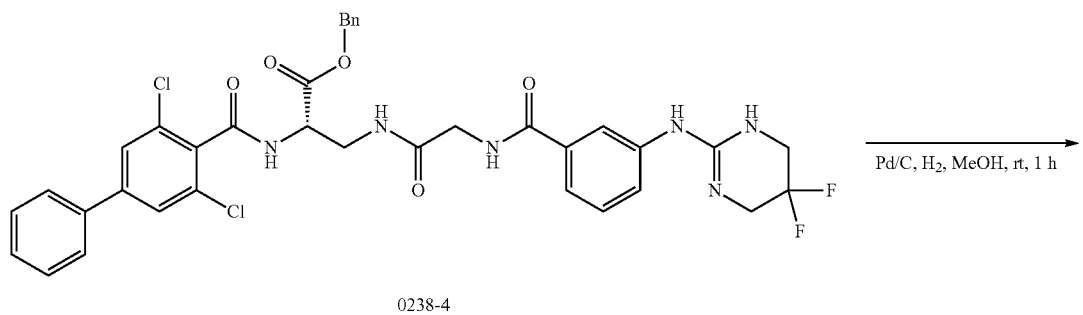

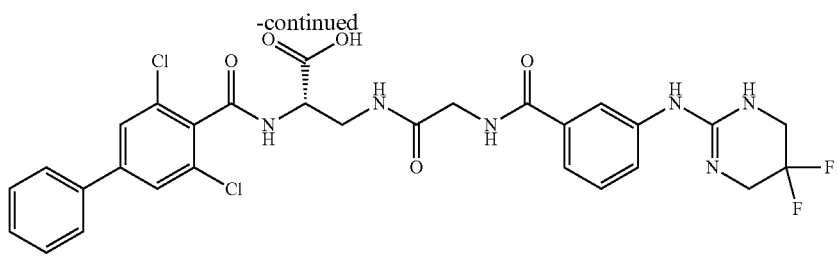

SU15210-0238

To a solution of 0238-4 (100 mg, 0.13 mmol) in MeOH (5.0 mL) was added Pd/C (10 mg). The mixture was stirred at room temperature for 1 h. Filtrated to remove the solid, the filtrate was concentrated and purified by prep-HPLC to get SU15210-00238-01 (20 mg, 23% yield) as a white solid.

Agilent LCMS 1200-6120, Column: Waters X-Bridge-C18 (100 mm*4.6 mm*3.5 μm); Column Temperature: 40° C.; Flow Rate: 2.0 mL/min; Mobile Phase: from 95% [water+10 mM TFA] and 5% [$CH_3CN$] to 0% [water+10 mM TFA] and 100% [$CH_3CN$] in 1.6 min, then under this condition for 1.4 min, finally changed to 95% [water+10 mM TFA] and 5% [$CH_3CN$] in 0.1 min. Purity is 100%. Rt=1.559 min; MS Calcd.: 646.2; MS Found: 647.2 [M+H]$^+$.

Agilent HPLC 1200; Column: Waters X-Bridge C18 (50 mm*4.6 mm*3.5 μm); Column Temperature: 30° C.; Flow Rate: 2.0 mL/min; Mobile Phase: from 95% [water+0.1% $NH_4HCO_3$] and 5% [$CH_3CN$] to 0% [water+0.1% $NH_4HCO_3$] and 100% [$CH_3CN$] in 10 min, then under this condition for 5 min, finally changed to 95% [water+0.1% $NH_4HCO_3$] and 5% [$CH_3CN$] in 0.1 min and under this condition for 5 min. Purity is 100%. Rt=6.808 min.

$^1$H NMR (400 MHz, DMSO-$d_6$) δ 10.17 (br, 2H), 8.90 (t, J=5.6 Hz, 1H), 8.36 (d, J=8.0 Hz, 1H), 8.10 (s, 1H), 7.74-7.79 (m, 5H), 7.64 (d, J=8.0 Hz, 1H), 7.42-7.52 (m, 4H), 7.37 (d, J=8.0 Hz, 1H), 4.19-4.23 (m, 1H), 3.85 (d, J=5.2 Hz, 2H), 3.70-3.77 (m, 4H), 3.59-3.66 (m, 2H), 3.16-3.21 (m, 2H).

Scheme: Route for SU15210-0241-01

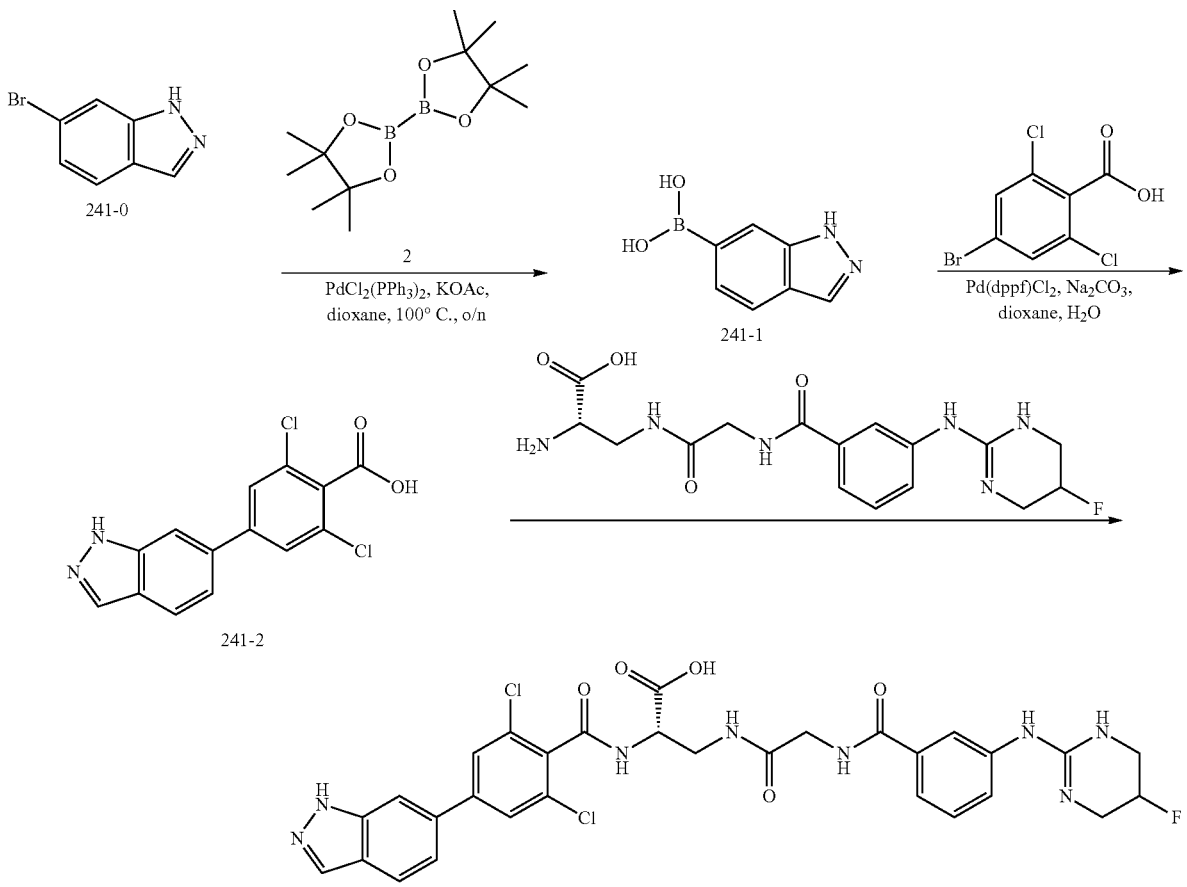

SU15210-0241-01

1H-indazol-6-ylboronic acid (241-1)

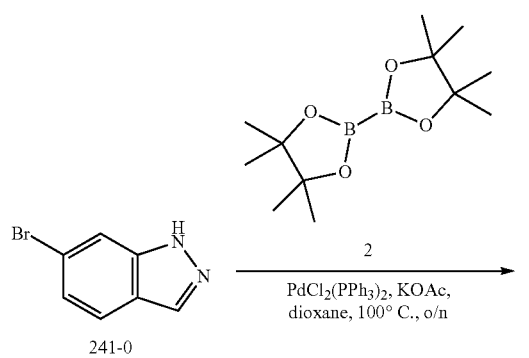

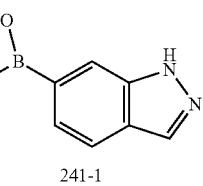

To a 1-neck round bottom flask, 6-bromo-1H-indazole (1 g, 5.08 mmol) and 4,4,5,5-tetramethyl-2-(4,4,5,5-tetramethyl-1,3,2-dioxaborolan-2-yl)-1,3,2-dioxaborolane (1.42 g, 5.58 mmol), dichloropalladium triphenylphosphane (1.78 g, 2.54 mmol), potassium acetate (1.49 g, 15.23 mmol, 951.79 uL) were added along with 1,4-dioxane (30 mL). The subsequent reaction mixture, then stirred at 98° C. overnight under nitrogen atmosphere, and was the diluted with water, extracted with EA, dried to get crude oil, and it was purified by prep-HPLC to afford 6-(4,4,5,5-tetramethyl-1,3,2-dioxaborolan-2-yl)-1H-indazole (190 mg, 778.38 umol, 15.34% yield) as light-light powder.

LC-MS (Agilent LCMS 1260-6120, Column: Waters X-Bridge C18 (50 mm*4.6 mm*3.5 μm); Column Temperature: 40° C.; Flow Rate: 1.5 mL/min; Mobile Phase: from 95% [water+10MmNH4HCO3] and 5% [CH$_3$CN] to 5% [water+10MmNH4HCO3] and 95% [CH$_3$CN] in 2 min, then under this condition for 2 min. Purity is 94.00%. Rt=1.396 min; MS Calcd.: 163.0; MS Found: 162.9 [M+H]$^+$.

2,6-dichloro-4-(1H-indazol-6-yl)benzoic acid (241-2)

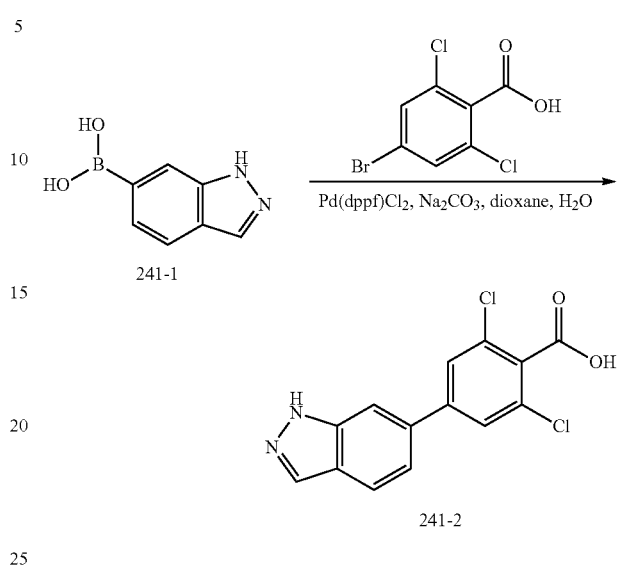

1H-indazol-6-ylboronic acid (170 mg, 1.05 mmol) 4-bromo-2,6-dichloro-benzoic acid (283.32 mg, 1.05 mmol), cyclopentyl(diphenyl)phosphane; dichloropalladium; iron (76.81 mg, 104.97 umol), disodium carbonate (333.76 mg, 3.15 mmol, 131.92 uL) was dissolved in 4-dioxane (3 mL) and water (0.5 mL) under nitrogen atmosphere. The subsequent reaction mixture was then it stirred at 100° C. overnight then diluted with water, extracted with EA, the aqueous layer was adjust the pH to 2 with HCl (2 M in water), and it was extracted with EA, dried with Na$_2$SO$_4$, concentrated to get crude product, it was purified by prep-HPLC to afford 2,6-dichloro-4-(1H-indazol-6-yl)benzoic acid (93 mg, 302.80 umol, 28.85% yield).

LC-MS (Agilent LCMS 1260-6120, Column: Waters X-Bridge C18 (50 mm*4.6 mm*3.5 μm); Column Temperature: 40° C.; Flow Rate: 1.5 mL/min; Mobile Phase: from 95% [water+10MmNH4HCO3] and 5% [CH$_3$CN] to 5% [water+10MmNH4HCO3] and 95% [CH$_3$CN] in 2 min, then under this condition for 2 min. Purity is 97.8%. Rt=1.503 min; MS Calcd.: 306.9; MS Found: 306.8 [M+H]$^+$.

(2S)-2-(2,6-dichloro-4-(1H-indazol-6-yl)benzamido)-3-(2-(3-(5-fluoro-1,4,5,6-tetrahydropyrimidin-2-ylamino)benzamido)acetamido)propanoic acid (SU15210-0241-01)

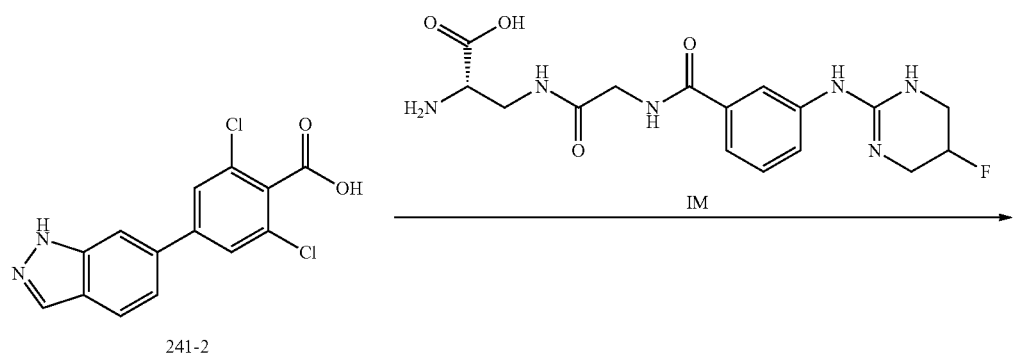

-continued

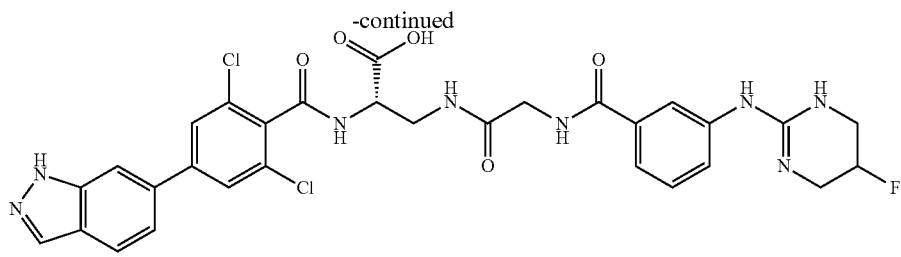

SU15210-0241-01

In a 50 mL 1-neck round bottom flask, 2,6-dichloro-4-(1H-indazol-6-yl)benzoic acid (7.5 mg, 24.42 umol) N,N,N',N'-tetramethyl-1-(3-oxido-2,3-dihydrotriazolo[4,5-b]pyridin-3-ium-1-yl)methanediamine; hexafluorophosphate (8.87 mg, 23.20 umol) and N-ethyl-N-isopropyl-propan-2-amine (15.78 mg, 122.10 umol, 21.27 uL) in DMF (2.5 mL) was stirred at RT for 1 h, then (2S)-2-amino-3-[[2-[[3-[(5-fluoro-1,4,5,6-tetrahydropyrimidin-2-yl)amino]benzoyl]amino]acetyl]amino]propanoic acid (10 mg, 26.29 umol) was added, it was stirred at RT for 2 h, LCMS detected the start material was consumed, then it was filtered, the filtrate was purified by prep-HPLC to afford (2S)-2-[[2,6-dichloro-4-(1H-indazol-6-yl)benzoyl]amino]-3-[[2-[[3-[(5-fluoro-1,4,5,6-tetrahydropyrimidin-2-yl)amino]benzoyl]amino]acetyl]amino]propanoic acid (4 mg, 5.97 umol, 24.47% yield) as white powder.

LC-MS (Agilent LCMS 1260-6120, Column: Waters X-Bridge C18 (50 mm*4.6 mm*3.5 μm); Column Temperature: 40° C.; Flow Rate: 1.5 mL/min; Mobile Phase: from 95% [water+10MmNH4HCO3] and 5% [CH$_3$CN] to 5% [water+10MmNH4HCO3] and 95% [CH$_3$CN] in 2 min, then under this condition for 2 min. Purity is 91.95%. Rt=1.772 min; MS Calcd.: 669.1 MS Found: 668.7 [M+H]$^+$.

$^1$H NMR (400 MHz, MeOD) δ 7.99 (s, 1H), 7.72 (dd, J=49.6, 16.6 Hz, 5H), 7.38 (dd, J=49.9, 8.6 Hz, 4H), 5.16 (s, 1H), 4.50 (s, 2H), 3.97 (d, J=4.8 Hz, 2H), 3.77-3.30 (m, 7H).

1H-indazol-6-ylboronic acid (SU15210-0247-01)

A mixture of 2,6-dichloro-4-(3-pyridyl)benzoic acid (20 mg, 74.60 umol) N,N,N',N'-tetramethyl-1-(3-oxido-2,3-dihydrotriazolo[4,5-b]pyridin-3-ium-1-yl)methanediamine; hexafluorophosphate (27.09 mg, 70.87 umol), N-ethyl-N-isopropyl-propan-2-amine (48.21 mg, 373.00 umol, 64.97 uL) in DMF (3 mL) was stirred at RT for 1 h, then 240-7 (25 mg, 53.14 umol) was added, it was stirred at RT for further 2 h, then it was filtered, the filtrate was purified by prep-HPLC to afford benzyl (2S)-2-[[2,6-dichloro-4-(3-pyridyl)benzoyl]amino]-3-[[2-[[3-[(5-fluoro-1,4,5,6-tetrahydropyrimidin-2-yl)amino]benzoyl]amino]acetyl]amino]propanoate (3.8 mg, 5.27 umol, 7.07% yield) as white solid.

LC-MS (Agilent LCMS 1260-6120, Column: Waters X-Bridge C18 (50 mm*4.6 mm*3.5 μm); Column Temperature: 40° C.; Flow Rate: 1.5 mL/min; Mobile Phase: from 95% [water+10MmNH4HCO3] and 5% [CH$_3$CN] to 5% [water+10MmNH4HCO3] and 95% [CH$_3$CN] in 2 min, then under this condition for 2 min. Purity is 94.00%. Rt=1.441 min; MS Calcd.: 629.2; MS Found: 629.7 [M+H]$^+$.

$^1$H NMR (400 MHz, MeOD) δ 8.74 (d, J=2.0 Hz, 1H), 8.50 (dd, J=4.9, 1.4 Hz, 1H), 8.08-7.98 (m, 1H), 7.84-7.55 (m, 4H), 7.53-7.39 (m, 2H), 7.30 (d, J=8.2 Hz, 1H), 5.12 (d, J=46.6 Hz, 2H), 4.56-4.39 (m, 4H), 3.96 (d, J=7.0 Hz, 2H), 3.72-3.29 (m, 6H).

Scheme: Route for SU15210-0247-01

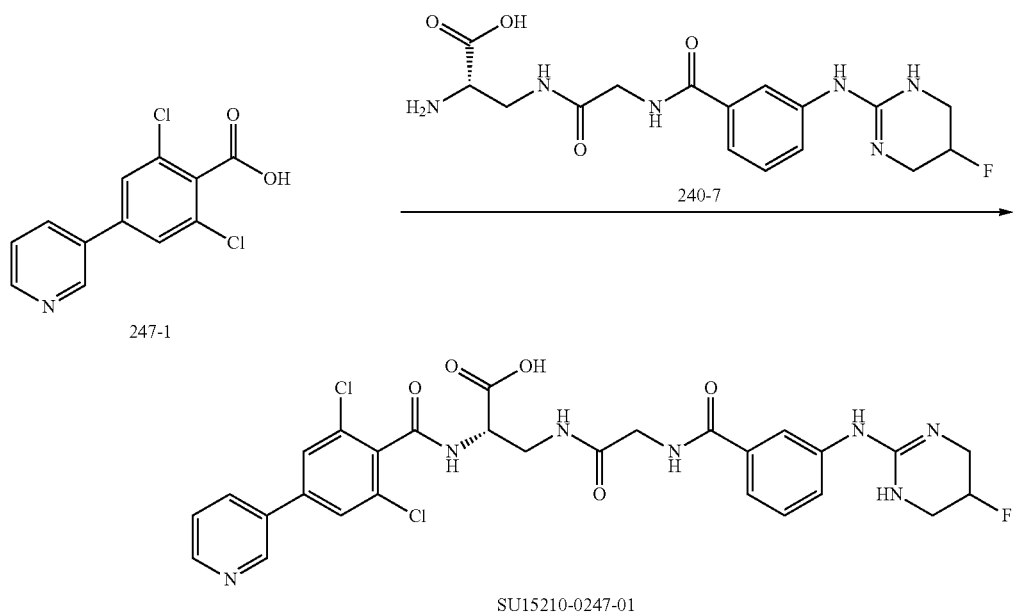

SU15210-0247-01

Scheme: Route for SU15210-0248-01

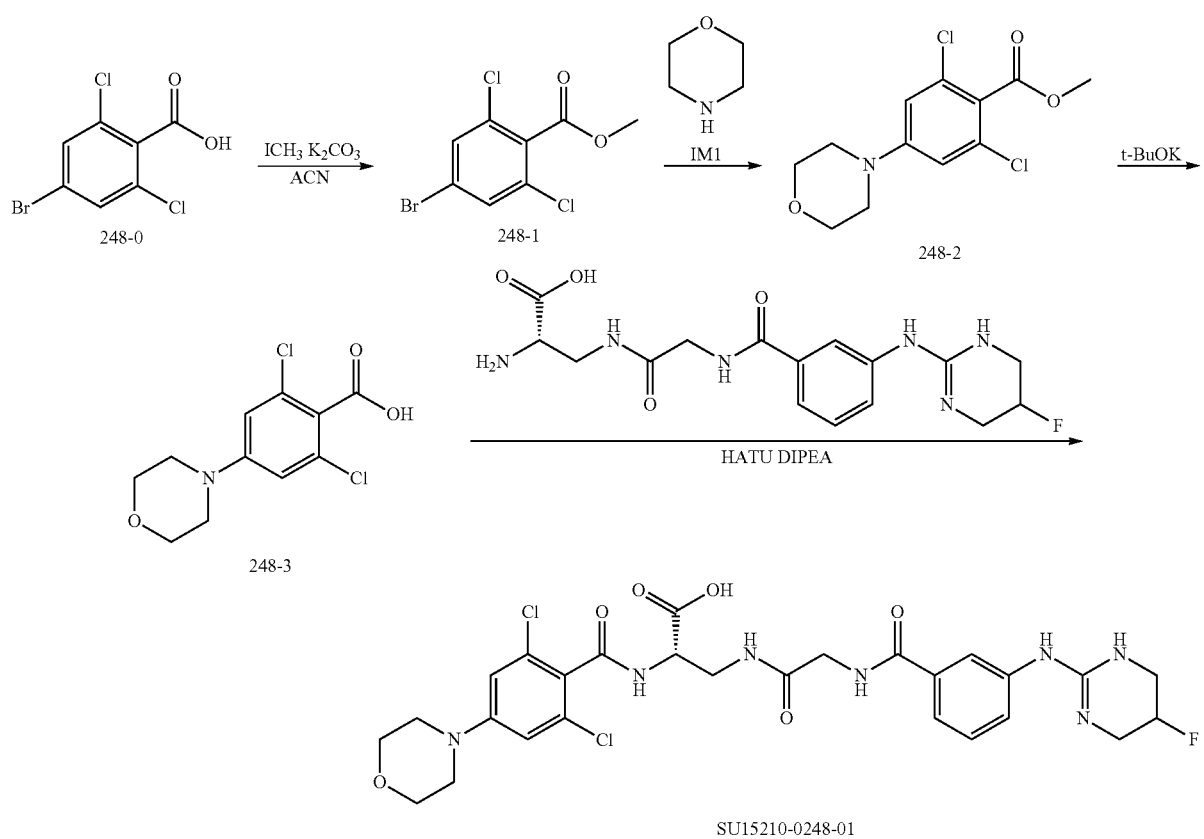

methyl 4-bromo-2,6-dichlorobenzoate (248-1)

methyl 2,6-dichloro-4-morpholinobenzoate (248-2)

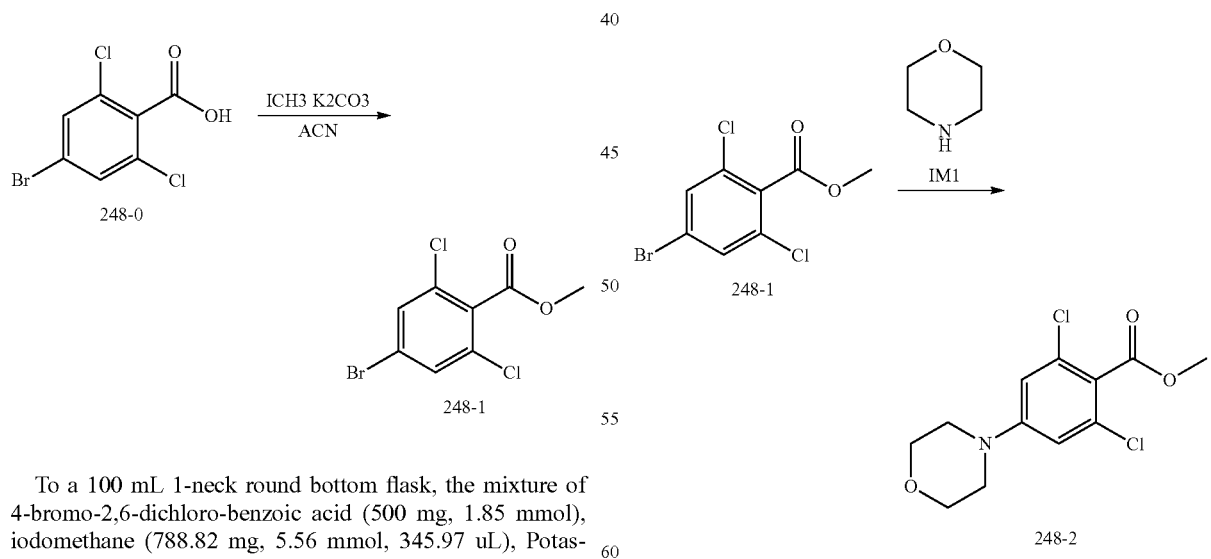

To a 100 mL 1-neck round bottom flask, the mixture of 4-bromo-2,6-dichloro-benzoic acid (500 mg, 1.85 mmol), iodomethane (788.82 mg, 5.56 mmol, 345.97 uL), Potassium carbonate (1.28 g, 9.26 mmol, 559.01 uL) in acetonitrile (20 mL) was stirred at RT for 6 h, then it was diluted with water, extracted with EA, dried with $Na_2SO_4$, concentrated to afford methyl 4-bromo-2,6-dichloro-benzoate (516 mg, 1.82 mmol, 98.10% yield) as yellow oil, it was used to next step without further purification. 1H NMR (400 MHz, CDCl3) δ 7.51 (s, 2H), 3.97 (s, 3H).

Methyl 4-bromo-2,6-dichloro-benzoate (200 mg, 704.39 umol), diacetoxypalladium (7.91 mg, 35.22 umol), Binap (26.32 mg, 42.26 umol), Cesium carbonate (688.51 mg, 2.11 mmol), morpholine (92.05 mg, 1.06 mmol, 92.42 uL) in toluene (5 mL) were added to a nitrogen-filled high-pressure sealed tube, and it was stirred at 100° C. overnight, TLC demonstrated that the starting material was consumed, then the reaction mixture was diluted with DCM, and it was filtered to collect the filtrate, purified by silica gel column (PE:EA=10:1) to afford methyl 2,6-dichloro-4-morpholino-benzoate (170 mg, 585.92 umol, 83.18% yield) as white powder.

LC-MS (Agilent LCMS 1260-6120, Column: Waters X-Bridge C18 (50 mm*4.6 mm*3.5 μm); Column Temperature: 40° C.; Flow Rate: 1.5 mL/min; Mobile Phase: from 95% [water+10MmNH4HCO3] and 5% [CH$_3$CN] to 5% [water+10MmNH4HCO3] and 95% [CH$_3$CN] in 2 min, then under this condition for 2 min. Purity is 97.8%. Rt=2.555 min; MS Calcd.: 290.0; MS Found: 289.8 [M+H]$^+$.

2,6-dichloro-4-morpholinobenzoic acid (248-3)

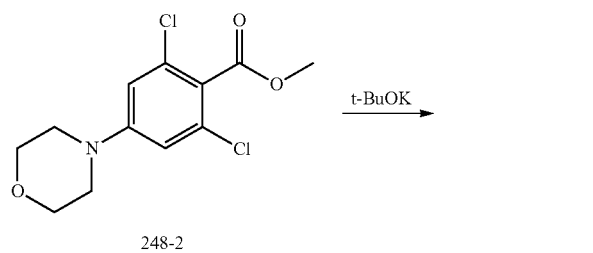

To a 50 mL 1-neck round bottom flask, the mixture of methyl 2,6-dichloro-4-morpholino-benzoate (100 mg, 344.66 umol), Potassium tert-butoxide (174.04 mg, 1.55 mmol) in DMSO (10 mL) and water (3 mL) was stirred at 90° C. for 4 h, TLC showed that the starting material was consumed, then the reaction mixture was diluted with water, extracted with EA, dried with Na$_2$SO$_4$, concentrated to get 2,6-dichloro-4-morpholino-benzoic acid (82 mg, 296.98 umol, 86.17% yield) as yellow solid, it was used to next step without further purification.

LC-MS (Agilent LCMS 1260-6120, Column: Waters X-Bridge C18 (50 mm*4.6 mm*3.5 μm); Column Temperature: 40° C.; Flow Rate: 1.5 mL/min; Mobile Phase: from 95% [water+10MmNH4HCO3] and 5% [CH$_3$CN] to 5% [water+10MmNH4HCO3] and 95% [CH$_3$CN] in 2 min, then under this condition for 2 min. Purity is 100%. Rt=2.603 min; MS Calcd.: 276.0 MS Found: 275.8 [M+H]$^+$.

(2 S)-2-(2,6-dichloro-4-morpholinobenzamido)-3-(2-(3-(5-fluoro-1,4,5,6-tetrahydropyrimidin-2-ylamino)benzamido)acetamido)propanoic acid (SU15210-0248-01)

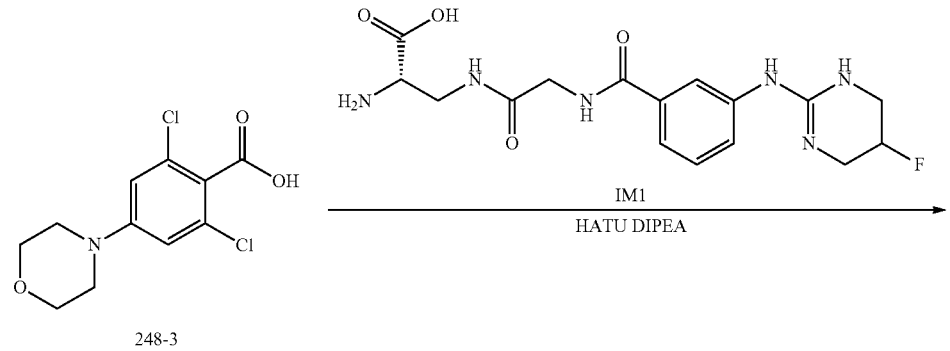

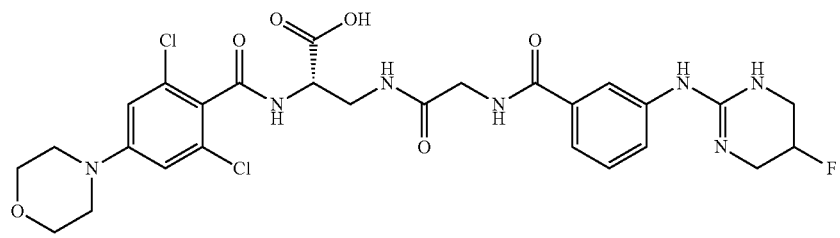

To a 50 mL 1-neck round bottom flask, A mixture of 2,6-dichloro-4-morpholino-benzoic acid (12.3 mg, 44.55 umol), HATU (16.18 mg, 42.32 umol), DIPEA (28.79 mg, 222.73 umol, 38.80 uL) in DMF (3 mL) was stirred at RT for 1 h, then IM1(15 mg, 31.88 umol) was added, it was stirred at RT for a further 2 h, then it was filtered, the filtrate was purified by prep-HPLC to afford the product (5 mg, 6.86 umol, 15.41% yield) as a white powder.

LC-MS (Agilent LCMS 1260-6120, Column: Waters X-Bridge C18 (50 mm*4.6 mm*3.5 μm); Column Temperature: 40° C.; Flow Rate: 1.5 mL/min; Mobile Phase: from 95% [water+10MmNH4HCO3] and 5% [CH$_3$CN] to 5% [water+10MmNH4HCO3] and 95% [CH$_3$CN] in 2 min, then under this condition for 2 min. Purity is 100%. Rt=1.598 min; MS Calcd.: 638.1 MS Found: 637.7 [M+H]$^+$.

$^1$H NMR (400 MHz, MeOD) δ 7.69 (t, J=4.3 Hz, 2H), 7.43 (t, J=7.9 Hz, 1H), 7.30 (dd, J=7.2, 1.3 Hz, 1H), 6.82 (s, 2H), 5.12 (d, J=44.4 Hz, 2H), 4.43 (s, 2H), 3.95 (d, J=3.2 Hz, 2H), 3.78-3.64 (m, 4H), 3.55 (dd, J=14.4, 4.9 Hz, 5H), 3.43 (s, 1H), 3.14-3.04 (m, 4H).

Scheme: Route for SU15210-0253-01

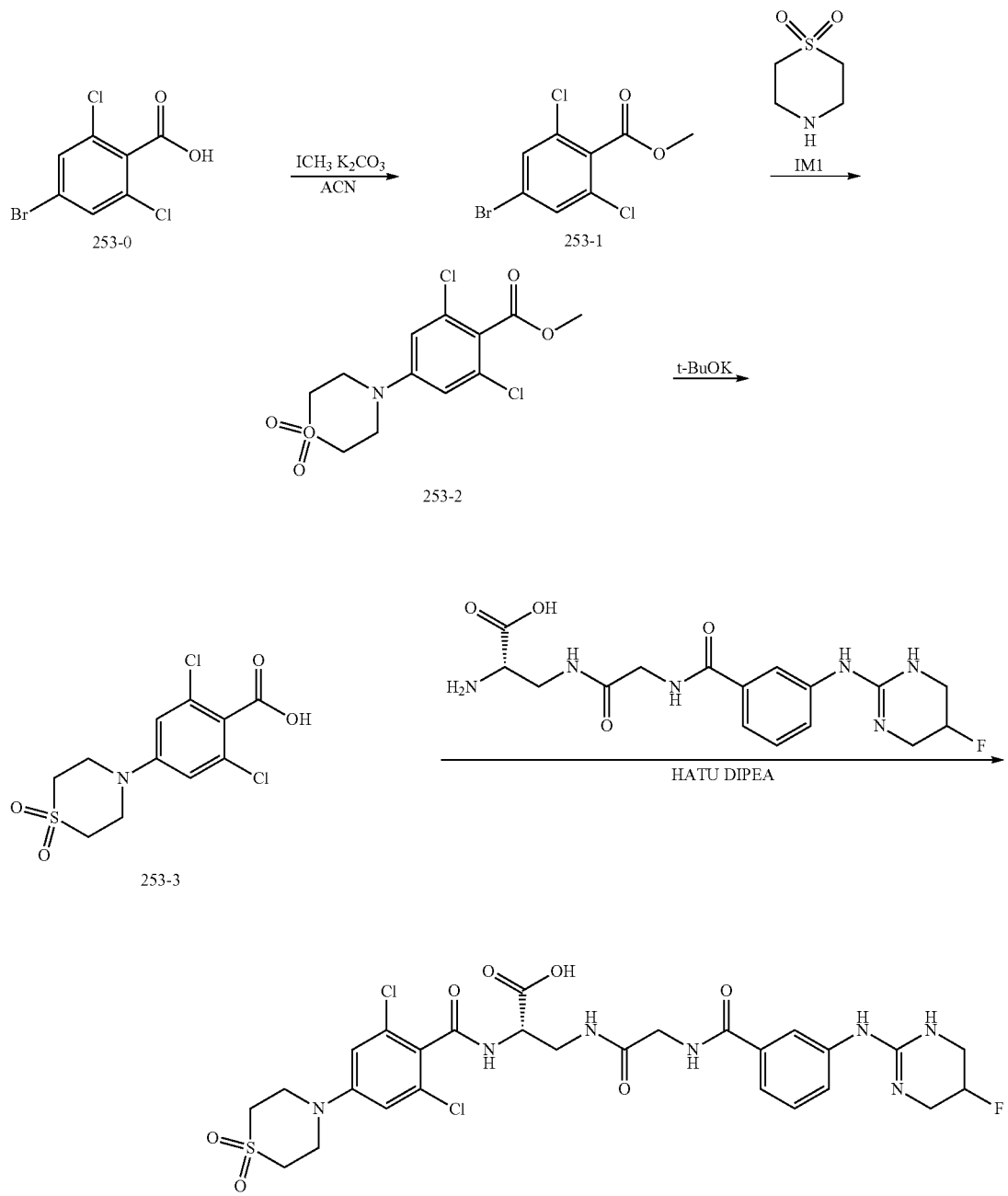

methyl 4-bromo-2,6-dichlorobenzoate (253-1)

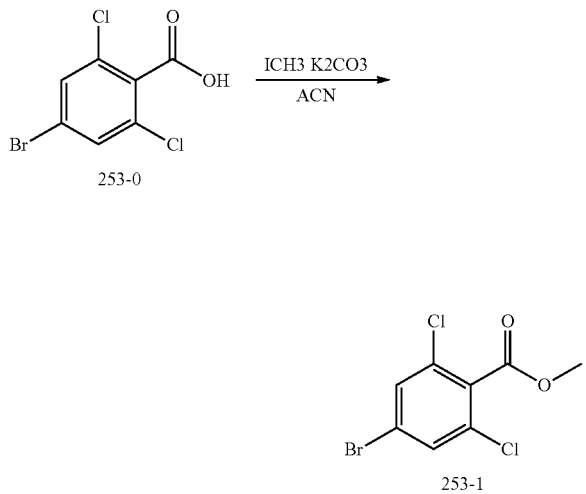

To a 100 mL 1-neck round bottom flask, a mixture of 4-bromo-2,6-dichloro-benzoic acid (500 mg, 1.85 mmol), iodomethane (788.82 mg, 5.56 mmol, 345.97 uL), Potassium carbonate (1.28 g, 9.26 mmol, 559.01 uL) was added to acetonitrile (20 mL). The subsequent reaction mixture was stirred at RT for 6 h, then it was diluted with water, extracted with EA, dried with $Na_2SO_4$, concentrated to afford methyl 4-bromo-2,6-dichloro-benzoate (516 mg, 1.82 mmol, 98.10% yield) as yellow oil, it was used to next step without further purification. $^1$H NMR (400 MHz, CDCl$_3$) δ 7.51 (s, 2H), 3.97 (s, 3H).

methyl 2,6-dichloro-4-(1,1-dioxo-1,4-thiazinan-4-yl)benzoate (253-2)

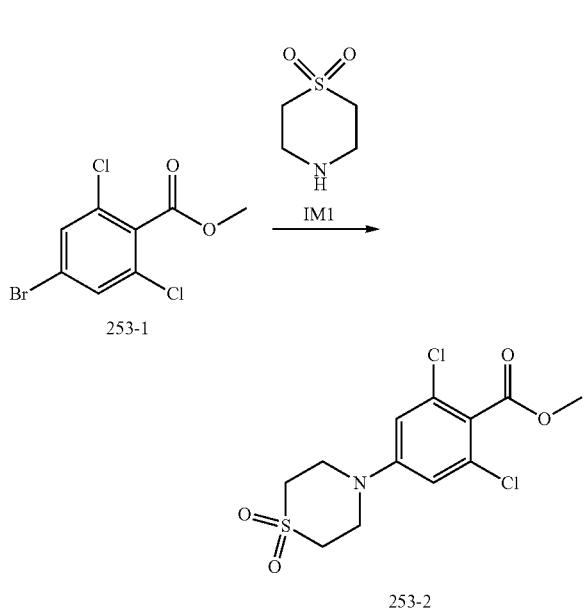

Methyl 4-bromo-2,6-dichloro-benzoate (70 mg, 246.54 umol), 1,4-thiazinane1,1-dioxide hydrochloride (50.78 mg, 295.84 umol), diacetoxypalladium (2.77 mg, 12.33 umol), binap (9.21 mg, 14.79 umol), Cesium carbonate (240.98 mg, 739.61 umol) in toluene (5 mL) was added to a nitrogen-filled sealed tube, and the subsequent reaction mixture was stirred at 100° C. overnight, TLC showed that the starting material was consumed, then the reaction mixture was diluted with DCM, and filtered to collect the filtrate. The crude material was purified by silica gel column (PE:EA=4:1) to afford methyl 2,6-dichloro-4-(1,1-dioxo-1,4-thiazinan-4-yl)benzoate (63 mg, 186.28 umol, 75.56% yield)

LC-MS (Agilent LCMS 1260-6120, Column: Waters X-Bridge C18 (50 mm*4.6 mm*3.5 μm); Column Temperature: 40° C.; Flow Rate: 1.5 mL/min; Mobile Phase: from 95% [water+10MmNH4HCO3] and 5% [CH$_3$CN] to 5% [water+10MmNH4HCO3] and 95% [CH$_3$CN] in 2 min, then under this condition for 2 min. Purity is 100%. Rt=2.362 min; MS Calcd.: 337.0; MS Found: 337.8 [M+H]$^+$. $^1$H NMR (400 MHz, CDCl$_3$) δ 6.80 (s, 2H), 3.95 (s, 3H), 3.92-3.85 (m, 4H), 3.13-3.05 (m, 4H).

2,6-dichloro-4-(1,1-dioxo-1,4-thiazinan-4-yl)benzoic acid (253-3)

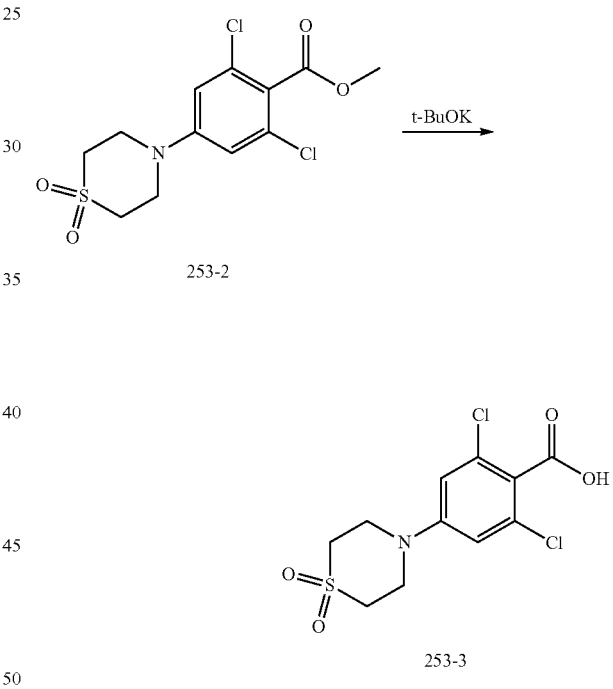

A mixture of methyl 2,6-dichloro-4-(1,1-dioxo-1,4-thiazinan-4-yl)benzoate (140 mg, 413.95 umol) and potassium; 2-methylpropan-2-olate (209.02 mg, 1.86 mmol) in DMSO (10 mL) and water (3 mL) was stirred at 90° C. for 4 h. TLC showed that the s starting material was consumed, then the reaction mixture was diluted with water, washed with EA for 3 times, then adjusted to pH to 2.5, extracted with EA, dried with $Na_2SO_4$, concentrated to give 2,6-dichloro-4-(1,1-dioxo-1,4-thiazinan-4-yl)benzoic acid (100 mg, 308.47 umol, 74.52% yield) as yellow solid, which was used to next step without further purification. $^1$H NMR (400 MHz, DMSO) δ 7.14 (s, 2H), 3.89 (s, 4H), 3.12 (s, 4H).

(benzyl (2 S)-2-[[2,6-dichloro-4-(1,1-di oxo-1,4-thiazinan-4-yl)benzoyl]amino]-3-[[2-[[3-[(5-fluoro-1,4,5,6-tetrahydropyrimidin-2-yl)amino]benzoyl]amino]acetyl]amino] propanoate (SU15210-0253-01)

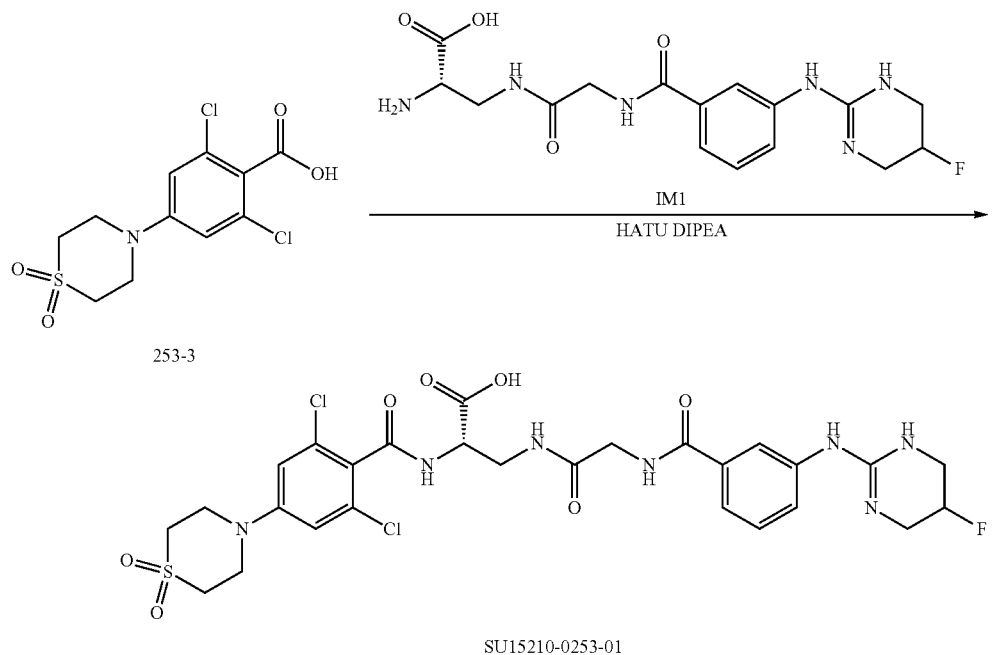

A mixture of 2,6-dichloro-4-(1,1-dioxo-1,4-thiazinan-4-yl)benzoic acid (30 mg, 92.54 umol), HATU (33.60 mg, 87.91 umol), DIPEA (59.80 mg, 462.71 umol, 80.59 uL) in DMF (3 mL) was stirred at RT for 1 h, then IM1 (30 mg, 63.76 umol) was added. The subsequent reaction mixture was stirred at RT for a further 2 h, then it was filtered, the filtrate was purified by prep-HPLC to afford benzyl (2S)-2-[[2,6-dichloro-4-(1,1-dioxo-1,4-thiazinan-4-yl)benzoyl]amino]-3-[[2-[[3-[(5-fluoro-1,4,5,6-tetrahydropyrimidin-2-yl)amino]benzoyl]amino]acetyl]amino]propanoate (3.8 mg, 4.89 umol, 5.29% yield) as a white powder.

LC-MS (Agilent LCMS 1260-6120, Column: Waters X-Bridge C18 (50 mm*4.6 mm*3.5 μm); Column Temperature: 40° C.; Flow Rate: 1.5 mL/min; Mobile Phase: from 95% [water+10MmNH4HCO3] and 5% [CH$_3$CN] to 5% [water+10MmNH4HCO3] and 95% [CH$_3$CN] in 2 min, then under this condition for 2 min. Purity is 100%. Rt=1.416 min; MS Calcd.: 686.1 MS Found: 685.7 [M+H]$^+$.

$^1$H NMR (400 MHz, MeOD) δ 7.83-7.76 (m, 2H), 7.54 (t, J=8.2 Hz, 1H), 7.40 (d, J=8.5 Hz, 1H), 7.03 (d, J=4.1 Hz, 2H), 5.22 (d, J=46.4 Hz, 2H), 4.04 (d, J=4.8 Hz, 2H), 3.92 (s, 4H), 3.74-3.47 (m, 7H), 3.12 (s, 4H).

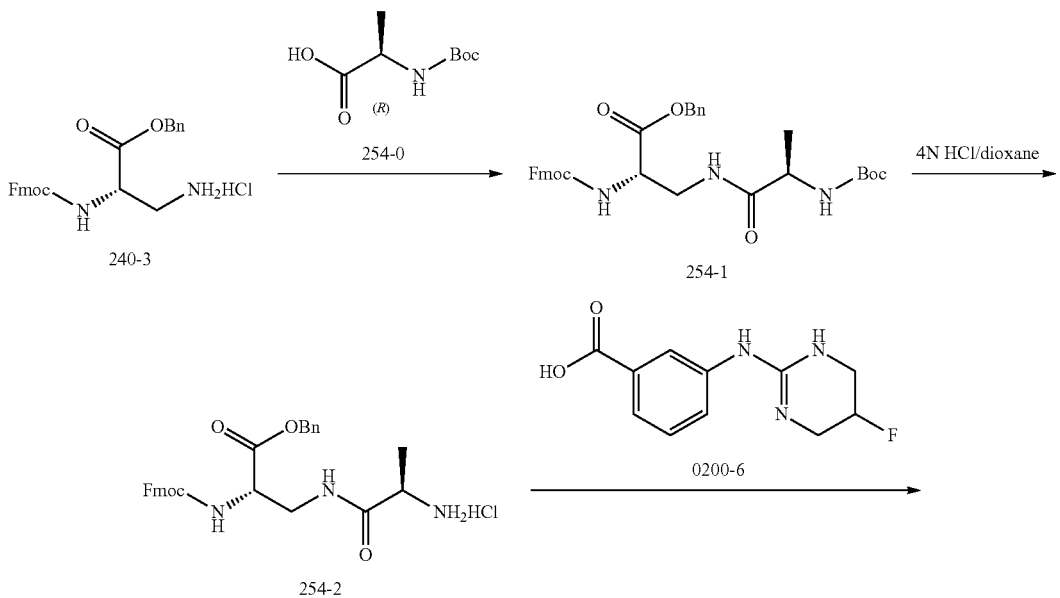

-continued

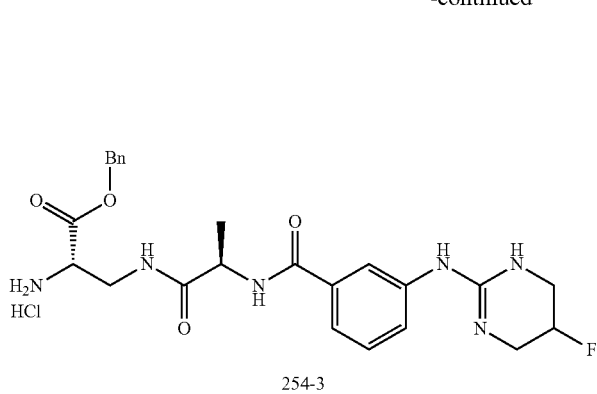

254-3

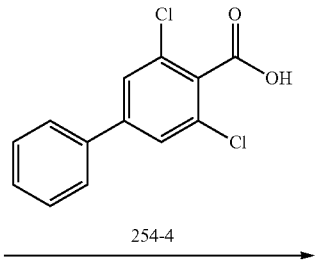

→ 254-4

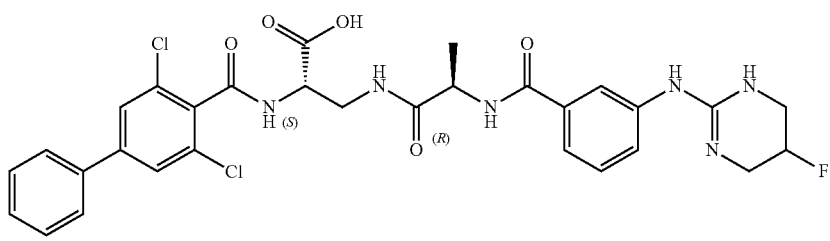

SU15210-0254

The Synthesis of benzyl (2S)-3-[[(2R)-2-(tert-butoxycarbonylamino)propanoyl]amino]-2-(9H-fluoren-9-ylmethoxycarbonylamino)propanoate (254-1)

The Synthesis of benzyl (2S)-3-[[(2R)-2-aminopropanoyl]amino]-2-(9H-fluoren-9-ylmethoxycarbonylamino)propanoate hydrochloride (254-2)

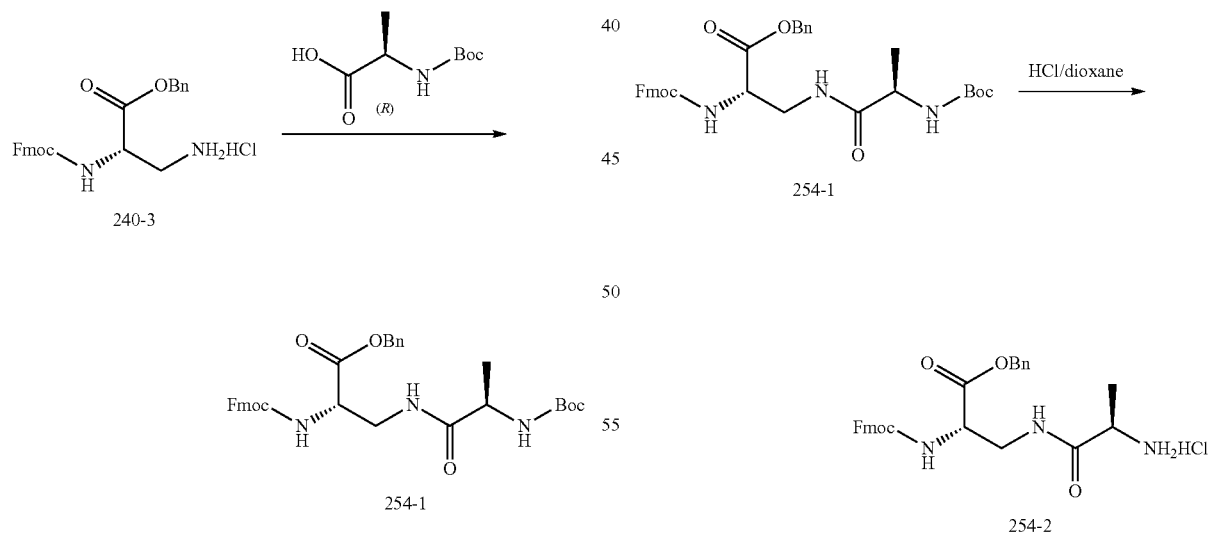

Benzyl (2S)-3-amino-2-(9H-fluoren-9-ylmethoxycarbonylamino) propanoate hydrochloride (4 g, 8.83 mmol) was added to a solution of (2R)-2-(tert-butoxycarbonylamino) propanoic acid (208.87 mg, 1.10 mmol), HATU (839.49 mg, 2.21 mmol) and DIPEA (428.01 mg, 3.31 mmol, 576.84 uL) in DMF (20 mL). After stirring at rt for 2 h, the reaction mixture was purified by CC (PE:EA=3:1) to afford 254-1 (4.9 g, 72.7% yield) as a white solid.

A solution of benzyl (2S)-3-[[(2R)-2-(tert-butoxycarbonylamino) propanoyl]amino]-2-(9H-fluoren-9-ylmethoxycarbonylamino) propanoate (4.9 g, 8.34 mmol) in 10 mL 4 N HCl/dioxane was stirred at rt for 16 h. Then the reaction mixture was filtered and the solid material was dried to afford 254-2 (4.1 g, 93.8% yield) as a white solid.

The Synthesis of benzyl (2S)-2-amino-3-[[(2R)-2-[[3-[(5-fluoro-1,4,5,6-tetrahydropyrimidin-2-yl)amino]benzoyl]amino]propanoyl]amino]propanoate hydrochloride (254-3)

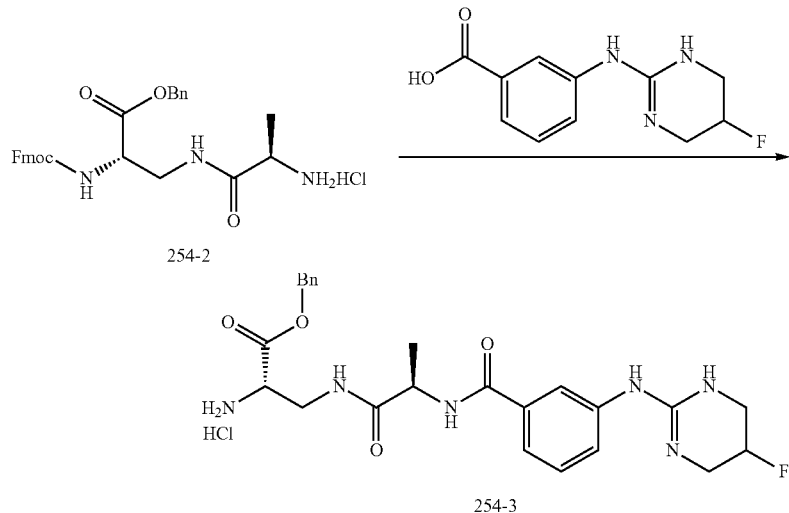

A mixture of 3-[(5-fluoro-1,4,5,6-tetrahydropyrimidin-2-yl)amino]benzoic acid (452.72 mg, 1.91 mmol) and SOCl$_2$ (190.84 mmol) was reflux under nitrogen atmosphere for 3 h then concentrated in vacuo to remove the residual SOCl$_2$. Then this residue was added to a solution of benzyl (2S)-3-[[(2R)-2-aminopropanoyl]amino]-2-(9H-fluoren-9-yl-methoxycarbonylamino)propanoate hydrochloride (1 g, 1.91 mmol) and TEA (965.54 mg, 9.54 mmol, 1.33 mL) in DCM (30 mL). After stirring at RT for 3 h, the reaction mixture was washed with 100 mL water twice, concentrated and purified by prep-HPLC to afford 254-3 (400 mg, 43.3% yield) as a white solid.

The Synthesis of (2S)-2-[(2,6-dichloro-4-phenyl-benzoyl)amino]-3-[[(2R)-2-[[3-[(5-fluoro-1,4,5,6-tetrahydropyrimidin-2-yl)amino]benzoyl]amino]propanoyl]amino]propanoic acid (SU15210-0254)

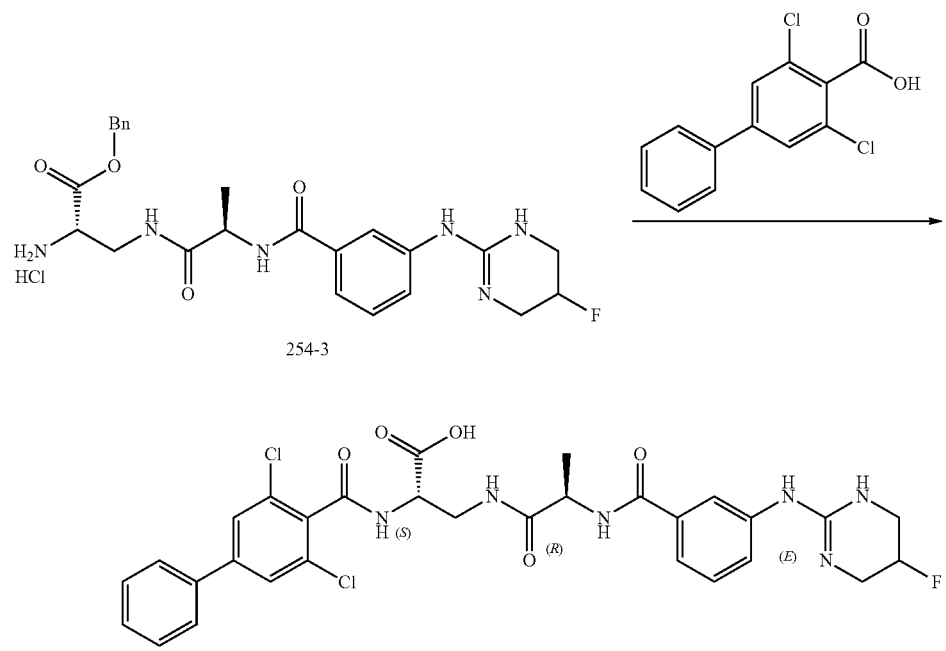

A mixture of 2,6-dichloro-4-phenyl-benzoic acid (55.13 mg, 206.39 umol) and SOCl$_2$ (41.28 mmol) was reflux under nitrogen atmosphere for 3 h and then concentrated in vacuo to remove the residual SOCl$_2$. Then this residue was added to a solution of benzyl (2S)-2-amino-3-[[(2R)-2-[[3-[(5-fluoro-1,4,5,6-tetrahydropyrimidin-2-yl)amino]benzoyl]amino]propanoyl]amino]propanoate hydrochloride (100 mg, 0.206 mmol) and TEA (104.42 mg, 1.03 mmol, 143.83 uL) in DCM (10 mL). After stirring at rt for 3 h, the reaction mixture concentrated in vacuo and purified by prep-HPLC to afford SU15210-0254 (7 mg, 5.2% yield) as a white solid.

$^1$H NMR (400 MHz, MeOD) δ 7.78 (d, J=7.1 Hz, 2H), 7.62 (d, J=6.5 Hz, 4H), 7.56-7.30 (m, 5H), 4.66-4.47 (m, 8H), 3.79-3.43 (m, 6H), 1.47 (d, J=7.2 Hz, 3H).

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min), Purity: 100%, Rt=1.810 min; MS Found: 642.7 [M+H]$^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 0.7 min), Purity: 98.84%, Rt=7.889 min.

Scheme: Route for SU15210-0255

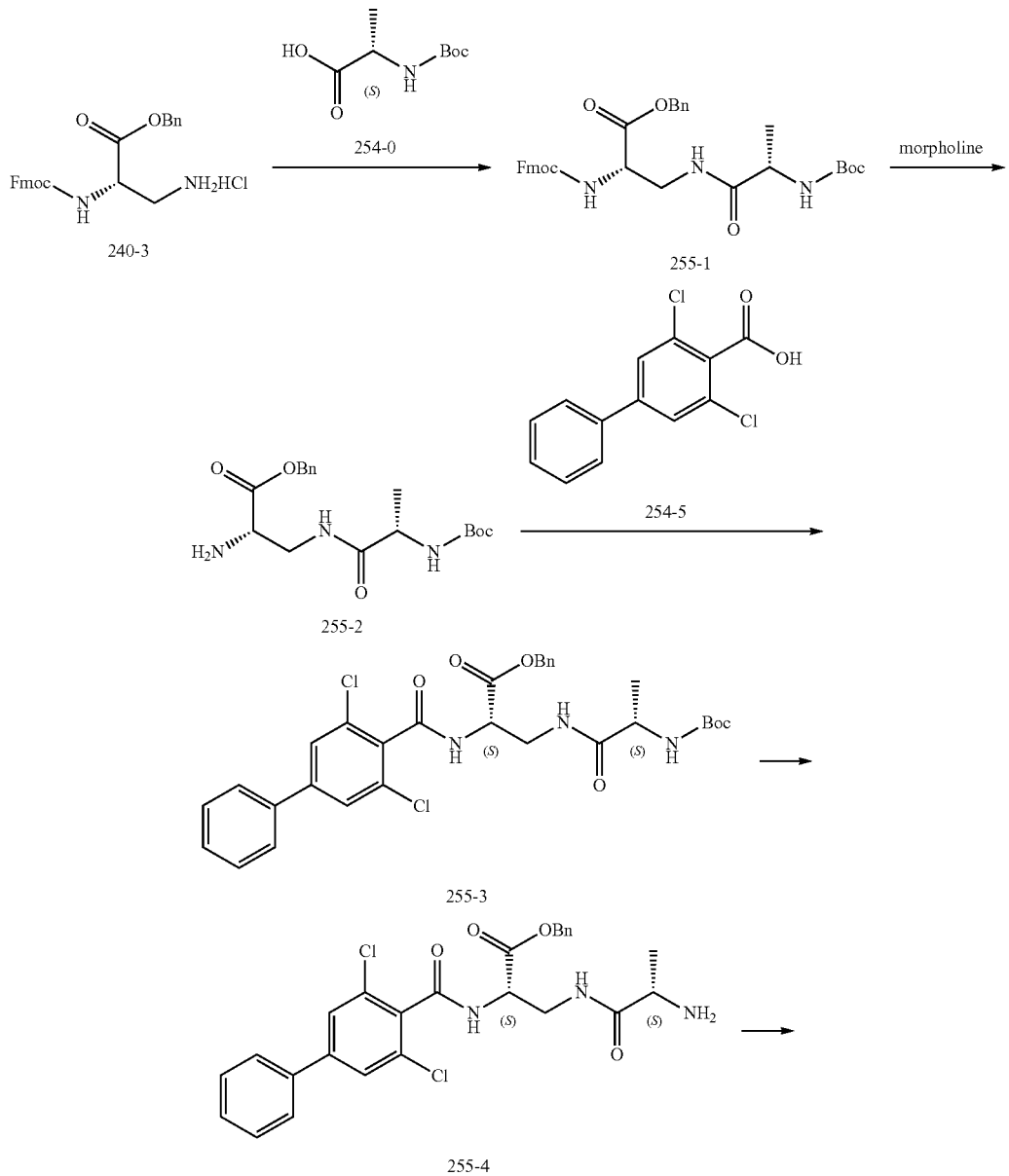

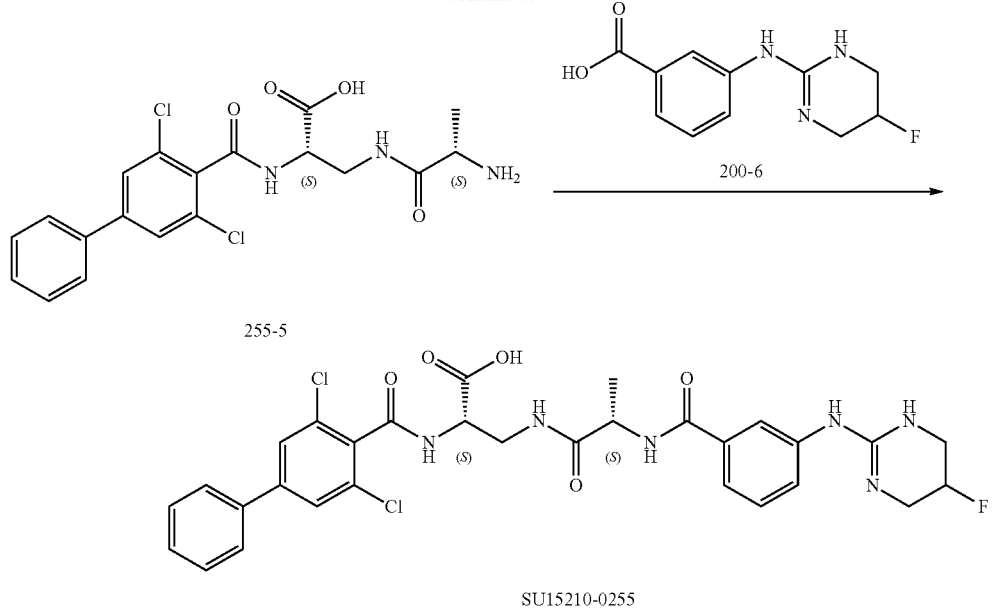

255-5

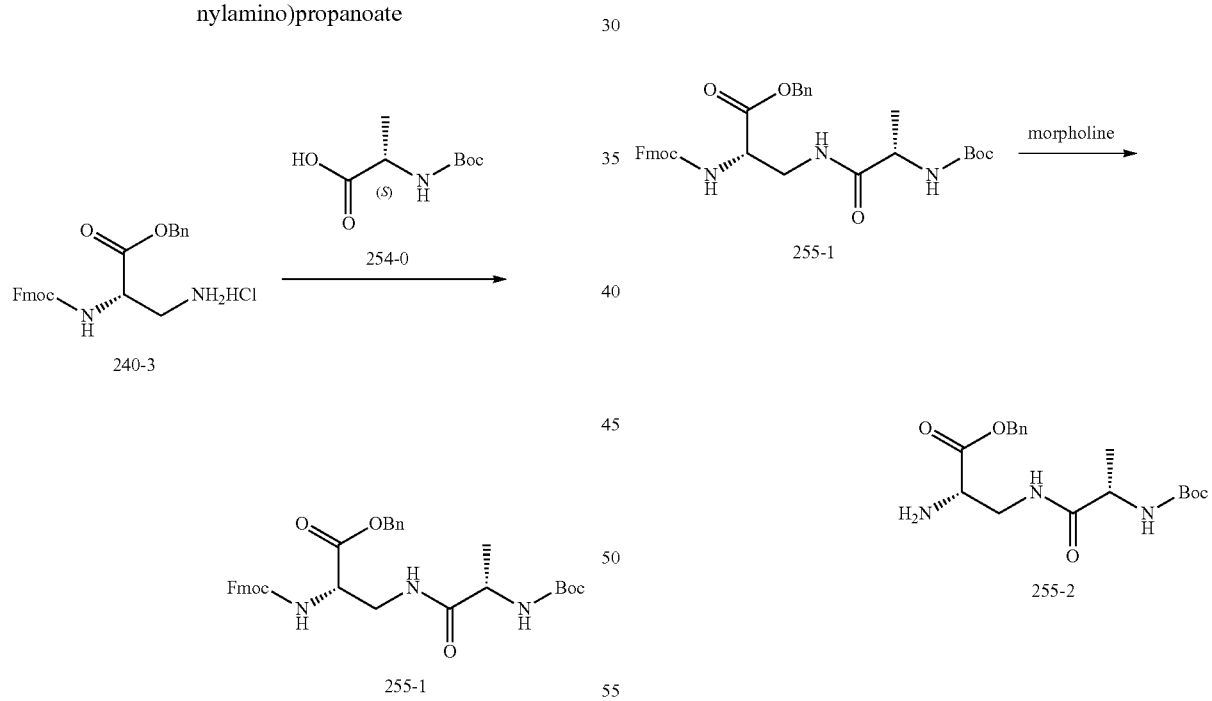

Benzyl (2S)-3-[[(2S)-2-(tert-butoxycarbonylamino)propanoyl]amino]-2-(9H-fluoren-9-ylmethoxycarbonylamino)propanoate (2S)-2-amino-3-[[(2S)-2-(tert-butoxycarbonylamino)propanoyl]amino]propanoate To a 100 mL round bottom flask, 240-3 (567 mg, 3.00 mmol), HATU (254.05 mg, 664.61 umol), DIPEA (429.47 mg, 3.32 mmol, 578.81 uL) in DMF was stirred at RT for 15 min, then 254-0 (1.13 g, 2.72 mmol) was added, the subsequent reaction mixture was stirred at RT overnight, then it was poured into water, and extracted with EA, dried with $Na_2SO_4$, concentrated to provide the crude oil, which was purified by silica gel column to afford 255-1 (1.38 g, 2.35 mmol, 424.00% yield) as a yellow solid.

A mixture of 255-1 (1.3 g, 2.21 mmol) and morpholine (6.50 g, 74.61 mmol, 6.53 mL) in DMF (25 mL) was stirred at RT for 30 min, LCMS showed that the starting material was consumed, then the reaction mixture was poured into water, extracted with EA, dried with $Na_2SO_4$, concentrated to give a crude yellow oil which was purified by silica gel column to afford 255-2 (730 mg, 2.00 mmol, 90.30% yield).

(S)-benzyl 3-((S)-2-(tert-butoxycarbonylamino)propanamido)-2-(3,5-dichlorobiphenyl-4-ylcarboxamido)propanoate (255-3)

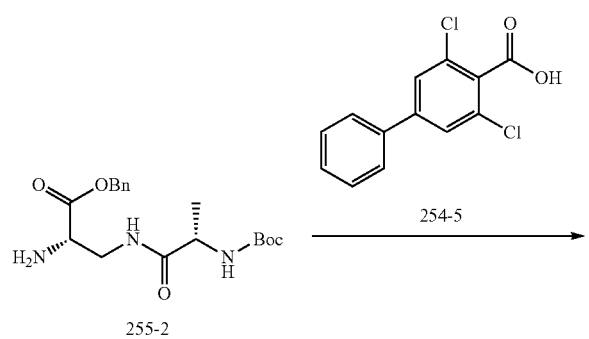

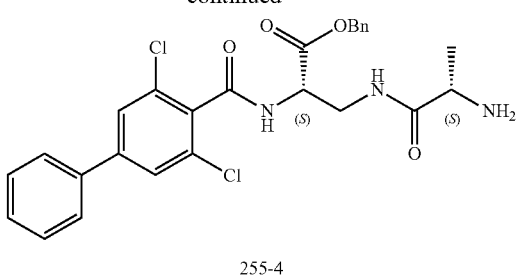

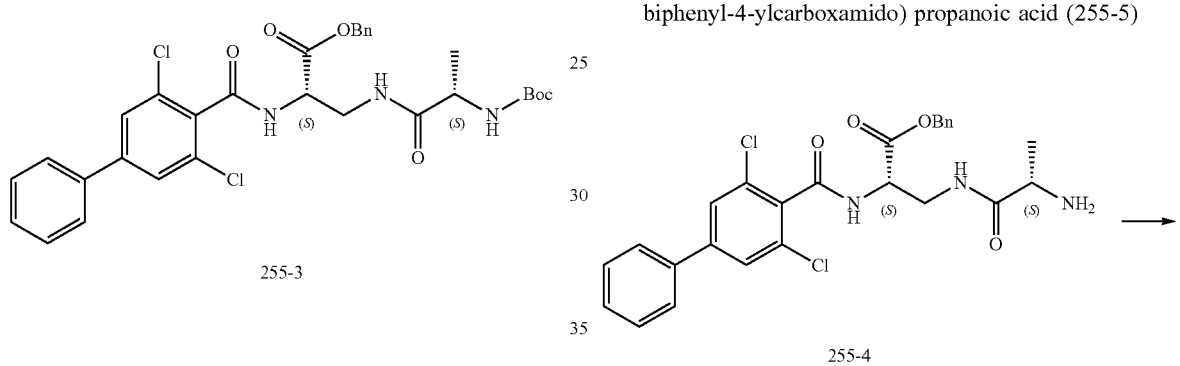

To a 50 mL one neck round bottom flask, 254-5 (445.88 mg, 1.67 mmol), HATU (957.12 mg, 2.50 mmol) and DIPEA (431.49 mg, 3.34 mmol, 581.52 uL) was added to DMF (5 mL), and the subsequent reaction mixture was stirred at RT for 1 h. Then 255-2 (610 mg, 1.67 mmol) was added. This reaction mixture stirred at RT overnight, then it was diluted with water, extracted with EA, dried with Na₂SO₄, and it was purified by silica gel column to afford 255-3 (600 mg, 951.60 umol, 57.01% yield).

4. (S)-benzyl 3-((S)-2-aminopropanamido)-2-(3,5-dichlorobiphenyl-4-ylcarboxamido) propanoate (255-4)

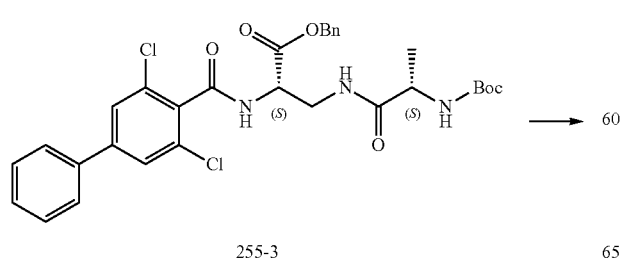

A mixture of 255-3 (580 mg, 919.88 umol) in HCl in 1,4-Dioxane (4 M) (20 mL) was stirred at RT overnight, LCMS showed that the starting material was consumed, then the solvent was removed in vacuo to afford the crude yellow oil 255-4 (320 mg, 603.32 umol, 65.59% yield), which was used in the next step without further purification.

5. (S)-3-((S)-2-aminopropanamido)-2-(3,5-dichlorobiphenyl-4-ylcarboxamido) propanoic acid (255-5)

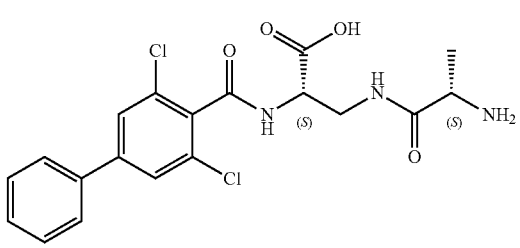

To a stirred solution of 255-4 (130 mg, 245.10 umol) in MeOH (2 mL), Pd/C (10%) (65.00 mg, 822.21 umol) was added, it was stirred at RT under hydrogen atmosphere (1 ATM) for 24 h, LCMS showed target product present and the reaction mixture was filtered and concentrated in vacuo. The crude product was purified by prep-HPLC to afford 255-5 (100 mg, 227.13 umol, 92.67% yield) as a white powder.

6. (2S)-2-(3,5-dichlorobiphenyl-4-ylcarboxamido)-3-((2S)-2-(3-(5-fluoro-1,4,5,6-tetrahydropyrimidin-2-ylamino)benzamido)propanamido)propanoic acid (SU15210-0255)

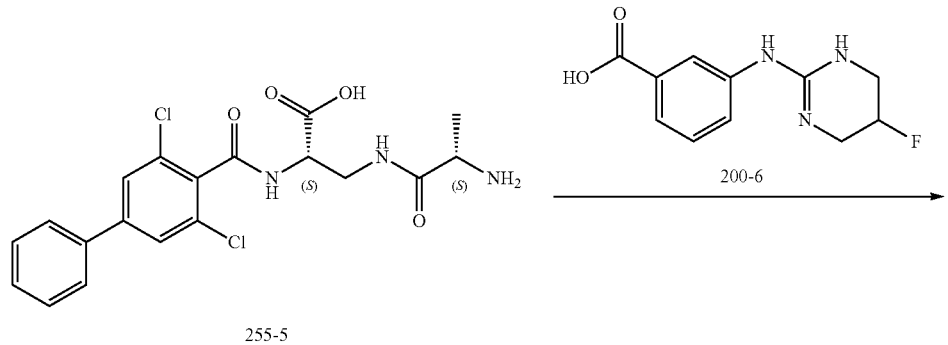

255-5

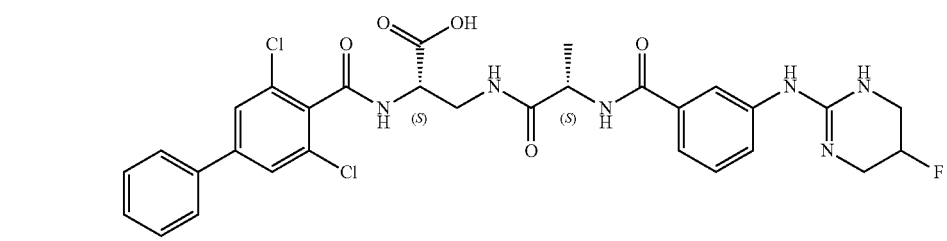

SU15210-0255

A 50 mL one neck round bottom flask was charged with 200-6 (30 mg, 126.46 umol), HATU (72.51 mg, 189.69 umol) and DIPEA (49.03 mg, 379.38 umol, 66.08 uL) and DMF (10 mL). The reaction mixture was stirred at 70° C. for 30 min until it was all solids completely dissolved, then 255-5 (40 mg, 90.85 umol) was added. The reaction mixture it was stirred at rt for 72 h, then filtered, and the filtrate was purified by prep-HPLC to afford SU15210-0255 (5 mg, 7.58 umol, 6.00% yield) as a white powder.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min), Purity: 100%, Rt=1.808 min; MS Found: 642.7 [M+H]$^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 0.7 min), Purity: 97.81%, Rt=7.927 min; MS Found: 642.7 [M+H]$^+$.

$^1$H NMR (400 MHz, MeOD) δ 7.71 (d, J=1.6 Hz, 2H), 7.58-7.52 (m, 4H), 7.37 (d, J=7.7 Hz, 5H), 5.06 (s, 1H), 4.50-4.44 (m, 7H), 3.59 (d, J=5.8 Hz, 6H), 1.39 (d, J=7.2 Hz, 3H).

Scheme: Route for SU15210-0269-01

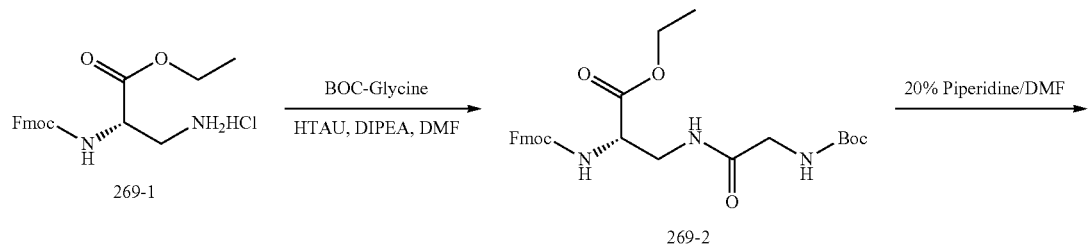

-continued
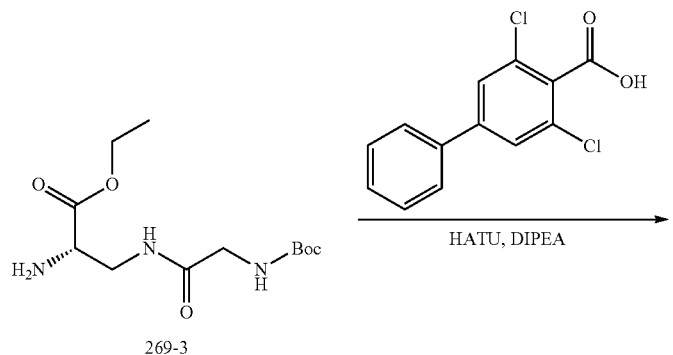
269-3
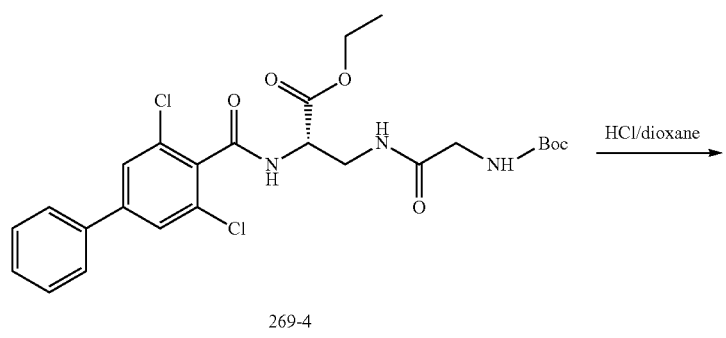
269-4
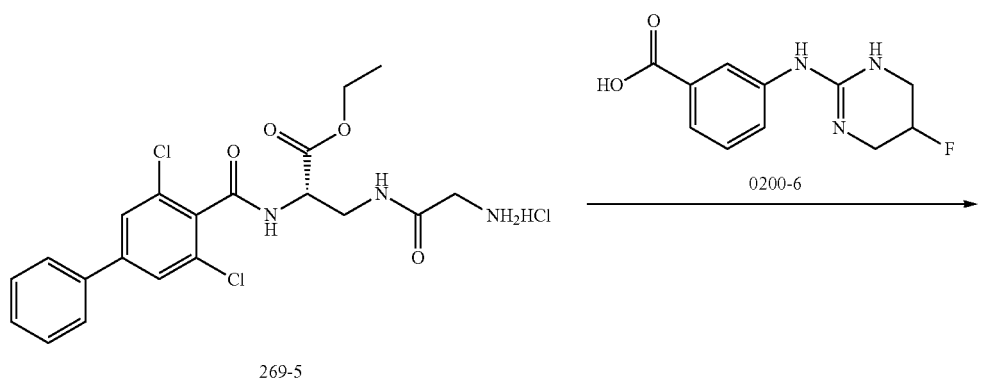
269-5
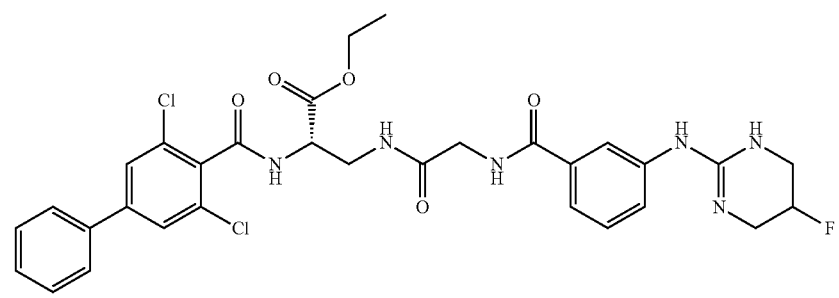
SU15210-0269-01

The Synthesis of (S)-ethyl 2-(((9H-fluoren-9-yl)methoxy)carbonylamino)-3-(2-(tert-butoxycarbonylamino)acetamido)propanoate (269-2)

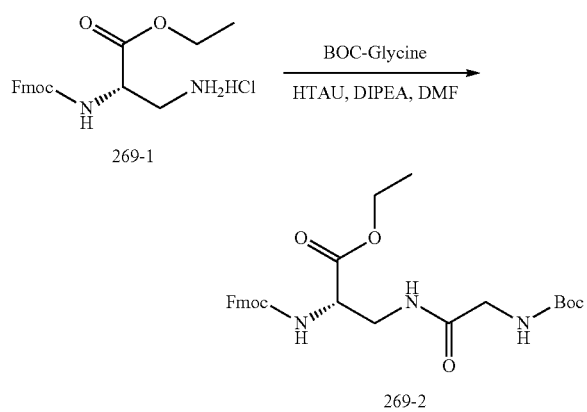

To a mixture of (S)-ethyl 2-(((9H-fluoren-9-yl) methoxy)carbonylamino)-3-aminopropanoate hydrochloride (1.5 g, 3.84 mmol) was added to a solution of 2-(tert-butoxycarbonylamino) acetic acid (672 mg, 3.84 mmol), HATU (2.19 g, 5.76 mmol) and DIPEA (1.49 g, 11.5 mmol) in DMF (25 mL). Then this reaction mixture was stirred at rt for 16 hr. It was then diluted with water, extracted with EA, dried with $Na_2SO_4$. The organic layer was purified by silica gel column (PE:EA=1:1) to afford 269-2 (1.5 g, 2.93 mmol, 76.40% yield) as a white solid.

The Synthesis of (S)-ethyl 2-amino-3-(2-(tert-butoxycarbonylamino) acetamido) propanoate (269-3)

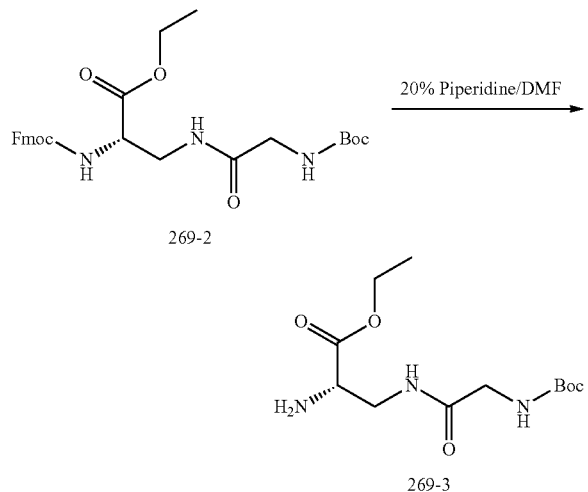

To a solution of ethyl (2S)-3-[[2-(tert-butoxycarbonylamino)acetyl]amino]-2-(9H-fluoren-9-ylmethoxycarbonylamino) propanoate (1.0 g, 1.95 mmol) in DMF (5 mL) was added morpholine (1 mL). The reaction was stirred at rt for 2 hr. Lyophilization and purification by silica gel column (DCM:MeOH=10:1) to afforded ethyl (2S)-2-amino-3-[[2-(tert-butoxycarbonylamino)acetyl]amino]propanoate (500 mg, 1.73 mmol, 88.41% yield) as a light yellow oil.

The Synthesis of (S)-ethyl 3-(2-(tert-butoxycarbonylamino)acetamido)-2-(3,5-dichlorobiphenyl-4-ylcarboxamido)propanoate (269-4)

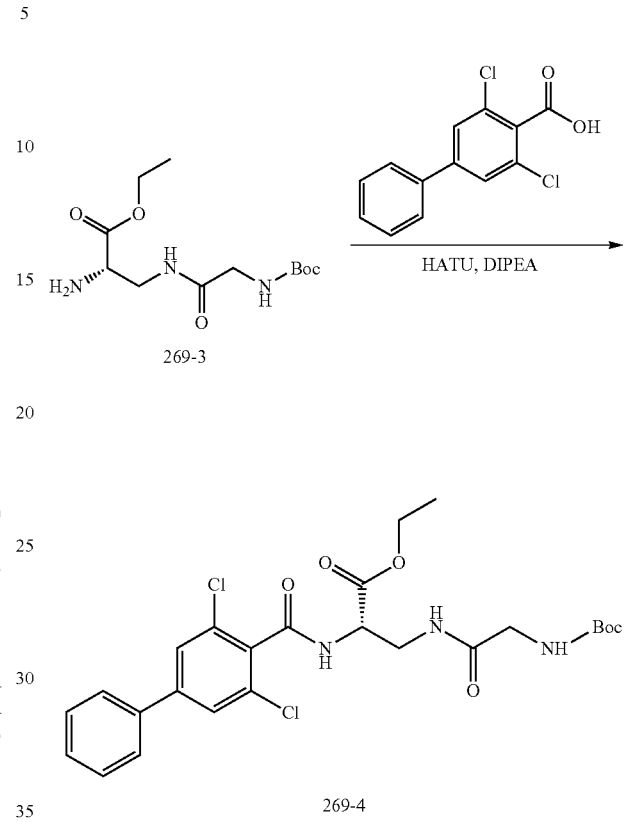

Ethyl (2S)-2-amino-3-[[2-(tert-butoxycarbonylamino)acetyl]amino]propanoate (324.96 mg, 1.12 mmol) was added to a solution of 2,6-dichloro-4-phenyl-benzoic acid (300 mg, 1.12 mmol), HATU (640.58 mg, 1.68 mmol) and DIPEA (435.47 mg, 3.37 mmol, 586.88 uL) in DMF (10 mL). After stirring at rt for 16 hr, 50 mL EA and 50 mL water was added. The organic layer was concentrated. The crude was purified by silica gel column (PE:EA=2:1) to afford ethyl (2S)-3-[[2-(tert-butoxycarbonylamino)acetyl]amino]-2-[(2,6-dichloro-4-phenyl-benzoyl)amino]propanoate (510 mg, 947.22 umol, 84.34% yield) as a light yellow oil.

The Synthesis of (S)-ethyl 3-(2-aminoacetamido)-2-(3,5-dichlorobiphenyl-4-ylcarboxamido)propanoate hydrochloride (269-5)

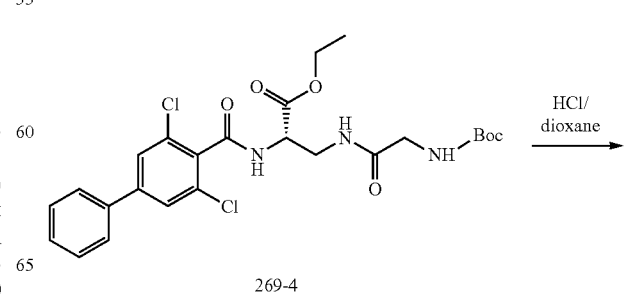

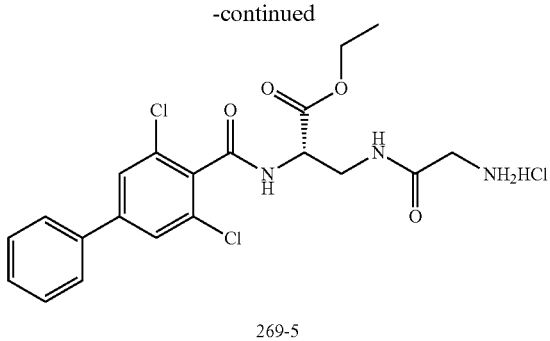

269-5

Ethyl (2S)-3-[[2-(tert-butoxycarbonylamino)acetyl]amino]-2-[(2,6-dichloro-4-phenyl-benzoyl)amino]propanoate (510 mg, 947.22 umol) was dissolved in 4 M HCl/dioxane (8 mL) and stirred at rt for 1 hr. The subsequent reaction mixture was concentrated to obtain (S)-ethyl 3-(2-aminoacetamido)-2-(3,5-dichlorobiphenyl-4-ylcarboxamido) propanoate hydrochloride (420 mg, 884.65 umol, 93.39% yield) as a light yellow solid.

The Synthesis of (2S)-ethyl 2-(3,5-dichlorobiphenyl-4-ylcarboxamido)-3-(2-(3-(5-fluoro-1,4,5,6-tetrahydropyrimidin-2-ylamino)benzamido)acetamido) propanoate (SU15210-0269-01)

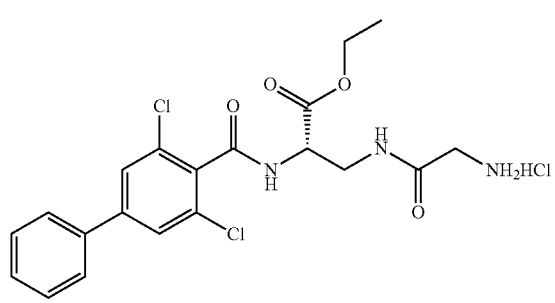

269-5

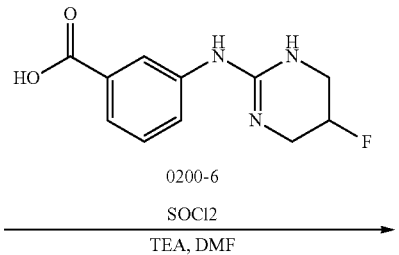

0200-6

→ SOCl2, TEA, DMF

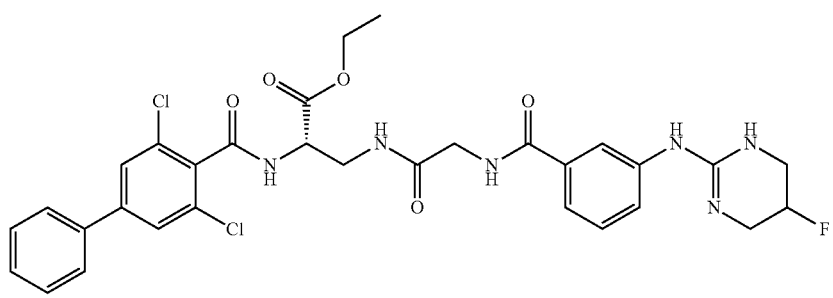

SU15210-0269-01

A mixture of 3-[(5-fluoro-1,4,5,6-tetrahydropyrimidin-2-yl)amino]benzoic acid (210 mg, 885.22 µmol) in SOCl₂ (8 mL) was heated and stirred at 80° C. for 2 hr. The reaction mixture was then concentrated to dryness and dissolved in 4 ml DMF. This mixture was added into the solution of (S)-ethyl 3-(2-aminoacetamido)-2-(3,5-dichlorobiphenyl-4-ylcarboxamido) propanoate hydrochloride (420 mg, 885.2 µmol) in 6 ml DMF. The subsequent reaction mixture was stirred at rt for 16 hr and was then concentrated in vacuo and purified by Prep-HPLC to give (2S)-ethyl 2-(3,5-dichlorobiphenyl-4-ylcarboxamido)-3-(2-(3-(5-fluoro-1, 4, 5, 6-tetrahydropyrimidin-2-ylamino)benzamido)acetamido) propanoate (31.75 mg, 47.15 µmol, 5.33% yield) as a white solid.

LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min), Purity: 100%, Rt=2.027 min; MS Found: 656.7 $[M+H]^+$.

HPLC (Agilent LCMS 1200-6120, Column: Waters X-Bridge C18 (150 mm*4.6 mm*3.5 µm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 0.7 min), Purity: 96.07%, Rt=7.767 min.

¹H NMR (400 MHz, DMSO) δ 7.70-7.56 (m, 6H), 7.52-7.39 (m, 4H), 7.26 (d, J=6.6 Hz, 1H), 5.08 (d, J=47.4 Hz, 1H), 4.29-4.16 (m, 2H), 4.06 (dt, J=23.2, 9.0 Hz, 2H), 3.84-3.74 (m, 1H), 3.68 (dd, J=13.8, 7.1 Hz, 1H), 3.64-3.46 (m, 4H), 3.46-3.38 (m, 1H), 1.32 (d, J=7.1 Hz, 3H).

Scheme: Route for SU15210-0271-01
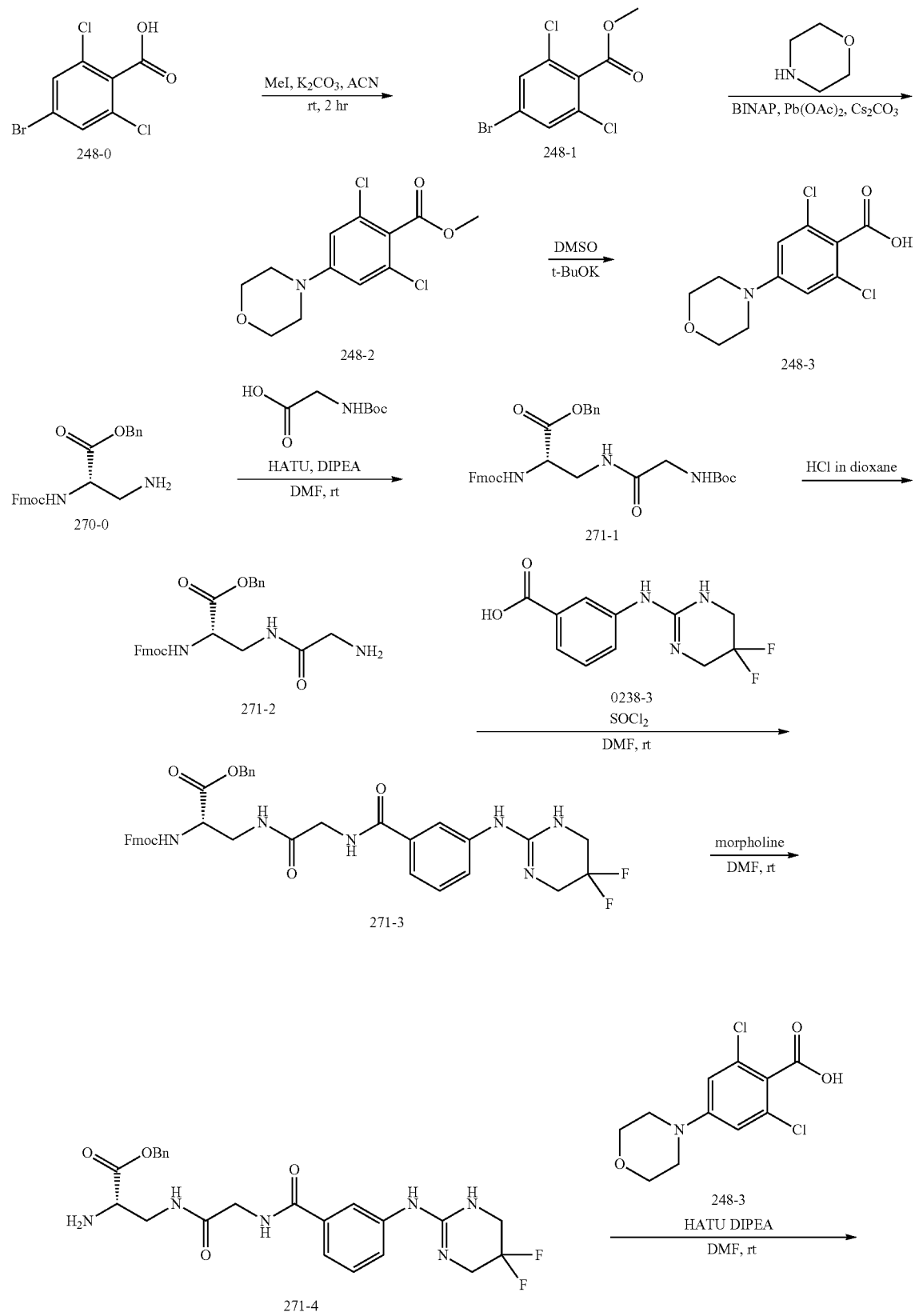

-continued

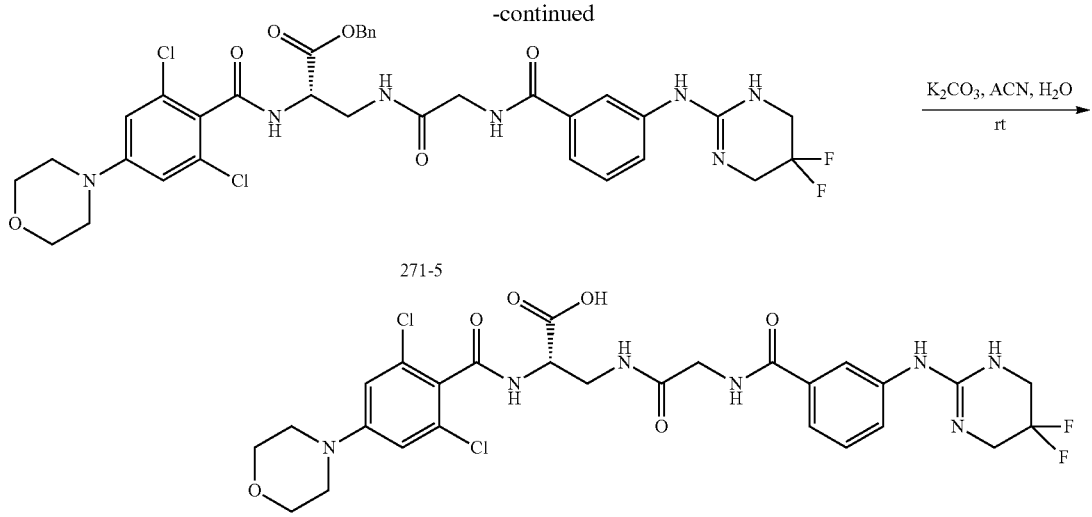

271-5

SU15210-0271-01

The Synthesis of methyl 4-bromo-2,6-dichlorobenzoate (248-1)

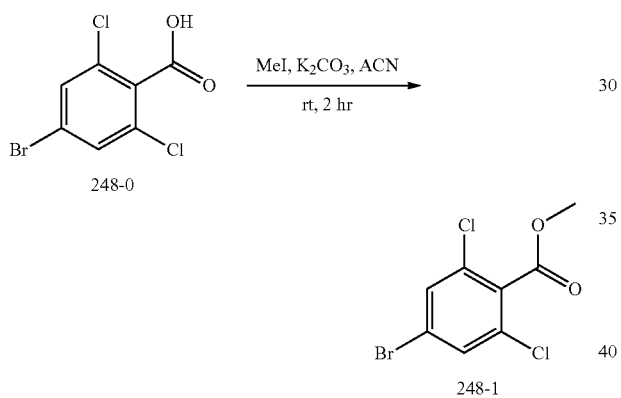

To a 100 mL round bottom flask, the mixture of 4-bromo-2,6-dichloro-benzoic acid (500 mg, 1.85 mmol), iodomethane (788 mg, 5.55 mmol), potassium carbonate (511 mg, 3.7 mmol) in acetonitrile (20 mL) was stirred at RT for 2 hr, then the reaction mixture was diluted with water, extracted with EA, dried with Na$_2$SO$_4$. Subsequent in vacuo concentration and purification by silica gel column (PE:EA=10:1) to afford methyl 4-bromo-2,6-dichloro-benzoate (380 mg, 1.34 mmol, 72.34% yield) as light yellow oil.

The Synthesis of methyl 2,6-dichloro-4-morpholinobenzoate (248-2)

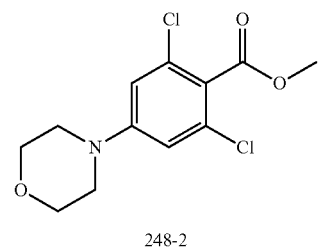

248-2

Methyl 4-bromo-2,6-dichloro-benzoate (380 mg, 1.34 mmol), diacetoxypalladium (30 mg, 134 umol), Binap (83 mg, 134 umol), cesium carbonate (1.31 g, 4.02 mmol), morpholine (175 mg, 2.01 mmol) in toluene (20 mL) were added to a nitrogen-filled sealed high pressure tube, which was stirred at 100° C. overnight, TLC showed that the starting material was consumed. Then the reaction mixture was diluted with DCM, and washed with brine. The organic layer was concentrated and purified by silica gel column (PE:EA=10:1) to afford methyl 2,6-dichloro-4-morpholino-benzoate (240 mg, 827.18 umol, 61.73% yield) as a yellow powder.

The Synthesis of 2,6-dichloro-4-morpholinobenzoic acid (248-3)

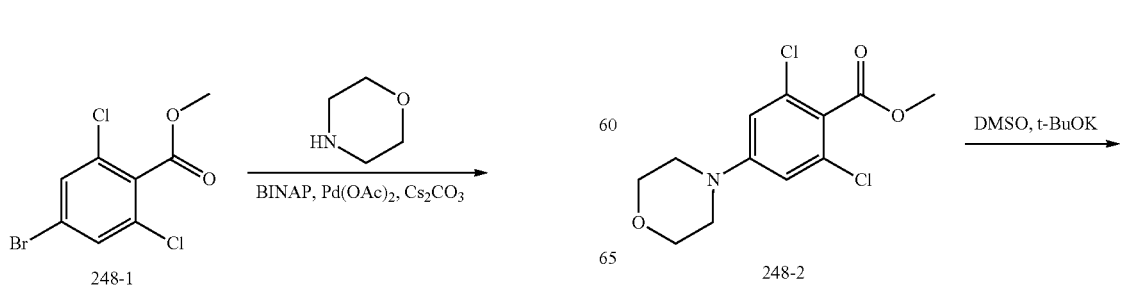

-continued

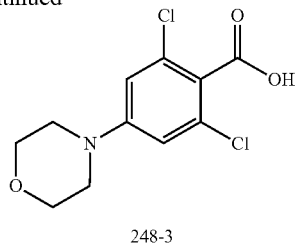

248-3

To a 50 mL 1-neck round bottom flask, a mixture of methyl 2,6-dichloro-4-morpholino-benzoate (240 mg, 827.18 umol), potassium tert-butoxide (278 mg, 2.48 mmol) in DMSO (6 mL) and water (2 mL) was stirred at 60° C. for 2 hr, TLC showed that the starting material was consumed, then the reaction mixture was diluted with water, extracted with EA, dried with $Na_2SO_4$, and concentrated to give 2,6-dichloro-4-morpholino-benzoic acid (90 mg, 325.95 umol, 39.4% yield) as a yellow solid which was used to next step without further purification.

The Synthesis of (R)-benzyl 1-(9H-fluoren-9-yl)-13,13-dimethyl-3,8,11-trioxo-2,12-dioxa-4,7,10-triazatetradecane-5-carboxylate (271-1)

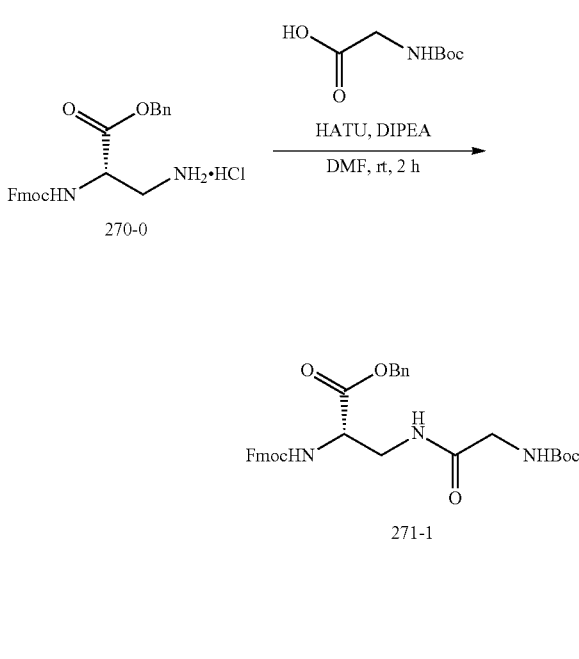

To a mixture of benzyl (2S)-3-amino-2-(9H-fluoren-9-ylmethoxycarbonylamino) propanoate hydrochloride (600 mg, 1.32 mmol) in DMF (5 mL) was added to a solution of 2-(tert-butoxycarbonylamino) acetic acid (232 mg, 1.32 mmol), HATU (1.01 g, 2.65 mmol) and DIPEA (514 mg, 3.17 mmol). Then the mixture was stirred at rt for 5 hr. It was diluted with water, extracted with EA, dried with $Na_2SO_4$. The organic layer was purified by silica gel column (PE: EA=3:1) to afford 271-1 (650 mg, 1.13 mmol, 85.54% yield) as a light-yellow solid.

The Synthesis of benzyl (2S)-3-[(2-aminoacetyl)amino]-2-(9H-fluoren-9-ylmethoxy carbonylamino) propanoate hydrochloride (271-2)

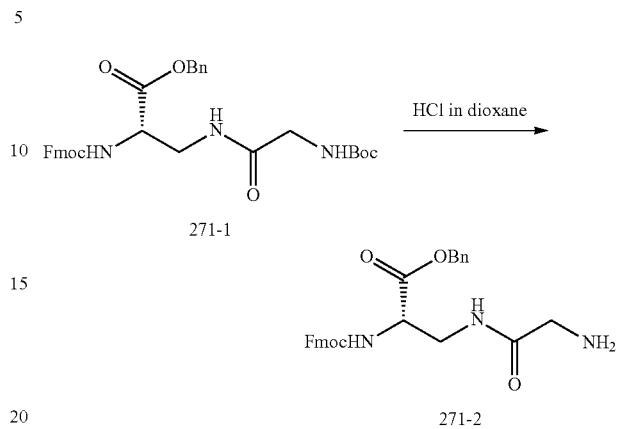

The solution of benzyl (2S)-3-[[2-(tert-butoxycarbonylamino)acetyl]amino]-2-(9H-fluoren-9-ylmethoxycarbonylamino)propanoate (650 mg, 1.13 mmol) in 3 mL 4 N HCl/dioxane was stirred at rt for 2 h. Then the reaction mixture was concentrated to dryness to afford 0271-2 (600 mg, 1.27 mmol, 100% yield) as a yellow solid.

The Synthesis of (R)-benzyl 11-(3-(5,5-difluoro-1,4,5,6-tetrahydropyrimidin-2-ylamino)phenyl)-1-(9H-fluoren-9-yl)-3,8,11-trioxo-2-oxa-4,7,10-triazaundecane-5-carboxylate (272-3)

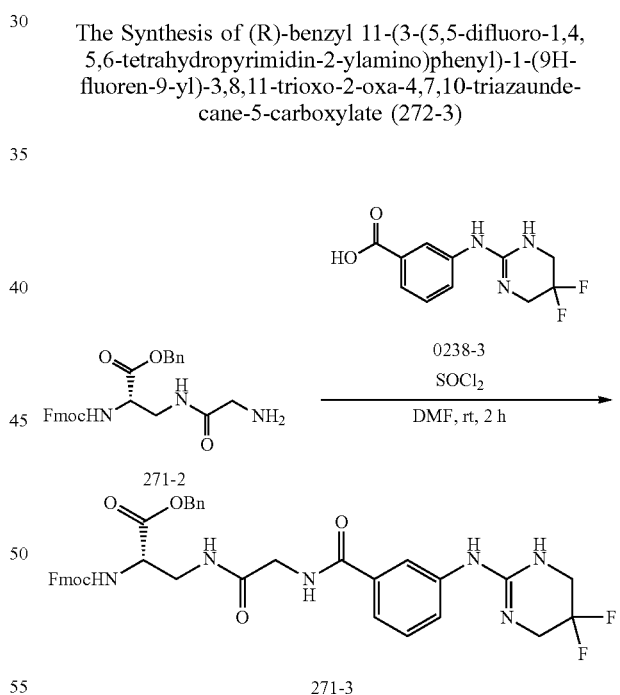

A mixture of 3-(5,5-difluoro-1,4,5,6-tetrahydropyrimidin-2-ylamino) benzoic acid (50 mg, 195.9 umol) in $SOCl_2$ (5 mL) was reflux under nitrogen atmosphere for 2 h. Then the reaction mixture was concentrated to remove $SOCl_2$. The residue was diluted with TEA (79.3 mg, 783.6 umol) and DCM (5 mL). Then benzyl (2S)-3-[(2-aminoacetyl)amino]-2-(9H-fluoren-9-ylmethoxycarbonylamino)propanoate (92.77 mg, 195.9 umol). The mixture was stirred at rt for 16 hr. The reaction mixture was concentrated to afford 271-3 (150 mg) as a crude solid.

The Synthesis of (S)-benzyl 2-amino-3-(2-(3-(5,5-difluoro-1,4,5,6-tetrahydropyrimidin-2-ylamino)benzamido)acetamido)propanoate (271-4)

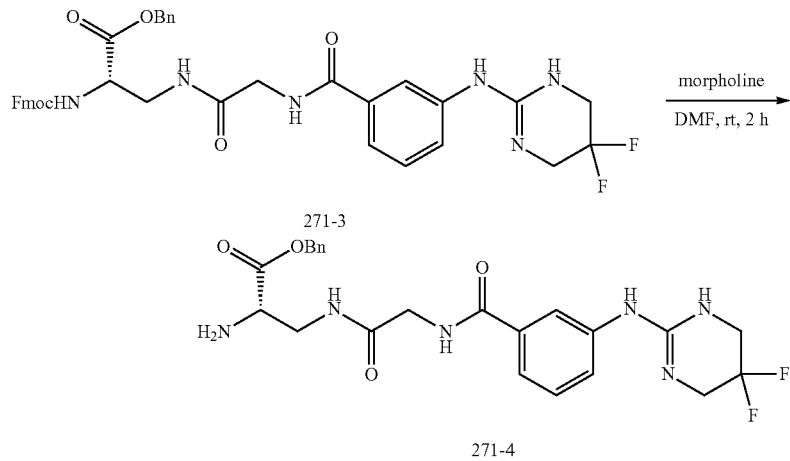

A mixture of benzyl (R)-benzyl 11-(3-(5,5-difluoro-1,4,5,6-tetrahydropyrimidin-2-yl amino)phenyl)-1-(9H-fluoren-9-yl)-3,8,11-tri oxo-2-oxa-4,7,10-triazaundecane-5-carboxylate (150 mg, 211 umol) and 0.2 ml morpholine in 2 ml DMF was stirred at rt for 0.5 hr. The reaction mixture was purified by prep-HPLC to afford 271-4 (42 mg, 85.98 umol, 40.7% yield) as a white solid.

The Synthesis of (S)-benzyl 2-(2,6-dichloro-4-morpholinobenzamido)-3-(2-(3-(5,5-difluoro-1,4,5,6-tetrahydropyrimidin-2-ylamino)benzamido)acetamido)propanoate (271-5)

Benzyl (2 S)-2-amino-3-[[2-[[3-[(5-fluoro-1,4,5,6-tetrahydropyrimidin-2-yl)amino]benzoyl]amino]acetyl]amino]propanoate (10 mg, 20.5 umol) was added to a mixture of 2,6-dichloro-4-(4-methoxyphenyl) benzoic acid (5.7 mg, 20.5 umol), HATU (8.6 mg, 22.5 umol), DIPEA (7.9 mg, 61.4 umol) in DMF (2 mL). Afterwards, the reaction mixture was stirred at rt for 5 h before it was diluted with water, extracted with EA, dried with $Na_2SO_4$. Then the crude product was purified by Prep-TLC (DCM:MeOH=6:1) to afford (S)-benzyl 2-(2,6-dichloro-4-morpholinobenzamido)-3-(2-(3-(5,5-difluoro-1,4,5,6-tetrahydropyrimidin-2-ylamino)benzamido)acetamido)propanoate (5 mg, 6.70 umol, 32.71% yield).

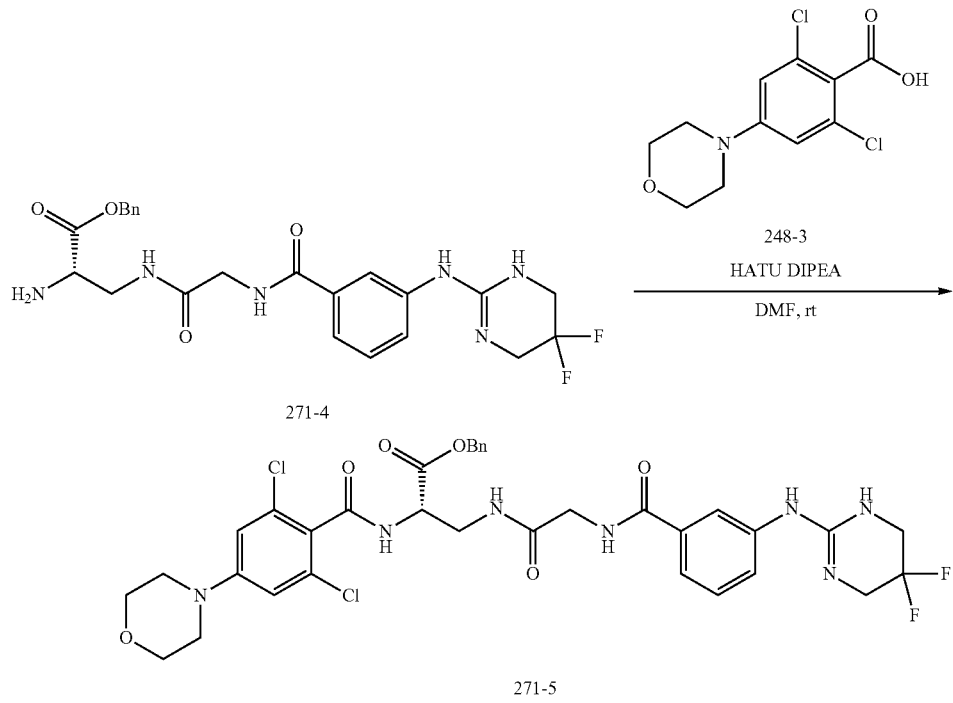

The Synthesis of (S)-2-(2,6-dichloro-4-morpholino-benzamido)-3-(2-(3-(5,5-difluoro-1,4,5,6-tetrahydro-pyrimidin-2-ylamino)benzamido)acetamido) propanoic acid (SU15210-0271-01)

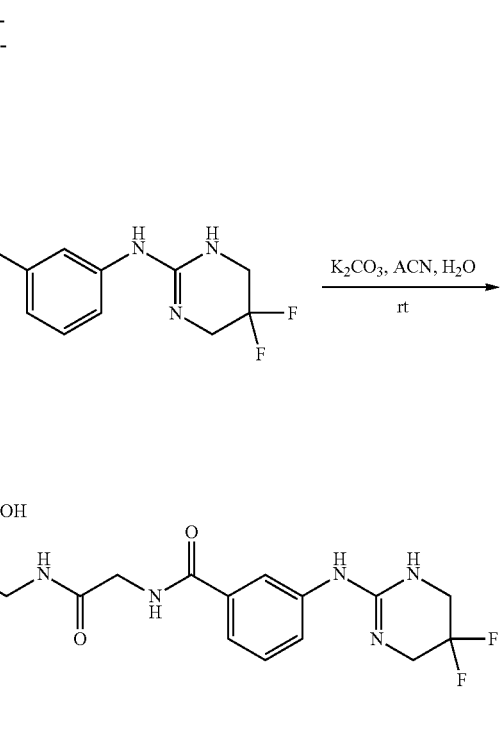

To a solution of compound 271-5 (8 mg, 10.7 umol) in ACN (2 mL) was added H₂O (0.2 mL) and K₂CO₃ (74 mg, 536 umol). The mixture was allowed to stir at rt for 2 hr. It was purified by pre-HPLC to give product SU521-0271-01 (1.57 mg, 2.39 umol, 22.32% yield) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min), Purity: 93.96%, Rt=1.360 min; MS Found: 655.8 [M+H]⁺.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 0.7 min), Purity: 92.09%, Rt=7.598 min.

¹H NMR (400 MHz, MeOD) δ 7.89-7.75 (m, 2H), 7.57 (t, J=7.9 Hz, 1H), 7.44 (d, J=8.0 Hz, 1H), 6.93 (s, 2H), 5.34 (t, J=4.6 Hz, 1H), 4.60 (s, 2H), 4.14-3.92 (m, 2H), 3.85-3.77 (m, 5H), 3.75 (s, 2H), 3.72 (s, 1H), 3.70-3.63 (m, 2H), 3.24-3.15 (m, 4H).

Scheme: Route for SU15210-0272-01

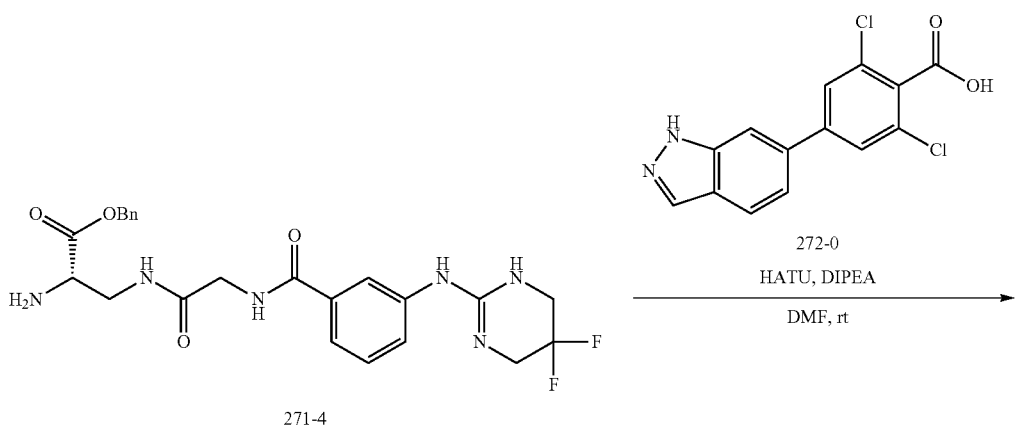

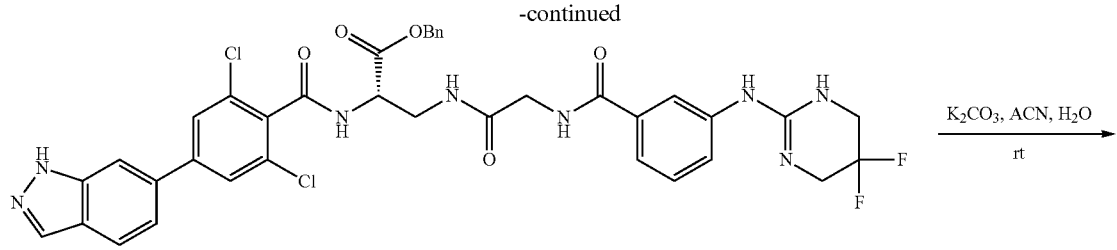

272-1

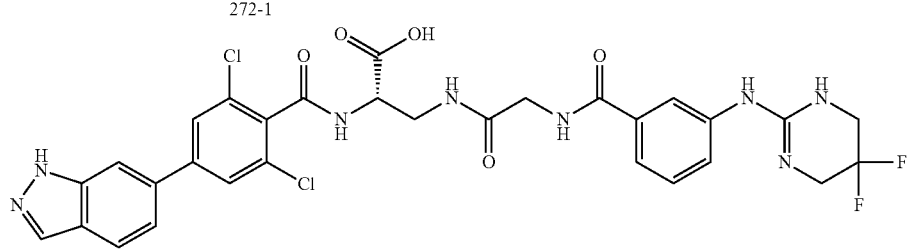

SU15210-0272-01

The Synthesis of (S)-benzyl 2-(2,6-dichloro-4-(1H-indazol-6-yl)benzamido)-3-(2-(3-(5,5-difluoro-1,4,5,6-tetrahydropyrimidin-2-ylamino)benzamido)acetamido)propanoate (272-1)

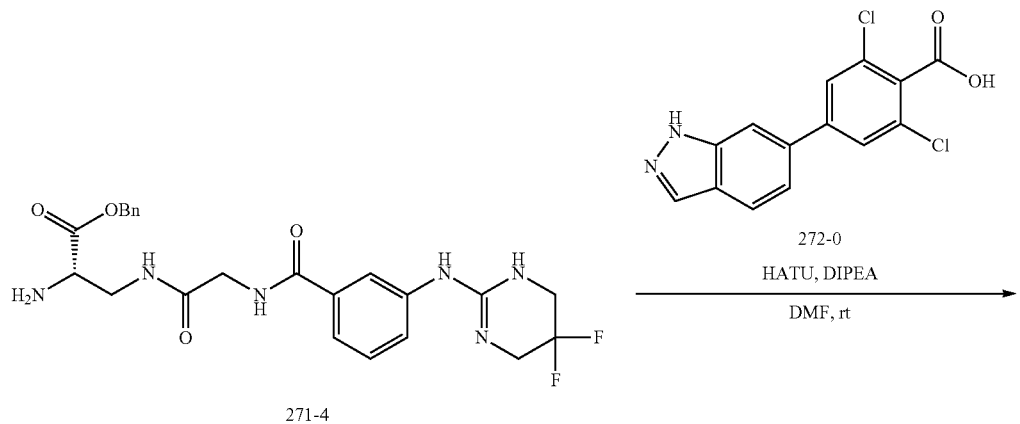

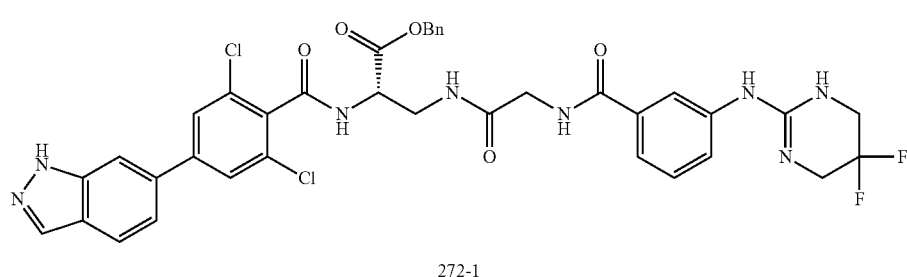

272-1

To Benzyl(2S)-2-amino-3-[[2-[[3-[(5-fluoro-1,4,5,6-tetrahydropyrimidin-2-yl) amino]benzoyl]amino]acetyl]amino]propanoate (15.9 mg, 32.56 umol) was added to a mixture of 2,6-dichloro-4-(4-methoxyphenyl) benzoic acid (10 mg, 32.56 umol), HATU (13.6 mg, 35.8 umol), DIPEA (12.6 mg, 97.7 umol) in DMF (1 mL). After stirring at rt for 2 h, the reaction mixture was diluted with water, extracted with EA, dried with $Na_2SO_4$. Then the crude product was purified by Prep-TLC (DCM:MeOH=6:1) to afford (S)-benzyl2-(2,6-dichloro-4-morpholinobenzamido)-3-(2-(3-(5,5-difluoro-1,4,5,6-tetrahydropyrimidin-2-ylamino)benzamido)acetamido)propanoate (9 mg, 11.6 umol, 35.55% yield) as a light yellow solid.

The Synthesis of (S)-2-(2,6-dichloro-4-(1H-indazol-6-yl)benzamido)-3-(2-(3-(5,5-difluoro-1,4,5,6-tetrahydropyrimidin-2-ylamino)benzamido)acetamido)propanoic acid (SU15210-0272-01)

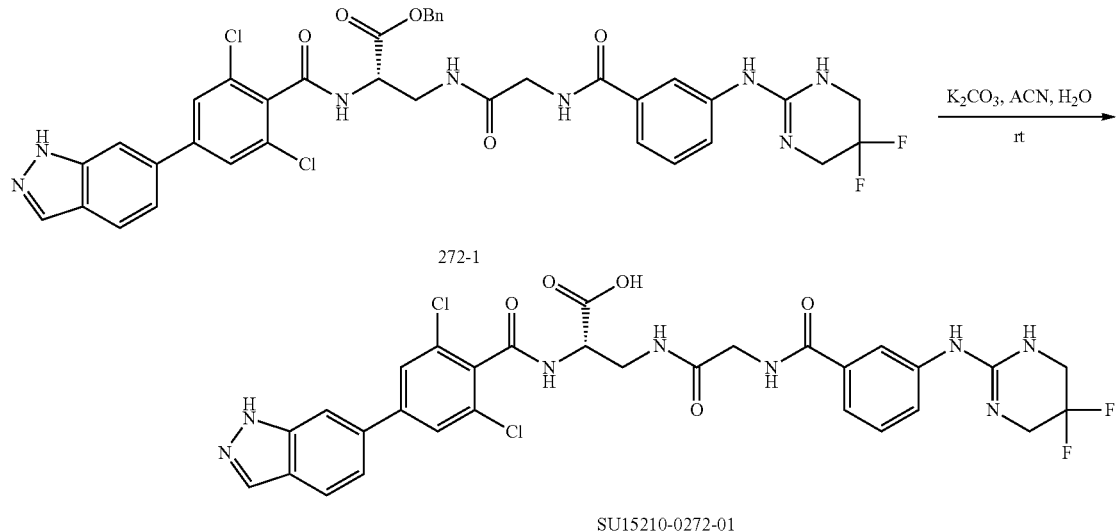

To a solution of compound 272-1 (9 mg, 11.6 umol) in ACN (2 mL) was added H$_2$O (0.5 mL) and K$_2$CO$_3$ (48 mg, 347.2 umol). The mixture was allowed to stir at rt for 2 hr before it was purified by pre-HPLC to give product SU521-0272-01 (3.03 mg, 4.41 umol, 38.07% yield) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min), Purity: 97.11%, Rt=1.666 min; MS Found: 686.7 [M+H]$^+$.

HPLC (Agilent LCMS 1200-6120, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 0.7 min), Purity: 96.57%, Rt=7.512 min.

$^1$H NMR (400 MHz, MeOD) δ 8.09 (d, J=0.8 Hz, 1H), 7.88 (d, J=8.5 Hz, 1H), 7.84-7.77 (m, 3H), 7.72 (d, J=6.0 Hz, 2H), 7.54 (t, J=8.1 Hz, 1H), 7.41 (ddd, J=8.0, 3.5, 1.3 Hz, 2H), 5.34 (t, J=4.6 Hz, 1H), 4.60 (d, J=5.9 Hz, 2H), 4.06 (q, J=16.7 Hz, 2H), 3.81-3.66 (m, 6H).

The section headings used herein are for organizational purposes only and are not to be construed as limiting the subject matter described. All documents, or portions of documents, cited in the application are hereby expressly incorporated by reference in their entirety for any purpose.

While various embodiments and aspects are shown and described herein, it will be obvious to those skilled in the art that such embodiments and aspects are provided by way of example only. Numerous variations, changes, and substitutions will now occur to those skilled in the art. Various alternatives to the embodiments and aspects described herein may be used.

What is claimed is:

1. A compound of Formula (I) or a pharmaceutically acceptable salt thereof:

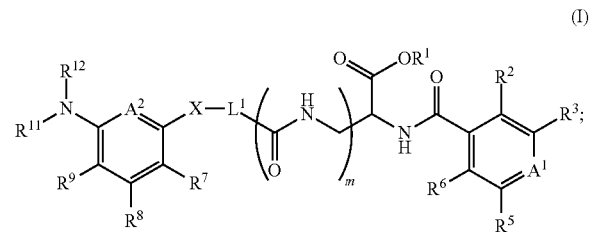

wherein:
m is 1 or 2;
A$^1$ is C(R$^4$) or N;
A$^2$ is C(R$^{10}$) or N;
X is a bond, —C(R$^{15}$)(R$^{16}$)— or —N(R$^{15}$)—;
L$^1$ is bond, —C(O)—, —C(O)O—, —O—, —S—, —NH—, —C(O)NH—, —NHC(O)—, —S(O)$_2$—, —S(O)NH—, —(CH$_2$)$_{z1}$—NH—, —(CH$_2$)$_{z3}$—N((CH$_2$)$_{z4}$CH$_3$)—C(=O)—, L$^{11}$-substituted or unsubstituted alkylene, unsubstituted heteroalkylene, L$^{11}$-substituted or unsubstituted cycloalkylene, L$^{11}$-substituted or unsubstituted heterocycloalkylene, L$^{11}$-substituted or unsubstituted arylene, or L$^{11}$-substituted or unsubstituted heteroarylene;
L$^{11}$ is independently halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, unsubstituted alkyl, unsubstituted heteroalkyl, unsubstituted cycloalkyl, unsubstituted heterocycloalkyl, unsubstituted aryl, or unsubstituted heteroaryl;

R$^1$ is hydrogen, R$^{100}$-substituted or unsubstituted alkyl, R$^{100}$-substituted or unsubstituted heteroalkyl, R$^{100}$-substituted or unsubstituted cycloalkyl, or —[P(=O)(OH)O—]$_n$—H, where n is an integer from 1 to 3;

R$^{100}$ is independently halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, R$^{101}$-substituted or unsubstituted alkyl, R$^{101}$-substituted or unsubstituted heteroalkyl, R$^{101}$-substituted or unsubstituted cycloalkyl, R$^{101}$-substituted or unsubstituted heterocycloalkyl, R$^{101}$-substituted or unsubstituted aryl, or R$^{101}$-substituted or unsubstituted heteroaryl;

R$^{101}$ is independently halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, unsubstituted alkyl, unsubstituted heteroalkyl, unsubstituted cycloalkyl, unsubstituted heterocycloalkyl, unsubstituted aryl, or unsubstituted heteroaryl;

R$^2$ is hydrogen, halogen, —CX$^2$$_3$, —CHX$^2$$_2$, —CH$_2$X$^2$, —OCX$^2$$_3$, —OCH$_2$X$^2$, —OCHX$^2$$_2$, —SO$_{n2}$R$^{2A}$, —SO$_{v2}$NR$^{2A}$R$^{2B}$, —CN, —C(O)R$^{2A}$, —C(O)OR$^{2A}$, —C(O)NR$^{2A}$R$^{2B}$, —OR$^{2A}$, —ONR$^{2A}$R$^{2B}$, —NHC(O)NR$^{2A}$R$^{2B}$, —N(O)$_{m2}$, —NR$^{2A}$R$^{2B}$, —NHNR$^{2A}$R$^{2B}$, —NR$^{2A}$SO$_2$R$^{2B}$, —NR$^{2A}$C(O)R$^{2B}$, —NR$^{2A}$C(O)OR$^{2B}$, —NR$^{2A}$OR$^{2B}$, —N$_3$, R$^{200}$-substituted or unsubstituted alkyl, R$^{200}$-substituted or unsubstituted heteroalkyl, R$^{200}$-substituted or unsubstituted cycloalkyl, R$^{200}$-substituted or unsubstituted heterocycloalkyl, R$^{200}$-substituted or unsubstituted aryl, or R$^{200}$-substituted or unsubstituted heteroaryl;

R$^{2A}$ and R$^{2B}$ are independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, R$^{200}$-substituted or unsubstituted alkyl, R$^{200}$-substituted or unsubstituted heteroalkyl, R$^{200}$-substituted or unsubstituted cycloalkyl, R$^{200}$-substituted or unsubstituted heterocycloalkyl, R$^{200}$-substituted or unsubstituted aryl, or R$^{200}$-substituted or unsubstituted heteroaryl;

R$^{200}$ is independently halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, R$^{201}$-substituted or unsubstituted alkyl, R$^{201}$-substituted or unsubstituted heteroalkyl, R$^{201}$-substituted or unsubstituted cycloalkyl, R$^{201}$-substituted or unsubstituted heterocycloalkyl, R$^{201}$-substituted or unsubstituted aryl, or R$^{201}$-substituted or unsubstituted heteroaryl;

R$^{201}$ is independently halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, unsubstituted alkyl, unsubstituted heteroalkyl, unsubstituted cycloalkyl, unsubstituted heterocycloalkyl, unsubstituted aryl, or unsubstituted heteroaryl;

R$^3$ is hydrogen, halogen, —CX$^3$$_3$, —CHX$^3$$_2$, —CH$_2$X$^3$, —OCX$^3$$_3$, —OCH$_2$X$^3$, —OCHX$^3$$_2$, —SO$_{n3}$R$^{3A}$, —SO$_{v3}$NR$^{3A}$R$^{3B}$, —CN, —C(O)R$^{3A}$, —C(O)OR$^{3A}$, —C(O)NR$^{3A}$R$^{3B}$, —OR$^{3A}$, —ONR$^{3A}$R$^{3B}$, —NHC(O)NR$^{3A}$R$^{3B}$, —N(O)$_{m3}$, —NR$^{3A}$R$^{3B}$, —NHNR$^{3A}$R$^{3B}$, —NR$^{3A}$SO$_2$R$^{3B}$, —NR$^{3A}$C(O)R$^{3B}$, —NR$^{3A}$C(O)OR$^{3B}$, —NR$^{3A}$OR$^{3B}$, —N$_3$, R$^{300}$-substituted or unsubstituted alkyl, R$^{300}$-substituted or unsubstituted heteroalkyl, R$^{300}$-substituted or unsubstituted cycloalkyl, R$^{300}$-substituted or unsubstituted heterocycloalkyl, R$^{300}$-substituted or unsubstituted aryl, or R$^{300}$-substituted or unsubstituted heteroaryl;

R$^{3A}$ and R$^{3B}$ are independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, R$^{300}$-substituted or unsubstituted alkyl, R$^{300}$-substituted or unsubstituted heteroalkyl, R$^{300}$-substituted or unsubstituted cycloalkyl, R$^{300}$-substituted or unsubstituted heterocycloalkyl, R$^{300}$-substituted or unsubstituted aryl, or R$^{300}$-substituted or unsubstituted heteroaryl;

R$^{300}$ is independently halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, R$^{301}$-substituted or unsubstituted alkyl, R$^{301}$-substituted or unsubstituted heteroalkyl, R$^{301}$-substituted or unsubstituted cycloalkyl, R$^{301}$-substituted or unsubstituted heterocycloalkyl, R$^{301}$-substituted or unsubstituted aryl, or R$^{301}$-substituted or unsubstituted heteroaryl;

$R^{301}$ is independently halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-N(O)_2$, $-NHSO_2H$, $-NHC(O)H$, $-NHC(O)OH$, $-NHOH$, $-N_3$, unsubstituted alkyl, unsubstituted heteroalkyl, unsubstituted cycloalkyl, unsubstituted heterocycloalkyl, unsubstituted aryl, or unsubstituted heteroaryl;

$R^4$ is hydrogen, halogen, $-CX^4{}_3$, $-CHX^4{}_2$, $-CH_2X^4$, $-OCX^4{}_3$, $-OCH_2X^4$, $-OCHX^4{}_2$, $-SO_{n4}R^{4A}$, $-SO_{v4}NR^{4A}R^{4B}$, $-CN$, $-C(O)R^{4A}$, $-C(O)OR^{4A}$, $-C(O)NR^{4A}R^{4B}$, $-ONR^{4A}R^{4B}$, $-NHC(O)NR^{4A}R^{4B}$, $-N(O)_{m4}$, $-NR^{4A}R^{4B}$, $-NHNR^{4A}R^{4B}$, $-NR^{4A}SO_2R^{4B}$, $-NR^{4A}C(O)R^{4B}$, $-NR^{4A}C(O)OR^{4B}$, $-NR^{4A}OR^{4B}$, $-N_3$, $R^{400}$-substituted or unsubstituted alkyl, $R^{400}$-substituted or unsubstituted cycloalkyl, $R^{400}$-substituted or unsubstituted heterocycloalkyl, $R^{400}$-substituted or unsubstituted aryl, or $R^{400}$-substituted or unsubstituted heteroaryl;

$R^{4A}$ and $R^{4B}$ are independently hydrogen, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $R^{400}$-substituted or unsubstituted alkyl, $R^{400}$-substituted or unsubstituted heteroalkyl, $R^{400}$-substituted or unsubstituted cycloalkyl, $R^{400}$-substituted or unsubstituted heterocycloalkyl, $R^{400}$-substituted or unsubstituted aryl, or $R^{400}$-substituted or unsubstituted heteroaryl;

$R^{400}$ is independently halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-N(O)_2$, $-NHSO_2H$, $-NHC(O)H$, $-NHC(O)OH$, $-NHOH$, $-N_3$, $R^{401}$-substituted or unsubstituted alkyl, $R^{401}$-substituted or unsubstituted heteroalkyl, $R^{401}$-substituted or unsubstituted cycloalkyl, $R^{401}$-substituted or unsubstituted heterocycloalkyl, $R^{401}$-substituted or unsubstituted aryl, or $R^{401}$-substituted or unsubstituted heteroaryl;

$R^{401}$ is independently halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-N(O)_2$, $-NHSO_2H$, $-NHC(O)H$, $-NHC(O)OH$, $-NHOH$, $-N_3$, unsubstituted alkyl, unsubstituted heteroalkyl, unsubstituted cycloalkyl, unsubstituted heterocycloalkyl, unsubstituted aryl, or unsubstituted heteroaryl;

$R^5$ is hydrogen, halogen, $-CX^5{}_3$, $-CHX^5{}_2$, $-CH_2X^5$, $-OCX^5{}_3$, $-OCH_2X^5$, $-OCHX^5{}_2$, $-SO_{n5}R^{5A}$, $-SO_{v5}NR^{5A}R^{5B}$, $-CN$, $-C(O)R^{5A}$, $-C(O)OR^{5A}$, $-C(O)NR^{5A}R^{5B}$, $-OR^{5A}$, $-ONR^{5A}R^{5B}$, $-NHC(O)NR^{5A}R^{5B}$, $-N(O)_{m5}$, $-NR^{5A}R^{5B}$, $-NHNR^{5A}R^{5B}$, $-NR^{5A}SO_2R^{5B}$, $-NR^{5A}C(O)R^{5B}$, $-NR^{5A}C(O)OR^{5B}$, $-NR^{5A}OR^{5B}$, $-N_3$, $R^{500}$-substituted or unsubstituted alkyl, $R^{500}$-substituted or unsubstituted heteroalkyl, $R^{500}$-substituted or unsubstituted cycloalkyl, $R^{500}$-substituted or unsubstituted heterocycloalkyl, $R^{500}$-substituted or unsubstituted aryl, or $R^{500}$-substituted or unsubstituted heteroaryl;

$R^{5A}$ and $R^{5B}$ are independently hydrogen, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $R^{500}$-substituted or unsubstituted alkyl, $R^{500}$-substituted or unsubstituted heteroalkyl, $R^{500}$-substituted or unsubstituted cycloalkyl, $R^{500}$-substituted or unsubstituted heterocycloalkyl, $R^{500}$-substituted or unsubstituted aryl, or $R^{500}$-substituted or unsubstituted heteroaryl;

$R^{500}$ is independently halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-N(O)_2$, $-NHSO_2H$, $-NHC(O)H$, $-NHC(O)OH$, $-NHOH$, $-N_3$, $R^{501}$-substituted or unsubstituted alkyl, $R^{501}$-substituted or unsubstituted heteroalkyl, $R^{501}$-substituted or unsubstituted cycloalkyl, $R^{501}$-substituted or unsubstituted heterocycloalkyl, $R^{501}$-substituted or unsubstituted aryl, or $R^{501}$-substituted or unsubstituted heteroaryl;

$R^{501}$ is independently halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-N(O)_2$, $-NHSO_2H$, $-NHC(O)H$, $-NHC(O)OH$, $-NHOH$, $-N_3$, unsubstituted alkyl, unsubstituted heteroalkyl, unsubstituted cycloalkyl, unsubstituted heterocycloalkyl, unsubstituted aryl, or unsubstituted heteroaryl;

$R^6$ is hydrogen, halogen, $-CX^6{}_3$, $-CHX^6{}_2$, $-CH_2X^6$, $-OCX^6{}_3$, $-OCH_2X^6$, $-OCHX^6{}_2$, $-SO_{n6}R^{6A}$, $-SO_{v6}NR^{6A}R^{6B}$, $-CN$, $-C(O)R^{6A}$, $-C(O)OR^{6A}$, $-C(O)NR^{6A}R^{6B}$, $-OR^{6A}$, $-ONR^{6A}R^{6B}$, $-NHC(O)NR^{6A}R^{6B}$, $-N(O)_{m6}$, $-NR^{6A}R^{6B}$, $-NHNR^{6A}R^{6B}$, $-NR^{6A}SO_2R^{6B}$, $-NR^{6A}C(O)R^{6B}$, $-NR^{6A}C(O)OR^{6B}$, $-NR^{6A}OR^{6B}$, $-N_3$, $R^{600}$-substituted or unsubstituted alkyl, $R^{600}$-substituted or unsubstituted heteroalkyl, $R^{600}$-substituted or unsubstituted cycloalkyl, $R^{600}$-substituted or unsubstituted heterocycloalkyl, $R^{600}$-substituted or unsubstituted aryl, or $R^{600}$-substituted or unsubstituted heteroaryl;

$R^{6A}$ and $R^{6B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{200}$-substituted or unsubstituted alkyl, $R^{600}$-substituted or unsubstituted heteroalkyl, $R^{600}$-substituted or unsubstituted cycloalkyl, $R^{600}$-substituted or unsubstituted heterocycloalkyl, $R^{600}$-substituted or unsubstituted aryl, or $R^{600}$-substituted or unsubstituted heteroaryl;

$R^{600}$ is independently halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$N(O)_2$, —$NHSO_2H$, —NHC(O)H, —NHC(O)OH, —NHOH, —$N_3$, $R^{601}$-substituted or unsubstituted alkyl, $R^{601}$-substituted or unsubstituted heteroalkyl, $R^{601}$-substituted or unsubstituted cycloalkyl, $R^{201}$-substituted or unsubstituted heterocycloalkyl, $R^{601}$-substituted or unsubstituted aryl, or $R^{601}$-substituted or unsubstituted heteroaryl;

$R^{601}$ is independently halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$N(O)_2$, —$NHSO_2H$, —NHC(O)H, —NHC(O)OH, —NHOH, —$N_3$, unsubstituted alkyl, unsubstituted heteroalkyl, unsubstituted cycloalkyl, unsubstituted heterocycloalkyl, unsubstituted aryl, or unsubstituted heteroaryl;

$R^7$ is hydrogen, halogen, —$CX^7_3$, —$CHX^7_2$, —$OCX^7_3$, —$OCH_2X^7$, —$OCHX^7_2$, —$SO_{n7}R^{7A}$, —$SO_{v7}NR^{7A}R^{7B}$, —CN, —C(O)$R^{7A}$, —C(O)$OR^{7A}$, —C(O)$NR^{7A}R^{7B}$, —$OR^{7A}$, —$ONR^{7A}R^{7B}$, —NHC(O)$NR^{7A}R^{7B}$, —$N(O)_{m7}$, —$NR^{7A}R^{7B}$, —$NHNR^{7A}R^{7B}$, —$NR^{7A}SO_2R^{7B}$, —$NR^{7A}C(O)R^{7B}$, —$NR^{7A}C(O)OR^{7B}$, —$NR^{7A}OR^{7B}$, —$N_3$, $R^{700}$-substituted or unsubstituted alkyl, $R^{700}$-substituted or unsubstituted heteroalkyl, $R^{700}$-substituted or unsubstituted cycloalkyl, $R^{700}$-substituted or unsubstituted heterocycloalkyl, $R^{700}$-substituted or unsubstituted aryl, or $R^{700}$-substituted or unsubstituted heteroaryl;

$R^{7A}$ and $R^{7B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, $R^{700}$-substituted or unsubstituted alkyl, $R^{700}$-substituted or unsubstituted heteroalkyl, $R^{700}$-substituted or unsubstituted cycloalkyl, $R^{700}$-substituted or unsubstituted heterocycloalkyl, $R^{700}$-substituted or unsubstituted aryl, or $R^{700}$-substituted or unsubstituted heteroaryl;

$R^{700}$ is independently halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$N(O)_2$, —$NHSO_2H$, —NHC(O)H, —NHC(O)OH, —NHOH, —$N_3$, $R^{701}$-substituted or unsubstituted alkyl, $R^{701}$-substituted or unsubstituted heteroalkyl, $R^{701}$-substituted or unsubstituted cycloalkyl, $R^{701}$-substituted or unsubstituted heterocycloalkyl, $R^{701}$-substituted or unsubstituted aryl, or $R^{701}$-substituted or unsubstituted heteroaryl;

$R^{701}$ is independently halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$N(O)_2$, —$NHSO_2H$, —NHC(O)H, —NHC(O)OH, —NHOH, —$N_3$, unsubstituted alkyl, unsubstituted heteroalkyl, unsubstituted cycloalkyl, unsubstituted heterocycloalkyl, unsubstituted aryl, or unsubstituted heteroaryl;

$R^7$ and $R^{15}$ are optionally joined to form a substituted or unsubstituted cycloalkyl, substituted or unsubstituted heterocycloalkyl, substituted or unsubstituted aryl, or substituted or unsubstituted heteroaryl, wherein the substituted cycloalkyl, substituted heterocycloalkyl, substituted aryl, or substituted heteroaryl is substituted with a substituent group;

$R^8$ is hydrogen, halogen, —$CX^8_3$, —$CHX^8_2$, —$CH_2X^8$, —$OCX^8_3$, —$OCH_2X^8$, —$OCHX^8_2$, —$SO_{n8}R^{8A}$, —$SO_{v8}NR^{8A}R^{8B}$, —CN, —C(O)$R^{8A}$, —C(O)$OR^{8A}$, —C(O)$NR^{8A}R^{8B}$, —$OR^{8A}$, —$ONR^{8A}R^{8B}$, —NHC(O)$NR^{8A}R^{8B}$, —$N(O)_{m8}$, —$NR^{8A}R^{8B}$, —$NHNR^{8A}R^{8B}$, —$NR^{8A}SO_2R^{8B}$, —$NR^{8A}C(O)R^{8B}$, —$NR^{8A}C(O)OR^{8B}$, —$NR^{8A}OR^{8B}$, —$N_3$, $R^{800}$-substituted or unsubstituted alkyl, $R^{800}$-substituted or unsubstituted heteroalkyl, $R^{800}$-substituted or unsubstituted cycloalkyl, $R^{800}$-substituted or unsubstituted heterocycloalkyl, $R^{800}$-substituted or unsubstituted aryl, or $R^{800}$-substituted or unsubstituted heteroaryl;

$R^{8A}$ and $R^{8B}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, $R^{800}$-substituted or unsubstituted alkyl, $R^{800}$-substituted or unsubstituted heteroalkyl, $R^{800}$-substituted or unsubstituted cycloalkyl, $R^{800}$-substituted or unsubstituted heterocycloalkyl, $R^{800}$-substituted or unsubstituted aryl, or $R^{800}$-substituted or unsubstituted heteroaryl;

$R^{800}$ is independently halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, R$^{801}$-substituted or unsubstituted alkyl, R$^{801}$-substituted or unsubstituted heteroalkyl, R$^{801}$-substituted or unsubstituted cycloalkyl, R$^{801}$-substituted or unsubstituted heterocycloalkyl, R$^{801}$-substituted or unsubstituted aryl, or R$^{801}$-substituted or unsubstituted heteroaryl;

R$^{801}$ is independently halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, unsubstituted alkyl, unsubstituted heteroalkyl, unsubstituted cycloalkyl, unsubstituted heterocycloalkyl, unsubstituted aryl, or unsubstituted heteroaryl;

R$^9$ is hydrogen, halogen, —CX$^9_3$, —CHX$^9_2$, —CH$_2$X$^9$, —OCX$^9_3$, —OCH$_2$X$^9$, —OCHX$^9_2$, —SO$_{n9}$R$^{9A}$, —SO$_{v9}$NR$^{9A}$R$^{9B}$, —CN, —C(O)R$^{9A}$, —C(O)OR$^{9A}$, —C(O)NR$^{9A}$R$^{9B}$, —OR$^{9A}$, —ONR$^{9A}$R$^{9B}$, —NHC(O)NR$^{9A}$R$^{9B}$, —N(O)$_{m9}$, —NR$^{9A}$R$^{9B}$, —NHNR$^{9A}$R$^{9B}$, —NR$^{9A}$SO$_2$R$^{9B}$, —NR$^{9A}$C(O)R$^{9B}$, —NR$^{9A}$C(O)OR$^{9B}$, —NR$^{9A}$OR$^{9B}$, —N$_3$, R$^{900}$-substituted or unsubstituted alkyl, R$^{900}$-substituted or unsubstituted heteroalkyl, R$^{900}$-substituted or unsubstituted cycloalkyl, R$^{900}$-substituted or unsubstituted heterocycloalkyl, R$^{900}$-substituted or unsubstituted aryl, or R$^{900}$-substituted or unsubstituted heteroaryl;

R$^{9A}$ and R$^{9B}$ are independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, R$^{900}$-substituted or unsubstituted alkyl, R$^{900}$-substituted or unsubstituted heteroalkyl, R$^{900}$-substituted or unsubstituted cycloalkyl, R$^{900}$-substituted or unsubstituted heterocycloalkyl, R$^{900}$-substituted or unsubstituted aryl, or R$^{900}$-substituted or unsubstituted heteroaryl;

R$^{900}$ is independently halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, R$^{901}$-substituted or unsubstituted alkyl, R$^{901}$-substituted or unsubstituted heteroalkyl, R$^{901}$-substituted or unsubstituted cycloalkyl, R$^{901}$-substituted or unsubstituted heterocycloalkyl, R$^{901}$-substituted or unsubstituted aryl, or R$^{901}$-substituted or unsubstituted heteroaryl;

R$^{901}$ is independently halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, unsubstituted alkyl, unsubstituted heteroalkyl, unsubstituted cycloalkyl, unsubstituted heterocycloalkyl, unsubstituted aryl, or unsubstituted heteroaryl;

R$^9$ and R$^{11}$ are optionally joined to form a substituted or unsubstituted cycloalkyl, substituted or unsubstituted heterocycloalkyl, substituted or unsubstituted aryl, or substituted or unsubstituted heteroaryl, wherein the substituted cycloalkyl, substituted heterocycloalkyl, substituted aryl, or substituted heteraryl is substituted with a substituent group;

R$^{10}$ is hydrogen, halogen, —CX$^{10}_3$, —CHX$^{10}_2$, —CH$_2$X$^{10}$, —OCX$^{10}_3$, —OCH$_2$X$^{10}$, —OCHX$^{10}_2$, —SO$_{n10}$R$^{10A}$, —SO$_{v10}$NR$^{10A}$R$^{10B}$, —CN, —C(O)R$^{10A}$, —C(O)OR$^{10A}$, —C(O)NR$^{10A}$R$^{10B}$, —OR$^{10A}$, —ONR$^{10A}$R$^{10B}$, —NHC(O)NR$^{10A}$R$^{10B}$, —N(O)$_{m10}$, —NR$^{10A}$R$^{10B}$, —NHNR$^{10A}$R$^{10B}$, —NR$^{10A}$, —SO$_2$R$^{10B}$, —NR$^{10A}$C(O)R$^{10B}$, —NR$^{10A}$C(O)OR$^{10B}$, —NR$^{10A}$OR$^{10B}$, —N$_3$, R$^{101}$-substituted or unsubstituted alkyl, R$^{101}$-substituted or unsubstituted heteroalkyl, R$^{101}$-substituted or unsubstituted cycloalkyl, R$^{101}$-substituted or unsubstituted heterocycloalkyl, R$^{101}$-substituted or unsubstituted aryl, or R$^{101}$-substituted or unsubstituted heteroaryl;

R$^{10A}$ and R$^{10B}$ are independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, R$^{101}$-substituted or unsubstituted alkyl, R$^{101}$-substituted or unsubstituted heteroalkyl, R$^{101}$-substituted or unsubstituted cycloalkyl, R$^{101}$-substituted or unsubstituted heterocycloalkyl, R$^{101}$-substituted or unsubstituted aryl, or R$^{101}$-substituted or unsubstituted heteroaryl;

R$^{101}$ is independently halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, R$^{102}$-substituted or unsubstituted alkyl, R$^{102}$-substituted or unsubstituted heteroalkyl, R$^{102}$-substituted or unsubstituted cycloalkyl, R$^{102}$-substituted or unsubstituted heterocycloalkyl, R$^{102}$-substituted or unsubstituted aryl, or R$^{102}$-substituted or unsubstituted heteroaryl;

R$^{102}$ is independently halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, unsubstituted alkyl, unsubstituted heteroalkyl, unsubstituted cycloalkyl, unsubstituted heterocycloalkyl, unsubstituted aryl, or unsubstituted heteroaryl;

R$^{11}$ is hydrogen, halogen, —CX$^{11}_3$, —CHX$^{11}_2$, —CH$_2$X$^{11}$, —OCX$^{11}_3$, —OCH$_2$X$^{11}$, —OCHX$^{11}_2$, —SO$_{n11}$R$^{11A}$, —SO$_{v11}$NR$^{11A}$R$^{11B}$, —CN, —C(O)R$^{11A}$, —C(O)OR$^{11A}$, —C(O)NR$^{11A}$R$^{11B}$, —OR$^{11A}$, —ONR$^{11A}$R$^{11B}$, —NHC(O)NR$^{11A}$R$^{11B}$, —N(O)$_{m11}$, —NR$^{11A}$R$^{11B}$, —NHNR$^{11A}$R$^{11B}$, —NR$^{11A}$SO$_2$R$^{11B}$, —NR$^{11A}$C(O)R$^{11B}$, —NR$^{11A}$C(O)OR$^{11B}$, —NR$^{11A}$R$^{11B}$, —N$_3$, R$^{110}$-substituted or unsubstituted alkyl, R$^{110}$-substituted or unsubstituted heteroalkyl, R$^{110}$-substituted or unsubstituted cycloalkyl, R$^{110}$-substituted or unsubstituted heterocycloalkyl, R$^{110}$-substituted or unsubstituted aryl, or R$^{110}$-substituted or unsubstituted heteroaryl;

R$^{11A}$ and R$^{11B}$ are independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, R$^{110}$-substituted or unsubstituted alkyl, R$^{110}$-substituted or unsubstituted heteroalkyl, R$^{110}$-substituted or unsubstituted cycloalkyl, R$^{110}$-substituted or unsubstituted heterocycloalkyl, R$^{110}$-substituted or unsubstituted aryl, or R$^{110}$-substituted or unsubstituted heteroaryl;

R$^{110}$ is independently halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, R$^{111}$-substituted or unsubstituted alkyl, R$^{111}$-substituted or unsubstituted heteroalkyl, R$^{111}$-substituted or unsubstituted cycloalkyl, R$^{111}$-substituted or unsubstituted heterocycloalkyl, R$^{111}$-substituted or unsubstituted aryl, or R$^{111}$-substituted or unsubstituted heteroaryl;

R$^{111}$ is independently halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, unsubstituted alkyl, unsubstituted heteroalkyl, unsubstituted cycloalkyl, unsubstituted heterocycloalkyl, unsubstituted aryl, or unsubstituted heteroaryl;

R$^{12}$ is hydrogen, halogen, —CX$^{12}_3$, —CHX$^{12}_2$, —CH$_2$X$^{12}$, —OCX$^{12}_3$, —OCH$_2$X$^{12}$, —OCHX$^{12}_2$, —SO$_{n12}$R$^{12A}$, —SO$_{v12}$NR$^{12A}$R$^{12B}$, —CN, —C(O)R$^{12A}$, —C(O)OR$^{12A}$, —C(O)NR$^{12A}$R$^{12B}$, —NR$^{12A}$, —ONR$^{12A}$R$^{12B}$, —NHC(O)NR$^{12A}$R$^{12B}$, —N(O)$_{m12}$, —NR$^{12A}$R$^{12B}$, —NHNR$^{12A}$R$^{12B}$, —NR$^{12A}$SO$_2$R$^{12B}$, —NR$^{12A}$C(O)R$^{12B}$, —NR$^{12A}$C(O)OR$^{12B}$, —NR$^{12A}$OR$^{12B}$, —N$_3$, R$^{120}$-substituted or unsubstituted alkyl, R$^{120}$-substituted or unsubstituted heteroalkyl, R$^{120}$-substituted or unsubstituted cycloalkyl, R$^{120}$-substituted or unsubstituted heterocycloalkyl, R$^{120}$-substituted or unsubstituted aryl, or R$^{120}$-substituted or unsubstituted heteroaryl;

R$^{12A}$ and R$^{12B}$ are independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, R$^{120}$-substituted or unsubstituted alkyl, R$^{120}$-substituted or unsubstituted heteroalkyl, R$^{120}$-substituted or unsubstituted cycloalkyl, R$^{120}$-substituted or unsubstituted heterocycloalkyl, R$^{120}$-substituted or unsubstituted aryl, or R$^{120}$-substituted or unsubstituted heteroaryl;

R$^{120}$ is independently halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, R$^{121}$-substituted or unsubstituted alkyl, R$^{121}$-substituted or unsubstituted heteroalkyl, R$^{121}$-substituted or unsubstituted cycloalkyl, R$^{121}$-substituted or unsubstituted heterocycloalkyl, R$^{121}$-substituted or unsubstituted aryl, or R$^{121}$-substituted or unsubstituted heteroaryl;

R$^{121}$ is independently halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —N(O)$_2$, —NHSO$_2$H, —NHC(O)H, —NHC(O)OH, —NHOH, —N$_3$, unsubstituted alkyl, unsubstituted heteroalkyl, unsubstituted cycloalkyl, unsubstituted heterocycloalkyl, unsubstituted aryl, or unsubstituted heteroaryl;

R$^{15}$ is hydrogen, —C(O)OR$^{15A}$, —C(O)R$^{15A}$, —SO$_2$R$^{15A}$, R$^{150}$-substituted or unsubstituted alkyl, R$^{150}$-substituted or unsubstituted heteroalkyl, R$^{150}$-substituted or unsubstituted cycloalkyl, R$^{150}$-substituted or unsubstituted heterocycloalkyl, R$^{150}$-substituted or unsubstituted aryl, or R$^{150}$-substituted or unsubstituted heteroaryl;

R$^{15A}$ is hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, R$^{150}$-substituted or unsubstituted alkyl, $R^{150}$-substituted or unsubstituted heteroalkyl, $R^{150}$-substituted or unsubstituted cycloalkyl, $R^{150}$-substituted or unsubstituted heterocycloalkyl, $R^{150}$-substituted or unsubstituted aryl, or $R^{150}$-substituted or unsubstituted heteroaryl;

$R^{150}$ is independently halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$N(O)_2$, —$NHSO_2H$, —NHC(O)H, —NHC(O)OH, —NHOH, —$N_3$, $R^{151}$-substituted or unsubstituted alkyl, $R^{151}$-substituted or unsubstituted heteroalkyl, $R^{151}$-substituted or unsubstituted cycloalkyl, $R^{151}$-substituted or unsubstituted heterocycloalkyl, $R^{151}$-substituted or unsubstituted aryl, or $R^{151}$-substituted or unsubstituted heteroaryl;

$R^{151}$ is independently halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$N(O)_2$, —$NHSO_2H$, —NHC(O)H, —NHC(O)OH, —NHOH, —$N_3$, unsubstituted alkyl, unsubstituted heteroalkyl, unsubstituted cycloalkyl, unsubstituted heterocycloalkyl, unsubstituted aryl, or unsubstituted heteroaryl;

$R^{16}$ is hydrogen, —C(O)O$R^{16A}$, —C(O)$R^{16A}$, —$SO_2R^{16A}$, $R^{160}$-substituted or unsubstituted alkyl, $R^{160}$-substituted or unsubstituted heteroalkyl, $R^{160}$-substituted or unsubstituted cycloalkyl, $R^{160}$-substituted or unsubstituted heterocycloalkyl, $R^{160}$-substituted or unsubstituted aryl, or $R^{160}$-substituted or unsubstituted heteroaryl;

$R^{16A}$ is hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —OC $HCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, $R^{160}$-substituted or unsubstituted alkyl, $R^{160}$-substituted or unsubstituted heteroalkyl, $R^{160}$-substituted or unsubstituted cycloalkyl, $R^{160}$-substituted or unsubstituted heterocycloalkyl, $R^{160}$-substituted or unsubstituted aryl, or $R^{160}$-substituted or unsubstituted heteroaryl;

$R^{160}$ is independently halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$N(O)_2$, —$NHSO_2H$, —NHC(O)H, —NHC(O)OH, —NHOH, —$N_3$, $R^{161}$-substituted or unsubstituted alkyl, $R^{161}$-substituted or unsubstituted heteroalkyl, $R^{161}$-substituted or unsubstituted cycloalkyl, $R^{161}$-substituted or unsubstituted heterocycloalkyl, $R^{161}$-substituted or unsubstituted aryl, or $R^{161}$-substituted or unsubstituted heteroaryl;

$R^{161}$ is independently halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$N(O)_2$, —$NHSO_2H$, —NHC(O)H, —NHC(O)OH, —NHOH, —$N_3$, unsubstituted alkyl, unsubstituted heteroalkyl, unsubstituted cycloalkyl, unsubstituted heterocycloalkyl, unsubstituted aryl, or unsubstituted heteroaryl;

$X^2, X^3, X^4, X^5, X^6, X^7, X^8, X^9, X^{10}, X^{11}$, and $X^{12}$ are each independently —F, —Cl, —Br, or —I;

n2, n3, n4, n5, n6, n7, n8, n9, n10, n11, and n12 are independently an integer from 0 to 4;

m2, m3, m4, m5, m6, m7, m8, m9, m10, m11, and m12 are independently 1 or 2;

v2, v3, v4, v5, v6, v7, v8, v9, v10, v11, and v12 are independently 1 or 2;

z1 is an integer from 1 to 10;

z3 is an integer from 1 to 10; and z4 is an integer from 0 to 9.

2. The compound of claim 1, wherein $A^1$ is C($R^4$), and $A^2$ is C($R^{10}$).

3. The compound of claim 1, wherein $A^1$ is N, and $A^2$ is C($R^{10}$) or N.

4. The compound of claim 1, wherein m is 2.

5. The compound of claim 1, wherein X is a bond.

6. The compound of claim 1, wherein $L^1$ is a bond, —NH—, —$(CH_2)_{z1}$—NH—, —$(CH_2)_{z2}$—, or —$(CH_2)_{z3}$—N(($CH_2)_{z4}CH_3$)—C(=O)—, wherein z2 is an integer from 1 to 10.

7. The compound of claim 1, wherein $R^2$ is hydrogen, halogen, —$CX^2_3$, —$CHX^2_2$, —$CH_2X^2$, —$OCX^2_3$, —$OCH_2X^2$, —$OCHX^2_2$, —$SO_{n2}R^{2A}$, —$SO_{v2}NR^{2A}R^{2B}$, —CN, —C(O)$R^{2A}$, —C(O)O$R^{2A}$, —C(O)N$R^{2A}R^{2B}$, —O$R^{2A}$, —ONR$^{2A}R^{2B}$, —NHC(O)N$R^{2A}R^{2B}$, —N(O)$_{m2}$, —N$R^{2A}R^{2B}$, —NHNR$^{2A}R^{2B}$, —N$R^{2A}R^{2B}$, —N$R^{2A}$C(O)$R^{2B}$, —N$R^{2A}$C(O)O$R^{2B}$, —N$R^{2A}$O$R^{2B}$, —$N_3$, $R^{200}$-substituted or unsubstituted alkyl, $R^{200}$-substituted or unsubstituted heteroalkyl, $R^{200}$-substituted or unsubstituted cycloalkyl, $R^{200}$-substituted or unsubstituted heterocycloalkyl, $R^{200}$-substituted or unsubstituted aryl, or $R^{200}$-substituted or unsubstituted heteroaryl.

8. The compound of claim 1, wherein $R^2$ is halogen, —$CX^2_3$, —$CHX^2_2$, —$CH_2X^2$, —$OCX^2_3$, —$OCH_2X^2$, or —$OCHX^2_2$; $R^6$ is halogen, —$CX^6_3$, —$CHX^6_2$, —$CH_2X^6$, —$OCX^6_3$, —$OCH_2X^6$, or —$OCHX^6_2$; and $X^2$ and $X^6$ are each independently chlorine or fluorine.

9. The compound of claim 1, wherein $R^2$ is halogen and $R^6$ is halogen or unsubstituted $C_{1-6}$ alkyl.

10. The compound of claim 1, wherein $R^4$ is hydrogen, halogen, $R^{400}$-substituted or unsubstituted alkyl, $R^{400}$-substituted or unsubstituted cycloalkyl, $R^{400}$-substituted or unsubstituted heterocycloalkyl, $R^{400}$-substituted or unsubstituted aryl, or $R^{400}$-substituted or unsubstituted heteroaryl.

11. The compound of claim 1, wherein $R^3$ is hydrogen; $R^5$ is hydrogen; $R^7$ is hydrogen; $R^8$ is hydrogen; $R^9$ is hydrogen; $R^{10}$ is hydrogen; $R^{11}$ is hydrogen; $R^{12}$ is hydrogen; or a combination of any two or more of the foregoing.

12. The compound of claim 1, wherein $R^{11}$ is $R^{110}$-substituted or unsubstituted heteroalkyl,

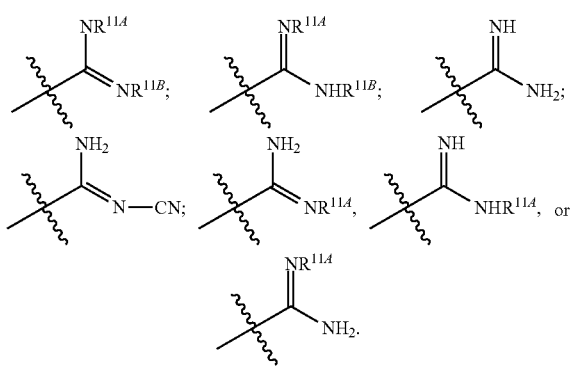

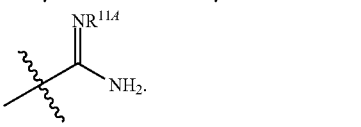

13. The compound of claim 1, wherein $R^9$ and $R^{11}$ are joined to form unsubstituted 5-6 membered heterocycloalkyl.

14. The compound of claim 1, wherein $R^7$ and $R^{15}$ are joined to form unsubstituted 6 membered heterocycloalkyl, wherein the heterocycloalkyl comprises (i) an oxygen atom, (ii) a nitrogen atom, or (iii) an oxygen atom and a nitrogen atom.

15. The compound of claim 1, wherein $R^7$ and $R^{15}$ are joined to form unsubstituted 6 membered aryl or an unsubstituted 6 membered cycloalkyl.

16. The compound of claim 1, wherein $R^7$ and $R^{15}$ are joined to form unsubstituted 5 or 6 membered heteroaryl, wherein the heteroaryl comprises 1 or 2 nitrogen atoms.

17. The compound of claim 1, wherein the compound of Formula (I) is a compound of Formula (JIB) or a pharmaceutically acceptable salt thereof, or a compound of Formula (IIIB) or a pharmaceutically acceptable salt thereof;

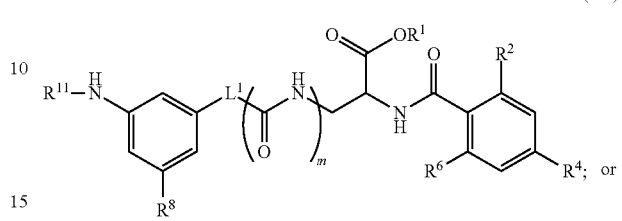

(IIB)

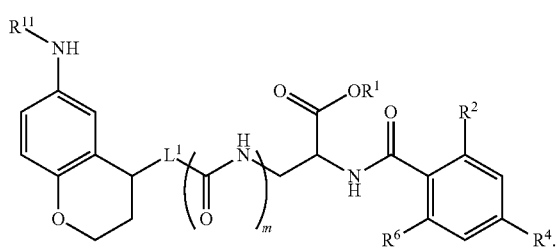

(IIIB)

18. The compound of claim 1, wherein the compound of Formula (I) is:

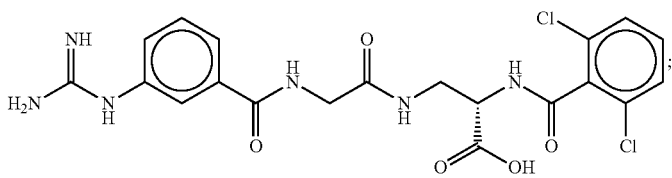

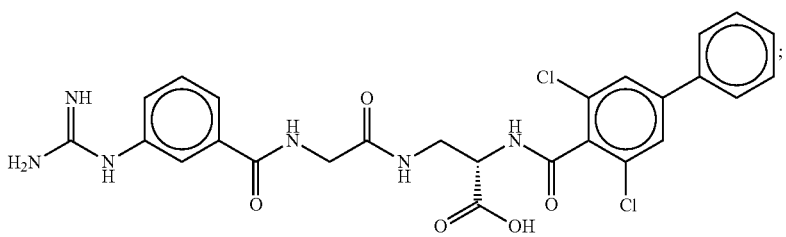

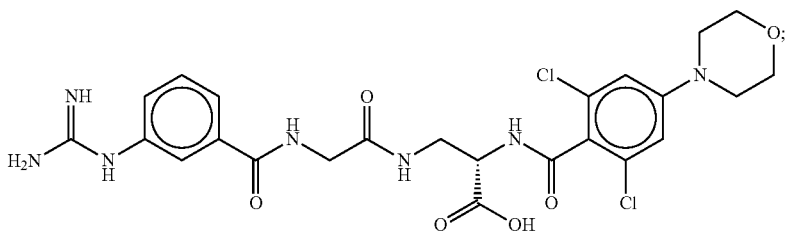

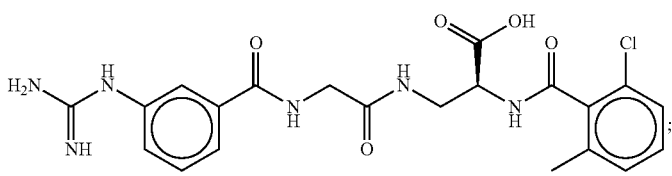

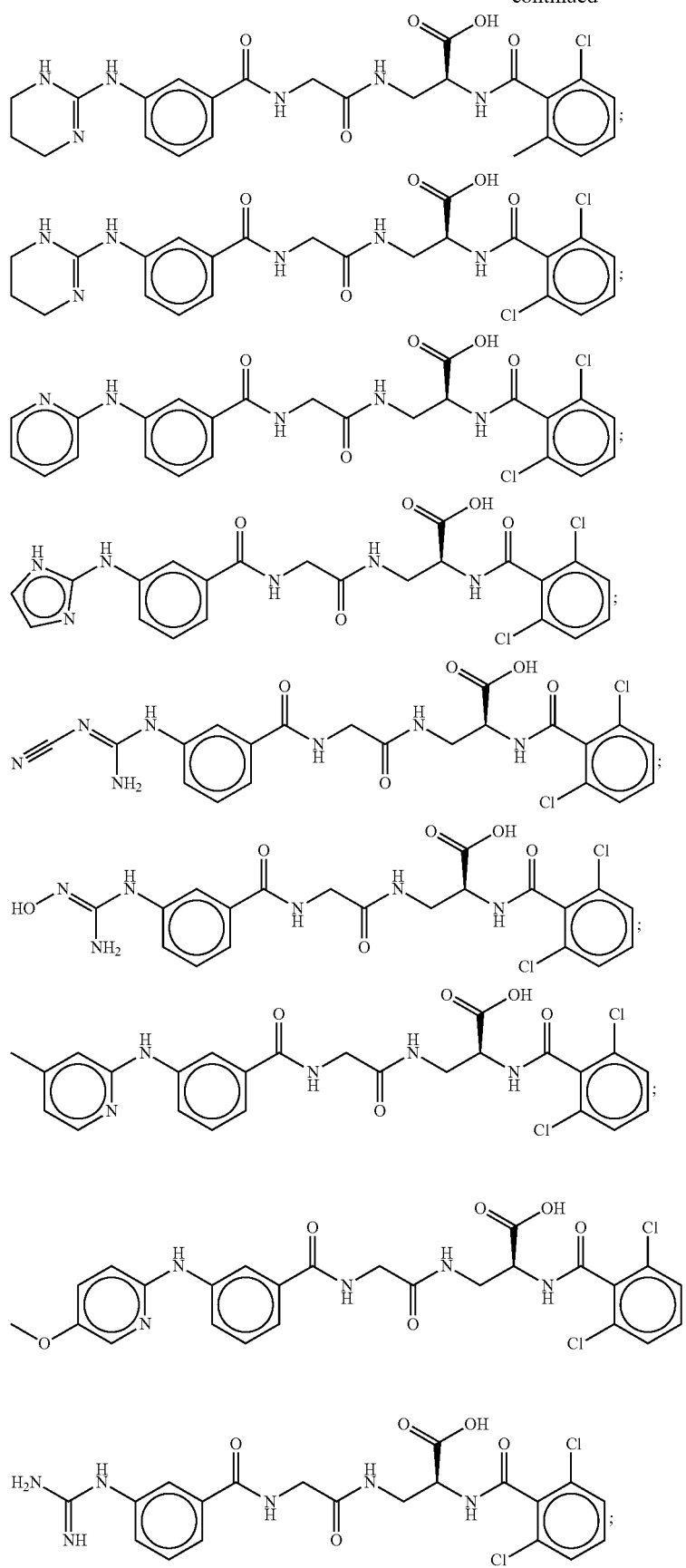

-continued
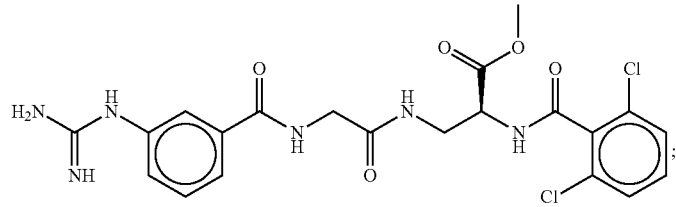
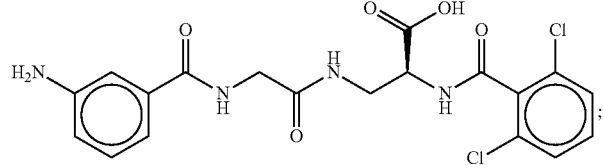
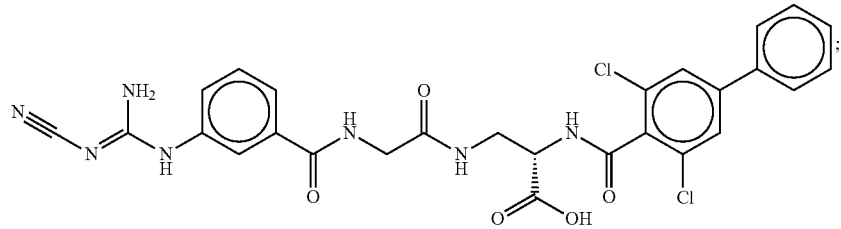
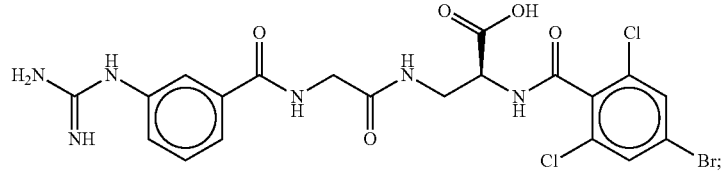
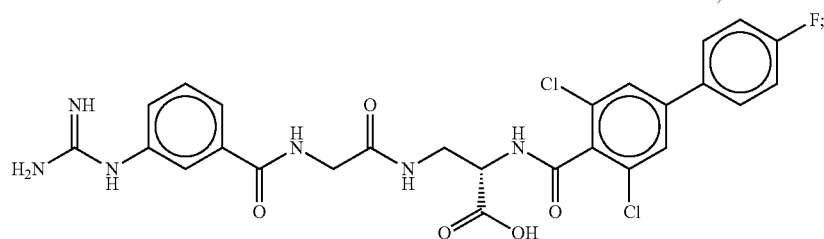
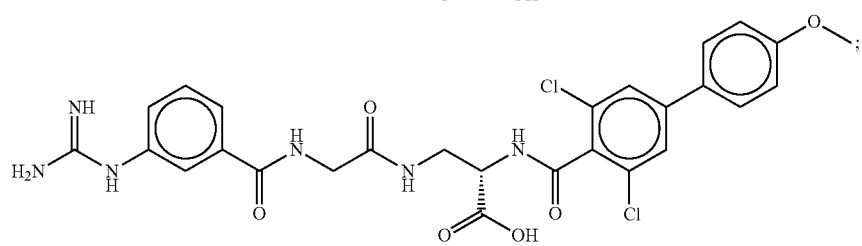
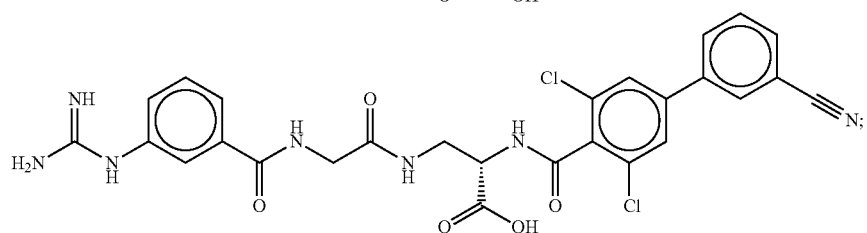
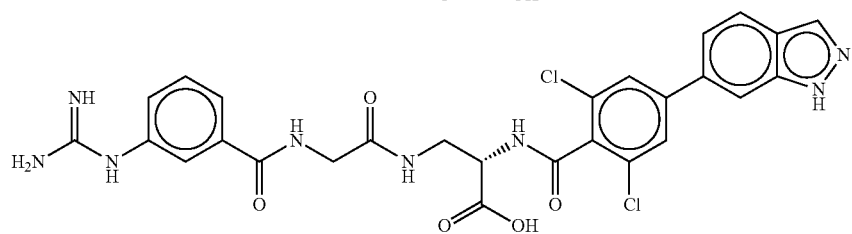

-continued
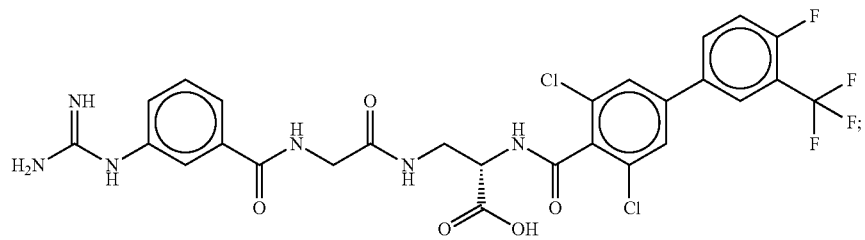
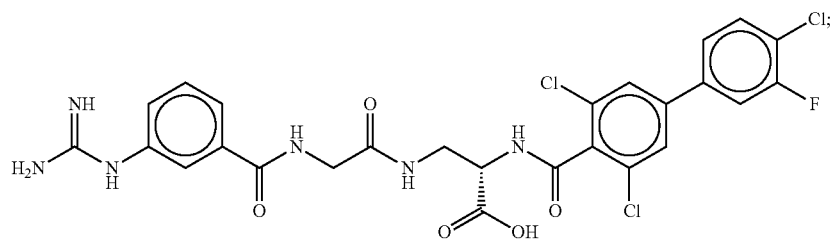
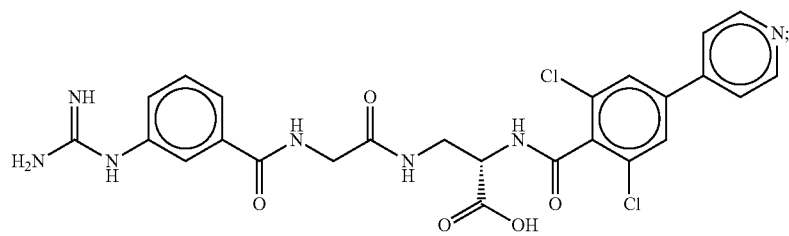
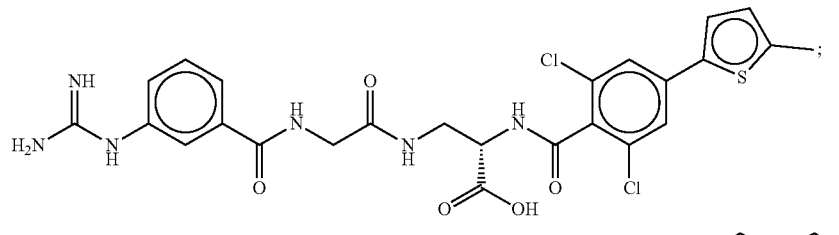
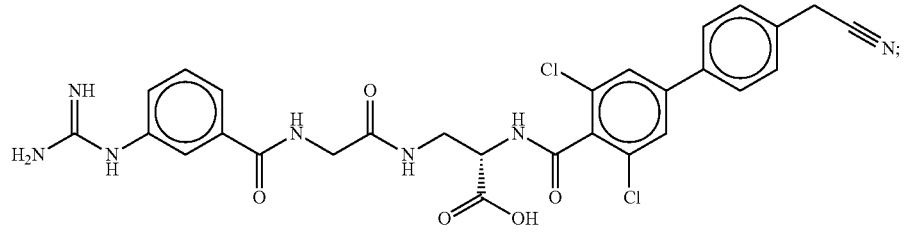
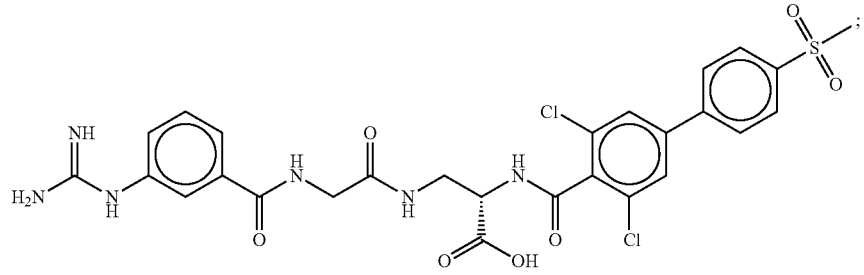
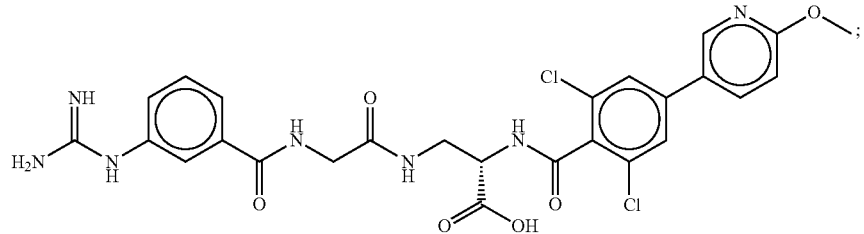

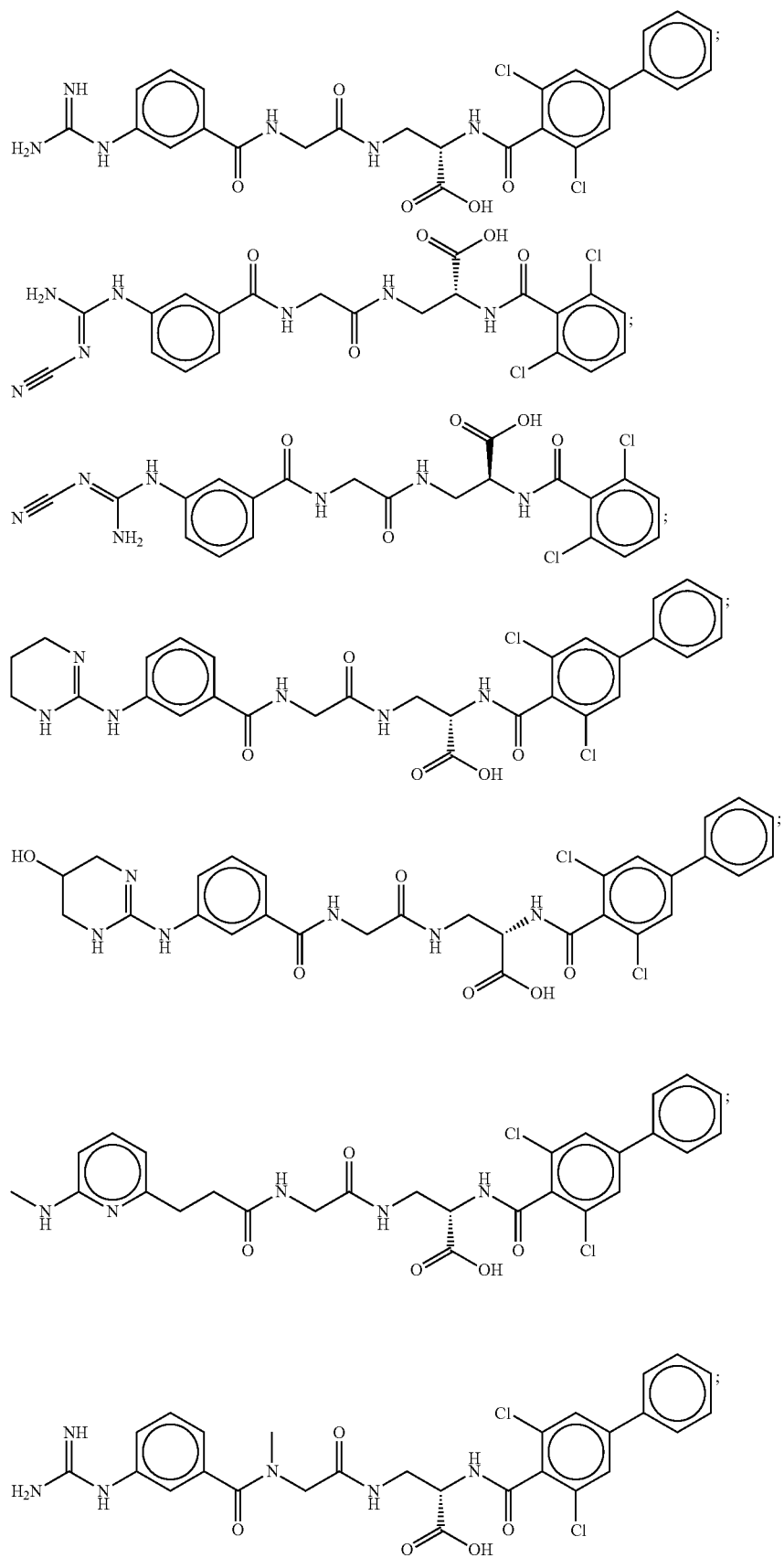

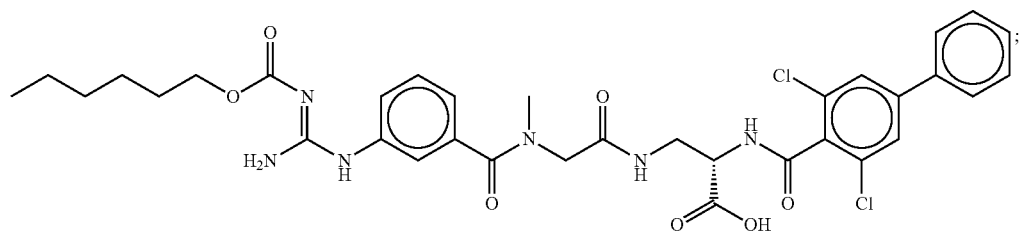
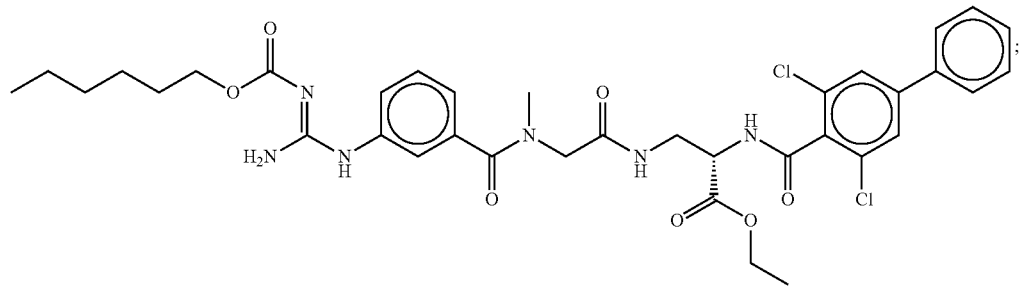
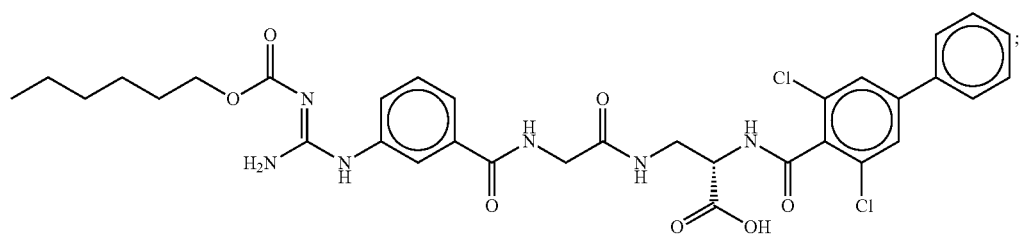
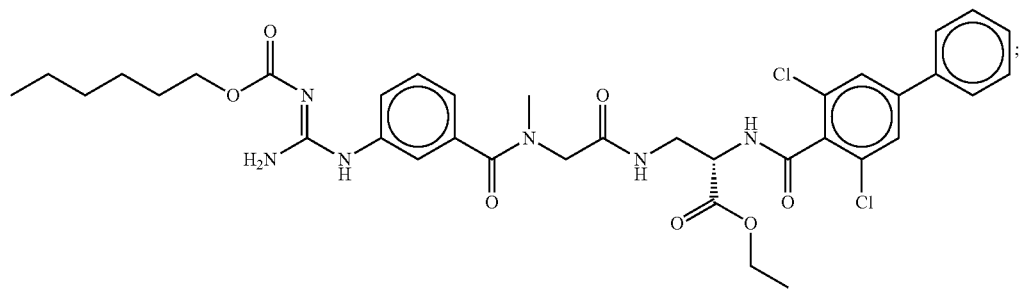
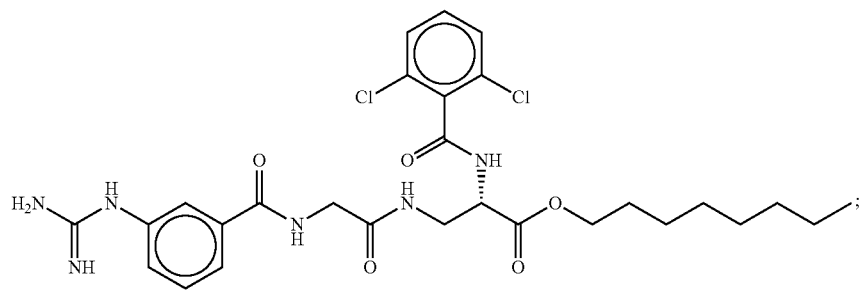
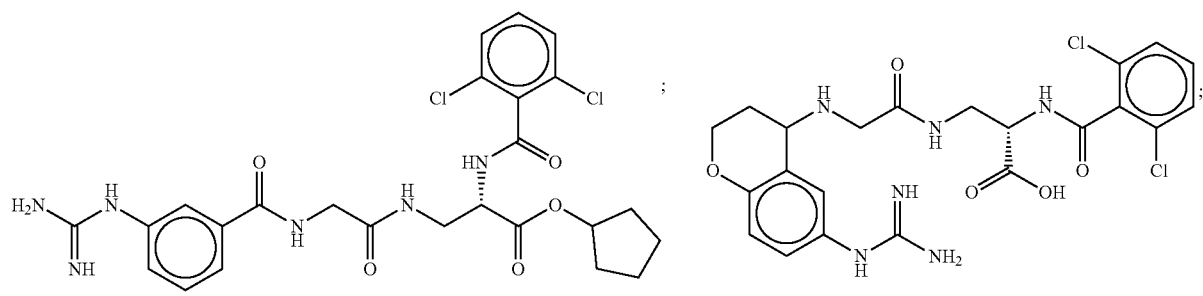

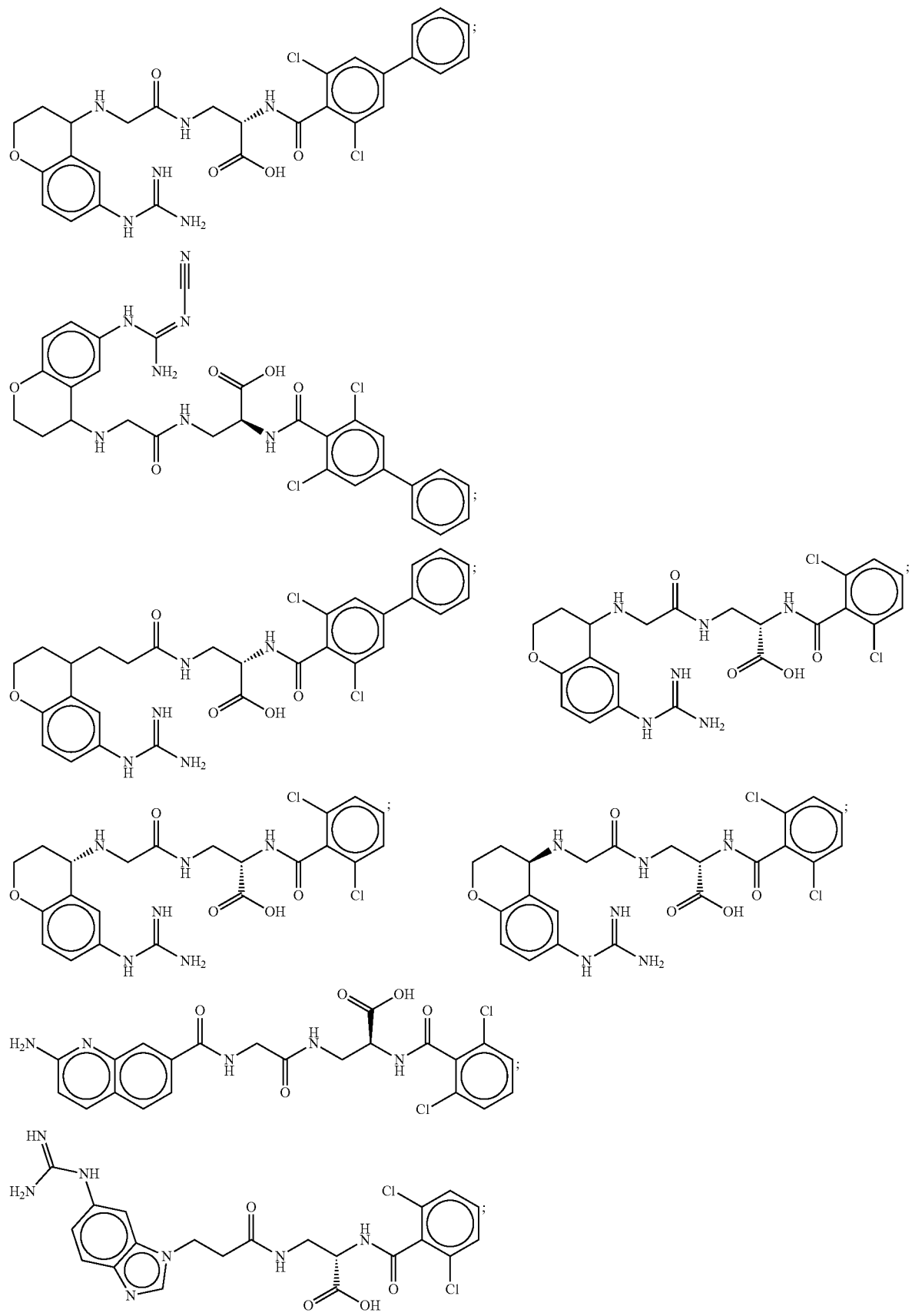

-continued
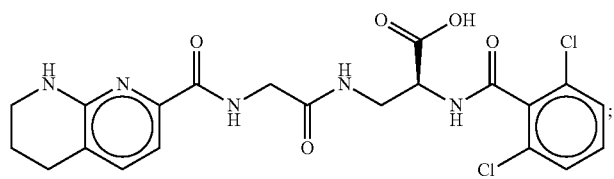
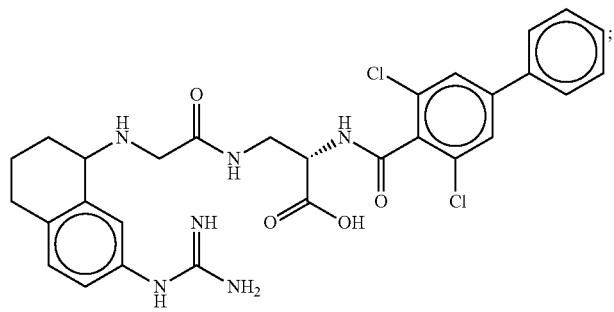
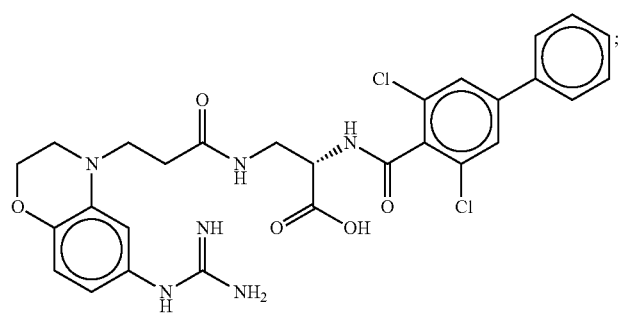
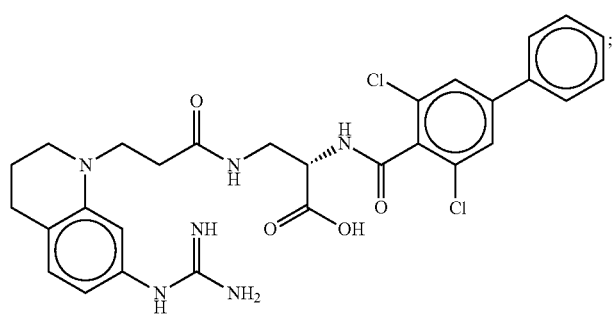
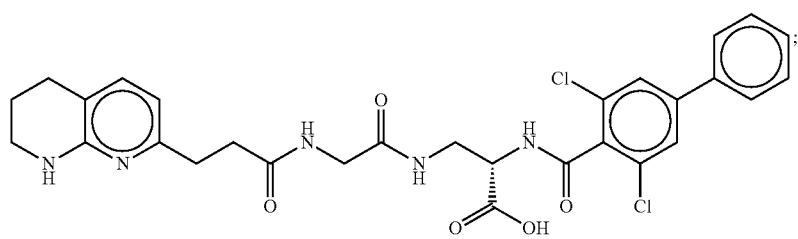
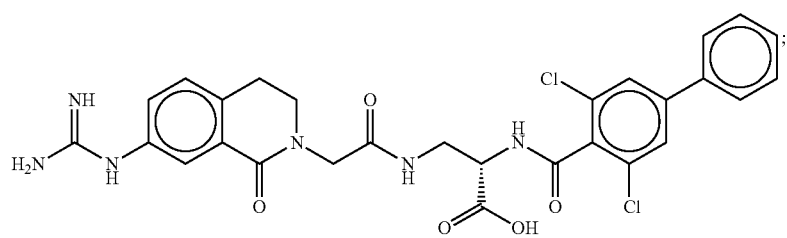

-continued
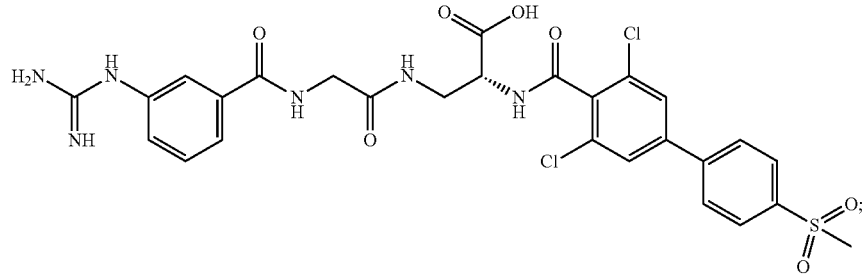
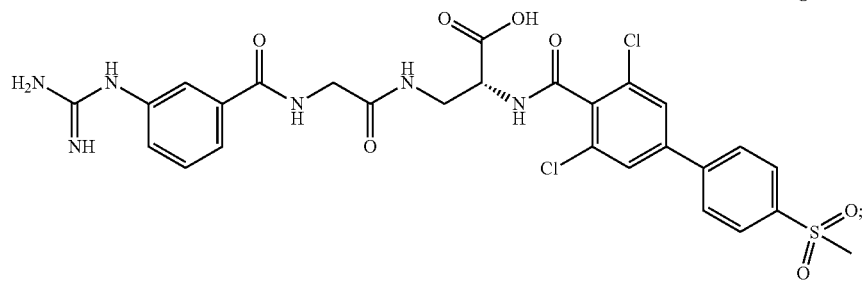
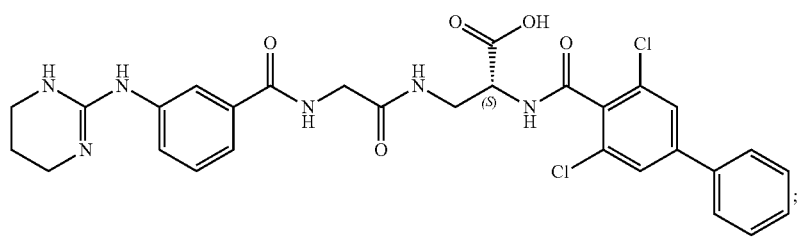
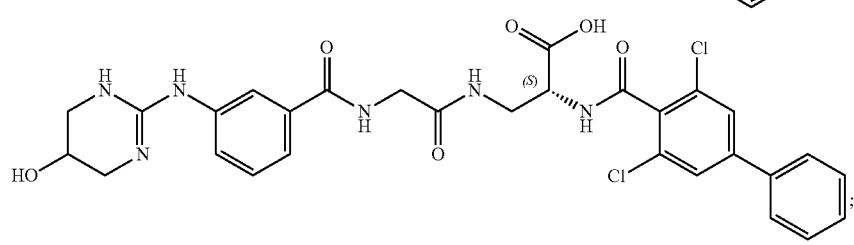
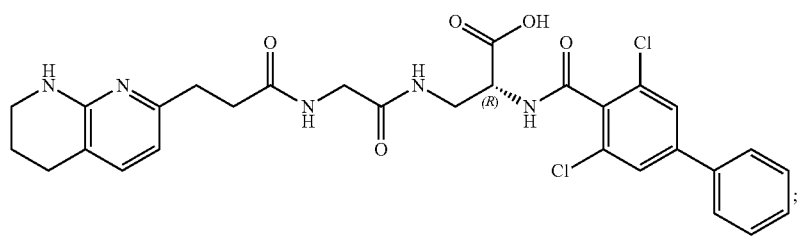
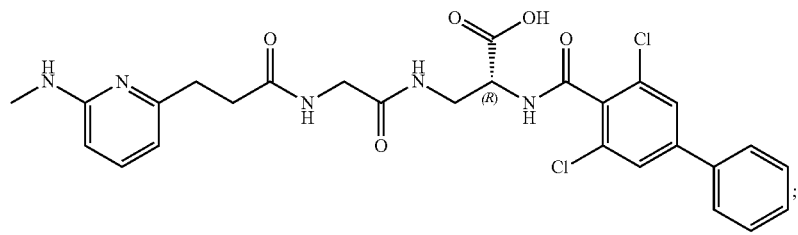
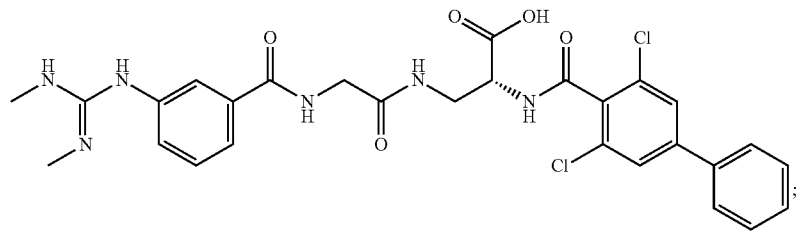

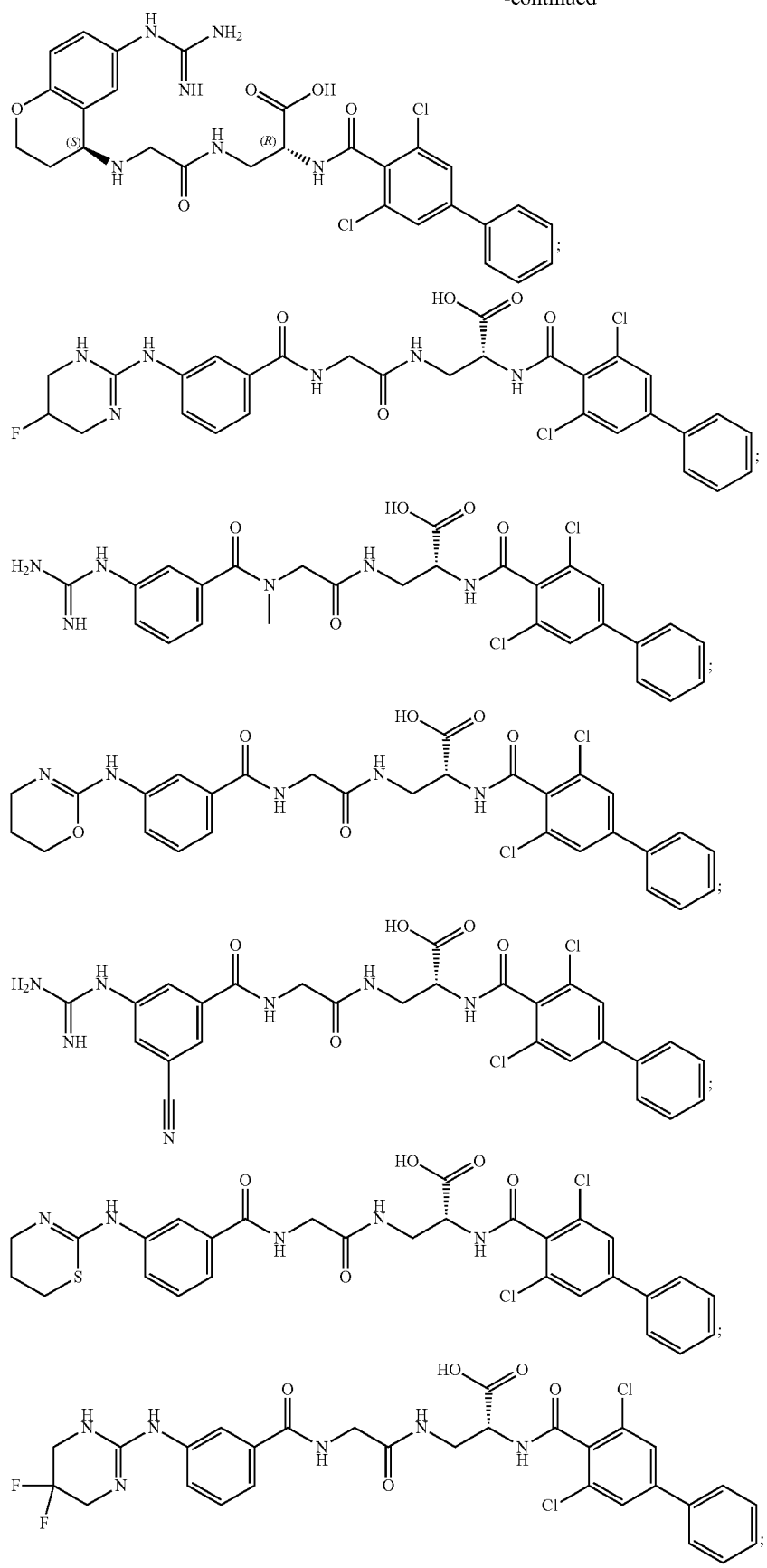

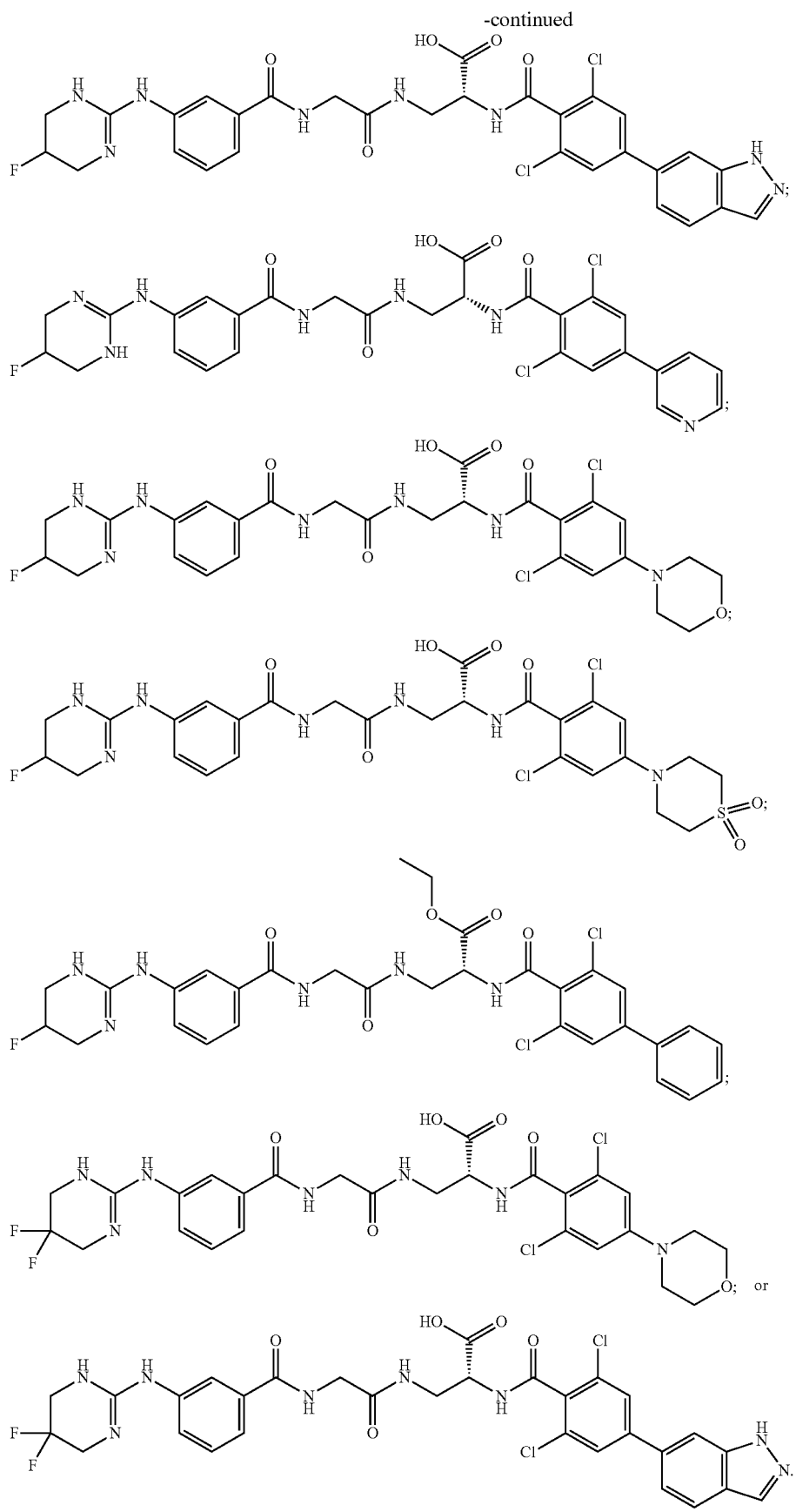

19. A pharmaceutical composition comprising the compound of claim 1 and a pharmaceutically acceptable carrier.

20. A method of treating asthma, rheumatoid arthritis, colorectal cancer, liver cancer, prostate cancer, renal cell carcinoma, breast cancer, esophageal cancer, non-small cell lung cancer, osteosarcoma, ovarian cancer, pancreatic cancer, thyroid cancer, melanoma, or rhabdomyosarcoma; or inhibiting angiogenesis in a patient in need thereof, the method comprising administering to the patient an effective amount of the compound of claim 1.

21. A compound, or a pharmaceutically acceptable salt thereof, having the formula:

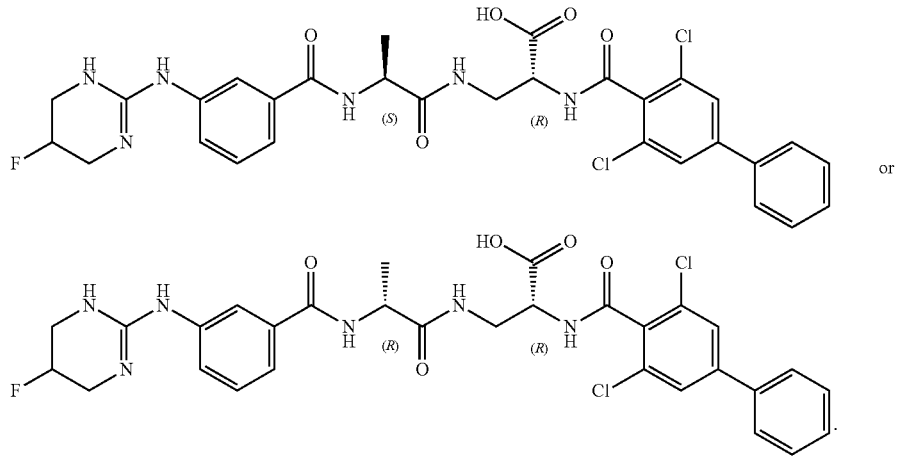

* * * * *